US010118927B2

United States Patent
Brown et al.

(10) Patent No.: US 10,118,927 B2
(45) Date of Patent: Nov. 6, 2018

(54) SUBSTITUTED PIPERIDIN-4-AMINO-TYPE COMPOUNDS AND USES THEREOF

(71) Applicants: SHIONOGI & CO., LTD., Chuo-ku, Osaka (JP); Kevin Brown, Philadelphia, PA (US); Dawit Tadesse, Parlin, NJ (US); Naoki Tsuno, Toyonaka-shi, Osaka (JP); Nobuyuki Tanaka, Toyonaka-shi, Osaka (JP); Xiaoming Zhou, Plainsboro, NJ (US)

(72) Inventors: Kevin Brown, Philadelphia, PA (US); Dawit Tadesse, Parlin, NJ (US); Nobuyuki Tanaka, Toyonaka (JP); Naoki Tsuno, Toyonaka (JP); Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/655,882

(22) PCT Filed: Dec. 23, 2013

(86) PCT No.: PCT/IB2013/002875
§ 371 (c)(1),
(2) Date: Jun. 26, 2015

(87) PCT Pub. No.: WO2014/102590
PCT Pub. Date: Jul. 3, 2014

(65) Prior Publication Data
US 2016/0272640 A1 Sep. 22, 2016

Related U.S. Application Data

(60) Provisional application No. 61/775,176, filed on Mar. 8, 2013, provisional application No. 61/746,373, filed on Dec. 27, 2012.

(51) Int. Cl.
*C07D 471/08* (2006.01)
*C07D 211/58* (2006.01)
*C07C 235/74* (2006.01)

(52) U.S. Cl.
CPC .......... *C07D 471/08* (2013.01); *C07C 235/74* (2013.01); *C07D 211/58* (2013.01); *C07C 2602/46* (2017.05)

(58) Field of Classification Search
CPC ... C07D 471/08; C07D 211/58; C07C 235/74; C07C 2102/46
See application file for complete search history.

(56) References Cited

U.S. PATENT DOCUMENTS 2,798,874 A * 7/1957 Archer .................. C07D 451/04
546/124
3,655,675 A * 4/1972 Carabateas .......... C07D 451/04
546/124

| | | | |
|---|---|---|---|
| 6,635,653 B2 | 10/2003 | Goehring et al. |
| 6,686,370 B2 | 2/2004 | Kyle et al. |
| 6,828,440 B2 | 12/2004 | Goehring et al. |
| 6,861,421 B2 | 3/2005 | Goehring et al. |
| 6,867,222 B2 | 3/2005 | Sun et al. |
| 6,872,733 B2 | 3/2005 | Goehring et al. |
| 6,984,664 B2 | 1/2006 | Kyle et al. |
| 6,995,168 B2 | 2/2006 | Chen et al. |

(Continued)

FOREIGN PATENT DOCUMENTS

| | | |
|---|---|---|
| EP | 2500345 A1 | 9/2012 |
| WO | WO-2004/113334 A1 | 12/2004 |

(Continued)

OTHER PUBLICATIONS

Riley & Bagley, 22(10) J. Med. Chem. 1167-71 (1979) (CAS Abstract) (Year: 1979).*
Gutkowska B et al: "Synthezy Niektorych Amidow Pochodnych 3-Aminotropanu O Spodziewanym Dzialaniu Farmakologicznym I Synthesis of Some Amide Derivatives of 3-Aminotropane With Potential Pharmacological Activity", Acta Poloniae Pharmaceutica—Drug Research, Polish Pharmaceutical Society, Warzsaw, PL, vol. 6 XLI, No. 6, Jan. 1, 1984:613-617.
Gutkowska Bozenna et al: "Synthesis of Some Amide Derivatives of 3-Aminotropane With Expected Pharmacological Activity. II", Acta Poloniae Pharmaceutica—Drug Research, Polish Pharmaceutical Society, Warzsaw, PL, vol. 43, No. 6, Dec. 31, 1985: 553-558.

(Continued)

*Primary Examiner* — Timothy R Rozof
(74) *Attorney, Agent, or Firm* — Purdue Pharma L.P.; Alan L. Koller; Weiying Yang

(57) ABSTRACT

The disclosure relates to Substituted Piperidin-4-amino-Type Compounds of Formula (I) and pharmaceutically acceptable salts and solvates thereof wherein $R^1$, $R^2$, $R^3$, $Q^1$, $Q^2$, $E^1$, $E^2$, A, B, D, W, Z, a, b, n, and x are as defined herein, compositions comprising an effective amount of a Substituted Piperidin-4-amino-Type Compound, and methods to treat or prevent a condition, such as pain, comprising administering to an animal in need thereof an effective amount of a Substituted Piperidin-4-amino-Type Compound.

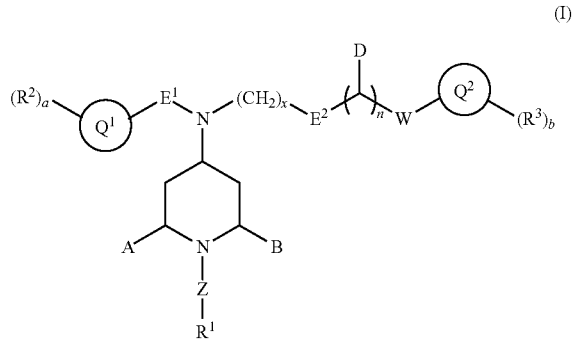

22 Claims, No Drawings

(56) References Cited

U.S. PATENT DOCUMENTS

| | | |
|---|---|---|
| 7,414,062 B2 | 8/2008 | Chen et al. |
| 7,456,198 B2 | 11/2008 | Kyle et al. |
| 7,495,109 B2 | 2/2009 | Sun et al. |
| 7,563,809 B2 | 7/2009 | Goehring et al. |
| 7,678,809 B2 | 3/2010 | Kyle et al. |
| 7,939,670 B2 | 5/2011 | Sun et al. |
| 8,110,602 B2 | 2/2012 | Brown et al. |
| 8,252,815 B2 | 8/2012 | Sun et al. |
| 8,476,271 B2 | 7/2013 | Tsuno et al. |
| 8,518,934 B2 | 8/2013 | Mikamiyama |
| 8,637,502 B2 | 1/2014 | Brown et al. |
| 8,846,929 B2 | 9/2014 | Fuchino et al. |
| 9,040,533 B2 | 5/2015 | Marra et al. |
| 9,085,561 B2 | 7/2015 | Tsuno et al. |
| 9,090,618 B2 | 7/2015 | Yamawaki et al. |
| 9,145,408 B2 | 9/2015 | Tsuno et al. |
| 2004/0087641 A1 | 5/2004 | Goehring et al. |
| 2004/0132757 A1 | 7/2004 | Kyle et al. |
| 2004/0259775 A1 | 12/2004 | Kyle |
| 2005/0192307 A1 | 9/2005 | Goehring et al. |
| 2006/0106114 A1 | 5/2006 | Kyle et al. |
| 2008/0214827 A1 | 9/2008 | Goehring et al. |
| 2009/0253727 A1 | 10/2009 | Goehring et al. |
| 2011/0092704 A1 | 4/2011 | Gharagozloo et al. |
| 2013/0274265 A1 | 10/2013 | Fuchino et al. |
| 2014/0045830 A1 | 2/2014 | Tsuno et al. |
| 2014/0128346 A1 | 5/2014 | Tadesse et al. |
| 2014/0187535 A1 | 7/2014 | Tanaka et al. |
| 2014/0187544 A1 | 7/2014 | Marra et al. |
| 2015/0011529 A1 | 1/2015 | Tafesse et al. |
| 2015/0141643 A1 | 5/2015 | Fuchino et al. |
| 2015/0238485 A1 | 8/2015 | Marra et al. |
| 2015/0315201 A1 | 11/2015 | Tafesse |
| 2015/0322066 A1 | 11/2015 | Yamawaki et al. |
| 2016/0002203 A1 | 1/2016 | Tadesse |

FOREIGN PATENT DOCUMENTS

| | | |
|---|---|---|
| WO | WO-2008/089201 A2 | 7/2008 |
| WO | WO-2010/010458 A1 | 1/2010 |
| WO | WO-2012/085648 A1 | 6/2012 |
| WO | WO-2014/020405 A8 | 2/2014 |
| WO | WO-2014/102589 A1 | 7/2014 |

OTHER PUBLICATIONS

Henderson et al., "The orphan opioid receptor and its endogenous ligand—nociceptin/orphanin FQ," Trends Pharmacol. Sci 18(8):293-300 (1997).

International Search Report dated Apr. 8, 2014 for corresponding international application No. PCT/IB2013/002875.

J.K. Baker: "Effect of Stereochemistry on the High-Performance Liquid Chromatographic Retention Index of Azabicycloalkanes", Anal.Chem., vol. 56, No. 14, 1984: 2932-2935.

Nurulain Zaveri et al., "Novel [alpha]3[beta]4 Nicotinic Acetylcholine Receptor-Seiective Ligands. Discovery, Structure-Activity Studies and Pharmacological Evaluation", J Med Chem., vol. 53, No. 22, Nov. 25, 2010: 8187-8191.

\* cited by examiner

SUBSTITUTED PIPERIDIN-4-AMINO-TYPE COMPOUNDS AND USES THEREOF

CROSS-REFERENCE TO RELATED APPLICATIONS

This application is the U.S. national phase, pursuant to 35 U.S.C. § 371, of PCT International Application Ser. No. PCT/IB2013/002875, filed Dec. 23, 2013, designating the United States and published in English on Jul. 3, 2014 as PCT Publication No. WO 2014/102590 A1, which claims priority to U.S. Provisional Application Ser. No. 61/746,373, filed Dec. 27, 2012, and U.S. Provisional Application Ser. No. 61/775,176, filed Mar. 8, 2013. The contents of the afore-mentioned patent applications are incorporated herein by their entirety.

1. FIELD

The disclosure relates to Substituted Piperidin-4-amino-Type Compounds, compositions comprising an effective amount of a Substituted Piperidin-4-amino-Type Compound and methods to treat or prevent a condition, such as pain, comprising administering to an animal in need thereof an effective amount of a Substituted Piperidin-4-amino-Type Compound.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as $\mu$, $\kappa$ and $\delta$. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for $\mu$, $\kappa$ and $\delta$ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand-nociceptin/orphanin FQ," *Trends Pharmacol. Sci.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication No. WO 2008/089201 describes heterocyclic-substituted piperidine compounds for use in treating a condition, such as pain.

International PCT Publication No. WO 2010/010458 describes substituted-quinoxaline-type bridged-piperidine compounds for use in treating a condition, such as pain.

International PCT Publication No. WO 2012/085648 describes phosphorus-substituted quinoxaline-type piperidine compounds for use in treating a condition, such as pain.

Citation of any reference in Section 2 of this application is not to be construed as an admission that such reference is prior art to the present application.

3. SUMMARY

In one aspect of the disclosure, new compounds that exhibit affinity for the ORL-1 receptor are described.

In some embodiments, such new compounds exhibit agonist activity or partial agonist activity at the ORL-1 receptor. In other embodiments, such new compounds exhibit agonist activity at the ORL-1 receptor. In other embodiments, such new compounds exhibit partial agonist activity at the ORL-1 receptor. In yet other embodiments, such new compounds exhibit antagonist activity at the ORL-1 receptor.

In another embodiment of the disclosure, such new compounds exhibit affinity for the ORL-1 receptor, and also for one or more of the $\mu$, $\kappa$ or $\delta$ receptors. In some embodiments, a new compound of the disclosure exhibits affinity for both the ORL-1 receptor and the receptor. In other embodiments, a new compound of the disclosure acts as an ORL-1 receptor agonist or partial agonist and as a $\mu$ receptor agonist or partial agonist. In other embodiments, a new compound of the disclosure acts as an ORL-1 receptor agonist and as a $\mu$ receptor agonist or partial agonist. In other embodiments, a new compound of the disclosure acts as an ORL-1 receptor partial agonist and as a $\mu$ receptor agonist or partial agonist. In other embodiments, a new compound of the disclosure acts as an ORL-1 receptor agonist or partial agonist and as a $\mu$ receptor agonist. In other embodiments, a new compound of the disclosure acts as an ORL-1 receptor agonist or partial agonist and as a $\mu$ receptor partial agonist. In other embodiments, a new compound of the disclosure acts as an ORL-1 receptor agonist and as a $\mu$ receptor agonist. In other embodiments, a new compound of the disclosure acts as an ORL-1 receptor agonist and as a $\mu$ receptor partial agonist. In other embodiments, a new compound of the disclosure acts as an ORL-1 receptor partial agonist and as a $\mu$ receptor agonist. In other embodiments, a new compound of the disclosure acts as an ORL-1 receptor partial agonist and as a $\mu$ receptor partial agonist. In other embodiments, a new compound of the disclosure acts as an ORL-1 receptor agonist or partial agonist and as a $\mu$ receptor antagonist. In other embodiments, a new compound of the disclosure acts as an ORL-1 receptor agonist and as a $\mu$ receptor antagonist. In other embodiments, a new compound of the disclosure acts as an ORL-1 receptor partial agonist and as a $\mu$ receptor antagonist. In other embodiments, a new compound of the disclosure acts as an ORL-1 receptor antagonist and as a $\mu$ receptor agonist or partial agonist. In other embodiments, a new compound of the disclosure acts as an ORL-1 receptor antagonist and as a $\mu$ receptor agonist. In other embodiments, a new compound of the disclosure acts as an ORL-1 receptor antagonist and as a 82 receptor partial agonist.

Certain new compounds of the disclosure can be used to treat an animal suffering from chronic or acute pain.

In another embodiment of the disclosure, methods for treating chronic or acute pain in an animal by administering one or more Substituted Piperidin-4-amino-Type Compounds to an animal in need of such treatment are described.

In certain embodiments, such new Substituted Piperidin-4-amino-Type Compounds effectively treat chronic or acute pain in the animal, while producing fewer or reduced side effects compared to previously available compounds.

Compounds of the disclosure include those of Formula (I):

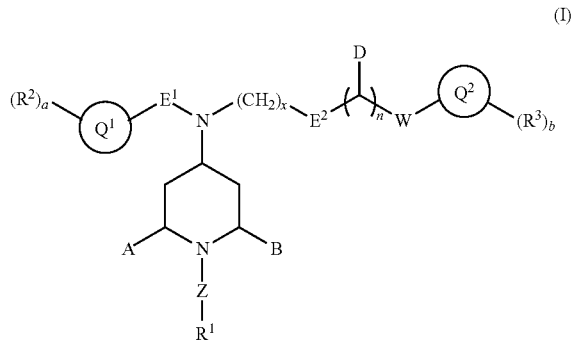

(I)

and the pharmaceutically acceptable salts and solvates thereof, wherein:

$Q^1$ is phenyl, naphthalenyl, pyridinyl, pyridazinyl, pyrimidinyl, pyrazinyl, or triazinyl;

$Q^2$ is $(C_3-C_{10})$cycloalkyl, (3- to 9-membered)heterocycle, or a direct bond;

$E^1$ and $E^2$ are, independently, C(=O), C(=S), S(=O)$_q$, CH$_2$, or a direct bond;

W is S, O, N(R*), or a direct bond;

D is H, OR*, SR*, NO$_2$, or N(R*)$_2$;

R* is, independently for each occurrence, H, $(C_1-C_6)$alkyl, $(C_2-C_6)$alkenyl, or $(C_2-C_6)$alkynyl each of which is unsubstituted or substituted with 1, 2, or 3 substituents independently selected from -halo, —CN, —NO$_2$, —N$_3$, —OH, —O(C$_1$-C$_6$)alkyl, —SH, —S(C$_1$-C$_6$)alkyl, —NH$_2$, —N(H)((C$_1$-C$_6$)alkyl), —N((C$_1$-C$_6$)alkyl)$_2$, =O, and =S;

each $R^2$ and $R^3$ is, independently for each occurrence:
(a) —H; or
(b) -halo, —CN, or —NO$_2$; or
(c) —X, —(C$_1$-C$_6$)alkyl-X, -(5- or 6-membered)heterocycle-X, or -(5- or 6-membered)heterocycle-(C$_1$-C$_6$)alkyl-X; or
(d) —C(=Y)CN, —C(=Y)X, —C(=Y)T$^3$, —C(=Y)YX, —C(=Y)YT$^3$, —C(=Y)N(T$^1$)(T$^2$), —C(=Y)N(R$^9$)CN, —C(=Y)N(R$^9$)X, —C(=Y)N(R$^9$)CH$_2$CH$_2$N(T$^1$)(T$^2$), —C(=Y)N(R$^9$)YH, —C(=Y)N(R$^9$)YX, —C(=Y)N(R$^9$)YCH$_2$X, —C(=Y)N(R$^9$)YCH$_2$CH$_2$X, or —C(=Y)N(R$^9$)S(=O)$_2$T$^3$; or
(e) —N(R$^9$)X, —N(R$^9$)—CH$_2$X, —N(R$^9$)—CH$_2$CH$_2$X, —N(R$^9$)—CH$_2$CH$_2$N(R$^9$)X, —N(R$^9$)CH$_2$CH$_2$N(T$^1$)(T$^2$), —N(R$^9$)CH$_2$C(=Y)X, —N((C$_1$-C$_6$)alkyl-C(=O)OR$^9$)$_2$, —N(R$^9$)CH$_2$N(R$^9$)C(=N(R$^{12}$))N(R$^{12}$)$_2$, —N(R$^9$)—CH$_2$CH$_2$N(R$^9$)C(=N(R$^{12}$))N(R$^{12}$)$_2$, —N(T$^1$)(T$^2$), —N(T$^3$)C(=Y)T$^3$, —N(T$^3$)C(=Y)YT$^3$, —N(T$^3$)C(=Y)N(T$^1$)(T$^2$), —N(T$^3$)S(=O)$_2$T$^3$, or —N(T$^3$)S(=O)$_2$N(T$^1$)(T$^2$); or
(f) —YH, —CH$_2$YH, —CH$_2$CH$_2$YH, —YX, or —YT$^3$; or
(g) —S(=O)T$^3$, —S(=O)$_2$T$^3$, —S(=O)N(T$^1$)(T$^2$), —S(=O)$_2$N(T$^1$)(T$^2$), —S(=O)X, or —S(=O)$_2$X;

X is, independently for each occurrence:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected R$^8$ groups; or
(b) -phenyl, -benzyl, -naphthalenyl, —(C$_{14}$)aryl, —(C$_1$-C$_6$)alkyl-(5- or 6-membered)heteroaryl or -(5- or 6-membered)heterocycle, each of which is unsubstituted or substituted with 1, 2 or 3 independently selected R$^7$ groups;

each Y is independently O or S;

A and B together form a $(C_2-C_6)$bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the $(C_2-C_6)$bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

$R^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

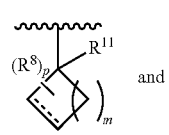

(i)

and

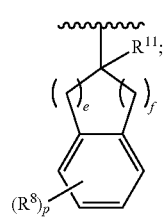

(ii)

and
(d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each $R^5$ is independently —(C$_1$-C$_4$)alkyl, —(C$_2$-C$_6$)alkenyl, —(C$_2$-C$_6$)alkynyl, -(5- to 9-membered)heteroaryl, (6-membered)aryl unsubstituted or substituted with OR$^9$, —(C$_1$-C$_6$)alkyl-C(=O)OR$^9$, —OR$^9$, —SR$^9$, —C(halo)$_3$, —CH(halo)$_2$, —CH$_2$(halo), —CN, =NH, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each $R^6$ is independently —H, —(C$_1$-C$_6$)alkyl, or —(C$_3$-C$_7$)cycloalkyl, or two R$^6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$^3$);

each $R^7$ is independently —$(C_1$-$C_4)$alkyl, —$(C_2$-$C_6)$alkenyl, —$(C_2$-$C_6)$alkynyl, —$OR^9$, —$SR^9$, —$C(halo)_3$, —$CH(halo)_2$, —$CH_2(halo)$, —CN, -halo, —$N_3$, —$NO_2$, —$CH$=$N(R^9)$, —$N(R^9)_2$, —$N(R^9)OH$, —$N(R^9)S$(=O)$R^{12}$, —$N(R^9)S$(=O)$_2R^{12}$, —$N(R^9)C$(=O)$R^{12}$, —$N(R^9)C$(=O)$N(T^1)(T^2)$, —$N(R^9)C$(=O)$OR^{12}$, —$C$(=O)$R^9$, —$C$(=O)$N(T^1)(T^2)$, —$C$(=O)$OR^9$, —$OC$(=O)$R^9$, —$OC$(=O)$N(T^1)(T^2)$, —$OC$(=O)$OR^9$, —$S$(=O)$R^9$, or —$S$(=O)$_2R^9$;

each $R^8$ is independently —$(C_1$-$C_4)$alkyl, —$(C_2$-$C_6)$alkenyl, —$(C_2$-$C_6)$alkynyl, -(5- to 9-membered)heteroaryl, —$(C_1$-$C_6)$alkyl-$C$(=O)$OR^9$, —$N(R^9)(C_1$-$C_6)$alkyl-$C$(=O)$OR^9$, —$OR^9$, —$SR^9$, —$C(halo)_3$, —$CH(halo)_2$, —$CH_2(halo)$, —CN, =O, =S, -halo, —$N_3$, —$NO_2$, —$CH$=$N(R^9)$, —$N(R^9)_2$, —$N(R^9)OH$, —$N(R^9)S$(=O)$R^{12}$, —$N(R^9)S$(=O)$_2R^{12}$, —$N(R^9)C$(=O)$R^{12}$, —$N(R^9)C$(=O)$N(T^1)(T^2)$, —$N(R^9)C$(=O)$OR^{12}$, $N(R^9)C$(=NH)$N(R^9)_2$, —$C$(=O)$R^9$, —$C$(=O)$N(T^1)(T^2)$, —$C$(=O)$OR^9$, —$OC$(=O)$R^9$, —$OC$(=O)$N(T^1)(T^2)$, —$OC$(=O)$OR^9$, —$S$(=O)$R^9$, or —$S$(=O)$_2R^9$;

each $R^9$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, -(3- to 7-membered)heterocycle, —$C(halo)_3$, —$CH(halo)_2$, or —$CH_2(halo)$;

if h is 0, then $R^{11}$ can be —H, —CN, —$C$(=O)$OR^9$, —$C$(=O)$N(R^6)_2$ or $R^{11}$ can be —$(C_1$-$C_4)$alkyl which is unsubstituted or substituted with —OH, —$(C_1$-$C_4)$alkoxy, —$N(R^6)_2$, —$C$(=O)$OR^9$, or —$C$(=O)$N(R^6)_2$;

if h is 1, then $R^{11}$ can be —H, —CN, —OH, -halo, —$C$(=O)$OR^9$, or —$C$(=O)$N(R^6)_2$ or $R^{11}$ can be —$(C_1$-$C_4)$alkyl which is unsubstituted or substituted with —OH, —$(C_1$-$C_4)$alkoxy, —$N(R^6)_2$, —$C$(=O)$OR^9$, or —$C$(=O)$N(R^6)_2$;

otherwise, when Z is —$[(C_2$-$C_{10})$alkenyl optionally substituted by $R^{13}]$— or —$[(C_1$-$C_{10})$alkyl-$N(R^6)C$(=Y)]—, then $R^{11}$ can be —H, —CN, —$C$(=O)$OR^9$, or —$C$(=O)$N(R^6)_2$ or $R^{11}$ can be —$(C_1$-$C_4)$alkyl which is unsubstituted or substituted with —OH, —$(C_1$-$C_4)$alkoxy, —$N(R^6)_2$, —$C$(=O)$OR^9$, or —$C$(=O)$N(R^6)_2$;

each $R^{12}$ is independently —H or —$(C_1$-$C_4)$alkyl;

$R^{13}$ is selected from:
(a) -halo, —CN, —OH, —$CH_2OH$, —$CH_2CH_2OH$, —$NO_2$, —$N(R^6)_2$, —$S$(=O)$NH_2$, —$S$(=O)$_2NH_2$, —$C$(=O)$OV^1$, and —$C$(=O)$CN$; and
(b) —$(C_1$-$C_{10})$alkyl, —$(C_2$-$C_{10})$alkenyl, —$(C_2$-$C_{10})$alkynyl, —$O(C_1$-$C_6)$alkyl, —$(C_3$-$C_7)$cycloalkoxy, —$(C_5$-$C_{10})$cycloalkenyl, and -(3- to 7-membered)heterocycle, each of which is unsubstituted or substituted with 1, 2, 3, or 4 independently selected $R^8$ groups; and
(c)

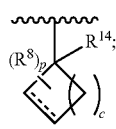

(iv)

and
(d) -phenyl and -(5- to 10-membered)heteroaryl, each of which is unsubstituted or substituted with 1, 2, or 3 independently selected $R^7$ groups;

$R^{14}$ is —H, —CN, —OH, -halo, —$C$(=O)$OR^9$, or —$C$(=O)$N(R^6)_2$ or $R^{14}$ can be —$(C_1$-$C_4)$alkyl which is unsubstituted or substituted with —OH, —$(C_1$-$C_4)$alkoxy, —$N(R^6)_2$, —$C$(=O)$OR^9$, or —$C$(=O)$N(R^6)_2$;

a is an integer selected from 0, 1, 2, 3, and 4;

b is an integer selected from 0, 1, 2, 3, and 4;

n is an integer selected from 0, 1, and 2;

x is an integer selected from 0, 1, 2, 3, 4, 5, and 6;

m is an integer selected from 0, 1, 2, 3, 4, 5, 6, 7, 8, 9, 10, and 11;

c is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4;

each q is, independently, an integer selected from 1 and 2;

each $T^1$ and $T^2$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^1$ or $T^2$ is attached is independently replaced by O, S, or $N(R^6)$, or $T^1$ and $T^2$ can together form a 5- to 8-membered ring wherein the number of atoms in the ring includes the nitrogen atom to which $T^1$ and $T^2$ are bonded, said 5- to 8-membered ring is unsubstituted or substituted with 1, 2, or 3 independently selected $R^5$ groups and, optionally, any carbon atom in said 5- to 8-membered ring is independently replaced by O, S, or $N(R^6)$;

each $T^3$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^3$ is attached is independently replaced by O, S, or $N(R^{12})$;

each $V^1$ is independently —H, —$(C_1$-$C_6)$alkyl, —$(C_3$-$C_7)$cycloalkyl, -phenyl, or -benzyl;

each halo is independently —F, —Cl, —Br, or —I;

with the proviso that when x is 0, $E^2$ is a direct bond, n is 0, W is a direct bond, $Q^2$ is a direct bond, b is 1, and $R^3$ is H, $R^2$ is not $NH_2$ or $NO_2$.

A compound of Formula (I) or a pharmaceutically acceptable salt or solvate thereof (referred to hereinafter as a "Substituted Piperidin-4-amino-Type Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Substituted Piperidin-4-amino-Type Compound is useful for treating and/or preventing pain (see, e.g., Courteix, et al. (2004). Evidence for an exclusive antinociceptive effect of nociceptin/orphanin FQ, an endogenous ligand for the ORL1 receptor, in two animal models of neuropathic pain. *Pain*, 110: 236-245; Reinscheid, et al. (1995). Orphanin FQ: a neuropeptide that activates an opioid-like G protein-coupled receptor. *Science*, 270: 792-794; Bignan et al. (2005). Recent advances towards the discovery of ORL-1 receptor agonists and antagonists. *Expert Opinion on Therapeutic Patents*, 15(4): 357-388; Meunier, et al. (1995). Isolation and structure of the endogenous agonist of opioid receptor-like ORL1 receptor. *Nature*, 377: 532-535; Briscini, et al (2002). Up-regulation of ORL-1 receptors in spinal tissue of allodynic rats after sciatic nerve injury. *Eur. J. Pharmacol.*, 447: 59-65; Li, et al. (2004). Role of nociceptin in the modulation of nociception in the arcuate nucleus of rats. *Brain Res.*, 1025: 67-74), anxiety (see, e.g., Jenck, et al. (1997). Orphanin FQ acts as an anxiolytic to attenuate behavioral responses to stress. *Proc. Natl. Acad. Sci., U.S.A.*, 94: 14854-14858; Koster, et al. (1999). Targeted disruption of the orphanin FQ/nociceptin gene increases stress susceptibility and impairs stress adaptation in mice. *Proc. Natl. Acad. Sci. U.S.A.*, 96: 10444-10449; Griebel, et al. (1999). Orphanin FQ, a novel neuropeptide with anti-stress-like activity. *Brain Res.*, 836: 221-224; Jenck, et al. (2000). A synthetic agonist at the orphanin FQ/nociceptin receptor ORL1: Anxiolytic profile in the rat. Proc. Natl. Acad. Sci., 97: 4938-4943), cough (see, e.g., Fischer, et al. (1998). Nociceptin-induced inhibition of tachykinergic neurotransmission in guinea pig bronchus. *J. Pharmacol. Ther.*, 285: 902-907; Rizzi, et al. (1999). Nociceptin receptor activation inhibits tachykinergic non adrenergic non cholinergic contraction of guinea pig isolated bronchus. *Life Sci.*, 64: L157-L163; Shah, et al. (1998). Nociceptin inhibits non-cholinergic contraction in guinea-pig airway. *Br. J. Pharmacol.*, 125: 510-516; Patel, et al., (1997). Naloxone-insensitive inhibition of acetylcholine release from parasympathetic nerves innervating guinea-pig trachea by the novel opioid, nociceptin. *Br. J. Pharmacol.*, 120: 735-736; Helyes, et al. (1997). Inhibition by nociceptin of neurogenic inflammation and the release of SP and CGRP from sensory nerve terminals. *Br. J. Pharmacol.*, 121: 613-615; Nemeth, et al., (1998). Inhibition of nociceptin on sensory neuropeptide release and mast cell-mediated plasma extravasation in rats. *Eur. J. Pharmacol.*, 347: 101-104; McLeod, et al. (2001). Nociceptin inhibits cough in the guinea-pig by activation of ORL1 receptors. *Br. J. Pharmacol.*, 132: 1175-1178; Corboz, et al. (2000). Nociceptin inhibits capsaicin-induced bronchoconstriction in isolated guinea pig lung. *Eir. J. Pharmacol.*, 402: 171-179), gut motility disorders (such as diarrhea and constipation) (see, e.g., Wang, et al. (1994). cDNA cloning of an orphan opiate receptor gene family member and its splice variant. *FEBS Lett.*, 348: 75-79; Calo', et al. (1996). The mouse deferens: a pharmacological preparation sensitive to nociceptin. *Eur. J. Pharmacol.*, 311: R3-R5; Zhang, et al. (1997). Orphanin FQ has an inuhibitory effect on the guinea pig ileum and the mouse vas deferens. *Brain Res.*, 772: 102-106; Osinski, et al. (1999). Cloning, expression and functional role of a nociceptin/orphanin FQ receptor in the porcine gastrointestinal tract. *Eur. J. Pharmacol.*, 365: 281-289; Yasdani, et al. (1999). Functional significance of a newly discovered neuropeptide, orphanin FQ, in rat gastrointestinal motility. *Gastroenterology*, 116: 108-117; Corbett, et al. (1998). The pharmacological actions of nociceptin in the isolated colon of rat, mouse, and man. *Naunyn Schmiedebergs Arch. Pharmacol.*, 358(Suppl 1): P40.47; Osinski, et al. (1999). Peripheral and central actions of orphanin FQ (nociceptin) on murine colon. *Am. J. Physiol.*, 276: G125-G131; Rizzi, et al. (1999). [Nphe$^1$]nociceptin(1-13)NH$_2$ antagonizes nociceptin effects in the mouse colon. *Eur. J. Pharmacol.*, 285: R3-R5; Taniguchi, et al. (1998). The effect of nociceptin an endogenous ligand for the ORL1 receptor, on rat colonic contraction and transit. *Eur. J. Pharmacol.*, 353: 265-271; Pheng, et al. (2000). [Nphe$^1$]nociceptin(1-13)NH$_2$ selectively antagonizes nociceptin effects in the rabbit isolated ileum. *Eur. J. Pharmacol.*, 397: 383-388), high blood pressure (see, e.g., Champion & Kadowitz (1997). Nociceptin, an endogenous ligand for the ORL1 receptor, has novel hypotensive activity in the rat. *Life Sci.*, 60: PL 241-245; Giuliani, et al. (1997). Effect of nociceptin on heart rate and blood pressure in anaesthetized rats. *Eur. J. Pharmacol.*, 333: 177-179; Kapusta, et al. (1997). Diuretic and antinatriuretic responses produced by the endogenous opioid-like peptide, noceptin (orphanin FQ). *Life Sci.*, 60: PL15-PL21; Kapusta, et al. (1999). Central administration of [Phe1psi(CH$_2$—NH)Gly2]nociceptin(1-13)-NH$_2$ and orphanin FQ/nociceptin (OFQ/N) produce similar cardiovascular and renal responses in conscious rats. *J. Pharmacol. Exp. Ther.*, 289: 173-180; Madeddu, et al. (1999). Cardiovascular effects of nociceptin in unanesthetized mice. *Hypertension*, 33: 914-919; Bigoni, et al. (1999). Characterization of nociceptin receptors in the periphery: in vitro and in vivo studies. *Naunyn Schmiedebergs Arch. Pharmacol.*, 359: 160-167; Chu, et al. (1999). Inhibition of cardiovascular activity following microinjection of novel opioid-like neuropeptide nociceptin (orphanin FQ) into the rat rostral ventrolateral medulla. *Brain Res.*, 829: 134-142; Chu, et al. (1999). The nociceptin receptor-mediated inhibition of the rat rostral ventrolateral medulla neurons in vitro. *Eur. J. Pharmacol.*, 364: 49-53; Arndt, et al. (1999). Nociceptin/orphanin FQ increases blood pressure and heart rate via sympathetic activation in sheep. Peptides, 20: 465-470; Gumusel, et al. (1997). Nociceptin: an endogenous agonist for central opioid-likel (ORL1) receptors possesses systemic vasorelaxant properties. *Life Sci.*, 69: PL 141-PL 145; Champion et al. (1998). Nociceptin, a novel endogenous ligand for the ORL1 receptor, dilates isolated resistance arteries from the rat. *Regul. Peptides*, 78: 69-74; Czapla, et al. (1997). Decreases in systemic arterial and hindquarters perfusion pressure in response to nociceptin are not inhibited by naloxone in the rat. *Peptides*, 18: 1197-1200; Armstead (1999), Nociceptin/orphanin FQ dilates pial arteries by K(ATP) and k(ca) channel activation. *Brain Res.*, 835: 315-323; Bucher (1998), ORL1 receptor-mediated inhibition by nociceptin of noradrenaline release from perivascular sympathetic nerve endings of the rat tail artery. *Naunyn Schmiedebergs Arch. Pharmacol.*, 358: 682-685; Champion et al. (1997). Nociceptin, a novel endogenous ligand for the ORL1 receptor, has potent erectile activity in the cat. *Am. J. Physiol.*, 73: E214-E219), epilepsy (see, e.g., Nicol, et al. (1996), Nociceptin induced inhibition of K+ evoked glutamate release from rat cerebrocortical slices. *Br. J. Pharmacol.*, 119: 1081-1083; Nicol, et al. (1998). Nociceptin inhibits glutamate release from rat cerebellar slices. *Br. J. Pharmacol.*, 123: 217P; Allen, et al. (1999). Orphanin-FQ/nociceptin (OFQ/N) modulates the activity of suprachiasmatic nucleus neurons. *J. Neurosci.*, 19: 2152-2160; Faber, et al. (1996). Depression of glutamatergic transmission by nociceptin in the neonatal rat hemisected spinal cord preparation in vitro. *Br. J. Pharmacol.*, 119: 189-190; Vaughn, et al. (1997). Actions of the ORL1 receptor ligand nociceptin on membrane properties of rat periaqueductal gray neurons in vitro. *J. Neurosci.*, 17: 996-1003; Wang, et al. (1996). Nociceptin (orphanin FQ), and endogenous ligand for the ORL1 (opioid receptor-like1) receptor, modulates responses of trigeminal neurons evoked by excitatory amino acids and somatosensory stimuli. *J. Neurophysiol.*, 76: 3568-3572; Yu & Xie (1998). Orphanin FQ/nociceptin inhibits synaptic transmission and long-term potentiation in rat dentate gyrus through postsynaptic mechanisms. *J. Neurophysiol.*, 80: 1277-1284; Bregola, et al. (1999). Limbic seizures increase pronociceptin mRNA levels in the thalamic reticular nucleus. *Neuroreport*, 19: 541-546; Sieklucka-Dziuba, et al. (2002). Nociceptin, OP4 receptor ligand in different models of experimental epilepsy. *Peptides*, 23: 497-505; Gutierrez, et al, (2001). Orphanin FQ/nociceptin inhibits kindling epileptogenesis and enhances hippocampal feed-forward inhibition. *Neuroscience,* 105: 325-333; Tallent, et al. (2001). Nociceptin reduces epileptiform events in CA3 hippocampus via presynaptic and postsynaptic mechanisms. *J. Neurosci.,* 21: 6940-6948), eating-related disorders (such as anorexia/cachexia and obesity) (see, e.g., Pomonis, et al. (1996). Orphanin FQ, agonist of orphan opioid receptor ORL1, stimulates feeding in rats. *Neuroreport,* 8: 369-371; Stratford et al. (1997). Injections of nociceptin into nucleus accumbens shell of ventromedial hypothalamic nucleus increase food intake. *Neuroreport,* 8: 423-426; Lee, et al. (1997). Nociceptin hyperpolarises neurones in the rt ventromedial hypothalamus. *Neurosci. Lett.,* 239: 37-40; Polidori, et al. (1999). Sensitivity of brain sites to the orexigenic effect of nociceptin or of its analog [Phe]psi ($CH_2$—NH)Gly2]NC(1-13)$NH_2$. Regul. Peptides, 80:126; Polidori, et al. (2000). Pharmacological characterization of the nociceptin receptor mediating hyperphagia: indentification of a selective antagonist. *Psychopharmacology,* 148: 430-437; Rowland, et al. (1996). The physiology and brain mechanisms of feeding. *Nutrition,* 12: 626-639), urinary incontinence (see, e.g., Giuliani, et al. (1998). The inhibitory effect of nociceptin on the micturition reflex in anaesthetized. *Br. J. Pharmacol.,* 24: 1566-1572; Giuliani, et al. (1999). Nociceptin protects capsaicin-sensitive afferent fibers in the rat urinary bladder from desensitization. Nanyn Schmiedeberg's *Arch. Pharmacol.,* 360: 202-208; Lecci, et al. (2000). Multiple sites of action in the inhibitory effect of nociceptin on the micturition reflex. *J. Urology,* 163: 638-645), renal function (see, e.g., Kapusta, et al. (1997). Diuretic and antinatriuretic responses produced by the endogenous opioid-like peptide, noceptin (orphanin FQ). *Life Sci.,* 60: PL15-PL21; Kapusta, et al. (1999). Central administration of [Phel psi(CH2-NH)Gly2]nociceptin(1-13)-NH2 and orphanin FQ/nociceptin (OFQ/N) produce similar cardiovascular and renal responses in conscious rats. *J. Pharmacol. Exp. Ther.,* 289: 173-180; drug abuse (see, e.g., Devine et al. (1996). The novel neuropeptide orphanin FQ fails to produce conditioned place preference or aversion. *Brain Res.,* 727: 225-229; Ciccocioppo, et al. (1999). Effect of nociceptin on alcohol intake in alcohol-preferring rats. *Psychopharmacology,* 141: 220-224; Angeletti, et al., (1999). Effect of nociceptin on morphine-induced conditioned place preference in rats. *Regulatory Peptides,* 80: 222; Murphy et a). (1999). Orphanin FQ/nociceptin blocks acquisition of morphine place preference. *Brain Res.,* 832: 168-170; Pieretti & Di Giannuario (1999). Orphanin FQ effects on morphine-induced dopamine release in the accumbens of rats. *Regulatory Peptides,* 80: 126; Walker et al. (1998). Nociceptin fails to affect heroin self-administration in the rat. *Neuroreport,* 9: 2243-2247; Narayanan & Maidment (1999). Orphanin FQ and behavioral sensitization to cocaine. *Pharmacol. Biochem. Behav.,* 63: 271-277), memory disorders (see, e.g., Sandin, et al. (1997). Nociceptin/orphanin FQ microinjected into hippocampus impairs spatial learning in rats. *Eur. J. Neurosci.,* 9: 194-197; Yu, et al. (1997). Orphanin FQ inhibits synaptic transmission and long-term potentiation in rat hippocampus. *Hippocampus,* 7: 88-94; Yu & Xie (1998). Orphanin FQ/nociceptin inhibits synaptic transmission and long-term potentiation in rat dentate gyrus through postsynaptic mechanisms. *J. Neurophysiol.,* 80: 1277-1284; Manabe, et al. (1998). Facilitation of long-term potentiation and memory in mice lacking nociceptin receptors. *Nature,* 394: 577-581; Hiramatsu & Inoue (1999). Effects of nocistatin on nociceptin-induced impairment of learning and memory in mice. *Eur. J. Pharmacol.,* 367: 151-155; Mamiya, et al. (1999). Nociceptin system plays a role in the memory retention: involvement of naloxone benzoylhydrazone binding sites. *Neuroreport,* 10: 1171-1175; Hiramatsu & Inoue (2000). Improvement by low doses of nociceptin on scopolamine-induced impairment of learning and/or memory. *Eur. J. Pharmacol.,* 395: 149-156), depression (see, e.g., Rizzi, et al. (2011). Nociceptin/orphanin FQ receptor knockout rats: in vitro and in vivo studies. Neuropharmacology, 60: 572-579; Goeldner, et al. (2010). Endogenous nociceptin/orphanin-FQ in the dorsal hippocampus fcilitates despair-related behavior. *Hippocampus,* 20: 911-916; Vitale, et al. (2009). Chronic treatment with the selective NOP receptor antagonist [Nphe 1, Arg 14, Lys 15]N/OFQ-NH2 (UFP-101) reverses the behavioural and biochemical effects of unpredictable chronic mild stress in rats. *Psychopharmacology,* 207: 173-189; Zambello, et al. (2008). Acute stress differentially affects corticotropin-releasing hormone mRNA expression in the central amygdala of the "epressed" flinders sensitive line and the control flinders resistant line rats. *Progress in Neuro-Psychopharmacology & Biological Psychiatry,* 32: 651-661; Gavioli & Calo' (2006). Antidepressant—an anxiolytic-like effects of nociceptin/orphanin FQ receptor ligands. *Naunyn-Schmiedebergs Arch. Pharmacol.,* 372: 319-330; Gavioli, et al. (2003). Blockade of nociceptin/orphanin FQ-NOP receptor signalling produces antidepressant-like effects: pharmacological and genetic evidences from the mouse forced swimming test. *Eur. J. Neurosci.,* 17: 1987-1990), dementia, or locomotor disorders (such as Parkinsonism) (see, e.g., Reinscheid, et al. (1995). Orphanin FQ: a neuropeptide that activates an opioidlike G protein-coupled receptor. *Science,* 270: 792-794; Calo' et al. (1999). Characterization of nociceptin receptors modulating locomotor activity in mice. *Fund. Clin. Pharmnacol.,* 13-S1: S27.6; Devine, et al, (1996). Rats rapidly develop tolerance to the locomotor-inhibiting effects of the novel neuropeptide orphanin FQ. *Neurochem. Res.,* 21: 1387-1396; Noble & Roques (1997). Association of aminopeptidase N and endopeptidase 14.15 inhibitors potentiate behavorial effects mediated by nociceptin/orphanin FQ in mice. *FEBS Lett.,* 401: 227-229; Florin, et al. (1996). Nociceptin stimulates locomotion and exploratory behaviour in mice. *Eur. J. Pharmacol.,* 317: 9-13) (each being a "Condition") in an animal. For a general discussion of ORL1 receptors see Calo' et al. (2000). Pharmacology of nociceptin and its receptor: a novel therapeutic target. *Br. J. Pharmacol.* 129: 1261-1283.

The present invention further provides compositions comprising an effective amount of a Substituted Piperidin-4-amino-Type Compound and a pharmaceutically acceptable carrier or excipient. The compositions are useful for treating or preventing a Condition in an animal.

The present disclosure further provides methods for treating or preventing a Condition, comprising administering to an animal in need thereof an effective amount of a Substituted Piperidin-4-amino-Type Compound.

The present disclosure further provides Substituted Piperidin-4-amino-Type Compounds for use in the manufacture of a medicament useful for treating a Condition or for preventing a Condition.

The present disclosure further provides methods for inhibiting ORL-1 receptor function in a cell, comprising contacting a cell capable of expressing the ORL-1 receptor with an ORL-1 receptor function-inhibiting amount of a Substituted Piperidin-4-amino-Type Compound. The present invention further provides methods for activating ORL-1 receptor function in a cell, comprising contacting a cell capable of expressing the ORL-1 receptor with an ORL-1 receptor function-activating amount of a Substituted Piperidin-4-amino-Type Compound.

The present invention further provides methods for preparing a composition, comprising the step of admixing a Substituted Piperidin-4-amino-Type Compound and a pharmaceutically acceptable carrier or excipient.

The present disclosure further provides a kit comprising a sterile container containing an effective amount of a Substituted Piperidin-4-amino-Type Compound.

The present disclosure further provides novel intermediates for use in making a Substituted Piperidin-4-amino-Type Compound.

The disclosure can be understood more fully by reference to the following detailed description and illustrative examples, which are intended to exemplify non-limiting embodiments of the disclosure.

4. DETAILED DESCRIPTION

In certain embodiments, the Substituted Piperidin-4-amino-Type Compounds of Formula (I) include the following:

(1) Compounds of Formula (I):

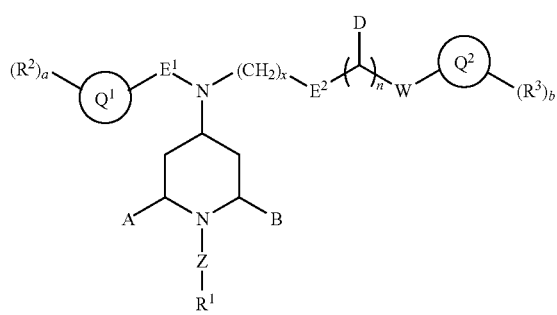

(I)

and the pharmaceutically acceptable salts and solvates thereof, wherein:

$Q^1$ is phenyl, naphthalenyl, pyridinyl, pyridazinyl, pyrimidinyl, pyrazinyl, or triazinyl;

$Q^2$ is $(C_3\text{-}C_{10})$cycloalkyl, (3- to 9-membered)heterocycle, or a direct bond;

$E^1$ and $E^2$ are, independently, C(=O), C(=S), S(=O)$_q$, CH$_2$, or a direct bond;

W is S, O, N(R*), or a direct bond;

D is H, OR*, SR*, NO$_2$, or N(R*)$_2$;

R* is, independently for each occurrence, H, (C$_1$-C$_6$) alkyl, (C$_2$-C$_6$)alkenyl, or (C$_2$-C$_6$)alkynyl each of which is unsubstituted or substituted with 1, 2, or 3 substituents independently selected from -halo, —CN, —NO$_2$, —N$_3$, —OH, —O(C$_1$-C$_6$)alkyl, —SH, —S(C$_1$-C$_6$)alkyl, —NH$_2$, —N(H)((C$_1$-C$_6$)alkyl), —N((C$_1$-C$_6$)alkyl)$_2$, =O, and =S;

each $R^2$ and $R^3$ is, independently for each occurrence:

(a) —H; or (b) -halo, —CN, or —NO$_2$; or (c) —X, —(C$_1$-C$_6$)alkyl-X, -(5- or 6-membered)heterocycle-X, or -(5- or 6-membered)heterocycle-(C$_1$-C$_6$)alkyl-X; or (d) —C(=Y)CN, —C(=Y)X, —C(=Y)T$^3$, —C(=Y)YX, —C(=Y)YT$^3$, —C(=Y)N(T$^1$)(T$^2$), —C(=Y)N(R$^9$)CN, —C(=Y)N(R$^9$)X, —C(=Y)N(R$^9$)CH$_2$CH$_2$N(T$^1$)(T$^2$), —C(=Y)N(R$^9$)YH, —C(=Y)N(R$^9$)YX, —C(=Y)N(R$^9$)YCH$_2$X, —C(=Y)N(R$^9$)YCH$_2$CH$_2$X, or —C(=Y)N(R$^9$)S(=O)$_2$T$^3$; or (e) —N(R$^9$)X, —N(R$^9$)—CH$_2$X, —N(R$^9$)—CH$_2$CH$_2$X, —N(R$^9$)—CH$_2$CH$_2$N(R$^9$)X, —N(R$^9$)CH$_2$CH$_2$N(T$^1$)(T$^2$), —N(R$^9$)CH$_2$C(=Y)X, —N((C$_1$-C$_6$)alkyl-C(=O)OR$^9$)$_2$, —N(R$^9$)CH$_2$N(R$^9$)C(=N(R$^{12}$))N(R$^{12}$)$_2$, —N(R$^9$)—CH$_2$CH$_2$N(R$^9$)C(=N(R$^{12}$))N(R$^{12}$)$_2$, —N(T$^1$)(T$^2$), —N(T$^3$)C(=Y)T$^3$, —N(T$^3$)C(=Y)YT$^3$, —N(T$^3$)C(=Y)N(T$^1$)(T$^2$), —N(T$^3$)S(=O)$_2$T$^3$, or —N(T$^3$)S(=O)$_2$N(T$^1$)(T$^2$); or (f) —YH, —CH$_2$YH, —CH$_2$CH$_2$YH, —YX, or —YT$^3$; or (g) —S(=O)T$^3$, —S(=O)$_2$T$^3$, —S(=O)N(T$^1$)(T$^2$), —S(=O)$_2$N(T)(T$^2$), —S(=O)X, or —S(=O)$_2$X;

X is, independently for each occurrence:

(a) —H, —(C$_1$-C$_6$)alkyl, —(C$_2$-C$_6$)alkenyl, —(C$_2$-C$_6$) alkynyl, —(C$_1$-C$_6$)alkoxy, —(C$_3$-C$_7$)cycloalkyl, —(C$_6$-C$_{14}$) bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered) bicycloheterocycle, each of which is unsubstituted or substituted with 1, 2 or 3 independently selected R$^8$ groups; or (b) -phenyl, -benzyl, -naphthalenyl, —(C$_{14}$)aryl, —(C$_1$-C$_6$)alkyl-(5- or 6-membered)heteroaryl or -(5- or 6-membered)heteroaryl, each of which is unsubstituted or substituted with 1, 2 or 3 independently selected R$^7$ groups;

each Y is independently O or S;

A and B together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:

(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$) tricycloalkyl, —(C$_5$-C$_{14}$)cycloalkenyl, —(C$_7$-C$_{14}$) bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

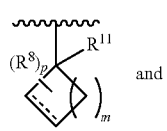

(i)

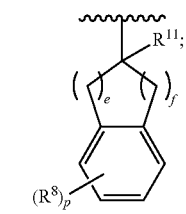

(ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each $R^5$ is independently —$(C_1$-$C_4)$alkyl, —$(C_2$-$C_6)$alkenyl, —$(C_2$-$C_6)$alkynyl, -(5- to 9-membered)heteroaryl, (6-membered)aryl unsubstituted or substituted with $OR^9$, —$(C_1$-$C_6)$alkyl-C(=O)$OR^9$, —$OR^9$, —$SR^9$, —C(halo)$_3$, —CH(halo)$_2$, —CH$_2$(halo), —CN, —NH, =O, =S, -halo, —N$_3$, —NO$_2$, —CH=N($R^9$), —N($R^9$)($C_1$-$C_6$)alkyl-C(=O)$OR^9$, —N($R^9$)$_2$, —N($R^9$)OH, —N($R^9$)S(=O)$R^{12}$, —N($R^9$)S(=O)$_2R^{12}$, —N($R^9$)C(=O)$R^{12}$, —N($R^9$)C(=O)$OR^{12}$, —C(=O)$R^9$, —C(=O)$OR^9$, —OC(=O)$R^9$, —OC(=O)$OR^9$, —S(=O)$R^9$, or —S(=O)$_2R^9$;

each $R^6$ is independently —H, —($C_1$-$C_6$)alkyl, or —($C_3$-$C_7$)cycloalkyl, or two $R^6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N($T^3$);

each $R^7$ is independently —($C_1$-$C_4$)alkyl, —($C_2$-$C_6$)alkenyl, —($C_2$-$C_6$)alkynyl, —$OR^9$, —$SR^9$, —C(halo)$_3$, —CH(halo)$_2$, —CH$_2$(halo), —CN, -halo, —N$_3$, —NO$_2$, —CH=N($R^9$), —N($R^9$)$_2$, —N($R^9$)OH, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, or —S(=O)$_2R^9$;

each $R^8$ is independently —($C_1$-$C_4$)alkyl, —($C_2$-$C_6$)alkenyl, —($C_2$-$C_6$)alkynyl, -(5- to 9-membered)heteroaryl, —($C_1$-$C_6$)alkyl-C(=O)$OR^9$, —N($R^9$)($C_1$-$C_6$)alkyl-C(=O)$OR^9$, —$OR^9$, —$SR^9$, —C(halo)$_3$, —CH(halo)$_2$, —CH$_2$(halo), —CN, =O, =S, -halo, —N$_3$, —NO$_2$, —CH=N($R^9$), —N($R^9$)$_2$, —N($R^9$)OH, —N($R^9$)S(=O)$R^{12}$, —N($R^9$)S(=O)$_2R^2$, —N($R^9$)C(=O)$R^{12}$, —N($R^9$)C(=O)N($T^1$)($T^2$), —N($R^9$)C(=O)$OR^{12}$, N($R^9$)C(=NH)N($R^9$)$_2$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, or —S(=O)$_2R^9$;

each $R^9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, or —CH$_2$(halo);

if h is 0, then $R^{11}$ can be —H, —CN, —C(=O)$OR^9$, —C(=O)N($R^6$)$_2$ or $R^{11}$ can be —($C_1$-$C_4$)alkyl which is unsubstituted or substituted with —OH, —($C_1$-$C_4$)alkoxy, —N($R^6$)$_2$, —C(=O)$OR^9$, or —C(=O)N($R^6$)$_2$;

if h is 1, then $R^{11}$ can be —H, —CN, —OH, -halo, —C(=O)$OR^9$, or —C(=O)N($R^6$)$_2$ or $R^{11}$ can be —($C_1$-$C_4$)alkyl which is unsubstituted or substituted with —OH, —($C_1$-$C_4$)alkoxy, —N($R^6$)$_2$, —C(=O)$OR^9$, or —C(=O)N($R^6$)$_2$;

otherwise, when Z is —[($C_2$-$C_{10}$)alkenyl optionally substituted by $R^{13}$]— or —[($C_1$-$C_{10}$)alkyl-N($R^6$)C(=Y)]—, then $R^{11}$ can be —H, —CN, —C(=O)$OR^9$, or —C(=O)N($R^6$)$_2$ or $R^{11}$ can be —($C_1$-$C_4$)alkyl which is unsubstituted or substituted with —OH, —($C_1$-$C_4$)alkoxy, —N($R^6$)$_2$, —C(=O)$OR^9$, or —C(=O)N($R^6$)$_2$;

each $R^{12}$ is independently —H or —($C_1$-$C_4$)alkyl;

$R^{13}$ is selected from:

(a) -halo, —CN, —OH, —CH$_2$OH, —CH$_2$CH$_2$OH, —NO$_2$, —N($R^6$)$_2$, —S(=O)NH$_2$, —S(=O)$_2$NH$_2$, —C(=O)$OV^1$, and —C(=O)CN; and (b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_5$-$C_{10}$)cycloalkenyl, and -(3- to 7-membered)heterocycle, each of which is unsubstituted or substituted with 1, 2, 3, or 4 independently selected $R^8$ groups; and (c)

(iv)

and (d) -phenyl and -(5- to 10-membered)heteroaryl, each of which is unsubstituted or substituted with 1, 2, or 3 independently selected $R^7$ groups;

$R^{14}$ is —H, —CN, —OH, -halo, —C(=O)$OR^9$, or —C(=O)N($R^6$)$_2$ or $R^{14}$ can be —($C_1$-$C_4$)alkyl which is unsubstituted or substituted with —OH, —($C_1$-$C_4$)alkoxy, —N($R^6$)$_2$, —C(=O)$OR^9$, or —C(=O)N($R^6$)$_2$;

a is an integer selected from 0, 1, 2, 3, and 4;
b is an integer selected from 0, 1, 2, 3, and 4;
n is an integer selected from 0, 1, and 2;
x is an integer selected from 0, 1, 2, 3, 4, 5, and 6;
m is an integer selected from 0, 1, 2, 3, 4, 5, 6, 7, 8, 9, 10, and 11;
c is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4;

each q is, independently, an integer selected from 1 and 2;

each $T^1$ and $T^2$ is independently —H or —($C_1$-$C_{10}$)alkyl which is unsubstituted or substituted with 1, 2, or 3 independently selected $R^5$ groups and, optionally, in which any —($C_1$-$C_{10}$)alkyl carbon atom except the carbon atom bonded directly to the atom to which $T^1$ or $T^2$ is attached is independently replaced by O, S, or N($R^6$), or $T^1$ and $T^2$ can together form a 5- to 8-membered ring wherein the number of atoms in the ring includes the nitrogen atom to which $T^1$ and $T^2$ are bonded, said 5- to 8-membered ring is unsubstituted or substituted with 1, 2, or 3 independently selected $R^5$ groups and, optionally, any carbon atom in said 5- to 8-membered ring is independently replaced by O, S, or N($R^6$);

each $T^3$ is independently —H or —($C_1$-$C_{10}$)alkyl which is unsubstituted or substituted with 1, 2, or 3 independently selected $R^5$ groups and, optionally, in which any —($C_1$-$C_{10}$) alkyl carbon atom except the carbon atom bonded directly to the atom to which $T^3$ is attached is independently replaced by O, S, or N($R^{12}$);

each $V^1$ is independently —H, —($C_1$-$C_6$)alkyl, —($C_3$-$C_7$)cycloalkyl, -phenyl, or -benzyl;

each halo is independently —F, —Cl, —Br, or —I;

with the proviso that when x is 0, $E^2$ is a direct bond, n is 0, W is a direct bond, $Q^2$ is a direct bond, b is 1, and $R^3$ is H, $R^2$ is not NH$_2$ or NO$_2$.

(i.e., "Substituted Piperidin-4-amino-Type Compounds").

(2) Substituted Piperidin-4-amino-Type Compounds, wherein:

$Q^1$ is phenyl;

$Q^2$ is ($C_3$-$C_{10}$)cycloalkyl, (3- to 9-membered)non-aromatic heterocycle, or a direct bond;

$E^1$ and $E^2$ are, independently, C(=O), S(=O)$_2$, CH$_2$, or a direct bond;

W is N($R^*$) or a direct bond;

D is H, NO$_2$, or N($R^*$)$_2$;

$R^*$ is, independently for each occurrence, H or ($C_1$-$C_6$) alkyl unsubstituted or substituted with 1 or 2 substituents independently selected from —OH, —O($C_1$-$C_6$)alkyl, and =O;

each $R^2$ and $R^3$ is, independently for each occurrence, —H, -halo, —$NO_2$, —X, —C(=Y)YX, —N($T^1$)($T^2$), —YH, or —YX;

X is, independently for each occurrence, —H, —($C_1$-$C_6$)alkyl, —($C_2$-$C_6$)alkenyl, or -(5- or 6-membered)heterocycle, each of which is unsubstituted or substituted with 1 or 2 independently selected $R^8$ groups;

each Y is O;
each $R^5$ is independently $OR^9$ or =O;
each $R^8$ is independently —$OR^9$, =O, or —C(=O)$OR^9$;
each $R^9$ is independently —H or —($C_1$-$C_6$)alkyl;
a is an integer selected from 0 and 1;
b is an integer selected from 0 and 1;
n is an integer selected from 0 and 1;
x is an integer selected from 0 and 1; and
each $T^1$ and $T^2$ is independently —H or —($C_1$-$C_{10}$)alkyl which is unsubstituted or substituted with 1, 2, or 3 independently selected $R^5$ groups.

(3) Substituted Piperidin-4-amino-Type Compounds of the above (1) or (2), wherein $R^1$ is selected from:
(a) -halo, —CN, —OH, —$CH_2OH$, —$CH_2CH_2OH$, —$NO_2$, —N($R^6$)$_2$, —S(=O)$NH_2$, —S(=O)$_2NH_2$, —C(=O)$OV^1$, and —C(=O)CN; and
(b) —($C_1$-$C_{10}$)alkyl, —O($C_1$-$C_6$)alkyl, —($C_3$-$C_7$)cycloalkyl, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c) -phenyl, -naphthalenyl, —($C_{14}$)aryl, and -(5- to 10-membered)heteroaryl, each of which is unsubstituted or substituted with 1, 2, or 3 independently selected $R^7$ groups.

(4) Substituted Piperidin-4-amino-Type Compounds of the above (1) or (2), wherein
Z is —[($C_1$-$C_{10}$)alkyl]$_h$—, wherein h is 0 or 1; and
$R^1$ is selected from:
(a) —CN, —OH, —$CH_2OH$, —$CH_2CH_2OH$, —$NO_2$, —N($R^6$)$_2$, —S(=O)$NH_2$, —S(=O)$_2NH_2$, —C(=O)$OV^1$, and —C(=O)CN; and
(b) —($C_1$-$C_{10}$)alkyl, —O($C_1$-$C_6$)alkyl, —($C_3$-$C_7$)cycloalkyl, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c)

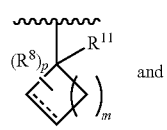

(i)

and

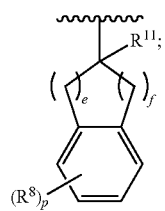

(ii)

and (d) -phenyl and -(5- to 0-membered)heteroaryl, each of which is unsubstituted or substituted with 1, 2, or 3 independently selected $R^7$ groups.

(5) Substituted Piperidin-4-amino-Type Compounds of any one of the above (1)-(4), wherein h is 1.

(6) Substituted Piperidin-4-amino-Type Compounds of any one of the above (1)-(3), or (5), wherein Z is —($C_1$-$C_3$)alkyl- optionally substituted by $R^{13}$.

(7) Substituted Piperidin-4-amino-Type Compounds of any one of the above (1)-(6), wherein $R^{13}$ is absent.

(8) Substituted Piperidin-4-amino-Type Compounds of any one of the above (1)-(7), wherein $R^{11}$ is absent and Z is —$CH_2$—$CH_2$—.

(9) Substituted Piperidin-4-amino-Type Compounds of any one of the above (1)-(8), wherein —Z—$R^1$ is:

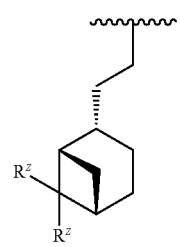

wherein each $R^z$ is independently —H, —($C_1$-$C_4$)alkyl, —OH, or —CN and preferably each $R^z$ is independently —H, —$CH_3$, or —$CH_2CH_3$.

(10) Substituted Piperidin-4-amino-Type Compounds of any one of the above (1)-(4), wherein h is 0.

(11) Substituted Piperidin-4-amino-Type Compounds of any one of the above (1)-(10), wherein A and B together form a bridge such that the bridged-piperidine is:

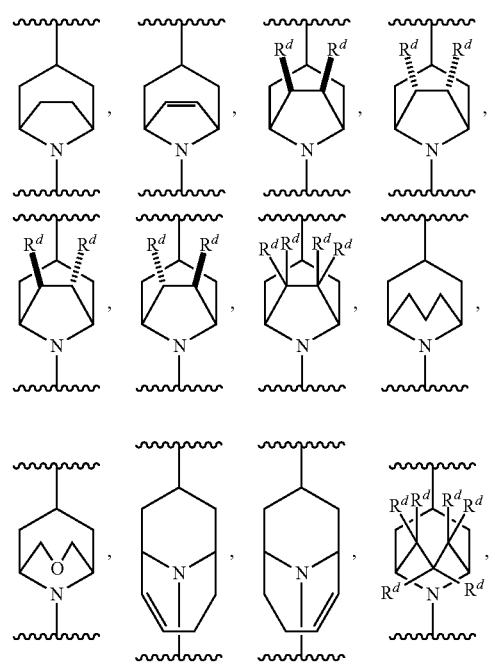

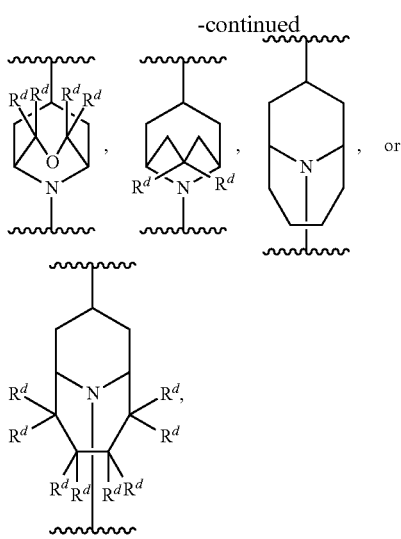

wherein each $R^d$ is independently —H, —$(C_1$-$C_4)$alkyl, -halo, or —C(halo)$_3$.

(12) Substituted Piperidin-4-amino-Type Compounds of any one of the above (1)-(11), wherein A and B together form a bridge such that the bridged-piperidine is:

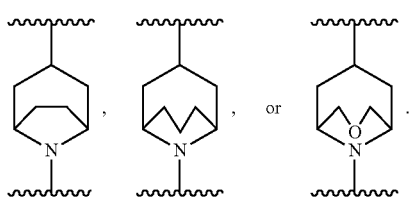

(13) Substituted Piperidin-4-amino-Type Compounds of any one of the above (1)-(12), wherein A and B together form a bridge such that the bridged-piperidine is:

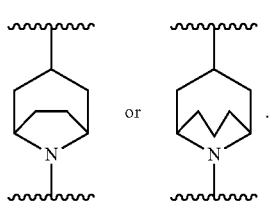 [SMILES: *C1CC2CCC(C1)N2* ; *C1CC2CCCC(C1)N2*]

(14) Substituted Piperidin-4-amino-Type Compounds of any one of the above (1)-(4) or (10)-(13), wherein:
  (a) h is 0;
  (b) $R^1$ is —$(C_1$-$C_{10})$alkyl, —$(C_3$-$C_{14})$cycloalkyl, —$(C_5$-$C_{14})$cycloalkenyl, —$(C_6$-$C_{14})$bicycloalkyl, —$(C_7$-$C_{14})$bicycloalkenyl, or —$(C_8$-$C_{20})$tricycloalkyl, each of which is unsubstituted or substituted with 1, 2, 3, or 4 independently selected $R^8$ groups and preferably $R^1$ is —$(C_3$-$C_{14})$cycloalkyl, —$(C_5$-$C_{14})$cycloalkenyl, —$(C_6$-$C_{14})$bicycloalkyl, —$(C_7$-$C_{14})$bicycloalkenyl, or —$(C_8$-$C_{20})$tricycloalkyl, each of which is unsubstituted or substituted with 1, 2, 3, or 4 independently selected $R^8$ groups; and
  (c) each $R^8$ is independently —$(C_1$-$C_4)$alkyl, —$(C_1$-$C_6)$alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, —C(=O)N(T$^1$)(T$^2$), or —C(=O)OR$^9$.

(15) Substituted Piperidin-4-amino-Type Compounds of any one of the above (1)-(4) or (10)-(14), wherein —Z—R$^1$ is:

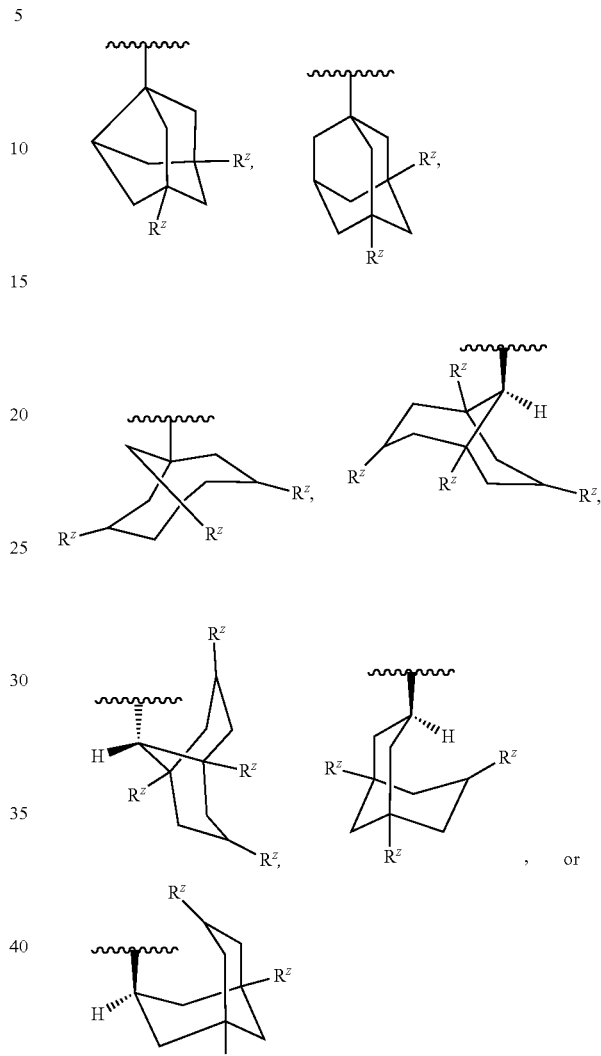

wherein each $R^z$ is independently —H, —$(C_1$-$C_4)$alkyl, —OH, or —CN and preferably each $R^z$ is independently —H, —CH$_3$, or —CH$_2$CH$_3$.

(16) Substituted Piperidin-4-amino-Type Compounds of any one of the above (1)-(4) or (10)-(14), wherein —Z—R$^1$ is:

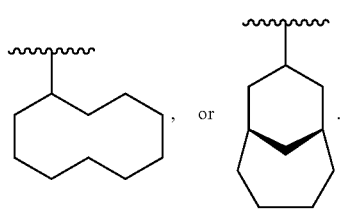 [SMILES: *C1CCCCCCCCC1 ; *C1C[C@H]2CCCC[C@@H](C1)C2]

(17) Substituted Piperidin-4-amino-Type Compounds of any one of the above (1)-(4) or (10)-(15), wherein —Z—R$^1$ is:

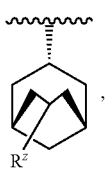

wherein R$^1$ is —H, —CH$_3$, or —CH$_2$CH$_3$.

(18) Substituted Piperidin-4-amino-Type Compounds of any one of the above (1)-(4), (10)-(17), wherein the R$^1$ group is in the exo-configuration with respect to the A-B bridge of the bridged piperidine.

(19) Substituted Piperidin-4-amino-Type Compounds of any one of the above (1)-(18), wherein E$^1$ is S(=O)$_2$, CH$_2$, or a direct bond.

(20) Substituted Piperidin-4-amino-Type Compounds of any one of the above (1)-(19), wherein Q$^1$ is phenyl.

(21) Substituted Piperidin-4-amino-Type Compounds of any one of the above (1)-(20), wherein a is selected from 0 and 1.

(22) Substituted Piperidin-4-amino-Type Compounds of any one of the above (1)-(21), wherein b is 0 or 1.

(23) Substituted Piperidin-4-amino-Type Compounds of any one of the above (1)-(22), wherein x is 0 or 1.

(24) Substituted Piperidin-4-amino-Type Compounds of any one of the above (1)-(23), wherein E$^2$ is C(=O) or a direct bond.

(25) Substituted Piperidin-4-amino-Type Compounds of any one of the above (1)-(24), wherein n is 0 or 1.

(26) Substituted Piperidin-4-amino-Type Compounds of any one of the above (1)-(25), wherein:
(a) D is H, NO$_2$ or N(R*)$_2$; and
(b) each R* is, independently for each occurrence in D, H or (C$_1$-C$_6$)alkyl unsubstituted or substituted with 1 or 2 substituents independently selected from —OH, —O(C$_1$-C$_6$ alkyl), and =O.

(27) Substituted Piperidin-4-amino-Type Compounds of any one of the above (1)-(26), wherein D is selected from

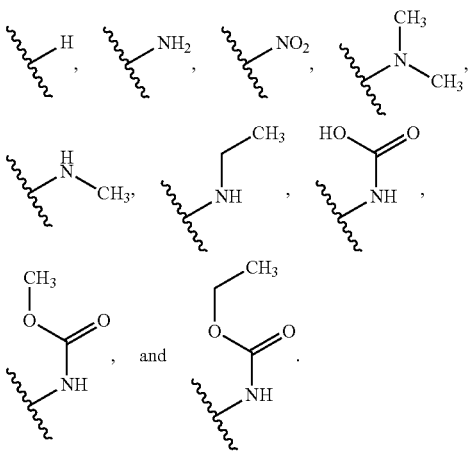

(28) Substituted Piperidin-4-amino-Type Compounds of any one of the above (1)-(27), wherein W is NH or a direct bond.

(29) Substituted Piperidin-4-amino-Type Compounds of any one of the above (1)-(28), wherein Q$^2$ is (C$_3$-C$_6$) cycloalkyl, non-aromatic (3- to 6-membered)heterocycle, or a direct bond.

(30) Substituted Piperidin-4-amino-Type Compounds of any one of the above (1)-(29), wherein Q$^2$-(R$^3$)$_b$ is selected from

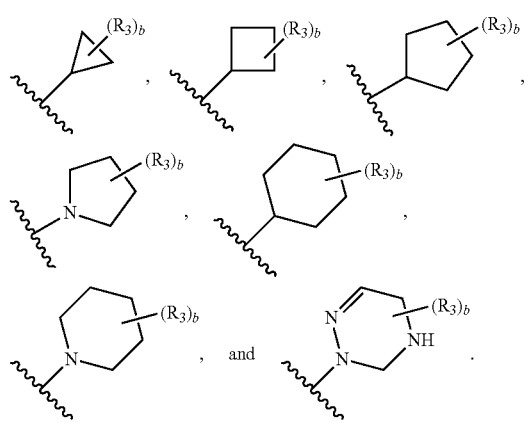

(31) Substituted Piperidin-4-amino-Type Compounds of any one of the above (1)-(30), wherein R$^2$ is, independently for each occurrence, -halo, —NO$_2$, —X, —C(=Y)YX, —N(T$^1$)(T$^2$), —YH, or —YX.

(32) Substituted Piperidin-4-amino-Type Compounds of any one of the above (1)-(31), wherein:
(a) R$^2$ is, independently for each occurrence, -halo, —NO$_2$, —X, —C(=Y)YX, —N(T$^1$)(T$^2$), —YH, or —YX;
(b) Y is O;
(b) each X is, independently for each occurrence in R$^2$, H, (C$_1$-C$_6$)alkyl, or (C$_2$-C$_6$)alkenyl unsubstituted or substituted with 1 or 2 substituents independently selected from —OH, —C(=O)OH, —C(=O)O(C$_1$-C$_6$)alkyl, —O(C$_1$-C$_6$ alkyl), and =O; and
(c) T$^1$ and T$^2$ are, independently for each occurrence in R$^2$, H or —(C$_1$-C$_{10}$)alkyl unsubstituted or substituted with 1, 2, or 3 substituents independently selected from —OH, —O(C$_1$-C$_6$)alkyl, and =O.

(33) Substituted Piperidin-4-amino-Type Compounds of any one of the above (1)-(32), wherein R$^2$ is selected from

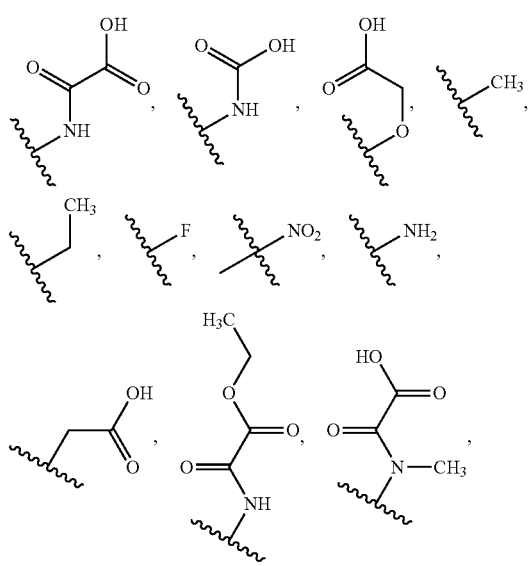

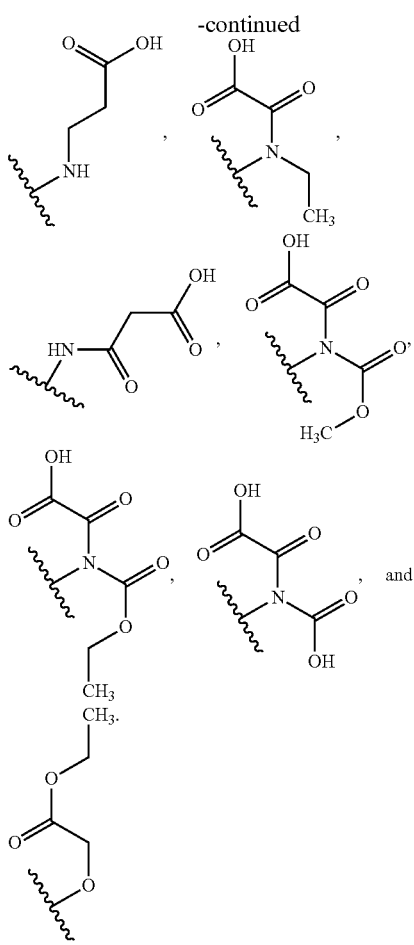

(34) Substituted Piperidin-4-amino-Type Compounds of any one of the above (1)-(32), wherein $R^2$ is selected from

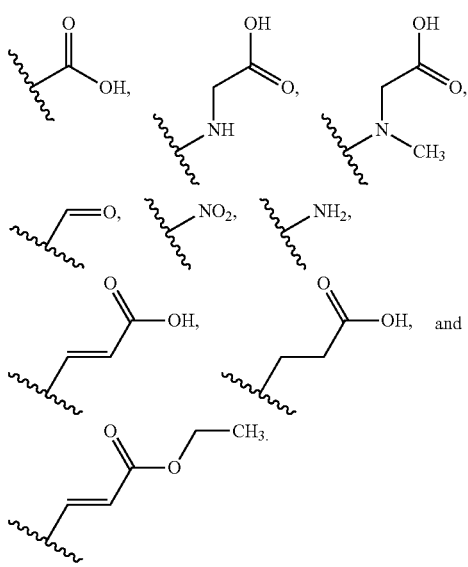

(35) Substituted Piperidin-4-amino-Type Compounds of any one of the above (1)-(34), wherein $R^3$ is, independently for each occurrence, H, $(C_1-C_6)$alkyl, halo, —C(=O)OH, —C(=O)O($C_1-C_6$alkyl), or tetrazolyl.

(36) Substituted Piperidin-4-amino-Type Compounds of any one of the above (1)-(35), wherein $R^3$ is selected from

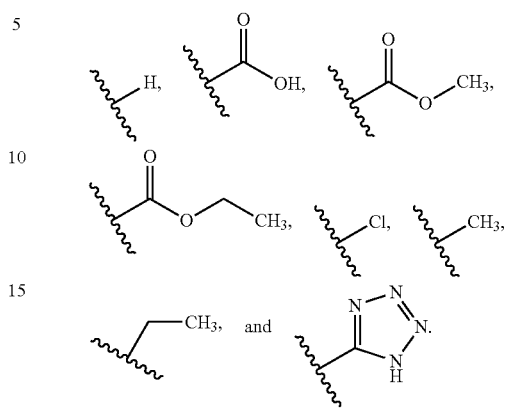

(37) Substituted Piperidin-4-amino-Type Compounds of any one of the above (1)-(35), wherein $R^3$ is selected from H and $CH_3$.

(38) Substituted Piperidin-4-amino-Type Compounds of any one of the above (1)-(33) and (35)-(36), wherein:

$E^1$ is a direct bond or $SO_2$;
$Q^1$ is phenyl;
a is selected from 0 and 1;
$R^2$ is selected from

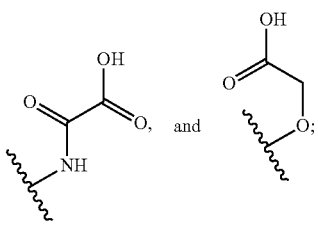 [SMILES: *NC(=O)C(=O)O ; *OCC(=O)O]

x is selected from 0 and;
$E^2$ is C(=O);
n is selected from 0 and 1;
D is selected from H and —N(CH_3)_2;
W is selected from —NH and a direct bond;
$Q^2$ is selected from pyrrolidinyl, cyclopropyl, cyclohexyl and a direct bond;
b is selected from 0 and 1; and
$R^3$ is selected from

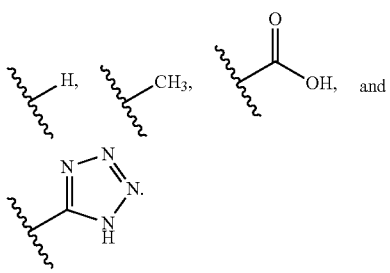

(39) Substituted Piperidin-4-amino-Type Compounds of the above (38), wherein:
$E^1$ is a direct bond;
$R^2$ is

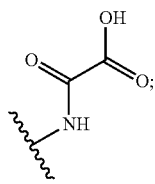

D is H;
W is a direct bond;
$Q^2$ is selected from pyrrolidinyl and a direct bond;
b is 1; and
$R^3$ is selected from

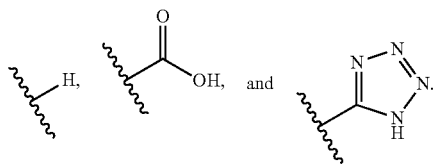

(40) Substituted Piperidin-4-amino-Type Compounds of any one of the above (1)-(32), (34)-(35), and (37), wherein:
$E^1$ is selected from a C(=O), $CH_2$, and a direct bond;
$Q^1$ is phenyl;
a is 1;
$R^2$ is selected from

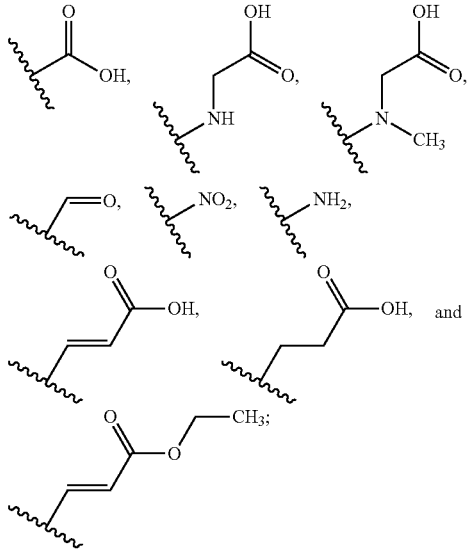

x is 0
$E^2$ is selected from C(=O) and a direct bond;
n is 0;
W is a direct bond;
$Q^2$ is a direct bond;
b is 1; and
$R^3$ is selected from H and $CH_3$.
(41) Substituted Piperidin-4-amino-Type Compounds of the above (40), wherein $R^2$ is selected from

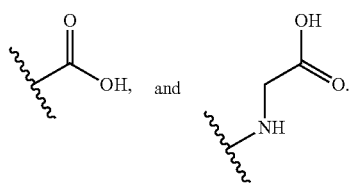

(42) A Substituted Piperidin-4-amino-Type Compound of any one of the above (1)-(33), (35)-(36), and (38), wherein the compound is:

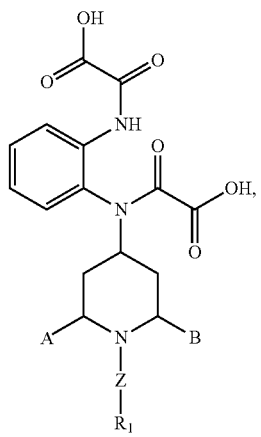

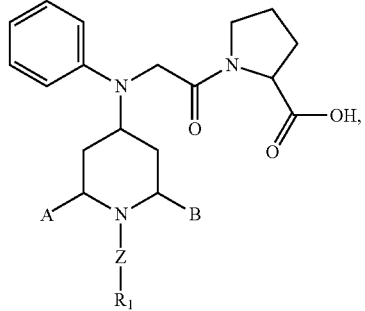

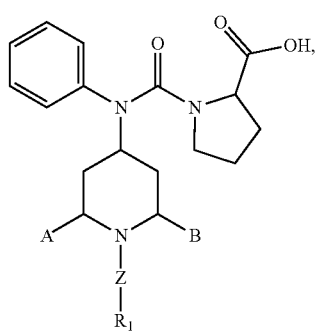

-continued
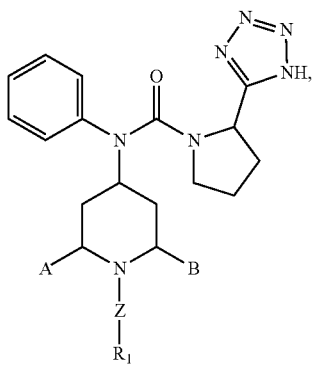
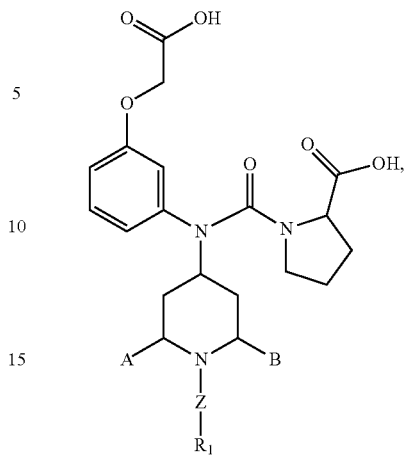
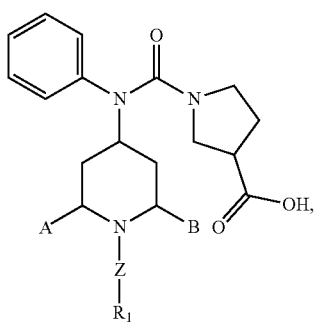
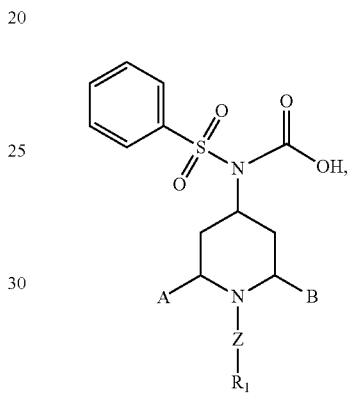
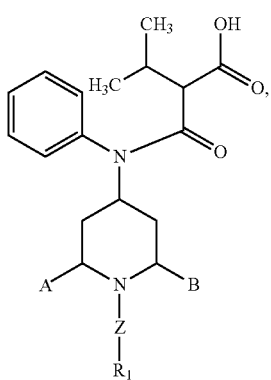
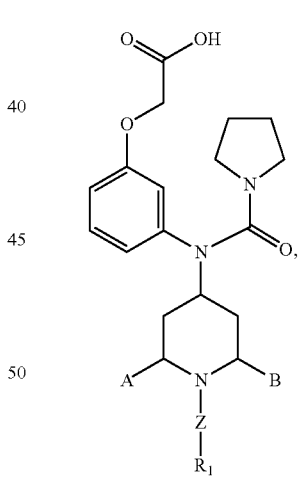
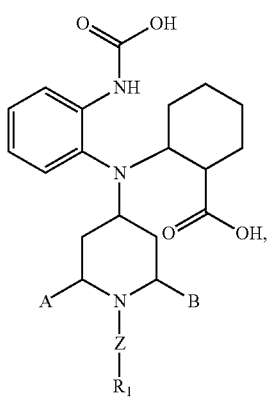
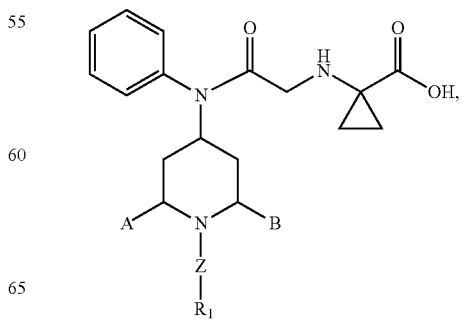

27
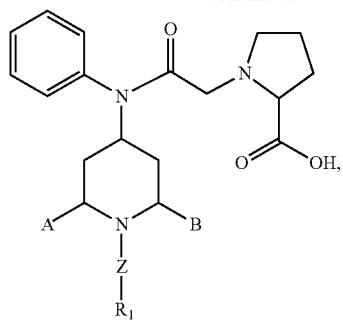
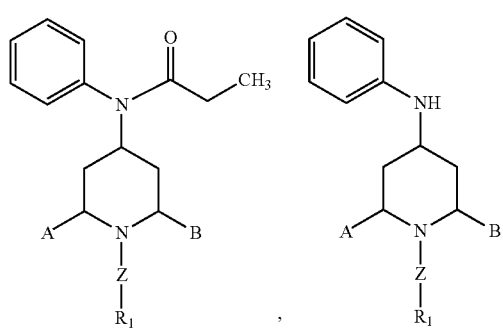
or a pharmaceutically acceptable salt or solvate thereof.
(43) A Substituted Piperidin-4-amino-Type Compound of the above (42), wherein the compound is:
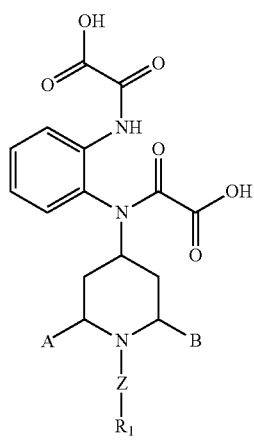
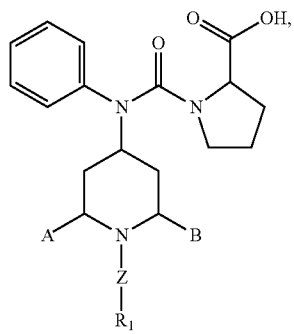
28
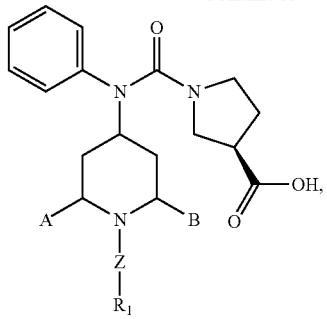
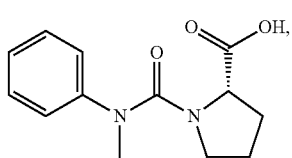
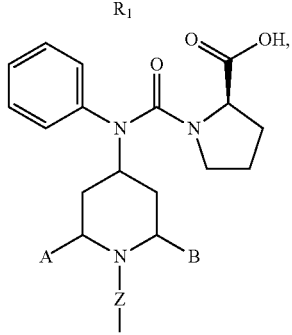
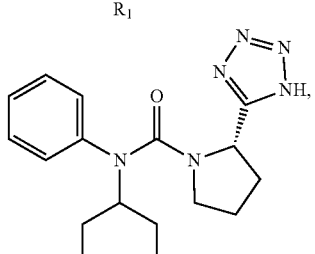
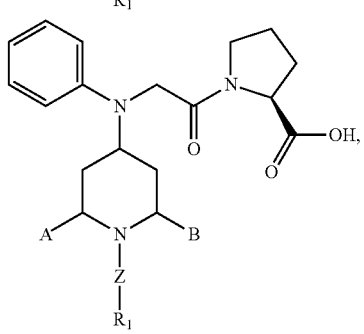

-continued
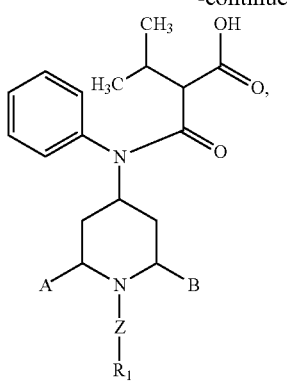
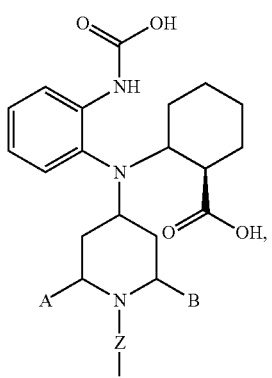
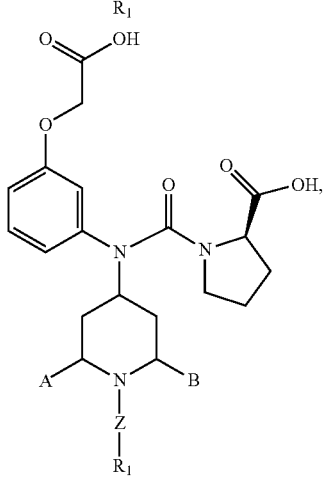
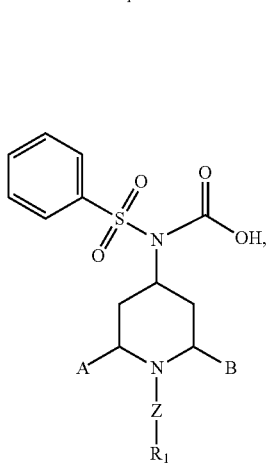
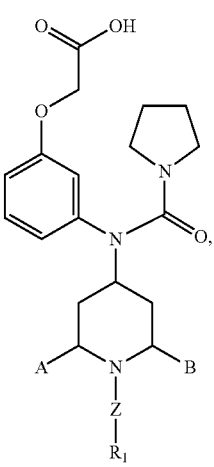
-continued
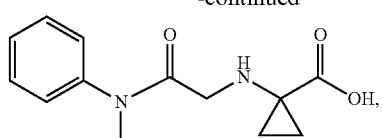
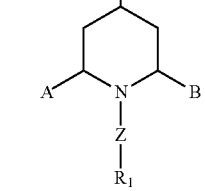
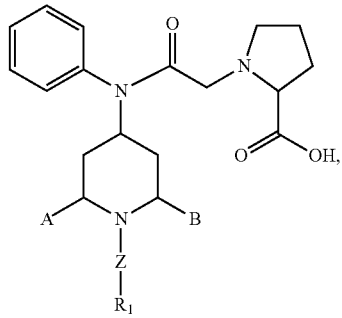
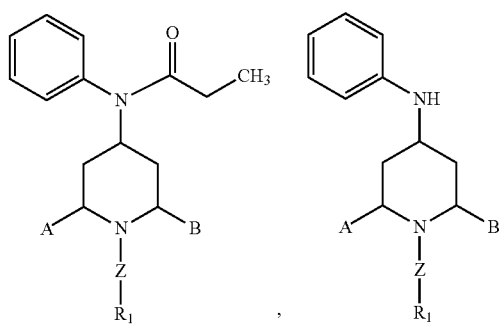
or a pharmaceutically acceptable salt or solvate thereof.
(44) A Substituted Piperidin-4-amino-Type Compound of any one of the above (1)-(32), (34), (37), and (40), wherein the compound is:
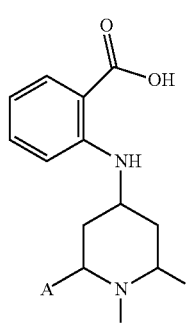
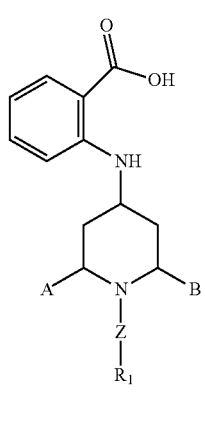

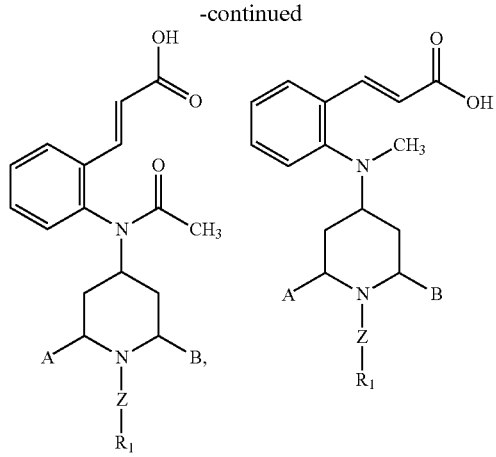
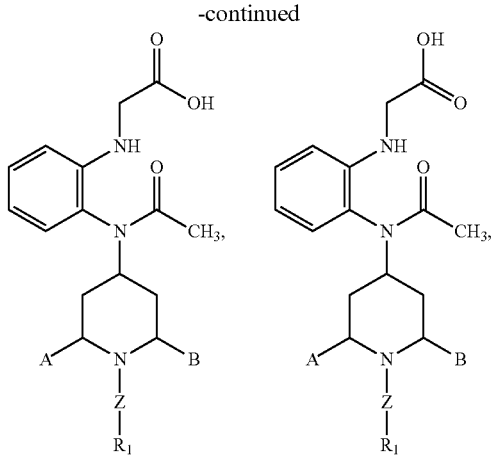
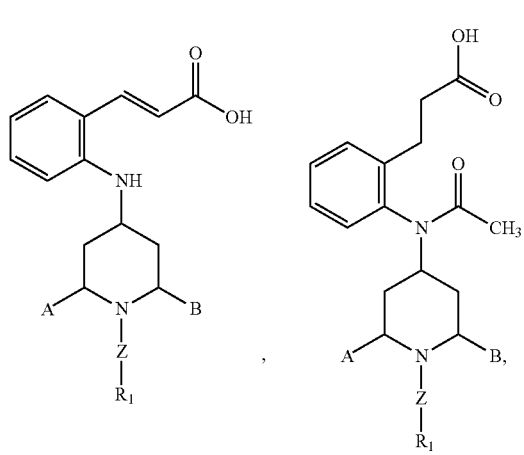
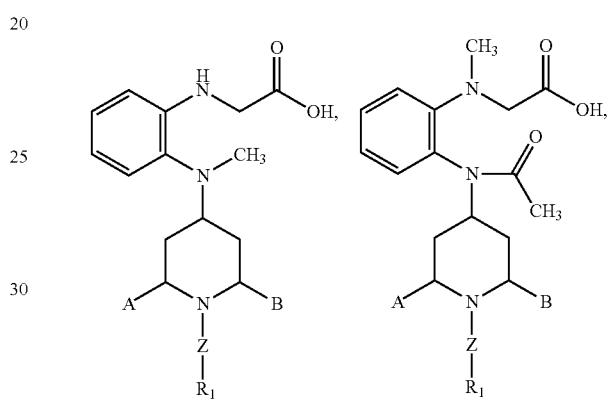
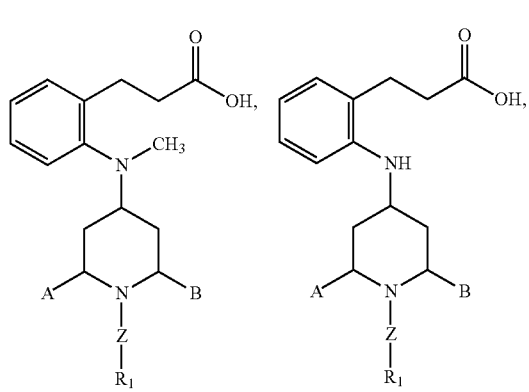
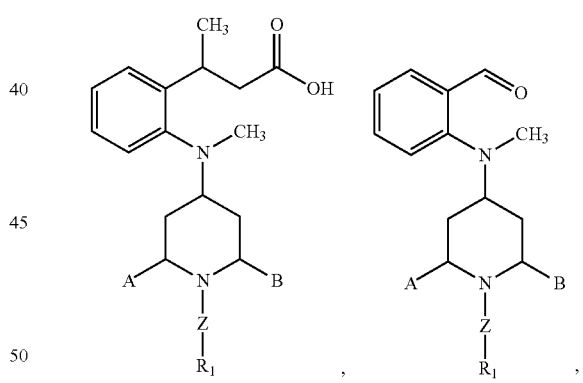
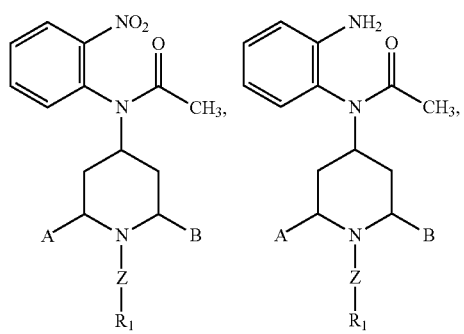
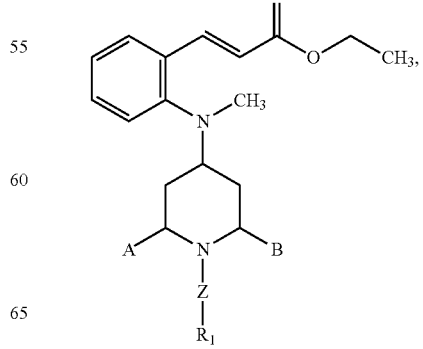

-continued
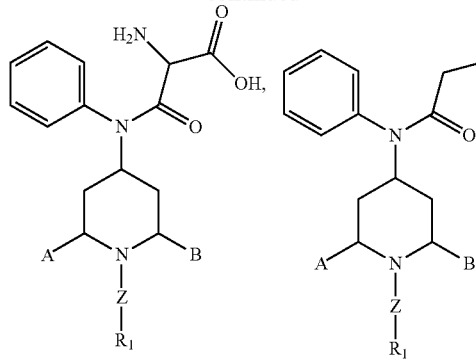 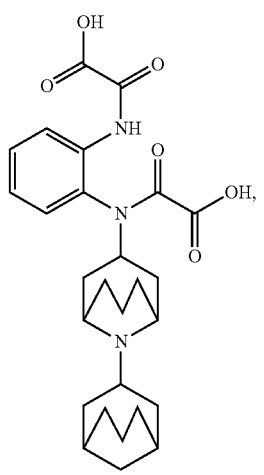
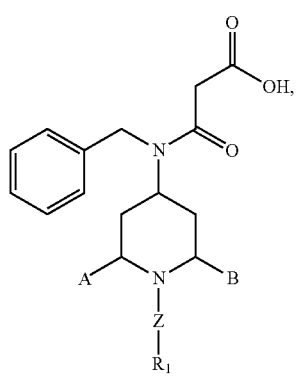 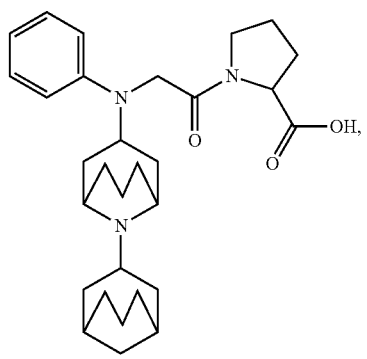
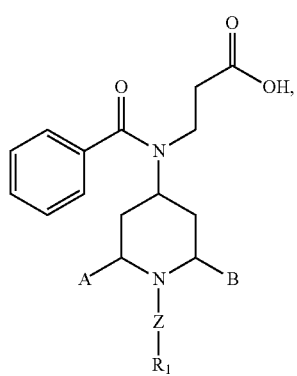 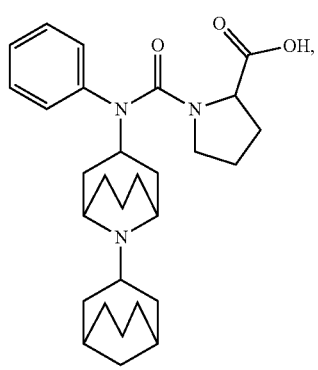
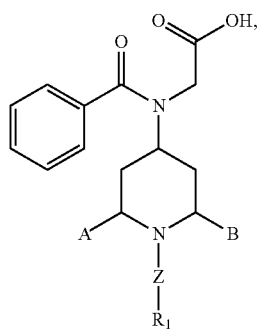 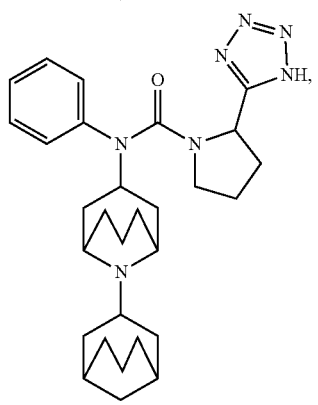
or a pharmaceutically acceptable salt or solvate thereof.
(45) A Substituted Piperidin-4-amino-Type Compound which is:

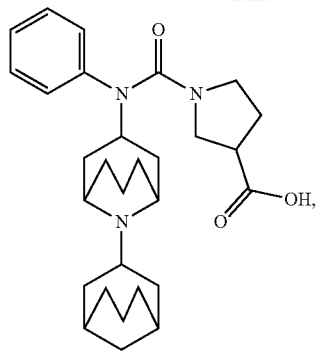
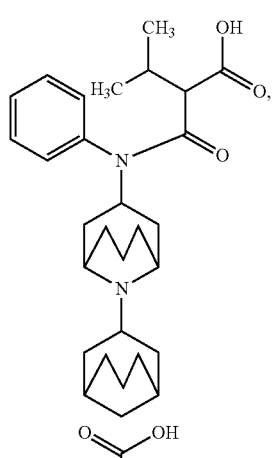
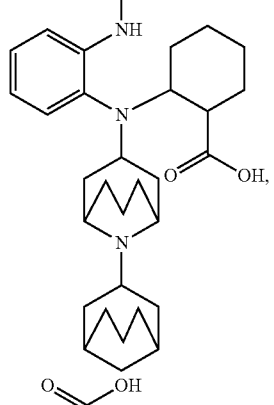
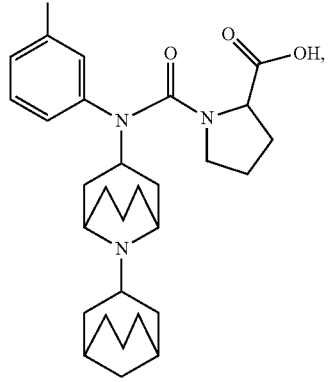
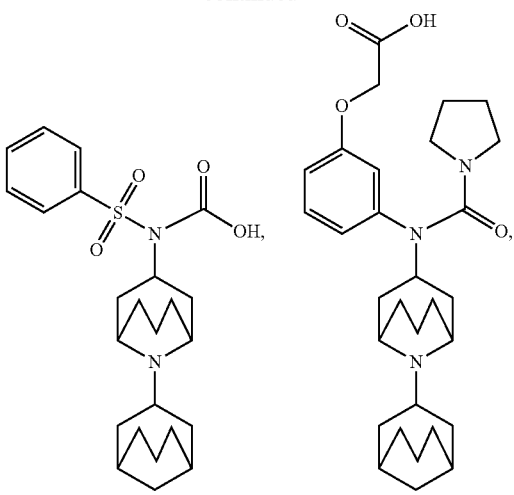
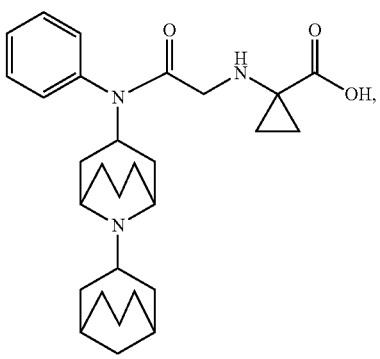
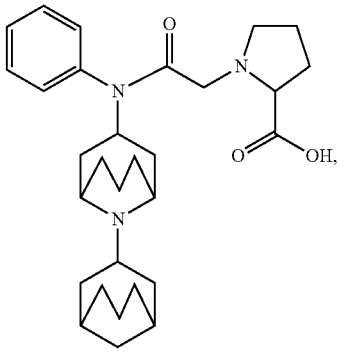
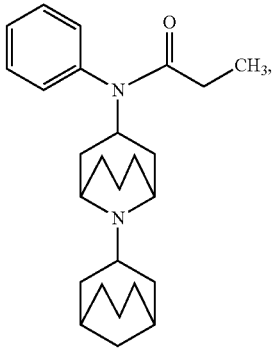

-continued
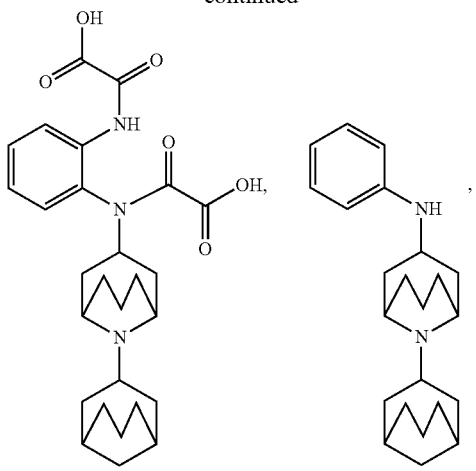
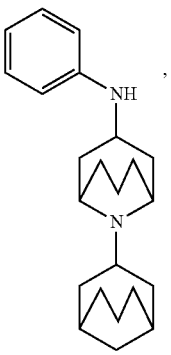
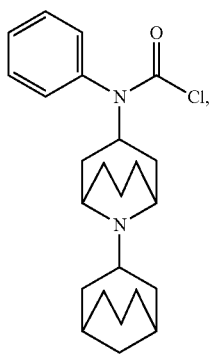
or a pharmaceutically acceptable salt or solvate thereof.
(46) The Substituted Piperidin-4-amino-Type Compound of the above (45), which is:
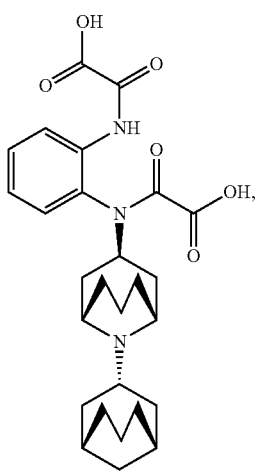
-continued
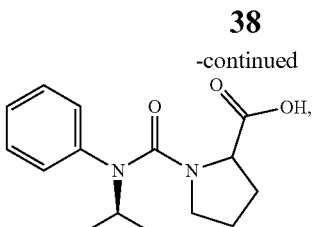
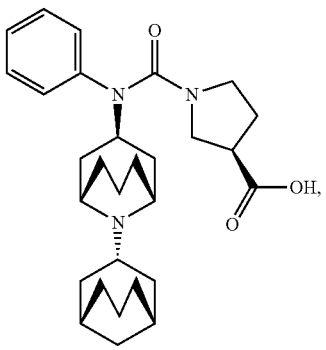
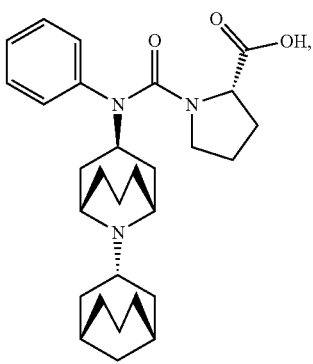
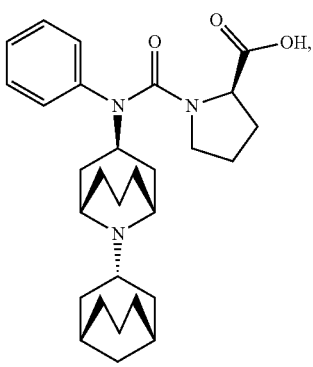

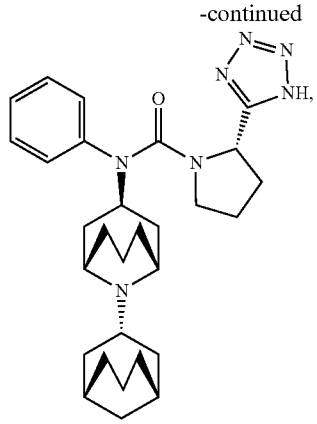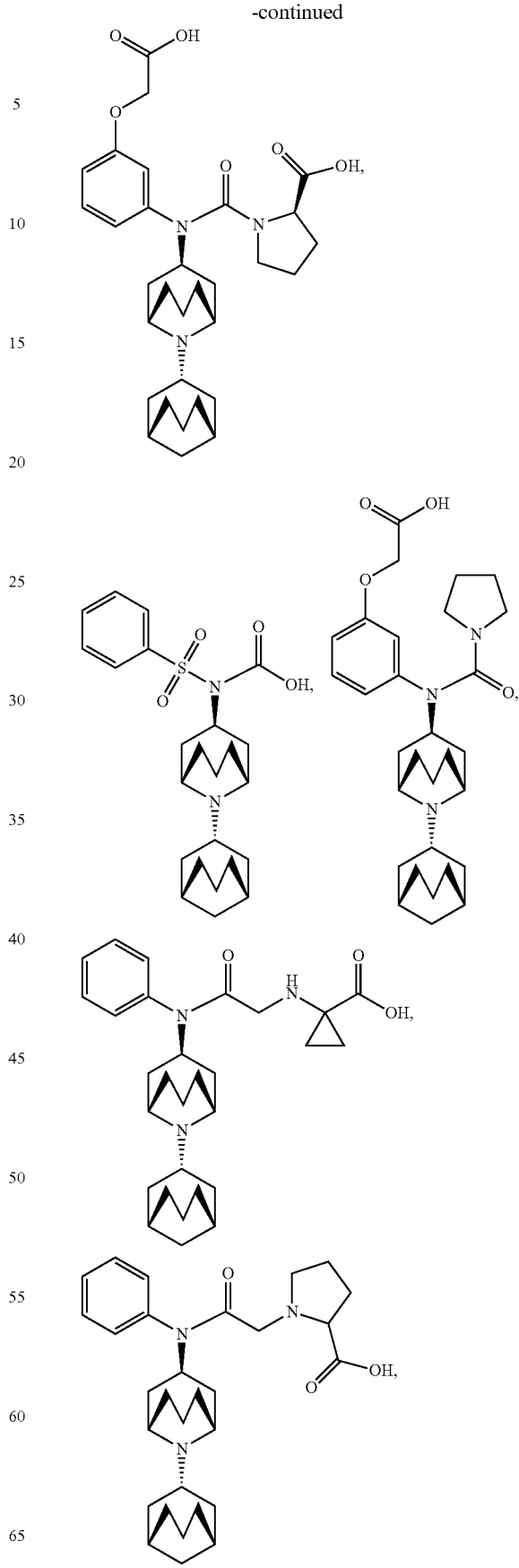

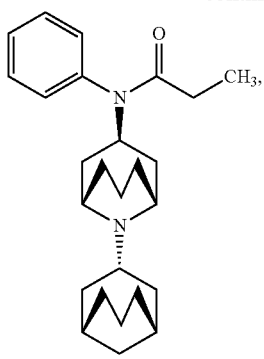

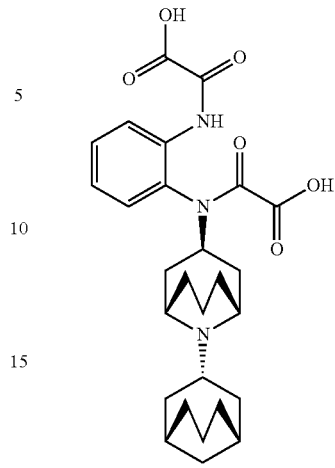

or a pharmaceutically acceptable salt or solvate thereof.

(48) The Substituted Piperidin-4-amino-Type Compound of the above (46), having the formula:

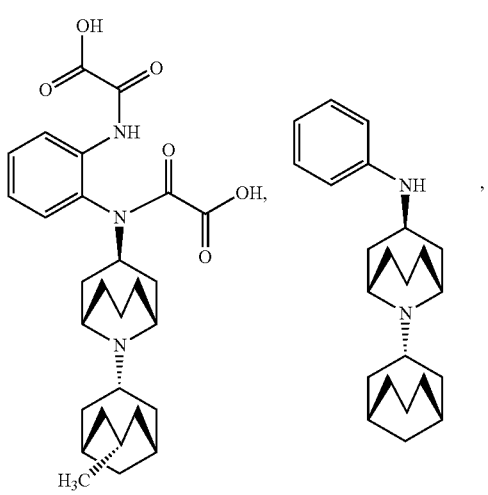

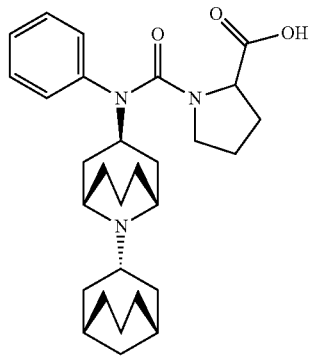

or a pharmaceutically acceptable salt or solvate thereof.

(49) The Substituted Piperidin-4-amino-Type Compound of the above (46), having the formula:

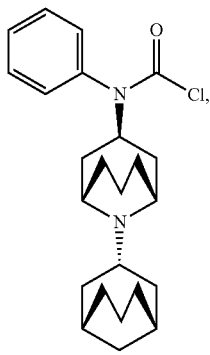 [SMILES: O=C(Cl)N(c1ccccc1)[C@H]1C[C@H]2CCC[C@@H](C1)N2[C@H]1C[C@@H]2CCC[C@@H](C2)C1]

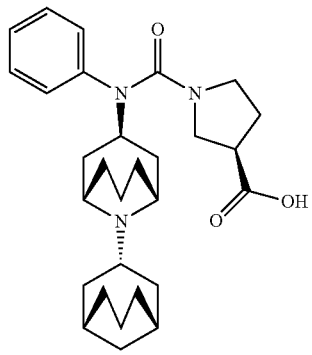

or a pharmaceutically acceptable salt or solvate thereof.

(47) The Substituted Piperidin-4-amino-Type Compound of the above (46), having the formula:

or a pharmaceutically acceptable salt or solvate thereof.

(50) The Substituted Piperidin-4-amino-Type Compound of the above (46), having the formula:

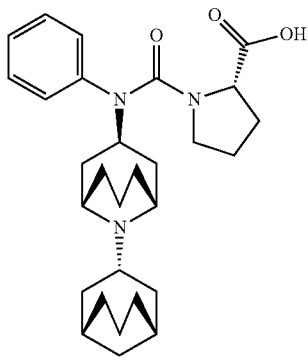 [SMILES: O=C(O)C1CCCN1C(=O)N(c1ccccc1)[C@H]1C[C@H]2CCC[C@@H](C1)N2[C@H]1C[C@@H]2CCC[C@@H](C2)C1]

or a pharmaceutically acceptable salt or solvate thereof.

(51) The Substituted Piperidin-4-amino-Type Compound of the above (46), having the formula:

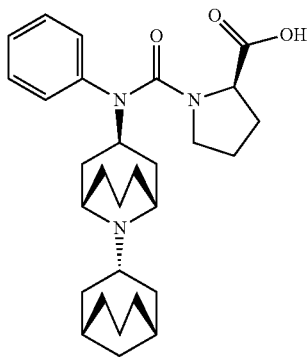 [SMILES: O=C(O)[C@H]1CCCN1C(=O)N(c1ccccc1)[C@H]1C[C@H]2CCC[C@@H](C1)N2[C@H]1C[C@@H]2CCC[C@@H](C2)C1]

or a pharmaceutically acceptable salt or solvate thereof.

(52) The Substituted Piperidin-4-amino-Type Compound of the above (46), having the formula:

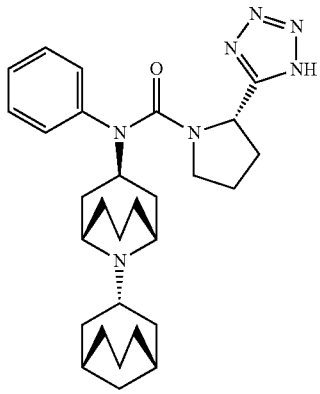 [SMILES: O=C(N1CCC[C@H]1c1nnn[nH]1)N(c1ccccc1)[C@H]1C[C@H]2CCC[C@@H](C1)N2[C@H]1C[C@@H]2CCC[C@@H](C2)C1]

or a pharmaceutically acceptable salt or solvate thereof.

(53) The Substituted Piperidin-4-amino-Type Compound of the above (46), having the formula:

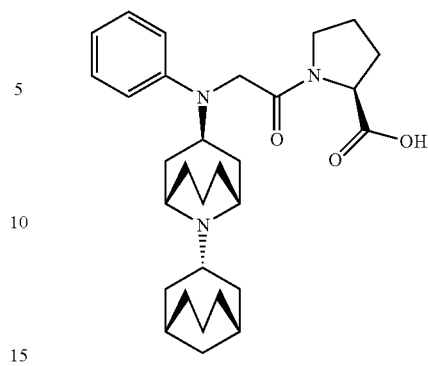

or a pharmaceutically acceptable salt or solvate thereof.

(54) The Substituted Piperidin-4-amino-Type Compound of the above (46), having the formula:

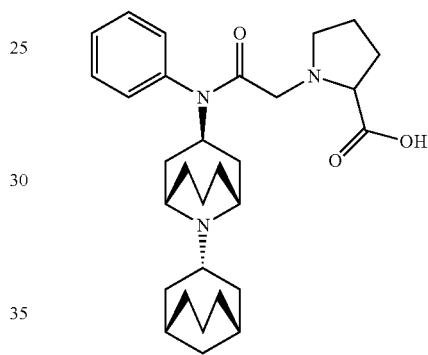

or a pharmaceutically acceptable salt or solvate thereof.

(55) The Substituted Piperidin-4-amino-Type Compound of the above (46), having the formula:

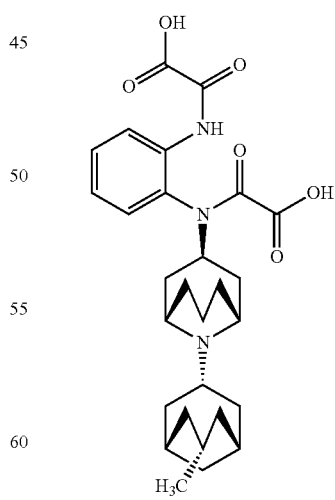

or a pharmaceutically acceptable salt or solvate thereof.

(56) The Substituted Piperidin-4-amino-Type Compound of the above (46), having the formula:

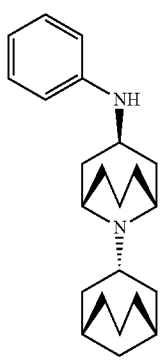 [SMILES: c1ccc(N[C@H]2C[C@H]3CCC[C@@H](C2)N3[C@H]2C[C@@H]3CCC[C@@H](C3)C2)cc1]
or a pharmaceutically acceptable salt or solvate thereof.
(57) The Substituted Piperidin-4-amino-Type Compound of the above (46), having the formula:
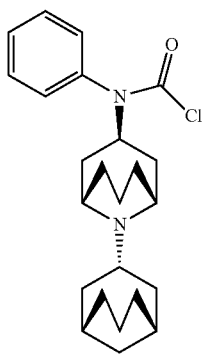 [SMILES: O=C(Cl)N(c1ccccc1)[C@H]1C[C@H]2CCC[C@@H](C1)N2[C@H]1C[C@@H]2CCC[C@@H](C2)C1]
or a pharmaceutically acceptable salt or solvate thereof.
(58) A Substituted Piperidin-4-amino-Type Compound which is:
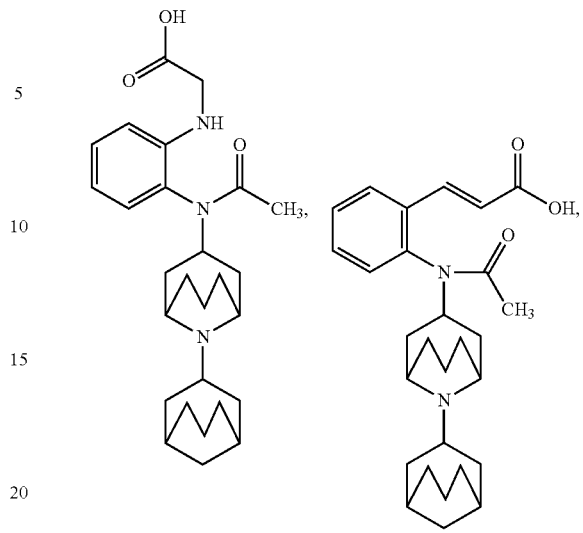
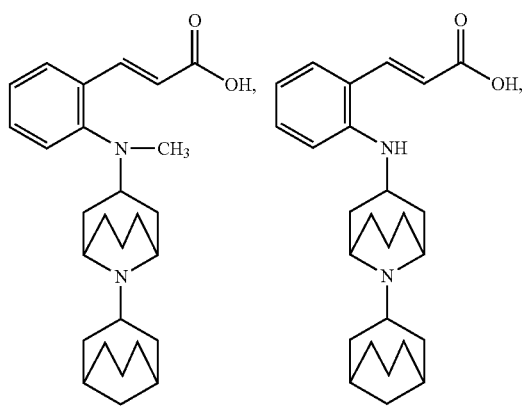
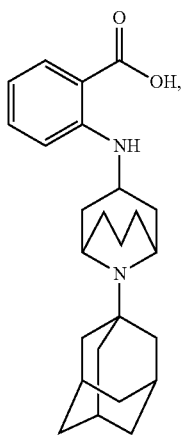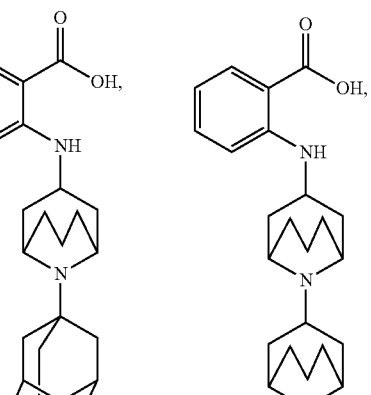
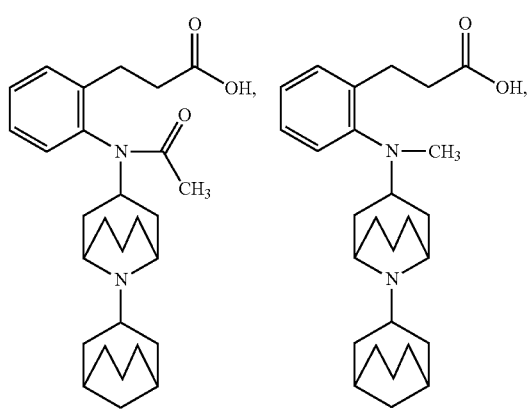

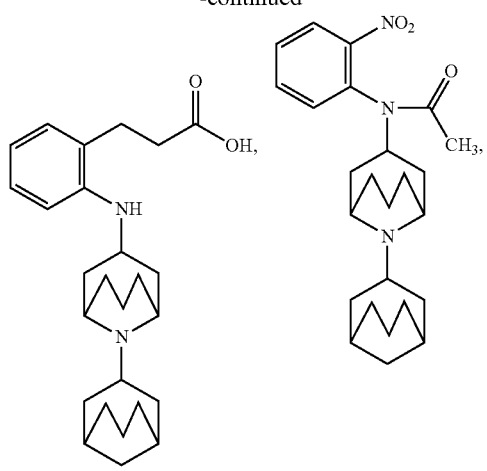
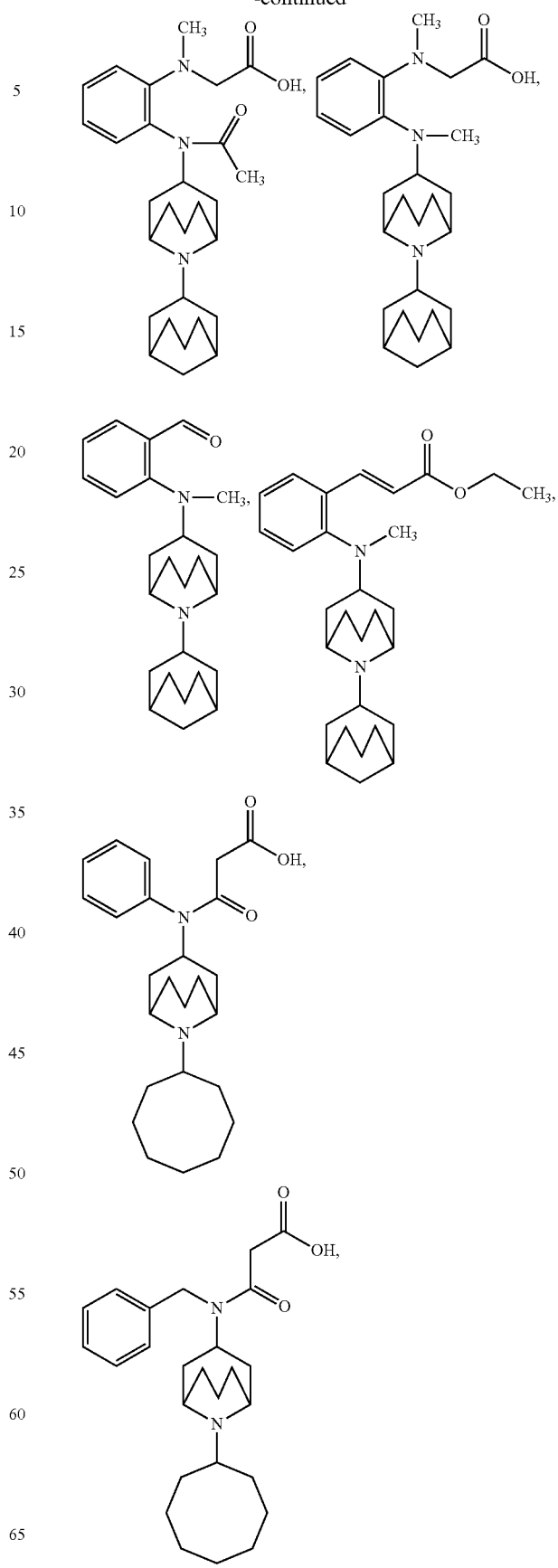

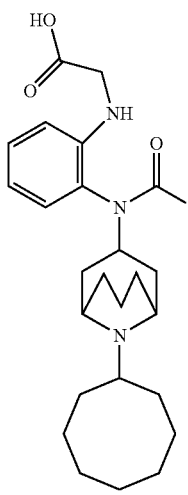
or a pharmaceutically acceptable salt or solvate thereof.
(59) The Substituted Piperidin-4-amino-Type Compound of the above (58), which is:
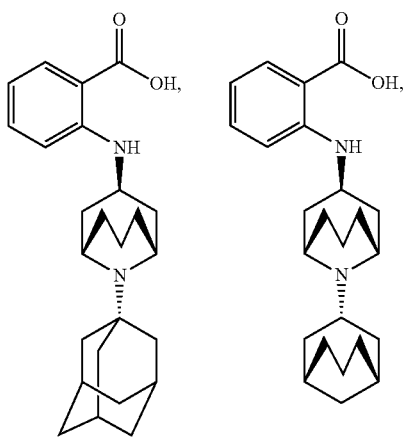
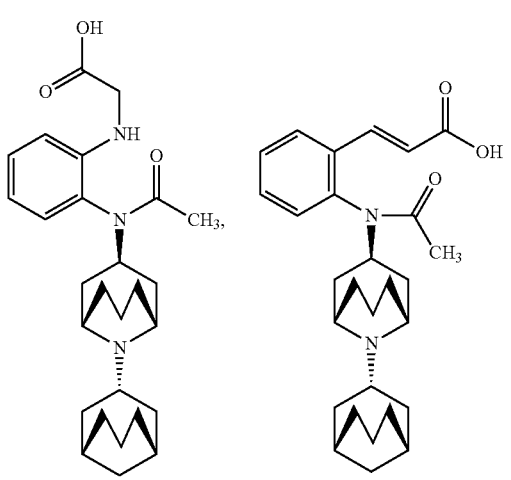
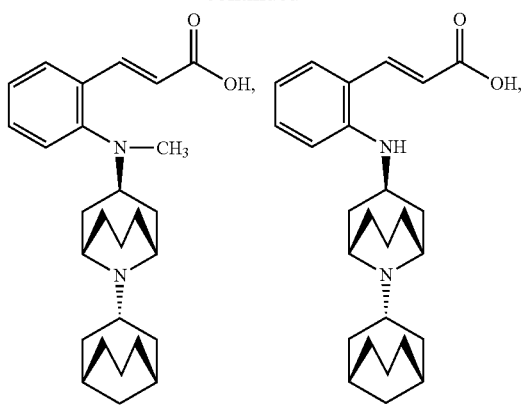
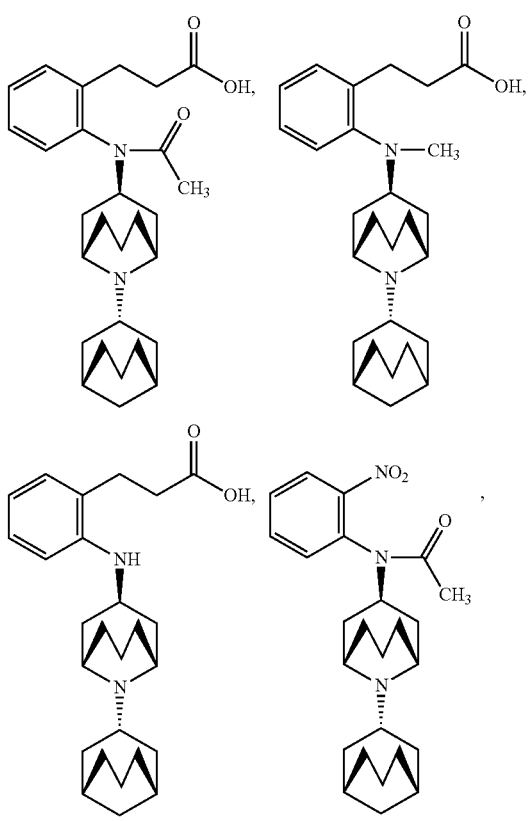

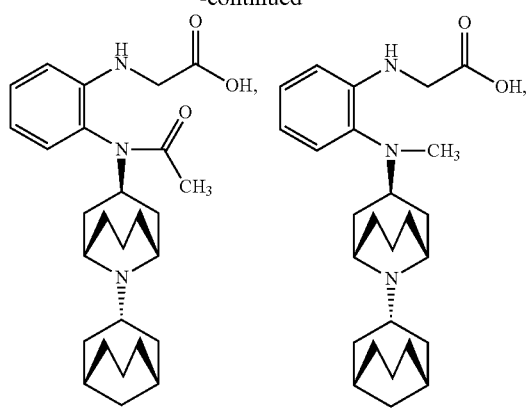
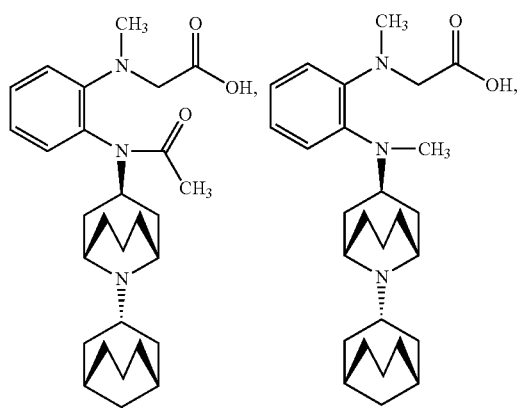
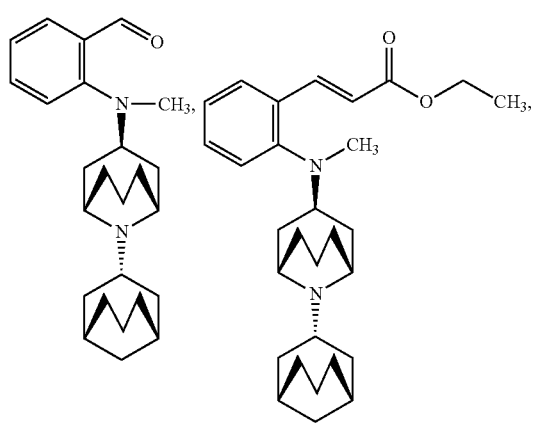
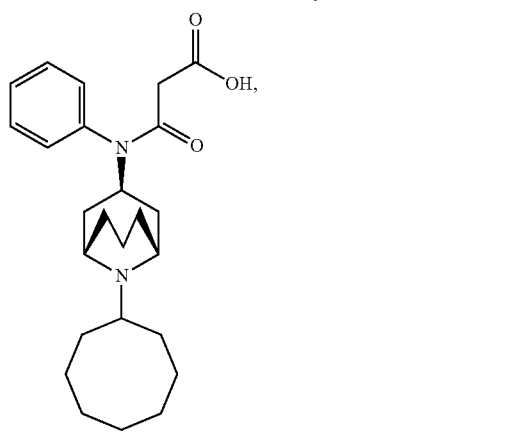
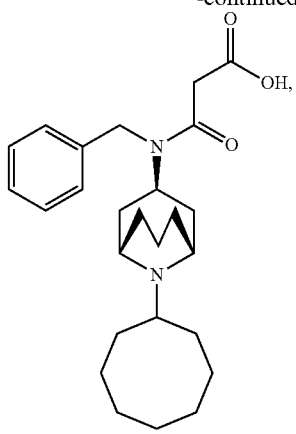
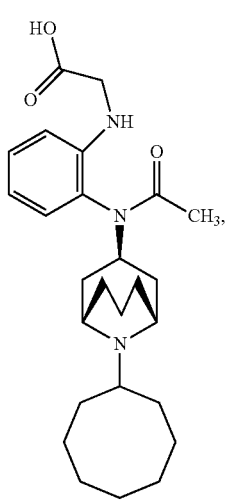
or a pharmaceutically acceptable salt or solvate thereof.
(60) The Substituted Piperidin-4-amino-Type Compound of the above (59), which is:
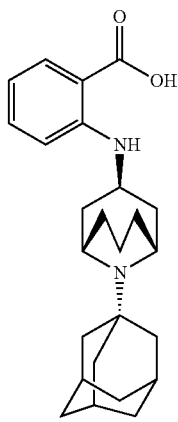
or a pharmaceutically acceptable salt or solvate thereof.
(61) The Substituted Piperidin-4-amino-Type Compound of the above (59), which is:

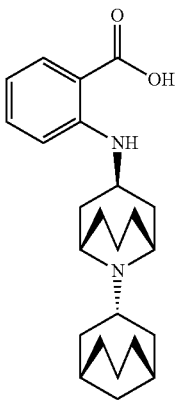 [SMILES: O=C(O)c1ccccc1N[C@H]1C[C@H]2CCC[C@@H](C1)N2[C@H]1C[C@@H]2CCC[C@@H](C2)C1]

or a pharmaceutically acceptable salt or solvate thereof.

(62) The Substituted Piperidin-4-amino-Type Compound of the above (59), which is:

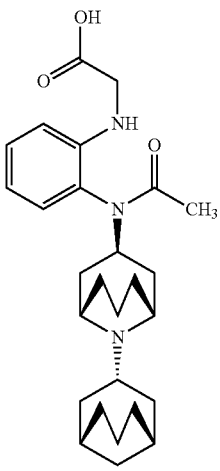 [SMILES: CC(=O)N(c1ccccc1NCC(=O)O)[C@H]1C[C@H]2CCC[C@@H](C1)N2[C@H]1C[C@@H]2CCC[C@@H](C2)C1]

or a pharmaceutically acceptable salt or solvate thereof.

(63) The Substituted Piperidin-4-amino-Type Compound of the above (59), which is:

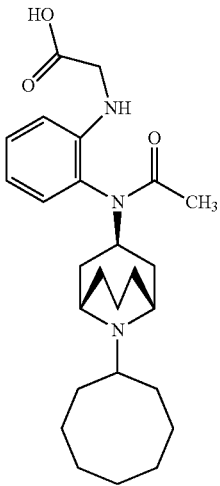 [SMILES: CC(=O)N(c1ccccc1NCC(=O)O)[C@H]1C[C@H]2CCC[C@@H](C1)N2C1CCCCCCC1]

or a pharmaceutically acceptable salt or solvate thereof.

(64) The Substituted Piperidin-4-amino-Type Compound of any one of the above (1)-(41), having the formula:

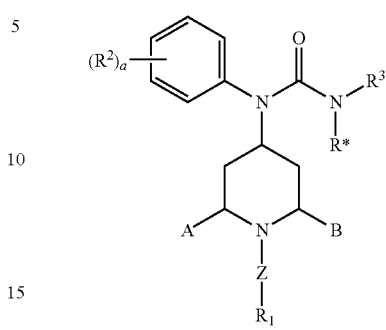

(65) The Substituted Piperidin-4-amino-Type Compounds of any one of the above (1)-(64), which is radiolabeled.

(66) The Substituted Piperidin-4-amino-Type Compounds of any one of the above (1)-(65), wherein the pharmaceutically acceptable salt is, for example, a hydrochloride-salt, a sodium-salt, a potassium-salt, or a para-toluenesulfonic acid-salt.

(67) The Substituted Piperidin-4-amino-Type Compounds of any one of the above (1)-(66), wherein the % de of the compound is at least about 95%.

(68) The Substituted Piperidin-4-amino-Type Compounds of the above (67), wherein the % de of the compound is at least about 99%.

(69) A composition comprising a Substituted Piperidin-4-amino-Type Compound of any one of the above (1)-(68) and a pharmaceutically acceptable carrier or excipient.

(70) A method for preparing a composition, comprising the step of admixing a Substituted Piperidin-4-amino-Type Compound of any one of the above (1)-(68) and a pharmaceutically acceptable carrier or excipient.

(71) A method for modulating ORL-1 receptor function in a cell, comprising contacting a cell capable of expressing the ORL-1 receptor with the composition or a Substituted Piperidin-4-amino-Type Compound of any one of the above (1)-(69).

(72) The method of the above (71), wherein the composition or the Substituted Piperidin-4-amino-Type Compound acts as an agonist at the ORL-1 receptor.

(73) The method of the above (71), wherein the composition or the Substituted Piperidin-4-amino-Type Compounds acts as a partial agonist at the ORL-1 receptor.

(74) The method of the above (71), wherein the composition or the Substituted Piperidin-4-amino-Type Compounds acts as an antagonist at the ORL-1 receptor.

(75) A method for treating pain in an animal, comprising administering to an animal in need thereof the composition or a Substituted Piperidin-4-amino-Type Compound of any one of the above (1)-(69).

(76) A method for treating a memory disorder, obesity, constipation, depression, Parkinsonism, anxiety, cough, diarrhea, high blood pressure, epilepsy, anorexia/cachexia, urinary incontinence, drug abuse, a sleep disorder (see, e.g., U.S. Pat. No. 8,003,669), a metabolic disorder (see, e.g., Matsushita, et al. (2009), a renal disorder, or a cardiovascular disorder in an animal, comprising administering to an animal in need thereof an effective amount of a Substituted Piperidin-4-amino-Type Compound of any one of the above (1)-(69).

(77) Use of a Substituted Piperidin-4-amino-Type Compound of any one of the above (1)-(68) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(78) A Substituted Piperidin-4-amino-Type Compound of any one of the above (1)-(68) for use in the treatment of pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(79) A kit, comprising a sterile container containing an amount of a Substituted Piperidin-4-amino-Type Compound of any one of the above (1)-(69).

4.1 Substituted Piperidin-4-amino-Type Compounds of Formula (I)

As stated above, the disclosure encompasses Substituted Piperidin-4-amino-Type Compounds of Formula (I):

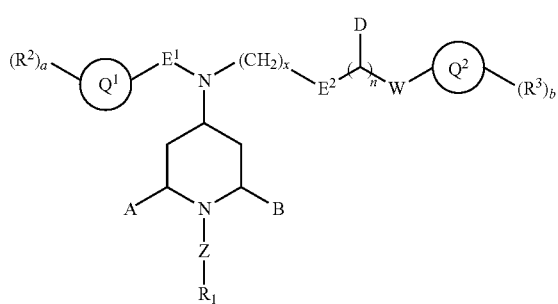

and pharmaceutically acceptable salts and solvates thereof, where $R^1$, $R^2$, $R^3$, $Q^1$, $Q^2$, $E^1$, $E^2$, A, B, D, W, Z, a, b, n, and x are defined above.

In one embodiment, $Q^1$ is phenyl, naphthalenyl, pyridinyl, pyridazinyl, pyrimidinyl, pyrazinyl, or triazinyl. In another embodiment, $Q^1$ is phenyl, naphthalenyl, pyridinyl, pyridazinyl, pyrimidinyl, or pyrazinyl. In another embodiment, $Q^1$ is phenyl, naphthalenyl, pyridinyl, pyridazinyl, pyrimidinyl, or triazinyl. In another embodiment, $Q^1$ is phenyl, naphthalenyl, pyridinyl, pyridazinyl, pyrazinyl, or triazinyl. In another embodiment, $Q^1$ is phenyl, naphthalenyl, pyridinyl, pyrimidinyl, pyrazinyl, or triazinyl. In another embodiment, $Q^1$ is phenyl, naphthalenyl, pyridazinyl, pyrimidinyl, pyrazinyl, or triazinyl. In another embodiment, $Q^1$ is phenyl, pyridinyl, pyridazinyl, pyrimidinyl, pyrazinyl, or triazinyl. In another embodiment, $Q^1$ is naphthalenyl, pyridinyl, pyridazinyl, pyrimidinyl, pyrazinyl, or triazinyl. In another embodiment, $Q^1$ is phenyl. In another embodiment, $Q^1$ is naphthalenyl. In another embodiment, $Q^1$ is pyridinyl. In another embodiment, $Q^1$ is pyridazinyl. In another embodiment, $Q^1$ is pyrimidinyl. In another embodiment, $Q^1$ is pyrazinyl. In another embodiment, $Q^1$ is triazinyl.

In another embodiment, $Q^2$ is $(C_3-C_{10})$cycloalkyl, (3- to 9-membered)heterocycle, or a direct bond. In another embodiment, $Q^2$ is $(C_3-C_{10})$cycloalkyl or (3- to 9-membered)heterocycle. In another embodiment, $Q^2$ is $(C_3-C_{10})$cycloalkyl or a direct bond. In another embodiment, $Q^2$ is (3- to 9-membered)heterocycle or a direct bond. In another embodiment, $Q^2$ is $(C_3-C_{10})$cycloalkyl. (3- to 9-membered) heterocycle. In another embodiment, $Q^2$ is a direct bond. In another embodiment, $Q^2$ is $(C_3-C_6)$cycloalkyl, non-aromatic (3- to 6-membered)heterocycle, or a direct bond. In another embodiment, $Q^2$ is non-aromatic (3- to 6-membered)heterocycle. In another embodiment, $Q^2$ is selected from pyrrolidinyl, cyclopropyl, cyclohexyl and a direct bond. In another embodiment, $Q^2$ is pyrrolidinyl. In another embodiment, $Q^2$ is cyclopropyl. In another embodiment, $Q^2$ is cyclohexyl.

In another embodiment, $Q^2$-$(R^3)_b$ is selected from

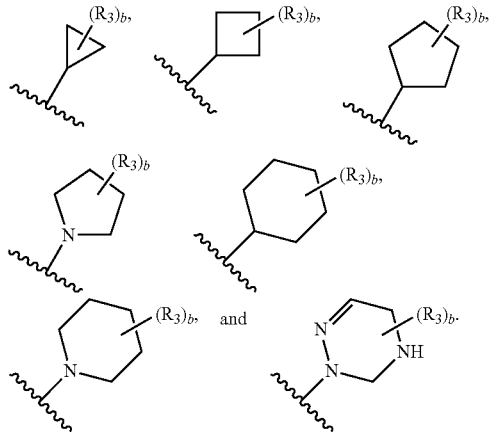

In another embodiment, $E^1$ is C(=O), S(=O)$_2$, CH$_2$, or a direct bond. In another embodiment, $E^1$ is C(=O), S(=O)$_2$, or CH$_2$. In another embodiment, $E^1$ is C(=O), S(=O)$_2$, or a direct bond. In another embodiment, $E^1$ is C(=O), CH$_2$, or a direct bond. In another embodiment, $E^1$ is S(=O)$_2$, CH$_2$, or a direct bond. In another embodiment, $E^1$ is a direct bond or S(=O)$_2$. In another embodiment, $E^1$ is C(=O). In another embodiment, $E^1$ is S(=O)$_2$. In another embodiment, $E^1$ is CH$_2$. In another embodiment, $E^1$ is a direct bond.

In another embodiment, $E^2$ is C(=O), S(=O)$_2$, CH$_2$, or a direct bond. In another embodiment, $E^2$ is C(=O), S(=O)$_2$, or CH$_2$. In another embodiment, $E^2$ is C(=O), S(=O)$_2$, or a direct bond. In another embodiment, $E^2$ is C(=O), CH$_2$, or a direct bond. In another embodiment, $E^2$ is S(=O)$_2$, CH$_2$, or a direct bond. In another embodiment, $E^2$ is C(=O). In another embodiment, $E^2$ is S(=O)$_2$. In another embodiment, $E^2$ is CH$_2$. In another embodiment, $E^2$ is a direct bond.

In another embodiment, W is S, O, N(R*), or a direct bond. In another embodiment, W is S, O, or N(R*). In another embodiment, W is S, O, or a direct bond. In another embodiment, W is S, N(R*), or a direct bond. In another embodiment, W is O, N(R*), or a direct bond. In another embodiment, W is S or O. In another embodiment, W is S or N(R*). In another embodiment, W is S or a direct bond. In another embodiment, W is O or N(R*). In another embodiment, W is O or a direct bond. In another embodiment, W is N(R*) or a direct bond. In another embodiment, W is S. In another embodiment, W is O. In another embodiment, W is N(R*). In another embodiment, W is a direct bond. In another embodiment, W is NH or a direct bond. In another embodiment, W is NH.

In another embodiment, D is H, OR*, SR*, NO$_2$, or N(R*)$_2$. In another embodiment, D is H, OR*, SR*, or NO$_2$. In another embodiment, D is H, OR*, NO$_2$, or N(R*)$_2$. In another embodiment, D is H, SR*, NO$_2$, or N(R*)$_2$. In another embodiment, D is OR*, SR*, NO$_2$, or N(R*)$_2$. In another embodiment, D is H, OR*, SR*, NO$_2$, or N(R*)$_2$. In another embodiment, D is H, OR*, or SR*. In another embodiment, D is H, OR*, or NO$_2$. In another embodiment, D is H, OR*, or N(R*)$_2$. In another embodiment, D is OR*, SR*, or NO$_2$. In another embodiment, D is OR*, SR*, or N(R*)$_2$. In another embodiment, D is SR*, NO$_2$, or N(R*)$_2$. In another embodiment, D is H or*. In another embodiment, D is H or SR*. In another embodiment, D is H or NO$_2$. In another embodiment, D is H or N(R*)$_2$. In another embodiment, D is OR* or SR*. In another embodiment, D is OR* or NO$_2$. In another embodiment, D is OR* or N(R*)$_2$. In another embodiment, D is SR* or NO$_2$. In another embodiment, D is SR* or N(R*)$_2$. In another embodiment, D is NO$_2$ or N(R*)$_2$. In another embodiment, D is H. In another embodiment, D is OR*. In another embodiment, D is SR*. In another embodiment, D is NO$_2$. In another embodiment, D is N(R*)$_2$. In another embodiment, D is selected from

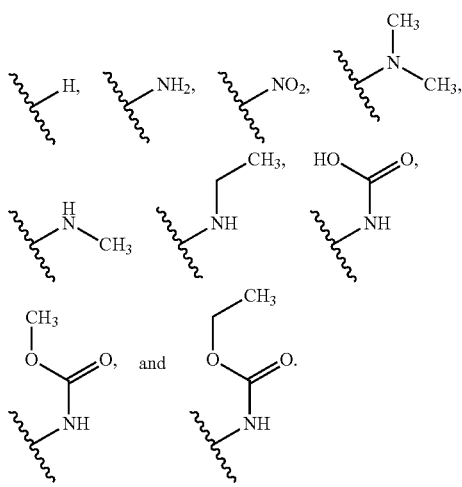

In another embodiment, D is H or —N(CH$_3$)$_2$. In another embodiment, D is —N(CH$_3$)$_2$.

In another embodiment, R* is, independently for each occurrence, H, (C$_1$-C$_6$)alkyl, (C$_2$-C$_6$)alkenyl, or (C$_2$-C$_6$)alkynyl each of which is unsubstituted or substituted with 1, 2, or 3 substituents independently selected from -halo, —CN, —NO$_2$, —N$_3$, —OH, —O(C$_1$-C$_6$)alkyl, —SH, —S(C$_1$-C$_6$)alkyl, —NH$_2$, —N(H)((C$_1$-C$_6$)alkyl), —N((C$_1$-C$_6$)alkyl)$_2$, =O, and =S. In another embodiment, R* is, independently for each occurrence, H or (C$_1$-C$_6$)alkyl unsubstituted or substituted with 1 or 2 substituents independently selected from —OH, —O(C$_1$-C$_6$)alkyl, and =O.

In another embodiment, each R$^2$ and R$^3$ is, independently for each occurrence:

(a) —H; or (b) -halo, —CN, or —NO$_2$; or (c) —X, —(C$_1$-C$_6$)alkyl-X, -(5- or 6-membered)heterocycle-X, or -(5- or 6-membered)heterocycle-(C$_1$-C$_6$)alkyl-X; or (d) —C(=Y)CN, —C(=Y)X, —C(=Y)T$^3$, —C(=Y)YX, —C(=Y)YT$^3$, —C(=Y)N(T$^1$)(T$^2$), —C(=Y)N(R$^9$)CN, —C(=Y)N(R$^9$)X, —C(=Y)N(R$^9$)CH$_2$CH$_2$N(T$^1$)(T$^2$), —C(=Y)N(R$^9$)YH, —C(=Y)N(R$^9$)YX, —C(=Y)N(R$^9$)YCH$_2$X, —C(=Y)N(R$^9$)YCH$_2$CH$_2$X, or —C(=Y)N(R$^9$)S(=O)$_2$T$^3$; or (e) —N(R$^9$)X, —N(R$^9$)—CH$_2$X, —N(R$^9$)—CH$_2$CH$_2$X, —N(R$^9$)—CH$_2$CH$_2$N(R$^9$)X, —N(R$^9$)CH$_2$CH$_2$N(T$^1$)(T$^2$), —N(R$^9$)CH$_2$C(=Y)X, —N((C$_1$-C$_6$)alkyl-C(=O)OR$^9$)$_2$, —N(R$^9$)CH$_2$N(R$^9$)C(=N(R$^{12}$))N(R$^{12}$)$_2$, —N(R$^9$))—CH$_2$CH$_2$N(R$^9$)C(=N(R$^{12}$))N(R$^{12}$)$_2$, —N(T$^1$)(T$^2$), —N(T$^3$)C(=Y)T$^3$, —N(T$^3$)C(=Y)YT$^3$, —N(T$^3$)C(=Y)N(T$^1$)(T$^2$), —N(T$^3$)S(=O)$_2$T$^3$, or —N(T$^3$)S(=O)$_2$N(T$^1$)(T$^2$); or (f) —YH, —CH$_2$YH, —CH$_2$CH$_2$YH, —YX, or —YT$^3$; or (g) —S(=O)T$^3$, —S(=O)$_2$T$^3$, —S(=O)N(T$^1$)(T$^2$), —S(=O)$_2$N(T$^1$)(T$^2$), —S(=O)X, or —S(=O)$_2$X.

In another embodiment, R$^2$ is, independently for each occurrence, H, -halo, —NO$_2$, —X, —C(=Y)YX, —N(T$^1$)(T$^2$), —YH, or —YX. In another embodiment, R$^2$ is H. In another embodiment, R$^2$ is -halo. In another embodiment, R$^2$ is —NO$_2$. In another embodiment, R$^2$ is —X. In another embodiment, R$^2$ is —C(=Y)YX. In another embodiment, R$^2$ is —N(T$^1$)(T$^2$). In another embodiment, R$^2$ is —YH. In another embodiment, R$^2$ is —YX. In another embodiment, each R$^2$ is independently selected from

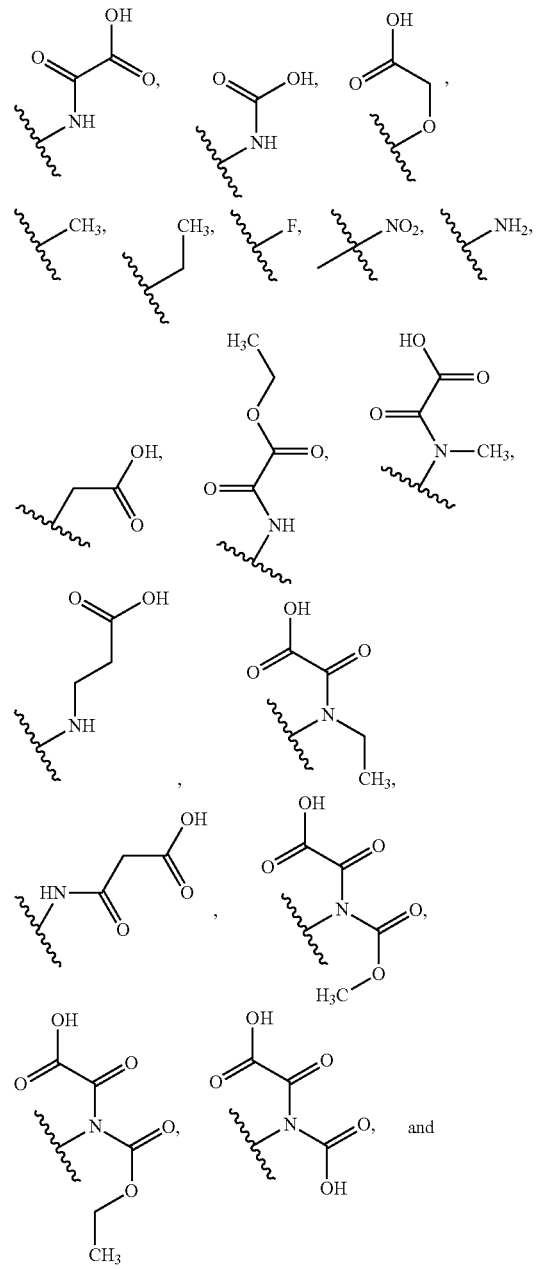

-continued

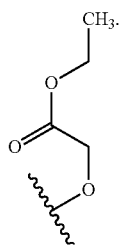

In another embodiment, each R² is independently selected from

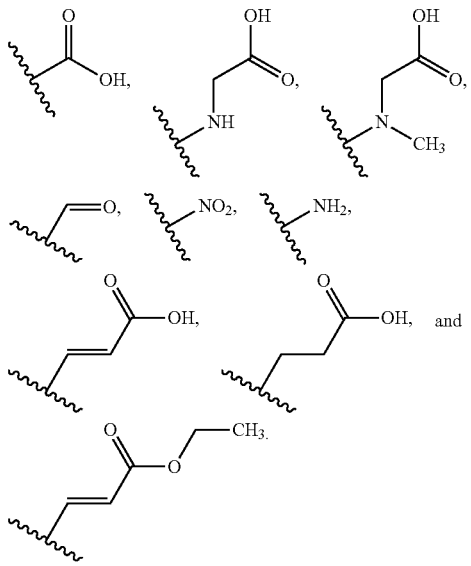

In another embodiment, each R² is independently selected from

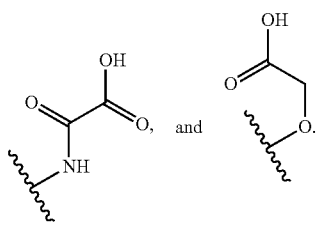 [SMILES: *NC(=O)C(=O)O ; *OCC(=O)O]

In another embodiment, R² is selected from

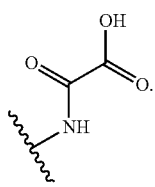 [SMILES: *NC(=O)C(=O)O]

In another embodiment, each R² is independently selected from

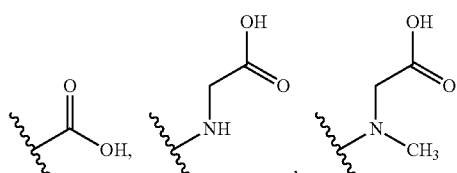

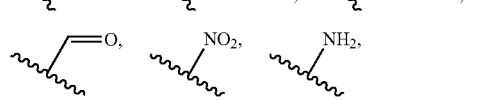

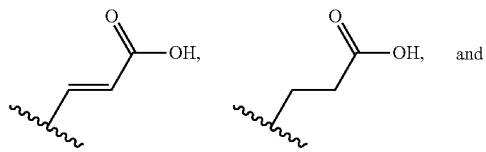

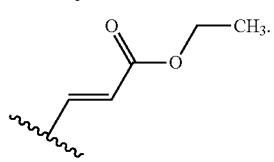

In another embodiment, each R² is independently selected from

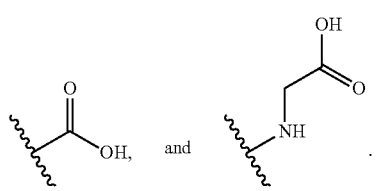

In another embodiment, R² is not NO₂. In another embodiment, R² is not NH₂. In another embodiment, R² is not a BOC protected amine. In another embodiment, R² is not an amine. In another embodiment, when Q¹ is phenyl, each R², if present, is not ortho to the 4-amino nitrogen of the Substituted Piperidin-4-Amino-type Compound. In another embodiment, when Q¹ is phenyl, each R², if present, is meta or para to the 4-amino nitrogen of the Substituted Piperidin-4-Amino-type Compound. In another embodiment, when Q¹ is phenyl, Q¹-(R²)ₐ is selected from

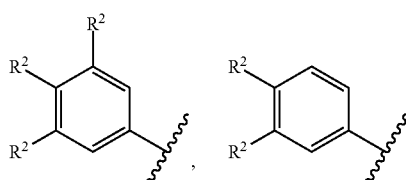

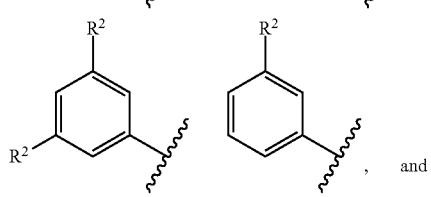

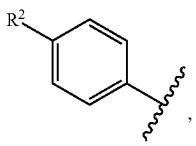

where each $R^2$ is independently selected and defined as above.

In another embodiment, each $R^3$ is independently selected from H, -halo, —$NO_2$, —X, —C(=Y)YX, —N($T^1$)($T^2$), —YH, or —YX. In another embodiment, $R^3$ is H. In another embodiment, $R^3$ is -halo. In another embodiment, $R^3$ is not -halo.

In another embodiment, $R^3$ is —$NO_2$. In another embodiment, $R^3$ is —X. In another embodiment, $R^3$ is —C(=Y)YX. In another embodiment, $R^3$ is —N($T^1$)($T^2$). In another embodiment, $R^3$ is —YH. In another embodiment, $R^3$ is —YX. In another embodiment, $R^3$ is H, ($C_1$-$C_6$)alkyl, halo, —C(=O)OH, —C(=O)O($C_1$-$C_6$alkyl), or tetrazolyl. In another embodiment, $R^3$ is ($C_1$-$C_6$)alkyl. In another embodiment, $R^3$ is —C(=O)OH. In another embodiment, $R^3$ is —C(=O)O($C_1$-$C_6$alkyl). In another embodiment, $R^3$ is tetrazolyl. In another embodiment, each $R^3$ is independently selected from

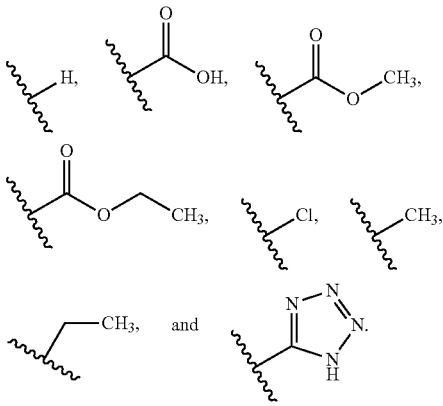

In another embodiment, each $R^3$ is independently selected from

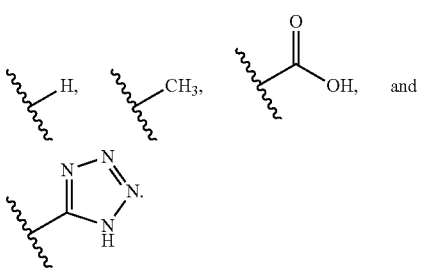

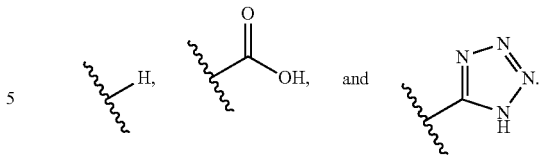

In another embodiment, each $R^3$ is independently selected from H and $CH_3$. In another embodiment, $R^3$ is H. In another embodiment, $R^3$ is $CH_3$.

In another embodiment, X is, independently for each occurrence:

(a) —H, —($C_1$-$C_6$)alkyl, —($C_2$-$C_6$)alkenyl, —($C_2$-$C_6$)alkynyl, —($C_1$-$C_6$)alkoxy, ($C_3$-$C_7$)cycloalkyl, ($C_6$-$C_{14}$)bicycloalkyl, —($C_8$-$C_{20}$)tricycloalkyl, —($C_5$-$C_{10}$)cycloalkenyl, ($C_7$-$C_{14}$)bicycloalkenyl, —($C_8$-$C_{20}$)tricycloalkenyl, (5- or 6-membered)heterocycle, or -(7- to 10-membered)bicycloheterocycle, each of which is unsubstituted or substituted with 1, 2 or 3 independently selected $R^8$ groups; or (b) phenyl, -benzyl, -naphthalenyl, —($C_{14}$)aryl, —($C_1$-$C_6$)alkyl-(5- or 6-membered)heteroaryl or -(5- or 6-membered)heteroaryl, each of which is unsubstituted or substituted with 1, 2 or 3 independently selected $R^7$ groups.

In another embodiment, $Q^1$ is phenyl and $E^1$ is a direct bond. In another embodiment, $Q^1$ is phenyl and $E^1$ is $CH_2$. In another embodiment, $Q^1$ is phenyl, $E^1$ is a direct bond, and $E^2$ is C(=O). In another embodiment, $Q^1$ is phenyl, $E^1$ is $CH_2$, and $E^2$ is C(=O). In another embodiment, $Q^1$ is phenyl, $E^1$ is a direct bond, $E^2$ is C(=O), and $Q^2$ is pyrrolidinyl. In another embodiment, $Q^1$ is phenyl, $E^1$ is $CH_2$, $E^2$ is C(=O), and $Q^2$ is pyrrolidinyl. In another embodiment, $Q^1$ is phenyl, $E^1$ is a direct bond, $E^2$ is C(=O), $Q^2$ is pyrrolidinyl, and $R^3$ is C(=O)OH or tetrazoyl). In another embodiment, $Q^1$ is phenyl, $E^1$ is $CH_2$, $E^2$ is C(=O), $Q^2$ is pyrrolidinyl, and $R^3$ is C(=O)OH or tetrazolyl.

In another embodiment, X is, independently for each occurrence, —H, —($C_1$-$C_6$)alkyl, —($C_2$-$C_6$)alkenyl, or -(5- or 6-membered)heterocycle, each of which is unsubstituted or substituted with 1 or 2 independently selected $R^8$ groups. In another embodiment, X is H. In another embodiment, X is —($C_1$-$C_6$)alkyl, unsubstituted or substituted with 1 or 2 independently selected $R^8$ groups. In another embodiment, X is —($C_2$-$C_6$)alkenyl unsubstituted or substituted with 1 or 2 independently selected $R^8$ groups. In another embodiment, X is -(5- or 6-membered)heterocycle unsubstituted or substituted with 1 or 2 independently selected $R^8$ groups. In another embodiment, each X is, independently for each occurrence, H, ($C_1$-$C_6$)alkyl, or ($C_2$-$C_6$)alkenyl unsubstituted or substituted with 1 or 2 substituents independently selected from —OH, —C(=O)OH, —C(=O)O($C_1$-$C_6$)alkyl, —O($C_1$-$C_6$ alkyl), and =O. In another embodiment, X is, independently for each occurrence, —H, —($C_1$-$C_6$) alkyl, —($C_2$-$C_6$)alkenyl, —($C_2$-$C_6$)alkynyl, —($C_1$-$C_6$) alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R^8$ groups.

In another embodiment, each $R^1$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O) $OR^9$, —N($R^9$)($C_1$-$C_6$)alkyl-C(=O)$OR^9$, —$OR^9$, —$SR^9$, —C(halo)$_3$, —CH(halo)$_2$, —$CH_2$(halo), —CN, =O, =S, -halo, —$NO_2$, —CH=N($R^9$), —N($R^9$)$_2$, —N($R^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —S(=O)R$^9$, and —S(=O)$_2$R$^9$. In another embodiment, each R$^5$ is independently selected from —(C$_1$-C$_4$)alkyl, —(C$_2$-C$_6$)alkenyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), =O, =S, -halo, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —S(=O)R$^9$, and —S(=O)$_2$R$^9$. In another embodiment, each R$^5$ is independently selected from —(C$_1$-C$_4$)alkyl, —(C$_2$-C$_6$)alkenyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —CH=N(R$^9$), —N(R$^9$)$_2$, —N(R$^9$)OH, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, -(5- or 6-membered)heteroaryl), —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, —(C$_1$-C$_6$)alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, and —C(=O)OR$^9$. In another embodiment, each R$^5$ is independently OR$^9$ or =O. In another embodiment, R$^5$ is OR$^9$. In another embodiment, R$^5$ is =O.

In another embodiment, each R$^7$ is independently selected from —(C$_1$-C$_4$)alkyl, —OR$^9$, —SR$^9$, —C(halo)$_3$, —CH(halo)$_2$, —CH$_2$(halo), -halo, —N(R$^9$)$_2$, —N(R$^9$)C(=O)OR$^{12}$, —C(=O)OR$^9$, and —OC(=O)R$^9$. In another embodiment, each R$^7$ is independently selected from —(C$_1$-C$_4$)alkyl, —OR$^9$, —C(halo)$_3$, —CH(halo)$_2$, —CH$_2$(halo), -halo, —N(R$^9$)$_2$, —C(=O)OR$^9$, and —OC(=O)R$^9$. In another embodiment, each R$^7$ is independently selected from —(C$_1$-C$_4$)alkyl, —OR$^9$, —C(halo)$_3$, -halo, —N(R$^9$)$_2$, and —C(=O)OR$^9$.

In another embodiment, each R$^8$ is independently selected from —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —S(=O)R$^9$, and —S(=O)$_2$R$^9$. In another embodiment, each R$^8$ is independently selected from —(C$_1$-C$_4$)alkyl, —(C$_1$-C$_6$)alkenyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), =O, =S, -halo, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each R$^8$ is independently selected from —(C$_1$-C$_4$)alkyl, —(C$_2$-C$_6$)alkenyl), -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —CH=N(R$^9$), —N(R$^9$)$_2$, —N(R$^9$)OH, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(O)N(T$^1$)(T$^2$), —C(=O)OR$^9$, —OC(=O)R$^9$, and —S(=O)$_2$R$^9$. In another embodiment, each R$^8$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each R$^8$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each R$^8$ is independently selected from —(C$_1$-C$_4$)alkyl, —(C$_1$-C$_6$)alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, —C(=O)N(T$^1$)(T$^2$), and —C(O)OR$^9$. In another embodiment, each R$^8$ is independently —OR$^9$, =O, or —C(=O)OR$^9$. In another embodiment, R$^8$ is —OR$^9$. In another embodiment, R$^8$ is =O. In another embodiment, R$^8$ is independently —C(=O)OR$^9$.

In another embodiment, each R$^9$ is independently —H, —(C$_1$-C$_6$)alkyl, —(C$_2$-C$_6$)alkenyl, —(C$_3$-C$_8$)cycloalkyl, -phenyl, -benzyl, -(3- to 7-membered)heterocycle, —C(halo)$_3$, —CH(halo)$_2$, or —CH$_2$(halo). In another embodiment, each R$^9$ is independently —H, —(C$_1$-C$_6$)alkyl, —(C$_3$-C$_8$)cycloalkyl, -phenyl, -benzyl, -(3- to 7-membered)heterocycle, —C(halo)$_3$, —CH(halo)$_2$, or —CH$_2$(halo). In another embodiment, each R$^9$ is independently —H, —(C$_1$-C$_6$)alkyl, —C(halo)$_3$, —CH(halo)$_2$, or —CH$_2$(halo). In another embodiment, each R$^9$ is independently —H or —(C$_1$-C$_3$)alkyl. In another embodiment, each R$^9$ is independently —H or —(C$_1$-C$_6$)alkyl. In another embodiment, R$^9$ is —H. In another embodiment, R$^9$ is —(C$_1$-C$_6$)alkyl.

In another embodiment, a is 0. In another embodiment, a is 1.

In another embodiment, b is 0. In another embodiment, b is 1.

In another embodiment, n is 0. In another embodiment, n is 1.

In another embodiment, x is 0. In another embodiment, x is 1.

In another embodiment, each T$^1$ and T$^2$ is independently —H or —(C$_1$-C$_{10}$)alkyl which is unsubstituted or substituted with 1, 2, or 3 independently selected R$^5$ groups. In another embodiment, each T$^1$ and T$^2$ is —H. In another embodiment, each T$^1$ and T$^2$ is —(C$_1$-C$_{10}$)alkyl which is unsubstituted or substituted with 1, 2, or 3 independently selected R$^5$ groups. In another embodiment, each T$^1$ and T$^2$ is independently —H or —(C$_1$-C$_3$)alkyl which is unsubstituted or substituted with an independently selected R$^5$ group. In another embodiment, each T$^1$ and T$^2$ is independently —H or —(C$_1$-C$_3$)alkyl which is unsubstituted. In another embodiment, each T$^1$ and T$^2$ is independently —H or —CH$_3$. In another embodiment, each T$^3$ is independently —H or —(C$_1$-C$_3$)alkyl which is unsubstituted or substituted with an independently selected R$^5$ group. In another embodiment, each $T^3$ is independently —H or —($C_1$-$C_3$)alkyl which is unsubstituted. In another embodiment, each $T^3$ is independently —H or —$CH_3$.

In another embodiment, $R^{11}$ is —H, —CN, or —C(=O)N($R^6$)$_2$ or $R^{11}$ is —($C_1$-$C_4$)alkyl which is unsubstituted or substituted with —OH, —($C_1$-$C_4$)alkoxy, or —N($R^6$)$_2$. In another embodiment, $R^{11}$ is —H or —($C_1$-$C_4$)alkyl which is unsubstituted or substituted with —OH, —($C_1$-$C_4$)alkoxy, or —N($R^6$)$_2$. In another embodiment, $R^{11}$ is —H. In another embodiment, $R^{11}$ is not —C(=O)OH. In another embodiment, $R^{14}$ is —H. In another embodiment, $R^{14}$ is not —C(=O)OH. In another embodiment, $R^{11}$ is —H and $R^{14}$ is —H. In another embodiment, $R^{11}$ is not —C(=O)OH and $R^{14}$ is not —C(=O)OH.

In another embodiment, h is 0. In another embodiment, h is 1. In another embodiment, h is 1 and $R^{13}$ is absent. In another embodiment, h is 0 and $R^{11}$ is —H. In another embodiment, h is 1 and $R^{11}$ is —H. In another embodiment, h is 0 or 1 and Z is —($C_1$-$C_{10}$)alkyl unsubstituted by $R^{13}$, i.e., Z is —[($C_1$-$C_{10}$)alkyl]$_h$.

In another embodiment, h is 1 and Z is —($C_1$-$C_3$)alkyl optionally substituted by $R^{13}$. In another embodiment, h is 1, $R^{13}$ is absent, and Z is —$CH_2$—. In another embodiment, h is 1, $R^{13}$ is absent, and Z is —$CH_2$—$CH_2$—. In another embodiment, h is 1, $R^{13}$ is absent and Z is —$CH_2$—$CH_2$—$CH_2$—. In another embodiment, h is 1, Z is —($C_1$-$C_3$)alkyl-, $R^1$ is phenyl, and the Z group (i.e., —($C_1$-$C_3$)alkyl-) is substituted by $R^{13}$. In another embodiment, h is 1, Z is a —($C_1$-$C_3$)alkyl-, $R^1$ is optionally-substituted phenyl, and the Z group is substituted by $R^{13}$ which is optionally-substituted phenyl. In another embodiment, h is 1, Z is a —($C_1$-$C_3$)alkyl-, $R^1$ is unsubstituted phenyl, and the Z group is substituted by $R^{13}$ which is unsubstituted phenyl. In another embodiment, h is 1, Z is a —($C_1$-$C_3$)alkyl-, and the Z group is substituted by $R^{13}$ which is —$CF_3$. In another embodiment, h is 1 and Z—$R^{13}$ is —$CH_2$—CH($CF_3$)—$CH_2$—.

In another embodiment, $R^1$ is —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, -(3- to 7-membered)heterocycle, or -(7- to 10-membered)bicycloheterocycle, each of which is unsubstituted or substituted with 1, 2, 3, or 4 independently selected $R^8$ groups.

In another embodiment, Z is —($C_2$-$C_{10}$)alkenyl-. In another embodiment, Z is —($C_2$-$C_6$)alkenyl-. In another embodiment, Z is —$CH_2$—CH=CH—. In another embodiment, Z is —$CH_2$—CH=CH—$CH_2$—. In another embodiment, Z is a —($C_3$)alkenyl-. In another embodiment, Z is n-prop-1,3-diyl and $R^1$ is an optionally substituted —($C_6$-$C_{14}$)bicycloalkyl or optionally substituted —($C_8$-$C_{20}$)tricycloalkyl. In another embodiment, Z—$R^1$ is —$CH_2$—CH=$R_1$. In another embodiment, Z—$R^1$ is —$CH_2$—$CH_2$—CH=$R_1$ or —CH($CH_3$)—CH=$R_1$ where $R^1$ is —($C_6$-$C_{14}$)bicycloalkyl or —($C_8$-$C_{20}$)tricycloalkyl, each of which is optionally substituted. In another embodiment, h is 1, and Z—$R^1$ is

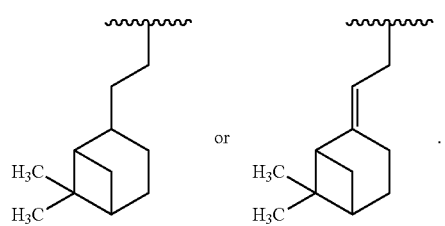 [SMILES: *CCC1CCC2CC1C2(C)C ; *C/C=C1\CCC2CC1C2(C)C]

In another embodiment, Y is O. In another embodiment, Y is S.

In another embodiment, Z is —$CH_2$—NH—C(=O)—. In another embodiment, Z is —$CH_2$—$CH_2$—NH—C(=O)—. In another embodiment, Z is —$CH_2$—NH—C(=S)—. In another embodiment, Z is —$CH_2$—$CH_2$—NH—C(=S)—. In another embodiment, Z is —$CH_2$—N($CH_3$)—C(=O)—. In another embodiment, Z is —$CH_2$—$CH_2$—N($CH_3$)—C(=O)—. In another embodiment, Z is —$CH_2$—N($CH_3$)—C(=S)—. In another embodiment, Z is —$CH_2$—$CH_2$—N($CH_3$)—C(=S)—.

In another embodiment, $R^1$ is selected from:
(a) -halo, —CN, —OH, —$CH_2$OH, —$CH_2CH_2$OH, —$NO_2$, —N($R^6$)$_2$, —S(=O)$NH_2$, —S(=O)$_2NH_2$, —C(=O)O$V^1$, and —C(=O)CN; and
(b) —($C_1$-$C_{10}$)alkyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c) -phenyl, -naphthalenyl, —($C_{14}$)aryl, and -(5- to 10-membered)heteroaryl, each of which is unsubstituted or substituted with 1, 2, or 3 independently selected $R^7$ groups.

In another embodiment, $R^1$ is selected from:
(a) -halo, —CN, —OH, —$CH_2$OH, —$CH_2CH_2$OH, —$NO_2$, —N($R^6$)$_2$, —S(=O)$NH_2$, —S(=O)$_2NH_2$, —C(=O)O$V^1$, and —C(=O)CN; and
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c)

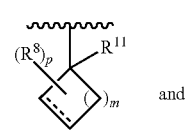 (i)

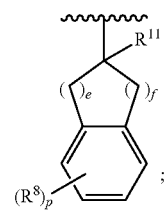 (ii)

and
(d) -phenyl, -naphthalenyl, —($C_{14}$)aryl, and -(5- to 10-membered)heteroaryl, each of which is unsubstituted or substituted with 1, 2, or 3 independently selected $R^7$ groups.

In another embodiment, $R^1$ is selected from:
(a) -halo, —CN, —OH, —$CH_2$OH, —$CH_2CH_2$OH, —$NO_2$, —N($R^6$)$_2$, —S(=O)$NH_2$, —S(=O)$_2NH_2$, —C(=O)O$V^1$, and —C(=O)CN; and
(b) —($C_1$-$C_{10}$)alkyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

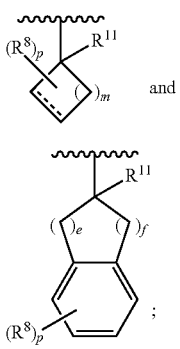

(i)

and (ii)

and (d) -phenyl and -(5- to (10-membered)heteroaryl, each of which is unsubstituted or substituted with 1, 2, or 3 independently selected R$^7$ groups.

In another embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_3$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_4$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, and —(C$_8$-C$_{20}$)tricycloalkenyl, each of which is unsubstituted or substituted with 1, 2, 3, or 4 independently selected R$^8$ groups; and (c)

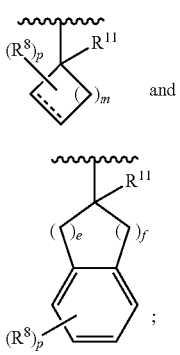

(i)

and (ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups; and wherein m is an integer selected from 1, 2, 3, 4, 5, 6, 7, 8, 9, 10, and 11.

In another embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, and —C(=O)CN; and (b) —(C$_3$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_4$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, and —(C$_8$-C$_{20}$)tricycloalkenyl, each of which is unsubstituted or substituted with 1, 2, 3, or 4 independently selected R$^8$ groups; wherein the and (c)

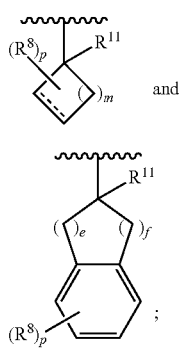

(i)

and (ii)

and (d) -naphthalenyl, —(C$_{14}$)aryl, and -(5- to 10-membered) heteroaryl, each of which is unsubstituted or substituted with 1, 2, 3, or 4 independently selected R$^7$ groups;

wherein each V$^1$ is independently —H, —(C$_1$-C$_6$)alkyl, —(C$_3$-C$_7$)cycloalkyl, -phenyl, or -benzyl.

and wherein the —(C$_1$-C$_6$)alkyl with the definition of V$^1$ is not tert-butyl; and m is an integer selected from 1, 2, 3, 4, 5, 6, 7, 8, 9, 10, and 11.

In another embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

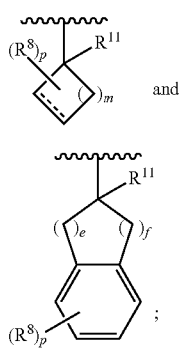

(i)

and (ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups.

In one embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_3$-C$_{10}$)alkenyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_4$-C$_{12}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

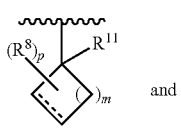
(i)

and

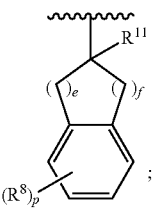
(ii)

and (d) -naphthalenyl, —(C$_{14}$)aryl, and -(5- to 10-membered) heteroaryl, each of which is unsubstituted or substituted with 1, 2, 3, or 4 independently selected R$^7$ groups; and wherein m is an integer selected from 1, 2, 3, 4, 5, 6, 7, 8, 9, 10, and 11.

In another embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, and —(C$_8$-C$_{20}$)tricycloalkenyl, each of which is unsubstituted or substituted with 1, 2, 3, or 4 independently selected R$^8$ groups; and (c)

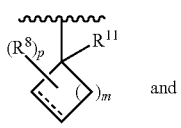
(i)

and

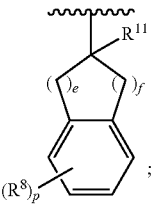
(ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups; and wherein each V$^1$ is independently —H, —(C$_1$-C$_6$)alkyl, —(C$_3$-C$_7$)cycloalkyl, -phenyl, or -benzyl, wherein the —(C$_1$-C$_6$)alkyl group in the definition of V$^1$ is not tert-butyl.

In another embodiment, R$^1$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

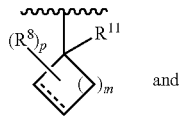
(i)

and

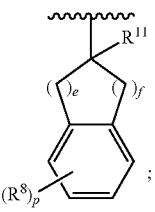
(ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

In another embodiment, m is 1, 2, 3, 4, 5, 6, 7, 8, or 9. In another embodiment, m is 2, 3, 4, 5, 6, 7, or 8. In another embodiment, m is 2, 3, 4, 5, 6, or 7. In another embodiment, m is 2, 3, 4, 5, or 6. In another embodiment, m is 2, 3, 4, or 5. In another embodiment, m is 2. In another embodiment, m is 3. In another embodiment, m is 4. In another embodiment, m is 5. In another embodiment, m is 6. In another embodiment, m is 7.

In another embodiment, c is 2, 3, 4, 5, 6, 7, or 8. In another embodiment, c is 2, 3, 4, 5, 6, or 7. In another embodiment, c is 2, 3, 4, 5, or 6. In another embodiment, c is 2, 3, 4, or 5. In another embodiment, c is 2. In another embodiment, c is 3. In another embodiment, c is 4. In another embodiment, c is 5. In another embodiment, c is 6. In another embodiment, c is 7.

In another embodiment, m is 1, 2, 3, 4, 5, 6, 7, 8, or 9 and c is 2, 3, 4, 5, 6, 7, or 8. In another embodiment, m is 2, 3, 4, 5, 6, 7, or 8 and c is 2, 3, 4, 5, 6, 7, or 8. In another embodiment, m is 2, 3, 4, 5, 6, or 7 and c is 2, 3, 4, 5, 6, or 7. In another embodiment, m is 2, 3, 4, 5, or 6 and c is 2, 3, 4, 5, or 6. In another embodiment, m is 2, 3, 4, or 5 and c is 2, 3, 4, or 5. In another embodiment, m=c. In another embodiment, m and c are each 2. In another embodiment, m and c are each 3. In another embodiment, m and c are each 4. In another embodiment, m and c are each 5. In another embodiment, m and c are each 6. In another embodiment, m and c are each 7.

In another embodiment, e is 0 and f is 0. In another embodiment, e is 0 and f is 1. In another embodiment, e is 1 and f is 0. In another embodiment, e is 1 and f is 1. In another embodiment, e is 1 and f is 2. In another embodiment, e is 2 and f is 1. In another embodiment, e is 2 and f is 2.

In another embodiment, p is 0, 1, 2, or 3. In another embodiment, p is 0, 1, or 2. In another embodiment, p is 1 or 2. In another embodiment, p is 2. In another embodiment, p is 1. In another embodiment, p is 0.

In another embodiment, $R^1$ is optionally substituted cyclooctyl. In another embodiment, $R^1$ is optionally substituted cyclooctenyl. In another embodiment, $R^1$ is optionally substituted anthryl.

In another embodiment, h is 0 and $R^1$ is optionally substituted cyclooctyl. In another embodiment, h is 0 and $R^1$ is optionally substituted cycloundecyl. In another embodiment, h is 0 and $R^1$ is optionally substituted cyclooctenyl. In another embodiment, h is 0 and $R^1$ is optionally substituted anthryl. In another embodiment, h is 0 and $R^1$ is optionally substituted —($C_6$-$C_{14}$)bicycloalkyl. In another embodiment, h is 0 and $R^1$ is optionally substituted bicyclo[3.3.1]nonyl. In another embodiment, h is 0 and $R^1$ is optionally substituted bicyclo[2.2.1.]heptyl. In another embodiment, h is 0 and $R^1$ is optionally substituted —($C_8$-$C_{20}$)tricycloalkyl. In another embodiment, h is 0 and $R^1$ is optionally substituted adamantyl. In another embodiment, h is 0 and $R^1$ is optionally substituted noradamantyl.

In another embodiment, —Z—$R^1$ is:

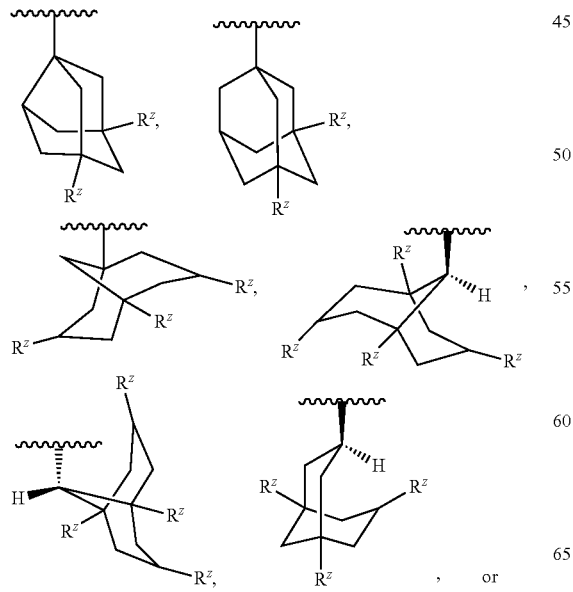

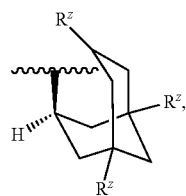

where each $R^z$ is independently —H, —($C_1$-$C_4$)alkyl, —OH, or —CN and preferably each $R^z$ is independently —H, —$CH_3$, or —$CH_2CH_3$. In another embodiment, —Z—$R^1$ is:

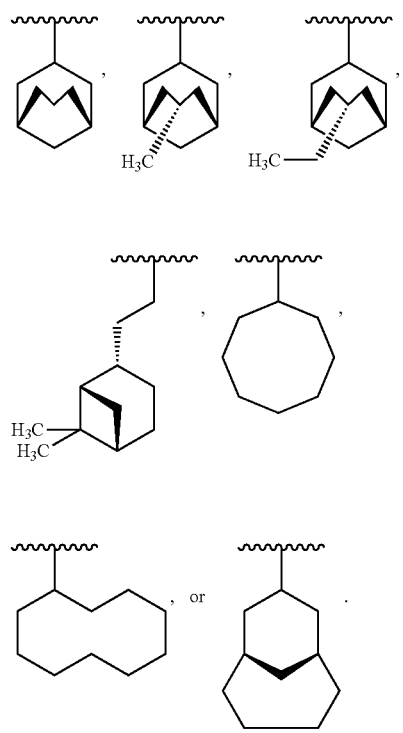

In another embodiment, —Z—$R^1$ is:

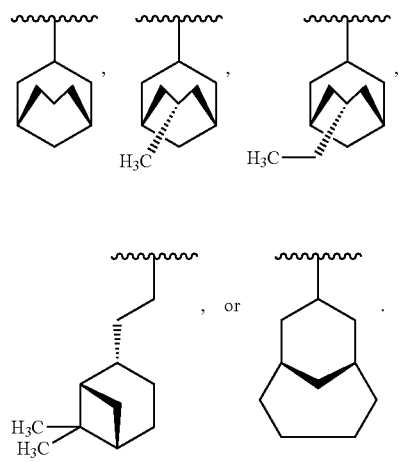

In another embodiment, —Z—R$^1$ is:

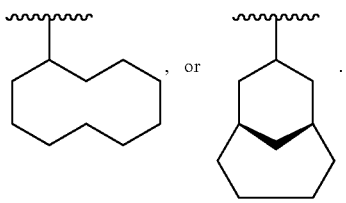 [SMILES: *C1CCCCCCCCC1 ; *C1C[C@H]2CCCC[C@@H](C1)C2]

In another embodiment, —Z—R$^1$ is:

where R$^z$ is —H, —CH$_3$, or —CH$_2$CH$_3$.

In another embodiment, A-B together form a (C$_2$-C$_6$) bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge.

In another embodiment, A-B together form a (C$_2$)bridge which bridge is substituted or unsubstituted. In another embodiment, A-B together form a (C$_2$)bridge which bridge is unsubstituted. In another embodiment, A-B together form a (C$_2$)bridge which bridge is substituted by one or two methyl groups. In another embodiment, A-B together form a (C$_3$)bridge which bridge is substituted or unsubstituted. In another embodiment, A-B together form a (C$_3$)bridge which bridge is unsubstituted. In another embodiment, A-B together form a (C$_3$)bridge which bridge is substituted by one or two methyl groups. In another embodiment, A-B together form a (C$_4$) bridge which bridge is substituted or unsubstituted. In another embodiment, A-B together form a (C$_4$) bridge which bridge is unsubstituted. In another embodiment, A-B together form a (C$_4$) bridge which bridge is substituted by one or two methyl groups. In another embodiment, A-B together form a (C$_5$)bridge which bridge is substituted or unsubstituted. In another embodiment, A-B together form a (C$_5$)bridge which bridge is unsubstituted. In another embodiment, A-B together form a (C$_5$)bridge which bridge is substituted by one or two methyl groups. In another embodiment, A-B together form a (C$_6$)bridge which bridge is substituted or unsubstituted. In another embodiment, A-B together form a (C$_6$)bridge which bridge is unsubstituted. In another embodiment, A-B together form a (C$_6$)bridge which bridge is substituted by one or two methyl groups.

In another embodiment, A-B together form a (C$_2$)bridge which bridge is —HC=CH— and is substituted or unsubstituted. In another embodiment, A-B together form a (C$_2$) bridge which bridge is —HC=CH— and is unsubstituted. In another embodiment, A-B together form a (C$_2$)bridge which is —HC=CH— and is substituted by one or two methyl groups. In another embodiment, A-B together form a (C$_3$)bridge which is —CH$_2$—HC=CH— or —HC=CH—CH$_2$— and is substituted or unsubstituted. In another embodiment, A-B together form a (C$_3$)bridge which is —CH$_2$—HC=CH— or —HC=CH—CH$_2$— and is unsubstituted. In another embodiment, A-B together form a (C$_3$)bridge which is —CH$_2$—HC=CH— or —HC=CH—CH$_2$— and is substituted by one or two methyl groups. In another embodiment, A-B together form a (C$_4$) bridge which is —CH$_2$—CH$_2$—HC=CH—, —CH$_2$—HC=CH—CH$_2$—, or —HC=CH—CH$_2$—CH$_2$— and is substituted or unsubstituted. In another embodiment, A-B together form a (C$_4$) bridge which is —CH$_2$—CH$_2$—HC=CH—, —CH$_2$—HC=C—CH$_2$—, or —HC=CH—CH$_2$—CH$_2$— and is unsubstituted. In another embodiment, A-B together form a (C$_4$) bridge which is —CH$_2$—CH$_2$—HC=CH—, —CH$_2$—HC=CH—CH$_2$—, or —HC=CH—CH$_2$—CH$_2$— and is substituted by one or two methyl groups.

In another embodiment, A-B together form a (C$_2$)bridge which is —CH$_2$—O—CH$_2$— and is substituted or unsubstituted. In another embodiment, A-B together form a (C$_2$) bridge which is —CH$_2$—O—CH$_2$— and is unsubstituted. In another embodiment, A-B together form a (C$_2$)bridge which is —CH$_2$—O—CH$_2$— and is substituted by one or two methyl groups. In another embodiment, A-B together form a (C$_3$)bridge which is —CH$_2$—O—CH$_2$—CH$_2$— or —CH$_2$—CH$_2$—O—CH$_2$— and is substituted or unsubstituted. In another embodiment, A-B together form a (C$_3$) bridge which is —CH$_2$—O—CH$_2$—CH$_2$— or —CH$_2$—CH$_2$—O—CH$_2$— and is unsubstituted. In another embodiment, A-B together form a (C$_3$)bridge which is —CH$_2$—O—CH$_2$—CH$_2$— or —CH$_2$—CH$_2$—O—CH$_2$— and is substituted by one or two methyl groups. In another embodiment, A-B together form a (C$_4$) bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted or unsubstituted. In another embodiment, A-B together form a (C$_4$) bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is unsubstituted. In another embodiment, A-B together form a (C$_4$) bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted by one or two methyl groups.

In another embodiment, A and B together form a bridge such that the bridged-piperidine is:

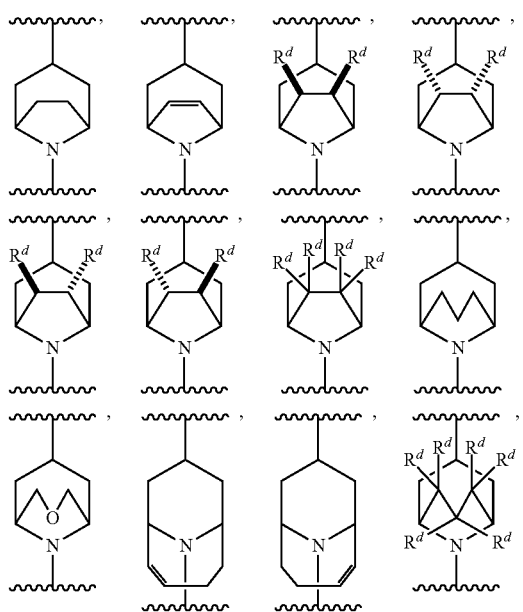

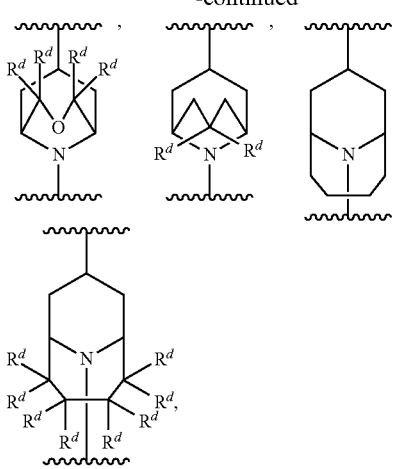

wherein each $R_d$ is independently —H, —($C_1$-$C_4$)alkyl, -halo, or —C(halo)$_3$.

In another embodiment, A and B together form a bridge such that the bridged-piperidine is:

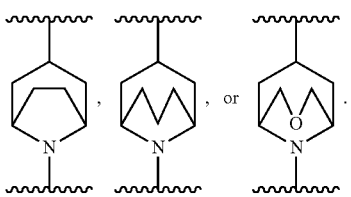

In another embodiment, A and B together form a bridge such that the bridged-piperidine is:

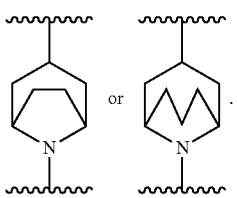

In another embodiment, the Substituted Piperidin-4-amino-Type Compound is in the form of a pharmaceutically acceptable salt. In another embodiment, the pharmaceutically acceptable salt is a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is a para-toluenesulfonic acid salt. In certain embodiments, the pharmaceutically acceptable salt includes two or more salt groups, such as two halide salt groups, and/or a combination of salt types, such as a chloride salt group and a bromide salt group. For example, in some embodiments, the pharmaceutically acceptable salt includes both a base addition salt group and an acid addition salt group. In certain embodiments, the pharmaceutically acceptable salt is a zwitterion.

In other embodiments, the Substituted Piperidin-4-amino-Type Compound has one of the formulae of Table 1.

TABLE 1

| Formula | Compound |
|---------|----------|
| IA | |
| IB | |
| IB$_1$ | |
| IB$_2$ | |
| IC | |

TABLE 1-continued

| Formula | Compound |
|---|---|
| IC₁ | 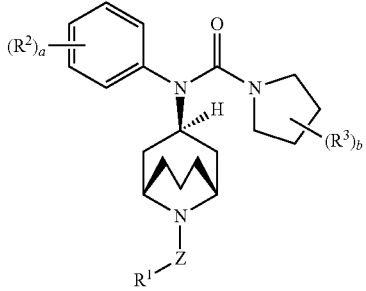 |
| IC₂ | 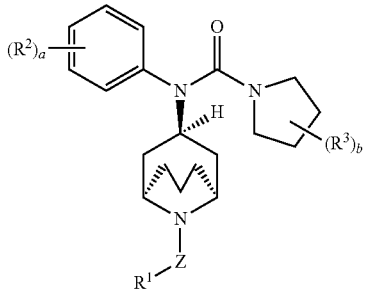 |
| ID | 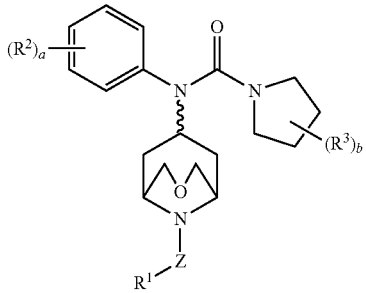 |
| ID₁ | 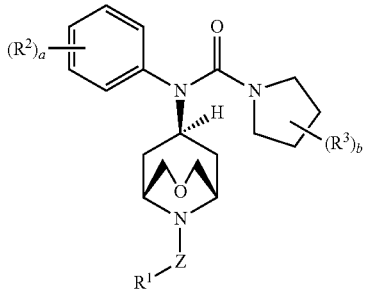 |
| ID₂ | 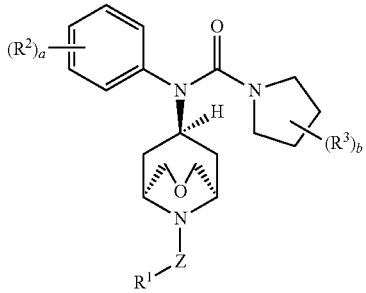 | where $R^1$, $R^2$, $R^3$, Z, A, B, a, and b are as defined above.

Illustrative Substituted Piperidin-4-amino-Type Compound are listed below in Tables 2-16.

TABLE 2

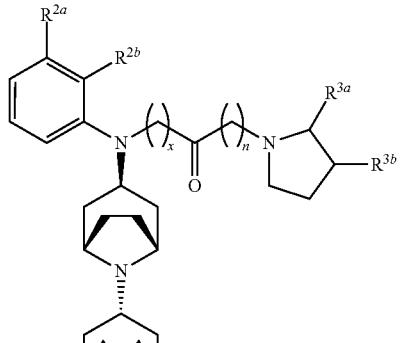 (a)

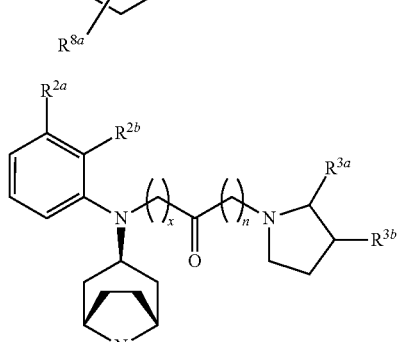 (b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| A1 a or b | H | H | 0 | 0 | H | H |
| A2 a or b | H | H | 1 | 0 | H | H |
| A3 a or b | H | H | 1 | 1 | H | H |
| A4 a or b | H | H | 0 | 1 | H | H |
| A5 a or b | N(H)C(=O)E³OH | H | 0 | 0 | H | H |
| A6 a or b | N(H)C((=O)E³OH | H | 1 | 0 | H | H |
| A7 a or b | N(H)C((=O)E³OH | H | 1 | 1 | H | H |
| A8 a or b | N(H)C((=O)E³OH | H | 0 | 1 | H | H |
| A9 a or b | OCH₂C(=O)OH | H | 0 | 0 | H | H |
| A10 a or b | OCH₂C(=O)OH | H | 1 | 0 | H | H |
| A11 a or b | OCH₂C(=O)OH | H | 1 | 1 | H | H |
| A12 a or b | OCH₂C(=O)OH | H | 0 | 1 | H | H |
| A13 a or b | H | N(H)C(=O)E³OH | 0 | 0 | H | H |
| A14 a or b | H | N(H)C(=O)E³OH | 1 | 0 | H | H |
| A15 a or b | H | N(H)C(=O)E³OH | 1 | 1 | H | H |

TABLE 2-continued

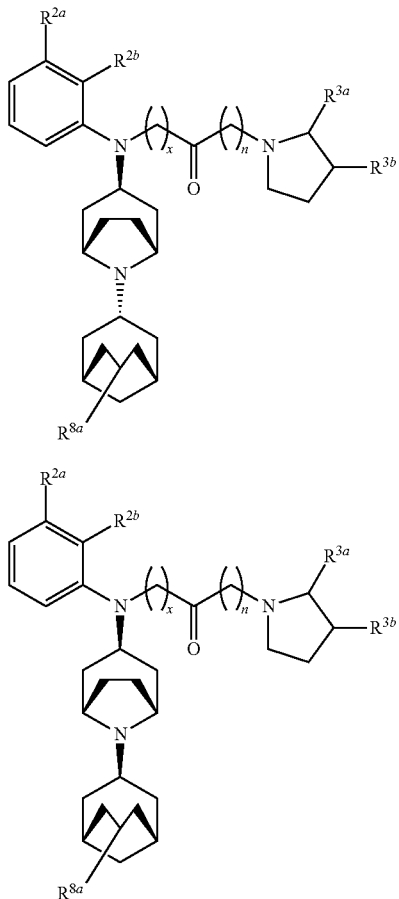

(a)

(b)

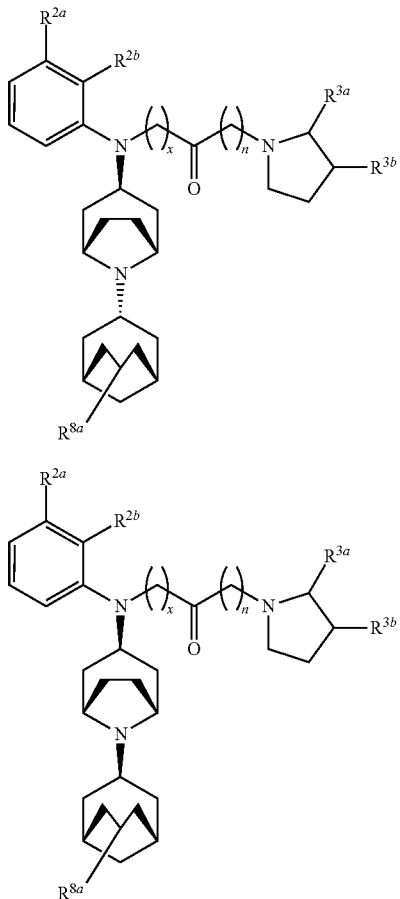

(a)

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| A16 a or b | H | $N(H)C(=O)E^3OH$ | 0 | 1 | H | H |
| A17 a or b | H | $OCH_2C(=O)OH$ | 0 | 0 | H | H |
| A18 a or b | H | $OCH_2C(=O)OH$ | 1 | 0 | H | H |
| A19 a or b | H | $OCH_2C(=O)OH$ | 1 | 1 | H | H |
| A20 a or b | H | $OCH_2C(=O)OH$ | 0 | 1 | H | H |
| A21 a or b | H | H | 0 | 0 | $C(=O)OH$ | H |
| A22 a or b | H | H | 1 | 0 | $C(=O)OH$ | H |
| A23 a or b | H | H | 1 | 1 | $C(=O)OH$ | H |
| A24 a or b | H | H | 0 | 1 | $C(=O)OH$ | H |
| A25 a or b | $N(H)C(=O)E^3OH$ | H | 0 | 0 | $C(=O)OH$ | H |
| A26 a or b | $N(H)C(=O)E^3OH$ | H | 1 | 0 | $C(=O)OH$ | H |
| A27 a or b | $N(H)C(=O)E^3OH$ | H | 1 | 1 | $C(=O)OH$ | H |
| A28 a or b | $N(H)C(=O)E^3OH$ | H | 0 | 1 | $C(=O)OH$ | H |
| A29 a or b | $OCH_2C(=O)OH$ | H | 0 | 0 | $C(=O)OH$ | H |
| A30 a or b | $OCH_2C(=O)OH$ | H | 1 | 0 | $C(=O)OH$ | H |
| A31 a or b | $OCH_2C(=O)OH$ | H | 1 | 1 | $C(=O)OH$ | H |
| A32 a or b | $OCH_2C(=O)OH$ | H | 0 | 1 | $C(=O)OH$ | H |
| A33 a or b | H | $N(H)C(=O)E^3OH$ | 0 | 0 | $C(=O)OH$ | H |
| A34 a or b | H | $N(H)C(=O)E^3OH$ | 1 | 0 | $C(=O)OH$ | H |
| A35 a or b | H | $N(H)C(=O)E^3OH$ | 1 | 1 | $C(=O)OH$ | H |
| A36 a or b | H | $N(H)C(=O)E^3OH$ | 0 | 1 | $C(=O)OH$ | H |
| A37 a or b | H | $OCH_2C(=O)OH$ | 0 | 0 | $C(=O)OH$ | H |
| A38 a or b | H | $OCH_2C(=O)OH$ | 1 | 0 | $C(=O)OH$ | H |
| A39 a or b | H | $OCH_2C(=O)OH$ | 1 | 1 | $C(=O)OH$ | H |
| A40 a or b | H | $OCH_2C(=O)OH$ | 0 | 1 | $C(=O)OH$ | H |
| A41 a or b | H | H | 0 | 0 | H | $C(=O)OH$ |
| A42 a or b | H | H | 1 | 0 | H | $C(=O)OH$ |
| A43 a or b | H | H | 1 | 1 | H | $C(=O)OH$ |
| A44 a or b | H | H | 0 | 1 | H | $C(=O)OH$ |
| A45 a or b | $N(H)C(=O)E^3OH$ | H | 0 | 0 | H | $C(=O)OH$ |

TABLE 2-continued

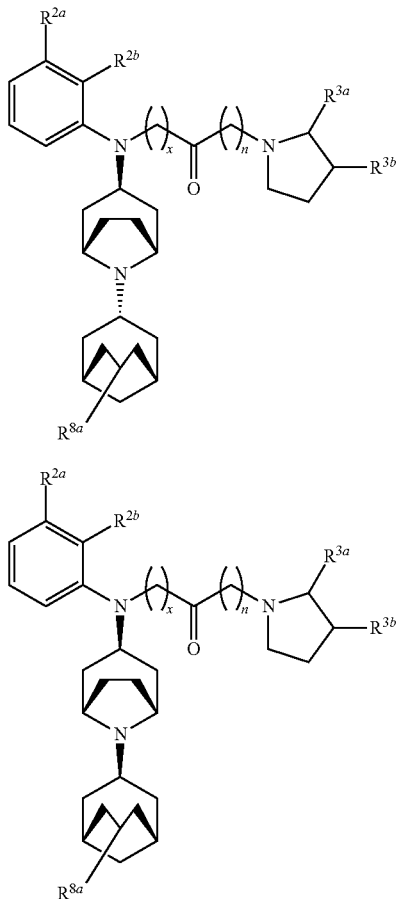

(a)

(b)

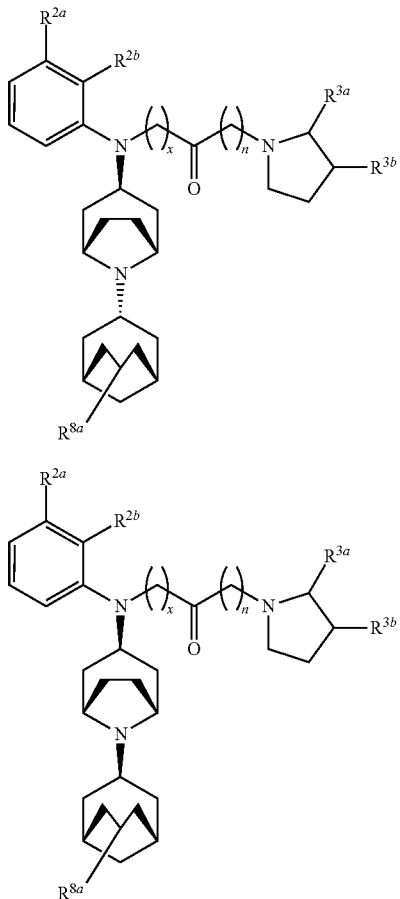

(a)

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| A46 a or b | $N(H)C(=O)E^3OH$ | H | 1 | 0 | H | $C(=O)OH$ |
| A47 a or b | $N(H)C(=O)E^3OH$ | H | 1 | 1 | H | $C(=O)OH$ |
| A48 a or b | $N(H)C(=O)E^3OH$ | H | 0 | 1 | H | $C(=O)OH$ |
| A49 a or b | $OCH_2C(=O)OH$ | H | 0 | 0 | H | $C(=O)OH$ |
| A50 a or b | $OCH_2C(=O)OH$ | H | 1 | 0 | H | $C(=O)OH$ |
| A51 a or b | $OCH_2C(=O)OH$ | H | 1 | 1 | H | $C(=O)OH$ |
| A52 a or b | $OCH_2C(=O)OH$ | H | 0 | 1 | H | $C(=O)OH$ |
| A53 a or b | H | $N(H)C(=O)E^3OH$ | 0 | 0 | H | $C(=O)OH$ |
| A54 a or b | H | $N(H)C(=O)E^3OH$ | 1 | 0 | H | $C(=O)OH$ |
| A55 a or b | H | $N(H)C(=O)E^3OH$ | 1 | 1 | H | $C(=O)OH$ |
| A56 a or b | H | $N(H)C(=O)E^3OH$ | 0 | 1 | H | $C(=O)OH$ |
| A57 a or b | H | $OCH_2C(=O)OH$ | 0 | 0 | H | $C(=O)OH$ |
| A58 a or b | H | $OCH_2C(=O)OH$ | 1 | 0 | H | $C(=O)OH$ |
| A59 a or b | H | $OCH_2C(=O)OH$ | 1 | 1 | H | $C(=O)OH$ |
| A60 a or b | H | $OCH_2C(=O)OH$ | 0 | 1 | H | $C(=O)OH$ |
| A61 a or b | H | H | 0 | 0 | tetrazolyl | H |
| A62 a or b | H | H | 1 | 0 | tetrazolyl | H |
| A63 a or b | H | H | 1 | 1 | tetrazolyl | H |
| A64 a or b | H | H | 0 | 1 | tetrazolyl | H |
| A65 a or b | $N(H)C(=O)E^3OH$ | H | 0 | 0 | tetrazolyl | H |
| A66 a or b | $N(H)C(=O)E^3OH$ | H | 1 | 0 | tetrazolyl | H |
| A67 a or b | $N(H)C(=O)E^3OH$ | H | 1 | 1 | tetrazolyl | H |
| A68 a or b | $N(H)C(=O)E^3OH$ | H | 0 | 1 | tetrazolyl | H |
| A69 a or b | $OCH_2C(=O)OH$ | H | 0 | 0 | tetrazolyl | H |
| A70 a or b | $OCH_2C(=O)OH$ | H | 1 | 0 | tetrazolyl | H |
| A71 a or b | $OCH_2C(=O)OH$ | H | 1 | 1 | tetrazolyl | H |
| A72 a or b | $OCH_2C(=O)OH$ | H | 0 | 1 | tetrazolyl | H |
| A73 a or b | H | $N(H)C(=O)E^3OH$ | 0 | 0 | tetrazolyl | H |
| A74 a or b | H | $N(H)C(=O)E^3OH$ | 1 | 0 | tetrazolyl | H |
| A75 a or b | H | $N(H)C(=O)E^3OH$ | 1 | 1 | tetrazolyl | H |

TABLE 2-continued

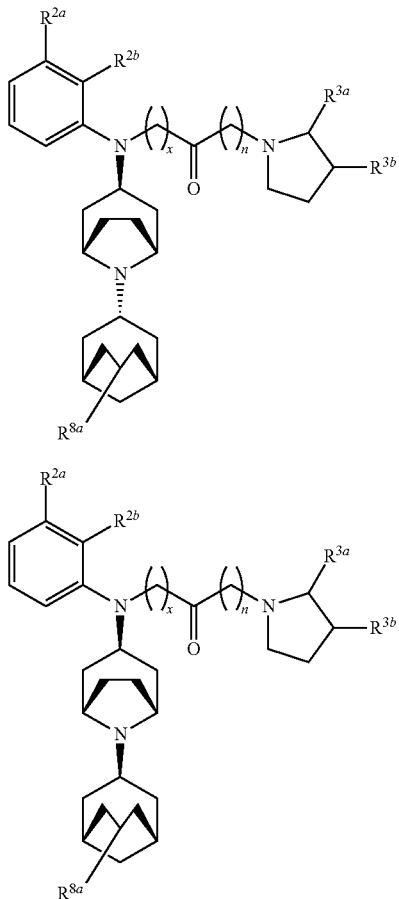

(a)

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| A76 a or b | H | N(H)C(=O)E³OH | 0 | 1 | tetrazolyl | H |
| A77 a or b | H | OCH₂C(=O)OH | 0 | 0 | tetrazolyl | H |
| A78 a or b | H | OCH₂C(=O)OH | 1 | 0 | tetrazolyl | H |
| A79 a or b | H | OCH₂C(=O)OH | 1 | 1 | tetrazolyl | H |
| A80 a or b | H | OCH₂C(=O)OH | 0 | 1 | tetrazolyl | H |
| A81 a or b | H | H | 0 | 0 | H | tetrazolyl |
| A82 a or b | H | H | 1 | 0 | H | tetrazolyl |
| A83 a or b | H | H | 1 | 1 | H | tetrazolyl |
| A84 a or b | H | H | 0 | 1 | H | tetrazolyl |
| A85 a or b | N(H)C(=O)E³OH | H | 0 | 0 | H | tetrazolyl |
| A86 a or b | N(H)C(=O)E³OH | H | 1 | 0 | H | tetrazolyl |
| A87 a or b | N(H)C(=O)E³OH | H | 1 | 1 | H | tetrazolyl |
| A88 a or b | N(H)C(=O)E³OH | H | 0 | 1 | H | tetrazolyl |
| A89 a or b | OCH₂C(=O)OH | H | 0 | 0 | H | tetrazolyl |
| A90 a or b | OCH₂C(=O)OH | H | 1 | 0 | H | tetrazolyl |
| A91 a or b | OCH₂C(=O)OH | H | 1 | 1 | H | tetrazolyl |
| A92 a or b | OCH₂C(=O)OH | H | 0 | 1 | H | tetrazolyl |
| A93 a or b | H | N(H)C(=O)E³OH | 0 | 0 | H | tetrazolyl |
| A94 a or b | H | N(H)C(=O)E³OH | 1 | 0 | H | tetrazolyl |
| A95 a or b | H | N(H)C(=O)E³OH | 1 | 1 | H | tetrazolyl |
| A96 a or b | H | N(H)C(=O)E³OH | 0 | 1 | H | tetrazolyl |
| A97 a or b | H | OCH₂C(=O)OH | 0 | 0 | H | tetrazolyl |
| A98 a or b | H | OCH₂C(=O)OH | 1 | 0 | H | tetrazolyl |
| A99 a or b | H | OCH₂C(=O)OH | 1 | 1 | H | tetrazolyl |
| A100 a or b | H | OCH₂C(=O)OH | 0 | 1 | H | tetrazolyl |

$R^{8a}$ is (i) H or (ii) $CH_3$; $E^3$ is (iii) a direct bond or (iv) C(=O).

TABLE 3

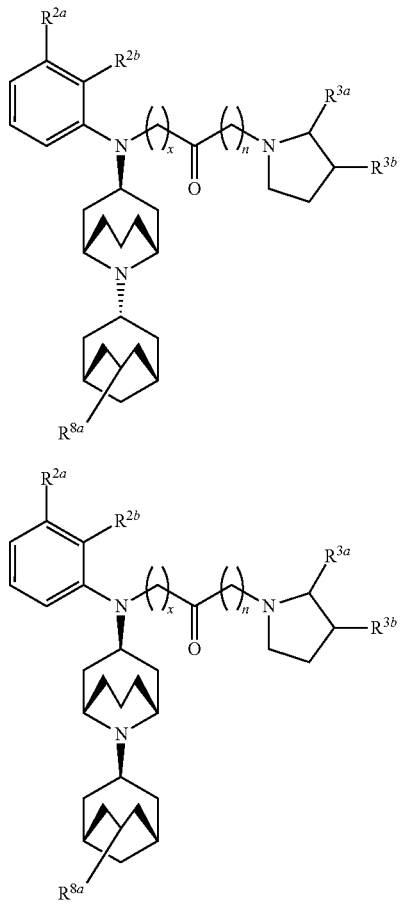

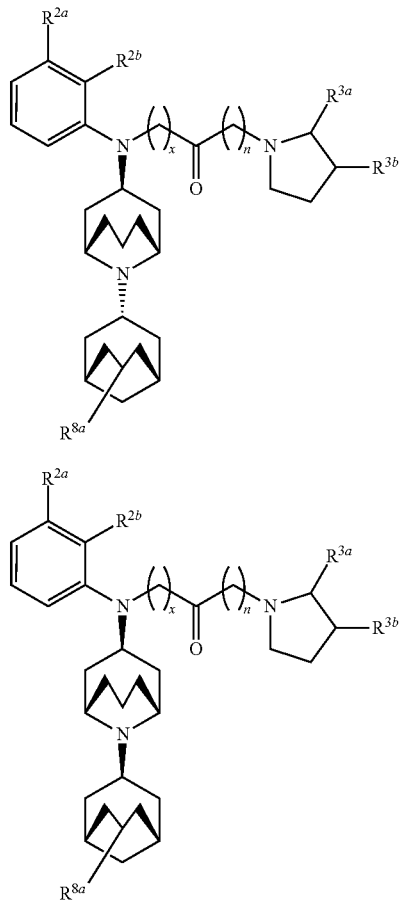

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| B1 a or b | H | H | 0 | 0 | H | H |
| B2 a or b | H | H | 1 | 0 | H | H |
| B3 a or b | H | H | 1 | 1 | H | H |
| B4 a or b | H | H | 0 | 1 | H | H |
| B5 a or b | N(H)C(=O)$E^3$OH | H | 0 | 0 | H | H |
| B6 a or b | N(H)C(=O)$E^3$OH | H | 1 | 0 | H | H |
| B7 a or b | N(H)C(=O)$E^3$OH | H | 1 | 1 | H | H |
| B8 a or b | N(H)C(=O)$E^3$OH | H | 0 | 1 | H | H |
| B9 a or b | OCH$_2$C(=O)OH | H | 0 | 0 | H | H |
| B10 a or b | OCH$_2$C(=O)OH | H | 1 | 0 | H | H |
| B11 a or b | OCH$_2$C(=O)OH | H | 1 | 1 | H | H |
| B12 a or b | OCH$_2$C(=O)OH | H | 0 | 1 | H | H |
| B13 a or b | H | N(H)C(=O)$E^3$OH | 0 | 0 | H | H |
| B14 a or b | H | N(H)C(=O)$E^3$OH | 1 | 0 | H | H |
| B15 a or b | H | N(H)C(=O)$E^3$OH | 1 | 1 | H | H |
| B16 a or b | H | N(H)C(=O)$E^3$OH | 0 | 1 | H | H |
| B17 a or b | H | OCH$_2$C(=O)OH | 0 | 0 | H | H |
| B18 a or b | H | OCH$_2$C(=O)OH | 1 | 0 | H | H |
| B19 a or b | H | OCH$_2$C(=O)OH | 1 | 1 | H | H |
| B20 a or b | H | OCH$_2$C(=O)OH | 0 | 1 | H | H |
| B21 a or b | H | H | 0 | 0 | C(=O)OH | H |
| B22 a or b | H | H | 1 | 0 | C(=O)OH | H |
| B23 a or b | H | H | 1 | 1 | C(=O)OH | H |
| B24 a or b | H | H | 0 | 1 | C(=O)OH | H |
| B25 a or b | N(H)C(=O)$E^3$OH | H | 0 | 0 | C(=O)OH | H |
| B26 a or b | N(H)C(=O)$E^3$OH | H | 1 | 0 | C(=O)OH | H |
| B27 a or b | N(H)C(=O)$E^3$OH | H | 1 | 1 | C(=O)OH | H |
| B28 a or b | N(H)C(=O)$E^3$OH | H | 0 | 1 | C(=O)OH | H |
| B29 a or b | OCH$_2$C(=O)OH | H | 0 | 0 | C(=O)OH | H |
| B30b a or b | OCH$_2$C(=O)OH | H | 1 | 0 | C(=O)OH | H |

TABLE 3-continued


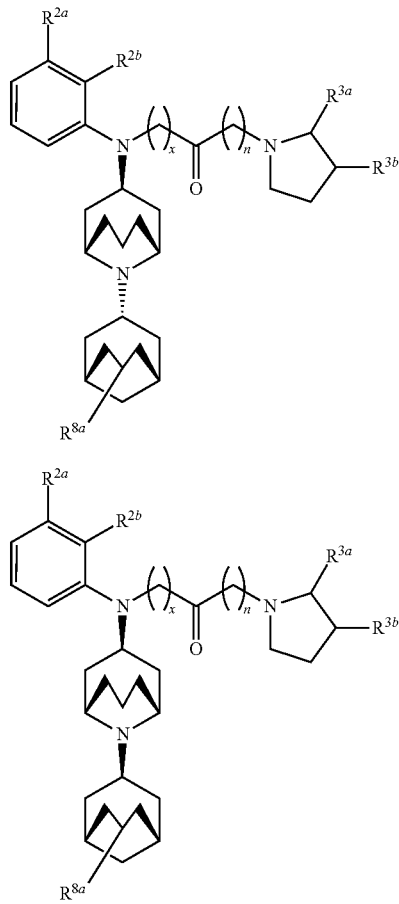

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| B31 a or b | $OCH_2C(=O)OH$ | H | 1 | 1 | $C(=O)OH$ | H |
| B32 a or b | $OCH_2C(=O)OH$ | H | 0 | 1 | $C(=O)OH$ | H |
| B33 a or b | H | $N(H)C(=O)E^3OH$ | 0 | 0 | $C(=O)OH$ | H |
| B34 a or b | H | $N(H)C(=O)E^3OH$ | 1 | 0 | $C(=O)OH$ | H |
| B35 a or b | H | $N(H)C(=O)E^3OH$ | 1 | 1 | $C(=O)OH$ | H |
| B36 a or b | H | $N(H)C(=O)E^3OH$ | 0 | 1 | $C(=O)OH$ | H |
| B37 a or b | H | $OCH_2C(=O)OH$ | 0 | 0 | $C(=O)OH$ | H |
| B38 a or b | H | $OCH_2C(=O)OH$ | 1 | 0 | $C(=O)OH$ | H |
| B39 a or b | H | $OCH_2C(=O)OH$ | 1 | 1 | $C(=O)OH$ | H |
| B40 a or b | H | $OCH_2C(=O)OH$ | 0 | 1 | $C(=O)OH$ | H |
| B41 a or b | H | H | 0 | 0 | H | $C(=O)OH$ |
| B42 a or b | H | H | 1 | 0 | H | $C(=O)OH$ |
| B43 a or b | H | H | 1 | 1 | H | $C(=O)OH$ |
| B44 a or b | H | H | 0 | 1 | H | $C(=O)OH$ |
| B45 a or b | $N(H)C(=O)E^3OH$ | H | 0 | 0 | H | $C(=O)OH$ |
| B46 a or b | $N(H)C(=O)E^3OH$ | H | 1 | 0 | H | $C(=O)OH$ |
| B47 a or b | $N(H)C(=O)E^3OH$ | H | 1 | 1 | H | $C(=O)OH$ |
| B48 a or b | $N(H)C(=O)E^3OH$ | H | 0 | 1 | H | $C(=O)OH$ |
| B49 a or b | $OCH_2C(=O)OH$ | H | 0 | 0 | H | $C(=O)OH$ |
| B50 a or b | $OCH_2C(=O)OH$ | H | 1 | 0 | H | $C(=O)OH$ |
| B51 a or b | $OCH_2C(=O)OH$ | H | 1 | 1 | H | $C(=O)OH$ |
| B52 a or b | $OCH_2C(=O)OH$ | H | 0 | 1 | H | $C(=O)OH$ |
| B53 a or b | H | $N(H)C(=O)E^3OH$ | 0 | 0 | H | $C(=O)OH$ |
| B54 a or b | H | $N(H)C(=O)E^3OH$ | 1 | 0 | H | $C(=O)OH$ |
| B55 a or b | H | $N(H)C(=O)E^3OH$ | 1 | 1 | H | $C(=O)OH$ |
| B56 a or b | H | $N(H)C(=O)E^3OH$ | 0 | 1 | H | $C(=O)OH$ |
| B57 a or b | H | $OCH_2C(=O)OH$ | 0 | 0 | H | $C(=O)OH$ |
| B58 a or b | H | $OCH_2C(=O)OH$ | 1 | 0 | H | $C(=O)OH$ |
| B59 a or b | H | $OCH_2C(=O)OH$ | 1 | 1 | H | $C(=O)OH$ |
| B60 a or b | H | $OCH_2C(=O)OH$ | 0 | 1 | H | $C(=O)OH$ |

TABLE 3-continued (a)

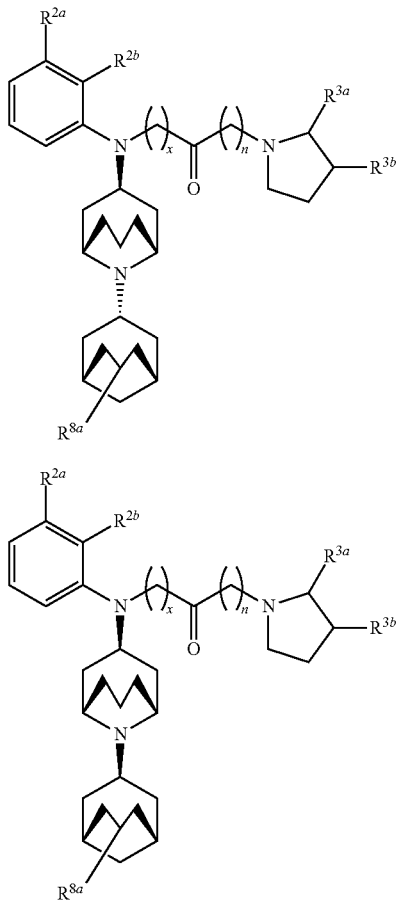

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| B61 a or b | H | H | 0 | 0 | tetrazolyl | H |
| B62 a or b | H | H | 1 | 0 | tetrazolyl | H |
| B63 a or b | H | H | 1 | 1 | tetrazolyl | H |
| B64 a or b | H | H | 0 | 1 | tetrazolyl | H |
| B65 a or b | $N(H)C(=O)E^3OH$ | H | 0 | 0 | tetrazolyl | H |
| B66b a or b | $N(H)C(=O)E^3OH$ | H | 1 | 0 | tetrazolyl | H |
| B67 a or b | $N(H)C(=O)E^3OH$ | H | 1 | 1 | tetrazolyl | H |
| B68 a or b | $N(H)C(=O)E^3OH$ | H | 0 | 1 | tetrazolyl | H |
| B69 a or b | $OCH_2C(=O)OH$ | H | 0 | 0 | tetrazolyl | H |
| B70 a or b | $OCH_2C(=O)OH$ | H | 1 | 0 | tetrazolyl | H |
| B71 a or b | $OCH_2C(=O)OH$ | H | 1 | 1 | tetrazolyl | H |
| B72 a or b | $OCH_2C(=O)OH$ | H | 0 | 1 | tetrazolyl | H |
| B73 a or b | H | $N(H)C(=O)E^3OH$ | 0 | 0 | tetrazolyl | H |
| B74 a or b | H | $N(H)C(=O)E^3OH$ | 1 | 0 | tetrazolyl | H |
| B75 a or b | H | $N(H)C(=O)E^3OH$ | 1 | 1 | tetrazolyl | H |

TABLE 3-continued (a)

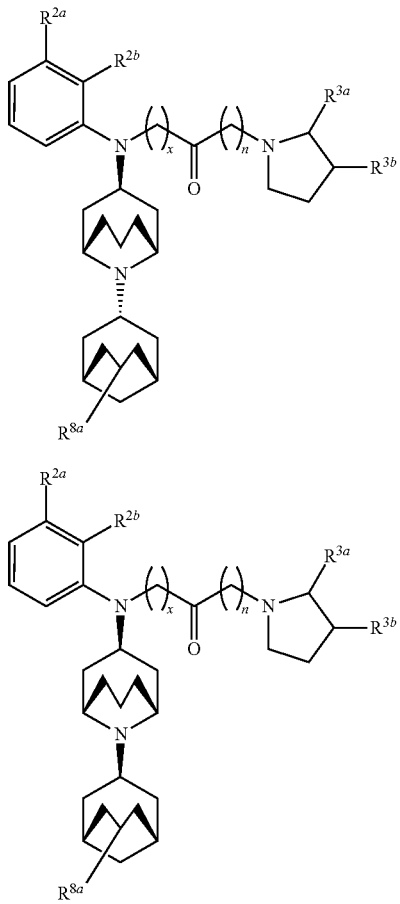

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| B76 a or b | H | $N(H)C(=O)E^3OH$ | 0 | 1 | tetrazolyl | H |
| B77 a or b | H | $OCH_2C(=O)OH$ | 0 | 0 | tetrazolyl | H |
| B78 a or b | H | $OCH_2C(=O)OH$ | 1 | 0 | tetrazolyl | H |
| B79 a or b | H | $OCH_2C(=O)OH$ | 1 | 1 | tetrazolyl | H |
| B80 a or b | H | $OCH_2C(=O)OH$ | 0 | 1 | tetrazolyl | H |
| B81 a or b | H | H | 0 | 0 | H | tetrazolyl |
| B82 a or b | H | H | 1 | 0 | H | tetrazolyl |
| B83 a or b | H | H | 1 | 1 | H | tetrazolyl |
| B84 a or b | H | H | 0 | 1 | H | tetrazolyl |
| B85 a or b | $N(H)C(=O)E^3OH$ | H | 0 | 0 | H | tetrazolyl |
| B86 a or b | $N(H)C(=O)E^3OH$ | H | 1 | 0 | H | tetrazolyl |
| B87 a or b | $N(H)C(=O)E^3OH$ | H | 1 | 1 | H | tetrazolyl |
| B88 a or b | $N(H)C(=O)E^3OH$ | H | 0 | 1 | H | tetrazolyl |
| B89 a or b | $OCH_2C(=O)OH$ | H | 0 | 0 | H | tetrazolyl |
| B90 a or b | $OCH_2C(=O)OH$ | H | 1 | 0 | H | tetrazolyl |

TABLE 3-continued

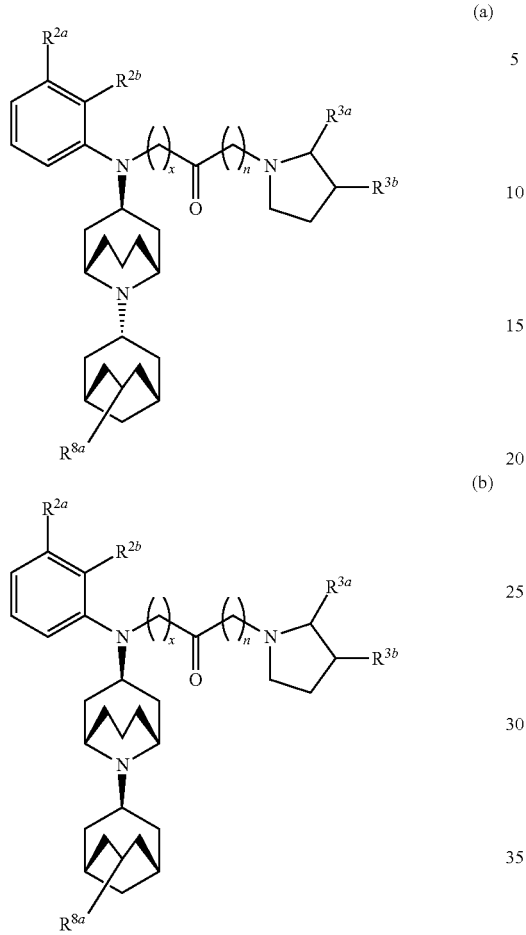

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| B91 a or b | OCH$_2$C(=O)OH | H | 1 | 1 | H | tetrazolyl |
| B92 a or b | OCH$_2$C(=O)OH | H | 0 | 1 | H | tetrazolyl |
| B93 a or b | H | N(H)C(=O)E$^3$OH | 0 | 0 | H | tetrazolyl |
| B94 a or b | H | N(H)C(=O)E$^3$OH | 1 | 0 | H | tetrazolyl |
| B95 a or b | H | N(H)C(=O)E$^3$OH | 1 | 1 | H | tetrazolyl |
| B96 a or b | H | N(H)C(=O)E$^3$OH | 0 | 1 | H | tetrazolyl |
| B97 a or b | H | OCH$_2$C(=O)OH | 0 | 0 | H | tetrazolyl |
| B98 a or b | H | OCH$_2$C(=O)OH | 1 | 0 | H | tetrazolyl |
| B99 a or b | H | OCH$_2$C(=O)OH | 1 | 1 | H | tetrazolyl |
| B100 a or b | H | OCH$_2$C(=O)OH | 0 | 1 | H | tetrazolyl |

$R^{8a}$ is (i) H or (ii) CH$_3$; E$^3$ is (iii) a direct bond or (iv) C(=O).

TABLE 4

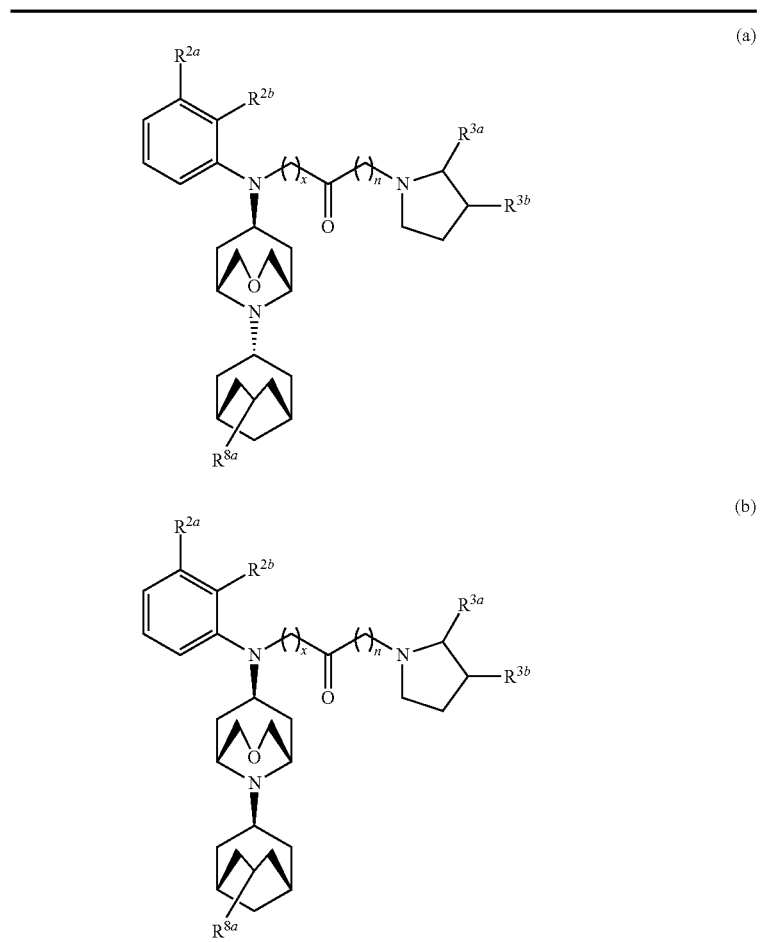

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| C1 a or b | H | H | 0 | 0 | H | H |
| C2 a or b | H | H | 1 | 0 | H | H |
| C3 a or b | H | H | 1 | 1 | H | H |
| C4 a or b | H | H | 0 | 1 | H | H |
| C5 a or b | $N(H)C(=O)E^3OH$ | H | 0 | 0 | H | H |
| C6 a or b | $N(H)C(=O)E^3OH$ | H | 1 | 0 | H | H |
| C7 a or b | $N(H)C(=O)E^3OH$ | H | 1 | 1 | H | H |
| C8 a or b | $N(H)C(=O)E^3OH$ | H | 0 | 1 | H | H |
| C9 a or b | $OCH_2C(=O)OH$ | H | 0 | 0 | H | H |
| C10 a or b | $OCH_2C(=O)OH$ | H | 1 | 0 | H | H |
| C11 a or b | $OCH_2C(=O)OH$ | H | 1 | 1 | H | H |
| C12 a or b | $OCH_2C(=O)OH$ | H | 0 | 1 | H | H |
| C13 a or b | H | $N(H)C(=O)E^3OH$ | 0 | 0 | H | H |
| C14 a or b | H | $N(H)C(=O)E^3OH$ | 1 | 0 | H | H |
| C15 a or b | H | $N(H)C(=O)E^3OH$ | 1 | 1 | H | H |
| C16 a or b | H | $N(H)C(=O)E^3OH$ | 0 | 1 | H | H |
| C17 a or b | H | $OCH_2C(=O)OH$ | 0 | 0 | H | H |
| C18 a or b | H | $OCH_2C(=O)OH$ | 1 | 0 | H | H |
| C19 a or b | H | $OCH_2C(=O)OH$ | 1 | 1 | H | H |
| C20 a or b | H | $OCH_2C(=O)OH$ | 0 | 1 | H | H |
| C21 a or b | H | H | 0 | 0 | $C(=O)OH$ | H |
| C22 a or b | H | H | 1 | 0 | $C(=O)OH$ | H |
| C23 a or b | H | H | 1 | 1 | $C(=O)OH$ | H |
| C24 a or b | H | H | 0 | 1 | $C(=O)OH$ | H |
| C25 a or b | $N(H)C(=O)E^3OH$ | H | 0 | 0 | $C(=O)OH$ | H |
| C26 a or b | $N(H)C(=O)E^3OH$ | H | 1 | 0 | $C(=O)OH$ | H |
| C27 a or b | $N(H)C(=O)E^3OH$ | H | 1 | 1 | $C(=O)OH$ | H |
| C28 a or b | $N(H)C(=O)E^3OH$ | H | 0 | 1 | $C(=O)OH$ | H |
| C29 a or b | $OCH_2C(=O)OH$ | H | 0 | 0 | $C(=O)OH$ | H |
| C30 a or b | $OCH_2C(=O)OH$ | H | 1 | 0 | $C(=O)OH$ | H |
| C31 a or b | $OCH_2C(=O)OH$ | H | 1 | 1 | $C(=O)OH$ | H |

TABLE 4-continued

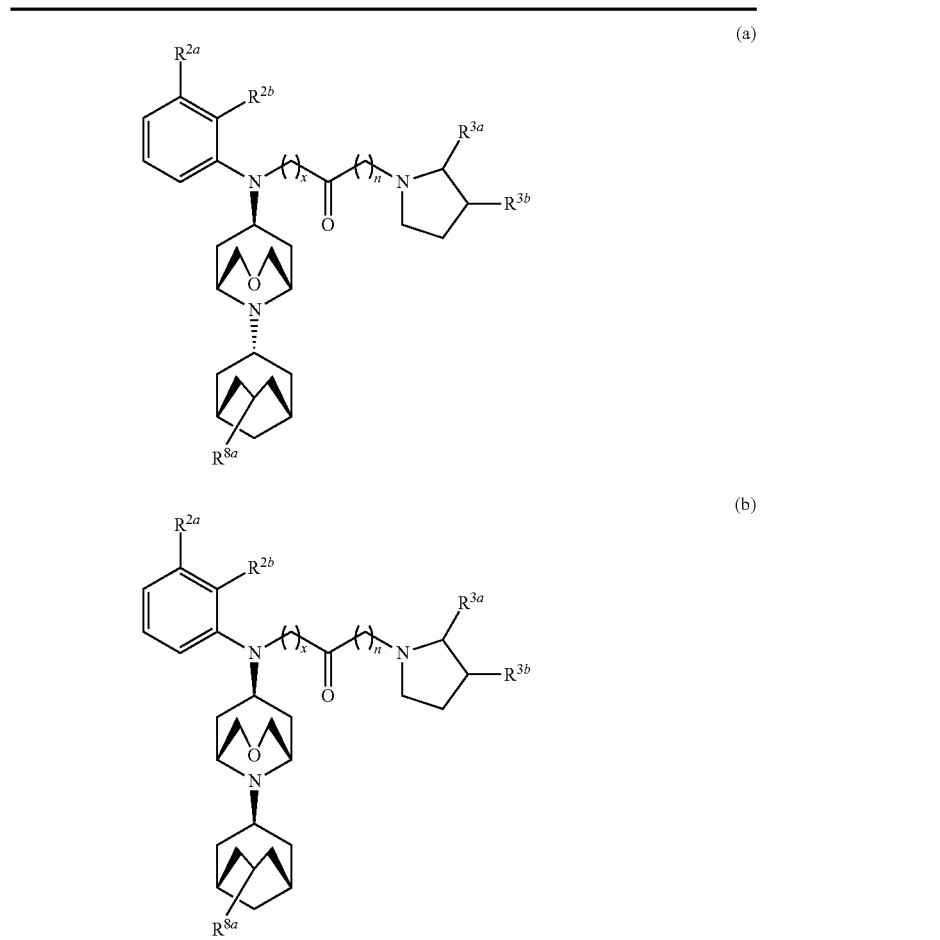

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| C32 a or b | $OCH_2C(=O)OH$ | H | 0 | 1 | $C(=O)OH$ | H |
| C33 a or b | H | $N(H)C(=O)E^3OH$ | 0 | 0 | $C(=O)OH$ | H |
| C34 a or b | H | $N(H)C(=O)E^3OH$ | 1 | 0 | $C(=O)OH$ | H |
| C35 a or b | H | $N(H)C(=O)E^3OH$ | 1 | 1 | $C(=O)OH$ | H |
| C36 a or b | H | $N(H)C(=O)E^3OH$ | 0 | 1 | $C(=O)OH$ | H |
| C37 a or b | H | $OCH_2C(=O)OH$ | 0 | 0 | $C(=O)OH$ | H |
| C38 a or b | H | $OCH_2C(=O)OH$ | 1 | 0 | $C(=O)OH$ | H |
| C39 a or b | H | $OCH_2C(=O)OH$ | 1 | 1 | $C(=O)OH$ | H |
| C40 a or b | H | $OCH_2C(=O)OH$ | 0 | 1 | $C(=O)OH$ | H |
| C41 a or b | H | H | 0 | 0 | H | $C(=O)OH$ |
| C42 a or b | H | H | 1 | 0 | H | $C(=O)OH$ |
| C43 a or b | H | H | 1 | 1 | H | $C(=O)OH$ |
| C44 a or b | H | H | 0 | 1 | H | $C(=O)OH$ |
| C45 a or b | $N(H)C(=O)E^3OH$ | H | 0 | 0 | H | $C(=O)OH$ |
| C46 a or b | $N(H)C(=O)E^3OH$ | H | 1 | 0 | H | $C(=O)OH$ |
| C47 a or b | $N(H)C(=O)E^3OH$ | H | 1 | 1 | H | $C(=O)OH$ |
| C48 a or b | $N(H)C(=O)E^3OH$ | H | 0 | 1 | H | $C(=O)OH$ |
| C49 a or b | $OCH_2C(=O)OH$ | H | 0 | 0 | H | $C(=O)OH$ |
| C50 a or b | $OCH_2C(=O)OH$ | H | 1 | 0 | H | $C(=O)OH$ |
| C51 a or b | $OCH_2C(=O)OH$ | H | 1 | 1 | H | $C(=O)OH$ |
| C52 a or b | $OCH_2C(=O)OH$ | H | 0 | 1 | H | $C(=O)OH$ |
| C53 a or b | H | $N(H)C(=O)E^3OH$ | 0 | 0 | H | $C(=O)OH$ |
| C54 a or b | H | $N(H)C(=O)E^3OH$ | 1 | 0 | H | $C(=O)OH$ |
| C55 a or b | H | $N(H)C(=O)E^3OH$ | 1 | 1 | H | $C(=O)OH$ |
| C56 a or b | H | $N(H)C(=O)E^3OH$ | 0 | 1 | H | $C(=O)OH$ |
| C57 a or b | H | $OCH_2C(=O)OH$ | 0 | 0 | H | $C(=O)OH$ |
| C58 a or b | H | $OCH_2C(=O)OH$ | 1 | 0 | H | $C(=O)OH$ |
| C59 a or b | H | $OCH_2C(=O)OH$ | 1 | 1 | H | $C(=O)OH$ |
| C60 a or b | H | $OCH_2C(=O)OH$ | 0 | 1 | H | $C(=O)OH$ |
| C61 a or b | H | H | 0 | 0 | tetrazolyl | H |
| C62 a or b | H | H | 1 | 0 | tetrazolyl | H |

TABLE 4-continued

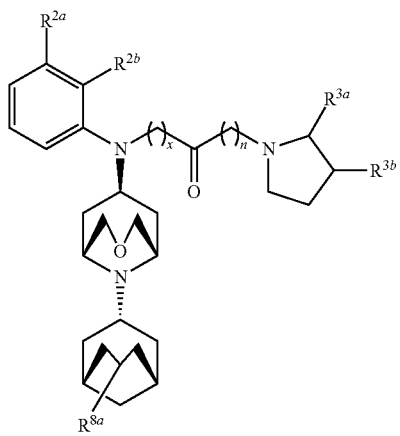

(a)

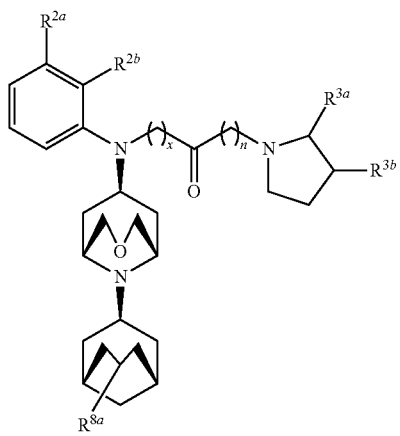

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| C63 a or b | H | H | 1 | 1 | tetrazolyl | H |
| C64 a or b | H | H | 0 | 1 | tetrazolyl | H |
| C65 a or b | N(H)C(=O)E$^3$OH | H | 0 | 0 | tetrazolyl | H |
| C66 a or b | N(H)C(=O)E$^3$OH | H | 1 | 0 | tetrazolyl | H |
| C67 a or b | N(H)C(=O)E$^3$OH | H | 1 | 1 | tetrazolyl | H |
| C68 a or b | N(H)C(=O)E$^3$OH | H | 0 | 1 | tetrazolyl | H |
| C69 a or b | OCH$_2$C(=O)OH | H | 0 | 0 | tetrazolyl | H |
| C70 a or b | OCH$_2$C(=O)OH | H | 1 | 0 | tetrazolyl | H |
| C71 a or b | OCH$_2$C(=O)OH | H | 1 | 1 | tetrazolyl | H |
| C72 a or b | OCH$_2$C(=O)OH | H | 0 | 1 | tetrazolyl | H |
| C73 a or b | H | N(H)C(=O)E$^3$OH | 0 | 0 | tetrazolyl | H |
| C74 a or b | H | N(H)C(=O)E$^3$OH | 1 | 0 | tetrazolyl | H |
| C75 a or b | H | N(H)C(=O)E$^3$OH | 1 | 1 | tetrazolyl | H |
| C76 a or b | H | N(H)C(=O)E$^3$OH | 0 | 1 | tetrazolyl | H |
| C77 a or b | H | OCH$_2$C(=O)OH | 0 | 0 | tetrazolyl | H |
| C78 a or b | H | OCH$_2$C(=O)OH | 1 | 0 | tetrazolyl | H |
| C79 a or b | H | OCH$_2$C(=O)OH | 1 | 1 | tetrazolyl | H |
| C80 a or b | H | OCH$_2$C(=O)OH | 0 | 1 | tetrazolyl | H |

TABLE 4-continued

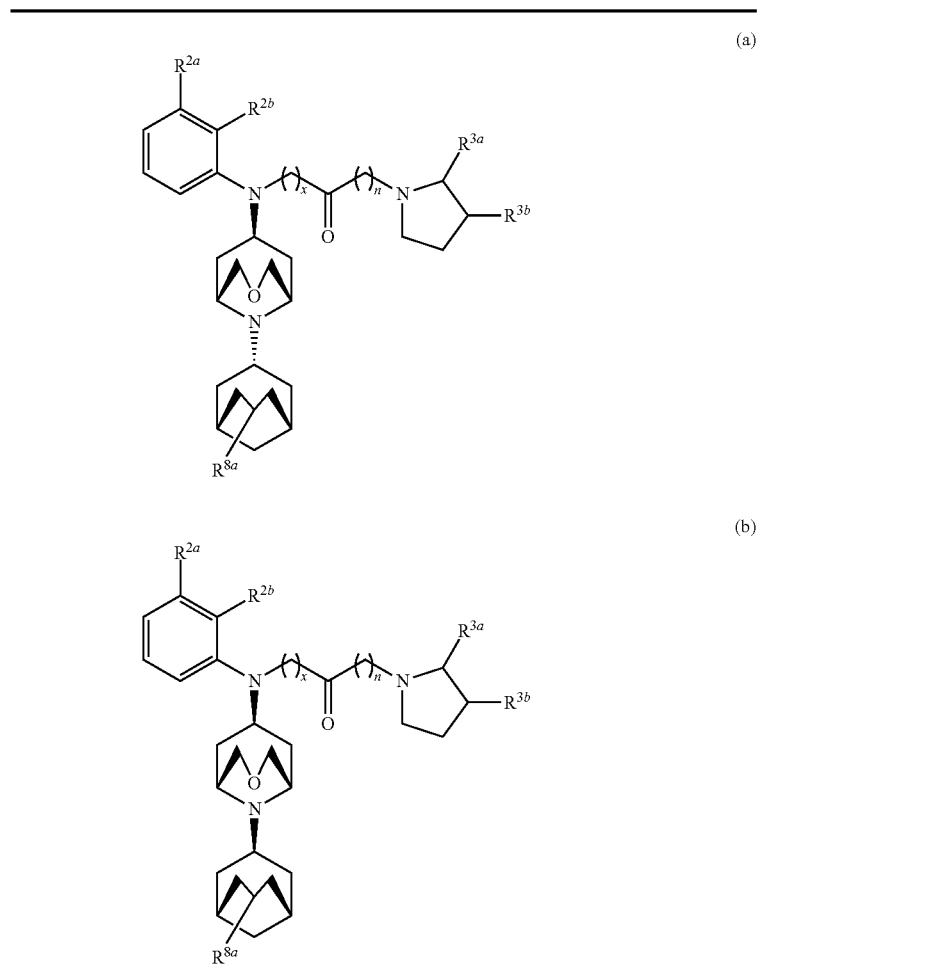

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| C81 a or b | H | H | 0 | 0 | H | tetrazolyl |
| C82 a or b | H | H | 1 | 0 | H | tetrazolyl |
| C83 a or b | H | H | 1 | 1 | H | tetrazolyl |
| C84 a or b | H | H | 0 | 1 | H | tetrazolyl |
| C85 a or b | N(H)C(=O)E³OH | H | 0 | 0 | H | tetrazolyl |
| C86 a or b | N(H)C(=O)E³OH | H | 1 | 0 | H | tetrazolyl |
| C87 a or b | N(H)C(=O)E³OH | H | 1 | 1 | H | tetrazolyl |
| C88 a or b | N(H)C(=O)E³OH | H | 0 | 1 | H | tetrazolyl |
| C89 a or b | OCH₂C(=O)OH | H | 0 | 0 | H | tetrazolyl |
| C90 a or b | OCH₂C(=O)OH | H | 1 | 0 | H | tetrazolyl |
| C91 a or b | OCH₂C(=O)OH | H | 1 | 1 | H | tetrazolyl |
| C92 a or b | OCH₂C(=O)OH | H | 0 | 1 | H | tetrazolyl |
| C93 a or b | H | N(H)C(=O)E³OH | 0 | 0 | H | tetrazolyl |
| C94 a or b | H | N(H)C(=O)E³OH | 1 | 0 | H | tetrazolyl |
| C95 a or b | H | N(H)C(=O)E³OH | 1 | 1 | H | tetrazolyl |
| C96 a or b | H | N(H)C(=O)E³OH | 0 | 1 | H | tetrazolyl |
| C97 a or b | H | OCH₂C(=O)OH | 0 | 0 | H | tetrazolyl |
| C98 a or b | H | OCH₂C(=O)OH | 1 | 0 | H | tetrazolyl |
| C99 a or b | H | OCH₂C(=O)OH | 1 | 1 | H | tetrazolyl |
| C100 a or b | H | OCH₂C(=O)OH | 0 | 1 | H | tetrazolyl |

$R^{8a}$ is (i) H or (ii) CH₃; $E^3$ is (iii) a direct bond or (iv) C(=O).

TABLE 5

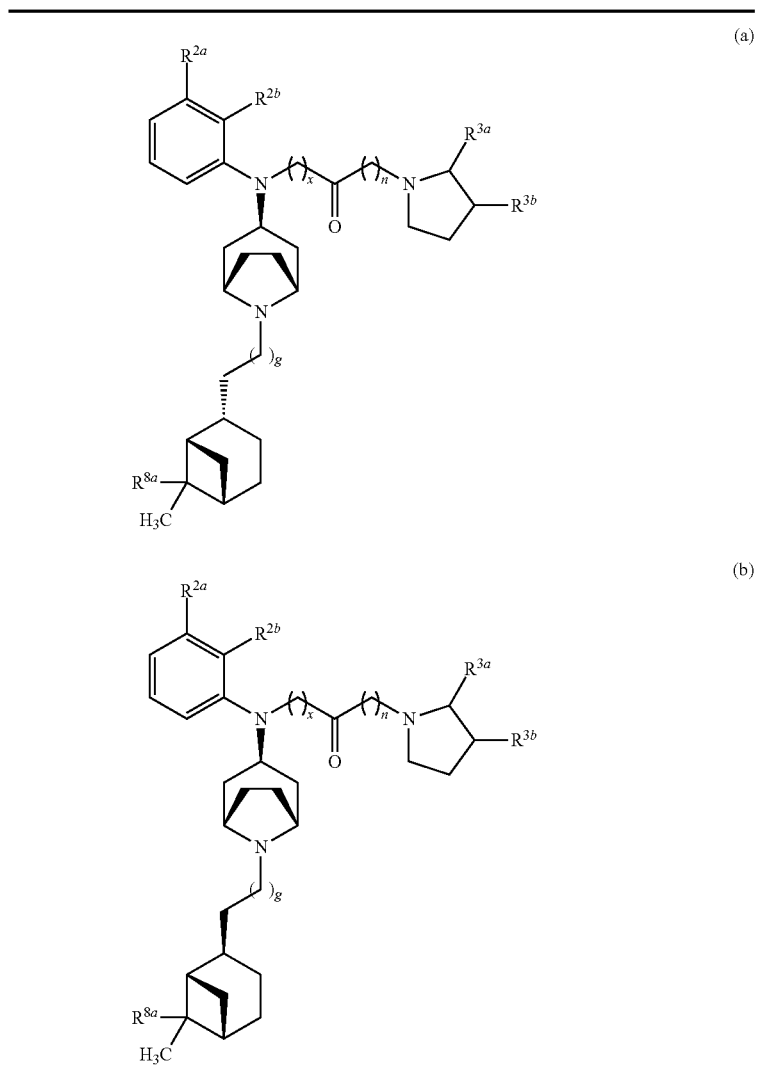

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| D1 a or b | H | H | 0 | 0 | H | H |
| D2 a or b | H | H | 1 | 0 | H | H |
| D3 a or b | H | H | 1 | 1 | H | H |
| D4 a or b | H | H | 0 | 1 | H | H |
| D5 a or b | N(H)C(=O)E³OH | H | 0 | 0 | H | H |
| D6 a or b | N(H)C(=O)E³OH | H | 1 | 0 | H | H |
| D7 a or b | N(H)C(=O)E³OH | H | 1 | 1 | H | H |
| D8 a or b | N(H)C(=O)E³OH | H | 0 | 1 | H | H |
| D9 a or b | OCH₂C(=O)OH | H | 0 | 0 | H | H |
| D10 a or b | OCH₂C(=O)OH | H | 1 | 0 | H | H |
| D11 a or b | OCH₂C(=O)OH | H | 1 | 1 | H | H |
| D12 a or b | OCH₂C(=O)OH | H | 0 | 1 | H | H |
| D13 a or b | H | N(H)C(=O)E³OH | 0 | 0 | H | H |
| D14 a or b | H | N(H)C(=O)E³OH | 1 | 0 | H | H |
| D15 a or b | H | N(H)C(=O)E³OH | 1 | 1 | H | H |
| D16 a or b | H | N(H)C(=O)E³OH | 0 | 1 | H | H |
| D17 a or b | H | OCH₂C(=O)OH | 0 | 0 | H | H |
| D18 a or b | H | OCH₂C(=O)OH | 1 | 0 | H | H |
| D19 a or b | H | OCH₂C(=O)OH | 1 | 1 | H | H |
| D20 a or b | H | OCH₂C(=O)OH | 0 | 1 | H | H |
| D21 a or b | H | H | 0 | 0 | C(=O)OH | H |
| D22 a or b | H | H | 1 | 0 | C(=O)OH | H |
| D23 a or b | H | H | 1 | 1 | C(=O)OH | H |
| D24 a or b | H | H | 0 | 1 | C(=O)OH | H |
| D25 a or b | N(H)C(=O)E³OH | H | 0 | 0 | C(=O)OH | H |

TABLE 5-continued

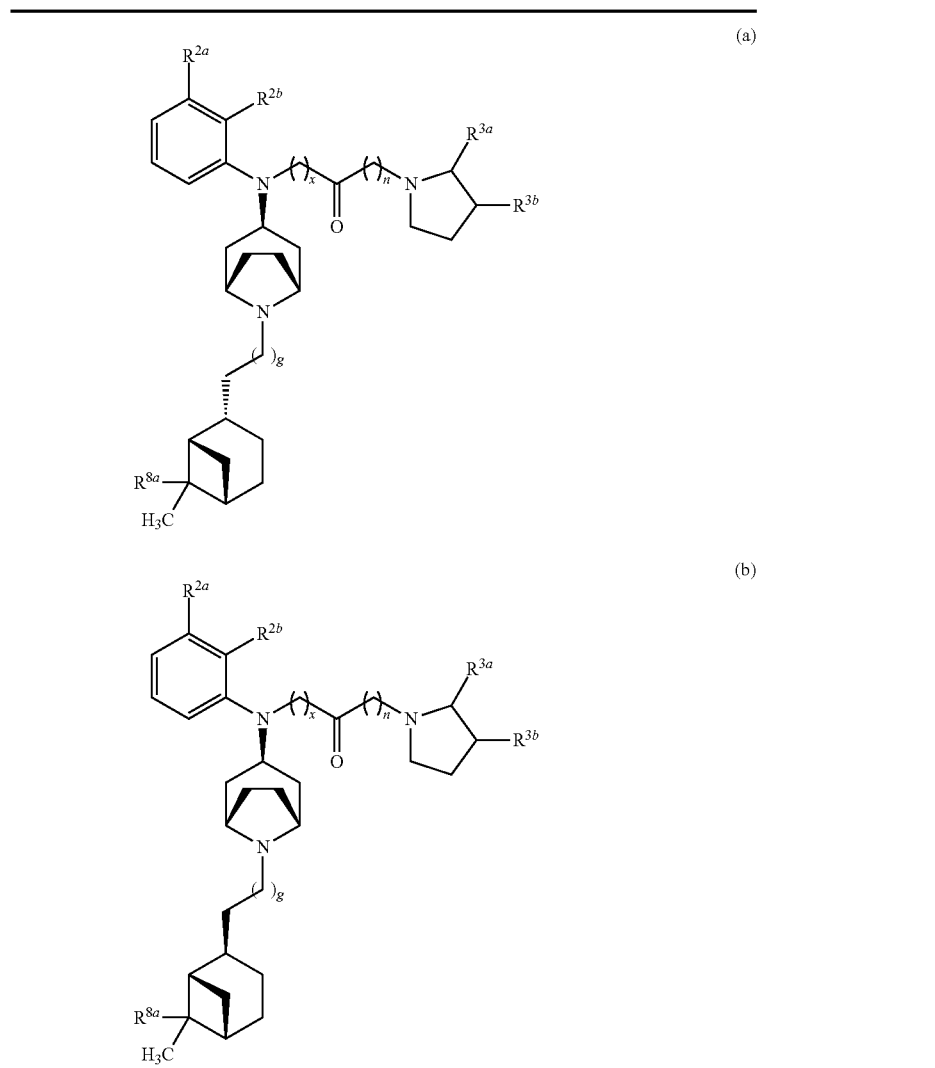

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| D26 a or b | N(H)C(=O)E$^3$OH | H | 1 | 0 | C(=O)OH | H |
| D27 a or b | N(H)C(=O)E$^3$OH | H | 1 | 1 | C(=O)OH | H |
| D28 a or b | N(H)C(=O)E$^3$OH | H | 0 | 1 | C(=O)OH | H |
| D29 a or b | OCH$_2$C(=O)OH | H | 0 | 0 | C(=O)OH | H |
| D30 a or b | OCH$_2$C(=O)OH | H | 1 | 0 | C(=O)OH | H |
| D31 a or b | OCH$_2$C(=O)OH | H | 1 | 1 | C(=O)OH | H |
| D32 a or b | OCH$_2$C(=O)OH | H | 0 | 1 | C(=O)OH | H |
| D33 a or b | H | N(H)C(=O)E$^3$OH | 0 | 0 | C(=O)OH | H |
| D34 a or b | H | N(H)C(=O)E$^3$OH | 1 | 0 | C(=O)OH | H |
| D35 a or b | H | N(H)C(=O)E$^3$OH | 1 | 1 | C(=O)OH | H |
| D36 a or b | H | N(H)C(=O)E$^3$OH | 0 | 1 | C(=O)OH | H |
| D37 a or b | H | OCH$_2$C(=O)OH | 0 | 0 | C(=O)OH | H |
| D38 a or b | H | OCH$_2$C(=O)OH | 1 | 0 | C(=O)OH | H |
| D39 a or b | H | OCH$_2$C(=O)OH | 1 | 1 | C(=O)OH | H |
| D40 a or b | H | OCH$_2$C(=O)OH | 0 | 1 | C(=O)OH | H |
| D41 a or b | H | H | 0 | 0 | H | C(=O)OH |
| D42 a or b | H | H | 1 | 0 | H | C(=O)OH |
| D43 a or b | H | H | 1 | 1 | H | C(=O)OH |
| D44 a or b | H | H | 0 | 1 | H | C(=O)OH |
| D45 a or b | N(H)C(=O)E$^3$OH | H | 0 | 0 | H | C(=O)OH |
| D46 a or b | N(H)C(=O)E$^3$OH | H | 1 | 0 | H | C(=O)OH |
| D47 a or b | N(H)C(=O)E$^3$OH | H | 1 | 1 | H | C(=O)OH |
| D48 a or b | N(H)C(=O)E$^3$OH | H | 0 | 1 | H | C(=O)OH |
| D49 a or b | OCH$_2$C(=O)OH | H | 0 | 0 | H | C(=O)OH |
| D50 a or b | OCH$_2$C(=O)OH | H | 1 | 0 | H | C(=O)OH |

TABLE 5-continued (a)

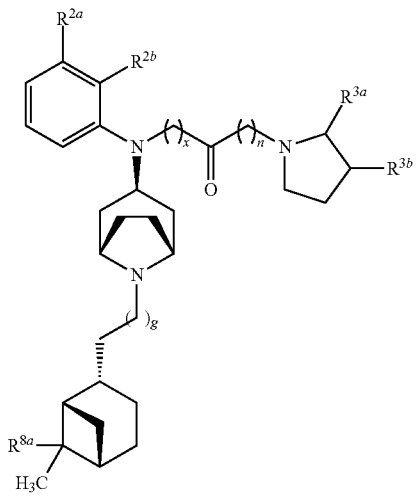

(b)

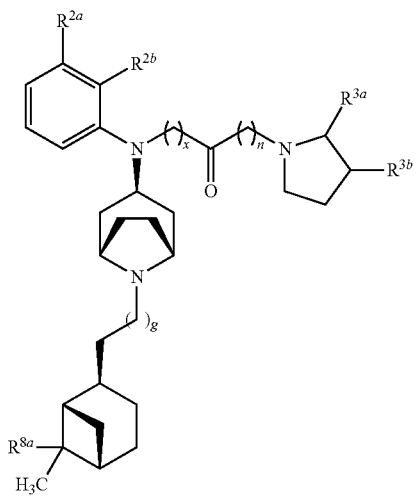

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| D51 a or b | $OCH_2C(=O)OH$ | H | 1 | 1 | H | $C(=O)OH$ |
| D52 a or b | $OCH_2C(=O)OH$ | H | 0 | 1 | H | $C(=O)OH$ |
| D53 a or b | H | $N(H)C(=O)E^3OH$ | 0 | 0 | H | $C(=O)OH$ |
| D54 a or b | H | $N(H)C(=O)E^3OH$ | 1 | 0 | H | $C(=O)OH$ |
| D55 a or b | H | $N(H)C(=O)E^3OH$ | 1 | 1 | H | $C(=O)OH$ |
| D56 a or b | H | $N(H)C(=O)E^3OH$ | 0 | 1 | H | $C(=O)OH$ |
| D57 a or b | H | $OCH_2C(=O)OH$ | 0 | 0 | H | $C(=O)OH$ |
| D58 a or b | H | $OCH_2C(=O)OH$ | 1 | 0 | H | $C(=O)OH$ |
| D59 a or b | H | $OCH_2C(=O)OH$ | 1 | 1 | H | $C(=O)OH$ |
| D60 a or b | H | $OCH_2C(=O)OH$ | 0 | 1 | H | $C(=O)OH$ |
| D61 a or b | H | H | 0 | 0 | tetrazolyl | H |
| D62 a or b | H | H | 1 | 0 | tetrazolyl | H |
| D63 a or b | H | H | 1 | 1 | tetrazolyl | H |
| D64 a or b | H | H | 0 | 1 | tetrazolyl | H |
| D65 a or b | $N(H)C(=O)E^3OH$ | H | 0 | 0 | tetrazolyl | H |
| D66 a or b | $N(H)C(=O)E^3OH$ | H | 1 | 0 | tetrazolyl | H |
| D67 a or b | $N(H)C(=O)E^3OH$ | H | 1 | 1 | tetrazolyl | H |
| D68 a or b | $N(H)C(=O)E^3OH$ | H | 0 | 1 | tetrazolyl | H |

TABLE 5-continued

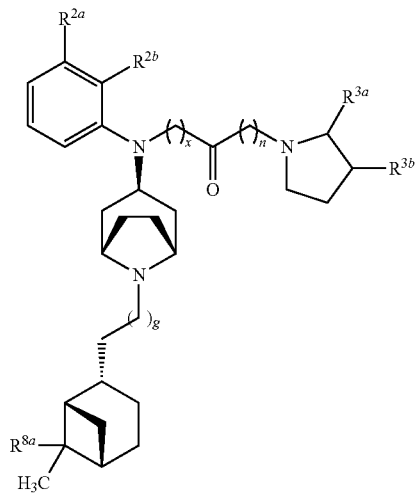

(a)

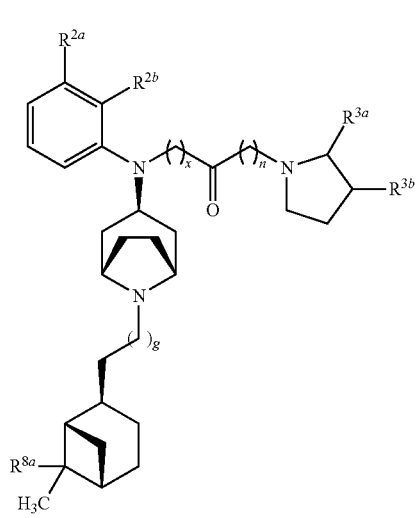

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| D69 a or b | $OCH_2C(=O)OH$ | H | 0 | 0 | tetrazolyl | H |
| D70 a or b | $OCH_2C(=O)OH$ | H | 1 | 0 | tetrazolyl | H |
| D71 a or b | $OCH_2C(=O)OH$ | H | 1 | 1 | tetrazolyl | H |
| D72 a or b | $OCH_2C(=O)OH$ | H | 0 | 1 | tetrazolyl | H |
| D73 a or b | H | $N(H)C(=O)E^3OH$ | 0 | 0 | tetrazolyl | H |
| D74 a or b | H | $N(H)C(=O)E^3OH$ | 1 | 0 | tetrazolyl | H |
| D75 a or b | H | $N(H)C(=O)E^3OH$ | 1 | 1 | tetrazolyl | H |
| D76 a or b | H | $N(H)C(=O)E^3OH$ | 0 | 1 | tetrazolyl | H |
| D77 a or b | H | $OCH_2C(=O)OH$ | 0 | 0 | tetrazolyl | H |
| D78 a or b | H | $OCH_2C(=O)OH$ | 1 | 0 | tetrazolyl | H |
| D79 a or b | H | $OCH_2C(=O)OH$ | 1 | 1 | tetrazolyl | H |
| D80 a or b | H | $OCH_2C(=O)OH$ | 0 | 1 | tetrazolyl | H |
| D81 a or b | H | H | 0 | 0 | H | tetrazolyl |
| D82 a or b | H | H | 1 | 0 | H | tetrazolyl |
| D83 a or b | H | H | 1 | 1 | H | tetrazolyl |
| D84 a or b | H | H | 0 | 1 | H | tetrazolyl |
| D85 a or b | $N(H)C(=O)E^3OH$ | H | 0 | 0 | H | tetrazolyl |
| D86 a or b | $N(H)C(=O)E^3OH$ | H | 1 | 0 | H | tetrazolyl |

TABLE 5-continued (a)

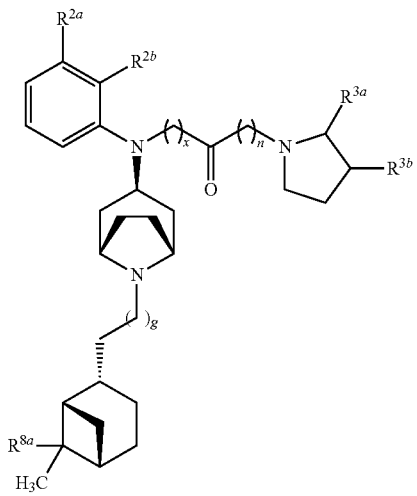

(b)

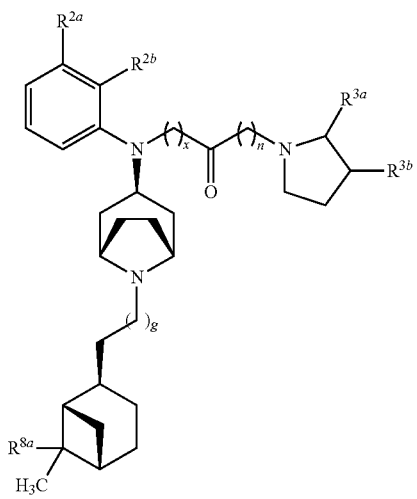

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| D87 a or b | N(H)C(=O)$E^3$OH | H | 1 | 1 | H | tetrazolyl |
| D88 a or b | N(H)C(=O)$E^3$OH | H | 0 | 1 | H | tetrazolyl |
| D89 a or b | OCH$_2$C(=O)OH | H | 0 | 0 | H | tetrazolyl |
| D90 a or b | OCH$_2$C(=O)OH | H | 1 | 0 | H | tetrazolyl |
| D91 a or b | OCH$_2$C(=O)OH | H | 1 | 1 | H | tetrazolyl |
| D92 a or b | OCH$_2$C(=O)OH | H | 0 | 1 | H | tetrazolyl |
| D93 a or b | H | N(H)C(=O)$E^3$OH | 0 | 0 | H | tetrazolyl |
| D94 a or b | H | N(H)C(=O)$E^3$OH | 1 | 0 | H | tetrazolyl |
| D95 a or b | H | N(H)C(=O)$E^3$OH | 1 | 1 | H | tetrazolyl |
| D96 a or b | H | N(H)C(=O)$E^3$OH | 0 | 1 | H | tetrazolyl |
| D97 a or b | H | OCH$_2$C(=O)OH | 0 | 0 | H | tetrazolyl |
| D98 a or b | H | OCH$_2$C(=O)OH | 1 | 0 | H | tetrazolyl |
| D99 a or b | H | OCH$_2$C(=O)OH | 1 | 1 | H | tetrazolyl |
| D100 a or b | H | OCH$_2$C(=O)OH | 0 | 1 | H | tetrazolyl |

$R^{8a}$ is (i) H or (ii) CH$_3$; $E^3$ is (iii) a direct bond or (iv) C(=O); g is 0, 1, 2, or 3.

TABLE 6

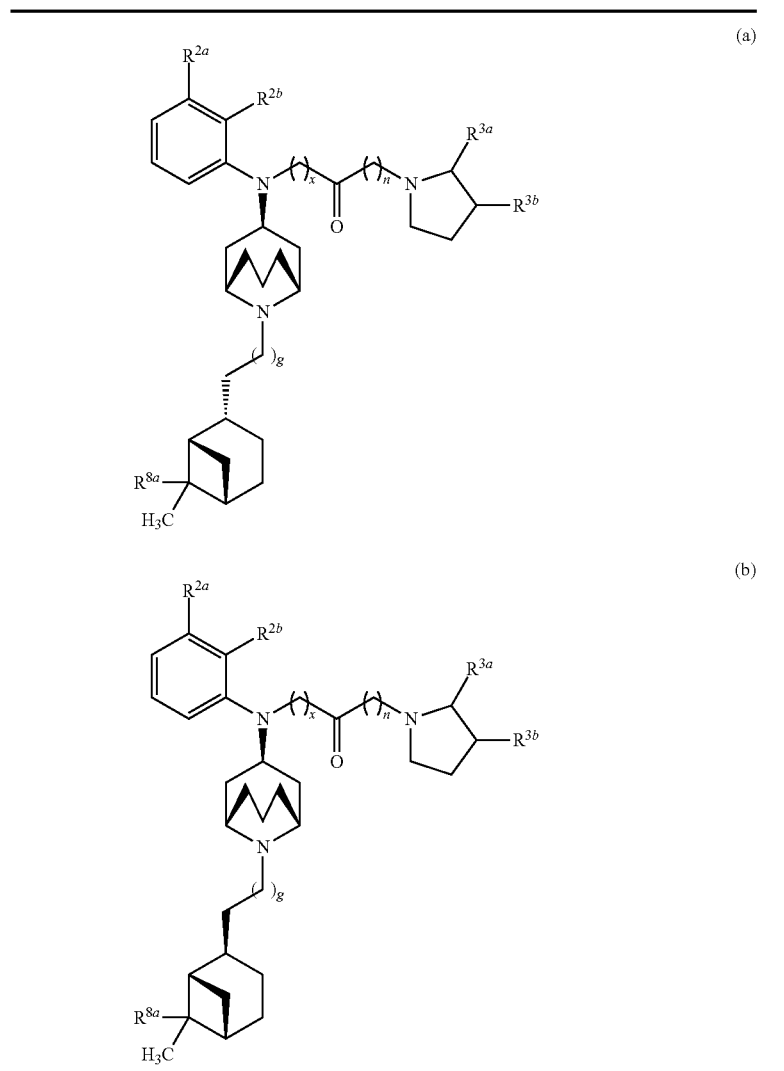

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| E1 a or b | H | H | 0 | 0 | H | H |
| E2 a or b | H | H | 1 | 0 | H | H |
| E3 a or b | H | H | 1 | 1 | H | H |
| E4 a or b | H | H | 0 | 1 | H | H |
| E5 a or b | N(H)C(=O)E$^3$OH | H | 0 | 0 | H | H |
| E6 a or b | N(H)C(=O)E$^3$OH | H | 1 | 0 | H | H |
| E7 a or b | N(H)C(=O)E$^3$OH | H | 1 | 1 | H | H |
| E8 a or b | N(H)C(=O)E$^3$OH | H | 0 | 1 | H | H |
| E9 a or b | OCH$_2$C(=O)OH | H | 0 | 0 | H | H |
| E10 a or b | OCH$_2$C(=O)OH | H | 1 | 0 | H | H |
| E11 a or b | OCH$_2$C(=O)OH | H | 1 | 1 | H | H |
| E12 a or b | OCH$_2$C(=O)OH | H | 0 | 1 | H | H |
| E13 a or b | H | N(H)C(=O)E$^3$OH | 0 | 0 | H | H |
| E14 a or b | H | N(H)C(=O)E$^3$OH | 1 | 0 | H | H |
| E15 a or b | H | N(H)C(=O)E$^3$OH | 1 | 1 | H | H |
| E16 a or b | H | N(H)C(=O)E$^3$OH | 0 | 1 | H | H |
| E17 a or b | H | OCH$_2$C(=O)OH | 0 | 0 | H | H |
| E18 a or b | H | OCH$_2$C(=O)OH | 1 | 0 | H | H |
| E19 a or b | H | OCH$_2$C(=O)OH | 1 | 1 | H | H |
| E20 a or b | H | OCH$_2$C(=O)OH | 0 | 1 | H | H |
| E21 a or b | H | H | 0 | 0 | C(=O)OH | H |
| E22 a or b | H | H | 1 | 0 | C(=O)OH | H |
| E23 a or b | H | H | 1 | 1 | C(=O)OH | H |
| E24 a or b | H | H | 0 | 1 | C(=O)OH | H |
| E25 a or b | N(H)C(=O)E$^3$OH | H | 0 | 0 | C(=O)OH | H |

TABLE 6-continued

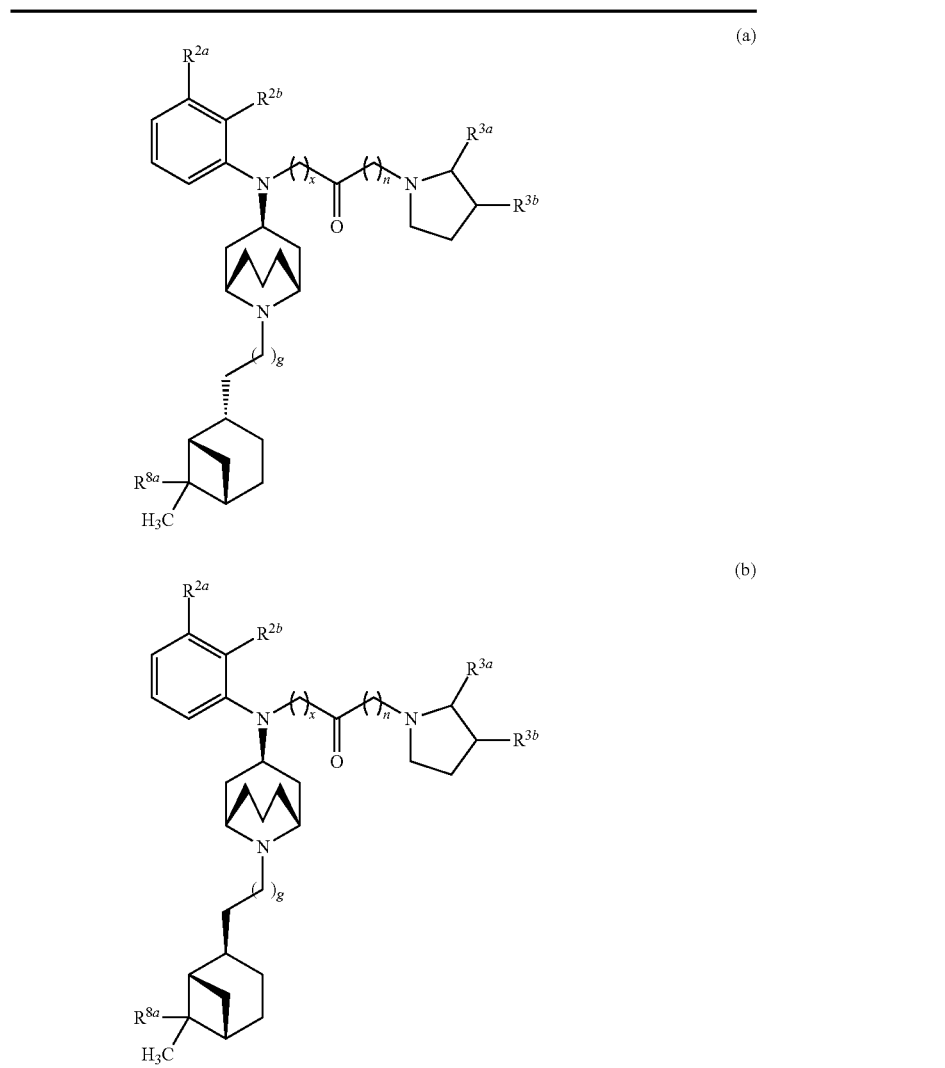

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| E26 a or b | N(H)C(=O)E$^3$OH | H | 1 | 0 | C(=O)OH | H |
| E27 a or b | N(H)C(=O)E$^3$OH | H | 1 | 1 | C(=O)OH | H |
| E28 a or b | N(H)C(=O)E$^3$OH | H | 0 | 1 | C(=O)OH | H |
| E29 a or b | OCH$_2$C(=O)OH | H | 0 | 0 | C(=O)OH | H |
| E30 a or b | OCH$_2$C(=O)OH | H | 1 | 0 | C(=O)OH | H |
| E31 a or b | OCH$_2$C(=O)OH | H | 1 | 1 | C(=O)OH | H |
| E32 a or b | OCH$_2$C(=O)OH | H | 0 | 1 | C(=O)OH | H |
| E33 a or b | H | N(H)C(=O)E$^3$OH | 0 | 0 | C(=O)OH | H |
| E34 a or b | H | N(H)C(=O)E$^3$OH | 1 | 0 | C(=O)OH | H |
| E35 a or b | H | N(H)C(=O)E$^3$OH | 1 | 1 | C(=O)OH | H |
| E36 a or b | H | N(H)C(=O)E$^3$OH | 0 | 1 | C(=O)OH | H |
| E37 a or b | H | OCH$_2$C(=O)OH | 0 | 0 | C(=O)OH | H |
| E38 a or b | H | OCH$_2$C(=O)OH | 1 | 0 | C(=O)OH | H |
| E39 a or b | H | OCH$_2$C(=O)OH | 1 | 1 | C(=O)OH | H |
| E40 a or b | H | OCH$_2$C(=O)OH | 0 | 1 | C(=O)OH | H |
| E41 a or b | H | H | 0 | 0 | H | C(=O)OH |
| E42 a or b | H | H | 1 | 0 | H | C(=O)OH |
| E43 a or b | H | H | 1 | 1 | H | C(=O)OH |
| E44 a or b | H | H | 0 | 1 | H | C(=O)OH |
| E45 a or b | N(H)C(=O)E$^3$OH | H | 0 | 0 | H | C(=O)OH |
| E46 a or b | N(H)C(=O)E$^3$OH | H | 1 | 0 | H | C(=O)OH |
| E47 a or b | N(H)C(=O)E$^3$OH | H | 1 | 1 | H | C(=O)OH |
| E48 a or b | N(H)C(=O)E$^3$OH | H | 0 | 1 | H | C(=O)OH |
| E49 a or b | OCH$_2$C(=O)OH | H | 0 | 0 | H | C(=O)OH |
| E50 a or b | OCH$_2$C(=O)OH | H | 1 | 0 | H | C(=O)OH |

TABLE 6-continued

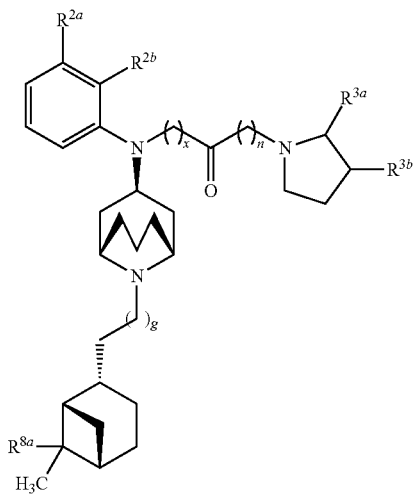

(a)

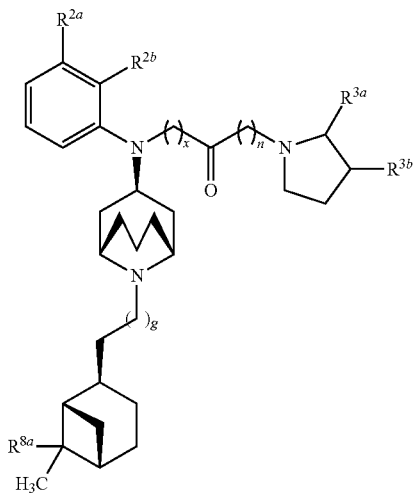

(b)

and pharmaceutically acceptable salts and solvates thereof, where:

| Compound  | $R^{2a}$          | $R^{2b}$          | x | n | $R^{3a}$  | $R^{3b}$  |
|-----------|-------------------|-------------------|---|---|-----------|-----------|
| E51 a or b | $OCH_2C(=O)OH$   | H                 | 1 | 1 | H         | $C(=O)OH$ |
| E52 a or b | $OCH_2C(=O)OH$   | H                 | 0 | 1 | H         | $C(=O)OH$ |
| E53 a or b | H                 | $N(H)C(=O)E^3OH$ | 0 | 0 | H         | $C(=O)OH$ |
| E54 a or b | H                 | $N(H)C(=O)E^3OH$ | 1 | 0 | H         | $C(=O)OH$ |
| E55 a or b | H                 | $N(H)C(=O)E^3OH$ | 1 | 1 | H         | $C(=O)OH$ |
| E56 a or b | H                 | $N(H)C(=O)E^3OH$ | 0 | 1 | H         | $C(=O)OH$ |
| E57 a or b | H                 | $OCH_2C(=O)OH$   | 0 | 0 | H         | $C(=O)OH$ |
| E58 a or b | H                 | $OCH_2C(=O)OH$   | 1 | 0 | H         | $C(=O)OH$ |
| E59 a or b | H                 | $OCH_2C(=O)OH$   | 1 | 1 | H         | $C(=O)OH$ |
| E60 a or b | H                 | $OCH_2C(=O)OH$   | 0 | 1 | H         | $C(=O)OH$ |
| E61 a or b | H                 | H                 | 0 | 0 | tetrazolyl | H        |
| E62 a or b | H                 | H                 | 1 | 0 | tetrazolyl | H        |
| E63 a or b | H                 | H                 | 1 | 1 | tetrazolyl | H        |
| E64 a or b | H                 | H                 | 0 | 1 | tetrazolyl | H        |
| E65 a or b | $N(H)C(=O)E^3OH$ | H                 | 0 | 0 | tetrazolyl | H        |
| E66 a or b | $N(H)C(=O)E^3OH$ | H                 | 1 | 0 | tetrazolyl | H        |
| E67 a or b | $N(H)C(=O)E^3OH$ | H                 | 1 | 1 | tetrazolyl | H        |
| E68 a or b | $N(H)C(=O)E^3OH$ | H                 | 0 | 1 | tetrazolyl | H        |
| E69 a or b | $OCH_2C(=O)OH$   | H                 | 0 | 0 | tetrazolyl | H        |

TABLE 6-continued

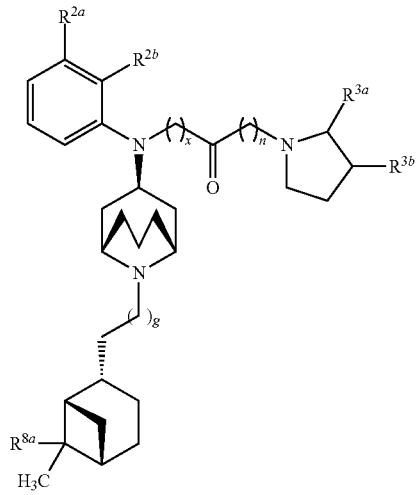

(a)

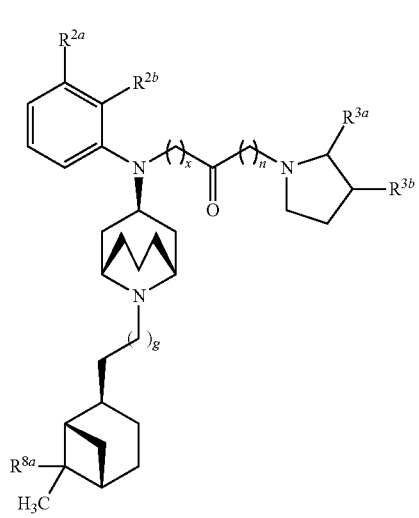

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| E70 a or b | $OCH_2C(=O)OH$ | H | 1 | 0 | tetrazolyl | H |
| E71 a or b | $OCH_2C(=O)OH$ | H | 1 | 1 | tetrazolyl | H |
| E72 a or b | $OCH_2C(=O)OH$ | H | 0 | 1 | tetrazolyl | H |
| E73 a or b | H | $N(H)C(=O)E^3OH$ | 0 | 0 | tetrazolyl | H |
| E74 a or b | H | $N(H)C(=O)E^3OH$ | 1 | 0 | tetrazolyl | H |
| E75 a or b | H | $N(H)C(=O)E^3OH$ | 1 | 1 | tetrazolyl | H |
| E76 a or b | H | $N(H)C(=O)E^3OH$ | 0 | 1 | tetrazolyl | H |
| E77 a or b | H | $OCH_2C(=O)OH$ | 0 | 0 | tetrazolyl | H |
| E78 a or b | H | $OCH_2C(=O)OH$ | 1 | 0 | tetrazolyl | H |
| E79 a or b | H | $OCH_2C(=O)OH$ | 1 | 1 | tetrazolyl | H |
| E80 a or b | H | $OCH_2C(=O)OH$ | 0 | 1 | tetrazolyl | H |
| E81 a or b | H | H | 0 | 0 | H | tetrazolyl |
| E82 a or b | H | H | 1 | 0 | H | tetrazolyl |
| E83 a or b | H | H | 1 | 1 | H | tetrazolyl |
| E84 a or b | H | H | 0 | 1 | H | tetrazolyl |
| E85 a or b | $N(H)C(=O)E^3OH$ | H | 0 | 0 | H | tetrazolyl |
| E86 a or b | $N(H)C(=O)E^3OH$ | H | 1 | 0 | H | tetrazolyl |
| E87 a or b | $N(H)C(=O)E^3OH$ | H | 1 | 1 | H | tetrazolyl |

TABLE 6-continued

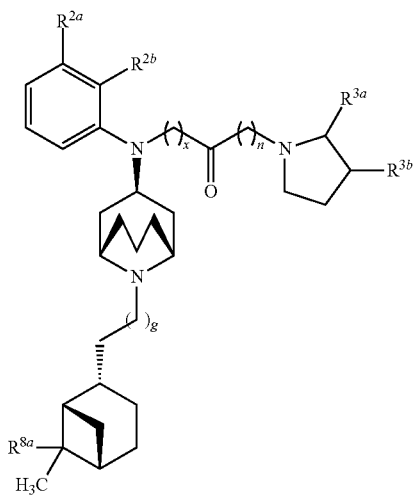

(a)

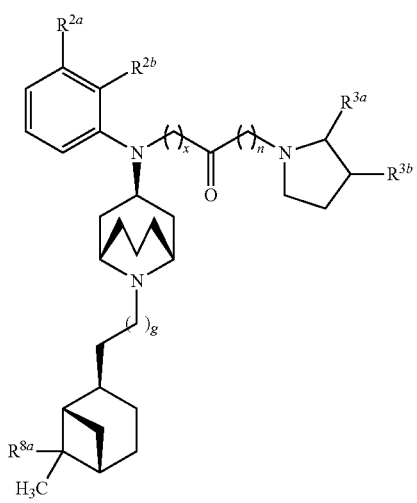

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| E88 a or b | N(H)C(=O)E³OH | H | 0 | 1 | H | tetrazolyl |
| E89 a or b | OCH₂C(=O)OH | H | 0 | 0 | H | tetrazolyl |
| E90 a or b | OCH₂C(=O)OH | H | 1 | 0 | H | tetrazolyl |
| E91 a or b | OCH₂C(=O)OH | H | 1 | 1 | H | tetrazolyl |
| E92 a or b | OCH₂C(=O)OH | H | 0 | 1 | H | tetrazolyl |
| E93 a or b | H | N(H)C(=O)E³OH | 0 | 0 | H | tetrazolyl |
| E94 a or b | H | N(H)C(=O)E³OH | 1 | 0 | H | tetrazolyl |
| E95 a or b | H | N(H)C(=O)E³OH | 1 | 1 | H | tetrazolyl |
| E96 a or b | H | N(H)C(=O)E³OH | 0 | 1 | H | tetrazolyl |
| E97 a or b | H | OCH₂C(=O)OH | 0 | 0 | H | tetrazolyl |
| E98 a or b | H | OCH₂C(=O)OH | 1 | 0 | H | tetrazolyl |
| E99 a or b | H | OCH₂C(=O)OH | 1 | 1 | H | tetrazolyl |
| E100 a or b | H | OCH₂C(=O)OH | 0 | 1 | H | tetrazolyl |

$R^{8a}$ is (i) H or (ii) CH₃; $E^3$ is (iii) a direct bond or (iv) C(=O); g is 0, 1, 2, or 3.

TABLE 7

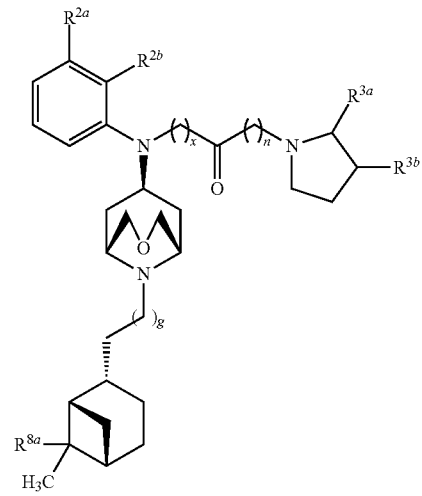

(a)

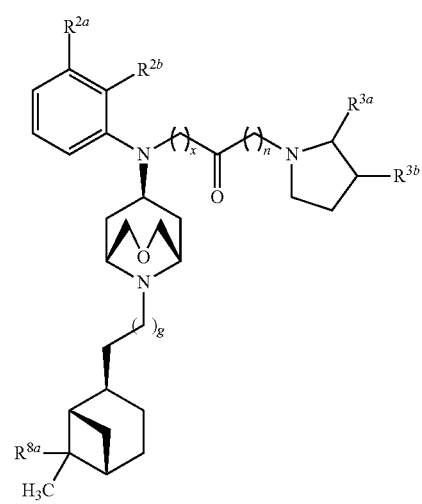

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| F1 a or b | H | H | 0 | 0 | H | H |
| F2 a or b | H | H | 1 | 0 | H | H |
| F3 a or b | H | H | 1 | 1 | H | H |
| F4 a or b | H | H | 0 | 1 | H | H |
| F5 a or b | N(H)C(=O)E³OH | H | 0 | 0 | H | H |
| F6 a or b | N(H)C(=O)E³OH | H | 1 | 0 | H | H |
| F7 a or b | N(H)C(=O)E³OH | H | 1 | 1 | H | H |
| F8 a or b | N(H)C(=O)E³OH | H | 0 | 1 | H | H |
| F9 a or b | OCH₂C(=O)OH | H | 0 | 0 | H | H |
| F10 a or b | OCH₂C(=O)OH | H | 1 | 0 | H | H |
| F11 a or b | OCH₂C(=O)OH | H | 1 | 1 | H | H |
| F12 a or b | OCH₂C(=O)OH | H | 0 | 1 | H | H |
| F13 a or b | H | N(H)C(=O)E³OH | 0 | 0 | H | H |
| F14 a or b | H | N(H)C(=O)E³OH | 1 | 0 | H | H |
| F15 a or b | H | N(H)C(=O)E³OH | 1 | 1 | H | H |
| F16 a or b | H | N(H)C(=O)E³OH | 0 | 1 | H | H |
| F17 a or b | H | OCH₂C(=O)OH | 0 | 0 | H | H |
| F18 a or b | H | OCH₂C(=O)OH | 1 | 0 | H | H |
| F19 a or b | H | OCH₂C(=O)OH | 1 | 1 | H | H |
| F20 a or b | H | OCH₂C(=O)OH | 0 | 1 | H | H |
| F21 a or b | H | H | 0 | 0 | C(=O)OH | H |
| F22 a or b | H | H | 1 | 0 | C(=O)OH | H |
| F23 a or b | H | H | 1 | 1 | C(=O)OH | H |
| F24 a or b | H | H | 0 | 1 | C(=O)OH | H |
| F25 a or b | N(H)C(=O)E³OH | H | 0 | 0 | C(=O)OH | H |
| F26 a or b | N(H)C(=O)E³OH | H | 1 | 0 | C(=O)OH | H |

TABLE 7-continued

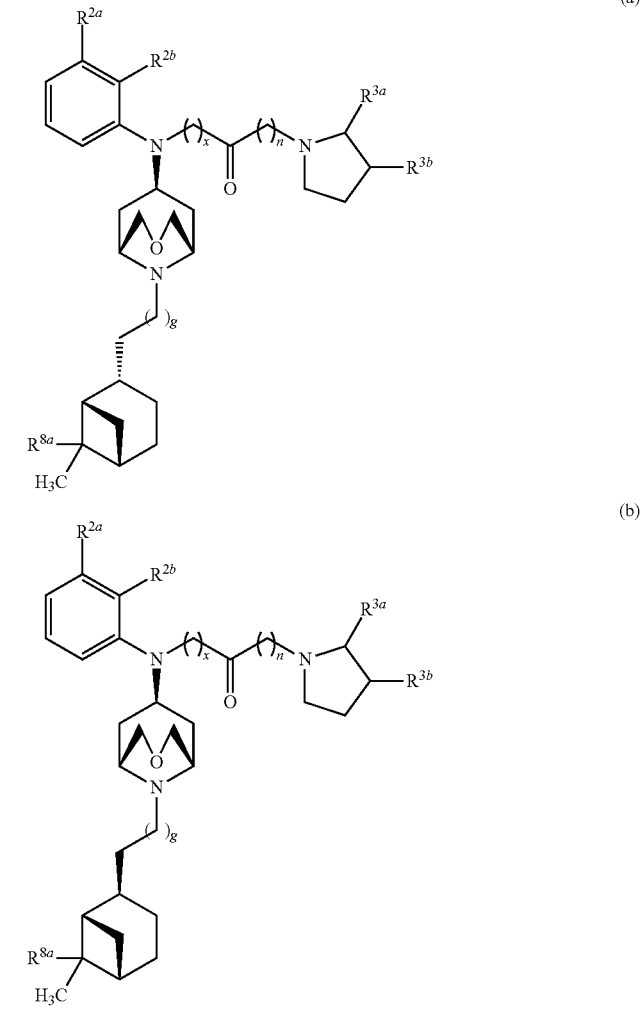

(a)

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| F27 a or b | N(H)C(=O)E$^3$OH | H | 1 | 1 | C(=O)OH | H |
| F28 a or b | N(H)C(=O)E$^3$OH | H | 0 | 1 | C(=O)OH | H |
| F29 a or b | OCH$_2$C(=O)OH | H | 0 | 0 | C(=O)OH | H |
| F30 a or b | OCH$_2$C(=O)OH | H | 1 | 0 | C(=O)OH | H |
| F31 a or b | OCH$_2$C(=O)OH | H | 1 | 1 | C(=O)OH | H |
| F32 a or b | OCH$_2$C(=O)OH | H | 0 | 1 | C(=O)OH | H |
| F33 a or b | H | N(H)C(=O)E$^3$OH | 0 | 0 | C(=O)OH | H |
| F34 a or b | H | N(H)C(=O)E$^3$OH | 1 | 0 | C(=O)OH | H |
| F35 a or b | H | N(H)C(=O)E$^3$OH | 1 | 1 | C(=O)OH | H |
| F36 a or b | H | N(H)C(=O)E$^3$OH | 0 | 1 | C(=O)OH | H |
| F37 a or b | H | OCH$_2$C(=O)OH | 0 | 0 | C(=O)OH | H |
| F38 a or b | H | OCH$_2$C(=O)OH | 1 | 0 | C(=O)OH | H |
| F39 a or b | H | OCH$_2$C(=O)OH | 1 | 1 | C(=O)OH | H |
| F40 a or b | H | OCH$_2$C(=O)OH | 0 | 1 | C(=O)OH | H |
| F41 a or b | H | H | 0 | 0 | H | C(=O)OH |
| F42 a or b | H | H | 1 | 0 | H | C(=O)OH |
| F43 a or b | H | H | 1 | 1 | H | C(=O)OH |
| F44 a or b | H | H | 0 | 1 | H | C(=O)OH |
| F45 a or b | N(H)C(=O)E$^3$OH | H | 0 | 0 | H | C(=O)OH |
| F46 a or b | N(H)C(=O)E$^3$OH | H | 1 | 0 | H | C(=O)OH |
| F47 a or b | N(H)C(=O)E$^3$OH | H | 1 | 1 | H | C(=O)OH |
| F48 a or b | N(H)C(=O)E$^3$OH | H | 0 | 1 | H | C(=O)OH |
| F49 a or b | OCH$_2$C(=O)OH | H | 0 | 0 | H | C(=O)OH |
| F50 a or b | OCH$_2$C(=O)OH | H | 1 | 0 | H | C(=O)OH |
| F51 a or b | OCH$_2$C(=O)OH | H | 1 | 1 | H | C(=O)OH |
| F52 a or b | OCH$_2$C(=O)OH | H | 0 | 1 | H | C(=O)OH |

TABLE 7-continued

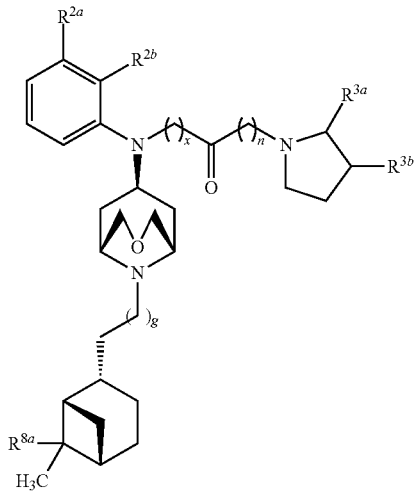

(a)


(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| F53 a or b | H | N(H)C(=O)E³OH | 0 | 0 | H | C(=O)OH |
| F54 a or b | H | N(H)C(=O)E³OH | 1 | 0 | H | C(=O)OH |
| F55 a or b | H | N(H)C(=O)E³OH | 1 | 1 | H | C(=O)OH |
| F56 a or b | H | N(H)C(=O)E³OH | 0 | 1 | H | C(=O)OH |
| F57 a or b | H | OCH₂C(=O)OH | 0 | 0 | H | C(=O)OH |
| F58 a or b | H | OCH₂C(=O)OH | 1 | 0 | H | C(=O)OH |
| F59 a or b | H | OCH₂C(=O)OH | 1 | 1 | H | C(=O)OH |
| F60 a or b | H | OCH₂C(=O)OH | 0 | 1 | H | C(=O)OH |
| F61 a or b | H | H | 0 | 0 | tetrazolyl | H |
| F62 a or b | H | H | 1 | 0 | tetrazolyl | H |
| F63 a or b | H | H | 1 | 1 | tetrazolyl | H |
| F64 a or b | H | H | 0 | 1 | tetrazolyl | H |
| F65 a or b | N(H)C(=O)E³OH | H | 0 | 0 | tetrazolyl | H |
| F66 a or b | N(H)C(=O)E³OH | H | 1 | 0 | tetrazolyl | H |
| F67 a or b | N(H)C(=O)E³OH | H | 1 | 1 | tetrazolyl | H |
| F68 a or b | N(H)C(=O)E³OH | H | 0 | 1 | tetrazolyl | H |
| F69 a or b | OCH₂C(=O)OH | H | 0 | 0 | tetrazolyl | H |
| F70 a or b | OCH₂C(=O)OH | H | 1 | 0 | tetrazolyl | H |
| F71 a or b | OCH₂C(=O)OH | H | 1 | 1 | tetrazolyl | H |
| F72 a or b | OCH₂C(=O)OH | H | 0 | 1 | tetrazolyl | H |
| F73 a or b | H | N(H)C(=O)E³OH | 0 | 0 | tetrazolyl | H |
| F74 a or b | H | N(H)C(=O)E³OH | 1 | 0 | tetrazolyl | H |
| F75 a or b | H | N(H)C(=O)E³OH | 1 | 1 | tetrazolyl | H |
| F76 a or b | H | N(H)C(=O)E³OH | 0 | 1 | tetrazolyl | H |
| F77 a or b | H | OCH₂C(=O)OH | 0 | 0 | tetrazolyl | H |
| F78 a or b | H | OCH₂C(=O)OH | 1 | 0 | tetrazolyl | H |

TABLE 7-continued (a)
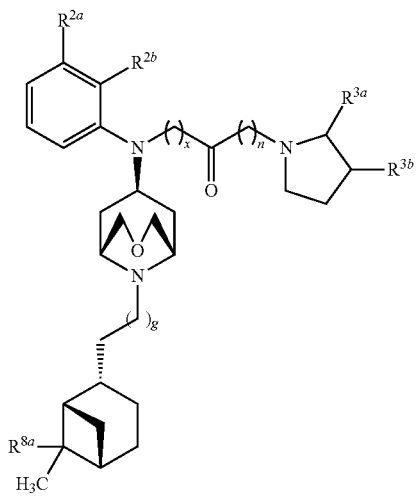

(b)
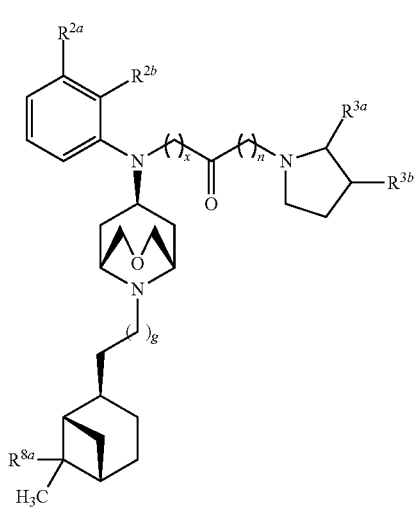

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| F79 a or b | H | OCH$_2$C(=O)OH | 1 | 1 | tetrazolyl | H |
| F80 a or b | H | OCH$_2$C(=O)OH | 0 | 1 | tetrazolyl | H |
| F81 a or b | H | H | 0 | 0 | H | tetrazolyl |
| F82 a or b | H | H | 1 | 0 | H | tetrazolyl |
| F83 a or b | H | H | 1 | 1 | H | tetrazolyl |
| F84 a or b | H | H | 0 | 1 | H | tetrazolyl |
| F85 a or b | N(H)C(=O)E$^3$OH | H | 0 | 0 | H | tetrazolyl |
| F86 a or b | N(H)C(=O)E$^3$OH | H | 1 | 0 | H | tetrazolyl |
| F87 a or b | N(H)C(=O)E$^3$OH | H | 1 | 1 | H | tetrazolyl |
| F88 a or b | N(H)C(=O)E$^3$OH | H | 0 | 1 | H | tetrazolyl |
| F89 a or b | OCH$_2$C(=O)OH | H | 0 | 0 | H | tetrazolyl |
| F90 a or b | OCH$_2$C(=O)OH | H | 1 | 0 | H | tetrazolyl |
| F91 a or b | OCH$_2$C(=O)OH | H | 1 | 1 | H | tetrazolyl |
| F92 a or b | OCH$_2$C(=O)OH | H | 0 | 1 | H | tetrazolyl |
| F93 a or b | H | N(H)C(=O)E$^3$OH | 0 | 0 | H | tetrazolyl |
| F94 a or b | H | N(H)C(=O)E$^3$OH | 1 | 0 | H | tetrazolyl |
| F95 a or b | H | N(H)C(=O)E$^3$OH | 1 | 1 | H | tetrazolyl |
| F96 a or b | H | N(H)C(=O)E$^3$OH | 0 | 1 | H | tetrazolyl |
| F97 a or b | H | OCH$_2$C(=O)OH | 0 | 0 | H | tetrazolyl |
| F98 a or b | H | OCH$_2$C(=O)OH | 1 | 0 | H | tetrazolyl |
| F99 a or b | H | OCH$_2$C(=O)OH | 1 | 1 | H | tetrazolyl |
| F100 a or b | H | OCH$_2$C(=O)OH | 0 | 1 | H | tetrazolyl |

$R^{8a}$ is (i) H or (ii) CH$_3$; E$^3$ is (iii) a direct bond or (iv) C(=O); g is 0, 1, 2, or 3.

TABLE 8
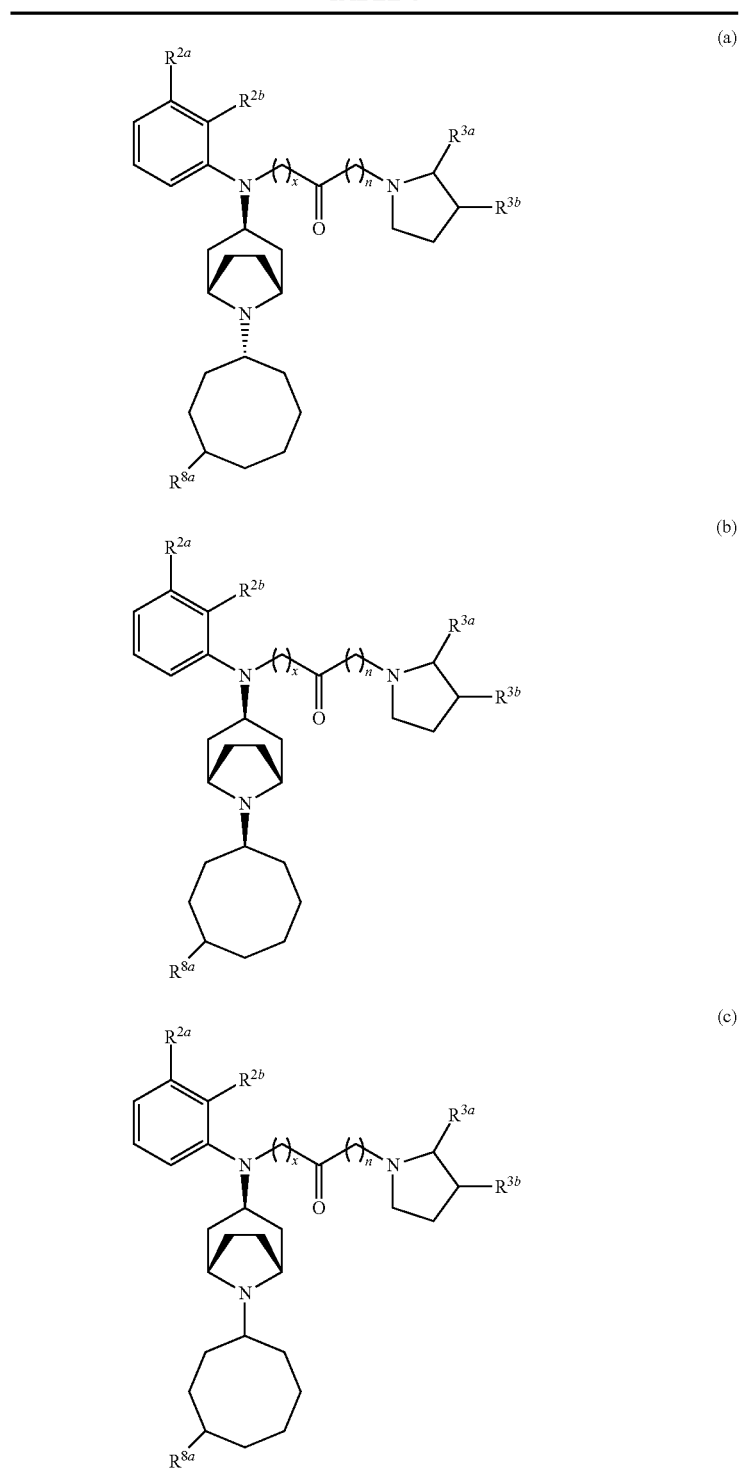
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G1 a, b, or c | H | H | 0 | 0 | H | H |
| G2 a, b, or c | H | H | 1 | 0 | H | H |
| G3 a, b, or c | H | H | 1 | 1 | H | H |
| G4 a, b, or c | H | H | 0 | 1 | H | H |
| G5 a, b, or c | N(H)C(=O)E$^3$OH | H | 0 | 0 | H | H |
| G6 a, b, or c | N(H)C(=O)E$^3$OH | H | 1 | 0 | H | H |
| G7 a, b, or c | N(H)C(=O)E$^3$OH | H | 1 | 1 | H | H |

TABLE 8-continued
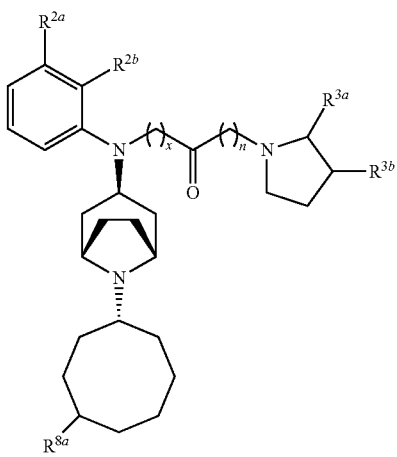
(a)
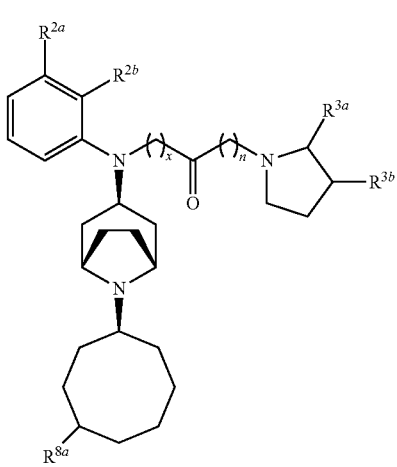
(b)
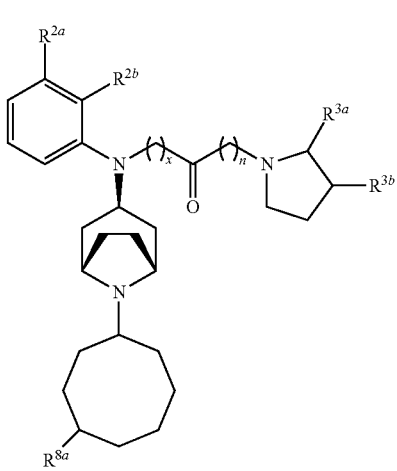
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G8 a, b, or c | N(H)C(=O)E$^3$OH | H | 0 | 1 | H | H |
| G9 a, b, or c | OCH$_2$C(=O)OH | H | 0 | 0 | H | H |
| G10 a, b, or c | OCH$_2$C(=O)OH | H | 1 | 0 | H | H |
| G11 a, b, or c | OCH$_2$C(=O)OH | H | 1 | 1 | H | H |
| G12 a, b, or c | OCH$_2$C(=O)OH | H | 0 | 1 | H | H |
| G13 a, b, or c | H | N(H)C(=O)E$^3$OH | 0 | 0 | H | H |
| G14 a, b, or c | H | N(H)C(=O)E$^3$OH | 1 | 0 | H | H |

TABLE 8-continued
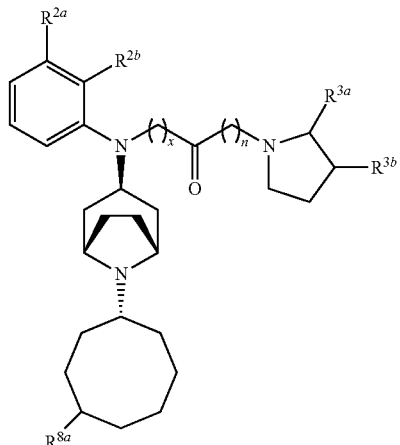
(a)
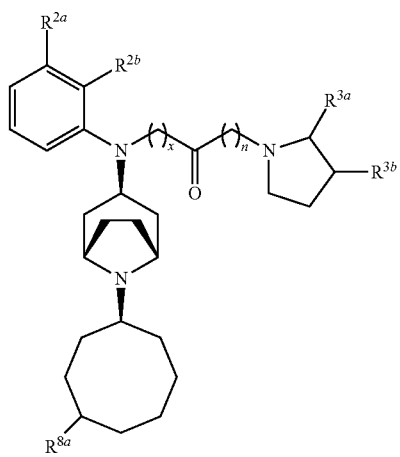
(b)
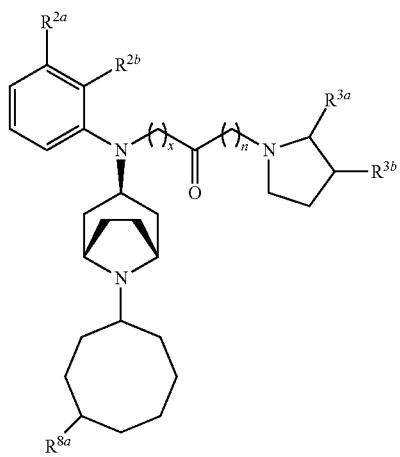
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G15 a, b, or c | H | N(H)C(=O)E³OH | 1 | 1 | H | H |
| G16 a, b, or c | H | N(H)C(=O)E³OH | 0 | 1 | H | H |
| G17 a, b, or c | H | OCH₂C(=O)OH | 0 | 0 | H | H |
| G18 a, b, or c | H | OCH₂C(=O)OH | 1 | 0 | H | H |
| G19 a, b, or c | H | OCH₂C(=O)OH | 1 | 1 | H | H |
| G20 a, b, or c | H | OCH₂C(=O)OH | 0 | 1 | H | H |
| G21 a, b, or c | H | H | 0 | 0 | C(=O)OH | H |

TABLE 8-continued
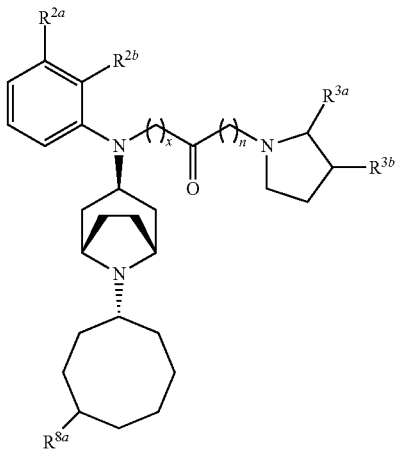
(a)
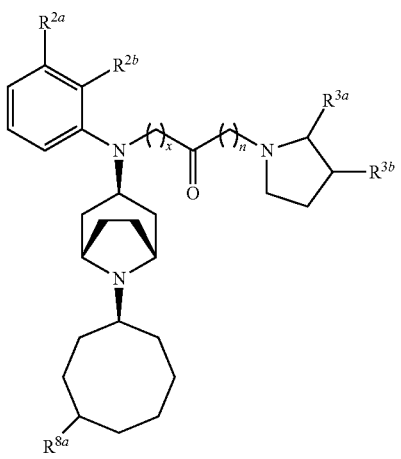
(b)
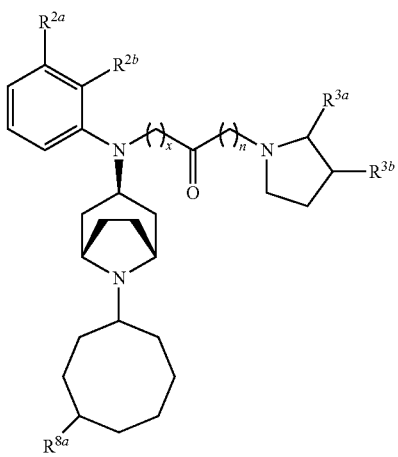
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G22 a, b, or c | H | H | 1 | 0 | C(=O)OH | H |
| G23 a, b, or c | H | H | 1 | 1 | C(=O)OH | H |
| G24 a, b, or c | H | H | 0 | 1 | C(=O)OH | H |
| G25 a, b, or c | N(H)C(=O)$E^3$OH | H | 0 | 0 | C(=O)OH | H |
| G26 a, b, or c | N(H)C(=O)$E^3$OH | H | 1 | 0 | C(=O)OH | H |
| G27 a, b, or c | N(H)C(=O)$E^3$OH | H | 1 | 1 | C(=O)OH | H |
| G28 a, b, or c | N(H)C(=O)$E^3$OH | H | 0 | 1 | C(=O)OH | H |

TABLE 8-continued
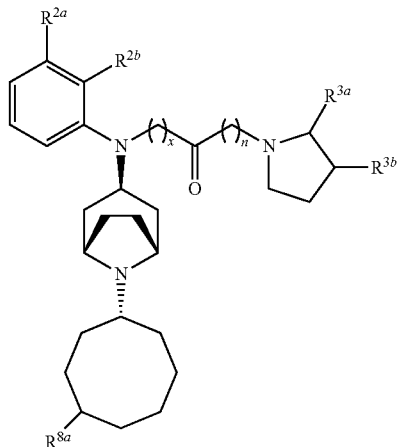
(a)
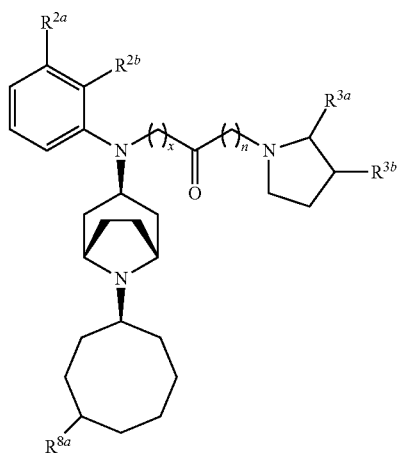
(b)
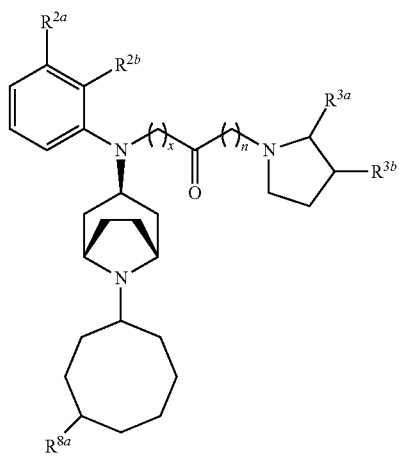
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G29 a, b, or c | $OCH_2C(=O)OH$ | H | 0 | 0 | $C(=O)OH$ | H |
| G30 a, b, or c | $OCH_2C(=O)OH$ | H | 1 | 0 | $C(=O)OH$ | H |
| G31 a, b, or c | $OCH_2C(=O)OH$ | H | 1 | 1 | $C(=O)OH$ | H |
| G32 a, b, or c | $OCH_2C(=O)OH$ | H | 0 | 1 | $C(=O)OH$ | H |
| G33 a, b, or c | H | $N(H)C(=O)E^3OH$ | 0 | 0 | $C(=O)OH$ | H |
| G34 a, b, or c | H | $N(H)C(=O)E^3OH$ | 1 | 0 | $C(=O)OH$ | H |
| G35 a, b, or c | H | $N(H)C(=O)E^3OH$ | 1 | 1 | $C(=O)OH$ | H |

TABLE 8-continued
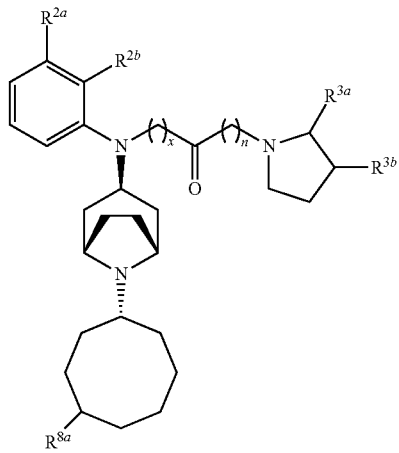
(a)
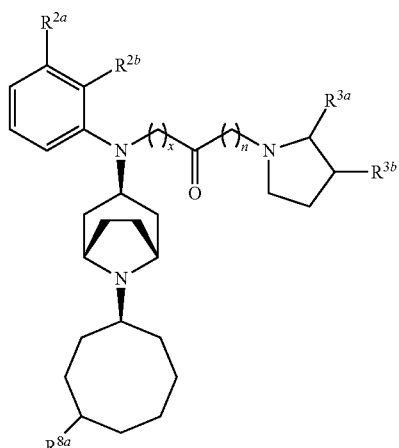
(b)
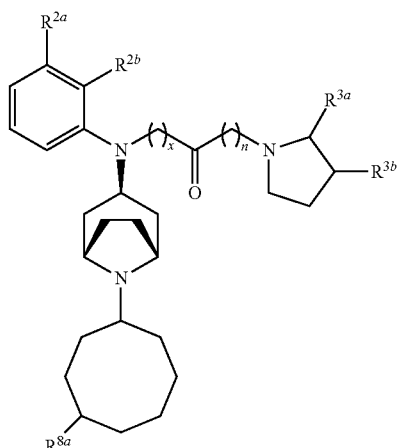
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G36 a, b, or c | H | $N(H)C(=O)E^3OH$ | 0 | 1 | $C(=O)OH$ | H |
| G37 a, b, or c | H | $OCH_2C(=O)OH$ | 0 | 0 | $C(=O)OH$ | H |
| G38 a, b, or c | H | $OCH_2C(=O)OH$ | 1 | 0 | $C(=O)OH$ | H |
| G39 a, b, or c | H | $OCH_2C(=O)OH$ | 1 | 1 | $C(=O)OH$ | H |
| G40 a, b, or c | H | $OCH_2C(=O)OH$ | 0 | 1 | $C(=O)OH$ | H |
| G41 a, b, or c | H | H | 0 | 0 | H | $C(=O)OH$ |
| G42 a, b, or c | H | H | 1 | 0 | H | $C(=O)OH$ |

TABLE 8-continued
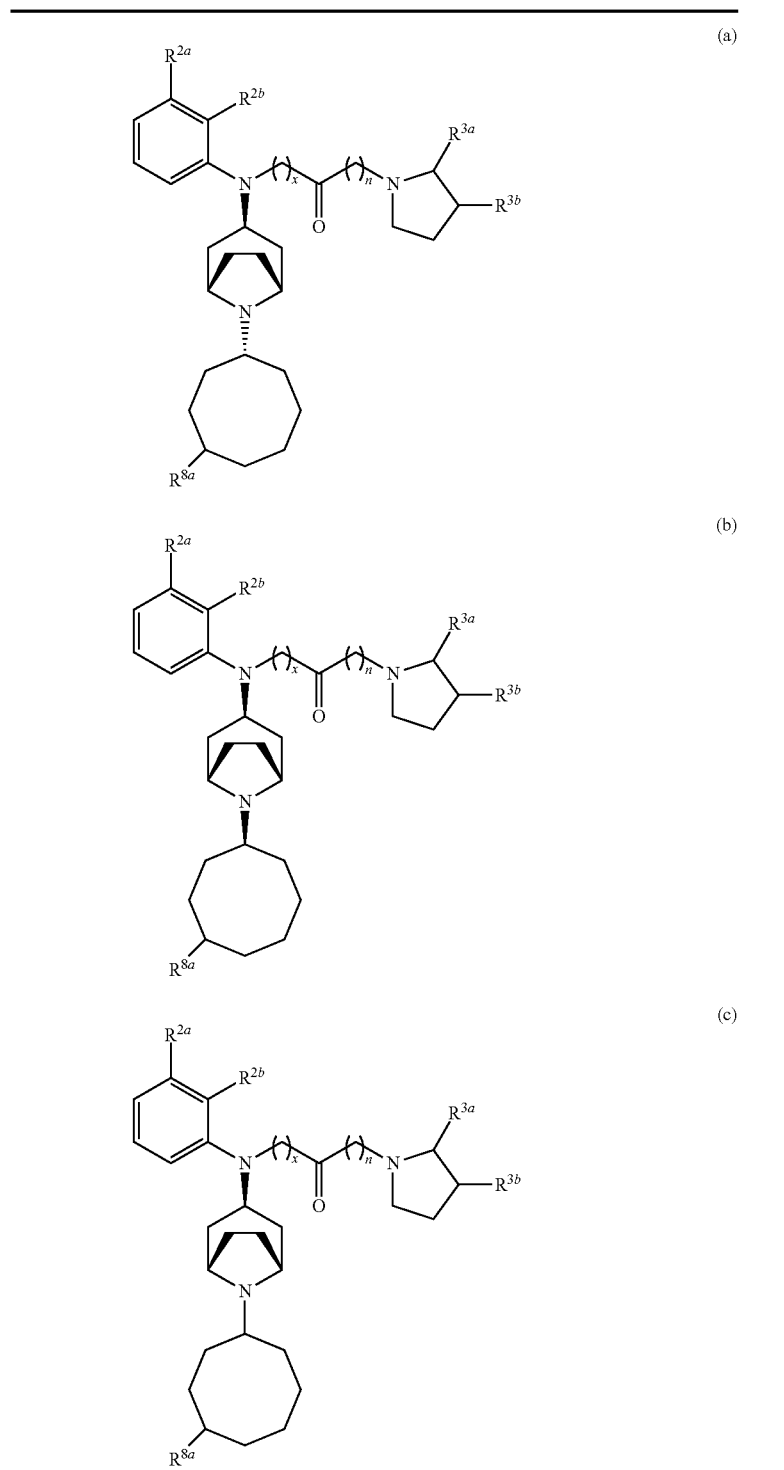
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G43 a, b, or c | H | H | 1 | 1 | H | C(=O)OH |
| G44 a, b, or c | H | H | 0 | 1 | H | C(=O)OH |
| G45 a, b, or c | N(H)C(=O)E$^3$OH | H | 0 | 0 | H | C(=O)OH |
| G46 a, b, or c | N(H)C(=O)E$^3$OH | H | 1 | 0 | H | C(=O)OH |
| G47 a, b, or c | N(H)C(=O)E$^3$OH | H | 1 | 1 | H | C(=O)OH |
| G48 a, b, or c | N(H)C(=O)E$^3$OH | H | 0 | 1 | H | C(=O)OH |
| G49 a, b, or c | OCH$_2$C(=O)OH | H | 0 | 0 | H | C(=O)OH |

TABLE 8-continued
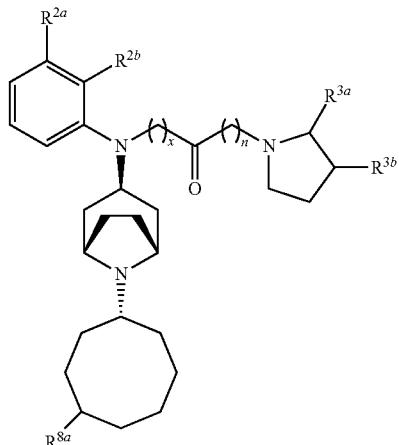
(a)
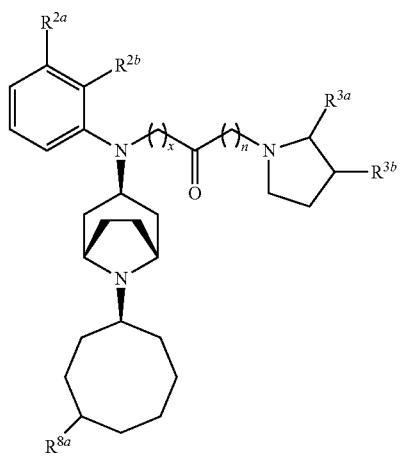
(b)
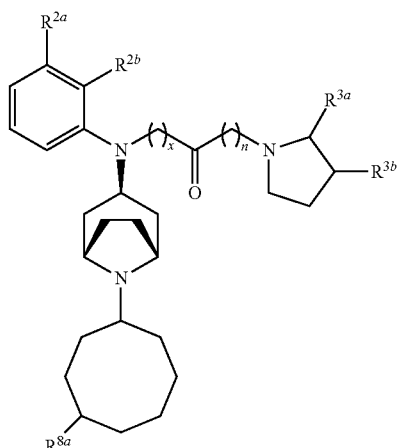
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G50 a, b, or c | $OCH_2C(=O)OH$ | H | 1 | 0 | H | $C(=O)OH$ |
| G51 a, b, or c | $OCH_2C(=O)OH$ | H | 1 | 1 | H | $C(=O)OH$ |
| G52 a, b, or c | $OCH_2C(=O)OH$ | H | 0 | 1 | H | $C(=O)OH$ |
| G53 a, b, or c | H | $N(H)C(=O)E^3OH$ | 0 | 0 | H | $C(=O)OH$ |
| G54 a, b, or c | H | $N(H)C(=O)E^3OH$ | 1 | 0 | H | $C(=O)OH$ |
| G55 a, b, or c | H | $N(H)C(=O)E^3OH$ | 1 | 1 | H | $C(=O)OH$ |
| G56 a, b, or c | H | $N(H)C(=O)E^3OH$ | 0 | 1 | H | $C(=O)OH$ |

TABLE 8-continued
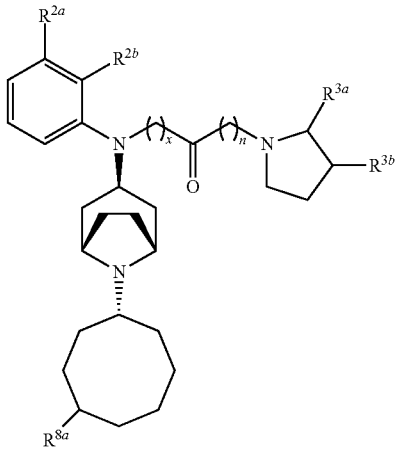
(a)
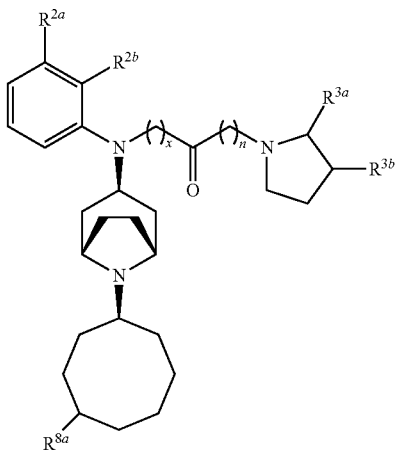
(b)
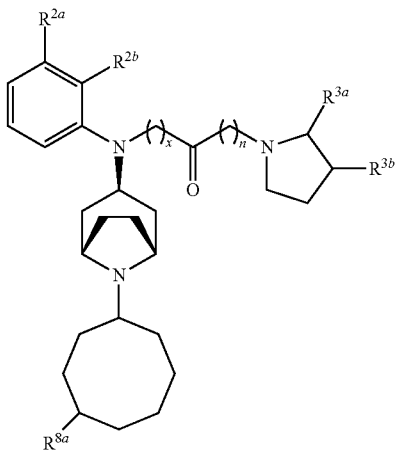
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G57 a, b, or c | H | $OCH_2C(=O)OH$ | 0 | 0 | H | $C(=O)OH$ |
| G58 a, b, or c | H | $OCH_2C(=O)OH$ | 1 | 0 | H | $C(=O)OH$ |
| G59 a, b, or c | H | $OCH_2C(=O)OH$ | 1 | 1 | H | $C(=O)OH$ |
| G60 a, b, or c | H | $OCH_2C(=O)OH$ | 0 | 1 | H | $C(=O)OH$ |
| G61 a, b, or c | H | H | 0 | 0 | tetrazolyl | H |
| G62 a, b, or c | H | H | 1 | 0 | tetrazolyl | H |
| G63 a, b, or c | H | H | 1 | 1 | tetrazolyl | H |

TABLE 8-continued
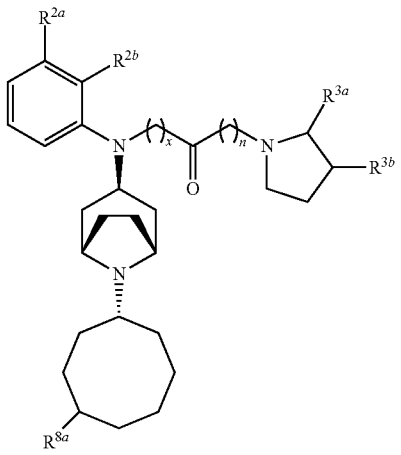
(a)
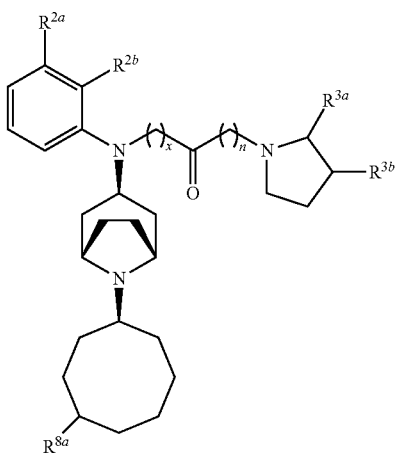
(b)
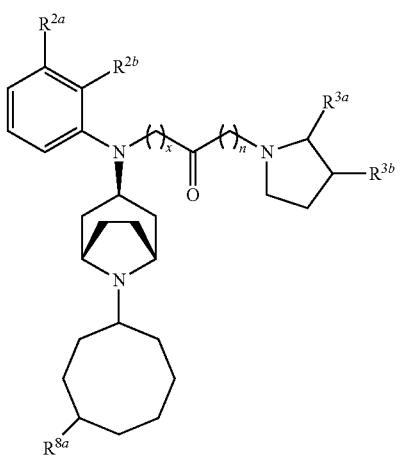
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G64 a, b, or c | H | H | 0 | 1 | tetrazolyl | H |
| G65 a, b, or c | N(H)C(=O)E³OH | H | 0 | 0 | tetrazolyl | H |
| G66 a, b, or c | N(H)C(=O)E³OH | H | 1 | 0 | tetrazolyl | H |
| G67 a, b, or c | N(H)C(=O)E³OH | H | 1 | 1 | tetrazolyl | H |
| G68 a, b, or c | N(H)C(=O)E³OH | H | 0 | 1 | tetrazolyl | H |
| G69 a, b, or c | OCH₂C(=O)OH | H | 0 | 0 | tetrazolyl | H |
| G70 a, b, or c | OCH₂C(=O)OH | H | 1 | 0 | tetrazolyl | H |

TABLE 8-continued

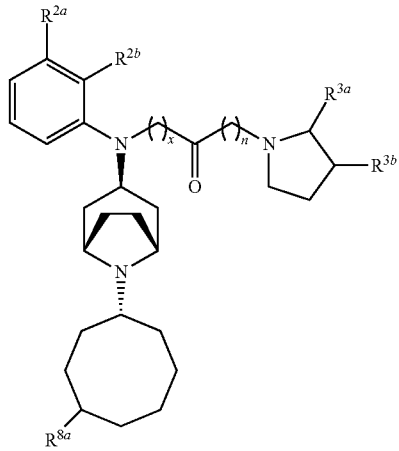

(a)

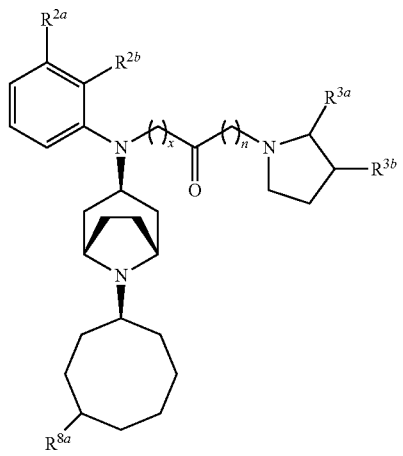

(b)

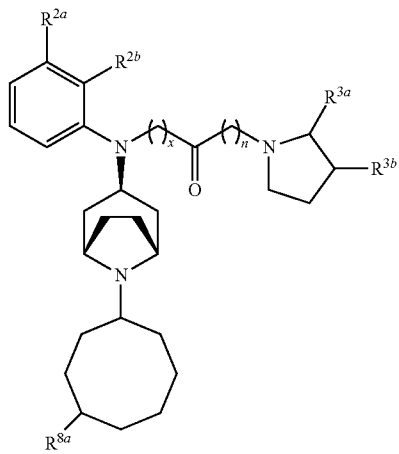

(c)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| G71 a, b, or c | OCH$_2$C(=O)OH | H | 1 | 1 | tetrazolyl | H |
| G72 a, b, or c | OCH$_2$C(=O)OH | H | 0 | 1 | tetrazolyl | H |
| G73 a, b, or c | H | N(H)C(=O)E$^3$OH | 0 | 0 | tetrazolyl | H |
| G74 a, b, or c | H | N(H)C(=O)E$^3$OH | 1 | 0 | tetrazolyl | H |
| G75 a, b, or c | H | N(H)C(=O)E$^3$OH | 1 | 1 | tetrazolyl | H |
| G76 a, b, or c | H | N(H)C(=O)E$^3$OH | 0 | 1 | tetrazolyl | H |
| G77 a, b, or c | H | OCH$_2$C(=O)OH | 0 | 0 | tetrazolyl | H |

TABLE 8-continued
(a)
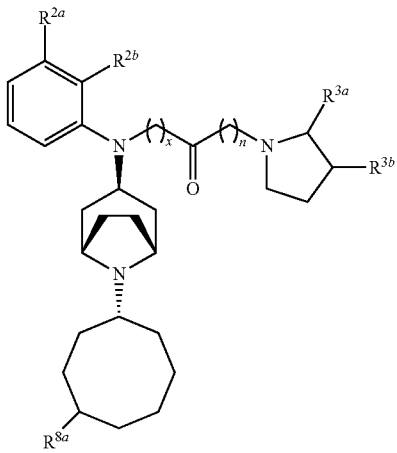
(b)
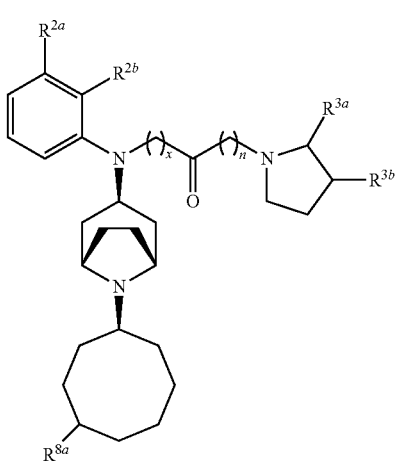
(c)
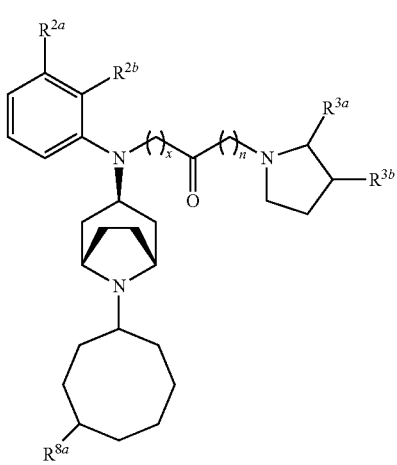
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G78 a, b, or c | H | OCH$_2$C(=O)OH | 1 | 0 | tetrazolyl | H |
| G79 a, b, or c | H | OCH$_2$C(=O)OH | 1 | 1 | tetrazolyl | H |
| G80 a, b, or c | H | OCH$_2$C(=O)OH | 0 | 1 | tetrazolyl | H |
| G81 a, b, or c | H | H | 0 | 0 | H | tetrazolyl |
| G82 a, b, or c | H | H | 1 | 0 | H | tetrazolyl |
| G83 a, b, or c | H | H | 1 | 1 | H | tetrazolyl |
| G84 a, b, or c | H | H | 0 | 1 | H | tetrazolyl |

TABLE 8-continued

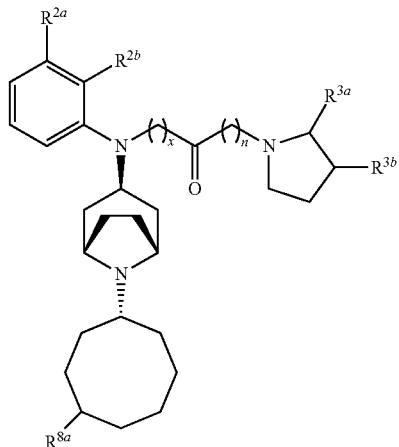

(a)

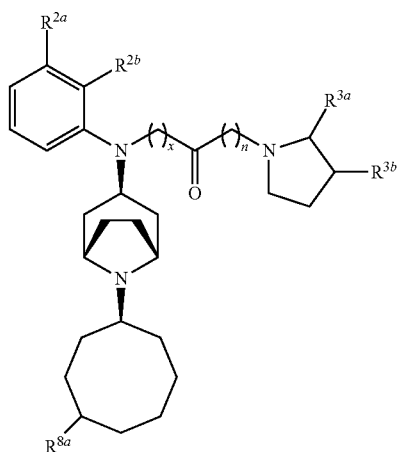

(b)

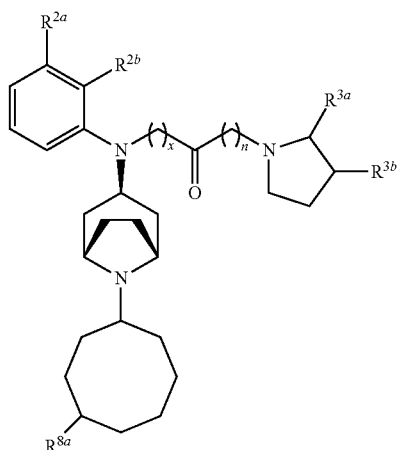

(c)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| G85 a, b, or c | $N(H)C(=O)E^3OH$ | H | 0 | 0 | H | tetrazolyl |
| G86 a, b, or c | $N(H)C(=O)E^3OH$ | H | 1 | 0 | H | tetrazolyl |
| G87 a, b, or c | $N(H)C(=O)E^3OH$ | H | 1 | 1 | H | tetrazolyl |
| G88 a, b, or c | $N(H)C(=O)E^3OH$ | H | 0 | 1 | H | tetrazolyl |
| G89 a, b, or c | $OCH_2C(=O)OH$ | H | 0 | 0 | H | tetrazolyl |
| G90 a, b, or c | $OCH_2C(=O)OH$ | H | 1 | 0 | H | tetrazolyl |
| G91 a, b, or c | $OCH_2C(=O)OH$ | H | 1 | 1 | H | tetrazolyl |

TABLE 8-continued

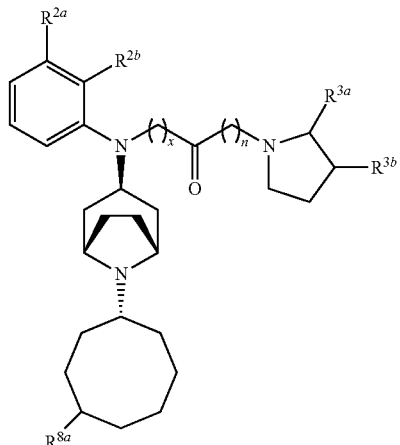

(a)

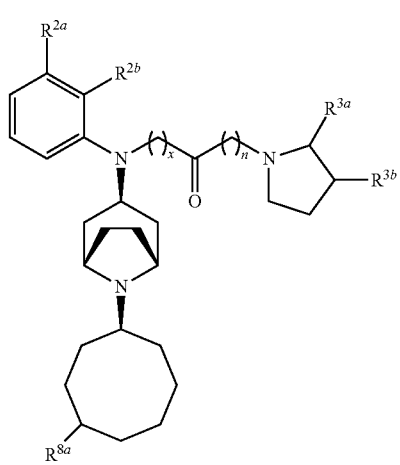

(b)

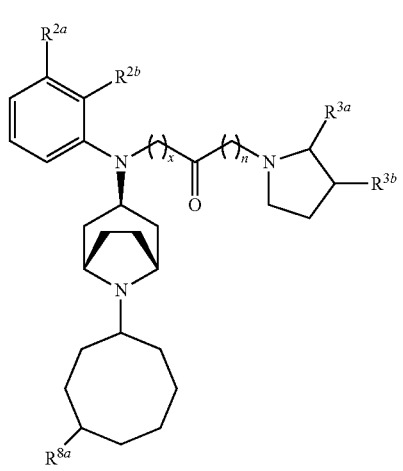

(c)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| G92 a, b, or c | $OCH_2C(=O)OH$ | H | 0 | 1 | H | tetrazolyl |
| G93 a, b, or c | H | $N(H)C(=O)E^3OH$ | 0 | 0 | H | tetrazolyl |
| G94 a, b, or c | H | $N(H)C(=O)E^3OH$ | 1 | 0 | H | tetrazolyl |
| G95 a, b, or c | H | $N(H)C(=O)E^3OH$ | 1 | 1 | H | tetrazolyl |
| G96 a, b, or c | H | $N(H)C(=O)E^3OH$ | 0 | 1 | H | tetrazolyl |
| G97 a, b, or c | H | $OCH_2C(=O)OH$ | 0 | 0 | H | tetrazolyl |
| G98 a, b, or c | H | $OCH_2C(=O)OH$ | 1 | 0 | H | tetrazolyl |

TABLE 8-continued
(a)
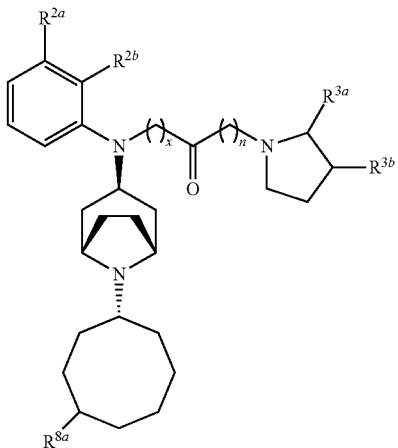
(b)
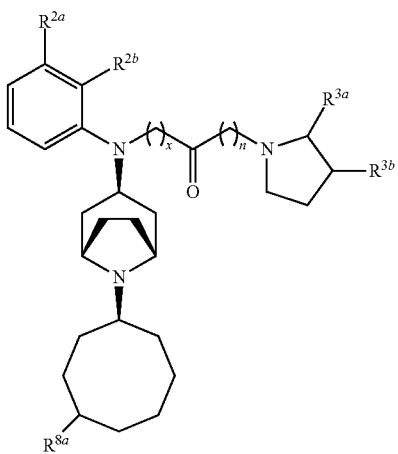
(c)
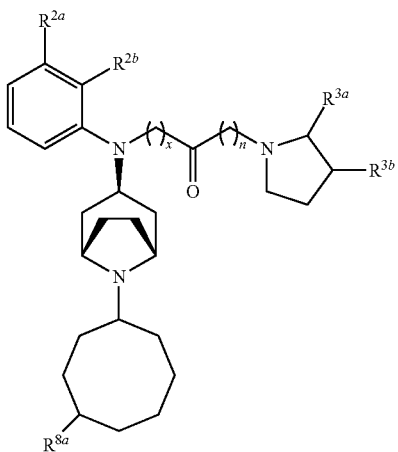
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| G99 a, b, or c | H | OCH$_2$C(=O)OH | 1 | 1 | H | tetrazolyl |
| G100 a, b, or c | H | OCH$_2$C(=O)OH | 0 | 1 | H | tetrazolyl |
$R^{8a}$ is (i) H or (ii) CH$_3$; $E^3$ is (iii) a direct bond or (iv) C(=O).

TABLE 9
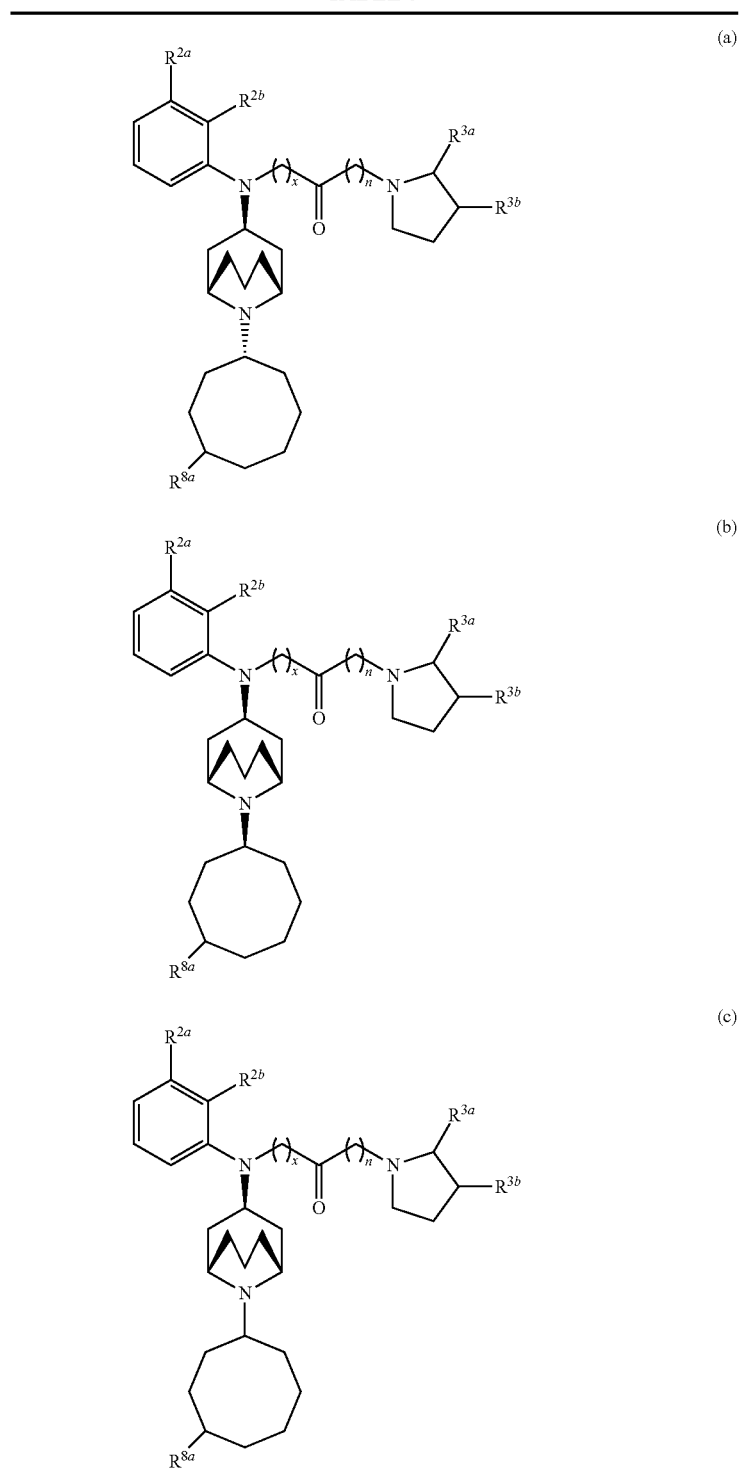
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H1 a, b, or c | H | H | 0 | 0 | H | H |
| H2 a, b, or c | H | H | 1 | 0 | H | H |
| H3 a, b, or c | H | H | 1 | 1 | H | H |
| H4 a, b, or c | H | H | 0 | 1 | H | H |
| H5 a, b, or c | N(H)C(=O)E³OH | H | 0 | 0 | H | H |
| H6 a, b, or c | N(H)C(=O)E³OH | H | 1 | 0 | H | H |
| H7 a, b, or c | N(H)C(=O)E³OH | H | 1 | 1 | H | H |

TABLE 9-continued
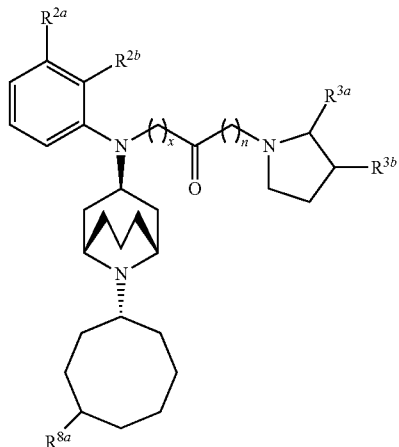
(a)
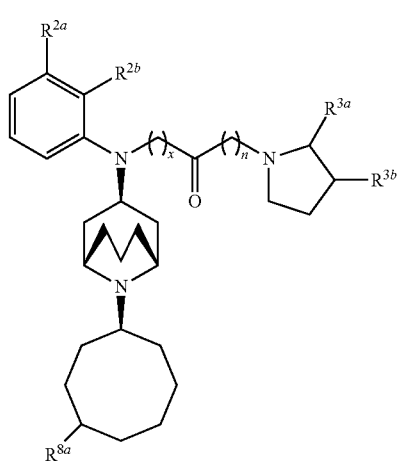
(b)
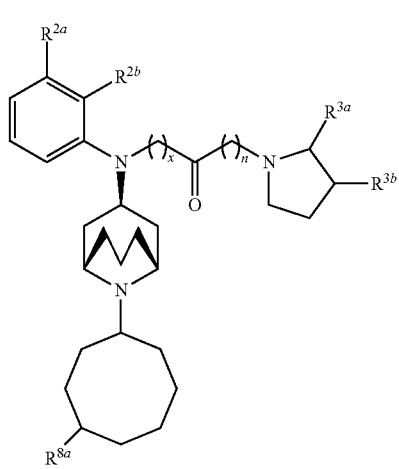
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H8 a, b, or c | N(H)C(=O)$E^3$OH | H | 0 | 1 | H | H |
| H9 a, b, or c | OCH$_2$C(=O)OH | H | 0 | 0 | H | H |
| H10 a, b, or c | OCH$_2$C(=O)OH | H | 1 | 0 | H | H |
| H11 a, b, or c | OCH$_2$C(=O)OH | H | 1 | 1 | H | H |
| H12 a, b, or c | OCH$_2$C(=O)OH | H | 0 | 1 | H | H |
| H13 a, b, or c | H | N(H)C(=O)$E^3$OH | 0 | 0 | H | H |
| H14 a, b, or c | H | N(H)C(=O)$E^3$OH | 1 | 0 | H | H |

TABLE 9-continued
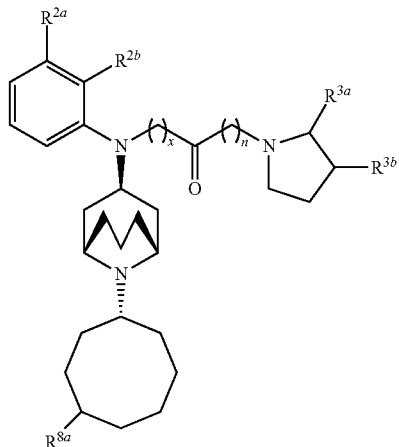
(a)
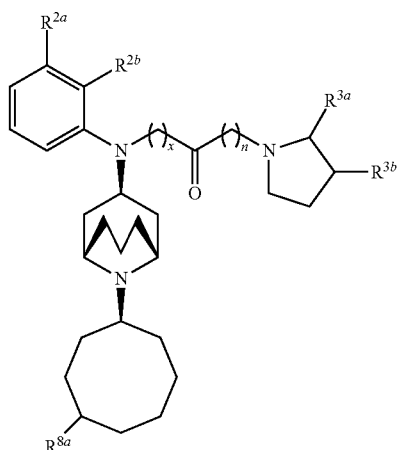
(b)
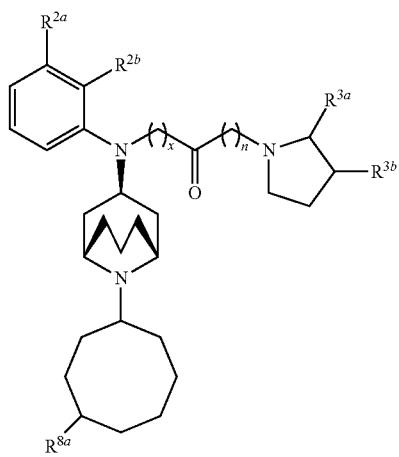
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H15 a, b, or c | H | N(H)C(=O)E$^3$OH | 1 | 1 | H | H |
| H16 a, b, or c | H | N(H)C(=O)E$^3$OH | 0 | 1 | H | H |
| H17 a, b, or c | H | OCH$_2$C(=O)OH | 0 | 0 | H | H |
| H18 a, b, or c | H | OCH$_2$C(=O)OH | 1 | 0 | H | H |
| H19 a, b, or c | H | OCH$_2$C(=O)OH | 1 | 1 | H | H |
| H20 a, b, or c | H | OCH$_2$C(=O)OH | 0 | 1 | H | H |
| H21 a, b, or c | H | H | 0 | 0 | C(=O)OH | H |

TABLE 9-continued
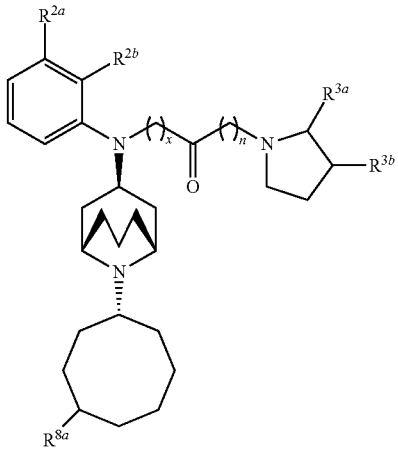
(a)
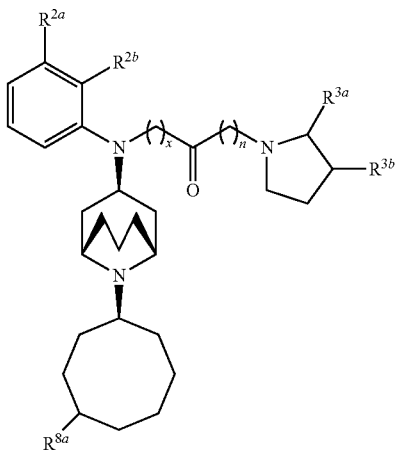
(b)
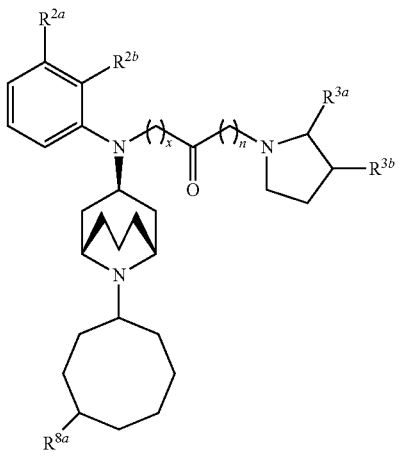
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H22 a, b, or c | H | H | 1 | 0 | C(=O)OH | H |
| H23 a, b, or c | H | H | 1 | 1 | C(=O)OH | H |
| H24 a, b, or c | H | H | 0 | 1 | C(=O)OH | H |
| H25 a, b, or c | N(H)C(=O)E$^3$OH | H | 0 | 0 | C(=O)OH | H |
| H26 a, b, or c | N(H)C(=O)E$^3$OH | H | 1 | 0 | C(=O)OH | H |
| H27 a, b, or c | N(H)C(=O)E$^3$OH | H | 1 | 1 | C(=O)OH | H |
| H28 a, b, or c | N(H)C(=O)E$^3$OH | H | 0 | 1 | C(=O)OH | H |

TABLE 9-continued
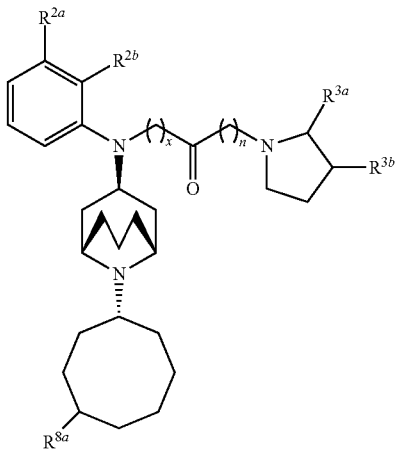
(a)
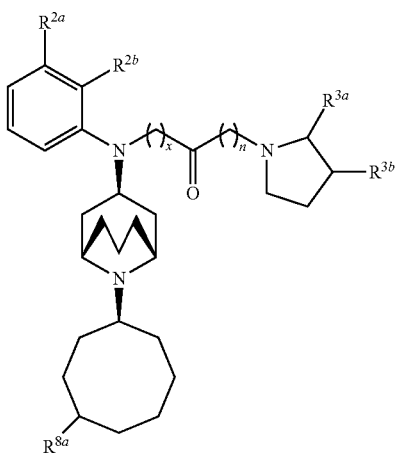
(b)
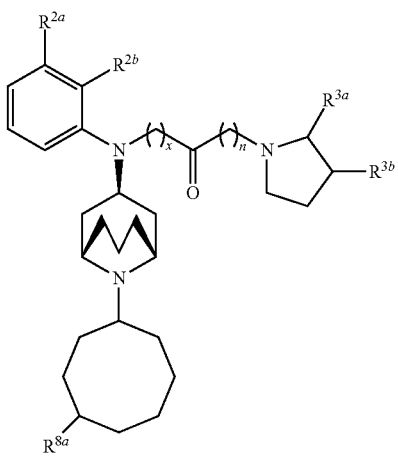
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H29 a, b, or c | OCH$_2$C(=O)OH | H | 0 | 0 | C(=O)OH | H |
| H30 a, b, or c | OCH$_2$C(=O)OH | H | 1 | 0 | C(=O)OH | H |
| H31 a, b, or c | OCH$_2$C(=O)OH | H | 1 | 1 | C(=O)OH | H |
| H32 a, b, or c | OCH$_2$C(=O)OH | H | 0 | 1 | C(=O)OH | H |
| H33 a, b, or c | H | N(H)C(=O)E$^3$OH | 0 | 0 | C(=O)OH | H |
| H34 a, b, or c | H | N(H)C(=O)E$^3$OH | 1 | 0 | C(=O)OH | H |
| H35 a, b, or c | H | N(H)C(=O)E$^3$OH | 1 | 1 | C(=O)OH | H |

TABLE 9-continued
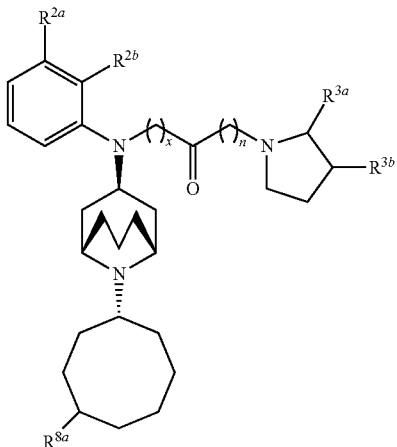
(a)

(b)

(c)
and pharmaceutically acceptable salts and solvates thereof, where:
| Compound      | $R^{2a}$ | $R^{2b}$            | x | n | $R^{3a}$   | $R^{3b}$   |
|---------------|----------|---------------------|---|---|------------|------------|
| H36 a, b, or c | H       | N(H)C(=O)E³OH      | 0 | 1 | C(=O)OH    | H          |
| H37 a, b, or c | H       | OCH₂C(=O)OH        | 0 | 0 | C(=O)OH    | H          |
| H38 a, b, or c | H       | OCH₂C(=O)OH        | 1 | 0 | C(=O)OH    | H          |
| H39 a, b, or c | H       | OCH₂C(=O)OH        | 1 | 1 | C(=O)OH    | H          |
| H40 a, b, or c | H       | OCH₂C(=O)OH        | 0 | 1 | C(=O)OH    | H          |
| H41 a, b, or c | H       | H                   | 0 | 0 | H          | C(=O)OH    |
| H42 a, b, or c | H       | H                   | 1 | 0 | H          | C(=O)OH    |

TABLE 9-continued
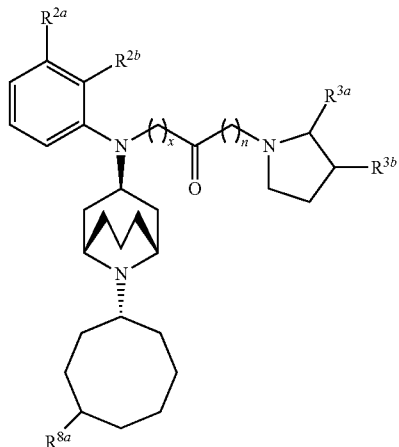
(a)
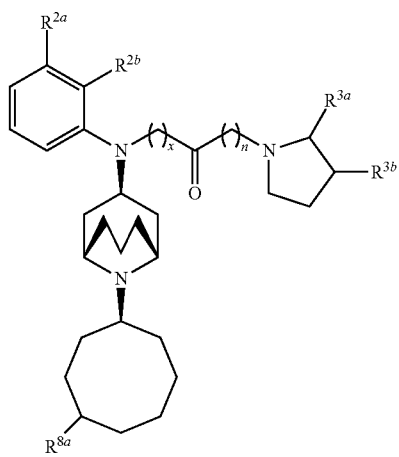
(b)
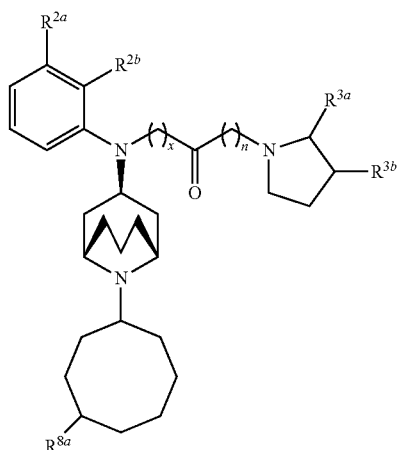
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H43 a, b, or c | H | H | 1 | 1 | H | C(=O)OH |
| H44 a, b, or c | H | H | 0 | 1 | H | C(=O)OH |
| H45 a, b, or c | N(H)C(=O)E$^3$OH | H | 0 | 0 | H | C(=O)OH |
| H46 a, b, or c | N(H)C(=O)E$^3$OH | H | 1 | 0 | H | C(=O)OH |
| H47 a, b, or c | N(H)C(=O)E$^3$OH | H | 1 | 1 | H | C(=O)OH |
| H48 a, b, or c | N(H)C(=O)E$^3$OH | H | 0 | 1 | H | C(=O)OH |
| H49 a, b, or c | OCH$_2$C(=O)OH | H | 0 | 0 | H | C(=O)OH |

TABLE 9-continued
(a)
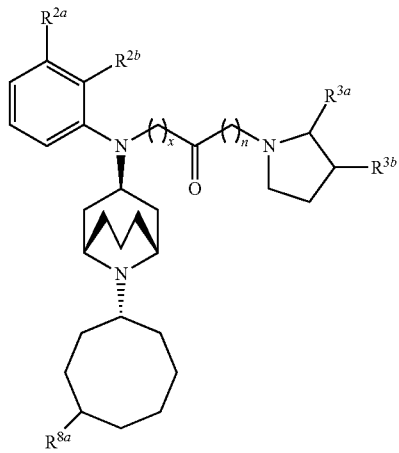
(b)
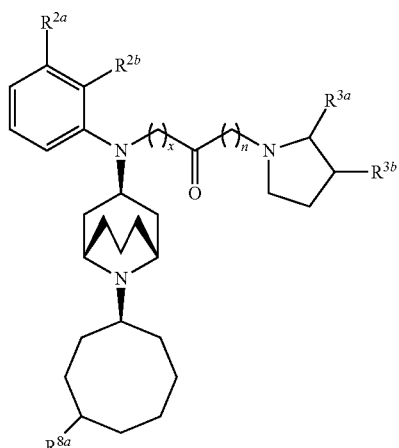
(c)
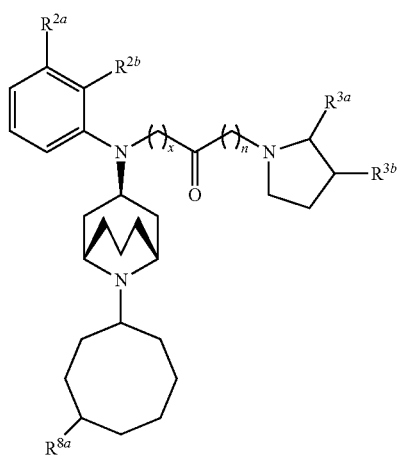
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H50 a, b, or c | $OCH_2C(=O)OH$ | H | 1 | 0 | H | $C(=O)OH$ |
| H51 a, b, or c | $OCH_2C(=O)OH$ | H | 1 | 1 | H | $C(=O)OH$ |
| H52 a, b, or c | $OCH_2C(=O)OH$ | H | 0 | 1 | H | $C(=O)OH$ |
| H53 a, b, or c | H | $N(H)C(=O)E^3OH$ | 0 | 0 | H | $C(=O)OH$ |
| H54 a, b, or c | H | $N(H)C(=O)E^3OH$ | 1 | 0 | H | $C(=O)OH$ |
| H55 a, b, or c | H | $N(H)C(=O)E^3OH$ | 1 | 1 | H | $C(=O)OH$ |
| H56 a, b, or c | H | $N(H)C(=O)E^3OH$ | 0 | 1 | H | $C(=O)OH$ |

TABLE 9-continued
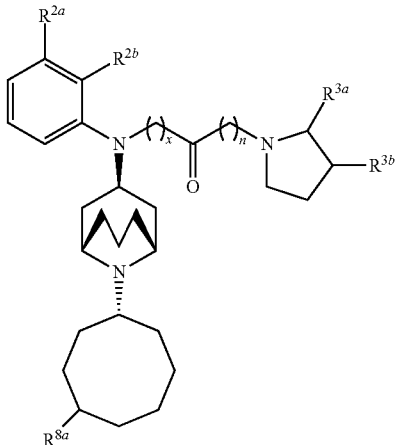
(a)
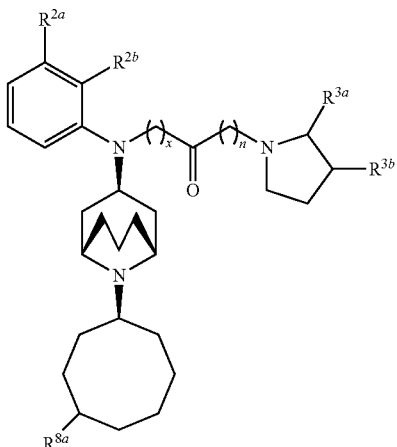
(b)
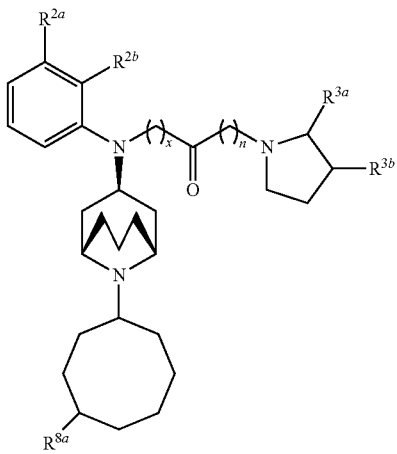
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H57 a, b, or c | H | OCH$_2$C(=O)OH | 0 | 0 | H | C(=O)OH |
| H58 a, b, or c | H | OCH$_2$C(=O)OH | 1 | 0 | H | C(=O)OH |
| H59 a, b, or c | H | OCH$_2$C(=O)OH | 1 | 1 | H | C(=O)OH |
| H60 a, b, or c | H | OCH$_2$C(=O)OH | 0 | 1 | H | C(=O)OH |
| H61 a, b, or c | H | H | 0 | 0 | tetrazolyl | H |
| H62 a, b, or c | H | H | 1 | 0 | tetrazolyl | H |
| H63 a, b, or c | H | H | 1 | 1 | tetrazolyl | H |

TABLE 9-continued
(a)
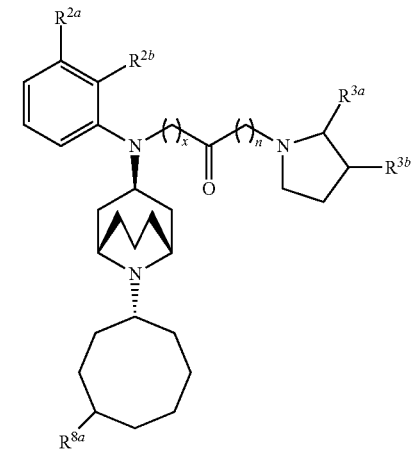
(b)
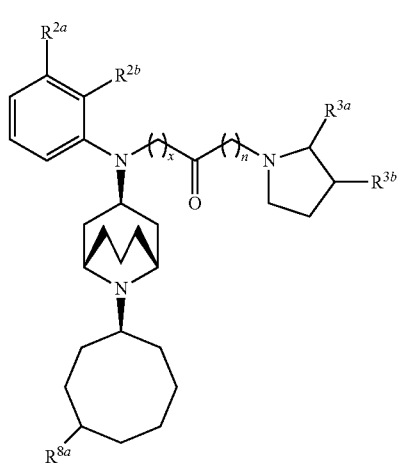
(c)
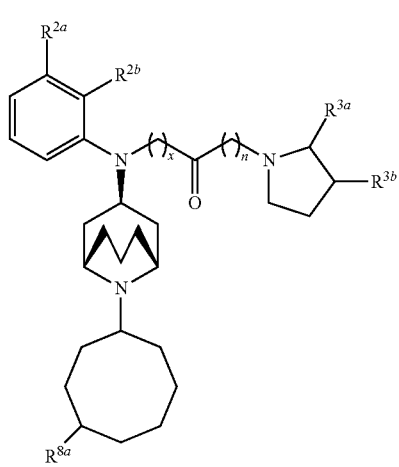
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H64 a, b, or c | H | H | 0 | 1 | tetrazolyl | H |
| H65 a, b, or c | N(H)C(=O)E$^3$OH | H | 0 | 0 | tetrazolyl | H |
| H66 a, b, or c | N(H)C(=O)E$^3$OH | H | 1 | 0 | tetrazolyl | H |
| H67 a, b, or c | N(H)C(=O)E$^3$OH | H | 1 | 1 | tetrazolyl | H |
| H68 a, b, or c | N(H)C(=O)E$^3$OH | H | 0 | 1 | tetrazolyl | H |
| H69 a, b, or c | OCH$_2$C(=O)OH | H | 0 | 0 | tetrazolyl | H |
| H70 a, b, or c | OCH$_2$C(=O)OH | H | 1 | 0 | tetrazolyl | H |

TABLE 9-continued (a)
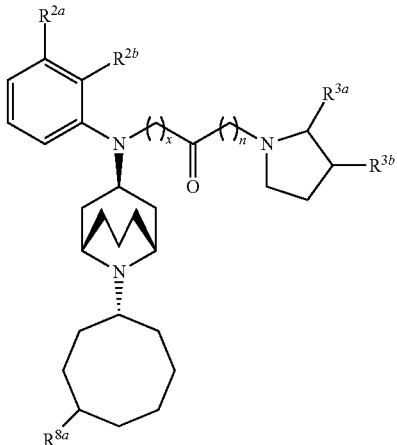

(b)
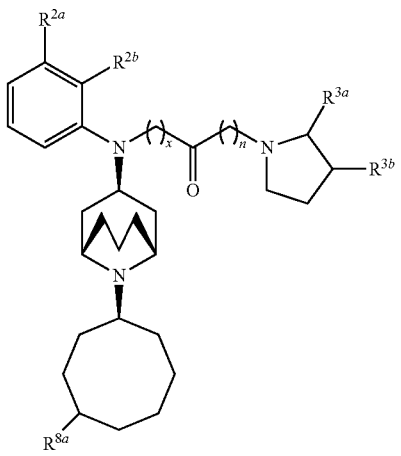

(c)
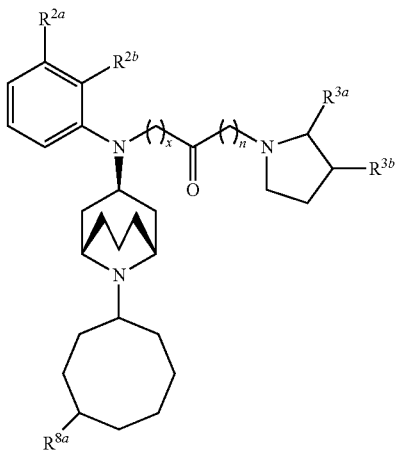

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| H71 a, b, or c | $OCH_2C(=O)OH$ | H | 1 | 1 | tetrazolyl | H |
| H72 a, b, or c | $OCH_2C(=O)OH$ | H | 0 | 1 | tetrazolyl | H |
| H73 a, b, or c | H | $N(H)C(=O)E^3OH$ | 0 | 0 | tetrazolyl | H |
| H74 a, b, or c | H | $N(H)C(=O)E^3OH$ | 1 | 0 | tetrazolyl | H |
| H75 a, b, or c | H | $N(H)C(=O)E^3OH$ | 1 | 1 | tetrazolyl | H |
| H76 a, b, or c | H | $N(H)C(=O)E^3OH$ | 0 | 1 | tetrazolyl | H |
| H77 a, b, or c | H | $OCH_2C(=O)OH$ | 0 | 0 | tetrazolyl | H |

TABLE 9-continued
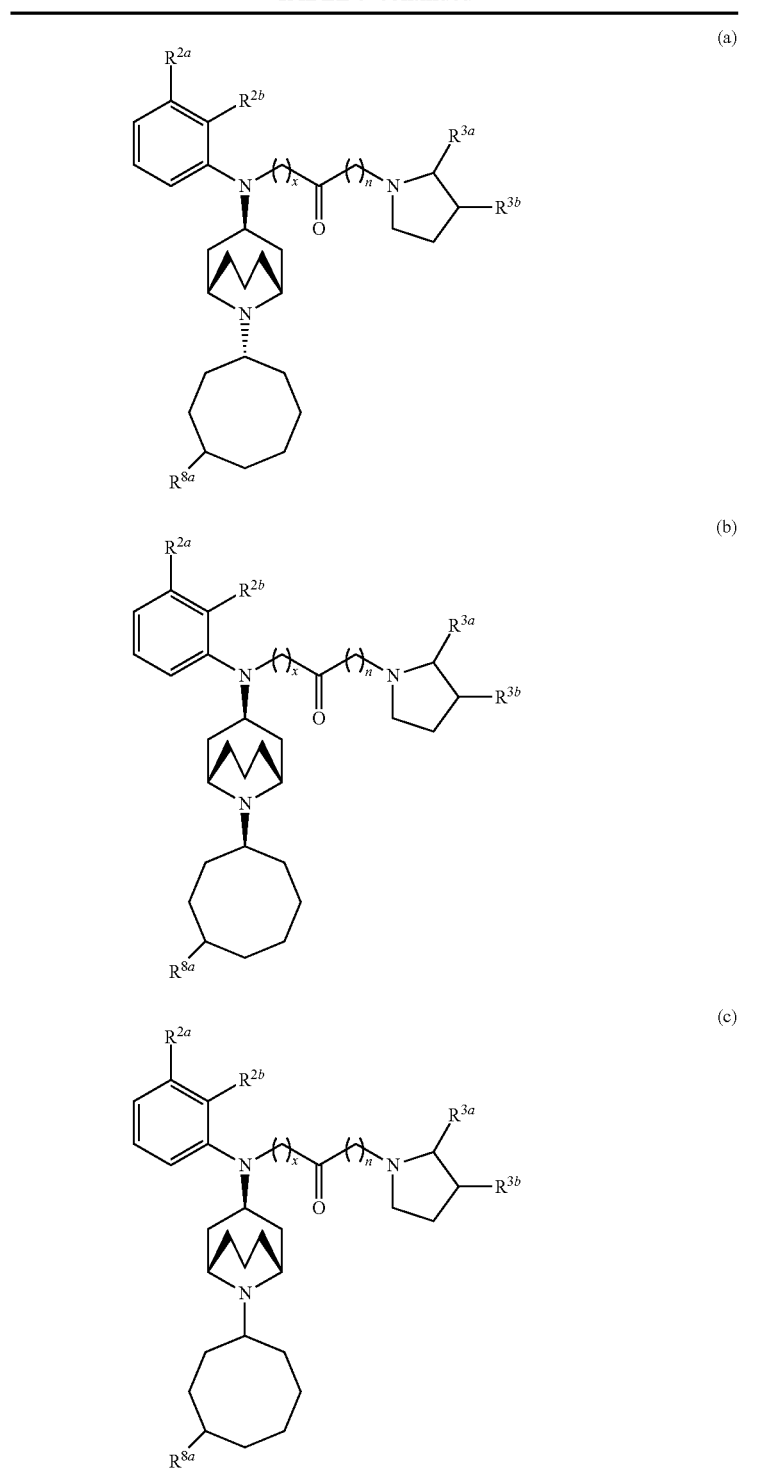
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H78 a, b, or c | H | OCH$_2$C(=O)OH | 1 | 0 | tetrazolyl | H |
| H79 a, b, or c | H | OCH$_2$C(=O)OH | 1 | 1 | tetrazolyl | H |
| H80 a, b, or c | H | OCH$_2$C(=O)OH | 0 | 1 | tetrazolyl | H |
| H81 a, b, or c | H | H | 0 | 0 | H | tetrazolyl |
| H82 a, b, or c | H | H | 1 | 0 | H | tetrazolyl |
| H83 a, b, or c | H | H | 1 | 1 | H | tetrazolyl |
| H84 a, b, or c | H | H | 0 | 1 | H | tetrazolyl |

TABLE 9-continued

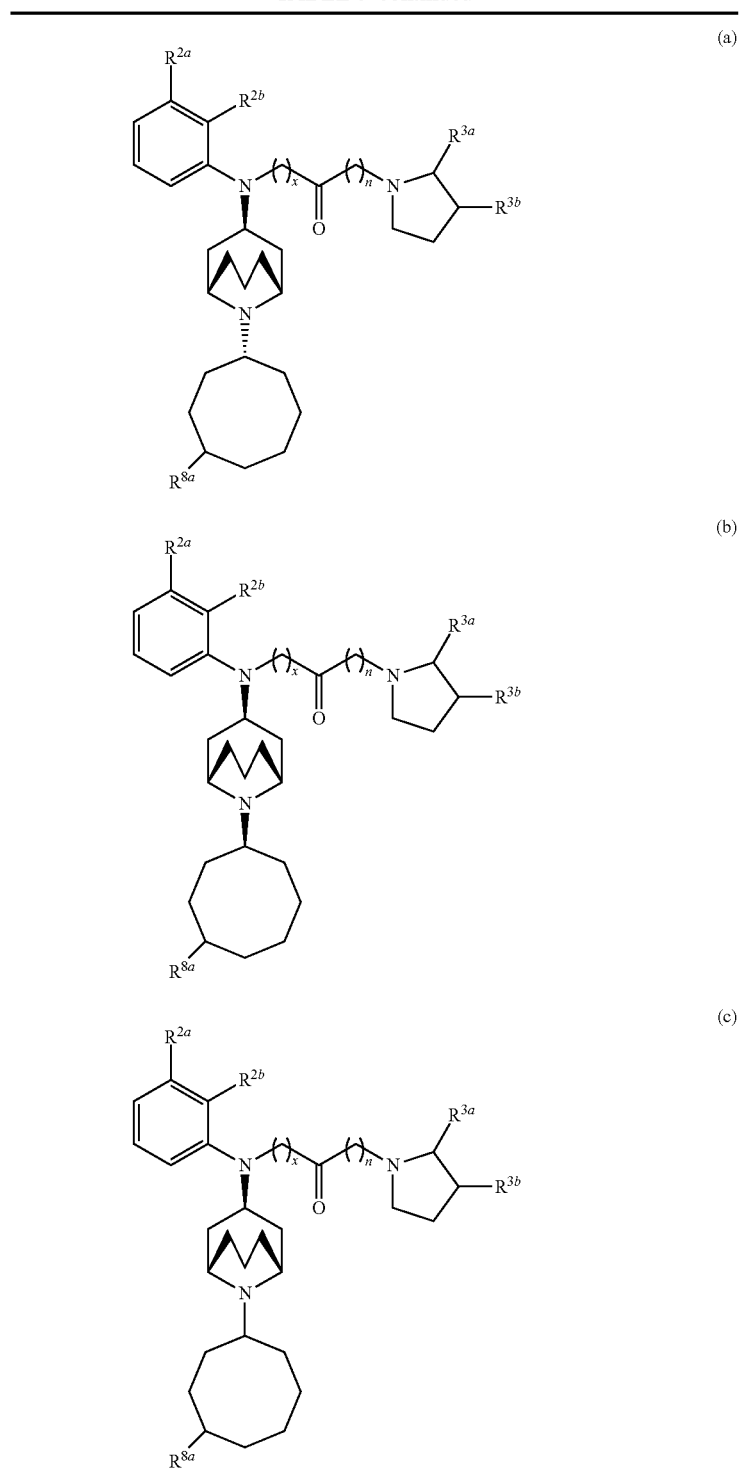

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| H85 a, b, or c | N(H)C(=O)E$^3$OH | H | 0 | 0 | H | tetrazolyl |
| H86 a, b, or c | N(H)C(=O)E$^3$OH | H | 1 | 0 | H | tetrazolyl |
| H87 a, b, or c | N(H)C(=O)E$^3$OH | H | 1 | 1 | H | tetrazolyl |
| H88 a, b, or c | N(H)C(=O)E$^3$OH | H | 0 | 1 | H | tetrazolyl |
| H89 a, b, or c | OCH$_2$C(=O)OH | H | 0 | 0 | H | tetrazolyl |
| H90 a, b, or c | OCH$_2$C(=O)OH | H | 1 | 0 | H | tetrazolyl |
| H91 a, b, or c | OCH$_2$C(=O)OH | H | 1 | 1 | H | tetrazolyl |

TABLE 9-continued (a)
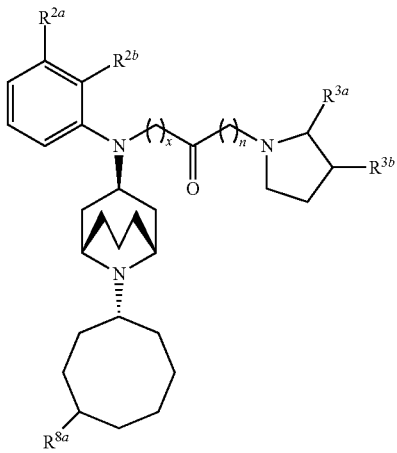

(b)
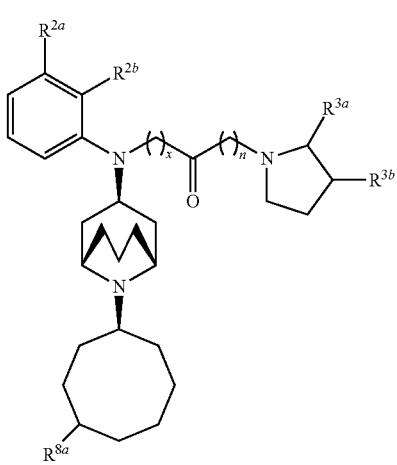

(c)
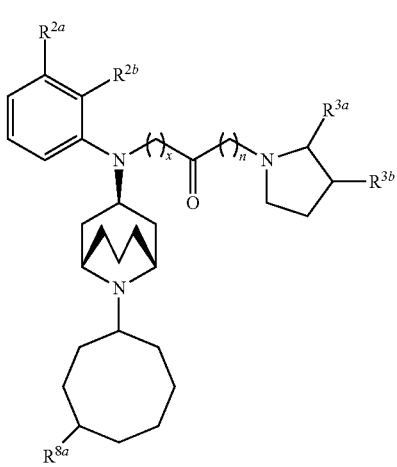

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| H92 a, b, or c | $OCH_2C(=O)OH$ | H | 0 | 1 | H | tetrazolyl |
| H93 a, b, or c | H | $N(H)C(=O)E^3OH$ | 0 | 0 | H | tetrazolyl |
| H94 a, b, or c | H | $N(H)C(=O)E^3OH$ | 1 | 0 | H | tetrazolyl |
| H95 a, b, or c | H | $N(H)C(=O)E^3OH$ | 1 | 1 | H | tetrazolyl |
| H96 a, b, or c | H | $N(H)C(=O)E^3OH$ | 0 | 1 | H | tetrazolyl |
| H97 a, b, or c | H | $OCH_2C(=O)OH$ | 0 | 0 | H | tetrazolyl |
| H98 a, b, or c | H | $OCH_2C(=O)OH$ | 1 | 0 | H | tetrazolyl |

TABLE 9-continued
(a)
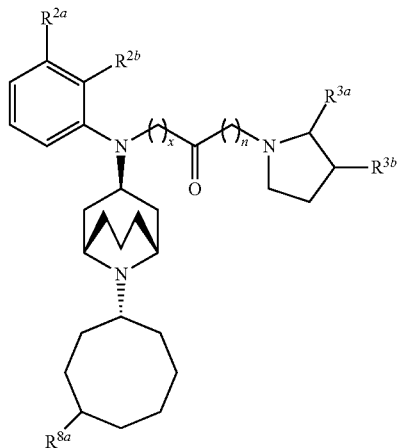
(b)
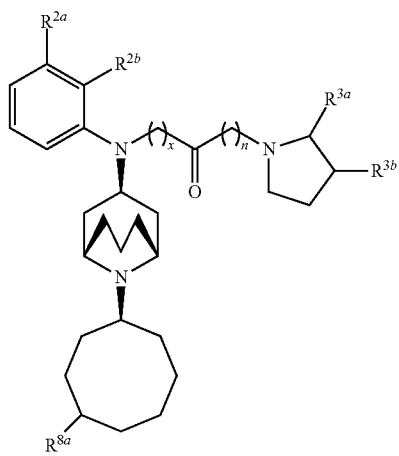
(c)
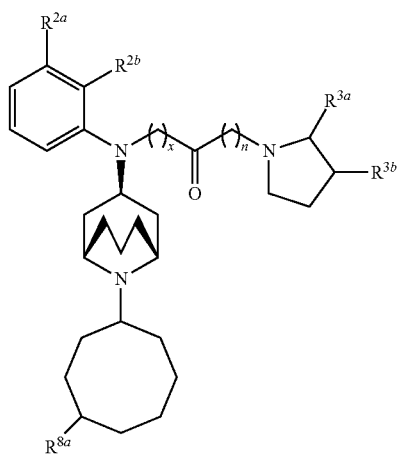
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| H99 a, b, or c | H | OCH$_2$C(=O)OH | 1 | 1 | H | tetrazolyl |
| H100 a, b, or c | H | OCH$_2$C(=O)OH | 0 | 1 | H | tetrazolyl |
$R^{8a}$ is (i) H or (ii) CH$_3$; $E^3$ is (iii) a direct bond or (iv) C(=O).

TABLE 10
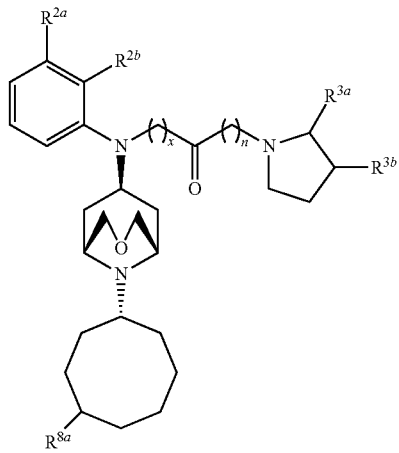
(a)
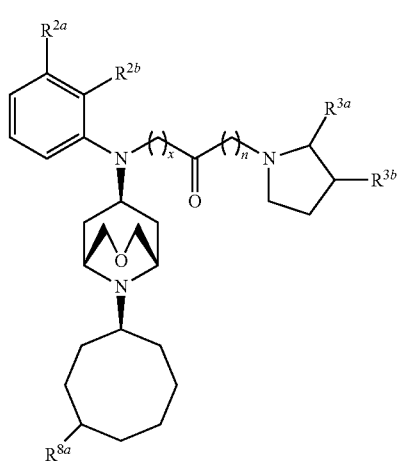
(b)
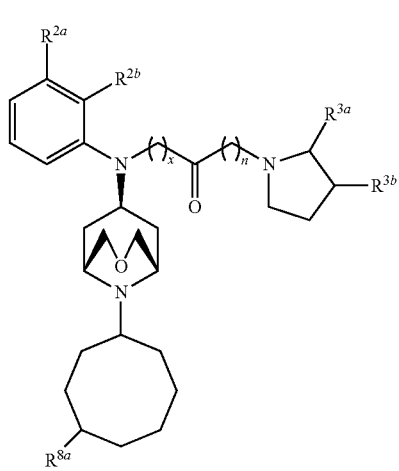
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I1 a, b, or c | H | H | 0 | 0 | H | H |
| I2 a, b, or c | H | H | 1 | 0 | H | H |
| I3 a, b, or c | H | H | 1 | 1 | H | H |
| I4 a, b, or c | H | H | 0 | 1 | H | H |
| I5 a, b, or c | N(H)C(=O)$E^3$OH | H | 0 | 0 | H | H |
| I6 a, b, or c | N(H)C(=O)$E^3$OH | H | 1 | 0 | H | H |
| I7 a, b, or c | N(H)C(=O)$E^3$OH | H | 1 | 1 | H | H |

TABLE 10-continued
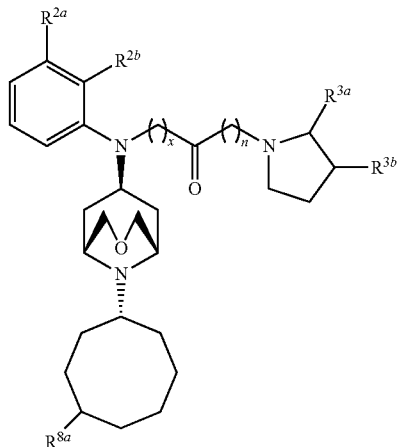
(a)
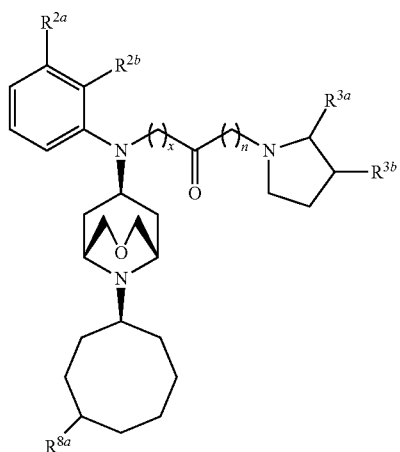
(b)
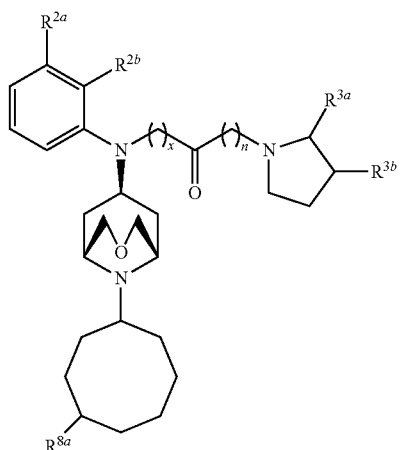
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I8 a, b, or c | N(H)C(=O)E³OH | H | 0 | 1 | H | H |
| I9 a, b, or c | OCH₂C(=O)OH | H | 0 | 0 | H | H |
| I10 a, b, or c | OCH₂C(=O)OH | H | 1 | 0 | H | H |
| I11 a, b, or c | OCH₂C(=O)OH | H | 1 | 1 | H | H |
| I12 a, b, or c | OCH₂C(=O)OH | H | 0 | 1 | H | H |
| I13 a, b, or c | H | N(H)C(=O)E³OH | 0 | 0 | H | H |
| I14 a, b, or c | H | N(H)C(=O)E³OH | 1 | 0 | H | H |

TABLE 10-continued
(a)
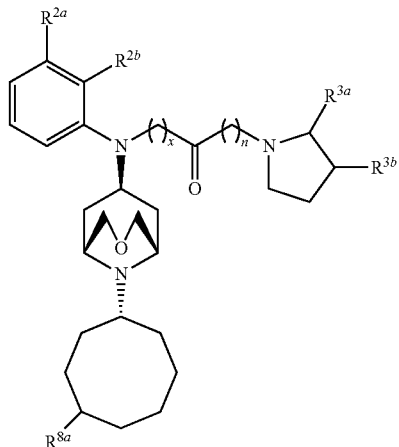
(b)
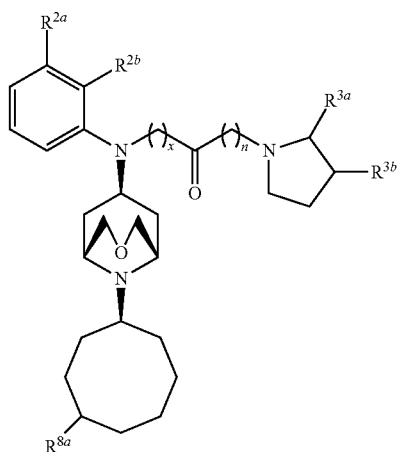
(c)
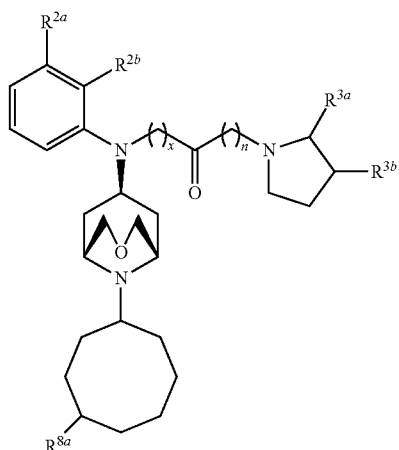
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I15 a, b, or c | H | N(H)C(=O)$E^3$OH | 1 | 1 | H | H |
| I16 a, b, or c | H | N(H)C(=O)$E^3$OH | 0 | 1 | H | H |
| I17 a, b, or c | H | OCH$_2$C(=O)OH | 0 | 0 | H | H |
| I18 a, b, or c | H | OCH$_2$C(=O)OH | 1 | 0 | H | H |
| I19 a, b, or c | H | OCH$_2$C(=O)OH | 1 | 1 | H | H |
| I20 a, b, or c | H | OCH$_2$C(=O)OH | 0 | 1 | H | H |
| I21 a, b, or c | H | H | 0 | 0 | C(=O)OH | H |

TABLE 10-continued
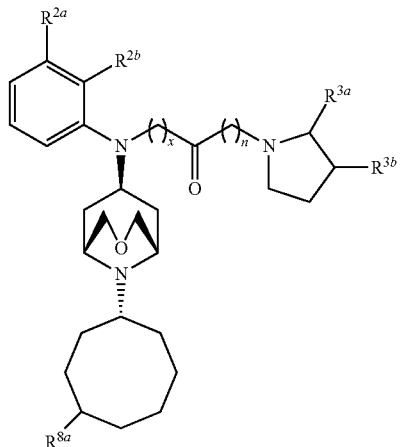
(a)
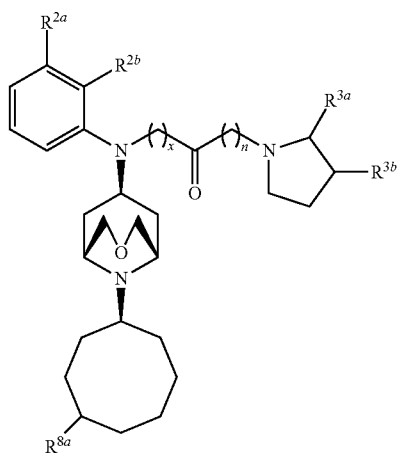
(b)
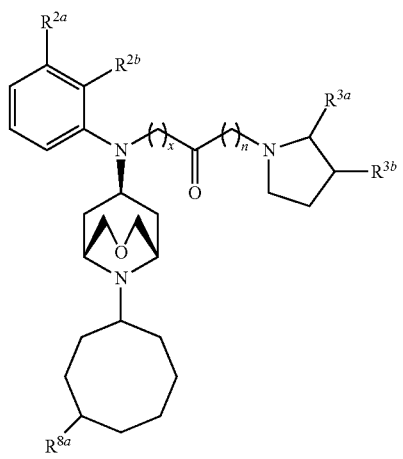
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I22 a, b, or c | H | H | 1 | 0 | C(=O)OH | H |
| I23 a, b, or c | H | H | 1 | 1 | C(=O)OH | H |
| I24 a, b, or c | H | H | 0 | 1 | C(=O)OH | H |
| I25 a, b, or c | N(H)C(=O)$E^3$OH | H | 0 | 0 | C(=O)OH | H |
| I26 a, b, or c | N(H)C(=O)$E^3$OH | H | 1 | 0 | C(=O)OH | H |
| I27 a, b, or c | N(H)C(=O)$E^3$OH | H | 1 | 1 | C(=O)OH | H |
| I28 a, b, or c | N(H)C(=O)$E^3$OH | H | 0 | 1 | C(=O)OH | H |

TABLE 10-continued
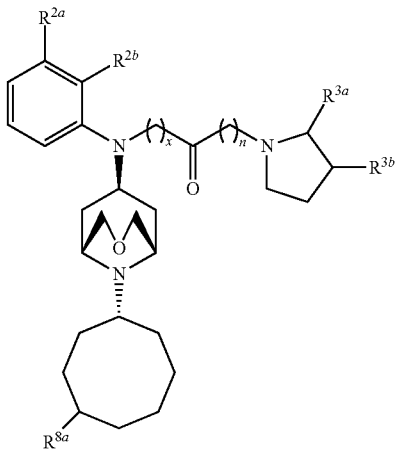
(a)
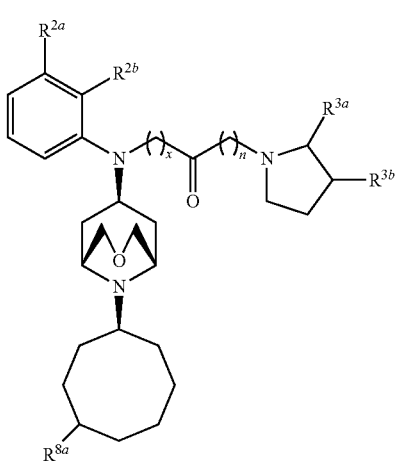
(b)
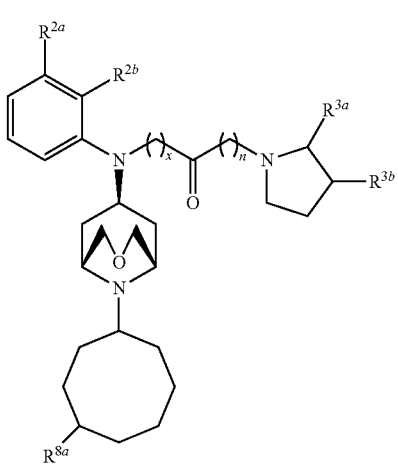
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I29 a, b, or c | $OCH_2C(=O)OH$ | H | 0 | 0 | $C(=O)OH$ | H |
| I30 a, b, or c | $OCH_2C(=O)OH$ | H | 1 | 0 | $C(=O)OH$ | H |
| I31 a, b, or c | $OCH_2C(=O)OH$ | H | 1 | 1 | $C(=O)OH$ | H |
| I32 a, b, or c | $OCH_2C(=O)OH$ | H | 0 | 1 | $C(=O)OH$ | H |
| I33 a, b, or c | H | $N(H)C(=O)E^3OH$ | 0 | 0 | $C(=O)OH$ | H |
| I34 a, b, or c | H | $N(H)C(=O)E^3OH$ | 1 | 0 | $C(=O)OH$ | H |
| I35 a, b, or c | H | $N(H)C(=O)E^3OH$ | 1 | 1 | $C(=O)OH$ | H |

TABLE 10-continued
(a)
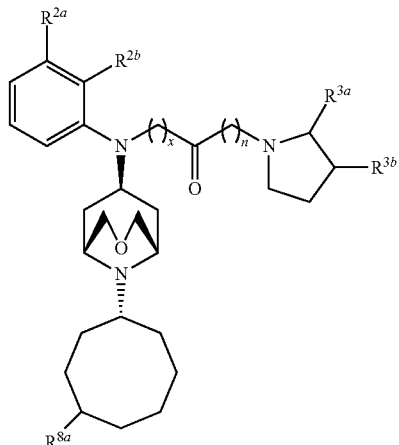
(b)
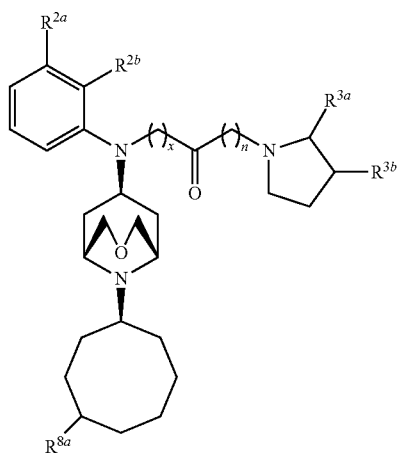
(c)
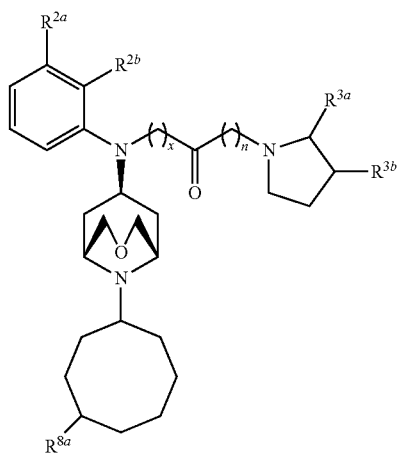
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I36 a, b, or c | H | N(H)C(=O)E$^3$OH | 0 | 1 | C(=O)OH | H |
| I37 a, b, or c | H | OCH$_2$C(=O)OH | 0 | 0 | C(=O)OH | H |
| I38 a, b, or c | H | OCH$_2$C(=O)OH | 1 | 0 | C(=O)OH | H |
| I39 a, b, or c | H | OCH$_2$C(=O)OH | 1 | 1 | C(=O)OH | H |
| I40 a, b, or c | H | OCH$_2$C(=O)OH | 0 | 1 | C(=O)OH | H |
| I41 a, b, or c | H | H | 0 | 0 | H | C(=O)OH |
| I42 a, b, or c | H | H | 1 | 0 | H | C(=O)OH |

TABLE 10-continued
(a)
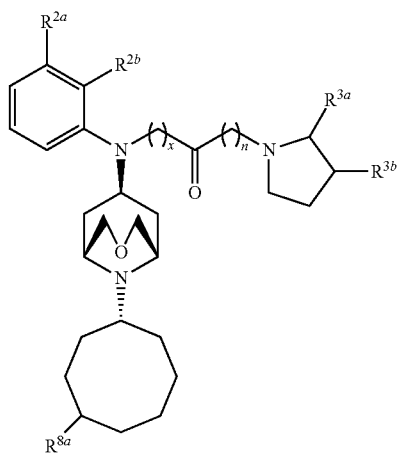
(b)
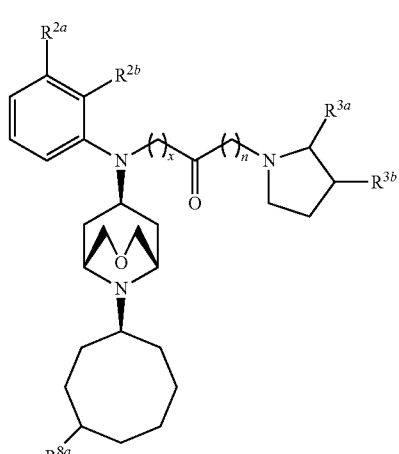
(c)
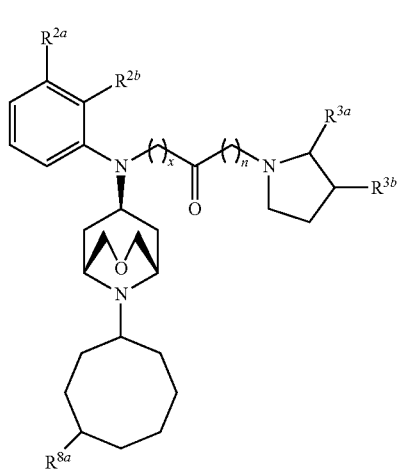
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I43 a, b, or c | H | H | 1 | 1 | H | C(=O)OH |
| I44 a, b, or c | H | H | 0 | 1 | H | C(=O)OH |
| I45 a, b, or c | N(H)C(=O)E$^3$OH | H | 0 | 0 | H | C(=O)OH |
| I46 a, b, or c | N(H)C(=O)E$^3$OH | H | 1 | 0 | H | C(=O)OH |
| I47 a, b, or c | N(H)C(=O)E$^3$OH | H | 1 | 1 | H | C(=O)OH |
| I48 a, b, or c | N(H)C(=O)E$^3$OH | H | 0 | 1 | H | C(=O)OH |
| I49 a, b, or c | OCH$_2$C(=O)OH | H | 0 | 0 | H | C(=O)OH |

TABLE 10-continued
(a)
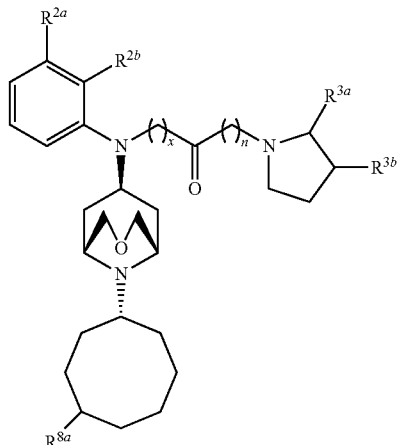
(b)
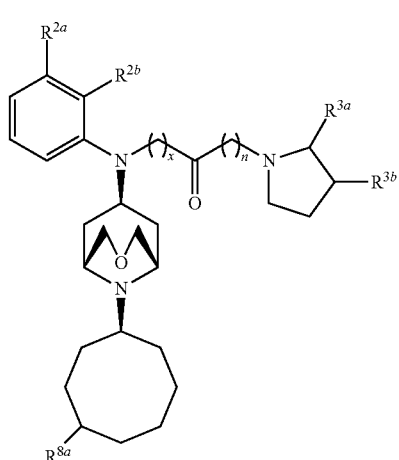
(c)
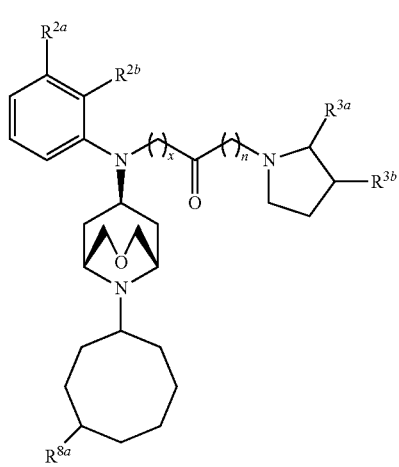
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I50 a, b, or c | $OCH_2C(=O)OH$ | H | 1 | 0 | H | $C(=O)OH$ |
| I51 a, b, or c | $OCH_2C(=O)OH$ | H | 1 | 1 | H | $C(=O)OH$ |
| I52 a, b, or c | $OCH_2C(=O)OH$ | H | 0 | 1 | H | $C(=O)OH$ |
| I53 a, b, or c | H | $N(H)C(=O)E^3OH$ | 0 | 0 | H | $C(=O)OH$ |
| I54 a, b, or c | H | $N(H)C(=O)E^3OH$ | 1 | 0 | H | $C(=O)OH$ |
| I55 a, b, or c | H | $N(H)C(=O)E^3OH$ | 1 | 1 | H | $C(=O)OH$ |
| I56 a, b, or c | H | $N(H)C(=O)E^3OH$ | 0 | 1 | H | $C(=O)OH$ |

TABLE 10-continued
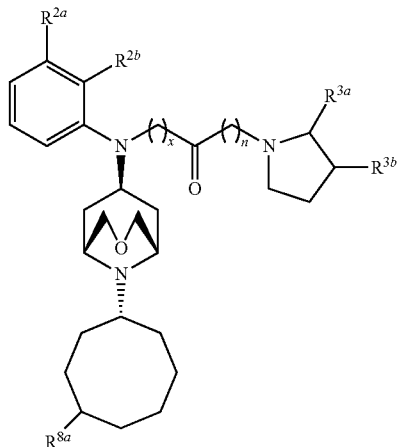
(a)
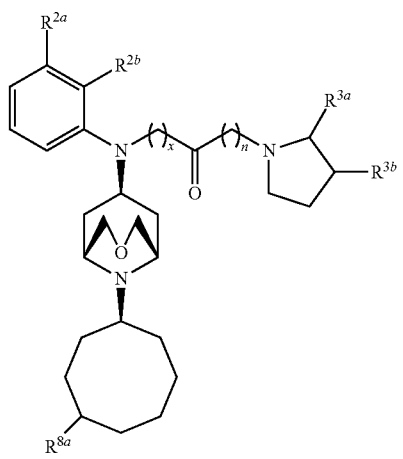
(b)
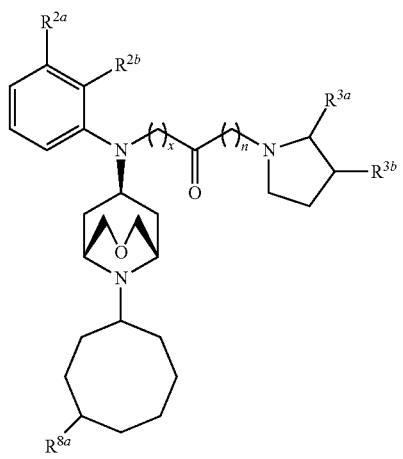
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I57 a, b, or c | H | $OCH_2C(=O)OH$ | 0 | 0 | H | $C(=O)OH$ |
| I58 a, b, or c | H | $OCH_2C(=O)OH$ | 1 | 0 | H | $C(=O)OH$ |
| I59 a, b, or c | H | $OCH_2C(=O)OH$ | 1 | 1 | H | $C(=O)OH$ |
| I60 a, b, or c | H | $OCH_2C(=O)OH$ | 0 | 1 | H | $C(=O)OH$ |
| I61 a, b, or c | H | H | 0 | 0 | tetrazolyl | H |
| I62 a, b, or c | H | H | 1 | 0 | tetrazolyl | H |
| I63 a, b, or c | H | H | 1 | 1 | tetrazolyl | H |

TABLE 10-continued
(a)
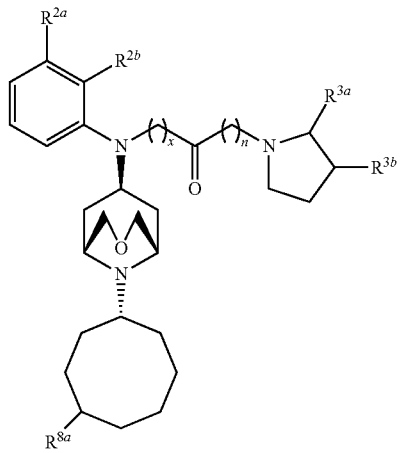
(b)
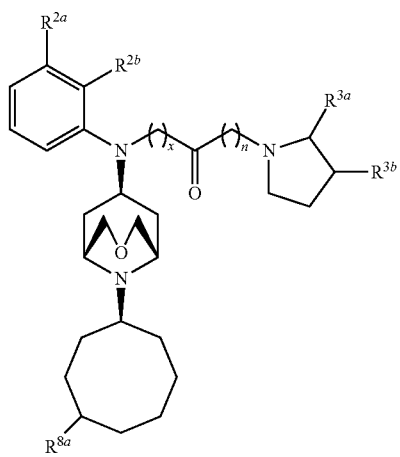
(c)
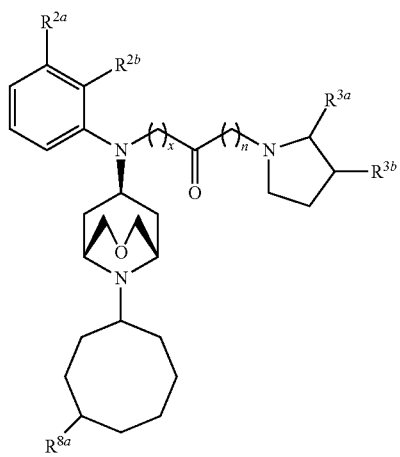
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I64 a, b, or c | H | H | 0 | 1 | tetrazolyl | H |
| I65 a, b, or c | N(H)C(=O)E$^3$OH | H | 0 | 0 | tetrazolyl | H |
| I66 a, b, or c | N(H)C(=O)E$^3$OH | H | 1 | 0 | tetrazolyl | H |
| I67 a, b, or c | N(H)C(=O)E$^3$OH | H | 1 | 1 | tetrazolyl | H |
| I68 a, b, or c | N(H)C(=O)E$^3$OH | H | 0 | 1 | tetrazolyl | H |
| I69 a, b, or c | OCH$_2$C(=O)OH | H | 0 | 0 | tetrazolyl | H |
| I70 a, b, or c | OCH$_2$C(=O)OH | H | 1 | 0 | tetrazolyl | H |

TABLE 10-continued (a)

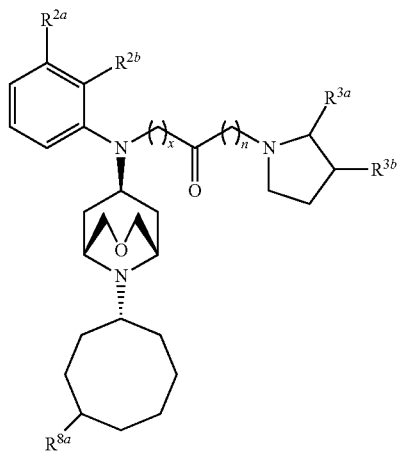

(b)

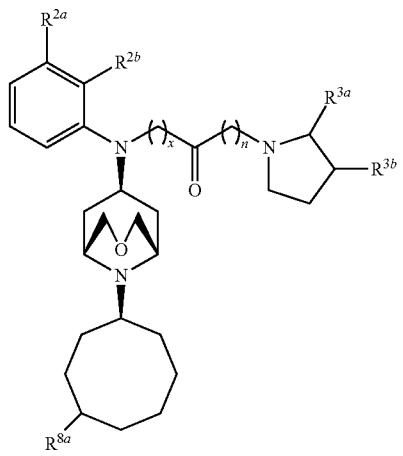

(c)

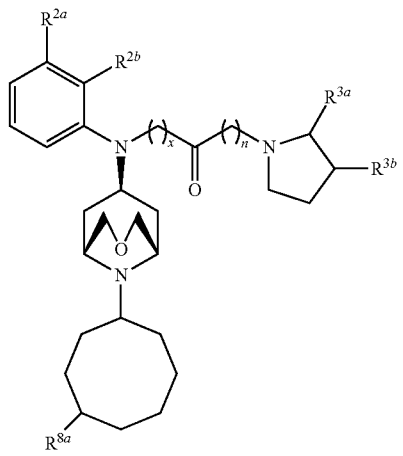

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| I71 a, b, or c | OCH$_2$C(=O)OH | H | 1 | 1 | tetrazolyl | H |
| I72 a, b, or c | OCH$_2$C(=O)OH | H | 0 | 1 | tetrazolyl | H |
| I73 a, b, or c | H | N(H)C(=O)E$^3$OH | 0 | 0 | tetrazolyl | H |
| I74 a, b, or c | H | N(H)C(=O)E$^3$OH | 1 | 0 | tetrazolyl | H |
| I75 a, b, or c | H | N(H)C(=O)E$^3$OH | 1 | 1 | tetrazolyl | H |
| I76 a, b, or c | H | N(H)C(=O)E$^3$OH | 0 | 1 | tetrazolyl | H |
| I77 a, b, or c | H | OCH$_2$C(=O)OH | 0 | 0 | tetrazolyl | H |

TABLE 10-continued
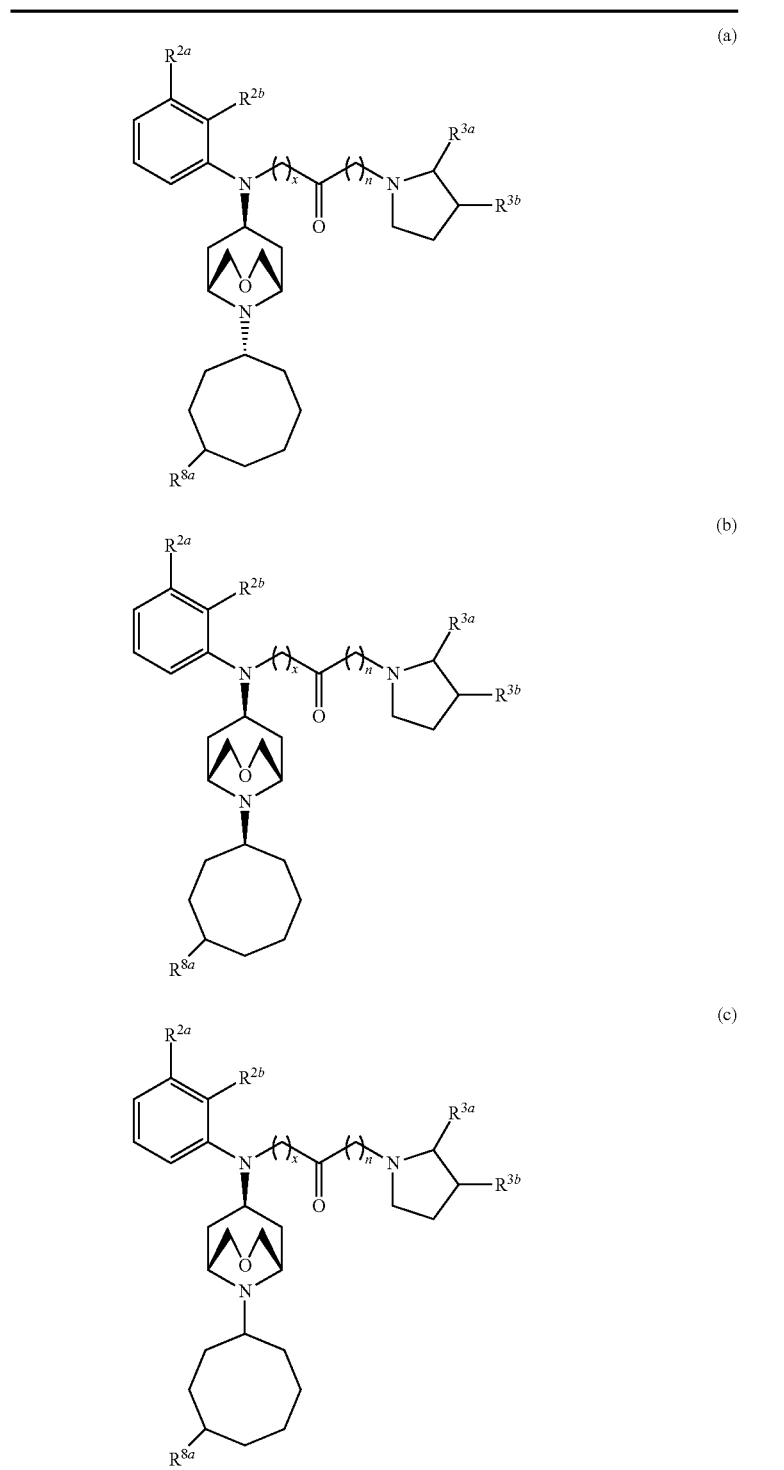
(a)
(b)
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I78 a, b, or c | H | OCH$_2$C(=O)OH | 1 | 0 | tetrazolyl | H |
| I79 a, b, or c | H | OCH$_2$C(=O)OH | 1 | 1 | tetrazolyl | H |
| I80 a, b, or c | H | OCH$_2$C(=O)OH | 0 | 1 | tetrazolyl | H |
| I81 a, b, or c | H | H | 0 | 0 | H | tetrazolyl |
| I82 a, b, or c | H | H | 1 | 0 | H | tetrazolyl |
| I83 a, b, or c | H | H | 1 | 1 | H | tetrazolyl |
| I84 a, b, or c | H | H | 0 | 1 | H | tetrazolyl |

TABLE 10-continued

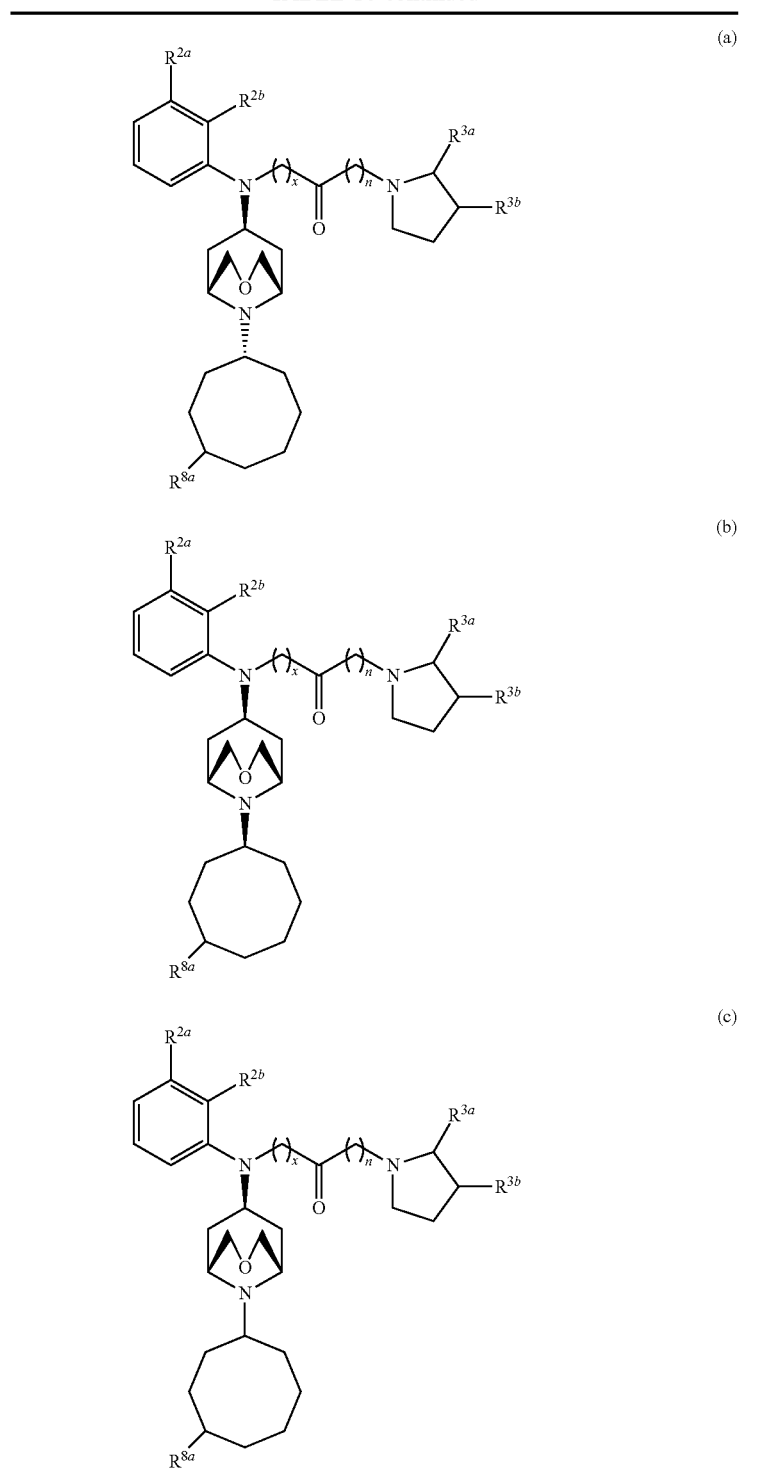

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| I85 a, b, or c | N(H)C(=O)$E^3$OH | H | 0 | 0 | H | tetrazolyl |
| I86 a, b, or c | N(H)C(=O)$E^3$OH | H | 1 | 0 | H | tetrazolyl |
| I87 a, b, or c | N(H)C(=O)$E^3$OH | H | 1 | 1 | H | tetrazolyl |
| I88 a, b, or c | N(H)C(=O)$E^3$OH | H | 0 | 1 | H | tetrazolyl |
| I89 a, b, or c | OCH$_2$C(=O)OH | H | 0 | 0 | H | tetrazolyl |
| I90 a, b, or c | OCH$_2$C(=O)OH | H | 1 | 0 | H | tetrazolyl |
| I91 a, b, or c | OCH$_2$C(=O)OH | H | 1 | 1 | H | tetrazolyl |

TABLE 10-continued

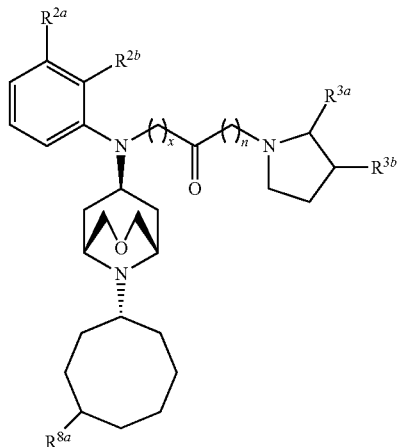
(a)

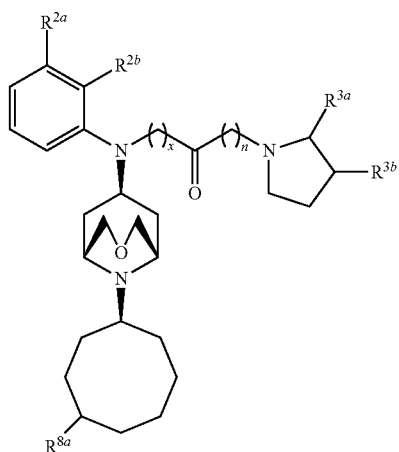
(b)

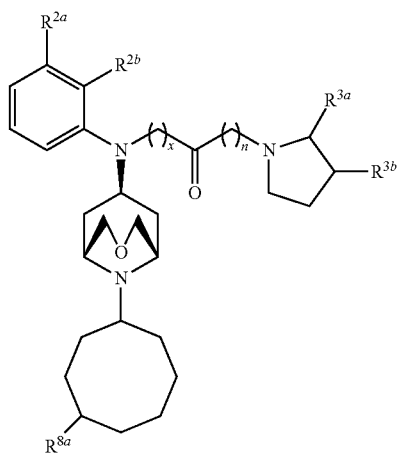
(c)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| I92 a, b, or c | OCH$_2$C(=O)OH | H | 0 | 1 | H | tetrazolyl |
| I93 a, b, or c | H | N(H)C(=O)E$^3$OH | 0 | 0 | H | tetrazolyl |
| I94 a, b, or c | H | N(H)C(=O)E$^3$OH | 1 | 0 | H | tetrazolyl |
| I95 a, b, or c | H | N(H)C(=O)E$^3$OH | 1 | 1 | H | tetrazolyl |
| I96 a, b, or c | H | N(H)C(=O)E$^3$OH | 0 | 1 | H | tetrazolyl |
| I97 a, b, or c | H | OCH$_2$C(=O)OH | 0 | 0 | H | tetrazolyl |
| I98 a, b, or c | H | OCH$_2$C(=O)OH | 1 | 0 | H | tetrazolyl |

TABLE 10-continued
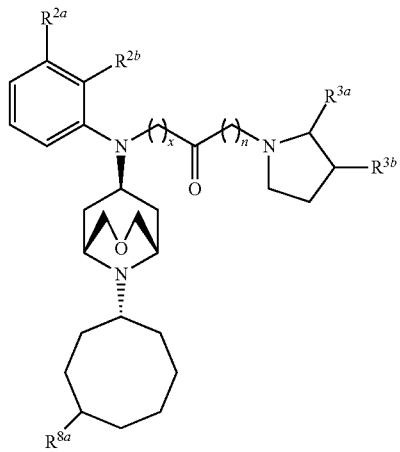
(a)
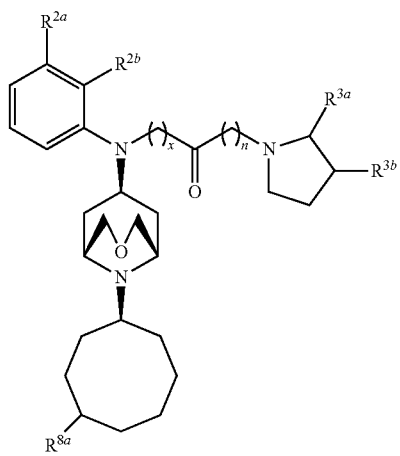
(b)
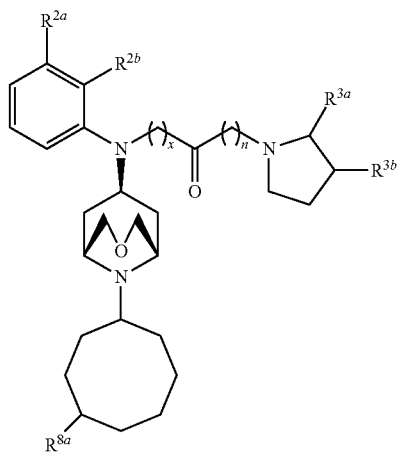
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| I99 a, b, or c | H | OCH$_2$C(=O)OH | 1 | 1 | H | tetrazolyl |
| I100 a, b, or c | H | OCH$_2$C(=O)OH | 0 | 1 | H | tetrazolyl |
$R^{8a}$ is (i) H or (ii) CH$_3$; E$^3$ is (iii) a direct bond or (iv) C(=O).

TABLE 11
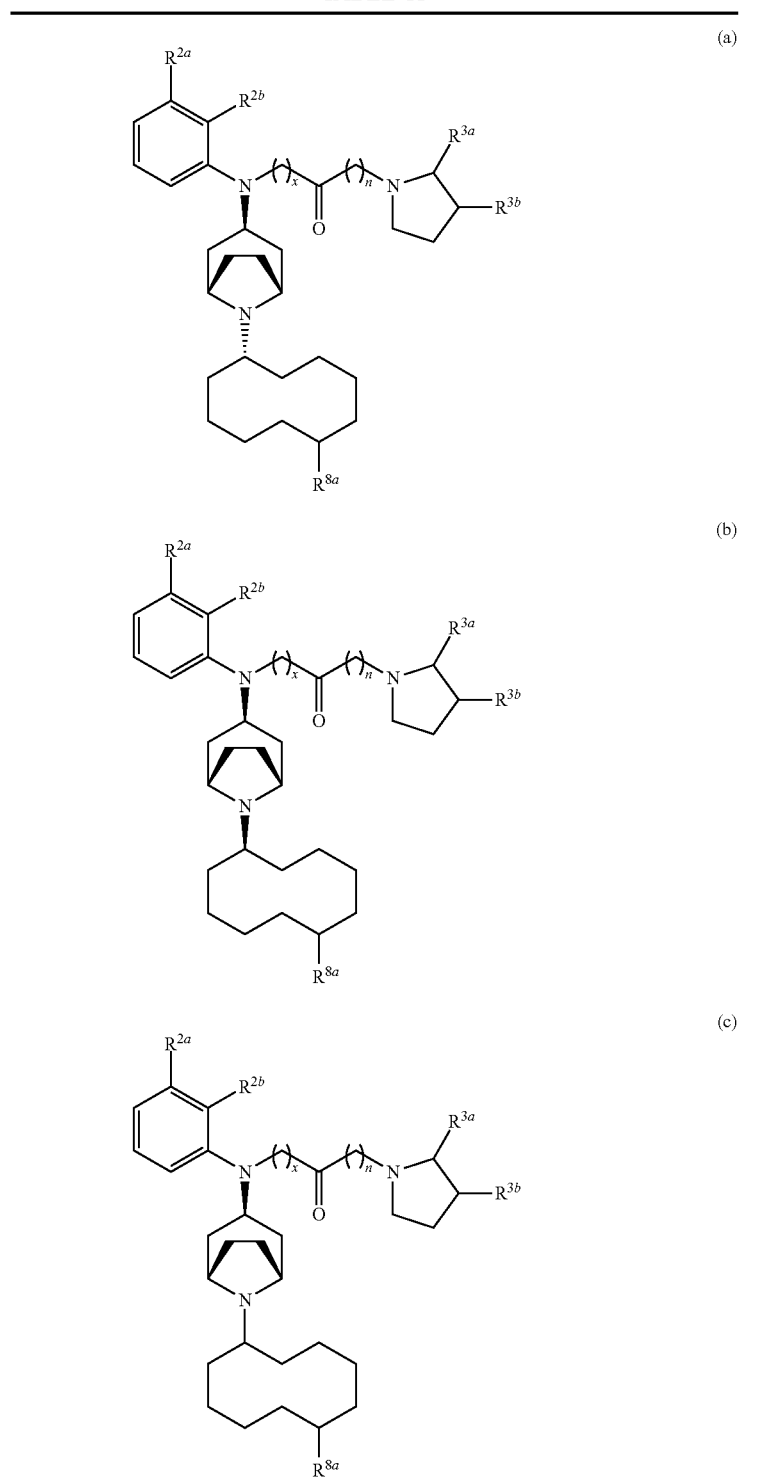
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J1 a, b, or c | H | H | 0 | 0 | H | H |
| J2 a, b, or c | H | H | 1 | 0 | H | H |
| J3 a, b, or c | H | H | 1 | 1 | H | H |
| J4 a, b, or c | H | H | 0 | 1 | H | H |
| J5 a, b, or c | N(H)C(=O)$E^3$OH | H | 0 | 0 | H | H |
| J6 a, b, or c | N(H)C(=O)$E^3$OH | H | 1 | 0 | H | H |

TABLE 11-continued
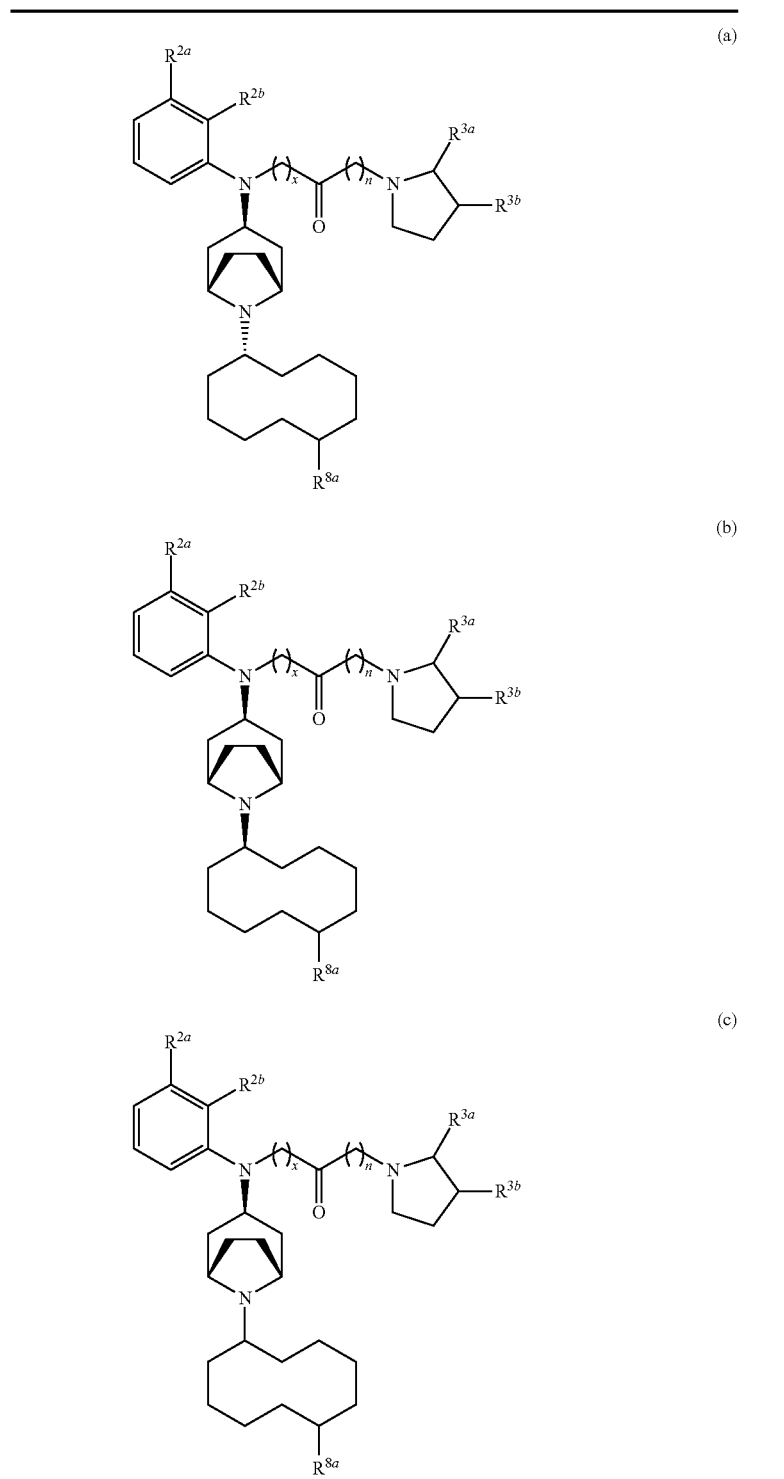
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J7 a, b, or c | N(H)C(=O)$E^3$OH | H | 1 | 1 | H | H |
| J8 a, b, or c | N(H)C(=O)$E^3$OH | H | 0 | 1 | H | H |
| J9 a, b, or c | OCH$_2$C(=O)OH | H | 0 | 0 | H | H |
| J10 a, b, or c | OCH$_2$C(=O)OH | H | 1 | 0 | H | H |
| J11 a, b, or c | OCH$_2$C(=O)OH | H | 1 | 1 | H | H |
| J12 a, b, or c | OCH$_2$C(=O)OH | H | 0 | 1 | H | H |

TABLE 11-continued
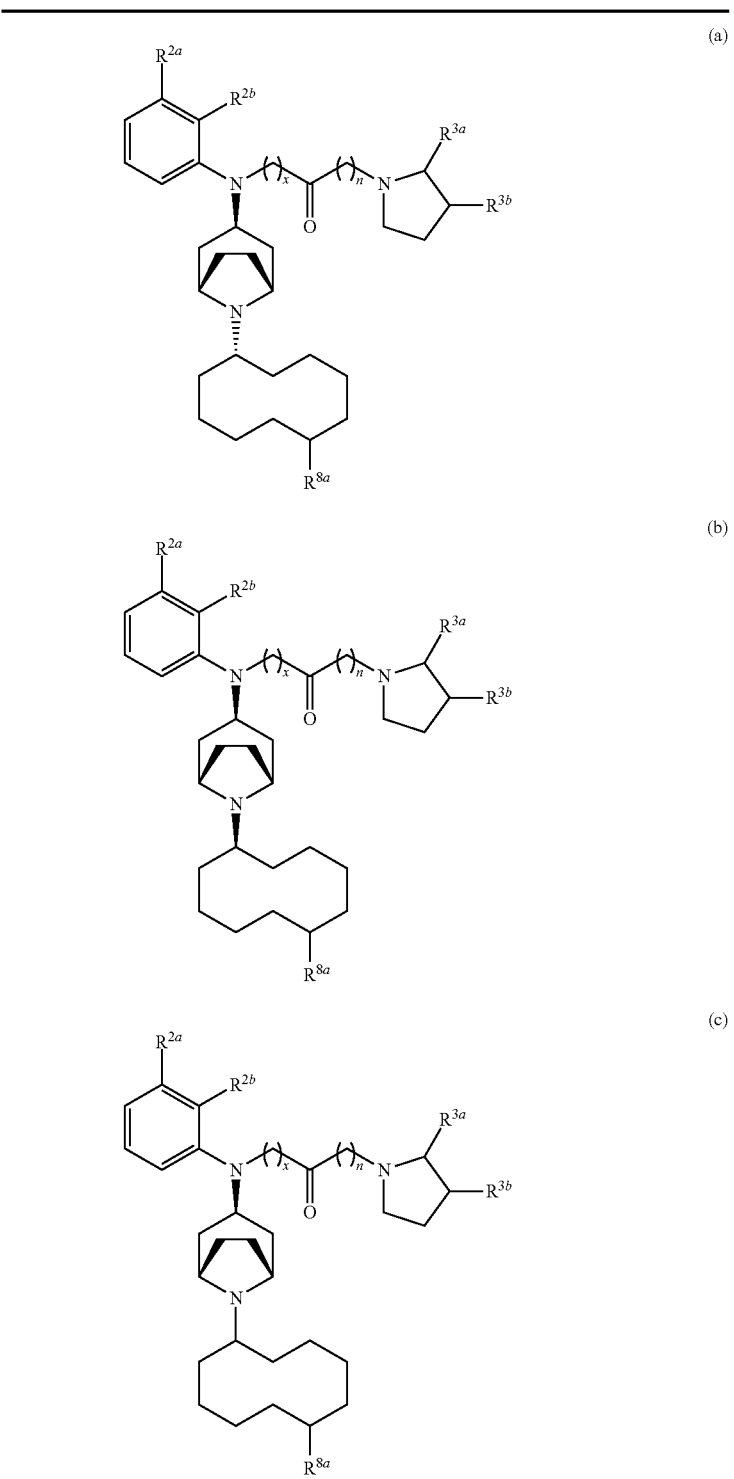
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J13 a, b, or c | H | N(H)C(=O)E$^3$OH | 0 | 0 | H | H |
| J14 a, b, or c | H | N(H)C(=O)E$^3$OH | 1 | 0 | H | H |
| J15 a, b, or c | H | N(H)C(=O)E$^3$OH | 1 | 1 | H | H |
| J16 a, b, or c | H | N(H)C(=O)E$^3$OH | 0 | 1 | H | H |
| J17 a, b, or c | H | OCH$_2$C(=O)OH | 0 | 0 | H | H |
| J18 a, b, or c | H | OCH$_2$C(=O)OH | 1 | 0 | H | H |

TABLE 11-continued
(a)
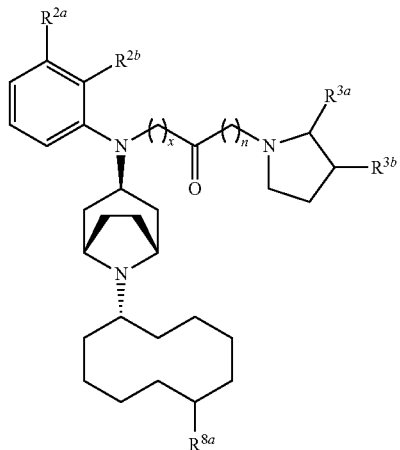
(b)
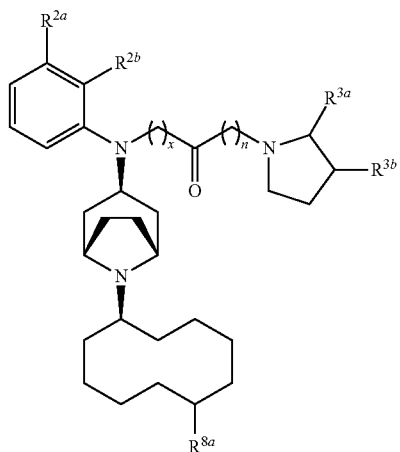
(c)
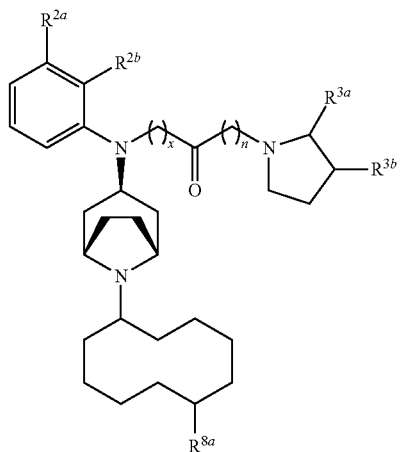
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J19 a, b, or c | H | OCH$_2$C(=O)OH | 1 | 1 | H | H |
| J20 a, b, or c | H | OCH$_2$C(=O)OH | 0 | 1 | H | H |
| J21 a, b, or c | H | H | 0 | 0 | C(=O)OH | H |
| J22 a, b, or c | H | H | 1 | 0 | C(=O)OH | H |
| J23 a, b, or c | H | H | 1 | 1 | C(=O)OH | H |
| J24 a, b, or c | H | H | 0 | 1 | C(=O)OH | H |

TABLE 11-continued
(a)
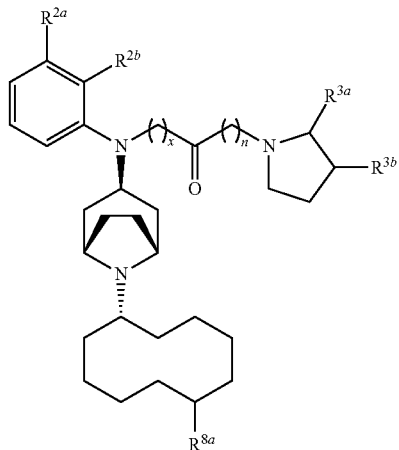
(b)
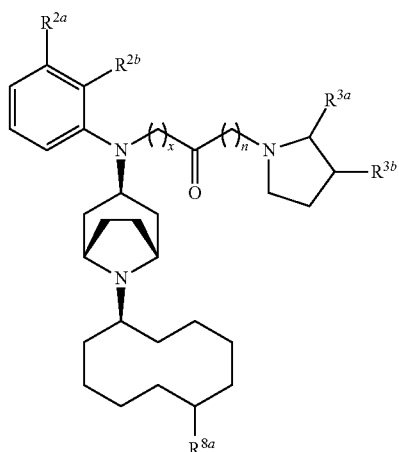
(c)
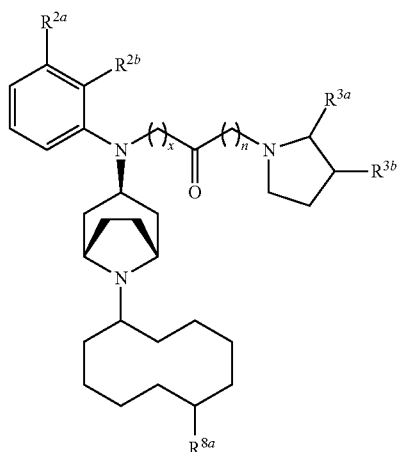
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J25 a, b, or c | N(H)C(=O)E³OH | H | 0 | 0 | C(=O)OH | H |
| J26 a, b, or c | N(H)C(=O)E³OH | H | 1 | 0 | C(=O)OH | H |
| J27 a, b, or c | N(H)C(=O)E³OH | H | 1 | 1 | C(=O)OH | H |
| J28 a, b, or c | N(H)C(=O)E³OH | H | 0 | 1 | C(=O)OH | H |
| J29 a, b, or c | OCH₂C(=O)OH | H | 0 | 0 | C(=O)OH | H |
| J30 a, b, or c | OCH₂C(=O)OH | H | 1 | 0 | C(=O)OH | H |

TABLE 11-continued
(a)
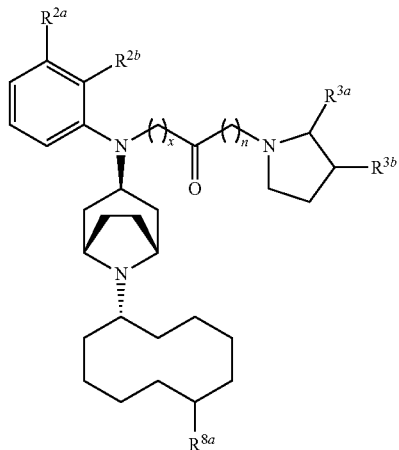
(b)
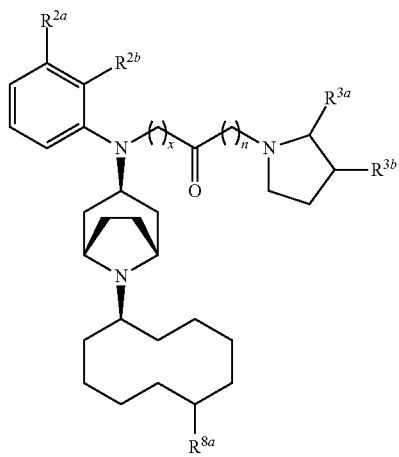
(c)
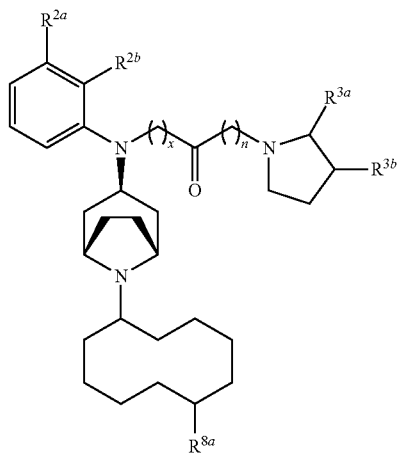
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J31 a, b, or c | $OCH_2C(=O)OH$ | H | 1 | 1 | $C(=O)OH$ | H |
| J32 a, b, or c | $OCH_2C(=O)OH$ | H | 0 | 1 | $C(=O)OH$ | H |
| J33 a, b, or c | H | $N(H)C(=O)E^3OH$ | 0 | 0 | $C(=O)OH$ | H |
| J34 a, b, or c | H | $N(H)C(=O)E^3OH$ | 1 | 0 | $C(=O)OH$ | H |
| J35 a, b, or c | H | $N(H)C(=O)E^3OH$ | 1 | 1 | $C(=O)OH$ | H |
| J36 a, b, or c | H | $N(H)C(=O)E^3OH$ | 0 | 1 | $C(=O)OH$ | H |

TABLE 11-continued
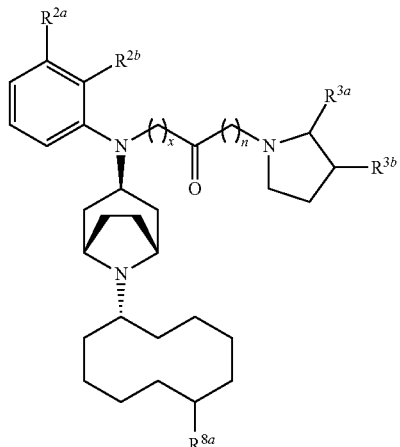
(a)
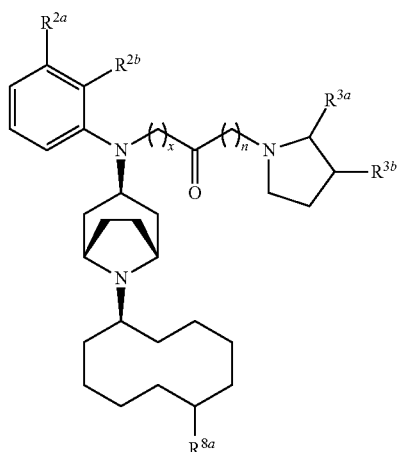
(b)
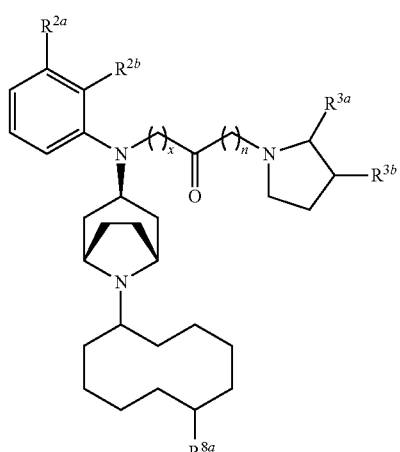
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J37 a, b, or c | H | OCH$_2$C(=O)OH | 0 | 0 | C(=O)OH | H |
| J38 a, b, or c | H | OCH$_2$C(=O)OH | 1 | 0 | C(=O)OH | H |
| J39 a, b, or c | H | OCH$_2$C(=O)OH | 1 | 1 | C(=O)OH | H |
| J40 a, b, or c | H | OCH$_2$C(=O)OH | 0 | 1 | C(=O)OH | H |
| J41 a, b, or c | H | H | 0 | 0 | H | C(=O)OH |
| J42 a, b, or c | H | H | 1 | 0 | H | C(=O)OH |

TABLE 11-continued
(a)
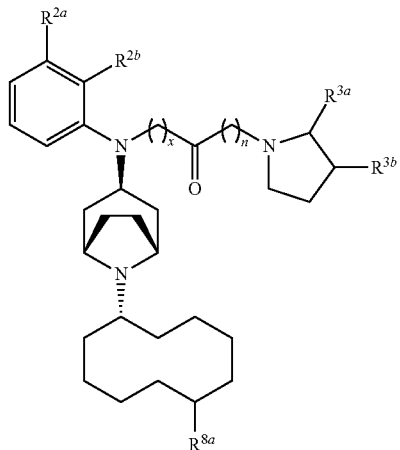
(b)
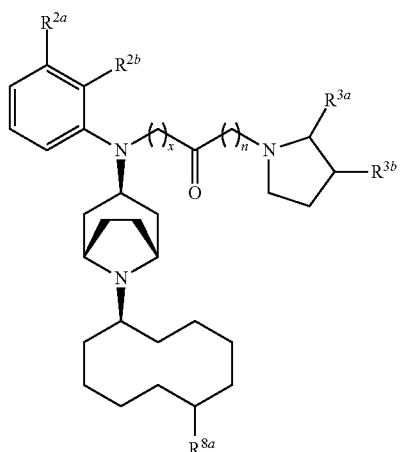
(c)
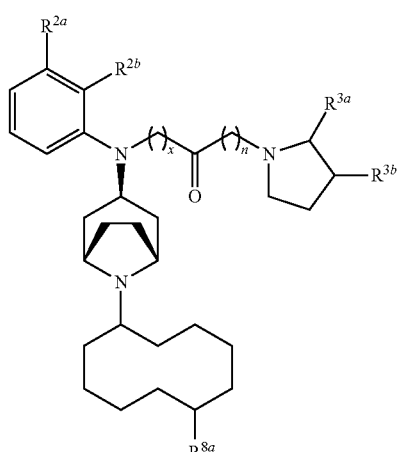
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J43 a, b, or c | H | H | 1 | 1 | H | C(=O)OH |
| J44 a, b, or c | H | H | 0 | 1 | H | C(=O)OH |
| J45 a, b, or c | N(H)C(=O)E$^3$OH | H | 0 | 0 | H | C(=O)OH |
| J46 a, b, or c | N(H)C(=O)E$^3$OH | H | 1 | 0 | H | C(=O)OH |
| J47 a, b, or c | N(H)C(=O)E$^3$OH | H | 1 | 1 | H | C(=O)OH |
| J48 a, b, or c | N(H)C(=O)E$^3$OH | H | 0 | 1 | H | C(=O)OH |

TABLE 11-continued
(a)
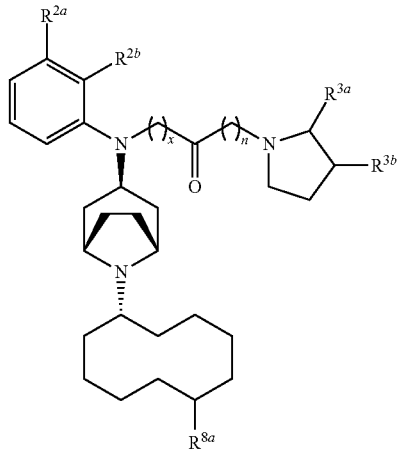
(b)
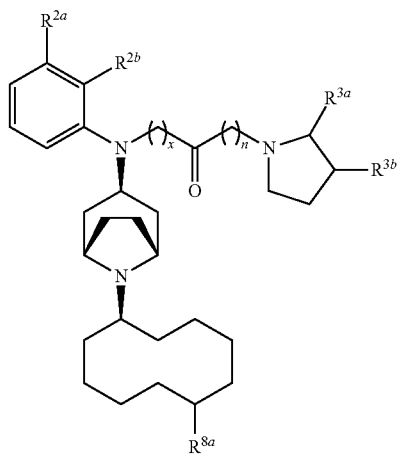
(c)
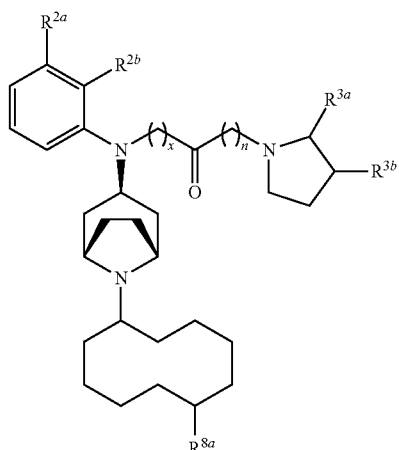
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J49 a, b, or c | OCH$_2$C(=O)OH | H | 0 | 0 | H | C(=O)OH |
| J50 a, b, or c | OCH$_2$C(=O)OH | H | 1 | 0 | H | C(=O)OH |
| J51 a, b, or c | OCH$_2$C(=O)OH | H | 1 | 1 | H | C(=O)OH |
| J52 a, b, or c | OCH$_2$C(=O)OH | H | 0 | 1 | H | C(=O)OH |
| J53 a, b, or c | H | N(H)C(=O)E$^3$OH | 0 | 0 | H | C(=O)OH |
| J54 a, b, or c | H | N(H)C(=O)E$^3$OH | 1 | 0 | H | C(=O)OH |

TABLE 11-continued
(a)
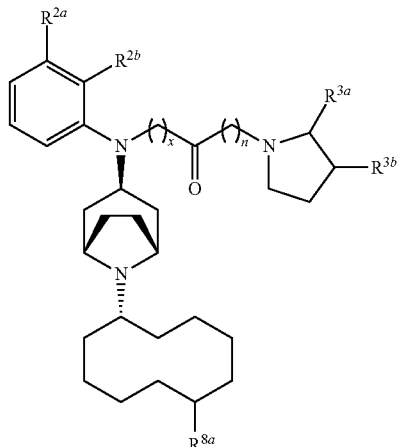
(b)
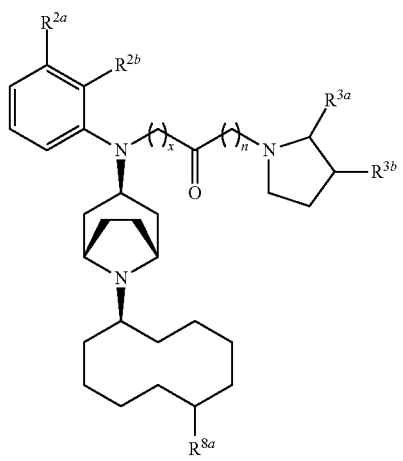
(c)
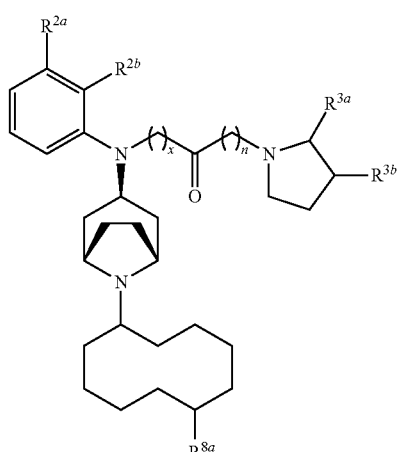
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J55 a, b, or c | H | N(H)C(=O)$E^3$OH | 1 | 1 | H | C(=O)OH |
| J56 a, b, or c | H | N(H)C(=O)$E^3$OH | 0 | 1 | H | C(=O)OH |
| J57 a, b, or c | H | OCH$_2$C(=O)OH | 0 | 0 | H | C(=O)OH |
| J58 a, b, or c | H | OCH$_2$C(=O)OH | 1 | 0 | H | C(=O)OH |
| J59 a, b, or c | H | OCH$_2$C(=O)OH | 1 | 1 | H | C(=O)OH |
| J60 a, b, or c | H | OCH$_2$C(=O)OH | 0 | 1 | H | C(=O)OH |

TABLE 11-continued
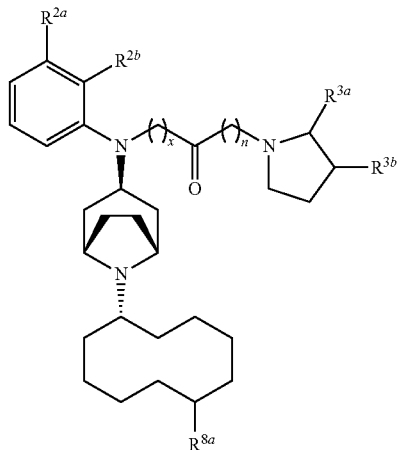
(a)
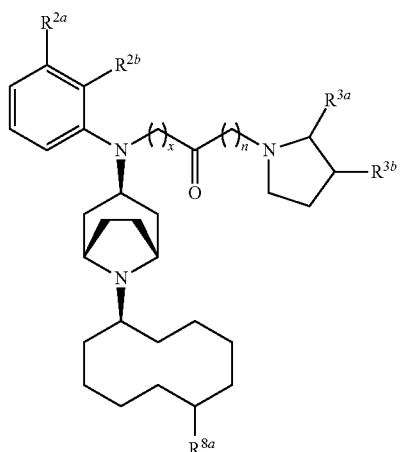
(b)
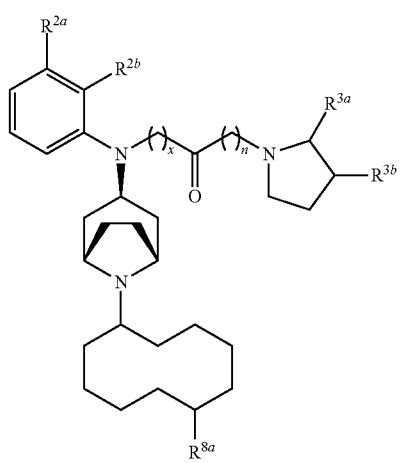
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J61 a, b, or c | H | H | 0 | 0 | tetrazolyl | H |
| J62 a, b, or c | H | H | 1 | 0 | tetrazolyl | H |
| J63 a, b, or c | H | H | 1 | 1 | tetrazolyl | H |
| J64 a, b, or c | H | H | 0 | 1 | tetrazolyl | H |
| J65 a, b, or c | N(H)C(=O)$E^3$OH | H | 0 | 0 | tetrazolyl | H |
| J66 a, b, or c | N(H)C(=O)$E^3$OH | H | 1 | 0 | tetrazolyl | H |

TABLE 11-continued
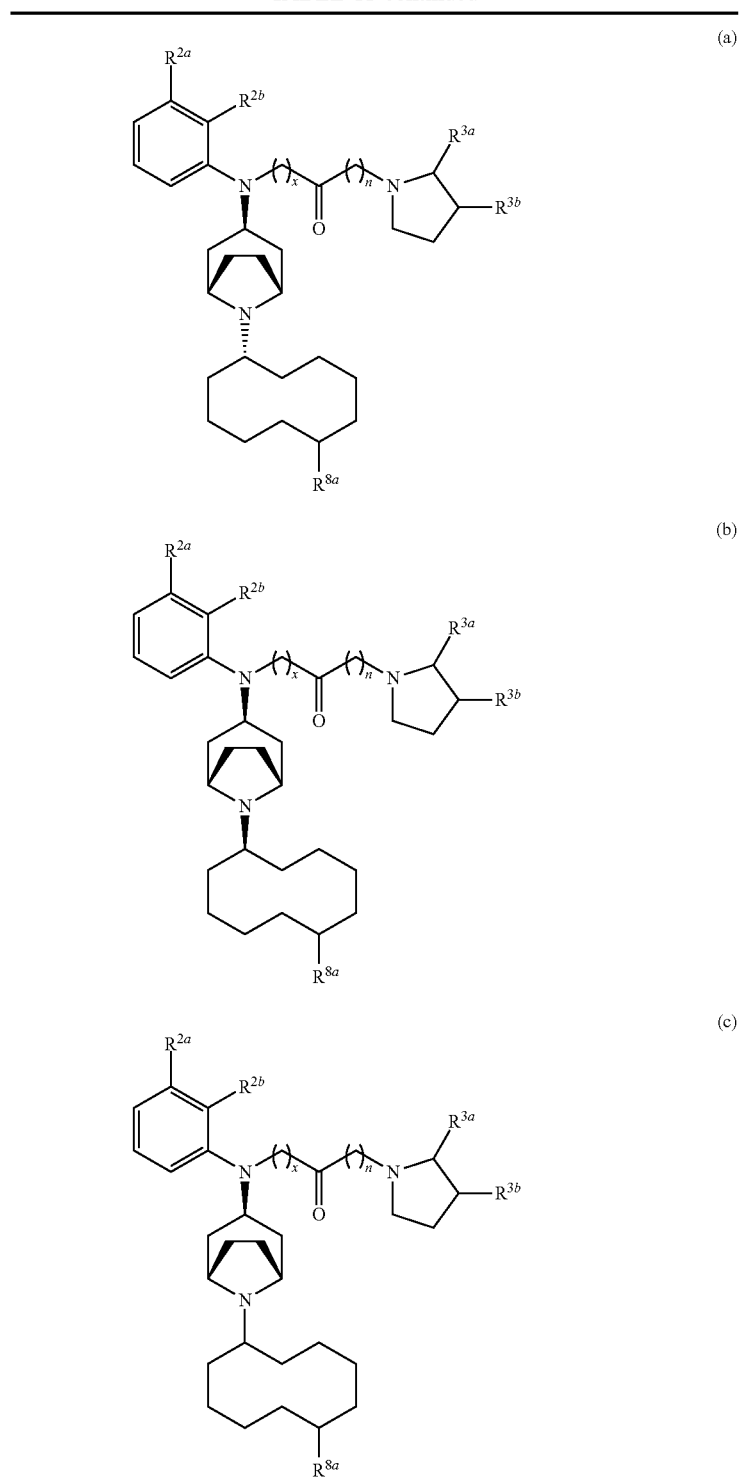
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J67 a, b, or c | N(H)C(=O)E³OH | H | 1 | 1 | tetrazolyl | H |
| J68 a, b, or c | N(H)C(=O)E³OH | H | 0 | 1 | tetrazolyl | H |
| J69 a, b, or c | OCH₂C(=O)OH | H | 0 | 0 | tetrazolyl | H |
| J70 a, b, or c | OCH₂C(=O)OH | H | 1 | 0 | tetrazolyl | H |
| J71 a, b, or c | OCH₂C(=O)OH | H | 1 | 1 | tetrazolyl | H |
| J72 a, b, or c | OCH₂C(=O)OH | H | 0 | 1 | tetrazolyl | H |

TABLE 11-continued
(a)
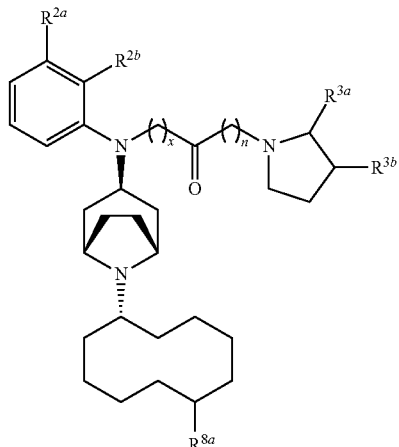
(b)
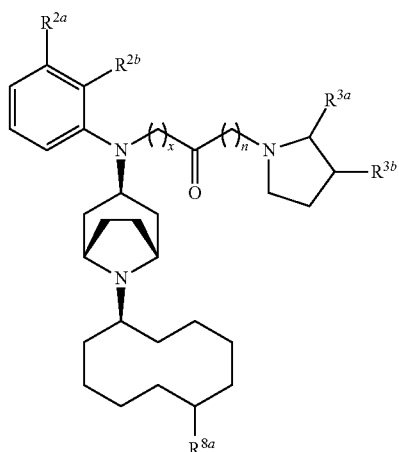
(c)
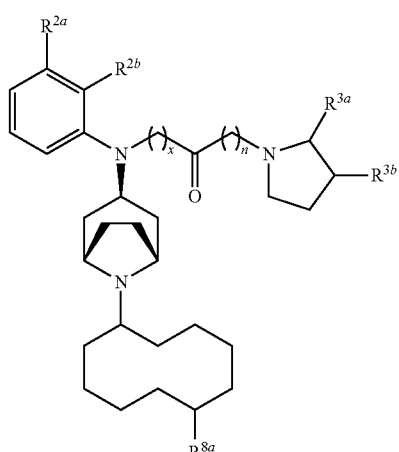
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J73 a, b, or c | H | N(H)C(=O)E³OH | 0 | 0 | tetrazolyl | H |
| J74 a, b, or c | H | N(H)C(=O)E³OH | 1 | 0 | tetrazolyl | H |
| J75 a, b, or c | H | N(H)C(=O)E³OH | 1 | 1 | tetrazolyl | H |
| J76 a, b, or c | H | N(H)C(=O)E³OH | 0 | 1 | tetrazolyl | H |
| J77 a, b, or c | H | OCH₂C(=O)OH | 0 | 0 | tetrazolyl | H |
| J78 a, b, or c | H | OCH₂C(=O)OH | 1 | 0 | tetrazolyl | H |

TABLE 11-continued
(a)
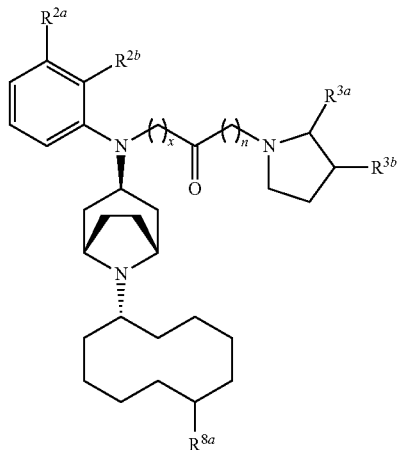
(b)
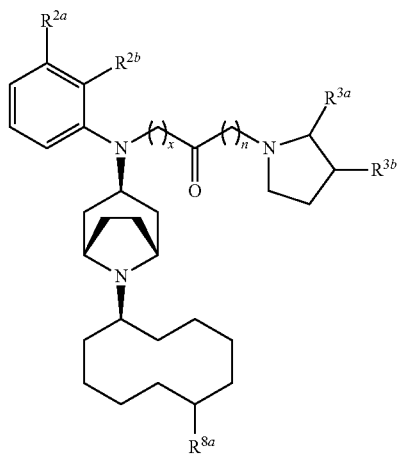
(c)
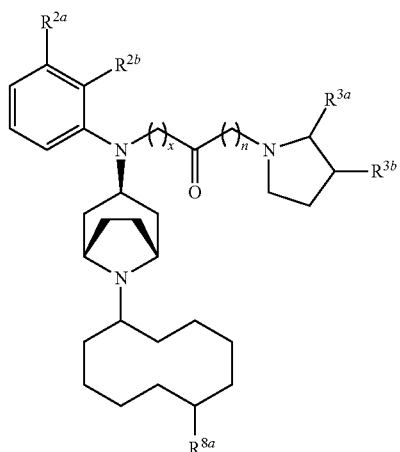
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J79 a, b, or c | H | OCH$_2$C(=O)OH | 1 | 1 | tetrazolyl | H |
| J80 a, b, or c | H | OCH$_2$C(=O)OH | 0 | 1 | tetrazolyl | H |
| J81 a, b, or c | H | H | 0 | 0 | H | tetrazolyl |
| J82 a, b, or c | H | H | 1 | 0 | H | tetrazolyl |
| J83 a, b, or c | H | H | 1 | 1 | H | tetrazolyl |
| J84 a, b, or c | H | H | 0 | 1 | H | tetrazolyl |

TABLE 11-continued
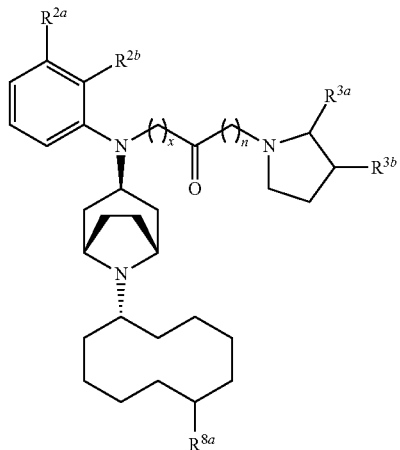
(a)

(b)

(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J85 a, b, or c | N(H)C(=O)E$^3$OH | H | 0 | 0 | H | tetrazolyl |
| J86 a, b, or c | N(H)C(=O)E$^3$OH | H | 1 | 0 | H | tetrazolyl |
| J87 a, b, or c | N(H)C(=O)E$^3$OH | H | 1 | 1 | H | tetrazolyl |
| J88 a, b, or c | N(H)C(=O)E$^3$OH | H | 0 | 1 | H | tetrazolyl |
| J89 a, b, or c | OCH$_2$C(=O)OH | H | 0 | 0 | H | tetrazolyl |
| J90 a, b, or c | OCH$_2$C(=O)OH | H | 1 | 0 | H | tetrazolyl |

TABLE 11-continued
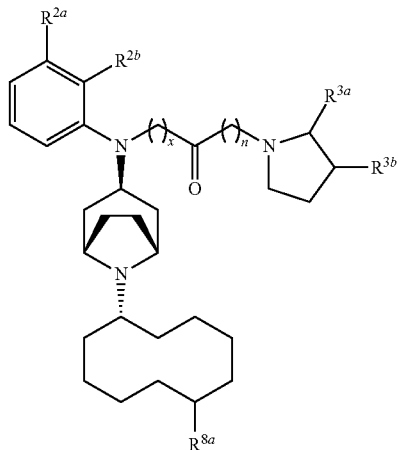
(a)
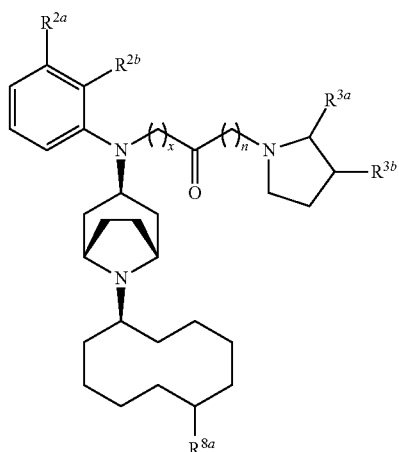
(b)
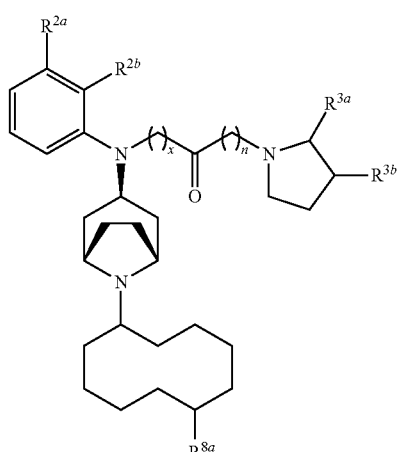
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J91 a, b, or c | OCH$_2$C(=O)OH | H | 1 | 1 | H | tetrazolyl |
| J92 a, b, or c | OCH$_2$C(=O)OH | H | 0 | 1 | H | tetrazolyl |
| J93 a, b, or c | H | N(H)C(=O)E$^3$OH | 0 | 0 | H | tetrazolyl |
| J94 a, b, or c | H | N(H)C(=O)E$^3$OH | 1 | 0 | H | tetrazolyl |
| J95 a, b, or c | H | N(H)C(=O)E$^3$OH | 1 | 1 | H | tetrazolyl |
| J96 a, b, or c | H | N(H)C(=O)E$^3$OH | 0 | 1 | H | tetrazolyl |

TABLE 11-continued
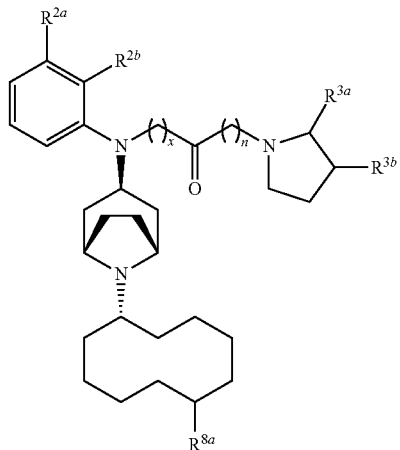
(a)
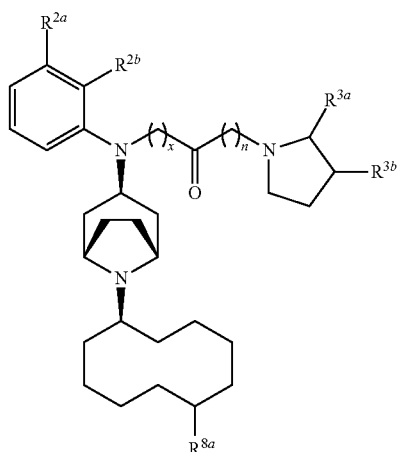
(b)
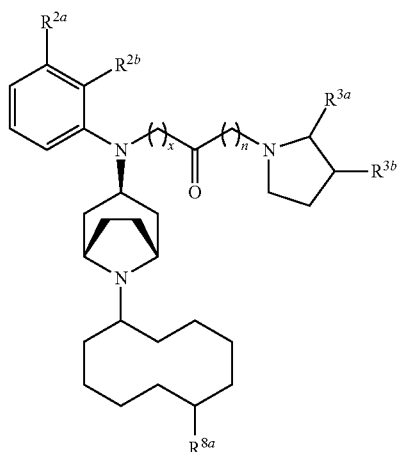
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| J97 a, b, or c | H | OCH$_2$C(=O)OH | 0 | 0 | H | tetrazolyl |
| J98 a, b, or c | H | OCH$_2$C(=O)OH | 1 | 0 | H | tetrazolyl |
| J99 a, b, or c | H | OCH$_2$C(=O)OH | 1 | 1 | H | tetrazolyl |
| J100 a, b, or c | H | OCH$_2$C(=O)OH | 0 | 1 | H | tetrazolyl |
$R^{8a}$ is (i) H or (ii) CH$_3$; E$^3$ is (iii) a direct bond or (iv) C(=O).

TABLE 12
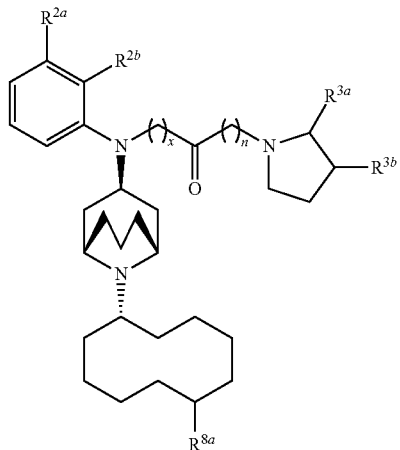
(a)
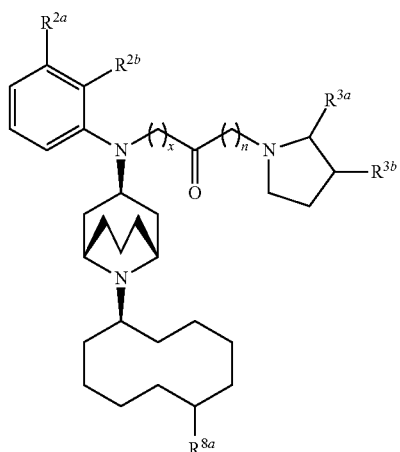
(b)
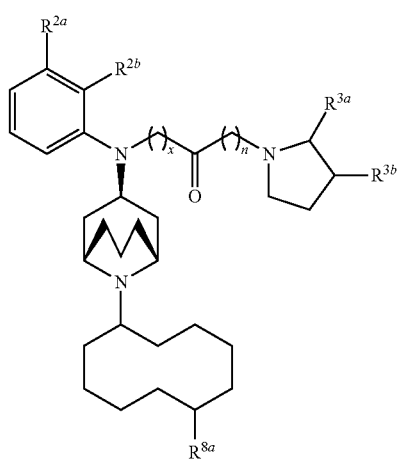
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K1 a, b, or c | H | H | 0 | 0 | H | H |
| K2 a, b, or c | H | H | 1 | 0 | H | H |
| K3 a, b, or c | H | H | 1 | 1 | H | H |
| K4 a, b, or c | H | H | 0 | 1 | H | H |
| K5 a, b, or c | N(H)C(=O)$E^3$OH | H | 0 | 0 | H | H |
| K6 a, b, or c | N(H)C(=O)$E^3$OH | H | 1 | 0 | H | H |

TABLE 12-continued
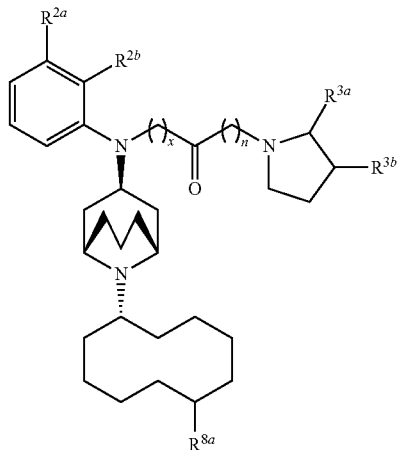
(a)
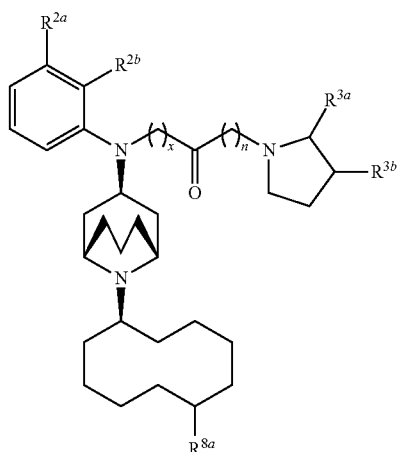
(b)
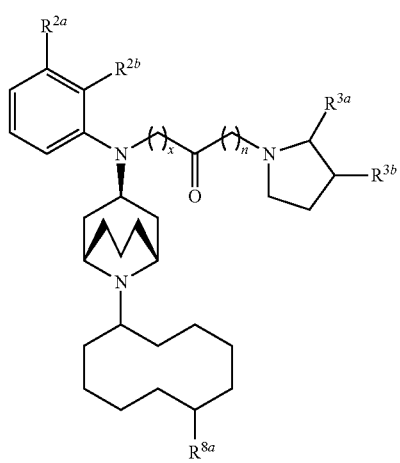
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K7 a, b, or c | $N(H)C(=O)E^3OH$ | H | 1 | 1 | H | H |
| K8 a, b, or c | $N(H)C(=O)E^3OH$ | H | 0 | 1 | H | H |
| K9 a, b, or c | $OCH_2C(=O)OH$ | H | 0 | 0 | H | H |
| K10 a, b, or c | $OCH_2C(=O)OH$ | H | 1 | 0 | H | H |
| K11 a, b, or c | $OCH_2C(=O)OH$ | H | 1 | 1 | H | H |
| K12 a, b, or c | $OCH_2C(=O)OH$ | H | 0 | 1 | H | H |

TABLE 12-continued
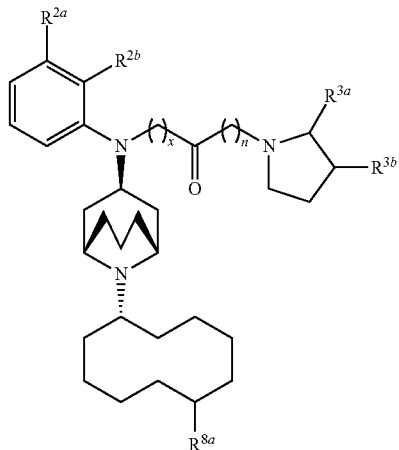
(a)
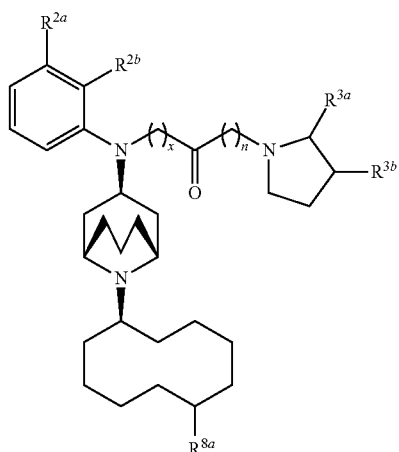
(b)
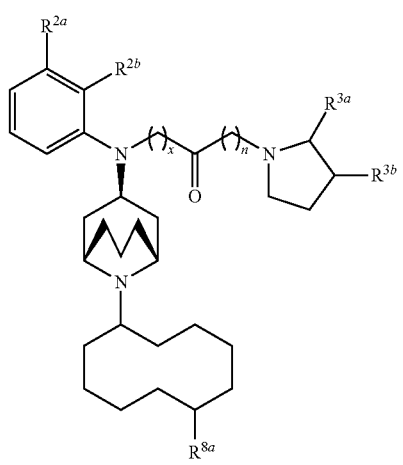
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K13 a, b, or c | H | N(H)C(=O)$E^3$OH | 0 | 0 | H | H |
| K14 a, b, or c | H | N(H)C(=O)$E^3$OH | 1 | 0 | H | H |
| K15 a, b, or c | H | N(H)C(=O)$E^3$OH | 1 | 1 | H | H |
| K16 a, b, or c | H | N(H)C(=O)$E^3$OH | 0 | 1 | H | H |
| K17 a, b, or c | H | OCH$_2$C(=O)OH | 0 | 0 | H | H |
| K18 a, b, or c | H | OCH$_2$C(=O)OH | 1 | 0 | H | H |

TABLE 12-continued
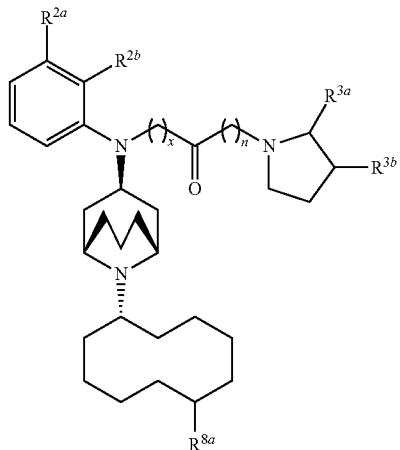
(a)
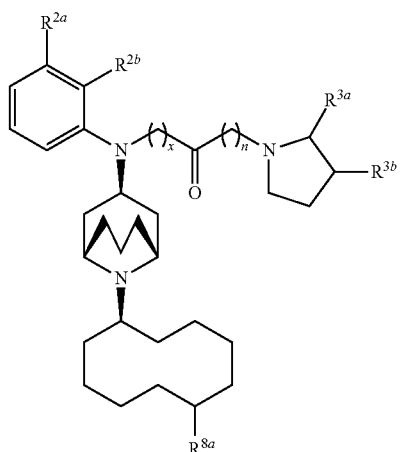
(b)
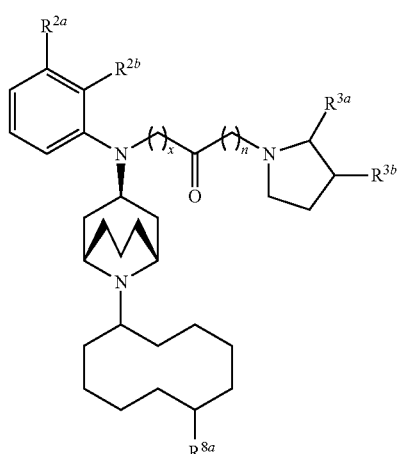
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K19 a, b, or c | H | $OCH_2C(=O)OH$ | 1 | 1 | H | H |
| K20 a, b, or c | H | $OCH_2C(=O)OH$ | 0 | 1 | H | H |
| K21 a, b, or c | H | H | 0 | 0 | $C(=O)OH$ | H |
| K22 a, b, or c | H | H | 1 | 0 | $C(=O)OH$ | H |
| K23 a, b, or c | H | H | 1 | 1 | $C(=O)OH$ | H |
| K24 a, b, or c | H | H | 0 | 1 | $C(=O)OH$ | H |

TABLE 12-continued
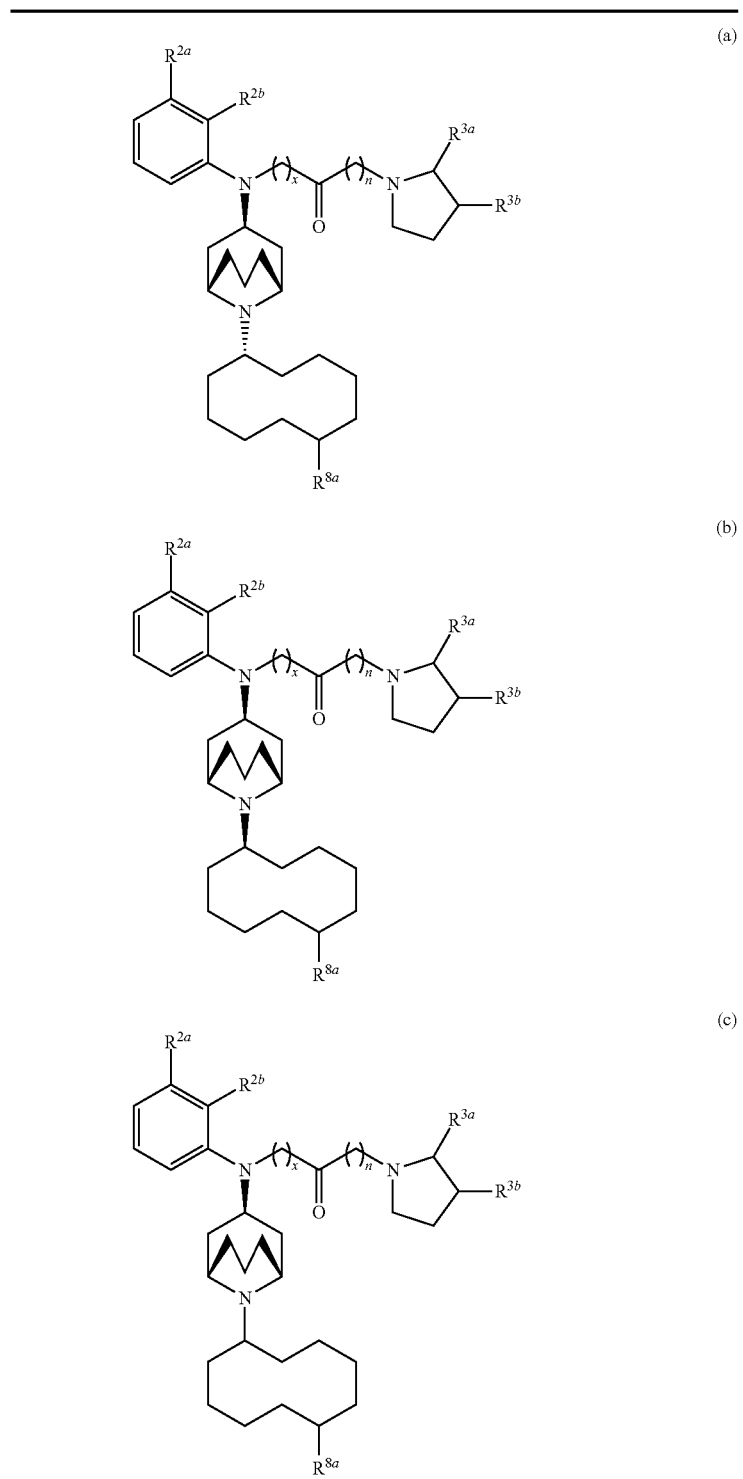
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K25 a, b, or c | N(H)C(=O)E$^3$OH | H | 0 | 0 | C(=O)OH | H |
| K26 a, b, or c | N(H)C(=O)E$^3$OH | H | 1 | 0 | C(=O)OH | H |
| K27 a, b, or c | N(H)C(=O)E$^3$OH | H | 1 | 1 | C(=O)OH | H |
| K28 a, b, or c | N(H)C(=O)E$^3$OH | H | 0 | 1 | C(=O)OH | H |
| K29 a, b, or c | OCH$_2$C(=O)OH | H | 0 | 0 | C(=O)OH | H |
| K30 a, b, or c | OCH$_2$C(=O)OH | H | 1 | 0 | C(=O)OH | H |

TABLE 12-continued
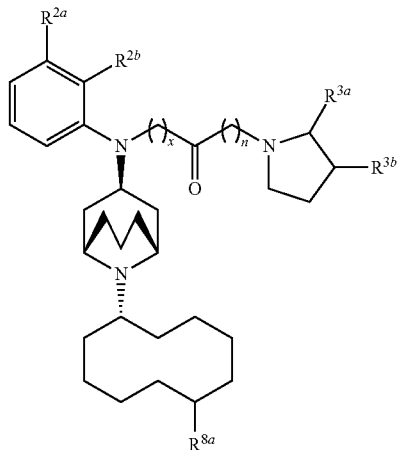
(a)
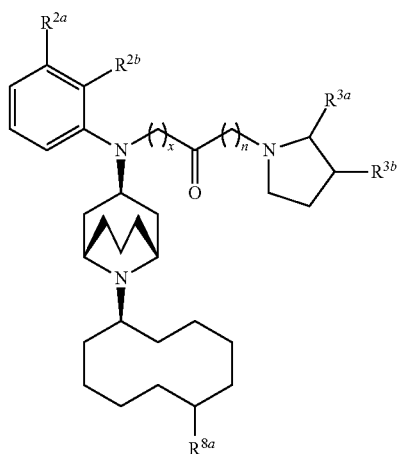
(b)
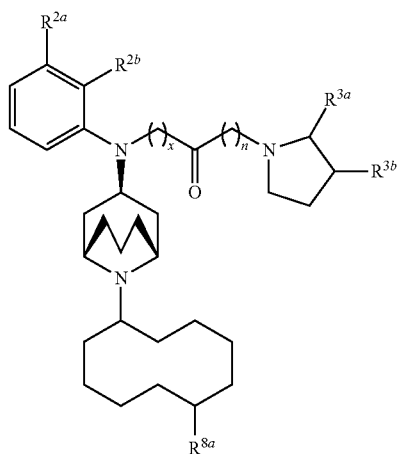
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K31 a, b, or c | $OCH_2C(=O)OH$ | H | 1 | 1 | $C(=O)OH$ | H |
| K32 a, b, or c | $OCH_2C(=O)OH$ | H | 0 | 1 | $C(=O)OH$ | H |
| K33 a, b, or c | H | $N(H)C(=O)E^3OH$ | 0 | 0 | $C(=O)OH$ | H |
| K34 a, b, or c | H | $N(H)C(=O)E^3OH$ | 1 | 0 | $C(=O)OH$ | H |
| K35 a, b, or c | H | $N(H)C(=O)E^3OH$ | 1 | 1 | $C(=O)OH$ | H |
| K36 a, b, or c | H | $N(H)C(=O)E^3OH$ | 0 | 1 | $C(=O)OH$ | H |

TABLE 12-continued
(a)
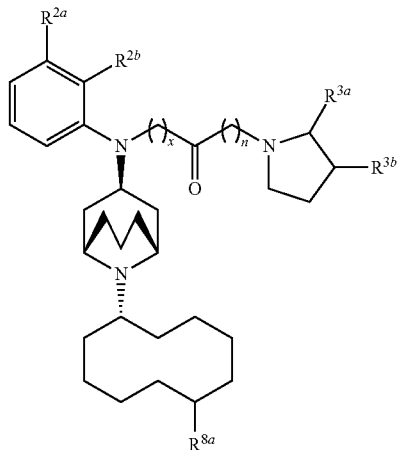
(b)
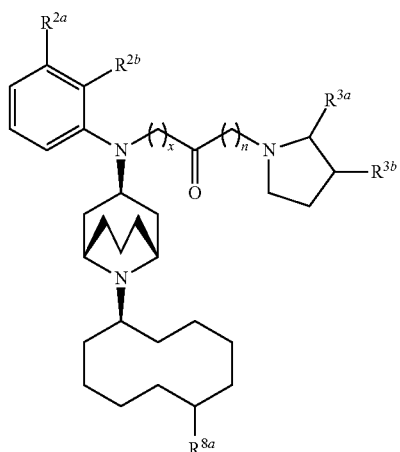
(c)
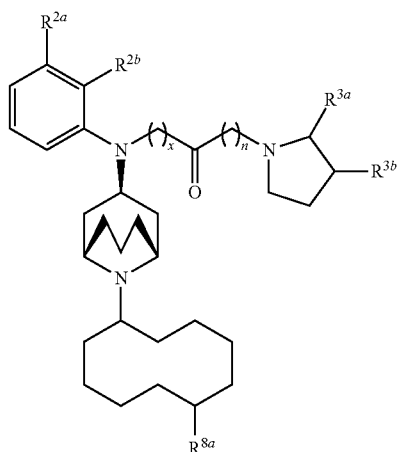
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K37 a, b, or c | H | $OCH_2C(=O)OH$ | 0 | 0 | $C(=O)OH$ | H |
| K38 a, b, or c | H | $OCH_2C(=O)OH$ | 1 | 0 | $C(=O)OH$ | H |
| K39 a, b, or c | H | $OCH_2C(=O)OH$ | 1 | 1 | $C(=O)OH$ | H |
| K40 a, b, or c | H | $OCH_2C(=O)OH$ | 0 | 1 | $C(=O)OH$ | H |
| K41 a, b, or c | H | H | 0 | 0 | H | $C(=O)OH$ |
| K42 a, b, or c | H | H | 1 | 0 | H | $C(=O)OH$ |

TABLE 12-continued
(a)
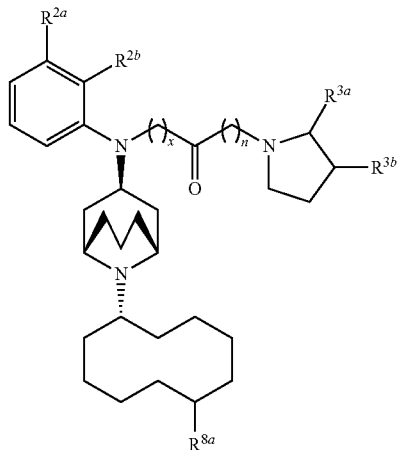
(b)
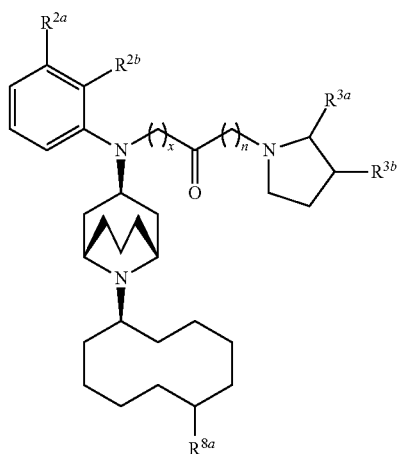
(c)
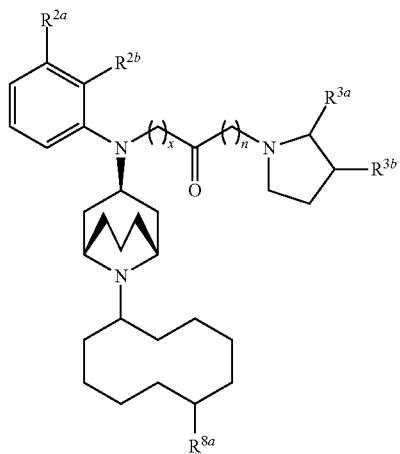
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K43 a, b, or c | H | H | 1 | 1 | H | C(=O)OH |
| K44 a, b, or c | H | H | 0 | 1 | H | C(=O)OH |
| K45 a, b, or c | N(H)C(=O)$E^3$OH | H | 0 | 0 | H | C(=O)OH |
| K46 a, b, or c | N(H)C(=O)$E^3$OH | H | 1 | 0 | H | C(=O)OH |
| K47 a, b, or c | N(H)C(=O)$E^3$OH | H | 1 | 1 | H | C(=O)OH |
| K48 a, b, or c | N(H)C(=O)$E^3$OH | H | 0 | 1 | H | C(=O)OH |

TABLE 12-continued
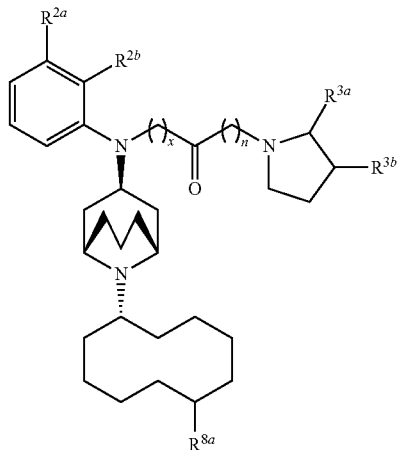
(a)
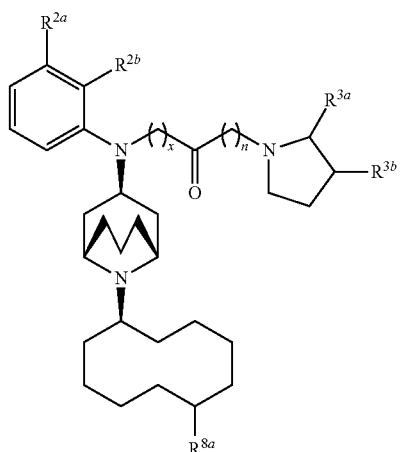
(b)
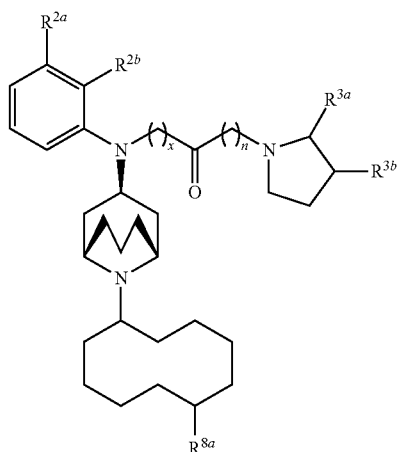
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K49 a, b, or c | $OCH_2C(=O)OH$ | H | 0 | 0 | H | $C(=O)OH$ |
| K50 a, b, or c | $OCH_2C(=O)OH$ | H | 1 | 0 | H | $C(=O)OH$ |
| K51 a, b, or c | $OCH_2C(=O)OH$ | H | 1 | 1 | H | $C(=O)OH$ |
| K52 a, b, or c | $OCH_2C(=O)OH$ | H | 0 | 1 | H | $C(=O)OH$ |
| K53 a, b, or c | H | $N(H)C(=O)E^3OH$ | 0 | 0 | H | $C(=O)OH$ |
| K54 a, b, or c | H | $N(H)C(=O)E^3OH$ | 1 | 0 | H | $C(=O)OH$ |

TABLE 12-continued
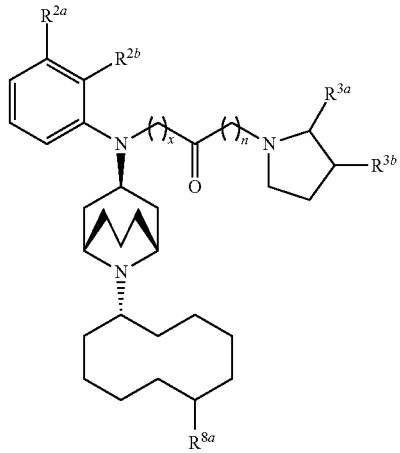
(a)
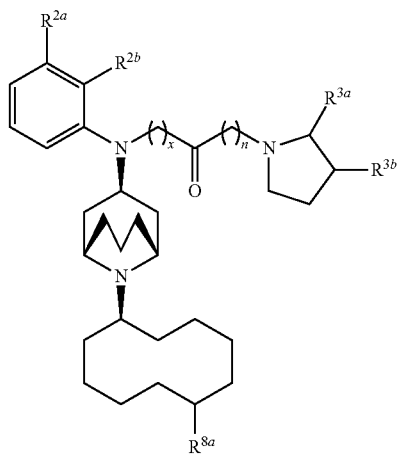
(b)
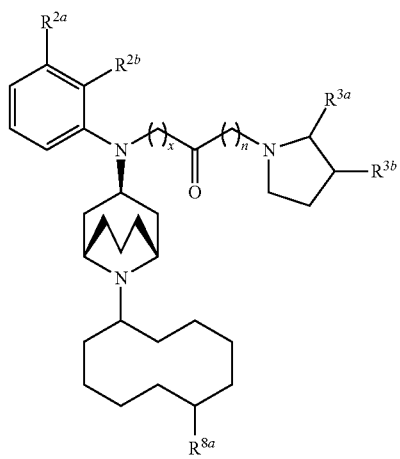
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K55 a, b, or c | H | $N(H)C(=O)E^3OH$ | 1 | 1 | H | $C(=O)OH$ |
| K56 a, b, or c | H | $N(H)C(=O)E^3OH$ | 0 | 1 | H | $C(=O)OH$ |
| K57 a, b, or c | H | $OCH_2C(=O)OH$ | 0 | 0 | H | $C(=O)OH$ |
| K58 a, b, or c | H | $OCH_2C(=O)OH$ | 1 | 0 | H | $C(=O)OH$ |
| K59 a, b, or c | H | $OCH_2C(=O)OH$ | 1 | 1 | H | $C(=O)OH$ |
| K60 a, b, or c | H | $OCH_2C(=O)OH$ | 0 | 1 | H | $C(=O)OH$ |

TABLE 12-continued
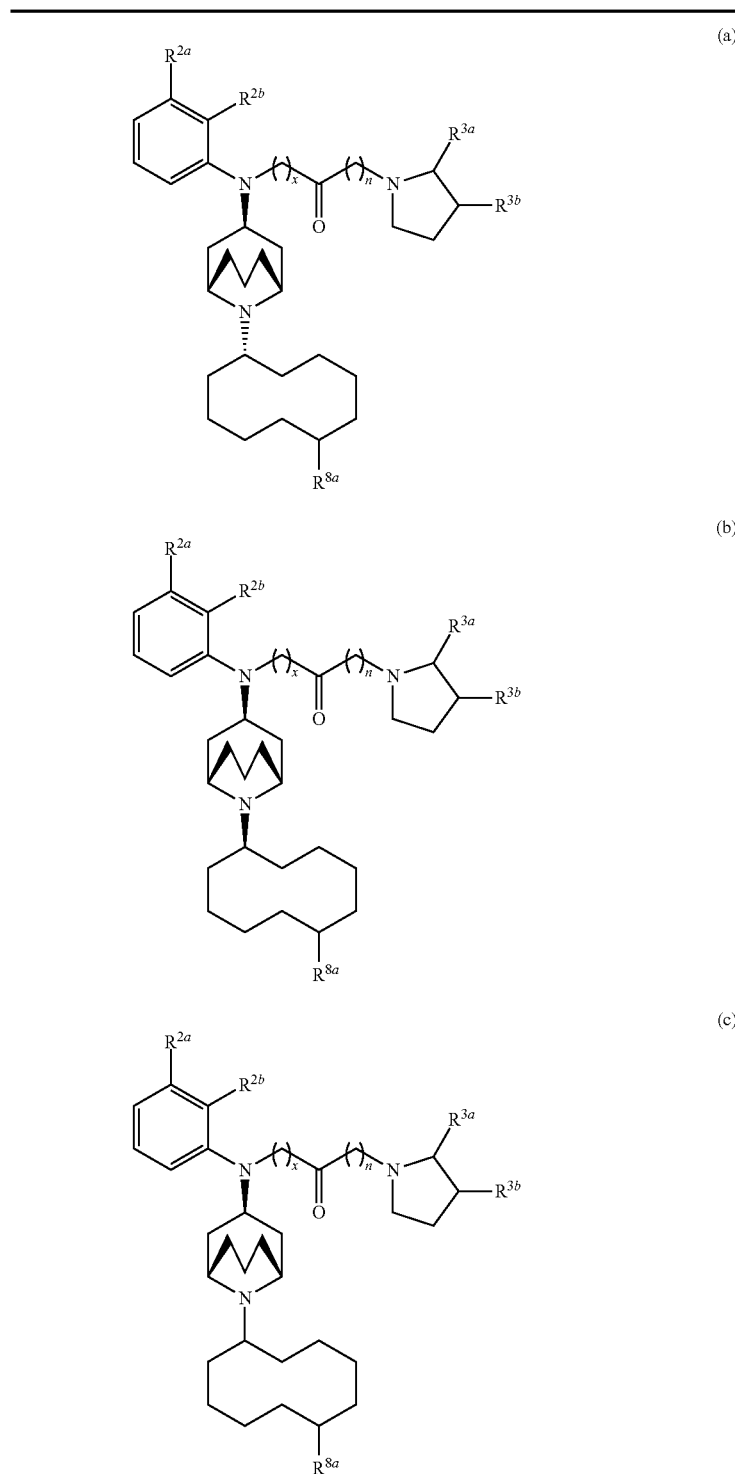
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K61 a, b, or c | H | H | 0 | 0 | tetrazolyl | H |
| K62 a, b, or c | H | H | 1 | 0 | tetrazolyl | H |
| K63 a, b, or c | H | H | 1 | 1 | tetrazolyl | H |
| K64 a, b, or c | H | H | 0 | 1 | tetrazolyl | H |
| K65 a, b, or c | N(H)C(=O)E$^3$OH | H | 0 | 0 | tetrazolyl | H |
| K66 a, b, or c | N(H)C(=O)E$^3$OH | H | 1 | 0 | tetrazolyl | H |

TABLE 12-continued
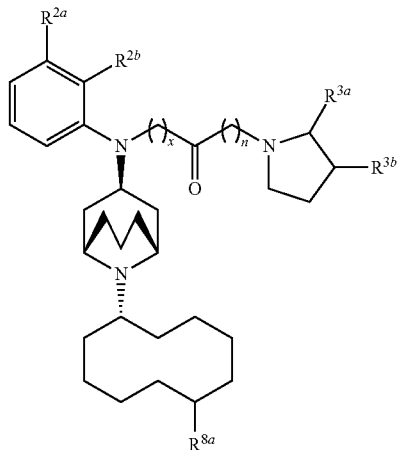
(a)
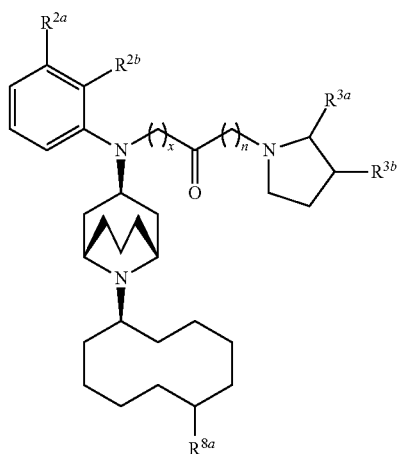
(b)
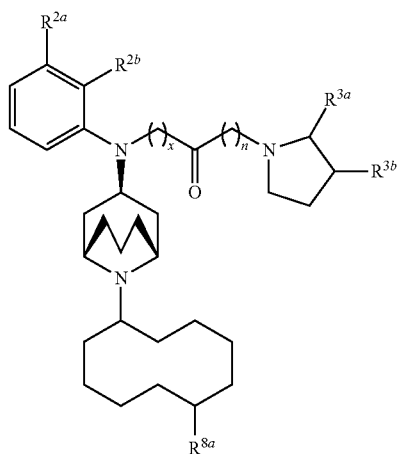
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K67 a, b, or c | N(H)C(=O)$E^3$OH | H | 1 | 1 | tetrazolyl | H |
| K68 a, b, or c | N(H)C(=O)$E^3$OH | H | 0 | 1 | tetrazolyl | H |
| K69 a, b, or c | OCH$_2$C(=O)OH | H | 0 | 0 | tetrazolyl | H |
| K70 a, b, or c | OCH$_2$C(=O)OH | H | 1 | 0 | tetrazolyl | H |
| K71 a, b, or c | OCH$_2$C(=O)OH | H | 1 | 1 | tetrazolyl | H |
| K72 a, b, or c | OCH$_2$C(=O)OH | H | 0 | 1 | tetrazolyl | H |

TABLE 12-continued
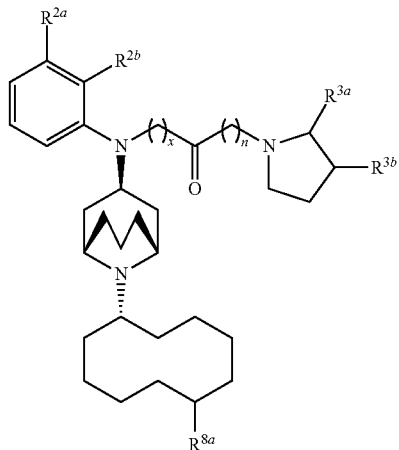
(a)
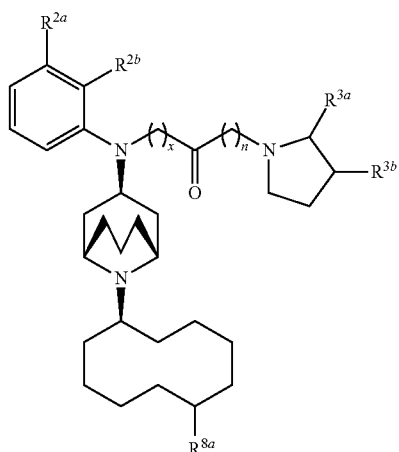
(b)
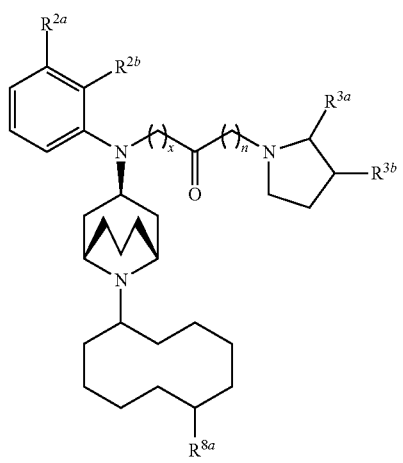
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K73 a, b, or c | H | N(H)C(=O)E$^3$OH | 0 | 0 | tetrazolyl | H |
| K74 a, b, or c | H | N(H)C(=O)E$^3$OH | 1 | 0 | tetrazolyl | H |
| K75 a, b, or c | H | N(H)C(=O)E$^3$OH | 1 | 1 | tetrazolyl | H |
| K76 a, b, or c | H | N(H)C(=O)E$^3$OH | 0 | 1 | tetrazolyl | H |
| K77 a, b, or c | H | OCH$_2$C(=O)OH | 0 | 0 | tetrazolyl | H |
| K78 a, b, or c | H | OCH$_2$C(=O)OH | 1 | 0 | tetrazolyl | H |

TABLE 12-continued
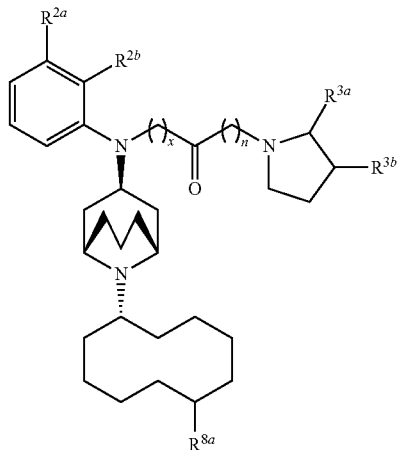
(a)
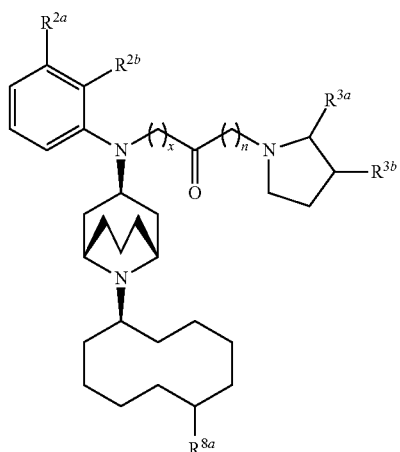
(b)
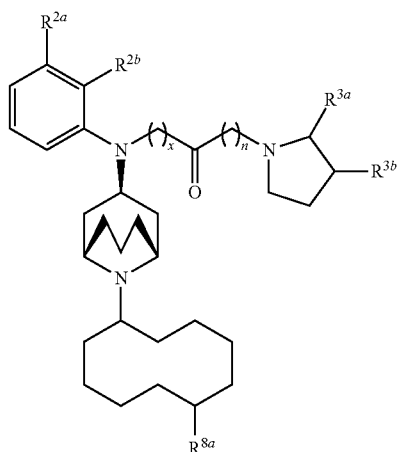
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K79 a, b, or c | H | OCH$_2$C(=O)OH | 1 | 1 | tetrazolyl | H |
| K80 a, b, or c | H | OCH$_2$C(=O)OH | 0 | 1 | tetrazolyl | H |
| K81 a, b, or c | H | H | 0 | 0 | H | tetrazolyl |
| K82 a, b, or c | H | H | 1 | 0 | H | tetrazolyl |
| K83 a, b, or c | H | H | 1 | 1 | H | tetrazolyl |
| K84 a, b, or c | H | H | 0 | 1 | H | tetrazolyl |

TABLE 12-continued
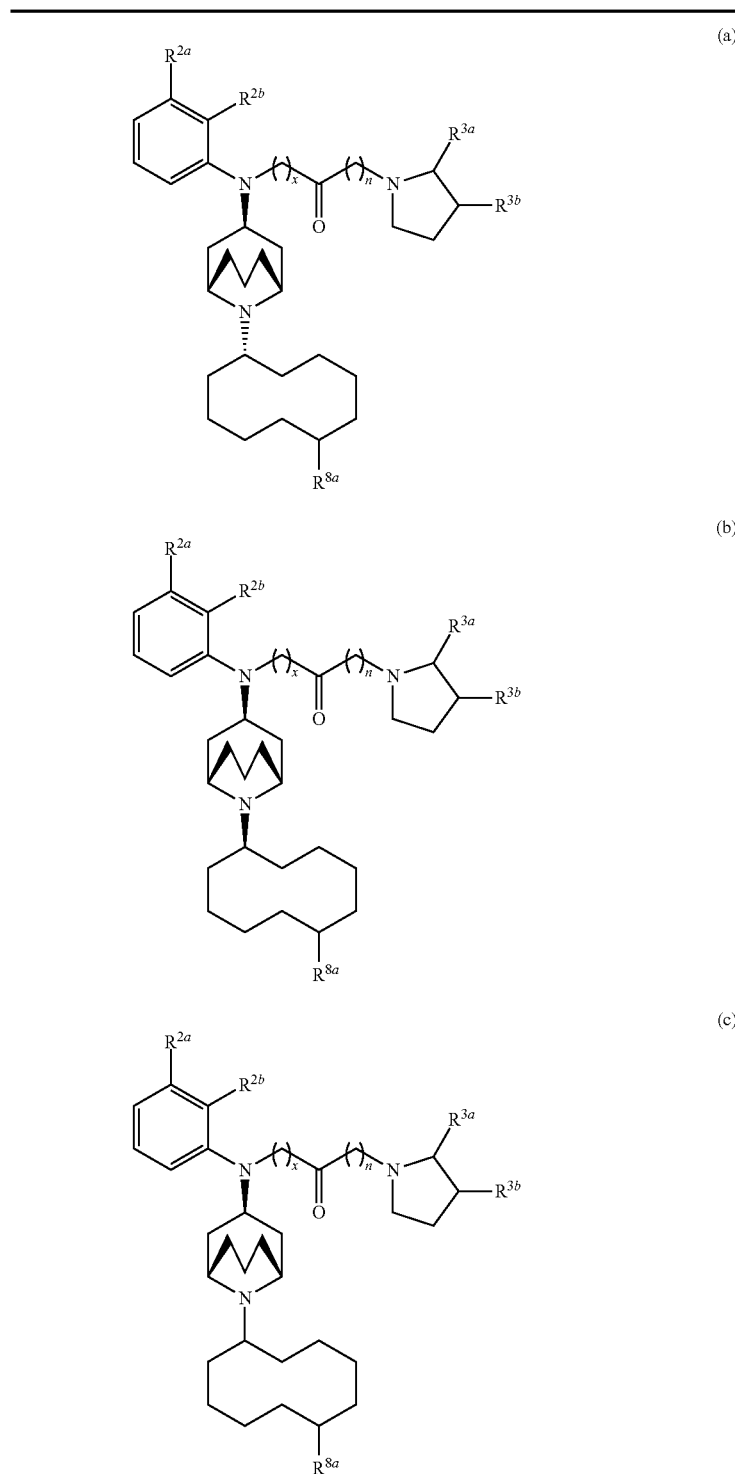
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K85 a, b, or c | $N(H)C(=O)E^3OH$ | H | 0 | 0 | H | tetrazolyl |
| K86 a, b, or c | $N(H)C(=O)E^3OH$ | H | 1 | 0 | H | tetrazolyl |
| K87 a, b, or c | $N(H)C(=O)E^3OH$ | H | 1 | 1 | H | tetrazolyl |
| K88 a, b, or c | $N(H)C(=O)E^3OH$ | H | 0 | 1 | H | tetrazolyl |
| K89 a, b, or c | $OCH_2C(=O)OH$ | H | 0 | 0 | H | tetrazolyl |
| K90 a, b, or c | $OCH_2C(=O)OH$ | H | 1 | 0 | H | tetrazolyl |

TABLE 12-continued
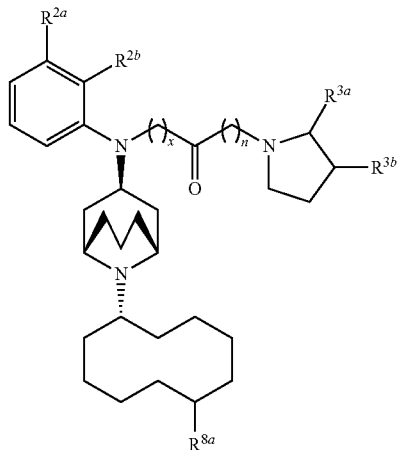
(a)
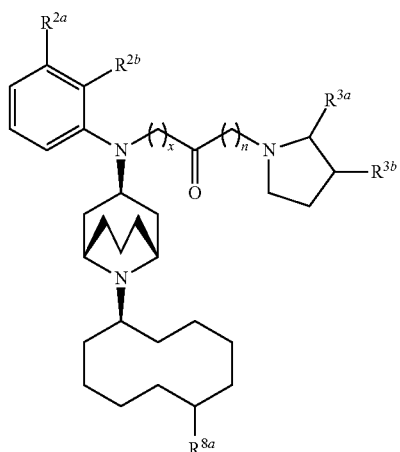
(b)
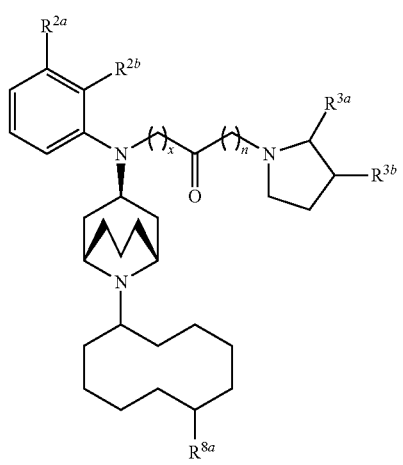
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K91 a, b, or c | OCH$_2$C(=O)OH | H | 1 | 1 | H | tetrazolyl |
| K92 a, b, or c | OCH$_2$C(=O)OH | H | 0 | 1 | H | tetrazolyl |
| K93 a, b, or c | H | N(H)C(=O)E$^3$OH | 0 | 0 | H | tetrazolyl |
| K94 a, b, or c | H | N(H)C(=O)E$^3$OH | 1 | 0 | H | tetrazolyl |
| K95 a, b, or c | H | N(H)C(=O)E$^3$OH | 1 | 1 | H | tetrazolyl |
| K96 a, b, or c | H | N(H)C(=O)E$^3$OH | 0 | 1 | H | tetrazolyl |

TABLE 12-continued
(a)
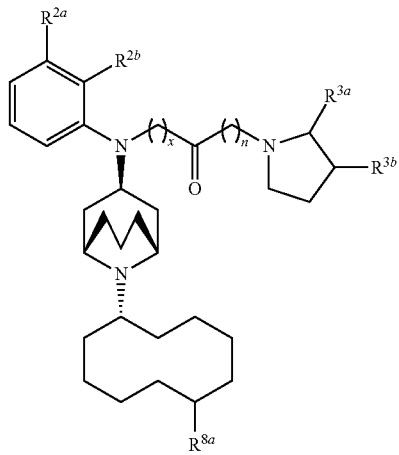
(b)
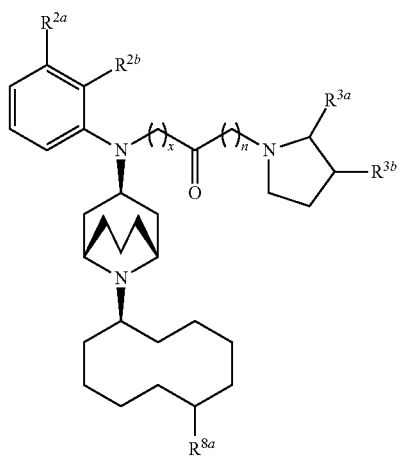
(c)
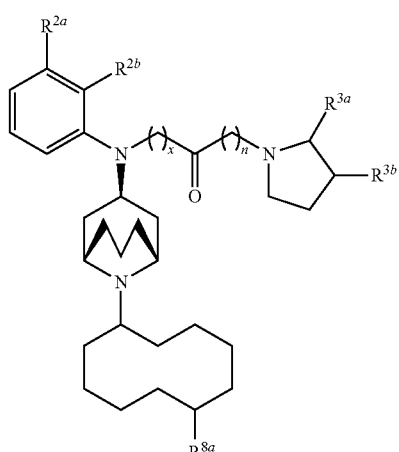
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| K97 a, b, or c | H | OCH$_2$C(=O)OH | 0 | 0 | H | tetrazolyl |
| K98 a, b, or c | H | OCH$_2$C(=O)OH | 1 | 0 | H | tetrazolyl |
| K99 a, b, or c | H | OCH$_2$C(=O)OH | 1 | 1 | H | tetrazolyl |
| K100 a, b, or c | H | OCH$_2$C(=O)OH | 0 | 1 | H | tetrazolyl |
$R^{8a}$ is (i) H or (ii) CH$_3$; $E^3$ is (iii) a direct bond or (iv) C(=O).

TABLE 13
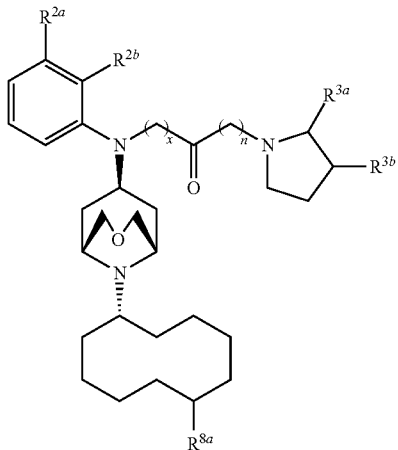
(a)
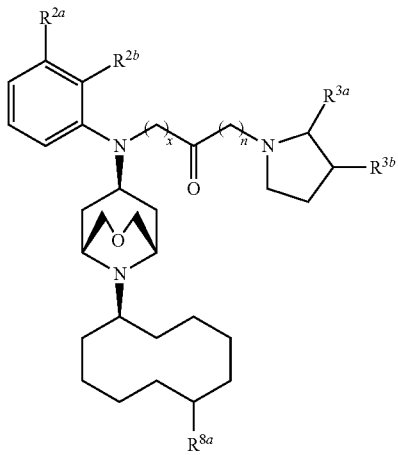
(b)
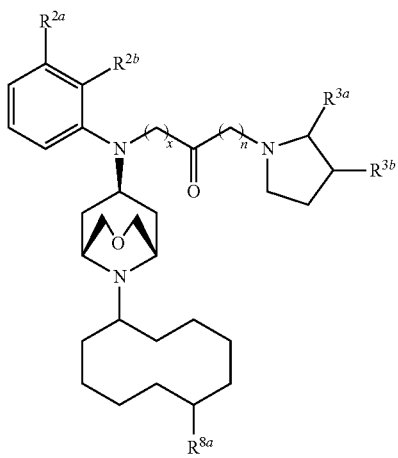
(c)
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L1 a, b, or c | H | H | 0 | 0 | H | H |
| L2 a, b, or c | H | H | 1 | 0 | H | H |
| L3 a, b, or c | H | H | 1 | 1 | H | H |
| L4 a, b, or c | H | H | 0 | 1 | H | H |
| L5 a, b, or c | N(H)C(=O)$E^3$OH | H | 0 | 0 | H | H |
| L6 a, b, or c | N(H)C(=O)$E^3$OH | H | 1 | 0 | H | H |

TABLE 13-continued
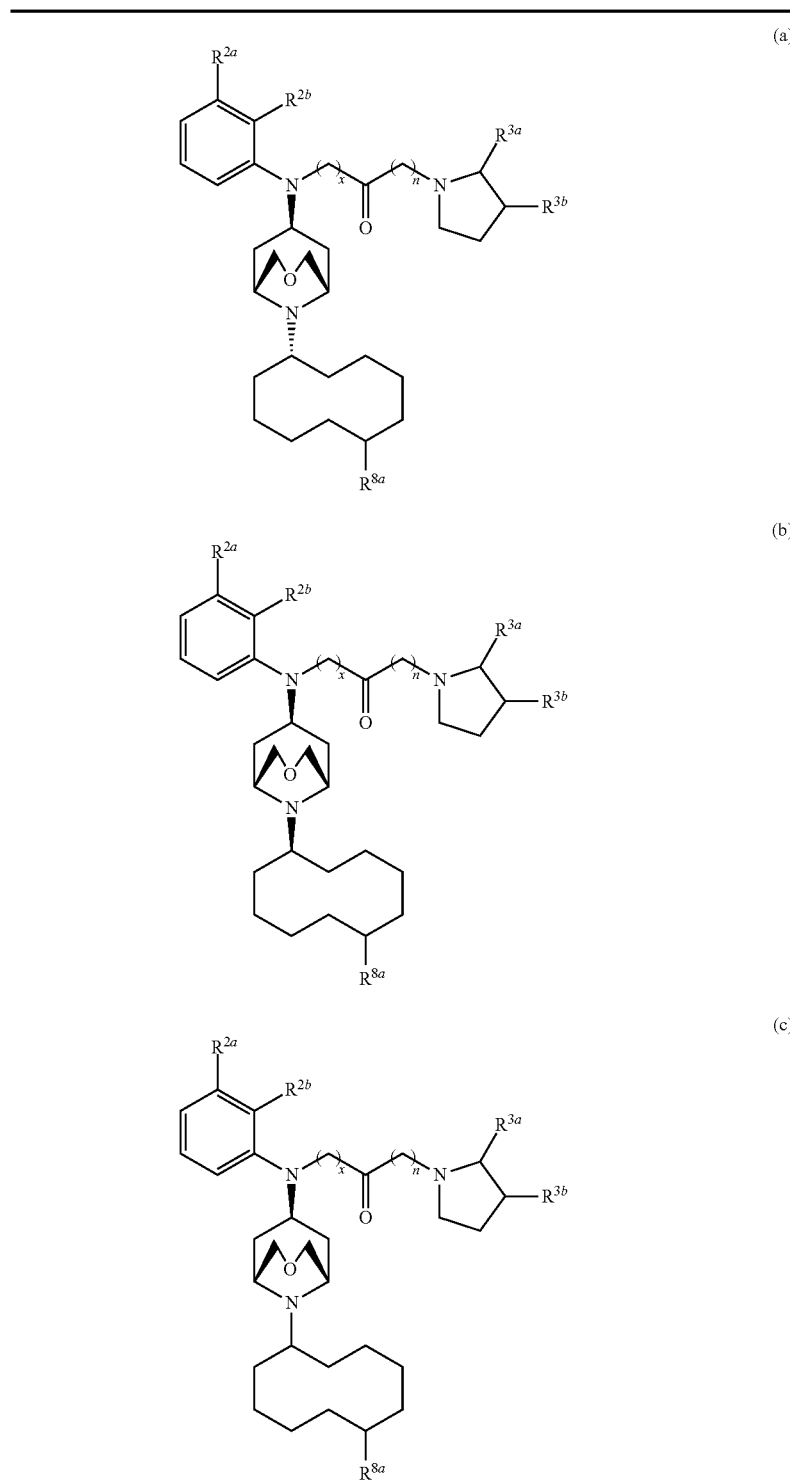
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L7 a, b, or c | N(H)C(=O)E³OH | H | 1 | 1 | H | H |
| L8 a, b, or c | N(H)C(=O)E³OH | H | 0 | 1 | H | H |
| L9 a, b, or c | OCH₂C(=O)OH | H | 0 | 0 | H | H |
| L10 a, b, or c | OCH₂C(=O)OH | H | 1 | 0 | H | H |
| L11 a, b, or c | OCH₂C(=O)OH | H | 1 | 1 | H | H |
| L12 a, b, or c | OCH₂C(=O)OH | H | 0 | 1 | H | H |

TABLE 13-continued
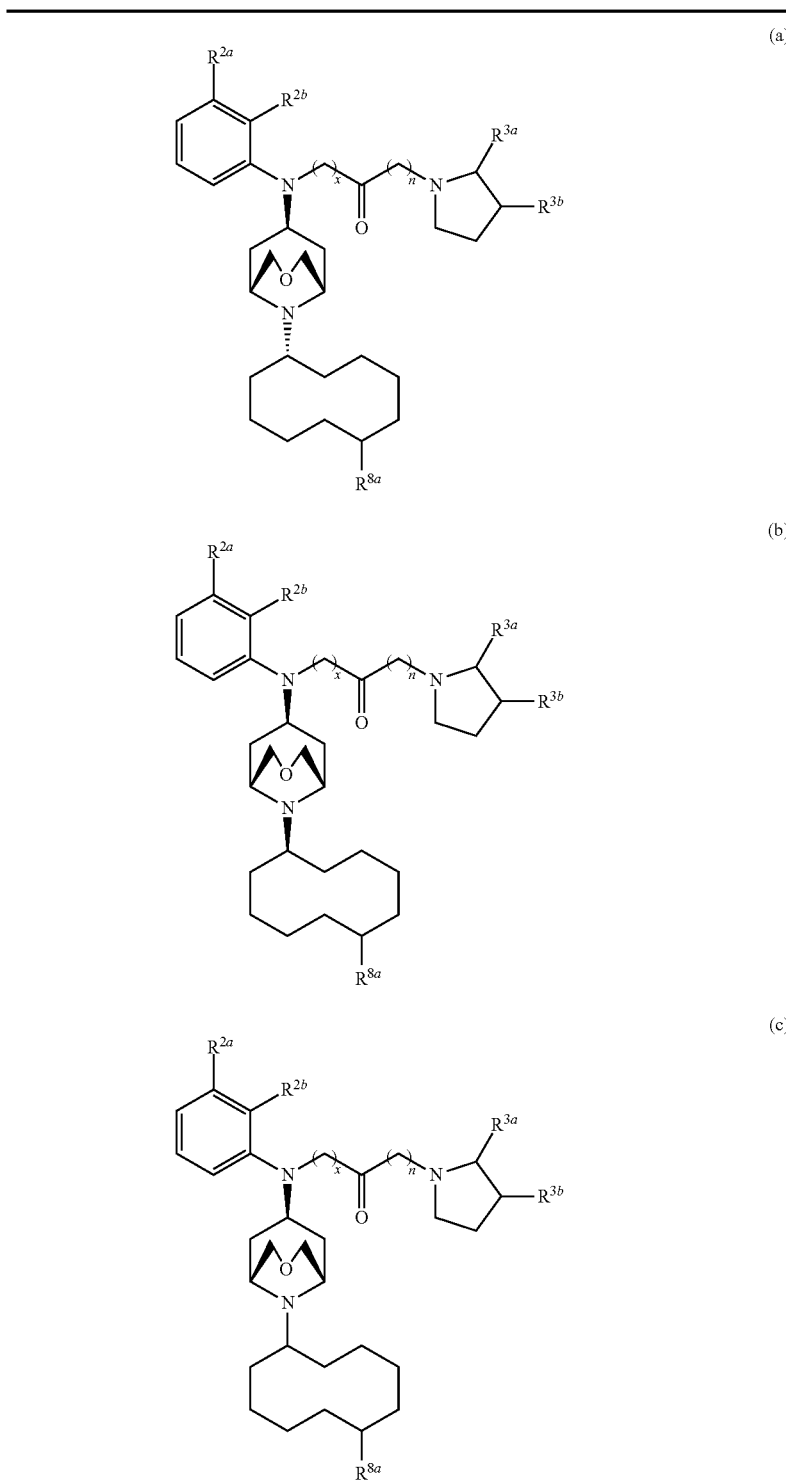
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L13 a, b, or c | H | N(H)C(=O)E³OH | 0 | 0 | H | H |
| L14 a, b, or c | H | N(H)C(=O)E³OH | 1 | 0 | H | H |
| L15 a, b, or c | H | N(H)C(=O)E³OH | 1 | 1 | H | H |
| L16 a, b, or c | H | N(H)C(=O)E³OH | 0 | 1 | H | H |
| L17 a, b, or c | H | OCH₂C(=O)OH | 0 | 0 | H | H |
| L18 a, b, or c | H | OCH₂C(=O)OH | 1 | 0 | H | H |

TABLE 13-continued
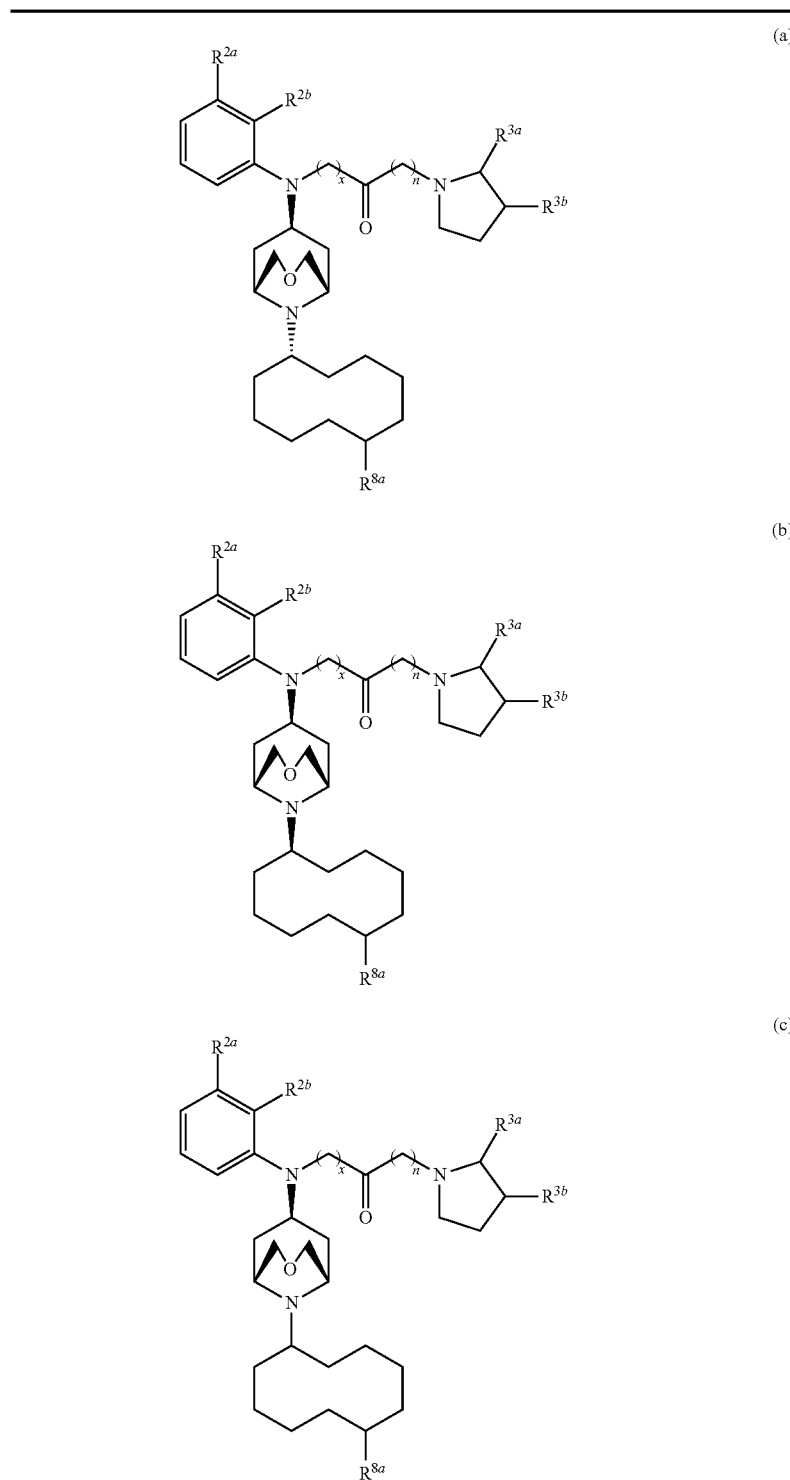
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L19 a, b, or c | H | OCH$_2$C(=O)OH | 1 | 1 | H | H |
| L20 a, b, or c | H | OCH$_2$C(=O)OH | 0 | 1 | H | H |
| L21 a, b, or c | H | H | 0 | 0 | C(=O)OH | H |
| L22 a, b, or c | H | H | 1 | 0 | C(=O)OH | H |
| L23 a, b, or c | H | H | 1 | 1 | C(=O)OH | H |
| L24 a, b, or c | H | H | 0 | 1 | C(=O)OH | H |

TABLE 13-continued
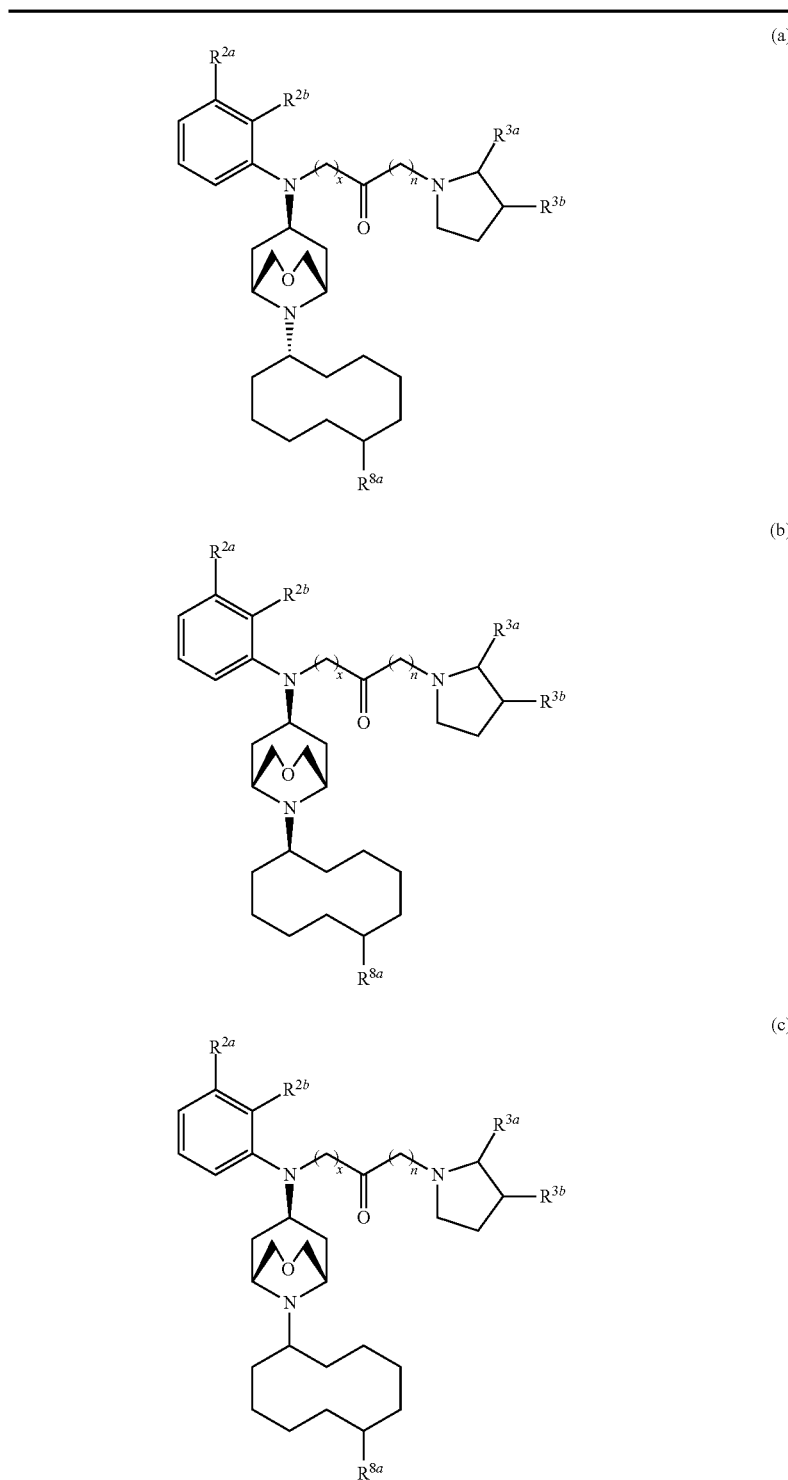
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L25 a, b, or c | N(H)C(=O)E³OH | H | 0 | 0 | C(=O)OH | H |
| L26 a, b, or c | N(H)C(=O)E³OH | H | 1 | 0 | C(=O)OH | H |
| L27 a, b, or c | N(H)C(=O)E³OH | H | 1 | 1 | C(=O)OH | H |
| L28 a, b, or c | N(H)C(=O)E³OH | H | 0 | 1 | C(=O)OH | H |
| L29 a, b, or c | OCH₂C(=O)OH | H | 0 | 0 | C(=O)OH | H |
| L30 a, b, or c | OCH₂C(=O)OH | H | 1 | 0 | C(=O)OH | H |

TABLE 13-continued
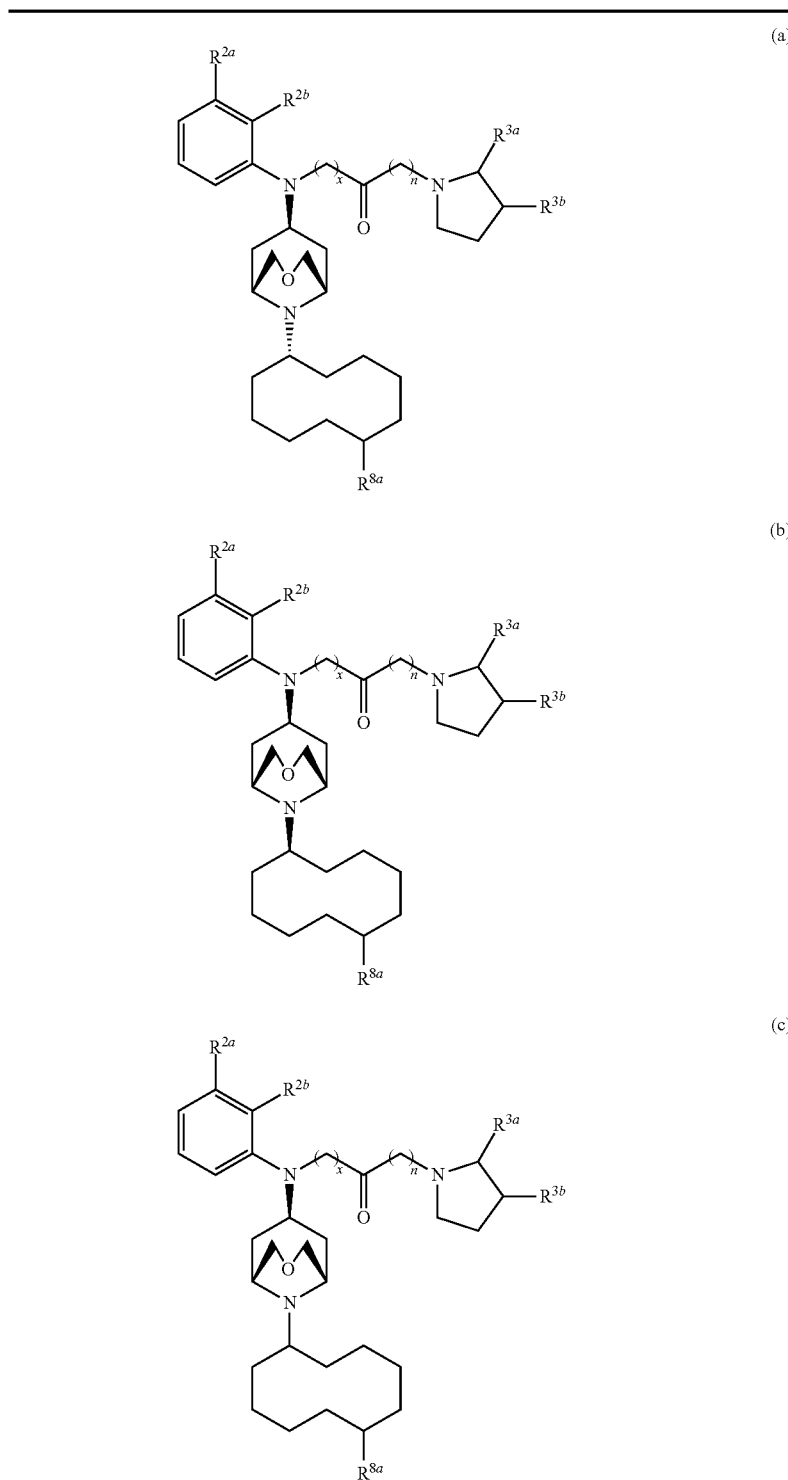
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L31 a, b, or c | OCH$_2$C(=O)OH | H | 1 | 1 | C(=O)OH | H |
| L32 a, b, or c | OCH$_2$C(=O)OH | H | 0 | 1 | C(=O)OH | H |
| L33 a, b, or c | H | N(H)C(=O)E$^3$OH | 0 | 0 | C(=O)OH | H |
| L34 a, b, or c | H | N(H)C(=O)E$^3$OH | 1 | 0 | C(=O)OH | H |
| L35 a, b, or c | H | N(H)C(=O)E$^3$OH | 1 | 1 | C(=O)OH | H |
| L36 a, b, or c | H | N(H)C(=O)E$^3$OH | 0 | 1 | C(=O)OH | H |

TABLE 13-continued
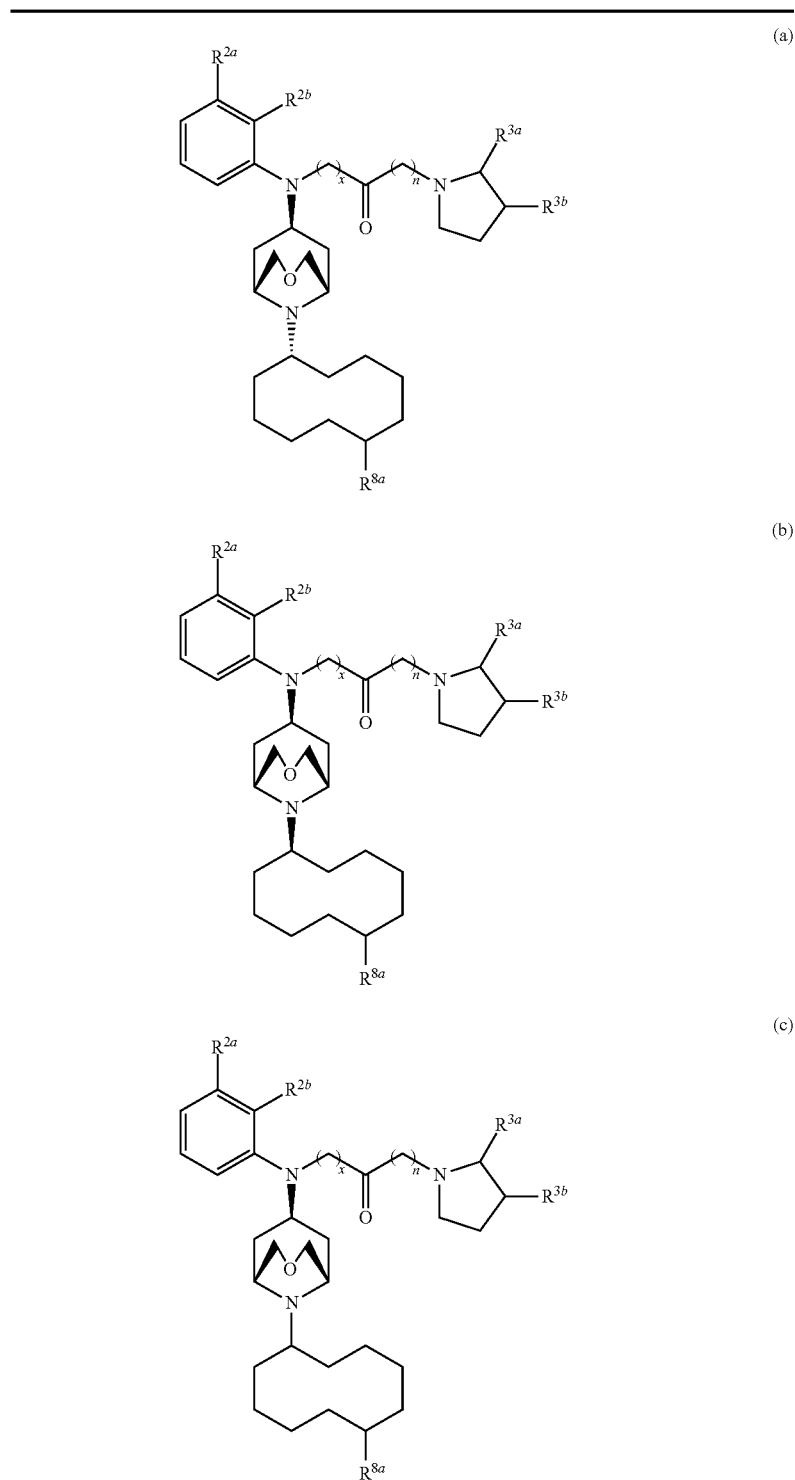
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L37 a, b, or c | H | OCH₂C(=O)OH | 0 | 0 | C(=O)OH | H |
| L38 a, b, or c | H | OCH₂C(=O)OH | 1 | 0 | C(=O)OH | H |
| L39 a, b, or c | H | OCH₂C(=O)OH | 1 | 1 | C(=O)OH | H |
| L40 a, b, or c | H | OCH₂C(=O)OH | 0 | 1 | C(=O)OH | H |
| L41 a, b, or c | H | H | 0 | 0 | H | C(=O)OH |
| L42 a, b, or c | H | H | 1 | 0 | H | C(=O)OH |

TABLE 13-continued
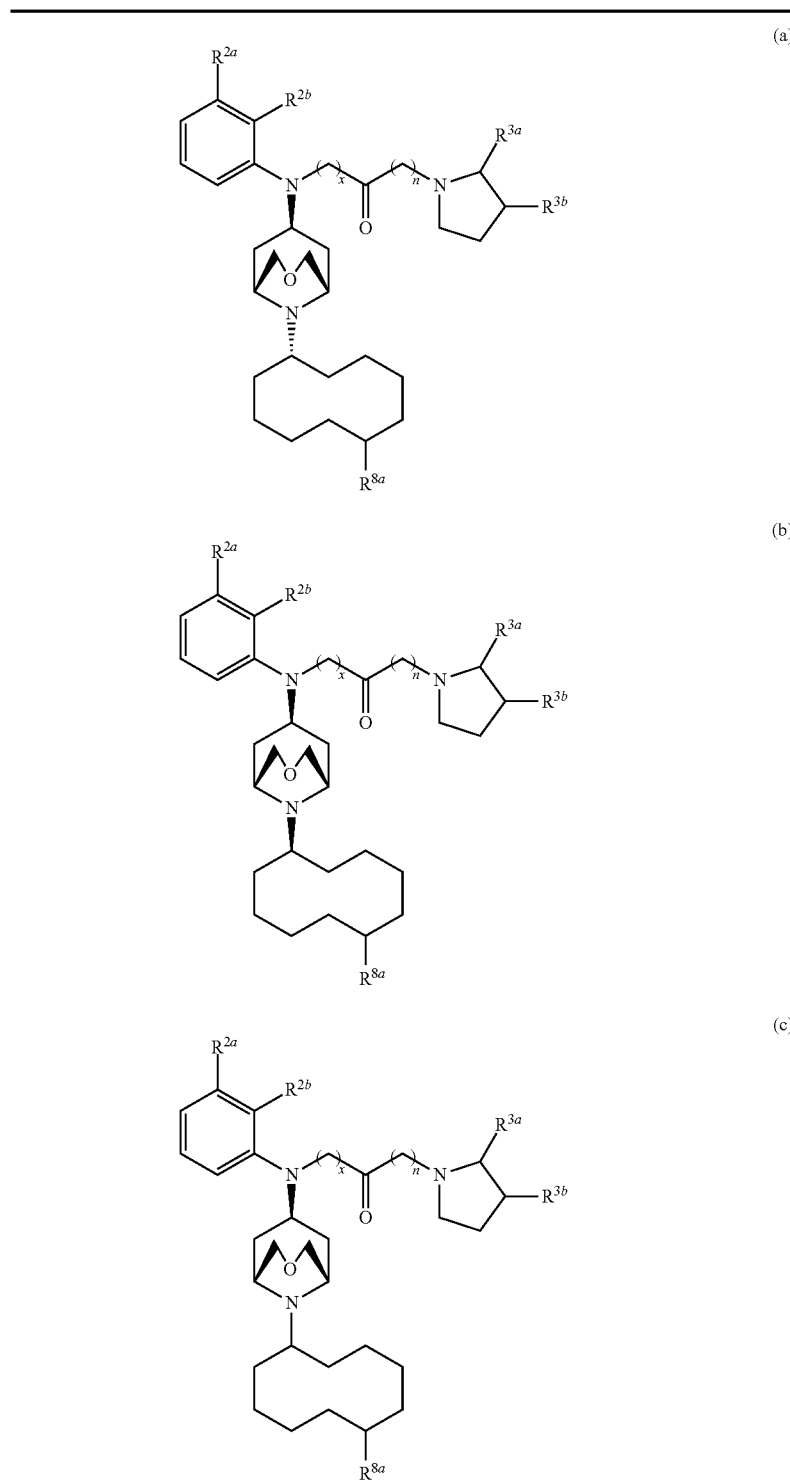
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L43 a, b, or c | H | H | 1 | 1 | H | C(=O)OH |
| L44 a, b, or c | H | H | 0 | 1 | H | C(=O)OH |
| L45 a, b, or c | N(H)C(=O)$E^3$OH | H | 0 | 0 | H | C(=O)OH |
| L46 a, b, or c | N(H)C(=O)$E^3$OH | H | 1 | 0 | H | C(=O)OH |
| L47 a, b, or c | N(H)C(=O)$E^3$OH | H | 1 | 1 | H | C(=O)OH |
| L48 a, b, or c | N(H)C(=O)$E^3$OH | H | 0 | 1 | H | C(=O)OH |

TABLE 13-continued
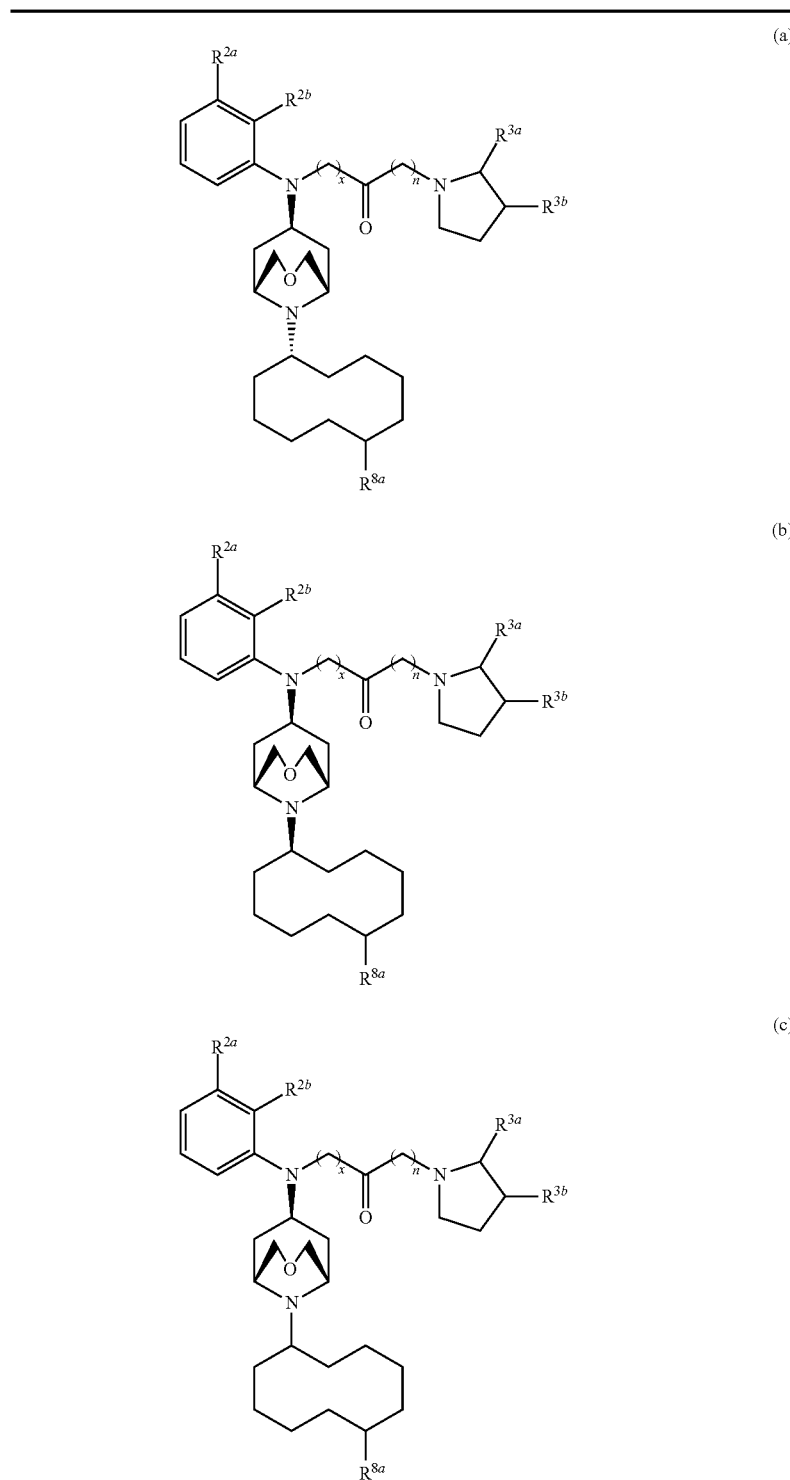
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L49 a, b, or c | $OCH_2C(=O)OH$ | H | 0 | 0 | H | $C(=O)OH$ |
| L50 a, b, or c | $OCH_2C(=O)OH$ | H | 1 | 0 | H | $C(=O)OH$ |
| L51 a, b, or c | $OCH_2C(=O)OH$ | H | 1 | 1 | H | $C(=O)OH$ |
| L52 a, b, or c | $OCH_2C(=O)OH$ | H | 0 | 1 | H | $C(=O)OH$ |
| L53 a, b, or c | H | $N(H)C(=O)E^3OH$ | 0 | 0 | H | $C(=O)OH$ |
| L54 a, b, or c | H | $N(H)C(=O)E^3OH$ | 1 | 0 | H | $C(=O)OH$ |

TABLE 13-continued
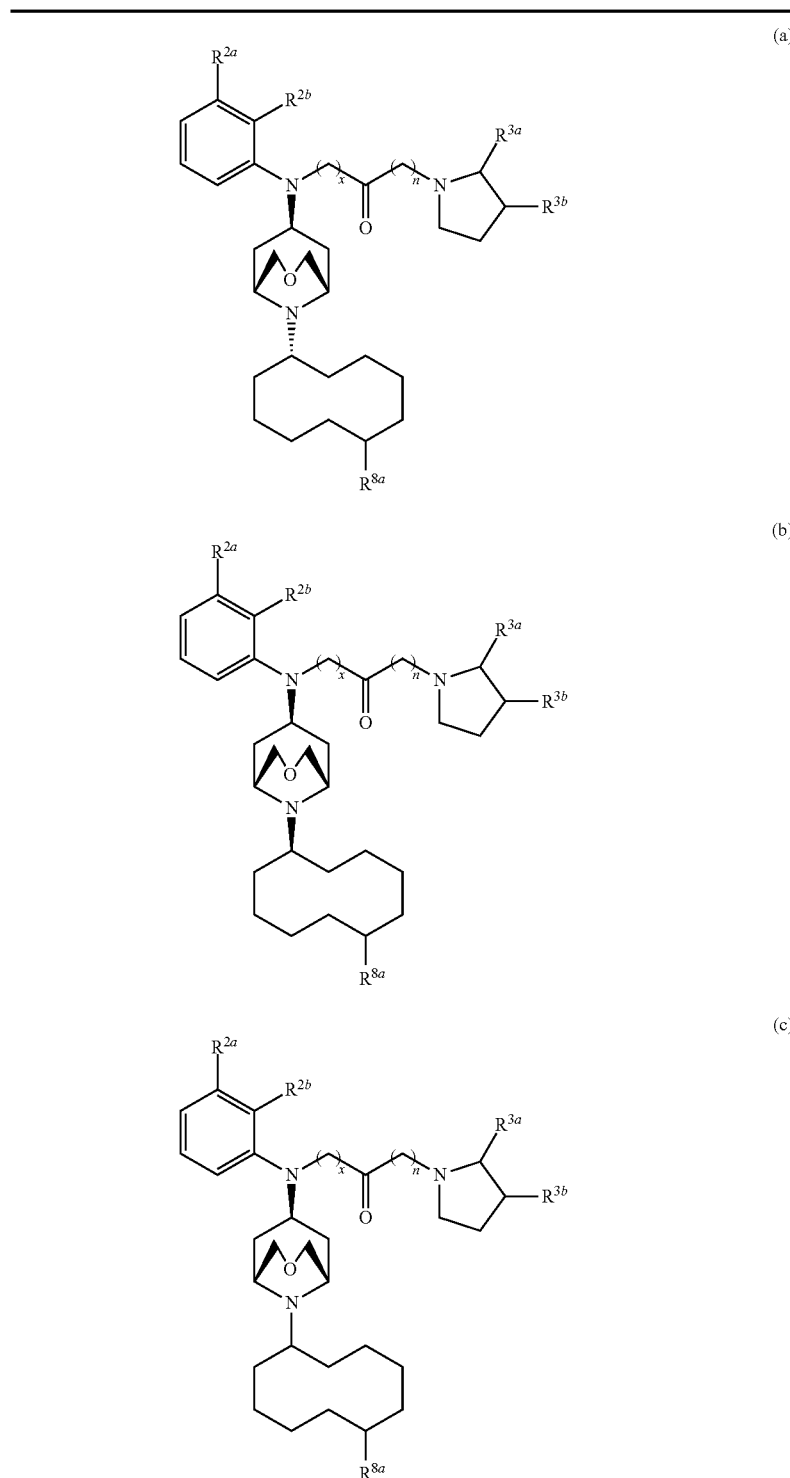
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L55 a, b, or c | H | N(H)C(=O)E³OH | 1 | 1 | H | C(=O)OH |
| L56 a, b, or c | H | N(H)C(=O)E³OH | 0 | 1 | H | C(=O)OH |
| L57 a, b, or c | H | OCH₂C(=O)OH | 0 | 0 | H | C(=O)OH |
| L58 a, b, or c | H | OCH₂C(=O)OH | 1 | 0 | H | C(=O)OH |
| L59 a, b, or c | H | OCH₂C(=O)OH | 1 | 1 | H | C(=O)OH |
| L60 a, b, or c | H | OCH₂C(=O)OH | 0 | 1 | H | C(=O)OH |

TABLE 13-continued
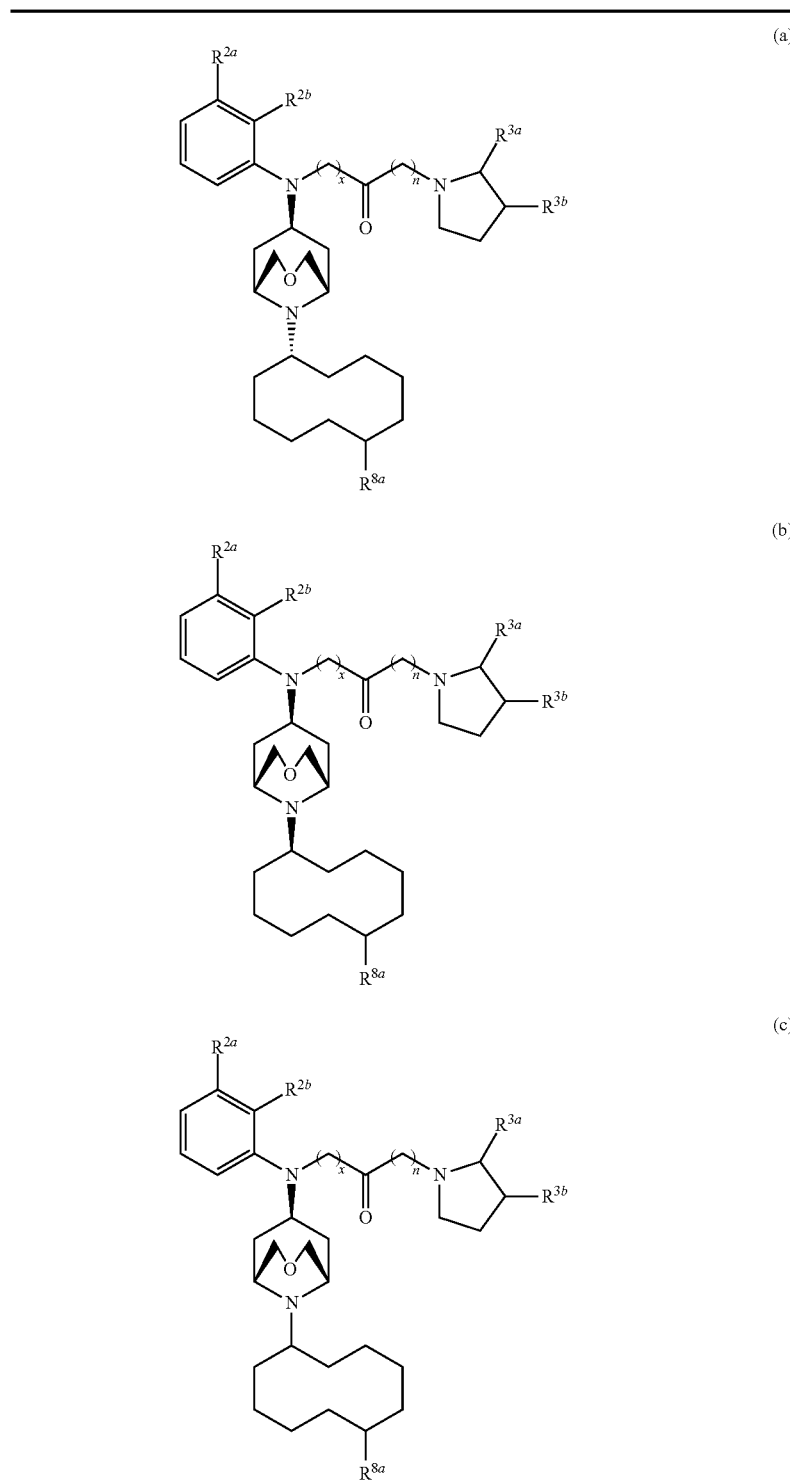
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L61 a, b, or c | H | H | 0 | 0 | tetrazolyl | H |
| L62 a, b, or c | H | H | 1 | 0 | tetrazolyl | H |
| L63 a, b, or c | H | H | 1 | 1 | tetrazolyl | H |
| L64 a, b, or c | H | H | 0 | 1 | tetrazolyl | H |
| L65 a, b, or c | N(H)C(=O)E$^3$OH | H | 0 | 0 | tetrazolyl | H |
| L66 a, b, or c | N(H)C(=O)E$^3$OH | H | 1 | 0 | tetrazolyl | H |

TABLE 13-continued
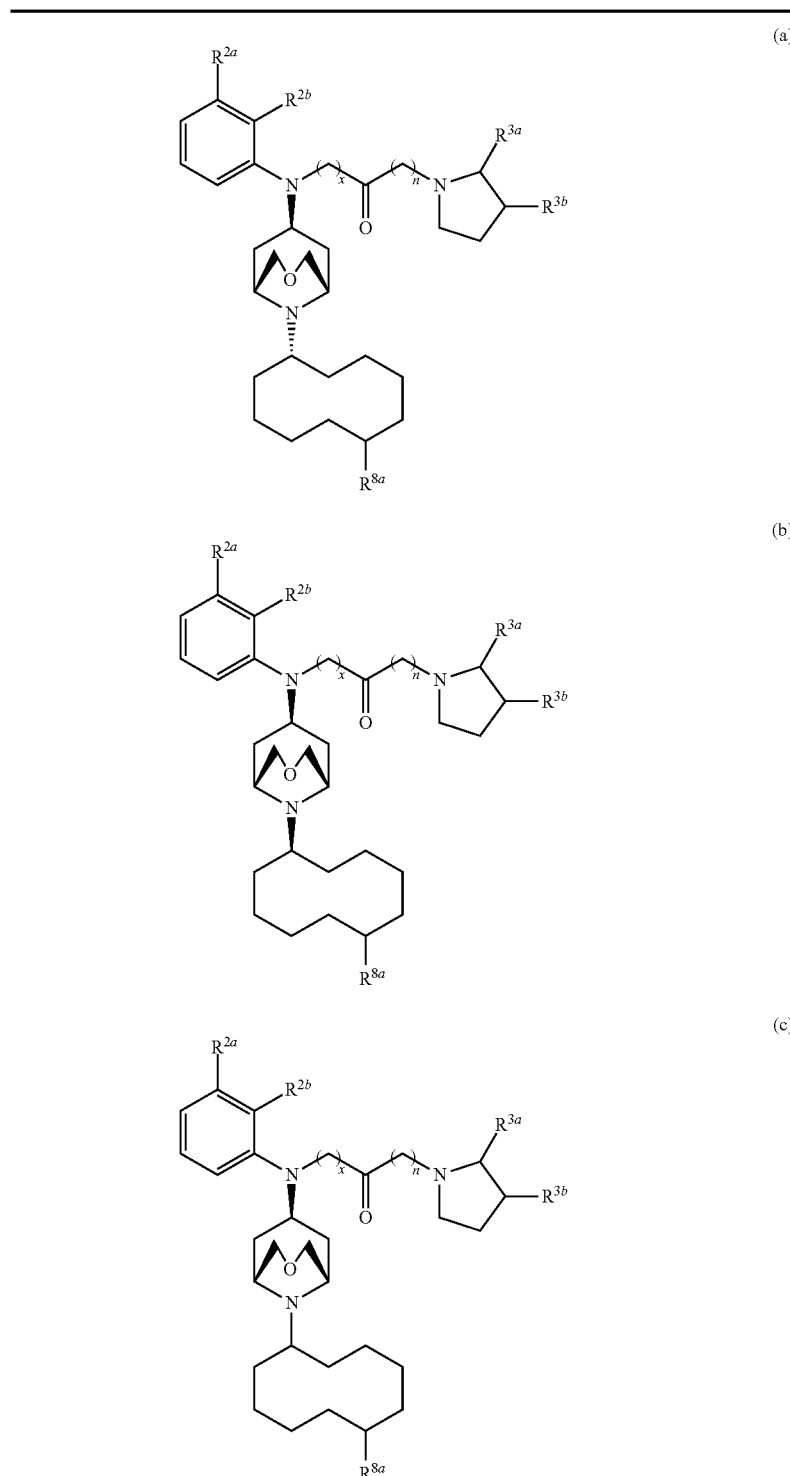
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L67 a, b, or c | N(H)C(=O)$E^3$OH | H | 1 | 1 | tetrazolyl | H |
| L68 a, b, or c | N(H)C(=O)$E^3$OH | H | 0 | 1 | tetrazolyl | H |
| L69 a, b, or c | OCH$_2$C(=O)OH | H | 0 | 0 | tetrazolyl | H |
| L70 a, b, or c | OCH$_2$C(=O)OH | H | 1 | 0 | tetrazolyl | H |
| L71 a, b, or c | OCH$_2$C(=O)OH | H | 1 | 1 | tetrazolyl | H |
| L72 a, b, or c | OCH$_2$C(=O)OH | H | 0 | 1 | tetrazolyl | H |

TABLE 13-continued
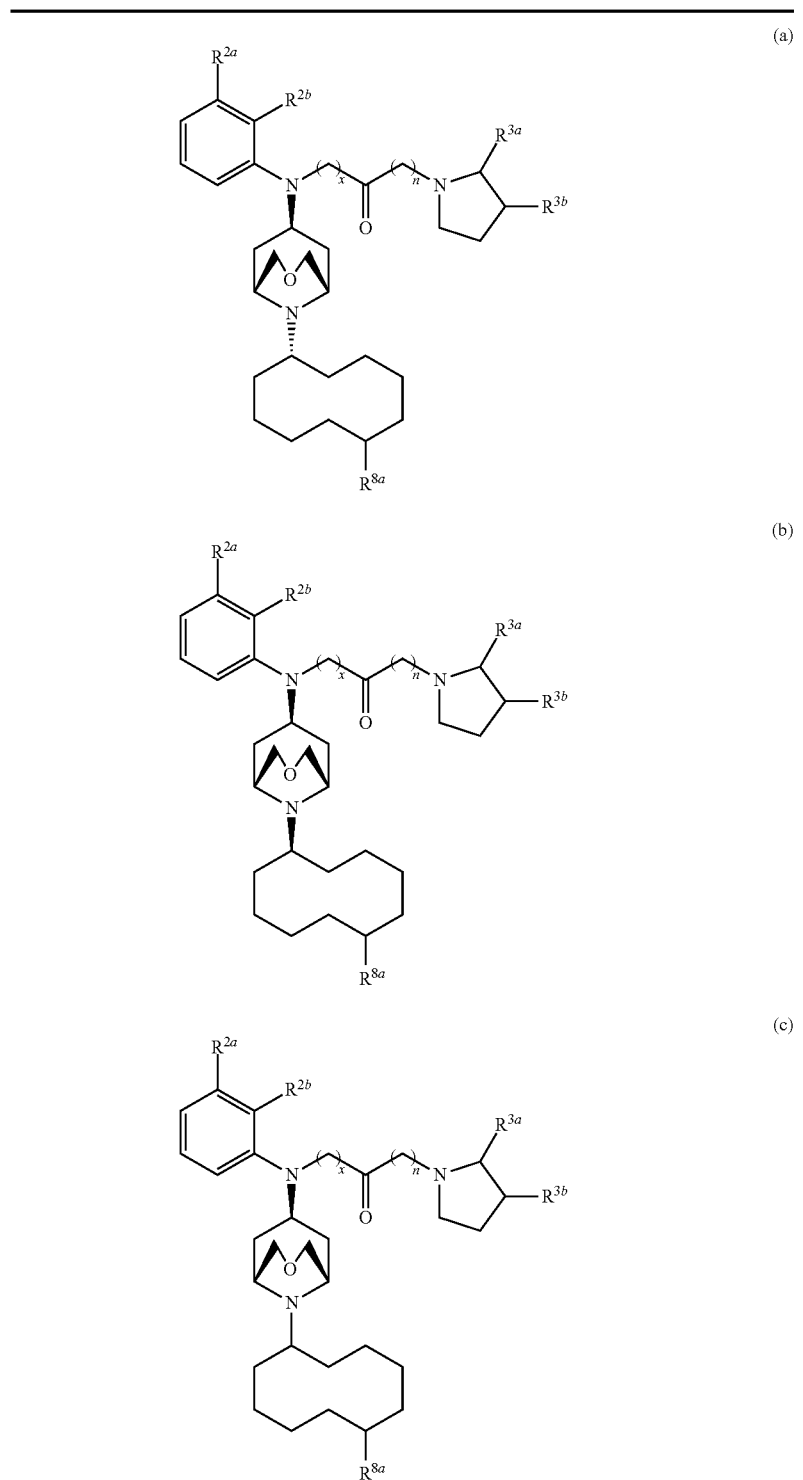
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L73 a, b, or c | H | N(H)C(=O)E$^3$OH | 0 | 0 | tetrazolyl | H |
| L74 a, b, or c | H | N(H)C(=O)E$^3$OH | 1 | 0 | tetrazolyl | H |
| L75 a, b, or c | H | N(H)C(=O)E$^3$OH | 1 | 1 | tetrazolyl | H |
| L76 a, b, or c | H | N(H)C(=O)E$^3$OH | 0 | 1 | tetrazolyl | H |
| L77 a, b, or c | H | OCH$_2$C(=O)OH | 0 | 0 | tetrazolyl | H |
| L78 a, b, or c | H | OCH$_2$C(=O)OH | 1 | 0 | tetrazolyl | H |

TABLE 13-continued
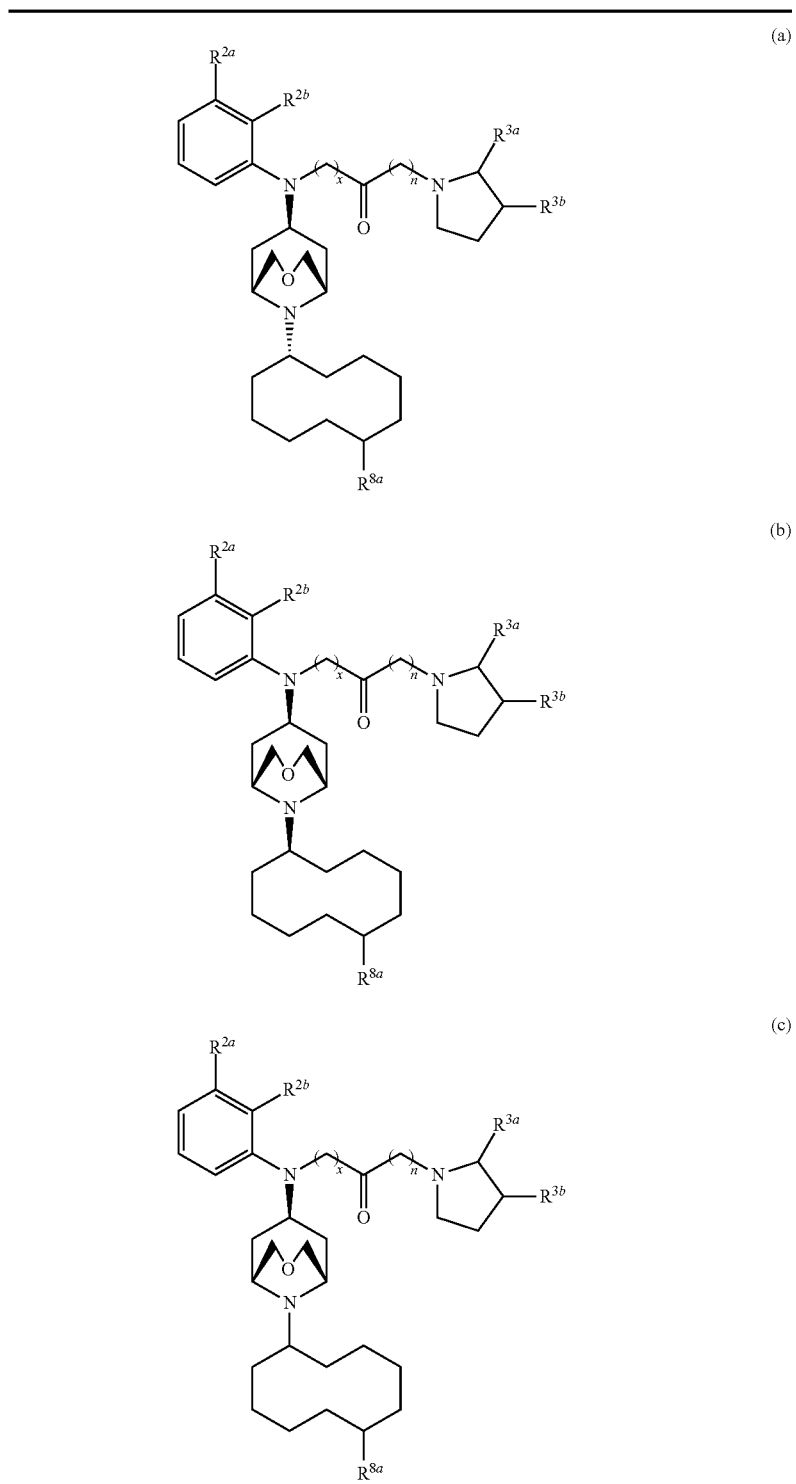
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L79 a, b, or c | H | OCH$_2$C(=O)OH | 1 | 1 | tetrazolyl | H |
| L80 a, b, or c | H | OCH$_2$C(=O)OH | 0 | 1 | tetrazolyl | H |
| L81 a, b, or c | H | H | 0 | 0 | H | tetrazolyl |
| L82 a, b, or c | H | H | 1 | 0 | H | tetrazolyl |
| L83 a, b, or c | H | H | 1 | 1 | H | tetrazolyl |
| L84 a, b, or c | H | H | 0 | 1 | H | tetrazolyl |

TABLE 13-continued
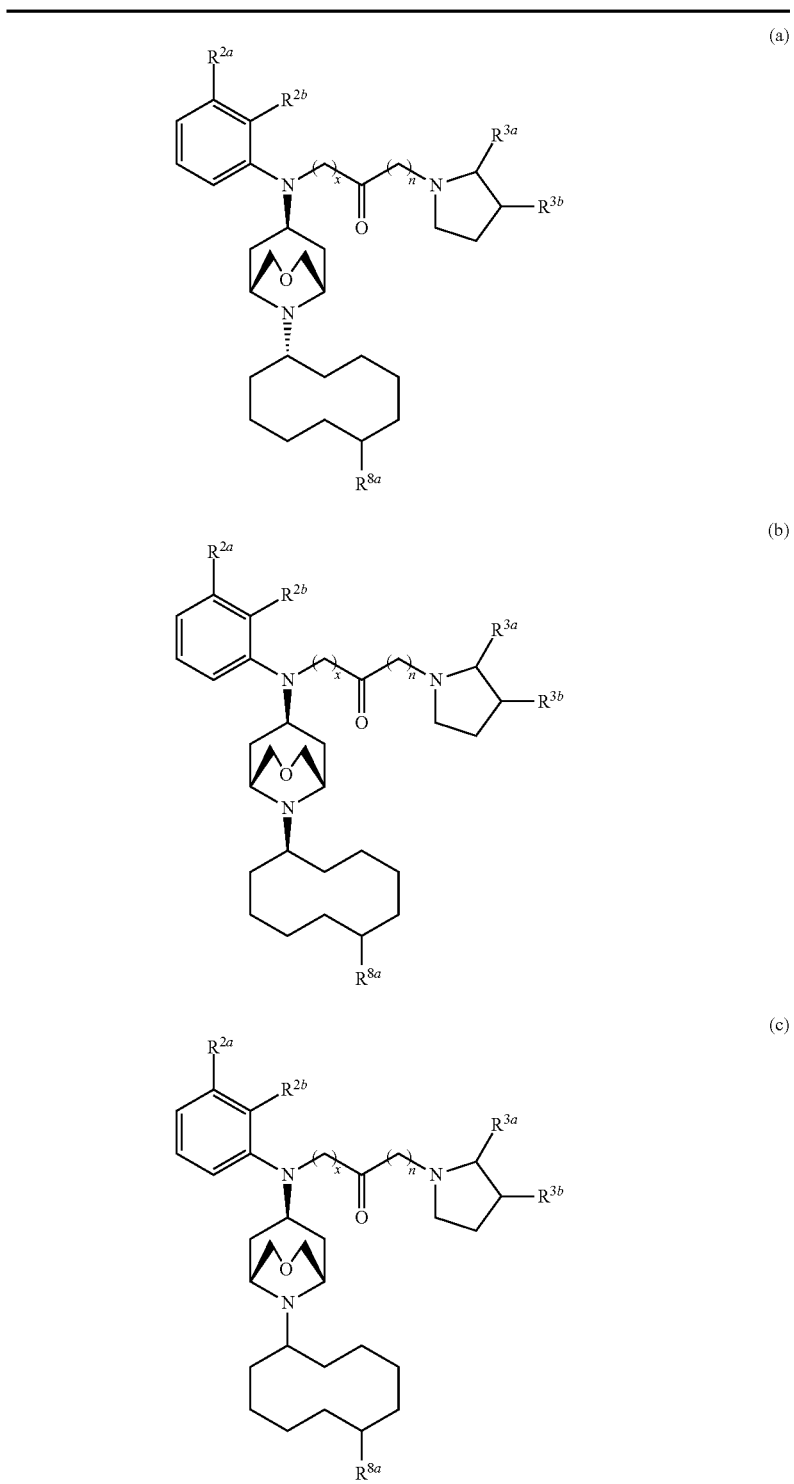
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L85 a, b, or c | N(H)C(=O)E$^3$OH | H | 0 | 0 | H | tetrazolyl |
| L86 a, b, or c | N(H)C(=O)E$^3$OH | H | 1 | 0 | H | tetrazolyl |
| L87 a, b, or c | N(H)C(=O)E$^3$OH | H | 1 | 1 | H | tetrazolyl |
| L88 a, b, or c | N(H)C(=O)E$^3$OH | H | 0 | 1 | H | tetrazolyl |
| L89 a, b, or c | OCH$_2$C(=O)OH | H | 0 | 0 | H | tetrazolyl |
| L90 a, b, or c | OCH$_2$C(=O)OH | H | 1 | 0 | H | tetrazolyl |

TABLE 13-continued
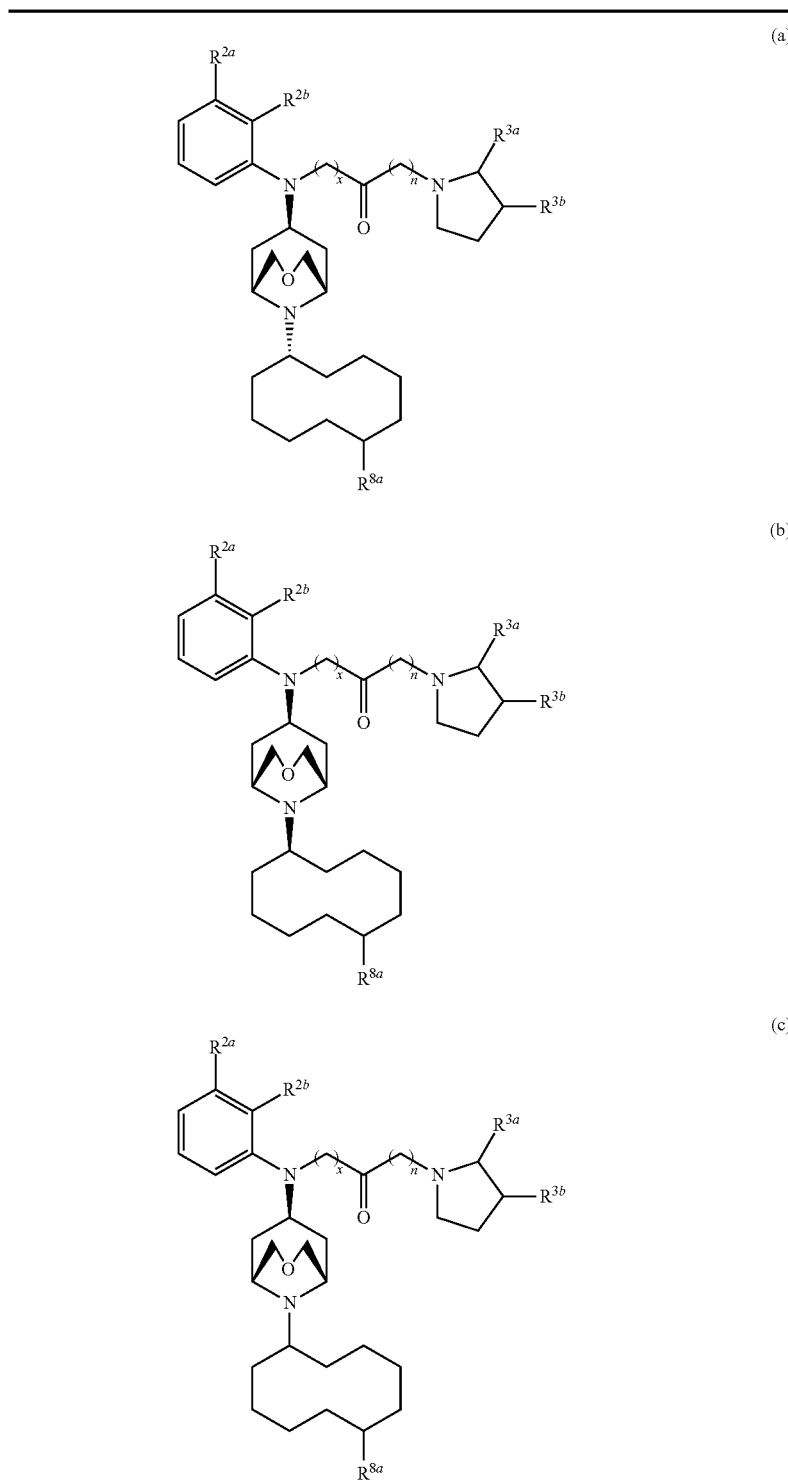
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L91 a, b, or c | $OCH_2C(=O)OH$ | H | 1 | 1 | H | tetrazolyl |
| L92 a, b, or c | $OCH_2C(=O)OH$ | H | 0 | 1 | H | tetrazolyl |
| L93 a, b, or c | H | $N(H)C(=O)E^3OH$ | 0 | 0 | H | tetrazolyl |
| L94 a, b, or c | H | $N(H)C(=O)E^3OH$ | 1 | 0 | H | tetrazolyl |
| L95 a, b, or c | H | $N(H)C(=O)E^3OH$ | 1 | 1 | H | tetrazolyl |
| L96 a, b, or c | H | $N(H)C(=O)E^3OH$ | 0 | 1 | H | tetrazolyl |

TABLE 13-continued
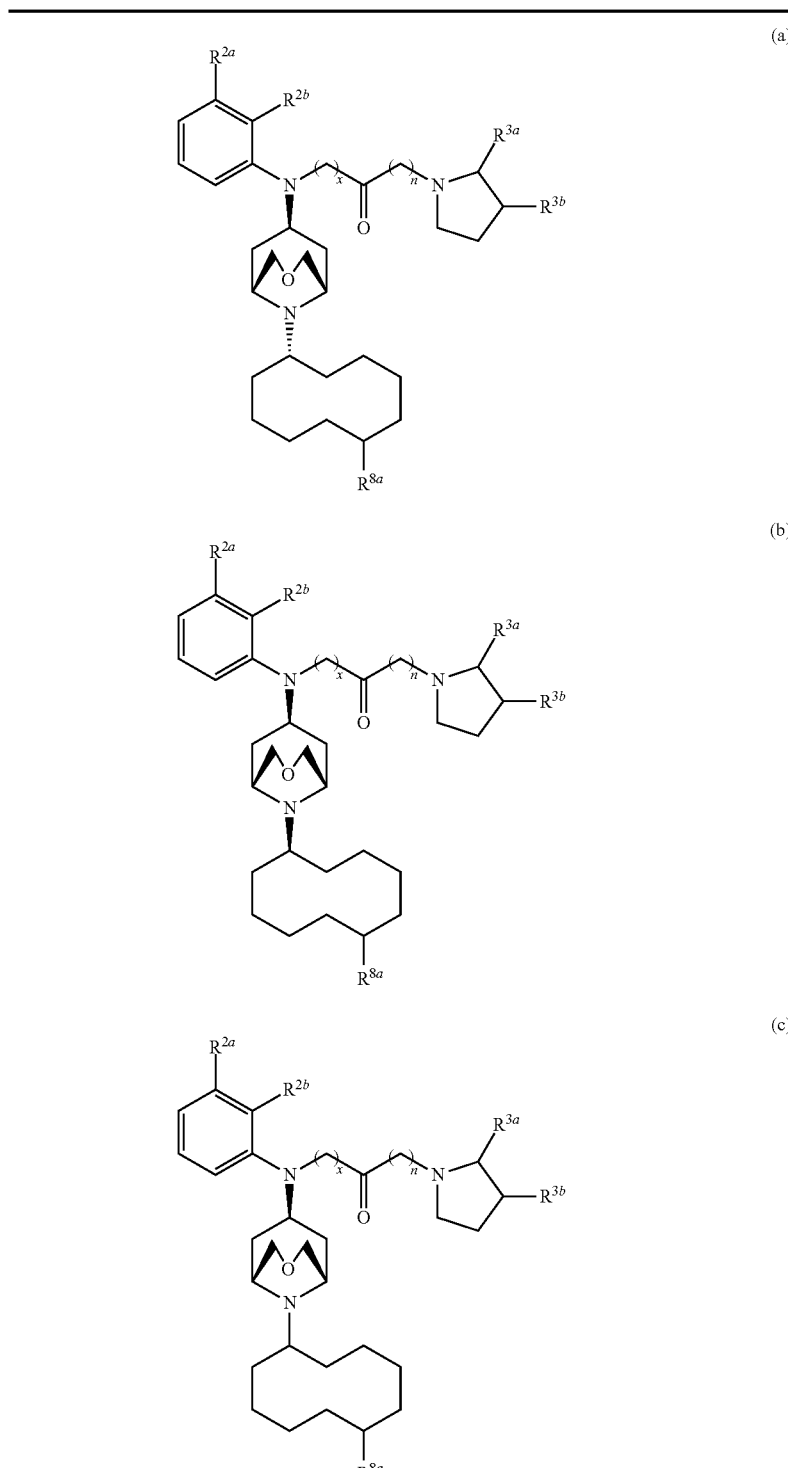
and pharmaceutically acceptable salts and solvates thereof, where:
| Compound | $R^{2a}$ | $R^{2b}$ | x | n | $R^{3a}$ | $R^{3b}$ |
|---|---|---|---|---|---|---|
| L97 a, b, or c | H | $OCH_2C(=O)OH$ | 0 | 0 | H | tetrazolyl |
| L98 a, b, or c | H | $OCH_2C(=O)OH$ | 1 | 0 | H | tetrazolyl |
| L99 a, b, or c | H | $OCH_2C(=O)OH$ | 1 | 1 | H | tetrazolyl |
| L100 a, b, or c | H | $OCH_2C(=O)OH$ | 0 | 1 | H | tetrazolyl |
$R^{8a}$ is (i) H or (ii) $CH_3$; $E^3$ is (iii) a direct bond or (iv) $C(=O)$.

TABLE 14

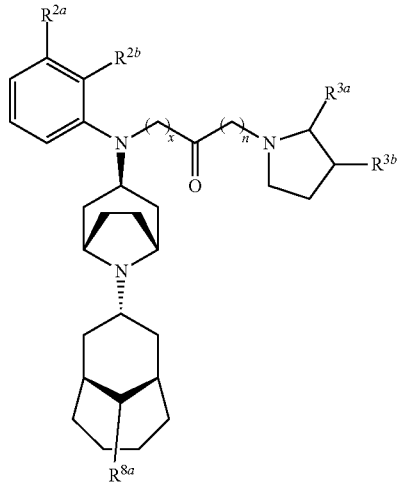

(a)

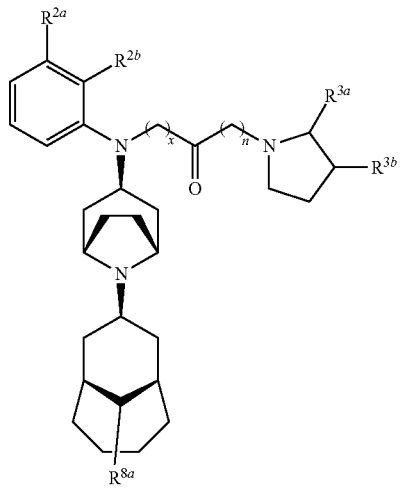

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| M1 a or b | H | H | 0 | 0 | H | H |
| M2 a or b | H | H | 1 | 0 | H | H |
| M3 a or b | H | H | 1 | 1 | H | H |
| M4 a or b | H | H | 0 | 1 | H | H |
| M5 a or b | N(H)C(=O)E³OH | H | 0 | 0 | H | H |
| M6 a or b | N(H)C(=O)E³OH | H | 1 | 0 | H | H |
| M7 a or b | N(H)C(=O)E³OH | H | 1 | 1 | H | H |
| M8 a or b | N(H)C(=O)E³OH | H | 0 | 1 | H | H |
| M9 a or b | OCH₂C(=O)OH | H | 0 | 0 | H | H |
| M10 a or b | OCH₂C(=O)OH | H | 1 | 0 | H | H |
| M11 a or b | OCH₂C(=O)OH | H | 1 | 1 | H | H |
| M12 a or b | OCH₂C(=O)OH | H | 0 | 1 | H | H |
| M13 a or b | H | N(H)C(=O)E³OH | 0 | 0 | H | H |
| M14 a or b | H | N(H)C(=O)E³OH | 1 | 0 | H | H |
| M15 a or b | H | N(H)C(=O)E³OH | 1 | 1 | H | H |
| M16 a or b | H | N(H)C(=O)E³OH | 0 | 1 | H | H |
| M17 a or b | H | OCH₂C(=O)OH | 0 | 0 | H | H |
| M18 a or b | H | OCH₂C(=O)OH | 1 | 0 | H | H |
| M19 a or b | H | OCH₂C(=O)OH | 1 | 1 | H | H |
| M20 a or b | H | OCH₂C(=O)OH | 0 | 1 | H | H |
| M21 a or b | H | H | 0 | 0 | C(=O)OH | H |
| M22 a or b | H | H | 1 | 0 | C(=O)OH | H |
| M23 a or b | H | H | 1 | 1 | C(=O)OH | H |
| M24 a or b | H | H | 0 | 1 | C(=O)OH | H |
| M25 a or b | N(H)C(=O)E³OH | H | 0 | 0 | C(=O)OH | H |
| M26 a or b | N(H)C(=O)E³OH | H | 1 | 0 | C(=O)OH | H |

TABLE 14-continued

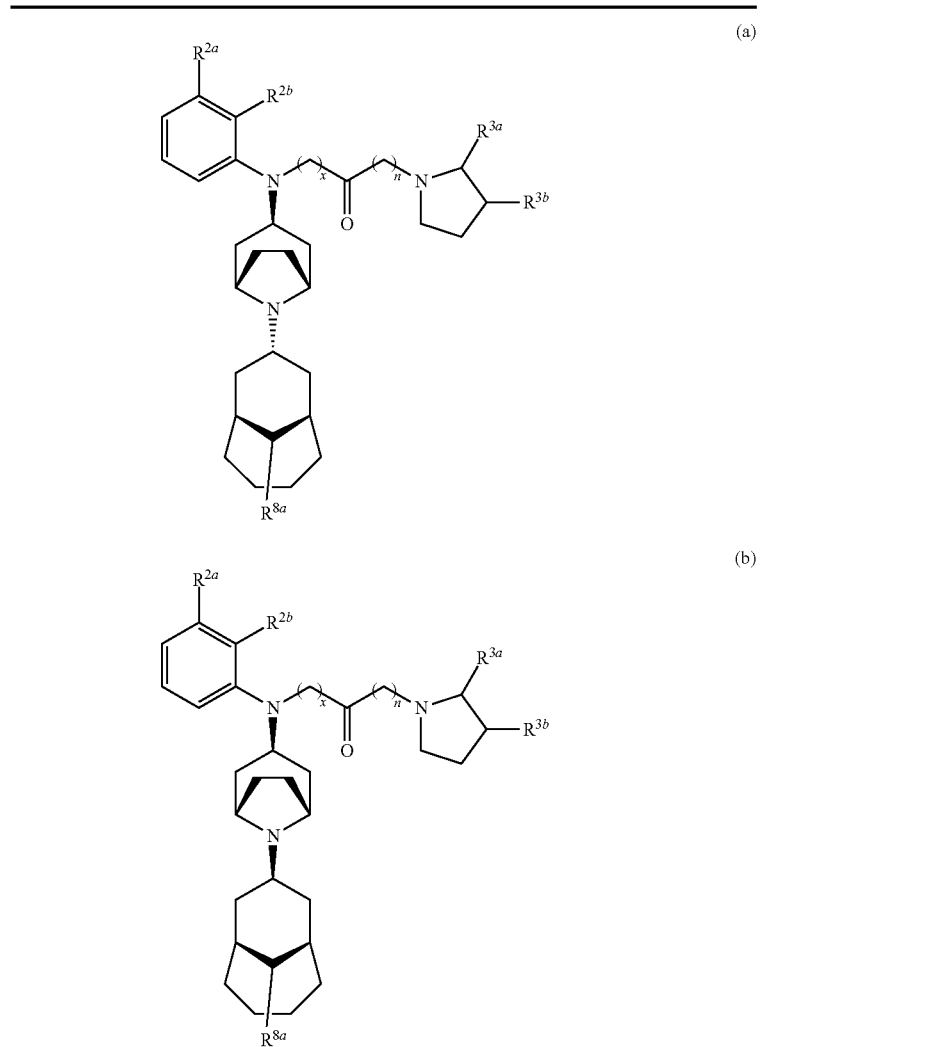

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| M27 a or b | N(H)C(=O)E$^3$OH | H | 1 | 1 | C(=O)OH | H |
| M28 a or b | N(H)C(=O)E$^3$OH | H | 0 | 1 | C(=O)OH | H |
| M29 a or b | OCH$_2$C(=O)OH | H | 0 | 0 | C(=O)OH | H |
| M30 a or b | OCH$_2$C(=O)OH | H | 1 | 0 | C(=O)OH | H |
| M31 a or b | OCH$_2$C(=O)OH | H | 1 | 1 | C(=O)OH | H |
| M32 a or b | OCH$_2$C(=O)OH | H | 0 | 1 | C(=O)OH | H |
| M33 a or b | H | N(H)C(=O)E$^3$OH | 0 | 0 | C(=O)OH | H |
| M34 a or b | H | N(H)C(=O)E$^3$OH | 1 | 0 | C(=O)OH | H |
| M35 a or b | H | N(H)C(=O)E$^3$OH | 1 | 1 | C(=O)OH | H |
| M36 a or b | H | N(H)C(=O)E$^3$OH | 0 | 1 | C(=O)OH | H |
| M37 a or b | H | OCH$_2$C(=O)OH | 0 | 0 | C(=O)OH | H |
| M38 a or b | H | OCH$_2$C(=O)OH | 1 | 0 | C(=O)OH | H |
| M39 a or b | H | OCH$_2$C(=O)OH | 1 | 1 | C(=O)OH | H |
| M40 a or b | H | OCH$_2$C(=O)OH | 0 | 1 | C(=O)OH | H |
| M41 a or b | H | H | 0 | 0 | H | C(=O)OH |
| M42 a or b | H | H | 1 | 0 | H | C(=O)OH |
| M43 a or b | H | H | 1 | 1 | H | C(=O)OH |
| M44 a or b | H | H | 0 | 1 | H | C(=O)OH |
| M45 a or b | N(H)C(=O)E$^3$OH | H | 0 | 0 | H | C(=O)OH |
| M46 a or b | N(H)C(=O)E$^3$OH | H | 1 | 0 | H | C(=O)OH |
| M47 a or b | N(H)C(=O)E$^3$OH | H | 1 | 1 | H | C(=O)OH |
| M48 a or b | N(H)C(=O)E$^3$OH | H | 0 | 1 | H | C(=O)OH |
| M49 a or b | OCH$_2$C(=O)OH | H | 0 | 0 | H | C(=O)OH |
| M50 a or b | OCH$_2$C(=O)OH | H | 1 | 0 | H | C(=O)OH |
| M51 a or b | OCH$_2$C(=O)OH | H | 1 | 1 | H | C(=O)OH |
| M52 a or b | OCH$_2$C(=O)OH | H | 0 | 1 | H | C(=O)OH |

TABLE 14-continued

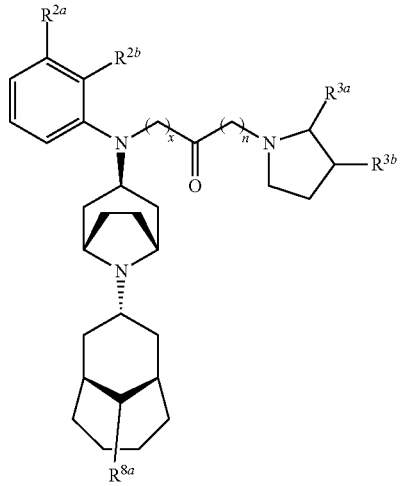

(a)

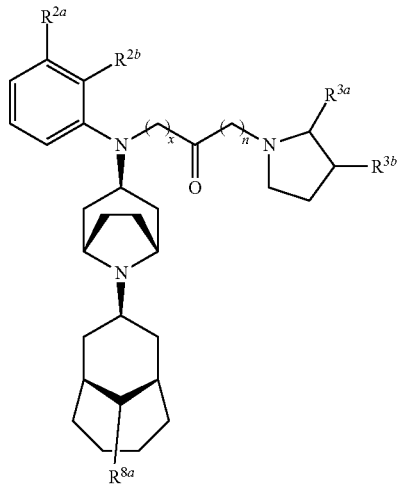

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| M53 a or b | H | N(H)C(=O)E$^3$OH | 0 | 0 | H | C(=O)OH |
| M54 a or b | H | N(H)C(=O)E$^3$OH | 1 | 0 | H | C(=O)OH |
| M55 a or b | H | N(H)C(=O)E$^3$OH | 1 | 1 | H | C(=O)OH |
| M56 a or b | H | N(H)C(=O)E$^3$OH | 0 | 1 | H | C(=O)OH |
| M57 a or b | H | OCH$_2$C(=O)OH | 0 | 0 | H | C(=O)OH |
| M58 a or b | H | OCH$_2$C(=O)OH | 1 | 0 | H | C(=O)OH |
| M59 a or b | H | OCH$_2$C(=O)OH | 1 | 1 | H | C(=O)OH |
| M60 a or b | H | OCH$_2$C(=O)OH | 0 | 1 | H | C(=O)OH |
| M61 a or b | H | H | 0 | 0 | tetrazolyl | H |
| M62 a or b | H | H | 1 | 0 | tetrazolyl | H |
| M63 a or b | H | H | 1 | 1 | tetrazolyl | H |
| M64 a or b | H | H | 0 | 1 | tetrazolyl | H |
| M65 a or b | N(H)C(=O)E$^3$OH | H | 0 | 0 | tetrazolyl | H |
| M66 a or b | N(H)C(=O)E$^3$OH | H | 1 | 0 | tetrazolyl | H |
| M67 a or b | N(H)C(=O)E$^3$OH | H | 1 | 1 | tetrazolyl | H |
| M68 a or b | N(H)C(=O)E$^3$OH | H | 0 | 1 | tetrazolyl | H |
| M69 a or b | OCH$_2$C(=O)OH | H | 0 | 0 | tetrazolyl | H |
| M70 a or b | OCH$_2$C(=O)OH | H | 1 | 0 | tetrazolyl | H |
| M71 a or b | OCH$_2$C(=O)OH | H | 1 | 1 | tetrazolyl | H |
| M72 a or b | OCH$_2$C(=O)OH | H | 0 | 1 | tetrazolyl | H |
| M73 a or b | H | N(H)C(=O)E$^3$OH | 0 | 0 | tetrazolyl | H |
| M74 a or b | H | N(H)C(=O)E$^3$OH | 1 | 0 | tetrazolyl | H |
| M75 a or b | H | N(H)C(=O)E$^3$OH | 1 | 1 | tetrazolyl | H |
| M76 a or b | H | N(H)C(=O)E$^3$OH | 0 | 1 | tetrazolyl | H |
| M77 a or b | H | OCH$_2$C(=O)OH | 0 | 0 | tetrazolyl | H |
| M78 a or b | H | OCH$_2$C(=O)OH | 1 | 0 | tetrazolyl | H |

TABLE 14-continued (a)
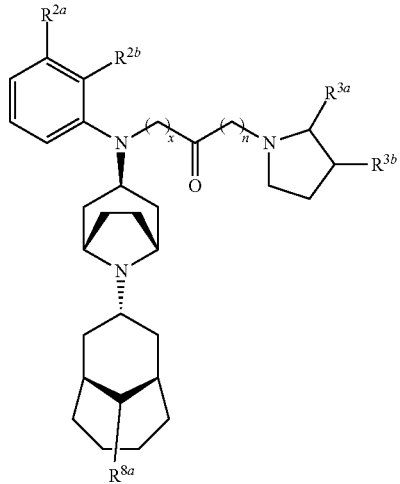

(b)
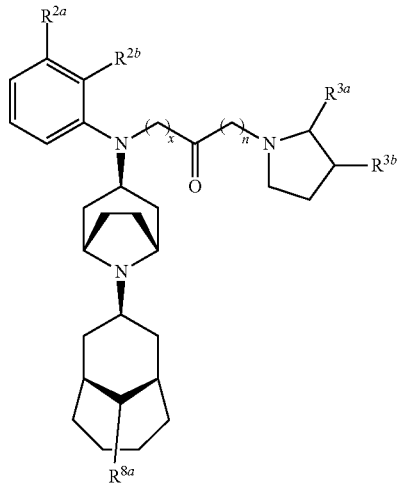

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| M79 a or b | H | OCH$_2$C(=O)OH | 1 | 1 | tetrazolyl | H |
| M80 a or b | H | OCH$_2$C(=O)OH | 0 | 1 | tetrazolyl | H |
| M81 a or b | H | H | 0 | 0 | H | tetrazolyl |
| M82 a or b | H | H | 1 | 0 | H | tetrazolyl |
| M83 a or b | H | H | 1 | 1 | H | tetrazolyl |
| M84 a or b | H | H | 0 | 1 | H | tetrazolyl |
| M85 a or b | N(H)C(=O)E$^3$OH | H | 0 | 0 | H | tetrazolyl |
| M86 a or b | N(H)C(=O)E$^3$OH | H | 1 | 0 | H | tetrazolyl |
| M87 a or b | N(H)C(=O)E$^3$OH | H | 1 | 1 | H | tetrazolyl |
| M88 a or b | N(H)C(=O)E$^3$OH | H | 0 | 1 | H | tetrazolyl |
| M89 a or b | OCH$_2$C(=O)OH | H | 0 | 0 | H | tetrazolyl |
| M90 a or b | OCH$_2$C(=O)OH | H | 1 | 0 | H | tetrazolyl |
| M91 a or b | OCH$_2$C(=O)OH | H | 1 | 1 | H | tetrazolyl |
| M92 a or b | OCH$_2$C(=O)OH | H | 0 | 1 | H | tetrazolyl |
| M93 a or b | H | N(H)C(=O)E$^3$OH | 0 | 0 | H | tetrazolyl |
| M94 a or b | H | N(H)C(=O)E$^3$OH | 1 | 0 | H | tetrazolyl |
| M95 a or b | H | N(H)C(=O)E$^3$OH | 1 | 1 | H | tetrazolyl |
| M96 a or b | H | N(H)C(=O)E$^3$OH | 0 | 1 | H | tetrazolyl |
| M97 a or b | H | OCH$_2$C(=O)OH | 0 | 0 | H | tetrazolyl |
| M98 a or b | H | OCH$_2$C(=O)OH | 1 | 0 | H | tetrazolyl |
| M99 a or b | H | OCH$_2$C(=O)OH | 1 | 1 | H | tetrazolyl |
| M100 a or b | H | OCH$_2$C(=O)OH | 0 | 1 | H | tetrazolyl |

$R^{8a}$ is (i) H or (ii) CH$_3$; E$^3$ is (iii) a direct bond or (iv) C(=O).

TABLE 15

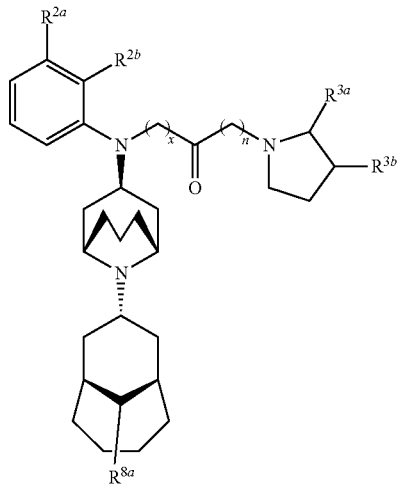

(a)

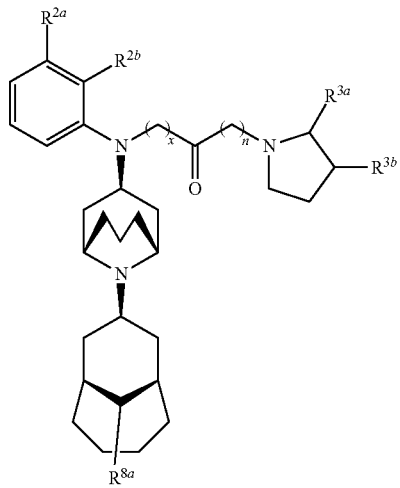

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| N1 a or b | H | H | 0 | 0 | H | H |
| N2 a or b | H | H | 1 | 0 | H | H |
| N3 a or b | H | H | 1 | 1 | H | H |
| N4 a or b | H | H | 0 | 1 | H | H |
| N5 a or b | N(H)C(=O)$E^3$OH | H | 0 | 0 | H | H |
| N6 a or b | N(H)C(=O)$E^3$OH | H | 1 | 0 | H | H |
| N7 a or b | N(H)C(=O)$E^3$OH | H | 1 | 1 | H | H |
| N8 a or b | N(H)C(=O)$E^3$OH | H | 0 | 1 | H | H |
| N9 a or b | OCH$_2$C(=O)OH | H | 0 | 0 | H | H |
| N10 a or b | OCH$_2$C(=O)OH | H | 1 | 0 | H | H |
| N11 a or b | OCH$_2$C(=O)OH | H | 1 | 1 | H | H |
| N12 a or b | OCH$_2$C(=O)OH | H | 0 | 1 | H | H |
| N13 a or b | H | N(H)C(=O)$E^3$OH | 0 | 0 | H | H |
| N14 a or b | H | N(H)C(=O)$E^3$OH | 1 | 0 | H | H |
| N15 a or b | H | N(H)C(=O)$E^3$OH | 1 | 1 | H | H |
| N16 a or b | H | N(H)C(=O)$E^3$OH | 0 | 1 | H | H |
| N17 a or b | H | OCH$_2$C(=O)OH | 0 | 0 | H | H |
| N18 a or b | H | OCH$_2$C(=O)OH | 1 | 0 | H | H |
| N19 a or b | H | OCH$_2$C(=O)OH | 1 | 1 | H | H |
| N20 a or b | H | OCH$_2$C(=O)OH | 0 | 1 | H | H |
| N21 a or b | H | H | 0 | 0 | C(=O)OH | H |
| N22 a or b | H | H | 1 | 0 | C(=O)OH | H |
| N23 a or b | H | H | 1 | 1 | C(=O)OH | H |
| N24 a or b | H | H | 0 | 1 | C(=O)OH | H |
| N25 a or b | N(H)C(=O)$E^3$OH | H | 0 | 0 | C(=O)OH | H |
| N26 a or b | N(H)C(=O)$E^3$OH | H | 1 | 0 | C(=O)OH | H |

TABLE 15-continued

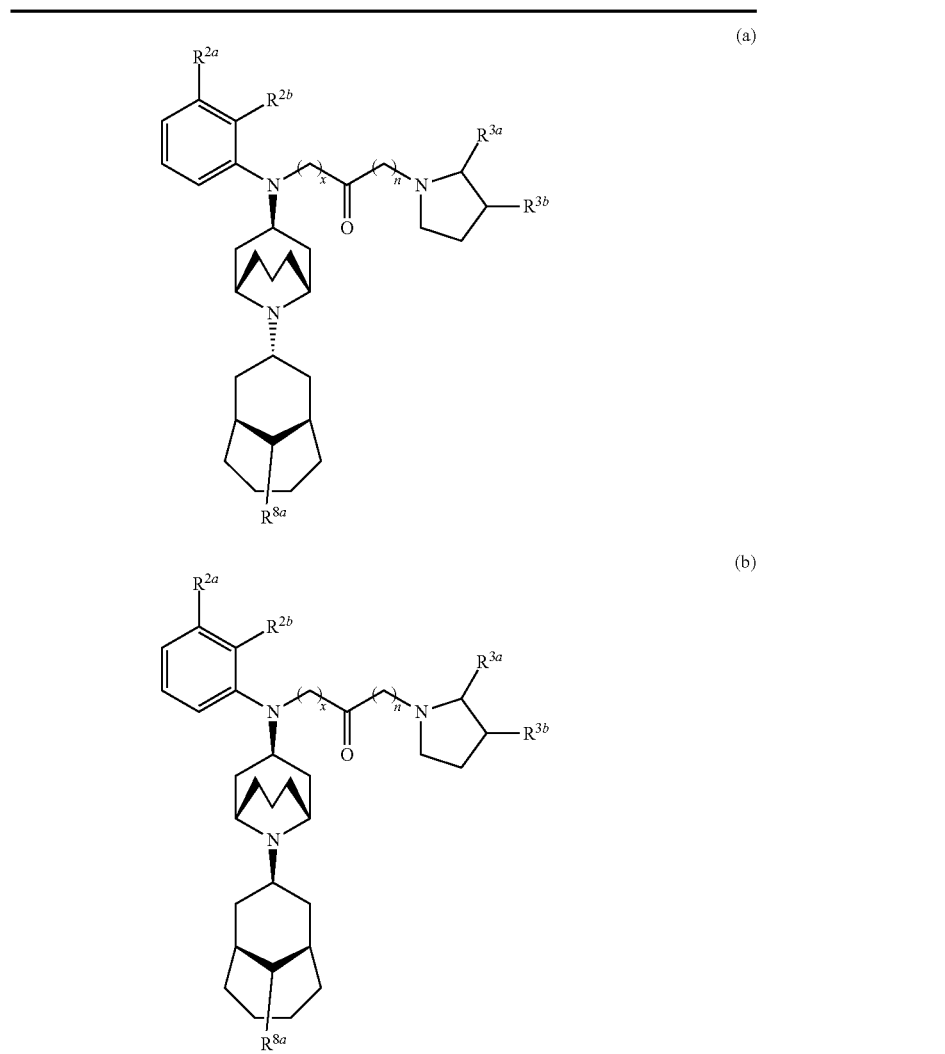

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| N27 a or b | N(H)C(=O)E$^3$OH | H | 1 | 1 | C(=O)OH | H |
| N28 a or b | N(H)C(=O)E$^3$OH | H | 0 | 1 | C(=O)OH | H |
| N29 a or b | OCH$_2$C(=O)OH | H | 0 | 0 | C(=O)OH | H |
| N30 a or b | OCH$_2$C(=O)OH | H | 1 | 0 | C(=O)OH | H |
| N31 a or b | OCH$_2$C(=O)OH | H | 1 | 1 | C(=O)OH | H |
| N32 a or b | OCH$_2$C(=O)OH | H | 0 | 1 | C(=O)OH | H |
| N33 a or b | H | N(H)C(=O)E$^3$OH | 0 | 0 | C(=O)OH | H |
| N34 a or b | H | N(H)C(=O)E$^3$OH | 1 | 0 | C(=O)OH | H |
| N35 a or b | H | N(H)C(=O)E$^3$OH | 1 | 1 | C(=O)OH | H |
| N36 a or b | H | N(H)C(=O)E$^3$OH | 0 | 1 | C(=O)OH | H |
| N37 a or b | H | OCH$_2$C(=O)OH | 0 | 0 | C(=O)OH | H |
| N38 a or b | H | OCH$_2$C(=O)OH | 1 | 0 | C(=O)OH | H |
| N39 a or b | H | OCH$_2$C(=O)OH | 1 | 1 | C(=O)OH | H |
| N40 a or b | H | OCH$_2$C(=O)OH | 0 | 1 | C(=O)OH | H |
| N41 a or b | H | H | 0 | 0 | H | C(=O)OH |
| N42 a or b | H | H | 1 | 0 | H | C(=O)OH |
| N43 a or b | H | H | 1 | 1 | H | C(=O)OH |
| N44 a or b | H | H | 0 | 1 | H | C(=O)OH |
| N45 a or b | N(H)C(=O)E$^3$OH | H | 0 | 0 | H | C(=O)OH |
| N46 a or b | N(H)C(=O)E$^3$OH | H | 1 | 0 | H | C(=O)OH |
| N47 a or b | N(H)C(=O)E$^3$OH | H | 1 | 1 | H | C(=O)OH |
| N48 a or b | N(H)C(=O)E$^3$OH | H | 0 | 1 | H | C(=O)OH |
| N49 a or b | OCH$_2$C(=O)OH | H | 0 | 0 | H | C(=O)OH |
| N50 a or b | OCH$_2$C(=O)OH | H | 1 | 0 | H | C(=O)OH |
| N51 a or b | OCH$_2$C(=O)OH | H | 1 | 1 | H | C(=O)OH |
| N52 a or b | OCH$_2$C(=O)OH | H | 0 | 1 | H | C(=O)OH |

TABLE 15-continued

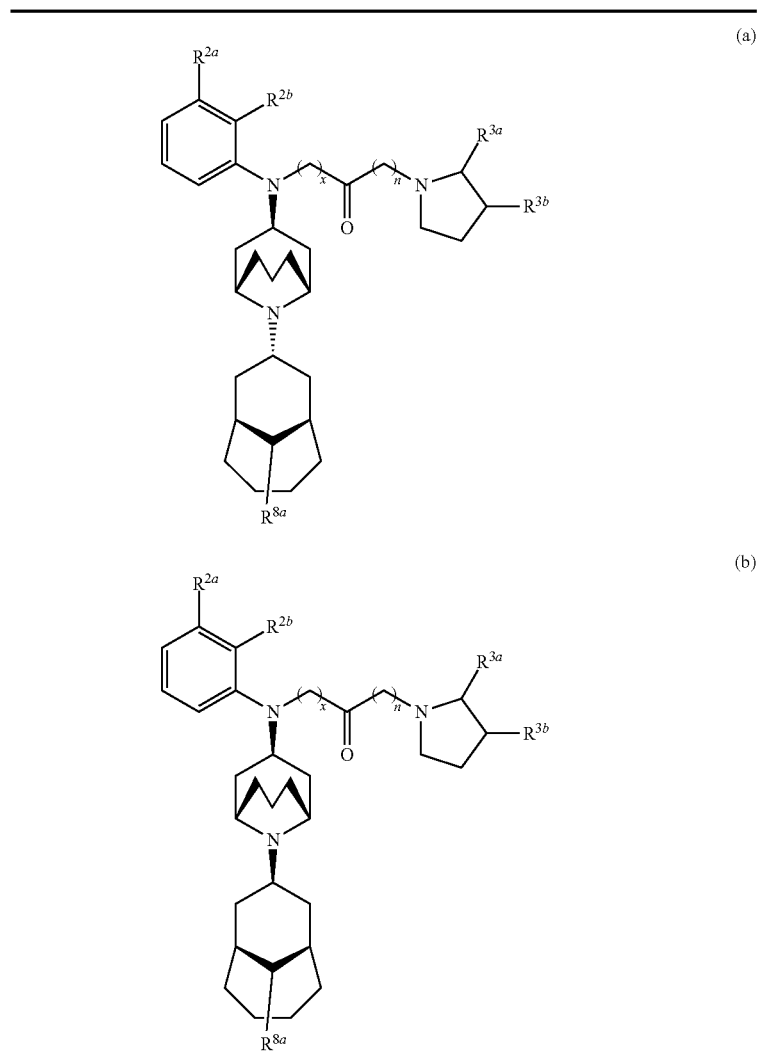

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| N53 a or b | H | N(H)C(=O)E³OH | 0 | 0 | H | C(=O)OH |
| N54 a or b | H | N(H)C(=O)E³OH | 1 | 0 | H | C(=O)OH |
| N55 a or b | H | N(H)C(=O)E³OH | 1 | 1 | H | C(=O)OH |
| N56 a or b | H | N(H)C(=O)E³OH | 0 | 1 | H | C(=O)OH |
| N57 a or b | H | OCH₂C(=O)OH | 0 | 0 | H | C(=O)OH |
| N58 a or b | H | OCH₂C(=O)OH | 1 | 0 | H | C(=O)OH |
| N59 a or b | H | OCH₂C(=O)OH | 1 | 1 | H | C(=O)OH |
| N60 a or b | H | OCH₂C(=O)OH | 0 | 1 | H | C(=O)OH |
| N61 a or b | H | H | 0 | 0 | tetrazolyl | H |
| N62 a or b | H | H | 1 | 0 | tetrazolyl | H |
| N63 a or b | H | H | 1 | 1 | tetrazolyl | H |
| N64 a or b | H | H | 0 | 1 | tetrazolyl | H |
| N65 a or b | N(H)C(=O)E³OH | H | 0 | 0 | tetrazolyl | H |
| N66 a or b | N(H)C(=O)E³OH | H | 1 | 0 | tetrazolyl | H |
| N67 a or b | N(H)C(=O)E³OH | H | 1 | 1 | tetrazolyl | H |
| N68 a or b | N(H)C(=O)E³OH | H | 0 | 1 | tetrazolyl | H |
| N69 a or b | OCH₂C(=O)OH | H | 0 | 0 | tetrazolyl | H |
| N70 a or b | OCH₂C(=O)OH | H | 1 | 0 | tetrazolyl | H |
| N71 a or b | OCH₂C(=O)OH | H | 1 | 1 | tetrazolyl | H |
| N72 a or b | OCH₂C(=O)OH | H | 0 | 1 | tetrazolyl | H |
| N73 a or b | H | N(H)C(=O)E³OH | 0 | 0 | tetrazolyl | H |
| N74 a or b | H | N(H)C(=O)E³OH | 1 | 0 | tetrazolyl | H |
| N75 a or b | H | N(H)C(=O)E³OH | 1 | 1 | tetrazolyl | H |
| N76 a or b | H | N(H)C(=O)E³OH | 0 | 1 | tetrazolyl | H |
| N77 a or b | H | OCH₂C(=O)OH | 0 | 0 | tetrazolyl | H |
| N78 a or b | H | OCH₂C(=O)OH | 1 | 0 | tetrazolyl | H |

TABLE 15-continued (a)
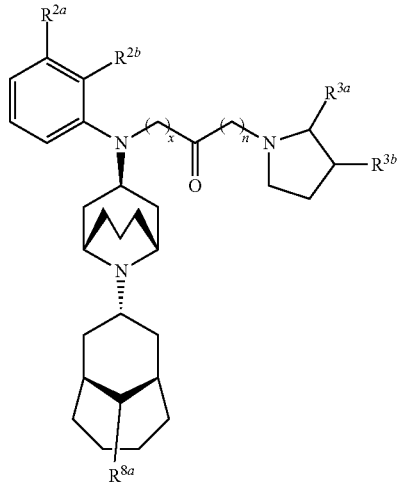

(b)
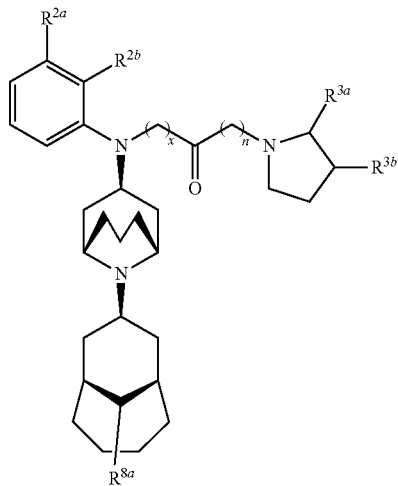

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| N79 a or b | H | OCH$_2$C(=O)OH | 1 | 1 | tetrazolyl | H |
| N80 a or b | H | OCH$_2$C(=O)OH | 0 | 1 | tetrazolyl | H |
| N81 a or b | H | H | 0 | 0 | H | tetrazolyl |
| N82 a or b | H | H | 1 | 0 | H | tetrazolyl |
| N83 a or b | H | H | 1 | 1 | H | tetrazolyl |
| N84 a or b | H | H | 0 | 1 | H | tetrazolyl |
| N85 a or b | N(H)C(=O)E$^3$OH | H | 0 | 0 | H | tetrazolyl |
| N86 a or b | N(H)C(=O)E$^3$OH | H | 1 | 0 | H | tetrazolyl |
| N87 a or b | N(H)C(=O)E$^3$OH | H | 1 | 1 | H | tetrazolyl |
| N88 a or b | N(H)C(=O)E$^3$OH | H | 0 | 1 | H | tetrazolyl |
| N89 a or b | OCH$_2$C(=O)OH | H | 0 | 0 | H | tetrazolyl |
| N90 a or b | OCH$_2$C(=O)OH | H | 1 | 0 | H | tetrazolyl |
| N91 a or b | OCH$_2$C(=O)OH | H | 1 | 1 | H | tetrazolyl |
| N92 a or b | OCH$_2$C(=O)OH | H | 0 | 1 | H | tetrazolyl |
| N93 a or b | H | N(H)C(=O)E$^3$OH | 0 | 0 | H | tetrazolyl |
| N94 a or b | H | N(H)C(=O)E$^3$OH | 1 | 0 | H | tetrazolyl |
| N95 a or b | H | N(H)C(=O)E$^3$OH | 1 | 1 | H | tetrazolyl |
| N96 a or b | H | N(H)C(=O)E$^3$OH | 0 | 1 | H | tetrazolyl |
| N97 a or b | H | OCH$_2$C(=O)OH | 0 | 0 | H | tetrazolyl |
| N98 a or b | H | OCH$_2$C(=O)OH | 1 | 0 | H | tetrazolyl |
| N99 a or b | H | OCH$_2$C(=O)OH | 1 | 1 | H | tetrazolyl |
| N100 a or b | H | OCH$_2$C(=O)OH | 0 | 1 | H | tetrazolyl |

$R^{8a}$ is (i) H or (ii) CH$_3$; E$^3$ is (iii) a direct bond or (iv) C(=O).

TABLE 16

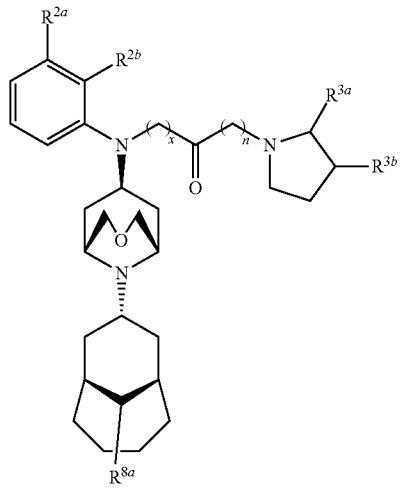

(a)

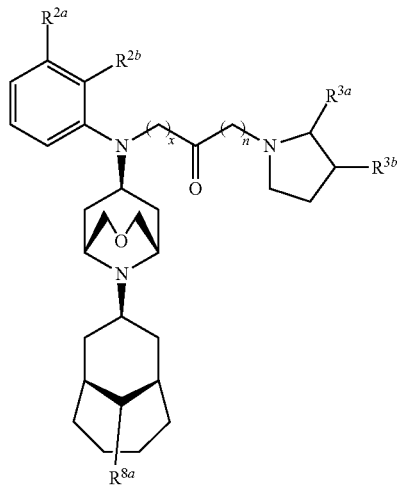

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| O1 a or b | H | H | 0 | 0 | H | H |
| O2 a or b | H | H | 1 | 0 | H | H |
| O3 a or b | H | H | 1 | 1 | H | H |
| O4 a or b | H | H | 0 | 1 | H | H |
| O5 a or b | N(H)C(=O)E$^3$OH | H | 0 | 0 | H | H |
| O6 a or b | N(H)C(=O)E$^3$OH | H | 1 | 0 | H | H |
| O7 a or b | N(H)C(=O)E$^3$OH | H | 1 | 1 | H | H |
| O8 a or b | N(H)C(=O)E$^3$OH | H | 0 | 1 | H | H |
| O9 a or b | OCH$_2$C(=O)OH | H | 0 | 0 | H | H |
| O10 a or b | OCH$_2$C(=O)OH | H | 1 | 0 | H | H |
| O11 a or b | OCH$_2$C(=O)OH | H | 1 | 1 | H | H |
| O12 a or b | OCH$_2$C(=O)OH | H | 0 | 1 | H | H |
| O13 a or b | H | N(H)C(=O)E$^3$OH | 0 | 0 | H | H |
| O14 a or b | H | N(H)C(=O)E$^3$OH | 1 | 0 | H | H |
| O15 a or b | H | N(H)C(=O)E$^3$OH | 1 | 1 | H | H |
| O16 a or b | H | N(H)C(=O)E$^3$OH | 0 | 1 | H | H |
| O17 a or b | H | OCH$_2$C(=O)OH | 0 | 0 | H | H |
| O18 a or b | H | OCH$_2$C(=O)OH | 1 | 0 | H | H |
| O19 a or b | H | OCH$_2$C(=O)OH | 1 | 1 | H | H |
| O20 a or b | H | OCH$_2$C(=O)OH | 0 | 1 | H | H |
| O21 a or b | H | H | 0 | 0 | C(=O)OH | H |
| O22 a or b | H | H | 1 | 0 | C(=O)OH | H |
| O23 a or b | H | H | 1 | 1 | C(=O)OH | H |
| O24 a or b | H | H | 0 | 1 | C(=O)OH | H |
| O25 a or b | N(H)C(=O)E$^3$OH | H | 0 | 0 | C(=O)OH | H |
| O26 a or b | N(H)C(=O)E$^3$OH | H | 1 | 0 | C(=O)OH | H |

TABLE 16-continued

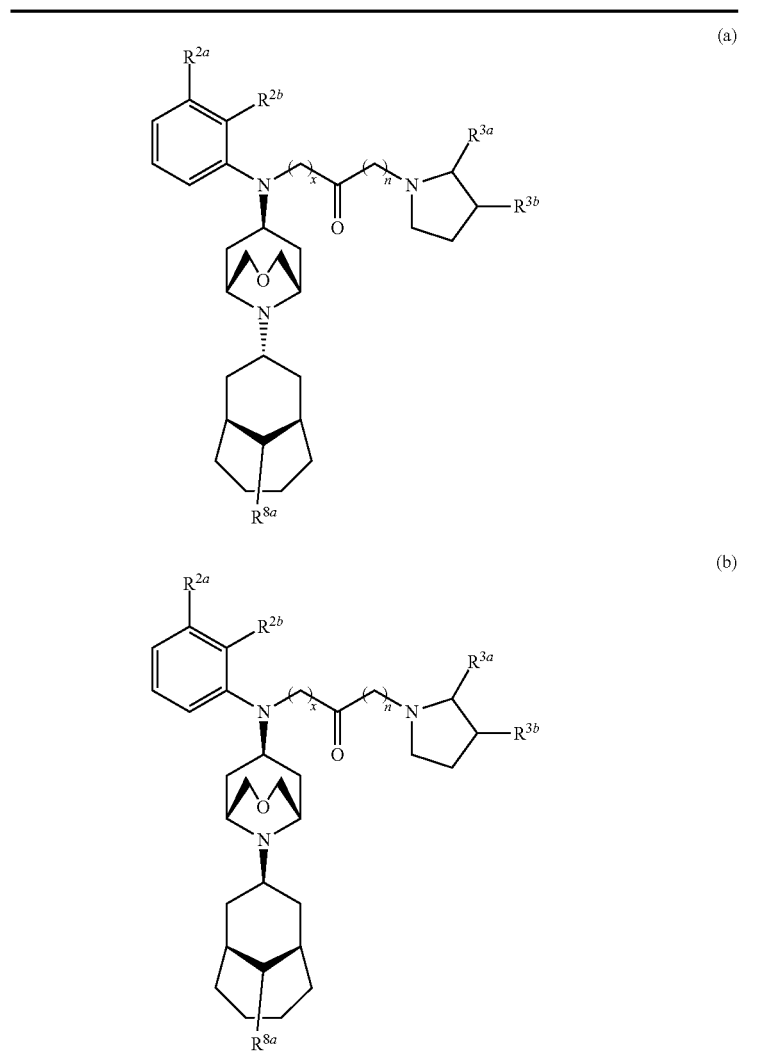

(a)

(b)

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| O27 a or b | N(H)C(=O)E³OH | H | 1 | 1 | C(=O)OH | H |
| O28 a or b | N(H)C(=O)E³OH | H | 0 | 1 | C(=O)OH | H |
| O29 a or b | OCH₂C(=O)OH | H | 0 | 0 | C(=O)OH | H |
| O30 a or b | OCH₂C(=O)OH | H | 1 | 0 | C(=O)OH | H |
| O31 a or b | OCH₂C(=O)OH | H | 1 | 1 | C(=O)OH | H |
| O32 a or b | OCH₂C(=O)OH | H | 0 | 1 | C(=O)OH | H |
| O33 a or b | H | N(H)C(=O)E³OH | 0 | 0 | C(=O)OH | H |
| O34 a or b | H | N(H)C(=O)E³OH | 1 | 0 | C(=O)OH | H |
| O35 a or b | H | N(H)C(=O)E³OH | 1 | 1 | C(=O)OH | H |
| O36 a or b | H | N(H)C(=O)E³OH | 0 | 1 | C(=O)OH | H |
| O37 a or b | H | OCH₂C(=O)OH | 0 | 0 | C(=O)OH | H |
| O38 a or b | H | OCH₂C(=O)OH | 1 | 0 | C(=O)OH | H |
| O39 a or b | H | OCH₂C(=O)OH | 1 | 1 | C(=O)OH | H |
| O40 a or b | H | OCH₂C(=O)OH | 0 | 1 | C(=O)OH | H |
| O41 a or b | H | H | 0 | 0 | H | C(=O)OH |
| O42 a or b | H | H | 1 | 0 | H | C(=O)OH |
| O43 a or b | H | H | 1 | 1 | H | C(=O)OH |
| O44 a or b | H | H | 0 | 1 | H | C(=O)OH |
| O45 a or b | N(H)C(=O)E³OH | H | 0 | 0 | H | C(=O)OH |
| O46 a or b | N(H)C(=O)E³OH | H | 1 | 0 | H | C(=O)OH |
| O47 a or b | N(H)C(=O)E³OH | H | 1 | 1 | H | C(=O)OH |
| O48 a or b | N(H)C(=O)E³OH | H | 0 | 1 | H | C(=O)OH |
| O49 a or b | OCH₂C(=O)OH | H | 0 | 0 | H | C(=O)OH |
| O50 a or b | OCH₂C(=O)OH | H | 1 | 0 | H | C(=O)OH |
| O51 a or b | OCH₂C(=O)OH | H | 1 | 1 | H | C(=O)OH |
| O52 a or b | OCH₂C(=O)OH | H | 0 | 1 | H | C(=O)OH |

TABLE 16-continued

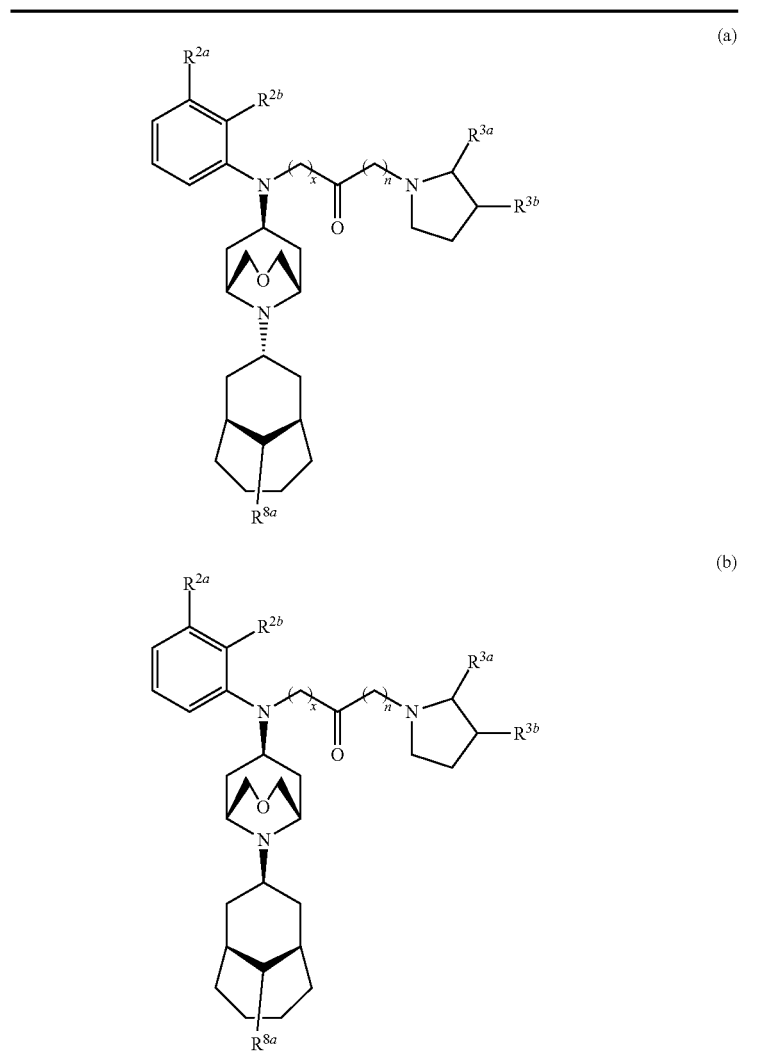

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| O53 a or b | H | N(H)C(=O)E$^3$OH | 0 | 0 | H | C(=O)OH |
| O54 a or b | H | N(H)C(=O)E$^3$OH | 1 | 0 | H | C(=O)OH |
| O55 a or b | H | N(H)C(=O)E$^3$OH | 1 | 1 | H | C(=O)OH |
| O56 a or b | H | N(H)C(=O)E$^3$OH | 0 | 1 | H | C(=O)OH |
| O57 a or b | H | OCH$_2$C(=O)OH | 0 | 0 | H | C(=O)OH |
| O58 a or b | H | OCH$_2$C(=O)OH | 1 | 0 | H | C(=O)OH |
| O59 a or b | H | OCH$_2$C(=O)OH | 1 | 1 | H | C(=O)OH |
| O60 a or b | H | OCH$_2$C(=O)OH | 0 | 1 | H | C(=O)OH |
| O61 a or b | H | H | 0 | 0 | tetrazolyl | H |
| O62 a or b | H | H | 1 | 0 | tetrazolyl | H |
| O63 a or b | H | H | 1 | 1 | tetrazolyl | H |
| O64 a or b | H | H | 0 | 1 | tetrazolyl | H |
| O65 a or b | N(H)C(=O)E$^3$OH | H | 0 | 0 | tetrazolyl | H |
| O66 a or b | N(H)C(=O)E$^3$OH | H | 1 | 0 | tetrazolyl | F1 |
| O67 a or b | N(H)C(=O)E$^3$OH | H | 1 | 1 | tetrazolyl | H |
| O68 a or b | N(H)C(=O)E$^3$OH | H | 0 | 1 | tetrazolyl | H |
| O69 a or b | OCH$_2$C(=O)OH | H | 0 | 0 | tetrazolyl | H |
| O70 a or b | OCH$_2$C(=O)OH | H | 1 | 0 | tetrazolyl | H |
| O71 a or b | OCH$_2$C(=O)OH | H | 1 | 1 | tetrazolyl | H |
| O72 a or b | OCH$_2$C(=O)OH | H | 0 | 1 | tetrazolyl | H |
| O73 a or b | H | N(H)C(=O)E$^3$OH | 0 | 0 | tetrazolyl | H |
| O74 a or b | H | N(H)C(=O)E$^3$OH | 1 | 0 | tetrazolyl | H |
| O75 a or b | H | N(H)C(=O)E$^3$OH | 1 | 1 | tetrazolyl | H |
| O76 a or b | H | N(H)C(=O)E$^3$OH | 0 | 1 | tetrazolyl | H |
| O77 a or b | H | OCH$_2$C(=O)OH | 0 | 0 | tetrazolyl | H |
| O78 a or b | H | OCH$_2$C(=O)OH | 1 | 0 | tetrazolyl | H |

TABLE 16-continued (a)

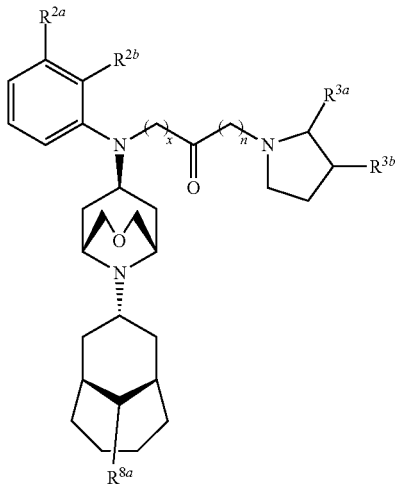

(b)

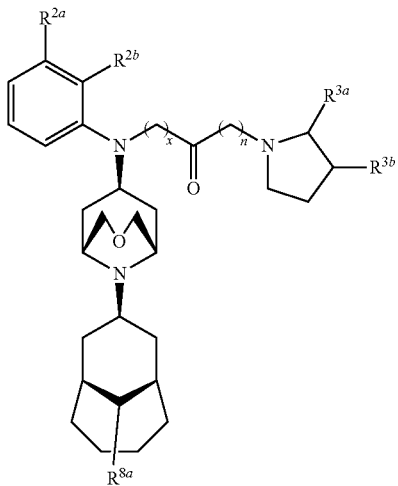

and pharmaceutically acceptable salts and solvates thereof, where:

| Compound | $R^{2a}$ | $R^{2b}$ | x | n | $R^{3a}$ | $R^{3b}$ |
|---|---|---|---|---|---|---|
| O79 a or b | H | OCH$_2$C(=O)OH | 1 | 1 | tetrazolyl | H |
| O80 a or b | H | OCH$_2$C(=O)OH | 0 | 1 | tetrazolyl | H |
| O81 a or b | H | H | 0 | 0 | H | tetrazolyl |
| O82 a or b | H | H | 1 | 0 | H | tetrazolyl |
| O83 a or b | H | H | 1 | 1 | H | tetrazolyl |
| O84 a or b | H | H | 0 | 1 | H | tetrazolyl |
| O85 a or b | N(H)C(=O)E$^3$OH | H | 0 | 0 | H | tetrazolyl |
| O86 a or b | N(H)C(=O)E$^3$OH | H | 1 | 0 | H | tetrazolyl |
| O87 a or b | N(H)C(=O)E$^3$OH | H | 1 | 1 | H | tetrazolyl |
| O88 a or b | N(H)C(=O)E$^3$OH | H | 0 | 1 | H | tetrazolyl |
| O89 a or b | OCH$_2$C(=O)OH | H | 0 | 0 | H | tetrazolyl |
| O90 a or b | OCH$_2$C(=O)OH | H | 1 | 0 | H | tetrazolyl |
| O91 a or b | OCH$_2$C(=O)OH | H | 1 | 1 | H | tetrazolyl |
| O92 a or b | OCH$_2$C(=O)OH | H | 0 | 1 | H | tetrazolyl |
| O93 a or b | H | N(H)C(=O)E$^3$OH | 0 | 0 | H | tetrazolyl |
| O94 a or b | H | N(H)C(=O)E$^3$OH | 1 | 0 | H | tetrazolyl |
| O95 a or b | H | N(H)C(=O)E$^3$OH | 1 | 1 | H | tetrazolyl |
| O96 a or b | H | N(H)C(=O)E$^3$OH | 0 | 1 | H | tetrazolyl |
| O97 a or b | H | OCH$_2$C(=O)OH | 0 | 0 | H | tetrazolyl |
| O98 a or b | H | OCH$_2$C(=O)OH | 1 | 0 | H | tetrazolyl |
| O99 a or b | H | OCH$_2$C(=O)OH | 1 | 1 | H | tetrazolyl |
| O100 a or b | H | OCH$_2$C(=O)OH | 0 | 1 | H | tetrazolyl |

$R^{8a}$ is (i) H or (ii) CH$_3$; E$^3$ is (iii) a direct bond or (iv) C(=O).

In other embodiments, the Substituted Piperidin-4-amino-Type Compound has one of the formulae of Table 17.

TABLE 17

| Formula | Compound |
| --- | --- |
| IA' | |
| IB' | |
| IB$_1$' | |
| IB$_2$' | |
| IC' | |

TABLE 17-continued

| Formula | Compound |
| --- | --- |
| IC$_1$' | |
| IC$_2$' | |
| ID' | |
| ID$_1$' | |
| ID$_2$' | |

Illustrative Substituted Piperidin-4-amino-Type Compounds are listed below in Tables 18-32.

TABLE 18

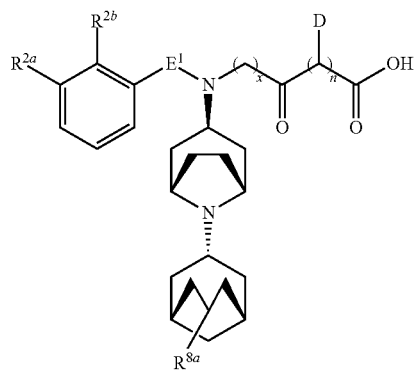

(a)

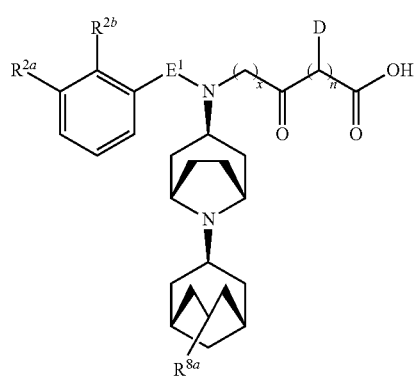

(b)

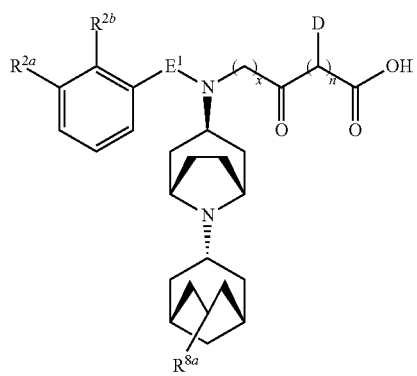

(a)

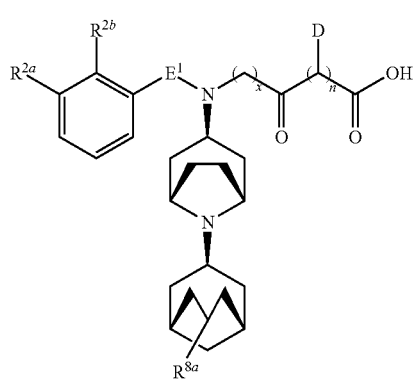

(b)

and pharmaceutically acceptable salts and solvates thereof, where:

| Compound | $R^{2a}$ | $R^{2b}$ | $E^1$ | x | n | D |
|---|---|---|---|---|---|---|
| P1 a or b | H | H | direct bond | 0 | 0 | absent |
| P2 a or b | H | H | direct bond | 0 | 1 | H |
| P3 a or b | H | H | direct bond | 0 | 1 | $N(CH_3)_2$ |
| P4 a or b | H | H | direct bond | 1 | 1 | H |
| P5 a or b | H | H | direct bond | 1 | 1 | $N(CH_3)_2$ |
| P6 a or b | H | H | $SO_2$ | 0 | 0 | absent |
| P7 a or b | H | H | $SO_2$ | 0 | 1 | H |
| P8 a or b | H | H | $SO_2$ | 0 | 1 | $N(CH_3)_2$ |
| P9 a or b | H | H | $SO_2$ | 1 | 1 | H |
| P10 a or b | H | H | $SO_2$ | 1 | 1 | $N(CH_3)_2$ |
| P11 a or b | H | $N(H)C(=O)E^3OH$ | direct bond | 0 | 0 | absent |
| P12 a or b | H | $N(H)C(=O)E^3OH$ | direct bond | 0 | 1 | H |
| P13 a or b | H | $N(H)C(=O)E^3OH$ | direct bond | 0 | 1 | $N(CH_3)_2$ |
| P14 a or b | H | $N(H)C(=O)E^3OH$ | direct bond | 1 | 1 | H |
| P15 a or b | H | $N(H)C(=O)E^3OH$ | direct bond | 1 | 1 | $N(CH_3)_2$ |
| P16 a or b | H | $N(H)C(=O)E^3OH$ | $SO_2$ | 0 | 0 | absent |
| P17 a or b | H | $N(H)C(=O)E^3OH$ | $SO_2$ | 0 | 1 | H |
| P18 a or b | H | $N(H)C(=O)E^3OH$ | $SO_2$ | 0 | 1 | $N(CH_3)_2$ |
| P19 a or b | H | $N(H)C(=O)E^3OH$ | $SO_2$ | 1 | 1 | H |
| P20 a or b | H | $N(H)C(=O)E^3OH$ | $SO_2$ | 1 | 1 | $N(CH_3)_2$ |
| P21 a or b | H | $OCH_2C(=O)OH$ | direct bond | 0 | 0 | absent |
| P22 a or b | H | $OCH_2C(=O)OH$ | direct bond | 0 | 1 | H |
| P23 a or b | H | $OCH_2C(=O)OH$ | direct bond | 0 | 1 | $N(CH_3)_2$ |
| P24 a or b | H | $OCH_2C(=O)OH$ | direct bond | 1 | 1 | H |
| P25 a or b | H | $OCH_2C(=O)OH$ | direct bond | 1 | 1 | $N(CH_3)_2$ |
| P26 a or b | H | $OCH_2C(=O)OH$ | $SO_2$ | 0 | 0 | absent |
| P27 a or b | H | $OCH_2C(=O)OH$ | $SO_2$ | 0 | 1 | H |
| P28 a or b | H | $OCH_2C(=O)OH$ | $SO_2$ | 0 | 1 | $N(CH_3)_2$ |
| P29 a or b | H | $OCH_2C(=O)OH$ | $SO_2$ | 1 | 1 | H |
| P30 a or b | H | $OCH_2C(=O)OH$ | $SO_2$ | 1 | 1 | $N(CH_3)_2$ |
| P31 a or b | $N(H)C(=O)E^3OH$ | H | direct bond | 0 | 0 | absent |
| P32 a or b | $N(H)C(=O)E^3OH$ | H | direct bond | 0 | 1 | H |
| P33 a or b | $N(H)C(=O)E^3OH$ | H | direct bond | 0 | 1 | $N(CH_3)_2$ |
| P34 a or b | $N(H)C(=O)E^3OH$ | H | direct bond | 1 | 1 | H |

TABLE 18-continued

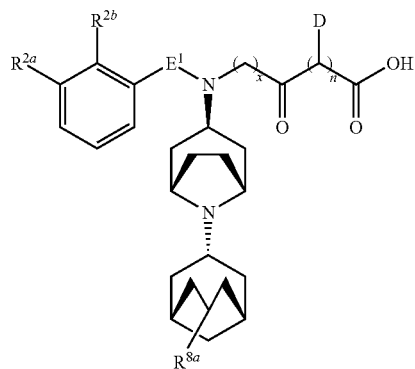

(a)

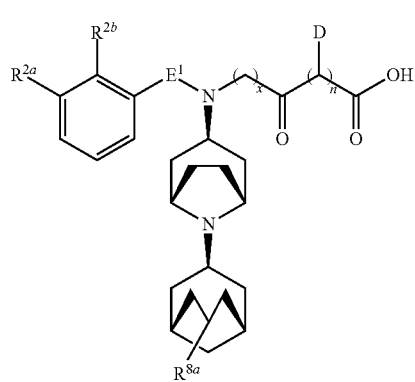

(b)

and pharmaceutically acceptable salts and solvates thereof, where:

| Compound | $R^{2a}$ | $R^{2b}$ | $E^1$ | x | n | D |
|---|---|---|---|---|---|---|
| P35 a or b | N(H)C(=O)E$^3$OH | H | direct bond | 1 | 1 | N(CH$_3$)$_2$ |
| P36 a or b | N(H)C(=O)E$^3$OH | H | SO$_2$ | 0 | 0 | absent |
| P37 a or b | N(H)C(=O)E$^3$OH | H | SO$_2$ | 0 | 1 | H |
| P38 a or b | N(H)C(=O)E$^3$OH | H | SO$_2$ | 0 | 1 | N(CH$_3$)$_2$ |
| P39 a or b | N(H)C(=O)E$^3$OH | H | SO$_2$ | 1 | 1 | H |
| P40 a or b | N(H)C(=O)E$^3$OH | H | SO$_2$ | 1 | 1 | N(CH$_3$)$_2$ |
| P41 a or b | OCH$_2$C(=O)OH | H | direct bond | 0 | 0 | absent |
| P42 a or b | OCH$_2$C(=O)OH | H | direct bond | 0 | 1 | H |
| P43 a or b | OCH$_2$C(=O)OH | H | direct bond | 0 | 1 | N(CH$_3$)$_2$ |
| P44 a or b | OCH$_2$C(=O)OH | H | direct bond | 1 | 1 | H |
| P45 a or b | OCH$_2$C(=O)OH | H | direct bond | 1 | 1 | N(CH$_3$)$_2$ |
| P46 a or b | OCH$_2$C(=O)OH | H | SO$_2$ | 0 | 0 | absent |
| P47 a or b | OCH$_2$C(=O)OH | H | SO$_2$ | 0 | 1 | H |
| P48 a or b | OCH$_2$C(=O)OH | H | SO$_2$ | 0 | 1 | N(CH$_3$)$_2$ |
| P49 a or b | OCH$_2$C(=O)OH | H | SO$_2$ | 1 | 1 | H |
| P50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 19

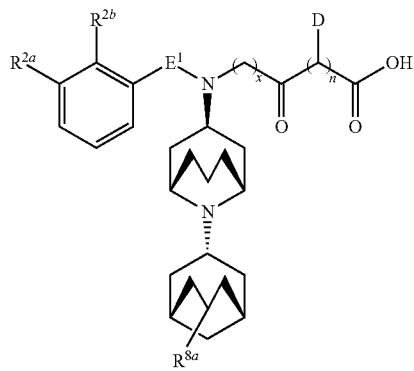

(a)

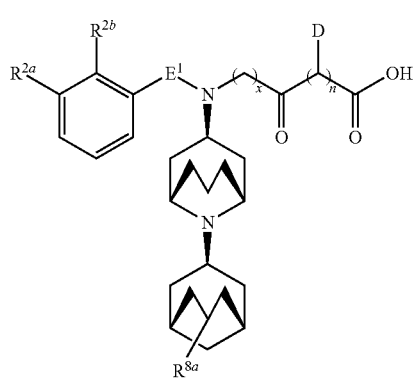

(b)

and pharmaceutically acceptable salts and solvates thereof, where:

| Compound | $R^{2a}$ | $R^{2b}$ | $E^1$ | x | n | D |
|---|---|---|---|---|---|---|
| Q1 a or b | H | H | direct bond | 0 | 0 | absent |
| Q2 a or b | H | H | direct bond | 0 | 1 | H |
| Q3 a or b | H | H | direct bond | 0 | 1 | N(CH$_3$)$_2$ |
| Q4 a or b | H | H | direct bond | 1 | 1 | H |
| Q5 a or b | H | H | direct bond | 1 | 1 | N(CH$_3$)$_2$ |
| Q6 a or b | H | H | SO$_2$ | 0 | 0 | absent |
| Q7 a or b | H | H | SO$_2$ | 0 | 1 | H |
| Q8 a or b | H | H | SO$_2$ | 0 | 1 | N(CH$_3$)$_2$ |
| Q9 a or b | H | H | SO$_2$ | 1 | 1 | H |
| Q10 a or b | H | H | SO$_2$ | 1 | 1 | N(CH$_3$)$_2$ |
| Q11 a or b | H | N(H)C(=O)E$^3$OH | direct bond | 0 | 0 | absent |
| Q12 a or b | H | N(H)C(=O)E$^3$OH | direct bond | 0 | 1 | H |
| Q13 a or b | H | N(H)C(=O)E$^3$OH | direct bond | 0 | 1 | N(CH$_3$)$_2$ |
| Q14 a or b | H | N(H)C(=O)E$^3$OH | direct bond | 1 | 1 | H |
| Q15 a or b | H | N(H)C(=O)E$^3$OH | direct bond | 1 | 1 | N(CH$_3$)$_2$ |
| Q16 a or b | H | N(H)C(=O)E$^3$OH | SO$_2$ | 0 | 0 | absent |
| Q17 a or b | H | N(H)C(=O)E$^3$OH | SO$_2$ | 0 | 1 | H |
| Q18 a or b | H | N(H)C(=O)E$^3$OH | SO$_2$ | 0 | 1 | N(CH$_3$)$_2$ |
| Q19 a or b | H | N(H)C(=O)E$^3$OH | SO$_2$ | 1 | 1 | H |
| Q20 a or b | H | N(H)C(=O)E$^3$OH | SO$_2$ | 1 | 1 | N(CH$_3$)$_2$ |
| Q21 a or b | H | OCH$_2$C(=O)OH | direct bond | 0 | 0 | absent |
| Q22 a or b | H | OCH$_2$C(=O)OH | direct bond | 0 | 1 | H |
| Q23 a or b | H | OCH$_2$C(=O)OH | direct bond | 0 | 1 | N(CH$_3$)$_2$ |

TABLE 19-continued (a)
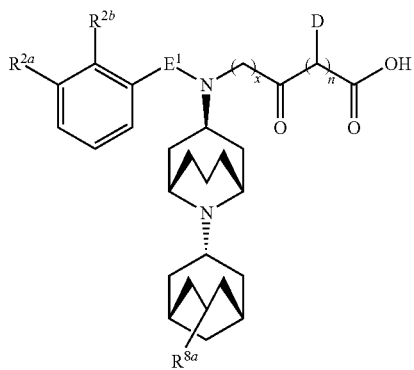

(b)
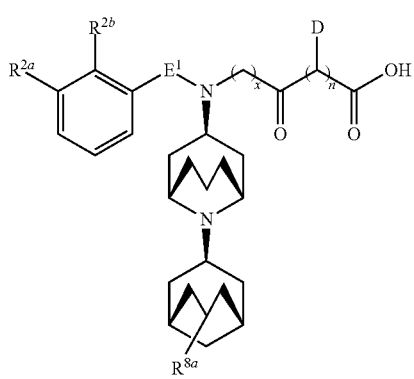

and pharmaceutically acceptable salts and solvates thereof, where:

| Compound | $R^{2a}$ | $R^{2b}$ | $E^1$ | x | n | D |
|---|---|---|---|---|---|---|
| Q24 a or b | H | OCH$_2$C(=O)OH | direct bond | 1 | 1 | H |
| Q25 a or b | H | OCH$_2$C(=O)OH | direct bond | 1 | 1 | N(CH$_3$)$_2$ |
| Q26 a or b | H | OCH$_2$C(=O)OH | SO$_2$ | 0 | 0 | absent |
| Q27 a or b | H | OCH$_2$C(=O)OH | SO$_2$ | 0 | 1 | H |
| Q28 a or b | H | OCH$_2$C(=O)OH | SO$_2$ | 0 | 1 | N(CH$_3$)$_2$ |
| Q29 a or b | H | OCH$_2$C(=O)OH | SO$_2$ | 1 | 1 | H |
| Q30 a or b | H | OCH$_2$C(=O)OH | SO$_2$ | 1 | 1 | N(CH$_3$)$_2$ |
| Q31 a or b | N(H)C(=O)E$^3$OH | H | direct bond | 0 | 0 | absent |
| Q32 a or b | N(H)C(=O)E$^3$OH | H | direct bond | 0 | 1 | H |
| Q33 a or b | N(H)C(=O)E$^3$OH | H | direct bond | 0 | 1 | N(CH$_3$)$_2$ |
| Q34 a or b | N(H)C(=O)E$^3$OH | H | direct bond | 1 | 1 | H |
| Q35 a or b | N(H)C(=O)E$^3$OH | H | direct bond | 1 | 1 | N(CH$_3$)$_2$ |
| Q36 a or b | N(H)C(=O)E$^3$OH | H | SO$_2$ | 0 | 0 | absent |
| Q37 a or b | N(H)C(=O)E$^3$OH | H | SO$_2$ | 0 | 1 | H |

TABLE 19-continued (a)
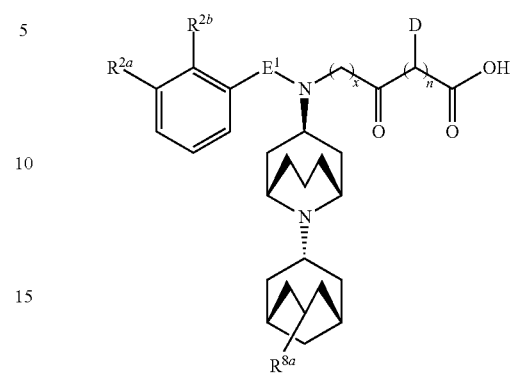

(b)
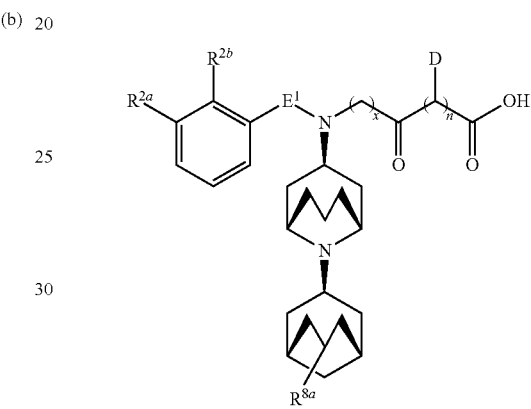

and pharmaceutically acceptable salts and solvates thereof, where:

| Compound | $R^{2a}$ | $R^{2b}$ | $E^1$ | x | n | D |
|---|---|---|---|---|---|---|
| Q38 a or b | N(H)C(=O)E$^3$OH | H | SO$_2$ | 0 | 1 | N(CH$_3$)$_2$ |
| Q39 a or b | N(H)C(=O)E$^3$OH | H | SO$_2$ | 1 | 1 | H |
| Q40 a or b | N(H)C(=O)E$^3$OH | H | SO$_2$ | 1 | 1 | N(CH$_3$)$_2$ |
| Q41 a or b | OCH$_2$C(=O)OH | H | direct bond | 0 | 0 | absent |
| Q42 a or b | OCH$_2$C(=O)OH | H | direct bond | 0 | 1 | H |
| Q43 a or b | OCH$_2$C(=O)OH | H | direct bond | 0 | 1 | N(CH$_3$)$_2$ |
| Q44 a or b | OCH$_2$C(=O)OH | H | direct bond | 1 | 1 | H |
| Q45 a or b | OCH$_2$C(=O)OH | H | direct bond | 1 | 1 | N(CH$_3$)$_2$ |
| Q46 a or b | OCH$_2$C(=O)OH | H | SO$_2$ | 0 | 0 | absent |
| Q47 a or b | OCH$_2$C(=O)OH | H | SO$_2$ | 0 | 1 | H |
| Q48 a or b | OCH$_2$C(=O)OH | H | SO$_2$ | 0 | 1 | N(CH$_3$)$_2$ |
| Q49 a or b | OCH$_2$C(=O)OH | H | SO$_2$ | 1 | 1 | H |
| Q50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 20

(a)
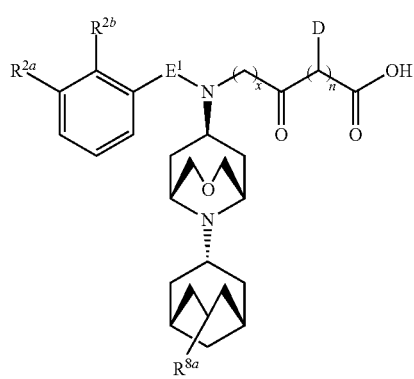

(b)
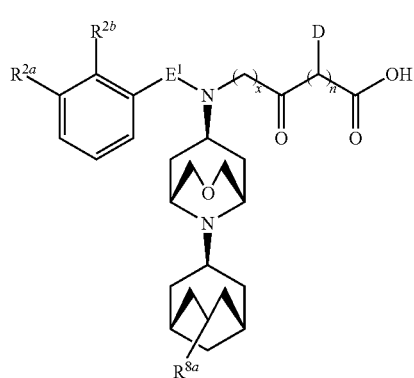

and pharmaceutically acceptable salts and solvates thereof, where:

| Compound | $R^{2a}$ | $R^{2b}$ | $E^1$ | x | n | D |
|---|---|---|---|---|---|---|
| R1 a or b | H | H | direct bond | 0 | 0 | absent |
| R2 a or b | H | H | direct bond | 0 | 1 | H |
| R3 a or b | H | H | direct bond | 0 | 1 | $N(CH_3)_2$ |
| R4 a or b | H | H | direct bond | 1 | 1 | H |
| R5 a or b | H | H | direct bond | 1 | 1 | $N(CH_3)_2$ |
| R6 a or b | H | H | $SO_2$ | 0 | 0 | absent |
| R7 a or b | H | H | $SO_2$ | 0 | 1 | H |
| R8 a or b | H | H | $SO_2$ | 0 | 1 | $N(CH_3)_2$ |
| R9 a or b | H | H | $SO_2$ | 1 | 1 | H |
| R10 a or b | H | H | $SO_2$ | 1 | 1 | $N(CH_3)_2$ |
| R11 a or b | H | $N(H)C(=O)E^3OH$ | direct bond | 0 | 0 | absent |
| R12 a or b | H | $N(H)C(=O)E^3OH$ | direct bond | 0 | 1 | H |
| R13 a or b | H | $N(H)C(=O)E^3OH$ | direct bond | 0 | 1 | $N(CH_3)_2$ |
| R14 a or b | H | $N(H)C(=O)E^3OH$ | direct bond | 1 | 1 | H |
| R15 a or b | H | $N(H)C(=O)E^3OH$ | direct bond | 1 | 1 | $N(CH_3)_2$ |
| R16 a or b | H | $N(H)C(=O)E^3OH$ | $SO_2$ | 0 | 0 | absent |
| R17 a or b | H | $N(H)C(=O)E^3OH$ | $SO_2$ | 0 | 1 | H |

TABLE 20-continued (a)
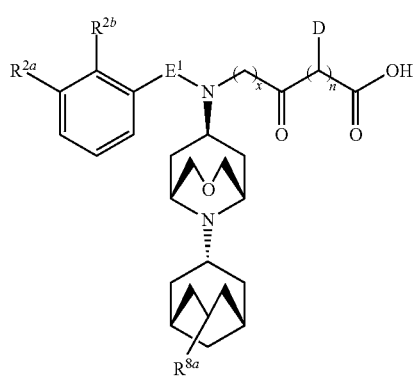

(b)
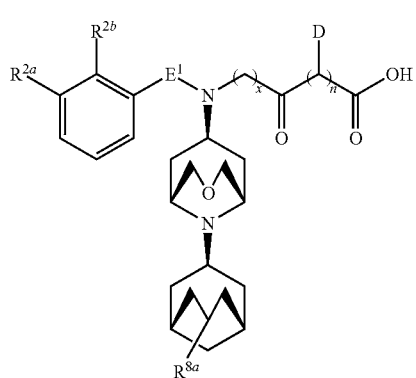

and pharmaceutically acceptable salts and solvates thereof, where:

| Compound | $R^{2a}$ | $R^{2b}$ | $E^1$ | x | n | D |
|---|---|---|---|---|---|---|
| R18 a or b | H | $N(H)C(=O)E^3OH$ | $SO_2$ | 0 | 1 | $N(CH_3)_2$ |
| R19 a or b | H | $N(H)C(=O)E^3OH$ | $SO_2$ | 1 | 1 | H |
| R20 a or b | H | $N(H)C(=O)E^3OH$ | $SO_2$ | 1 | 1 | $N(CH_3)_2$ |
| R21 a or b | H | $OCH_2C(=O)OH$ | direct bond | 0 | 0 | absent |
| R22 a or b | H | $OCH_2C(=O)OH$ | direct bond | 0 | 1 | H |
| R23 a or b | H | $OCH_2C(=O)OH$ | direct bond | 0 | 1 | $N(CH_3)_2$ |
| R24 a or 6 | H | $OCH_2C(=O)OH$ | direct bond | 1 | 1 | H |
| R25 a or b | H | $OCH_2C(=O)OH$ | direct bond | 1 | 1 | $N(CH_3)_2$ |
| R26 a or b | H | $OCH_2C(=O)OH$ | $SO_2$ | 0 | 0 | absent |
| R27 a or b | H | $OCH_2C(=O)OH$ | $SO_2$ | 0 | 1 | H |
| R28 a or b | H | $OCH_2C(=O)OH$ | $SO_2$ | 0 | 1 | $N(CH_3)_2$ |
| R29 a or b | H | $OCH_2C(=O)OH$ | $SO_2$ | 1 | 1 | H |
| R30 a or b | H | $OCH_2C(=O)OH$ | $SO_2$ | 1 | 1 | $N(CH_3)_2$ |
| R31 a or b | $N(H)C(=O)E^3OH$ | H | direct bond | 0 | 0 | absent |
| R32 a or b | $N(H)C(=O)E^3OH$ | H | direct bond | 0 | 1 | H |
| R33 a or b | $N(H)C(=O)E^3OH$ | H | direct bond | 0 | 1 | $N(CH_3)_2$ |
| R34 a or b | $N(H)C(=O)E^3OH$ | H | direct bond | 1 | 1 | H |

TABLE 20-continued (a)
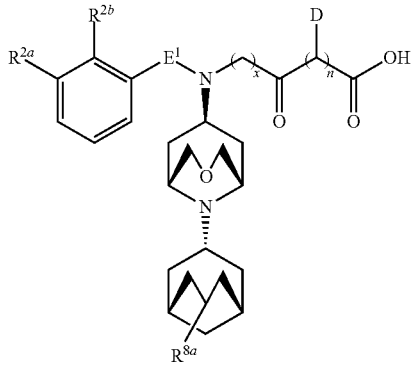

(b)
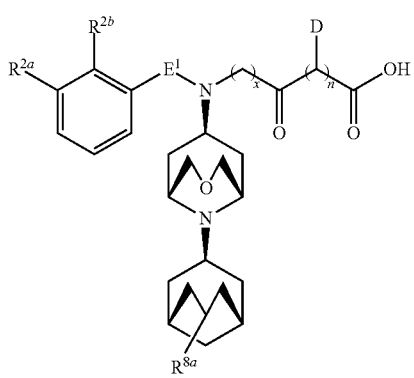

and pharmaceutically acceptable salts and solvates thereof, where:

| Compound | $R^{2a}$ | $R^{2b}$ | $E^1$ | x | n | D |
|---|---|---|---|---|---|---|
| R35 a or b | N(H)C(=O)E$^3$OH | H | direct bond | 1 | 1 | N(CH$_3$)$_2$ |
| R36 a or b | N(H)C(=O)E$^3$OH | H | SO$_2$ | 0 | 0 | absent |
| R37 a or b | N(H)C(=O)E$^3$OH | H | SO$_2$ | 0 | 1 | H |
| R38 a or b | N(H)C(=O)E$^3$OH | H | SO$_2$ | 0 | 1 | N(CH$_3$)$_2$ |
| R39 a or b | N(H)C(=O)E$^3$OH | H | SO$_2$ | 1 | 1 | H |
| R40 a or b | N(H)C(=O)E$^3$OH | H | SO$_2$ | 1 | 1 | N(CH$_3$)$_2$ |
| R41 a or b | OCH$_2$C(=O)OH | H | direct bond | 0 | 0 | absent |
| R42 a or b | OCH$_2$C(=O)OH | H | direct bond | 0 | 1 | H |
| R43 a or b | OCH$_2$C(=O)OH | H | direct bond | 0 | 1 | N(CH$_3$)$_2$ |
| R44 a or b | OCH$_2$C(=O)OH | H | direct bond | 1 | 1 | H |
| R45 a or b | OCH$_2$C(=O)OH | H | direct bond | 1 | 1 | N(CH$_3$)$_2$ |
| R46 a or b | OCH$_2$C(=O)OH | H | SO$_2$ | 0 | 0 | absent |
| R47 a or b | OCH$_2$C(=O)OH | H | SO$_2$ | 0 | 1 | H |
| R48 a or b | OCH$_2$C(=O)OH | H | SO$_2$ | 0 | 1 | N(CH$_3$)$_2$ |
| R49 a or b | OCH$_2$C(=O)OH | H | SO$_2$ | 1 | 1 | H |
| R50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 21

(a)
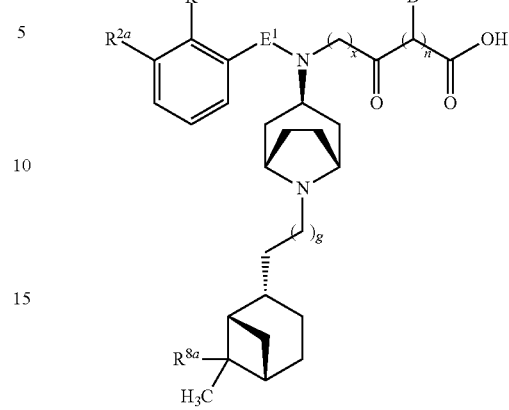

(b)
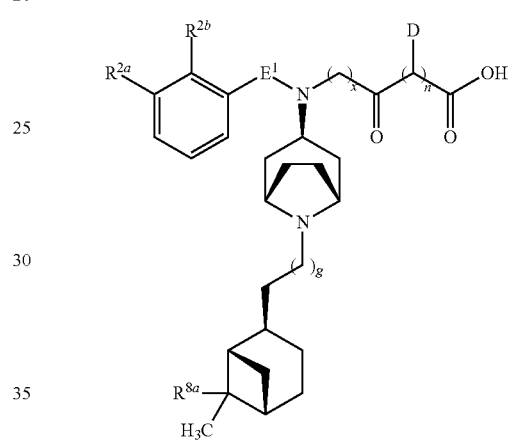

and pharmaceutically acceptable salts and solvates thereof, where:

| Compound | $R^{2a}$ | $R^{2b}$ | $E^1$ | x | n | D |
|---|---|---|---|---|---|---|
| S1 a or b | H | H | direct bond | 0 | 0 | absent |
| S2 a or b | H | H | direct bond | 0 | 1 | H |
| S3 a or b | H | H | direct bond | 0 | 1 | N(CH$_3$)$_2$ |
| S4 a or b | H | H | direct bond | 1 | 1 | H |
| S5 a or b | H | H | direct bond | 1 | 1 | N(CH$_3$)$_2$ |
| S6 a or b | H | H | SO$_2$ | 0 | 0 | absent |
| S7 a or b | H | H | SO$_2$ | 0 | 1 | H |
| S8 a or b | H | H | SO$_2$ | 0 | 1 | N(CH$_3$)$_2$ |
| S9 a or b | H | H | SO$_2$ | 1 | 1 | H |
| S10 a or b | H | H | SO$_2$ | 1 | 1 | N(CH$_3$)$_2$ |
| S11 a or b | H | N(H)C(=O)E$^3$OH | direct bond | 0 | 0 | absent |
| S12 a or b | H | N(H)C(=O)E$^3$OH | direct bond | 0 | 1 | H |
| S13 a or b | H | N(H)C(=O)E$^3$OH | direct bond | 0 | 1 | N(CH$_3$)$_2$ |
| S14 a or b | H | N(H)C(=O)E$^3$OH | direct bond | 1 | 1 | H |
| S15 a or b | H | N(H)C(=O)E$^3$OH | direct bond | 1 | 1 | N(CH$_3$)$_2$ |
| S16 a or b | H | N(H)C(=O)E$^3$OH | SO$_2$ | 0 | 0 | absent |
| S17 a or b | H | N(H)C(=O)E$^3$OH | SO$_2$ | 0 | 1 | H |
| S18 a or b | H | N(H)C(=O)E$^3$OH | SO$_2$ | 0 | 1 | N(CH$_3$)$_2$ |
| S19 a or b | H | N(H)C(=O)E$^3$OH | SO$_2$ | 1 | 1 | H |
| S20 a or b | H | N(H)C(=O)E$^3$OH | SO$_2$ | 1 | 1 | N(CH$_3$)$_2$ |

TABLE 21-continued (a)

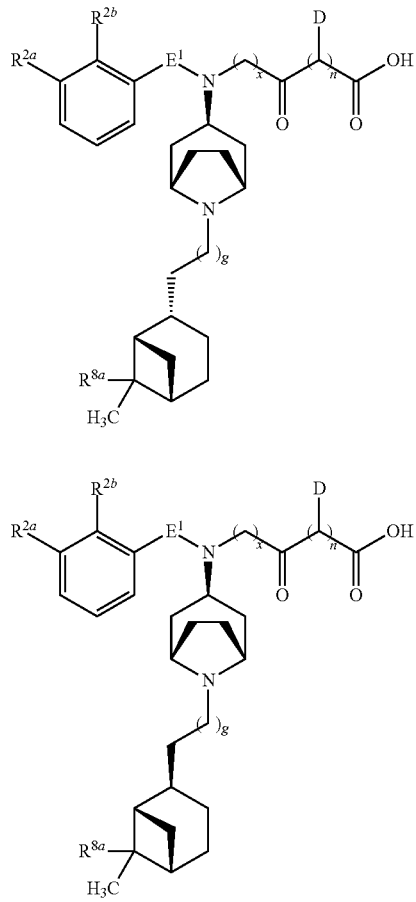

(b)

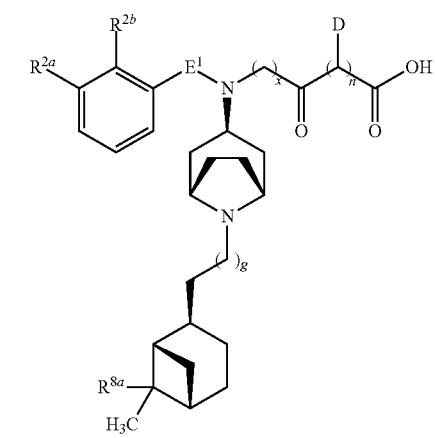

and pharmaceutically acceptable salts and solvates thereof, where:

| Compound | R$^{2a}$ | R$^{2b}$ | E$^1$ | x | n | D |
|---|---|---|---|---|---|---|
| S21 a or b | H | OCH$_2$C(=O)OH | direct bond | 0 | 0 | absent |
| S22 a or b | H | OCH$_2$C(=O)OH | direct bond | 0 | 1 | H |
| S23 a or b | H | OCH$_2$C(=O)OH | direct bond | 0 | 1 | N(CH$_3$)$_2$ |
| S24 a or b | H | OCH$_2$C(=O)OH | direct bond | 1 | 1 | H |
| S25 a or b | H | OCH$_2$C(=O)OH | direct bond | 1 | 1 | N(CH$_3$)$_2$ |
| S26 a or b | H | OCH$_2$C(=O)OH | SO$_2$ | 0 | 0 | absent |
| S27 a or b | H | OCH$_2$C(=O)OH | SO$_2$ | 0 | 1 | H |
| S28 a or b | H | OCH$_2$C(=O)OH | SO$_2$ | 0 | 1 | N(CH$_3$)$_2$ |
| S29 a or b | H | OCH$_2$C(=O)OH | SO$_2$ | 1 | 1 | H |
| S30 a or b | H | OCH$_2$C(=O)OH | SO$_2$ | 1 | 1 | N(CH$_3$)$_2$ |
| S31 a or b | N(H)C(=O)E$^3$OH | H | direct bond | 0 | 0 | absent |
| S32 a or b | N(H)C(=O)E$^3$OH | H | direct bond | 0 | 1 | H |
| S33 a or b | N(H)C(=O)E$^3$OH | H | direct bond | 0 | 1 | N(CH$_3$)$_2$ |
| S34 a or b | N(H)C(=O)E$^3$OH | H | direct bond | 1 | 1 | H |
| S35 a or b | N(H)C(=O)E$^3$OH | H | direct bond | 1 | 1 | N(CH$_3$)$_2$ |
| S36 a or b | N(H)C(=O)E$^3$OH | H | SO$_2$ | 0 | 0 | absent |
| S37 a or b | N(H)C(=O)E$^3$OH | H | SO$_2$ | 0 | 1 | H |
| S38 a or b | N(H)C(=O)E$^3$OH | H | SO$_2$ | 0 | 1 | N(CH$_3$)$_2$ |
| S39 a or b | N(H)C(=O)E$^3$OH | H | SO$_2$ | 1 | 1 | H |
| S40 a or b | N(H)C(=O)E$^3$OH | H | SO$_2$ | 1 | 1 | N(CH$_3$)$_2$ |

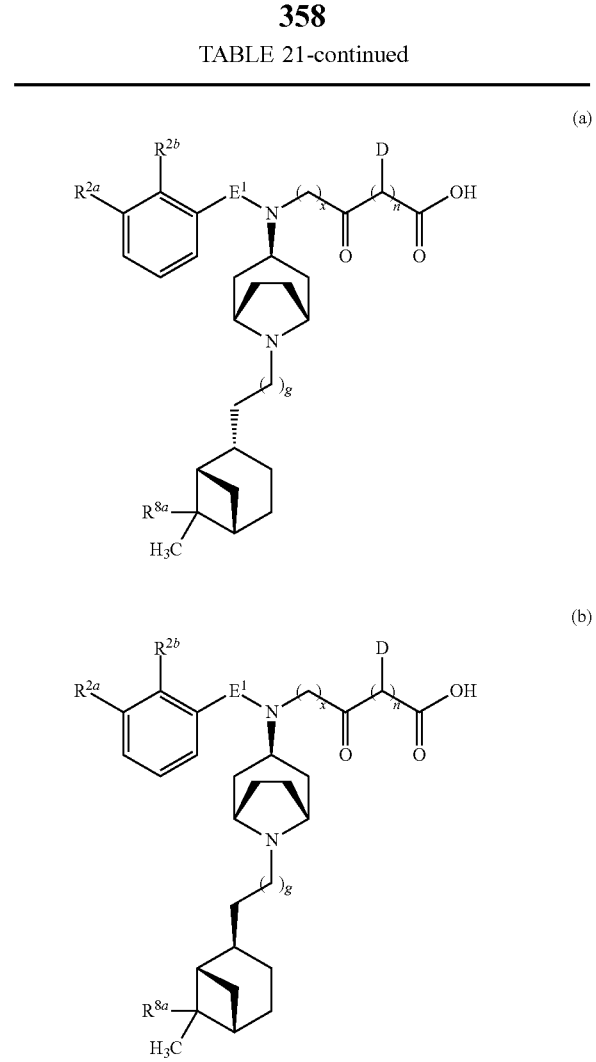

and pharmaceutically acceptable salts and solvates thereof, where:

| Compound | R$^{2a}$ | R$^{2b}$ | E$^1$ | x | n | D |
|---|---|---|---|---|---|---|
| S41 a or b | OCH$_2$C(=O)OH | H | direct bond | 0 | 0 | absent |
| S42 a or b | OCH$_2$C(=O)OH | H | direct bond | 1 | 0 | H |
| S43 a or b | OCH$_2$C(=O)OH | H | direct bond | 0 | 1 | N(CH$_3$)$_2$ |
| S44 a or b | OCH$_2$C(=O)OH | H | direct bond | 1 | 1 | H |
| S45 a or b | OCH$_2$C(=O)OH | H | direct bond | 1 | 1 | N(CH$_3$)$_2$ |
| S46 a or b | OCH$_2$C(=O)OH | H | SO$_2$ | 0 | 0 | absent |
| S47 a or b | OCH$_2$C(=O)OH | H | SO$_2$ | 0 | 1 | H |
| S48 a or b | OCH$_2$C(=O)OH | H | SO$_2$ | 0 | 1 | N(CH$_3$)$_2$ |
| S49 a or b | OCH$_2$C(=O)OH | H | SO$_2$ | 1 | 1 | H |
| S50 a or b | OCH$_2$C(=O)OH | H | SO$_2$ | 1 | 1 | N(CH$_3$)$_2$ |

R$^{8a}$ is (i) H or (ii) CH$_3$; E$^3$ is (iii) a direct bond or (iv) C(=O); g is 0, 1, 2 or 3.

TABLE 22

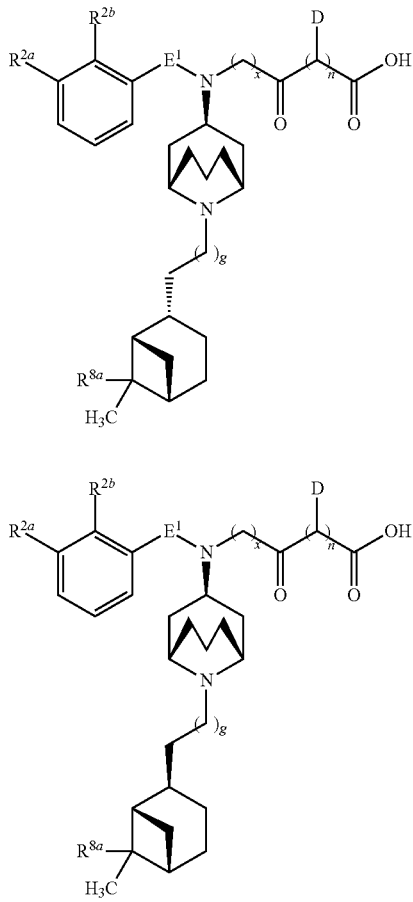

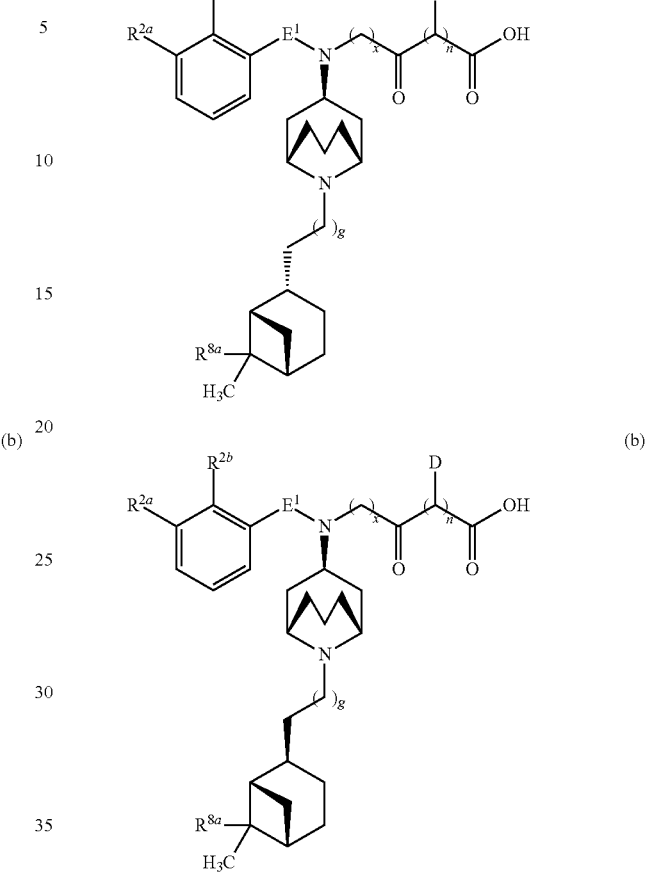

and pharmaceutically acceptable salts and solvates thereof, where:

| Compound | $R^{2a}$ | $R^{2b}$ | $E^1$ | x | n | D |
|---|---|---|---|---|---|---|
| T1 a or b | H | H | direct bond | 0 | 0 | absent |
| T2 a or b | H | H | direct bond | 0 | 1 | H |
| T3 a or b | H | H | direct bond | 0 | 1 | $N(CH_3)_2$ |
| T4 a or b | H | H | direct bond | 1 | 1 | H |
| T5 a or b | H | H | direct bond | 1 | 1 | $N(CH_3)_2$ |
| T6 a or b | H | H | $SO_2$ | 0 | 0 | absent |
| T7 a or b | H | H | $SO_2$ | 0 | 1 | H |
| T8 a or b | H | H | $SO_2$ | 0 | 1 | $N(CH_3)_2$ |
| T9 a or b | H | H | $SO_2$ | 1 | 1 | H |
| T10 a or b | H | H | $SO_2$ | 1 | 1 | $N(CH_3)_2$ |
| T11 a or b | H | $N(H)C(=O)E^3OH$ | direct bond | 0 | 0 | absent |
| T12 a or b | H | $N(H)C(=O)E^3OH$ | direct bond | 0 | 1 | H |
| T13 a or b | H | $N(H)C(=O)E^3OH$ | direct bond | 0 | 1 | $N(CH_3)_2$ |
| T14 a or b | H | $N(H)C(=O)E^3OH$ | direct bond | 1 | 1 | H |
| T15 a or b | H | $N(H)C(=O)E^3OH$ | direct bond | 1 | 1 | $N(CH_3)_2$ |
| T16 a or b | H | $N(H)C(=O)E^3OH$ | $SO_2$ | 0 | 0 | absent |
| T17 a or b | H | $N(H)C(=O)E^3OH$ | $SO_2$ | 0 | 1 | H |
| T18 a or b | H | $N(H)C(=O)E^3OH$ | $SO_2$ | 0 | 1 | $N(CH_3)_2$ |
| T19 a or b | H | $N(H)C(=O)E^3OH$ | $SO_2$ | 1 | 1 | H |
| T20 a or b | H | $N(H)C(=O)E^3OH$ | $SO_2$ | 1 | 1 | $N(CH_3)_2$ |
| T21 a or b | H | $OCH_2C(=O)OH$ | direct bond | 0 | 0 | absent |
| T22 a or b | H | $OCH_2C(=O)OH$ | direct bond | 0 | 1 | H |
| T23 a or b | H | $OCH_2C(=O)OH$ | direct bond | 0 | 1 | $N(CH_3)_2$ |
| T24 a or b | H | $OCH_2C(=O)OH$ | direct bond | 1 | 1 | H |
| T25 a or b | H | $OCH_2C(=O)OH$ | direct bond | 1 | 1 | $N(CH_3)_2$ |
| T26 a or b | H | $OCH_2C(=O)OH$ | $SO_2$ | 0 | 0 | absent |
| T27 a or b | H | $OCH_2C(=O)OH$ | $SO_2$ | 0 | 1 | H |
| T28 a or b | H | $OCH_2C(=O)OH$ | $SO_2$ | 0 | 1 | $N(CH_3)_2$ |
| T29 a or b | H | $OCH_2C(=O)OH$ | $SO_2$ | 1 | 1 | H |
| T30 a or b | H | $OCH_2C(=O)OH$ | $SO_2$ | 1 | 1 | $N(CH_3)_2$ |
| T31 a or b | $N(H)C(=O)E^3OH$ | H | direct bond | 0 | 0 | absent |
| T32 a or b | $N(H)C(=O)E^3OH$ | H | direct bond | 0 | 1 | H |
| T33 a or b | $N(H)C(=O)E^3OH$ | H | direct bond | 0 | 1 | $N(CH_3)_2$ |
| T34 a or b | $N(H)C(=O)E^3OH$ | H | direct bond | 1 | 1 | H |
| T35 a or b | $N(H)C(=O)E^3OH$ | H | direct bond | 1 | 1 | $N(CH_3)_2$ |
| T36 a or b | $N(H)C(=O)E^3OH$ | H | $SO_2$ | 0 | 0 | absent |
| T37 a or b | $N(H)C(=O)E^3OH$ | H | $SO_2$ | 0 | 1 | H |
| T38 a or b | $N(H)C(=O)E^3OH$ | H | $SO_2$ | 0 | 1 | $N(CH_3)_2$ |
| T39 a or b | $N(H)C(=O)E^3OH$ | H | $SO_2$ | 1 | 1 | H |
| T40 a or b | $N(H)C(=O)E^3OH$ | H | $SO_2$ | 1 | 1 | $N(CH_3)_2$ |

TABLE 22-continued

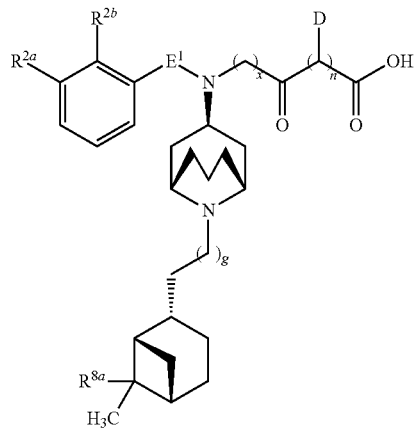

(a)

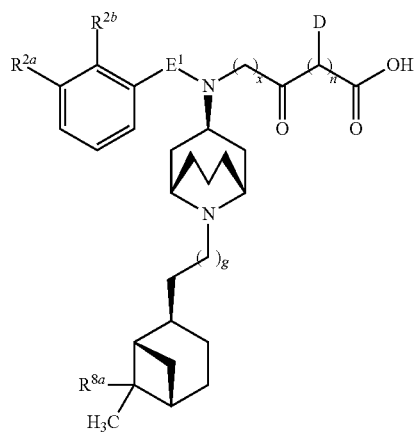

(b)

and pharmaceutically acceptable salts and solvates thereof, where:

| Compound | $R^{2a}$ | $R^{2b}$ | $E^1$ | x | n | D |
|---|---|---|---|---|---|---|
| T41 a or b | OCH$_2$C(=O)OH | H | direct bond | 0 | 0 | absent |
| T42 a or b | OCH$_2$C(=O)OH | H | direct bond | 0 | 1 | H |
| T43 a or b | OCH$_2$C(=O)OH | H | direct bond | 0 | 1 | N(CH$_3$)$_2$ |
| T44 a or b | OCH$_2$C(=O)OH | H | direct bond | 1 | 1 | H |
| T45 a or b | OCH$_2$C(=O)OH | H | direct bond | 1 | 1 | N(CH$_3$)$_2$ |
| T46 a or b | OCH$_2$C(=O)OH | H | SO$_2$ | 0 | 0 | absent |
| T47 a or b | OCH$_2$C(=O)OH | H | SO$_2$ | 0 | 1 | H |
| T48 a or b | OCH$_2$C(=O)OH | H | SO$_2$ | 0 | 1 | N(CH$_3$)$_2$ |
| T49 a or b | OCH$_2$C(=O)OH | H | SO$_2$ | 1 | 1 | H |
| T50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O); g is 0, 1, 2 or 3.

TABLE 23

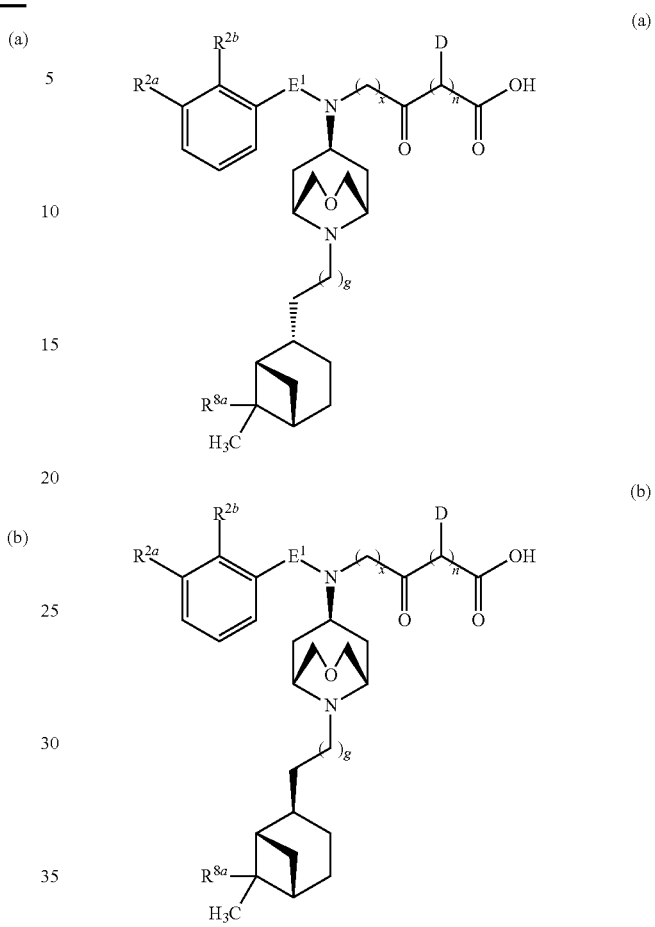

(a)

(b)

and pharmaceutically acceptable salts and solvates thereof, where:

| Compound | $R^{2a}$ | $R^{2b}$ | $E^1$ | x | n | D |
|---|---|---|---|---|---|---|
| U1 a or b | H | H | direct bond | 0 | 0 | absent |
| U2 a or b | H | H | direct bond | 0 | 1 | H |
| U3 a or b | H | H | direct bond | 0 | 1 | N(CH$_3$)$_2$ |
| U4 a or b | H | H | direct bond | 1 | 1 | H |
| U5 a or b | H | H | direct bond | 1 | 1 | N(CH$_3$)$_2$ |
| U6 a or b | H | H | SO$_2$ | 0 | 0 | absent |
| U7 a or b | H | H | SO$_2$ | 0 | 1 | H |
| U8 a or b | H | H | SO$_2$ | 0 | 1 | N(CH$_3$)$_2$ |
| U9 a or b | H | H | SO$_2$ | 1 | 1 | H |
| U10 a or b | H | H | SO$_2$ | 1 | 1 | N(CH$_3$)$_2$ |
| U11 a or b | H | N(H)C(=O)E$^3$OH | direct bond | 0 | 0 | absent |
| U12 a or b | H | N(H)C(=O)E$^3$OH | direct bond | 0 | 1 | H |
| U13 a or b | H | N(H)C(=O)E$^3$OH | direct bond | 0 | 1 | N(CH$_3$)$_2$ |
| U14 a or b | H | N(H)C(=O)E$^3$OH | direct bond | 1 | 1 | H |
| U15 a or b | H | N(H)C(=O)E$^3$OH | direct bond | 1 | 1 | N(CH$_3$)$_2$ |
| U16 a or b | H | N(H)C(=O)E$^3$OH | SO$_2$ | 0 | 0 | absent |
| U17 a or b | H | N(H)C(=O)E$^3$OH | SO$_2$ | 0 | 1 | H |
| U18 a or b | H | N(H)C(=O)E$^3$OH | SO$_2$ | 0 | 1 | N(CH$_3$)$_2$ |
| U19 a or b | H | N(H)C(=O)E$^3$OH | SO$_2$ | 1 | 1 | H |
| U20 a or b | H | N(H)C(=O)E$^3$OH | SO$_2$ | 1 | 1 | N(CH$_3$)$_2$ |

TABLE 23-continued (a)
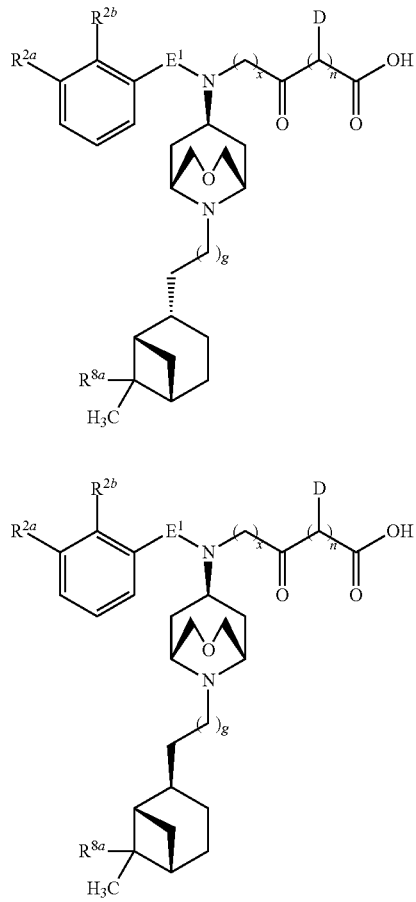

(b)
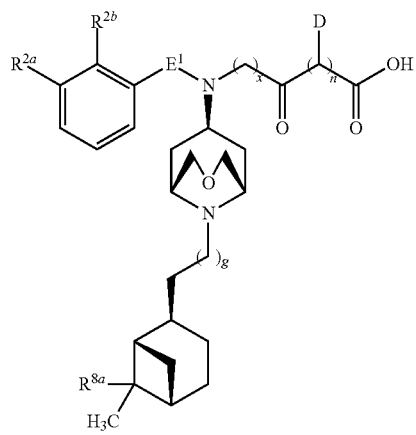

and pharmaceutically acceptable salts and solvates thereof, where:

| Compound | R$^{2a}$ | R$^{2b}$ | E$^1$ | x | n | D |
|---|---|---|---|---|---|---|
| U21 a or b | H | OCH$_2$C(=O)OH | direct bond | 0 | 0 | absent |
| U22 a or b | H | OCH$_2$C(=O)OH | direct bond | 0 | 1 | H |
| U23 a or b | H | OCH$_2$C(=O)OH | direct bond | 0 | 1 | N(CH$_3$)$_2$ |
| U24 a or b | H | OCH$_2$C(=O)OH | direct bond | 1 | 1 | H |
| U25 a or b | H | OCH$_2$C(=O)OH | direct bond | 1 | 1 | N(CH$_3$)$_2$ |
| U26 a or b | H | OCH$_2$C(=O)OH | SO$_2$ | 0 | 0 | absent |
| U27 a or b | H | OCH$_2$C(=O)OH | SO$_2$ | 0 | 1 | H |
| U28 a or b | H | OCH$_2$C(=O)OH | SO$_2$ | 0 | 1 | N(CH$_3$)$_2$ |
| U29 a or b | H | OCH$_2$C(=O)OH | SO$_2$ | 1 | 1 | H |
| U30 a or b | H | OCH$_2$C(=O)OH | SO$_2$ | 1 | 1 | N(CH$_3$)$_2$ |
| U31 a or b | N(H)C(=O)E$^3$OH | H | direct bond | 0 | 0 | absent |
| U32 a or b | N(H)C(=O)E$^3$OH | H | direct bond | 0 | 1 | H |
| U33 a or b | N(H)C(=O)E$^3$OH | H | direct bond | 0 | 1 | N(CH$_3$)$_2$ |
| U34 a or b | N(H)C(=O)E$^3$OH | H | direct bond | 1 | 1 | H |
| U35 a or b | N(H)C(=O)E$^3$OH | H | direct bond | 1 | 1 | N(CH$_3$)$_2$ |
| U36 a or b | N(H)C(=O)E$^3$OH | H | SO$_2$ | 0 | 0 | absent |
| U37 a or b | N(H)C(=O)E$^3$OH | H | SO$_2$ | 0 | 1 | H |
| U38 a or b | N(H)C(=O)E$^3$OH | H | SO$_2$ | 0 | 1 | N(CH$_3$)$_2$ |
| U39 a or b | N(H)C(=O)E$^3$OH | H | SO$_2$ | 1 | 1 | H |
| U40 a or b | N(H)C(=O)E$^3$OH | H | SO$_2$ | 1 | 1 | N(CH$_3$)$_2$ |

TABLE 23-continued (a)
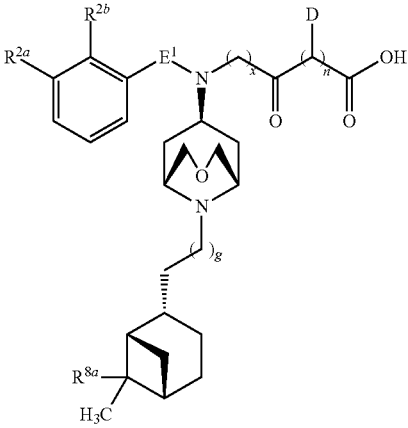

(b)
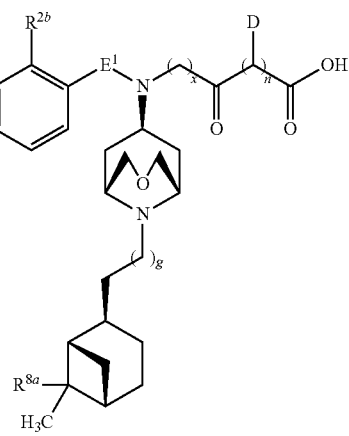

and pharmaceutically acceptable salts and solvates thereof, where:

| Compound | R$^{2a}$ | R$^{2b}$ | E$^1$ | x | n | D |
|---|---|---|---|---|---|---|
| U41 a or b | OCH$_2$C(=O)OH | H | direct bond | 0 | 0 | absent |
| U42 a or b | OCH$_2$C(=O)OH | H | direct bond | 0 | 1 | H |
| U43 a or b | OCH$_2$C(=O)OH | H | direct bond | 0 | 1 | N(CH$_3$)$_2$ |
| U44 a or b | OCH$_2$C(=O)OH | H | direct bond | 1 | 1 | H |
| U45 a or b | OCH$_2$C(=O)OH | H | direct bond | 1 | 1 | N(CH$_3$)$_2$ |
| U46 a or b | OCH$_2$C(=O)OH | H | SO$_2$ | 0 | 0 | absent |
| U47 a or b | OCH$_2$C(=O)OH | H | SO$_2$ | 0 | 1 | H |
| U48 a or b | OCH$_2$C(=O)OH | H | SO$_2$ | 0 | 1 | N(CH$_3$)$_2$ |
| U49 a or b | OCH$_2$C(=O)OH | H | SO$_2$ | 1 | 1 | H |
| U50 a or b | OCH$_2$C(=O)OH | H | SO$_2$ | 1 | 1 | N(CH$_3$)$_2$ |

R$^{8a}$ is (i) H or (ii) CH$_3$; E$^3$ is (iii) a direct bond or (iv) C(=O); g is 0, 1, 2 or 3.

TABLE 24

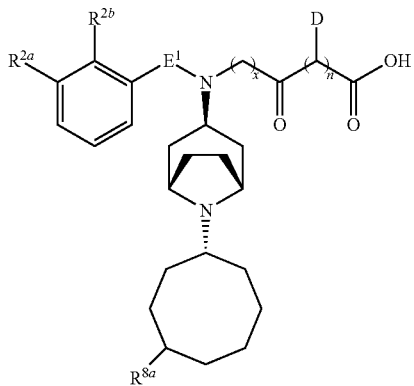
(a)

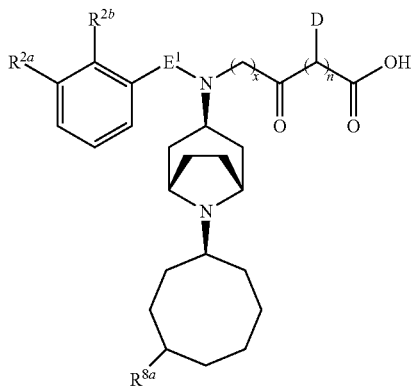
(b)

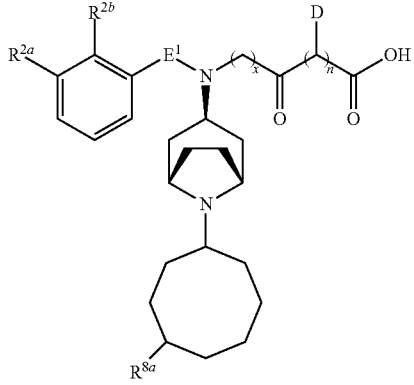
(c)

and pharmaceutically acceptable salts and solvates thereof, where:

| Compound | $R^{2a}$ | $R^{2b}$ | $E^1$ | x | n | D |
|---|---|---|---|---|---|---|
| V1 a, b, or c | H | H | direct bond | 0 | 0 | absent |
| V2 a, b, or c | H | H | direct bond | 0 | 1 | H |
| V3 a, b, or c | H | H | direct bond | 0 | 1 | $N(CH_3)_2$ |
| V4 a, b, or c | H | H | direct bond | 1 | 1 | H |
| V5 a, b, or c | H | H | direct bond | 1 | 1 | $N(CH_3)_2$ |
| V6 a, b, or c | H | H | $SO_2$ | 0 | 0 | absent |
| V7 a, b, or c | H | H | $SO_2$ | 0 | 1 | H |
| V8 a, b, or c | H | H | $SO_2$ | 0 | 1 | $N(CH_3)_2$ |
| V9 a, b, or c | H | H | $SO_2$ | 1 | 1 | H |
| V10 a, b, or c | H | H | $SO_2$ | 1 | 1 | $N(CH_3)_2$ |
| V11 a, b, or c | H | $N(H)C(=O)E^3OH$ | direct bond | 0 | 0 | absent |
| V12 a, b, or c | H | $N(H)C(=O)E^3OH$ | direct bond | 0 | 1 | H |
| V13 a, b, or c | H | $N(H)C(=O)E^3OH$ | direct bond | 0 | 1 | $N(CH_3)_2$ |
| V14 a, b, or c | H | $N(H)C(=O)E^3OH$ | direct bond | 1 | 1 | H |
| V15 a, b, or c | H | $N(H)C(=O)E^3OH$ | direct bond | 1 | 1 | $N(CH_3)_2$ |
| V16 a, b, or c | H | $N(H)C(=O)COH$ | $SO_2$ | 0 | 0 | absent |

TABLE 24-continued

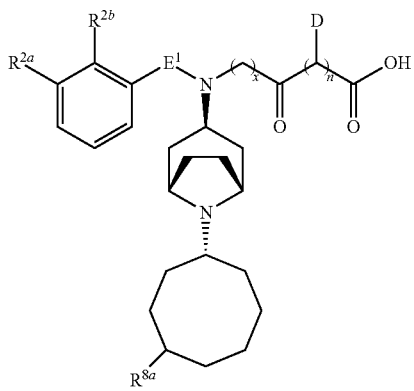

(a)

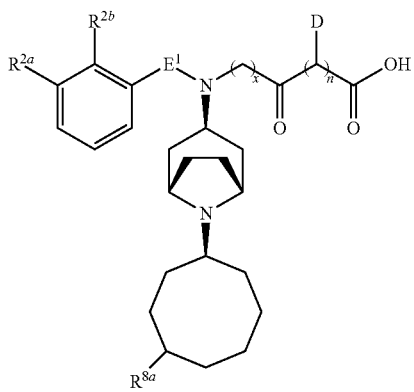

(b)

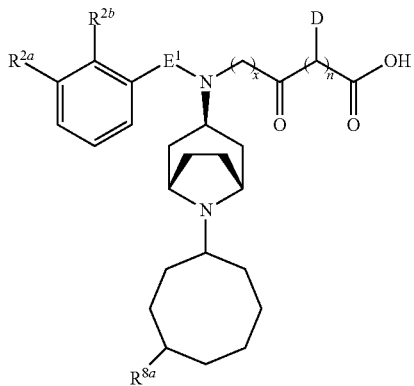

(c)

and pharmaceutically acceptable salts and solvates thereof, where:

| Compound | $R^{2a}$ | $R^{2b}$ | $E^1$ | x | n | D |
|---|---|---|---|---|---|---|
| V17 a, b, or c | H | N(H)C(=O)E$^3$OH | SO$_2$ | 0 | 1 | H |
| V18 a, b, or c | H | N(H)C(=O)E$^3$OH | SO$_2$ | 0 | 1 | N(CH$_3$)$_2$ |
| V19 a, b, or c | H | N(H)C(=O)E$^3$OH | SO$_2$ | 1 | 1 | H |
| V20 a, b, or c | H | N(H)C(=O)E$^3$OH | SO$_2$ | 1 | 1 | N(CH$_3$)$_2$ |
| V21 a, b, or c | H | OCH$_2$C(=O)OH | direct bond | 0 | 0 | absent |
| V22 a, b, or c | H | OCH$_2$C(=O)OH | direct bond | 0 | 1 | H |
| V23 a, b, or c | H | OCH$_2$C(=O)OH | direct bond | 0 | 1 | N(CH$_3$)$_2$ |
| V24 a, b, or c | H | OCH$_2$C(=O)OH | direct bond | 1 | 1 | H |
| V25 a, b, or c | H | OCH$_2$C(=O)OH | direct bond | 1 | 1 | N(CH$_3$)$_2$ |
| V26 a, b, or c | H | OCH$_2$C(=O)OH | SO$_2$ | 0 | 0 | absent |
| V27 a, b, or c, | H | OCH$_2$C(=O)OH | SO$_2$ | 0 | 1 | H |
| V28 a, b, or c | H | OCH$_2$C(=O)OH | SO$_2$ | 0 | 1 | N(CH$_3$)$_2$ |
| V29 a, b, or c | H | OCH$_2$C(=O)OH | SO$_2$ | 1 | 1 | H |
| V30 a, b, or c | H | OCH$_2$C(=O)OH | SO$_2$ | 1 | 1 | N(CH$_3$)$_2$ |
| V31 a, b, or c | N(H)C(=O)E$^3$OH | H | direct bond | 0 | 0 | absent |
| V32 a, b, or c | N(H)C(=O)E$^3$OH | H | direct bond | 0 | 1 | H |

TABLE 24-continued

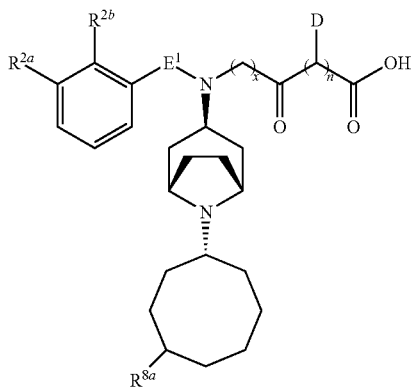

(a)

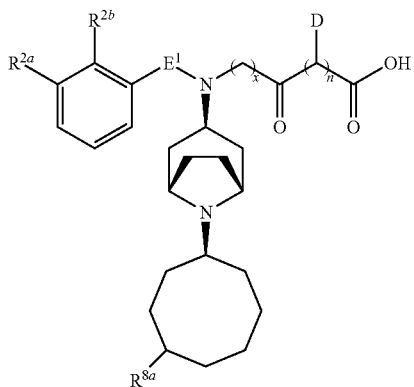

(b)

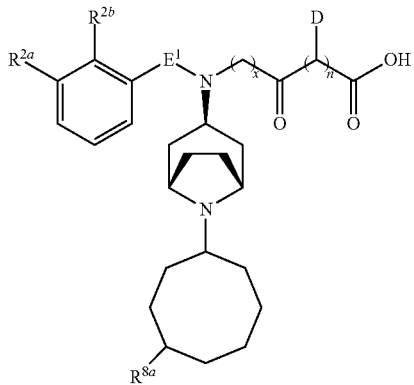

(c)

and pharmaceutically acceptable salts and solvates thereof, where:

| Compound | $R^{2a}$ | $R^{2b}$ | $E^1$ | x | n | D |
|---|---|---|---|---|---|---|
| V33 a, b, or c | N(H)C(=O)E$^3$OH | H | direct bond | 0 | 1 | N(CH$_3$)$_2$ |
| V34 a, b, or c | N(H)C(=O)E$^3$OH | H | direct bond | 1 | 1 | H |
| V35 a, b, or c | N(H)C(=O)E$^3$OH | H | direct bond | 1 | 1 | N(CH$_3$)$_2$ |
| V36 a, b, or c | N(H)C(=O)E$^3$OH | H | SO$_2$ | 0 | 0 | absent |
| V37 a, b, or c | N(H)C(=O)E$_3$OH | H | SO$_2$ | 0 | 1 | H |
| V38 a, b, or c | N(H)C(=O)E$^3$OH | H | SO$_2$ | 0 | 1 | N(CH$_3$)$_2$ |
| V39 a, b, or c | N(H)C(=O)E$^3$OH | H | SO$_2$ | 1 | 1 | H |
| V40 a, b, or c | N(H)C(=O)E$^3$OH | H | SO$_2$ | 1 | 1 | N(CH$_3$)$_2$ |
| V41 a, b, or c | OCH$_2$C(=O)OH | H | direct bond | 0 | 0 | absent |
| V42 a, b, or c | OCH$_2$C(=O)OH | H | direct bond | 0 | 1 | H |
| V43 a, b, or c | OCH$_2$C(=O)OH | H | direct bond | 0 | 1 | N(CH$_3$)$_2$ |
| V44 a, b, or c | OCH$_2$C(=O)OH | H | direct bond | 1 | 1 | H |

TABLE 24-continued (a)
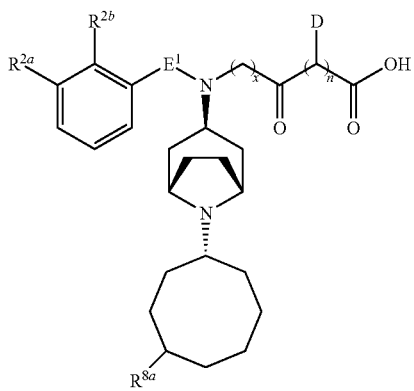

(b)
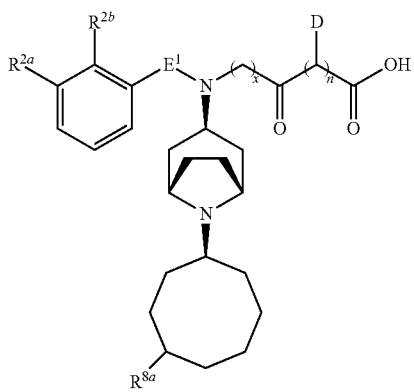

(c)
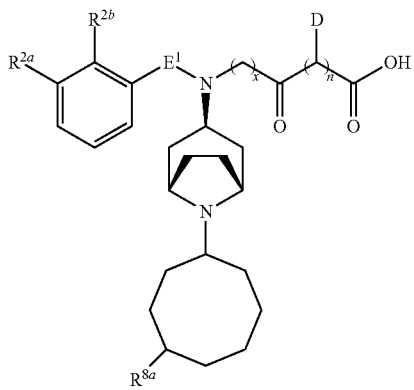

and pharmaceutically acceptable salts and solvates thereof, where:

| Compound | $R^{2a}$ | $R^{2b}$ | $E^1$ | x | n | D |
|---|---|---|---|---|---|---|
| V45 a, b, or c | OCH$_2$C(=O)OH | H | direct bond | 1 | 1 | N(CH$_3$)$_2$ |
| V46 a, b, or c | OCH$_2$C(=O)OH | H | SO$_2$ | 0 | 0 | absent |
| V47 a, b, or c | OCH$_2$C(=O)OH | H | SO$_2$ | 0 | 1 | H |
| V48 a, b, or c | OCH$_2$C(=O)OH | H | SO$_2$ | 0 | 1 | N(CH$_3$)$_2$ |
| V49 a, b, or c | OCH$_2$C(=O)OH | H | SO$_2$ | 1 | 1 | H |
| V50 a, b, or c | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 25

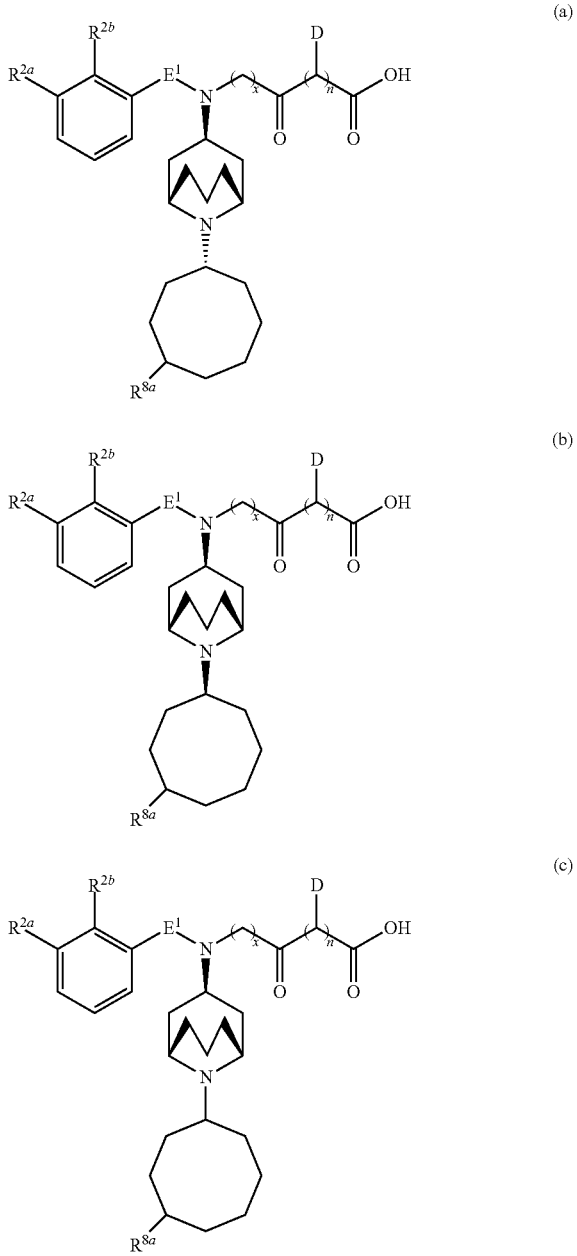

and pharmaceutically acceptable salts and solvates thereof, where:

| Compound | $R^{2a}$ | $R^{2b}$ | $E^1$ | x | n | D |
|---|---|---|---|---|---|---|
| W1 a, b, or c | H | H | direct bond | 0 | 0 | absent |
| W2 a, b, or c | H | H | direct bond | 0 | 1 | H |
| W3 a, b, or c | H | H | direct bond | 0 | 1 | $N(CH_3)_2$ |
| W4 a, b, or c | H | H | direct bond | 1 | 1 | H |
| W5 a, b, or c | H | H | direct bond | 1 | 1 | $N(CH_3)_2$ |
| W6 a, b, or c | H | H | $SO_2$ | 0 | 0 | absent |
| W7 a, b, or c | H | H | $SO_2$ | 0 | 1 | H |
| W8 a, b, or c | H | H | $SO_2$ | 0 | 1 | $N(CH_3)_2$ |
| W9 a, b, or c | H | H | $SO_2$ | 1 | 1 | H |
| W10 a, b, or c | H | H | $SO_2$ | 1 | 1 | $N(CH_3)_2$ |
| W11 a, b, or c | H | $N(H)C(=O)E^3OH$ | direct bond | 0 | 0 | absent |
| W12 a, b, or c | H | $N(H)C(=O)E^3OH$ | direct bond | 0 | 1 | H |
| W13 a, b, or c | H | $N(H)C(=O)E^3OH$ | direct bond | 0 | 1 | $N(CH_3)_2$ |
| W14 a, b, or c | H | $N(H)C(=O)E^3OH$ | direct bond | 1 | 1 | H |
| W15 a, b, or c | H | $N(H)C(=O)E^3OH$ | direct bond | 1 | 1 | $N(CH_3)_2$ |
| W16 a, b, or c | H | $N(H)C(=O)E^3OH$ | $SO_2$ | 0 | 0 | absent |

TABLE 25-continued

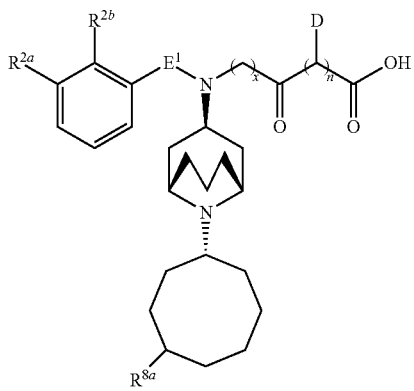

(a)

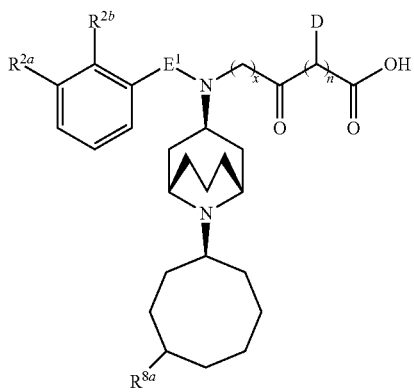

(b)

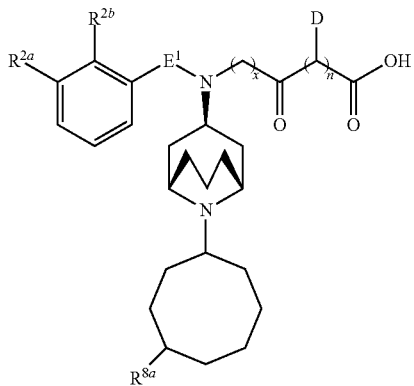

(c)

and pharmaceutically acceptable salts and solvates thereof, where:

| Compound | $R^{2a}$ | $R^{2b}$ | $E^1$ | x | n | D |
|---|---|---|---|---|---|---|
| W17 a, b, or c | H | N(H)C(=O)$E^3$OH | $SO_2$ | 0 | 1 | H |
| W18 a, b, or c | H | N(H)C(=O)$E^3$OH | $SO_2$ | 0 | 1 | $N(CH_3)_2$ |
| W19 a, b, or c | H | N(H)C(=O)$E^3$OH | $SO_2$ | 1 | 1 | H |
| W20 a, b, or c | H | N(H)C(=O)$E^3$OH | $SO_2$ | 1 | 1 | $N(CH_3)_2$ |
| W21 a, b, or c | H | $OCH_2$C(=O)OH | direct bond | 0 | 0 | absent |
| W22 a, b, or c | H | $OCH_2$C(=O)OH | direct bond | 0 | 1 | H |
| W23 a, b, or c | H | $OCH_2$C(=O)OH | direct bond | 0 | 1 | $N(CH_3)_2$ |
| W24 a, b, or c | H | $OCH_2$C(=O)OH | direct bond | 1 | 1 | H |
| W25 a, b, or c | H | $OCH_2$C(=O)OH | direct bond | 1 | 1 | $N(CH_3)_2$ |
| W26 a, b, or c | H | $OCH_2$C(=O)OH | $SO_2$ | 0 | 0 | absent |
| W27 a, b, or c | H | $OCH_2$C(=O)OH | $SO_2$ | 0 | 1 | H |
| W28 a, b, or c | H | $OCH_2$C(=O)OH | $SO_2$ | 0 | 1 | $N(CH_3)_2$ |
| W29 a, b, or c | H | $OCH_2$C(=O)OH | $SO_2$ | 1 | 1 | H |
| W30 a, b, or c | H | $OCH_2$C(=O)OH | $SO_2$ | 1 | 1 | $N(CH_3)_2$ |
| W31 a, b, or c | N(H)C(=O)$E^3$OH | H | direct bond | 0 | 0 | absent |
| W32 a, b, or c | N(H)C(=O)$E^3$OH | H | direct bond | 0 | 1 | H |

TABLE 25-continued (a)
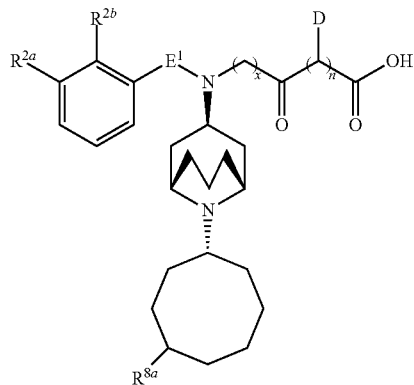

(b)
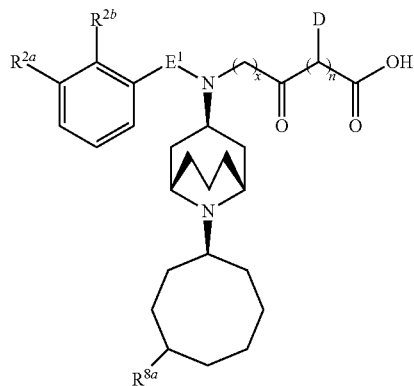

(c)
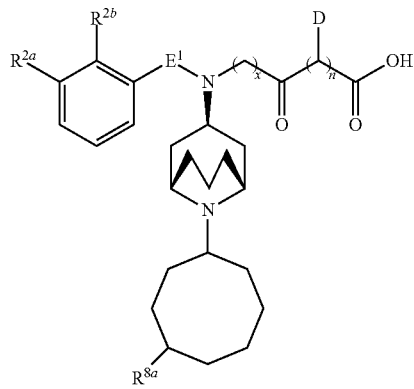

and pharmaceutically acceptable salts and solvates thereof, where:

| Compound | $R^{2a}$ | $R^{2b}$ | $E^1$ | x | n | D |
|---|---|---|---|---|---|---|
| W33 a, b, or c | $N(H)C(=O)E^3OH$ | H | direct bond | 0 | 1 | $N(CH_3)_2$ |
| W34 a, b, or c | $N(H)C(=O)E^3OH$ | H | direct bond | 1 | 1 | H |
| W35 a, b, or c | $N(H)C(=O)E^3OH$ | H | direct bond | 1 | 1 | $N(CH_3)_2$ |
| W36 a, b, or c | $N(H)C(=O)E^3OH$ | H | $SO_2$ | 0 | 0 | absent |
| W37 a, b, or c | $N(H)C(=O)E^3OH$ | H | $SO_2$ | 0 | 1 | H |
| W38 a, b, or c | $N(H)C(=O)E^3OH$ | H | $SO_2$ | 0 | 1 | $N(CH_3)_2$ |
| W39 a, b, or c | $N(H)C(=O)E^3OH$ | H | $SO_2$ | 1 | 1 | H |
| W40 a, b, or c | $N(H)C(=O)E^3OH$ | H | $SO_2$ | 1 | 1 | $N(CH_3)_2$ |
| W41 a, b, or c | $OCH_2C(=O)OH$ | H | direct bond | 0 | 0 | absent |
| W42 a, b, or c | $OCH_2C(=O)OH$ | H | direct bond | 0 | 1 | H |
| W43 a, b, or c | $OCH_2C(=O)OH$ | H | direct bond | 0 | 1 | $N(CH_3)_2$ |

TABLE 25-continued (a)
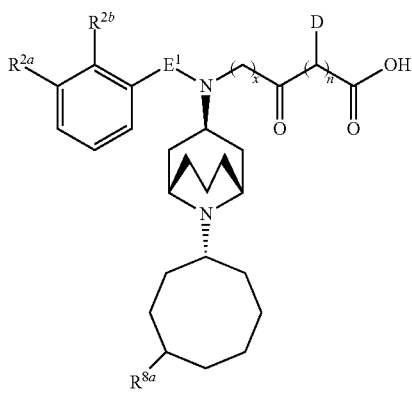

(b)
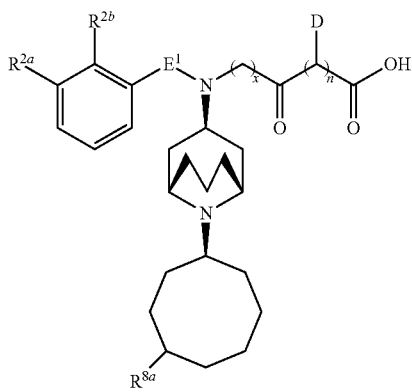

(c)
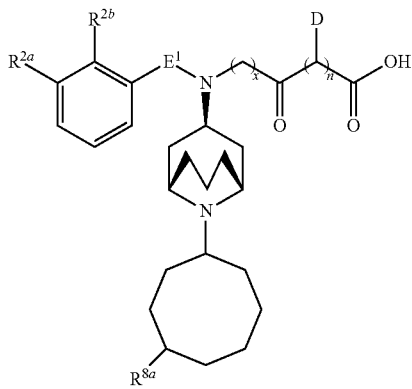

and pharmaceutically acceptable salts and solvates thereof, where:

| Compound | $R^{2a}$ | $R^{2b}$ | $E^1$ | x | n | D |
|---|---|---|---|---|---|---|
| W44 a, b, or c | OCH$_2$C(=O)OH | H | direct bond | 1 | 1 | H |
| W45 a, b, or c | OCH$_2$C(=O)OH | H | direct bond | 1 | 1 | N(CH$_3$)$_2$ |
| W46 a, b, or c | OCH$_2$C(=O)OH | H | SO$_2$ | 0 | 0 | absent |
| W47 a, b, or c | OCH$_2$C(=O)OH | H | SO$_2$ | 0 | 1 | H |
| W48 a, b, or c | OCH$_2$C(=O)OH | H | SO$_2$ | 0 | 1 | N(CH$_3$)$_2$ |
| W49 a, b, or c | OCH$_2$C(=O)OH | H | SO$_2$ | 1 | 1 | H |
| W50 a, b, or c | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 26

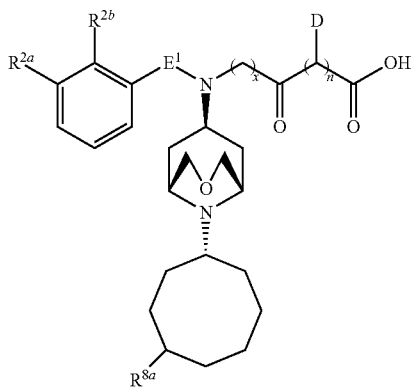

(a)

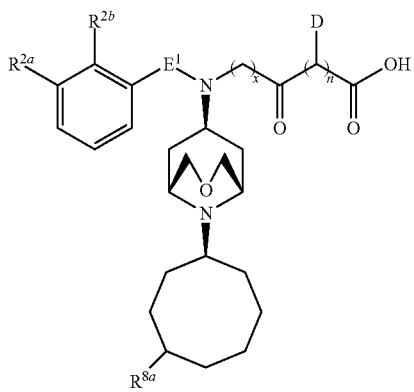

(b)

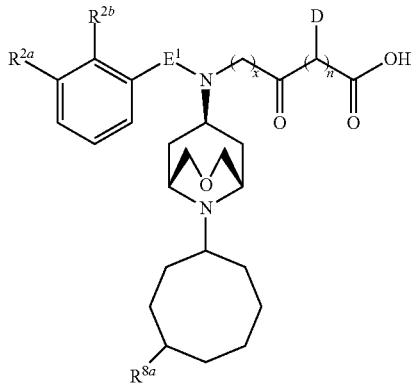

(c)

and pharmaceutically acceptable salts and solvates thereof, where:

| Compound | $R^{2a}$ | $R^{2b}$ | $E^1$ | x | n | D |
|---|---|---|---|---|---|---|
| X1 a, b, or c | H | H | direct bond | 0 | 0 | absent |
| X2 a, b, or c | H | H | direct bond | 0 | 1 | H |
| X3 a, b, or c | H | H | direct bond | 0 | 1 | $N(CH_3)_2$ |
| X4 a, b, or c | H | H | direct bond | 1 | 1 | H |
| X5 a, b, or c | H | H | direct bond | 1 | 1 | $N(CH_3)_2$ |
| X6 a, b, or c | H | H | $SO_2$ | 0 | 0 | absent |
| X7 a, b, or c | H | H | $SO_2$ | 0 | 1 | H |
| X8 a, b, or c | H | H | $SO_2$ | 0 | 1 | $N(CH_3)_2$ |
| X9 a, b, or c | H | H | $SO_2$ | 1 | 1 | H |
| X10 a, b, or c | H | H | $SO_2$ | 1 | 1 | $N(CH_3)_2$ |
| X11 a, b, or c | H | $N(H)C(=O)E^3OH$ | direct bond | 0 | 0 | absent |
| X12 a, b, or c | H | $N(H)C(=O)E^3OH$ | direct bond | 0 | 1 | H |
| X13 a, b, or c | H | $N(H)C(=O)E^3OH$ | direct bond | 0 | 1 | $N(CH_3)_2$ |
| X14 a, b, or c | H | $N(H)C(=O)E^3OH$ | direct bond | 1 | 1 | H |
| X15 a, b, or c | H | $N(H)C(=O)E^3OH$ | direct bond | 1 | 1 | $N(CH_3)_2$ |
| X16 a, b, or c | H | $N(H)C(=O)E^3OH$ | $SO_2$ | 0 | 0 | absent |

TABLE 26-continued

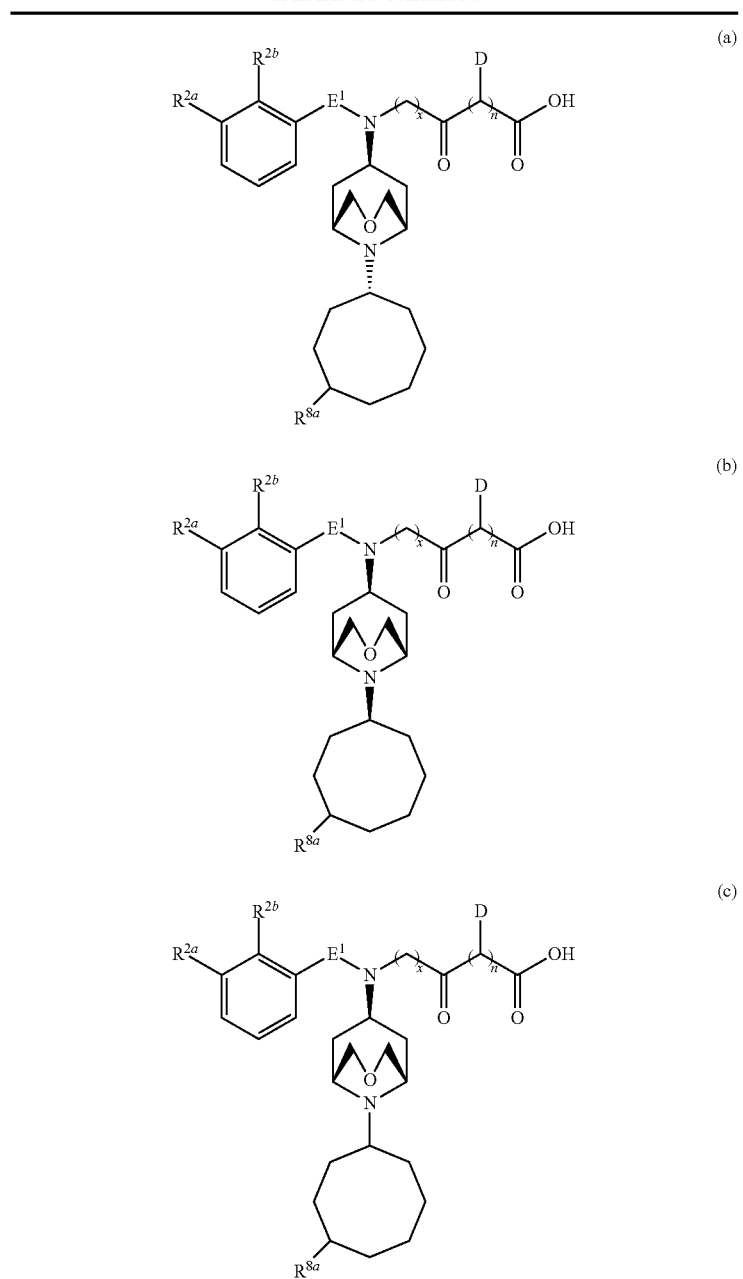

and pharmaceutically acceptable salts and solvates thereof, where:

| Compound | $R^{2a}$ | $R^{2b}$ | $E^1$ | x | n | D |
|---|---|---|---|---|---|---|
| X17 a, b, or c | H | N(H)C(=O)E$^3$OH | SO$_2$ | 0 | 1 | H |
| X18 a, b, or c | H | N(H)C(=O)E$^3$OH | SO$_2$ | 0 | 1 | N(CH$_3$)$_2$ |
| X19 a, b, or c | H | N(H)C(=O)E$^3$OH | SO$_2$ | 1 | 1 | H |
| X20 a, b, or c | H | N(H)C(=O)E$^3$OH | SO$_2$ | 1 | 1 | N(CH$_3$)$_2$ |
| X21 a, b, or c | H | OCH$_2$C(=O)OH | direct bond | 0 | 0 | absent |
| X22 a, b, or c | H | OCH$_2$C(=O)OH | direct bond | 0 | 1 | H |
| X23 a, b, or c | H | OCH$_2$C(=O)OH | direct bond | 0 | 1 | N(CH$_3$)$_2$ |
| X24 a, b, or c | H | OCH$_2$C(=O)OH | direct bond | 1 | 1 | H |
| X25 a, b, or c | H | OCH$_2$C(=O)OH | direct bond | 1 | 1 | N(CH$_3$)$_2$ |
| X26 a, b, or c | H | OCH$_2$C(=O)OH | SO$_2$ | 0 | 0 | absent |
| X27 a, b, or c | H | OCH$_2$C(=O)OH | SO$_2$ | 0 | 1 | H |
| X28 a, b, or c | H | OCH$_2$C(=O)OH | SO$_2$ | 0 | 1 | N(CH$_3$)$_2$ |
| X29 a, b, or c | H | OCH$_2$C(=O)OH | SO$_2$ | 1 | 1 | H |
| X30 a, b, or c | H | OCH$_2$C(=O)OH | SO$_2$ | 1 | 1 | N(CH$_3$)$_2$ |
| X31 a, b, or c | N(H)C(=O)E$^3$OH | H | direct bond | 0 | 0 | absent |
| X32 a, b, or c | N(H)C(=O)E$^3$OH | H | direct bond | 0 | 1 | H |

TABLE 26-continued

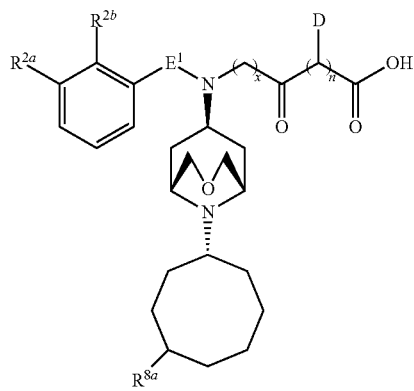

(a)

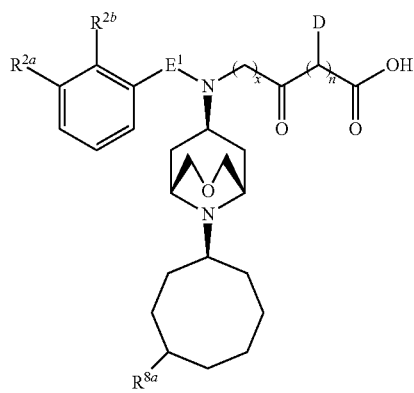

(b)

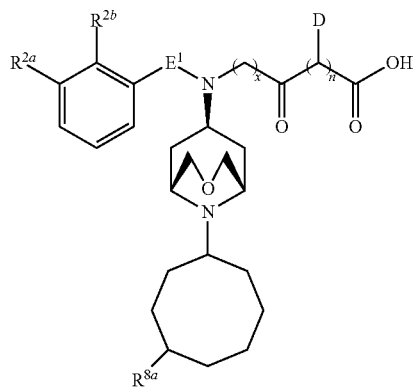

(c)

and pharmaceutically acceptable salts and solvates thereof, where:

| Compound | $R^{2a}$ | $R^{2b}$ | $E^1$ | x | n | D |
|---|---|---|---|---|---|---|
| X33 a, b, or c | N(H)C(=O)E$^3$OH | H | direct bond | 0 | 1 | N(CH$_3$)$_2$ |
| X34 a, b, or c | N(H)C(=O)E$^3$OH | H | direct bond | 1 | 1 | H |
| X35 a, b, or c | N(H)C(=O)E$^3$OH | H | direct bond | 1 | 1 | N(CH$_3$)$_2$ |
| X36 a, b, or c | N(H)C(=O)E$^3$OH | H | SO$_2$ | 0 | 0 | absent |
| X37 a, b, or c | N(H)C(=O)E$^3$OH | H | SO$_2$ | 0 | 1 | H |
| X38 a, b, or c | N(H)C(=O)E$^3$OH | H | SO$_2$ | 0 | 1 | N(CH$_3$)$_2$ |
| X39 a, b, or c | N(H)C(=O)E$^3$OH | H | SO$_2$ | 1 | 1 | H |
| X40 a, b, or c | N(H)C(=O)E$^3$OH | H | SO$_2$ | 1 | 1 | N(CH$_3$)$_2$ |
| X41 a, b, or c | OCH$_2$C(=O)OH | H | direct bond | 0 | 0 | absent |
| X42 a, b, or c | OCH$_2$C(=O)OH | H | direct bond | 0 | 1 | H |
| X43 a, b, or c | OCH$_2$C(=O)OH | H | direct bond | 0 | 1 | N(CH$_3$)$_2$ |

TABLE 26-continued (a)
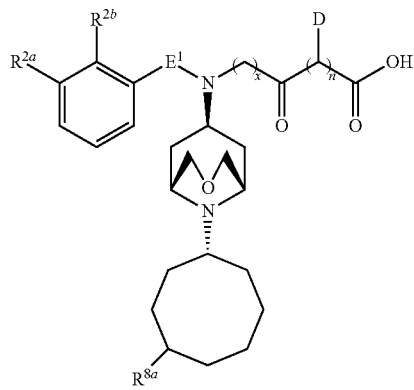

(b)
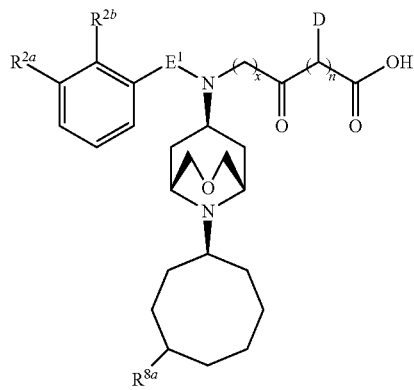

(c)
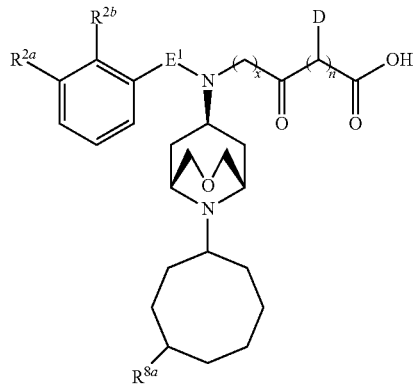

and pharmaceutically acceptable salts and solvates thereof, where:

| Compound | $R^{2a}$ | $R^{2b}$ | $E^1$ | x | n | D |
|---|---|---|---|---|---|---|
| X44 a, b, or c | $OCH_2C(=O)OH$ | H | direct bond | 1 | 1 | H |
| X45 a, b, or c | $OCH_2C(=O)OH$ | H | direct bond | 1 | 1 | $N(CH_3)_2$ |
| X46 a, b, or c | $OCH_2C(=O)OH$ | H | $SO_2$ | 0 | 0 | absent |
| X47 a, b, or c | $OCH_2C(=O)OH$ | H | $SO_2$ | 0 | 1 | H |
| X48 a, b, or c | $OCH_2C(=O)OH$ | H | $SO_2$ | 0 | 1 | $N(CH_3)_2$ |
| X49 a, b, or c | $OCH_2C(=O)OH$ | H | $SO_2$ | 1 | 1 | H |
| X50 a, b, or c | $OCH_2C(=O)OH$ | H | $SO_2$ | 1 | 1 | $N(CH_3)_2$ |

$R^{8a}$ is (i) H or (ii) $CH_3$; $E^3$ is (iii) a direct bond or (iv) $C(=O)$.

TABLE 27

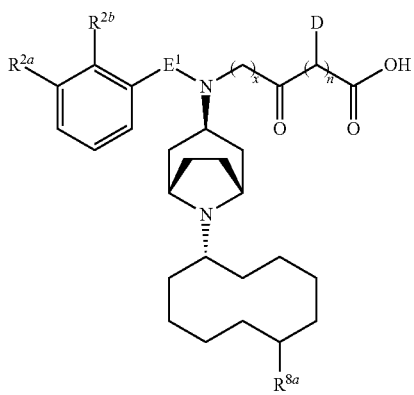

(a)

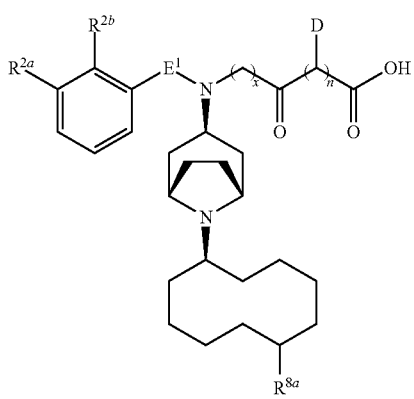

(b)

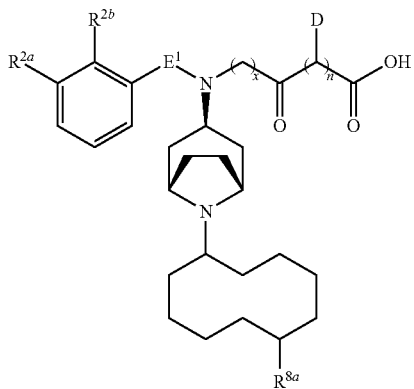

(c)

and pharmaceutically acceptable salts and solvates thereof, where:

| Compound | $R^{2a}$ | $R^{2b}$ | $E^1$ | x | n | D |
|---|---|---|---|---|---|---|
| Y1 a, b, or c | H | H | direct bond | 0 | 0 | absent |
| Y2 a, b, or c | H | H | direct bond | 0 | 1 | H |
| Y3 a, b, or c | H | H | direct bond | 0 | 1 | $N(CH_3)_2$ |
| Y4 a, b, or c | H | H | direct bond | 1 | 1 | H |
| Y5 a, b, or c | H | H | direct bond | 1 | 1 | $N(CH_3)_2$ |
| Y6 a, b, or c | H | H | $SO_2$ | 0 | 0 | absent |
| Y7 a, b, or c | H | H | $SO_2$ | 0 | 1 | H |
| Y8 a, b, or c | H | H | $SO_2$ | 0 | 1 | $N(CH_3)_2$ |
| Y9 a, b, or c | H | H | $SO_2$ | 1 | 1 | H |
| Y10 a, b, or c | H | H | $SO_2$ | 1 | 1 | $N(CH_3)_2$ |
| Y11 a, b, or c | H | $N(H)C(=O)E^3OH$ | direct bond | 0 | 0 | absent |
| Y12 a, b, or c | H | $N(H)C(=O)E^3OH$ | direct bond | 0 | 1 | H |
| Y13 a, b, or c | H | $N(H)C(=O)E^3OH$ | direct bond | 0 | 1 | $N(CH_3)_2$ |
| Y14 a, b, or c | H | $N(H)C(=O)E^3OH$ | direct bond | 1 | 1 | H |
| Y15 a, b, or c | H | $N(H)C(=O)E^3OH$ | direct bond | 1 | 1 | $N(CH_3)_2$ |

TABLE 27-continued

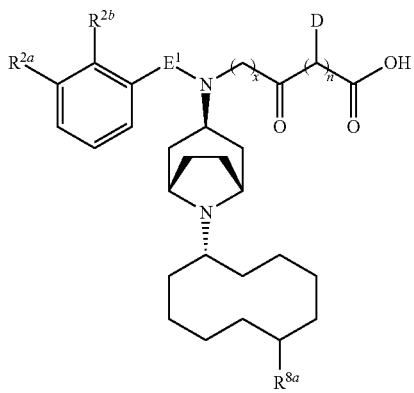

(a)

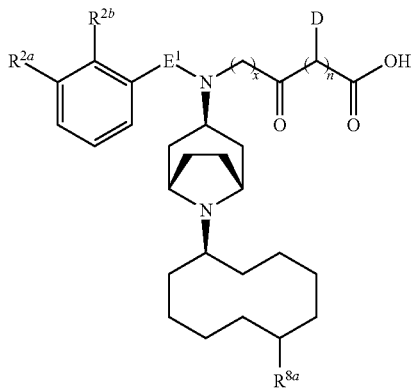

(b)

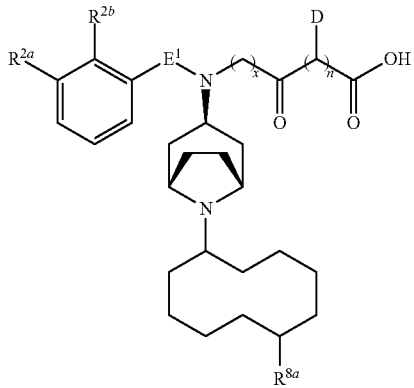

(c)

and pharmaceutically acceptable salts and solvates thereof, where:

| Compound | $R^{2a}$ | $R^{2b}$ | $E^1$ | x | n | D |
|---|---|---|---|---|---|---|
| Y16 a, b, or c | H | N(H)C(=O)E³OH | SO₂ | 0 | 0 | absent |
| Y17 a, b, or c | H | N(H)C(=O)E³OH | SO₂ | 0 | 1 | H |
| Y18 a, b, or c | H | N(H)C(=O)E³OH | SO₂ | 0 | 1 | N(CH₃)₂ |
| Y19 a, b, or c | H | N(H)C(=O)E³OH | SO₂ | 1 | 1 | H |
| Y20 a, b, or c | H | N(H)C(=O)E³OH | SO₂ | 1 | 1 | N(CH₃)₂ |
| Y21 a, b, or c | H | OCH₂C(=O)OH | direct bond | 0 | 0 | absent |
| Y22 a, b, or c | H | OCH₂C(=O)OH | direct bond | 0 | 1 | H |
| Y23 a, b, or c | H | OCH₂C(=O)OH | direct bond | 0 | 1 | N(CH₃)₂ |
| Y24 a, b, or c | H | OCH₂C(=O)OH | direct bond | 1 | 1 | H |
| Y25 a, b, or c | H | OCH₂C(=O)OH | direct bond | 1 | 1 | N(CH₃)₂ |
| Y26 a, b, or c | H | OCH₂C(=O)OH | SO₂ | 0 | 0 | absent |
| Y27 a, b, or c | H | OCH₂C(=O)OH | SO₂ | 0 | 1 | H |
| Y28 a, b, or c | H | OCH₂C(=O)OH | SO₂ | 0 | 1 | N(CH₃)₂ |
| Y29 a, b, or c | H | OCH₂C(=O)OH | SO₂ | 1 | 1 | H |
| Y30 a, b, or c | H | OCH₂C(=O)OH | SO₂ | 1 | 1 | N(CH₃)₂ |

TABLE 27-continued

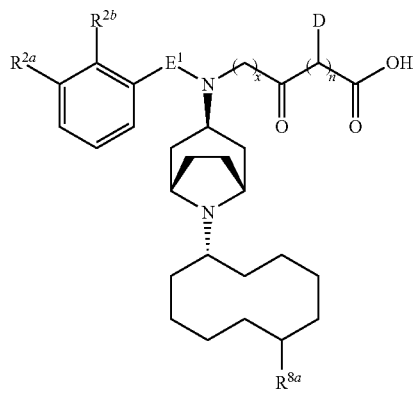

(a)

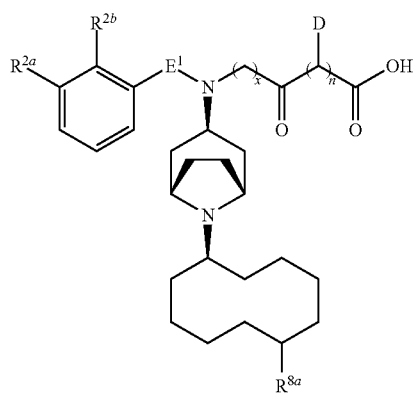

(b)

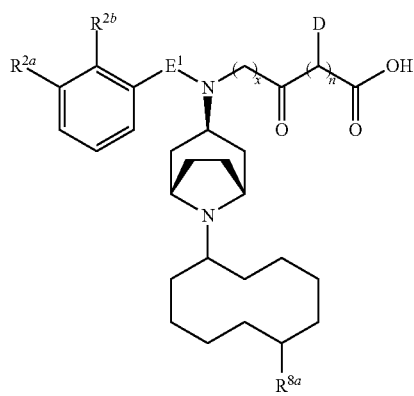

(c)

and pharmaceutically acceptable salts and solvates thereof, where:

| Compound | $R^{2a}$ | $R^{2b}$ | $E^1$ | x | n | D |
|---|---|---|---|---|---|---|
| Y31 a, b, or c | $N(H)C(=O)E^3OH$ | H | direct bond | 0 | 0 | absent |
| Y32 a, b, or c | $N(H)C(=O)E^3OH$ | H | direct bond | 0 | 1 | H |
| Y33 a, b, or c | $N(H)C(=O)E^3OH$ | H | direct bond | 0 | 1 | $N(CH_3)_2$ |
| Y34 a, b, or c | $N(H)C(=O)E^3OH$ | H | direct bond | 1 | 1 | H |
| Y35 a, b, or c | $N(H)C(=O)E^3OH$ | H | direct bond | 1 | 1 | $N(CH_3)_2$ |
| Y36 a, b, or c | $N(H)C(=O)E^3OH$ | H | $SO_2$ | 0 | 0 | absent |
| Y37 a, b, or c | $N(H)C(=O)E^3OH$ | H | $SO_2$ | 0 | 1 | H |
| Y38 a, b, or c | $N(H)C(=O)E^3OH$ | H | $SO_2$ | 0 | 1 | $N(CH_3)_2$ |
| Y39 a, b, or c | $N(H)C(=O)E^3OH$ | H | $SO_2$ | 1 | 1 | H |
| Y40 a, b, or c | $N(H)C(=O)E^3OH$ | H | $SO_2$ | 1 | 1 | $N(CH_3)_2$ |
| Y41 a, b, or c | $OCH_2C(=O)OH$ | H | direct bond | 0 | 0 | absent |
| Y42 a, b, or c | $OCH_2C(=O)OH$ | H | direct bond | 0 | 1 | H |
| Y43 a, b, or c | $OCH_2C(=O)OH$ | H | direct bond | 0 | 1 | $N(CH_3)_2$ |
| Y44 a, b, or c | $OCH_2C(=O)OH$ | H | direct bond | 1 | 1 | H |
| Y45 a, b, or c | $OCH_2C(=O)OH$ | H | direct bond | 1 | 1 | $N(CH_3)2$ |

TABLE 27-continued
(a)
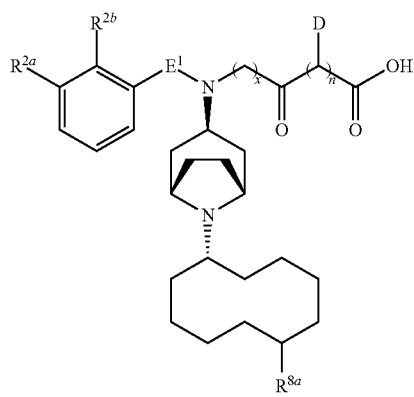
(b)
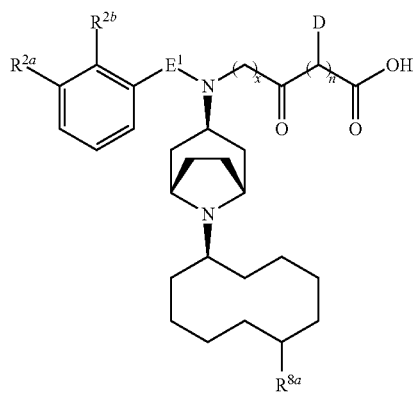
(c)
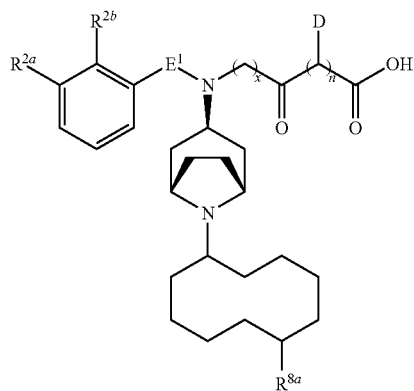
and pharmaceutically acceptable salts and solvates thereof, where:
| Compound | $R^{2a}$ | $R^{2b}$ | $E^1$ | x | n | D |
|---|---|---|---|---|---|---|
| Y46 a, b, or c | $OCH_2C(=O)OH$ | H | $SO_2$ | 0 | 0 | absent |
| Y47 a, b, or c | $OCH_2C(=O)OH$ | H | $SO_2$ | 0 | 1 | H |
| Y48 a, b, or c | $OCH_2C(=O)OH$ | H | $SO_2$ | 0 | 1 | $N(CH_3)_2$ |
| Y49 a, b, or c | $OCH_2C(=O)OH$ | H | $SO_2$ | 1 | 1 | H |
| Y50 a, b, or c | $OCH_2C(=O)OH$ | H | $SO_2$ | 1 | 1 | $N(CH_3)_2$ |
$R^{8a}$ is (i) H or (ii) $CH_3$; $E^3$ is (iii) a direct bond or (iv) $C(=O)$.

TABLE 28

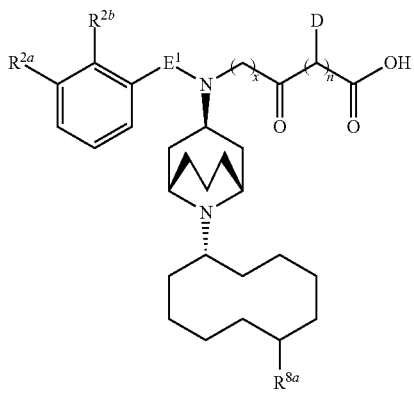

(a)

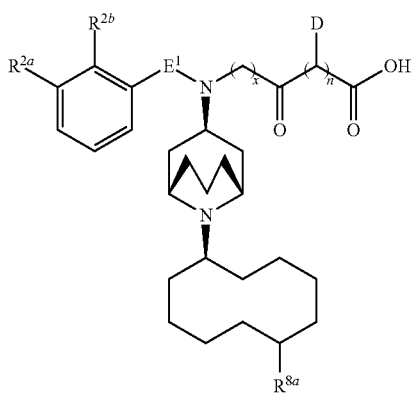

(b)

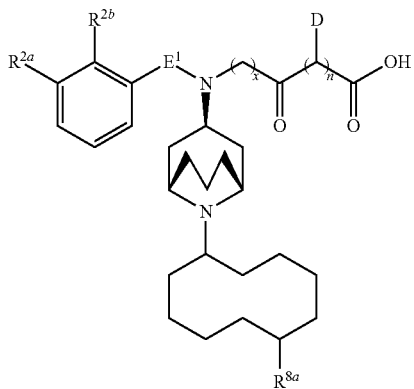

(c)

and pharmaceutically acceptable salts and solvates thereof, where:

| Compound | $R^{2a}$ | $R^{2b}$ | $E^1$ | x | n | D |
|---|---|---|---|---|---|---|
| Z1 a, b, or c | H | H | direct bond | 0 | 0 | absent |
| Z2 a, b, or c | H | H | direct bond | 0 | 1 | H |
| Z3 a, b, or c | H | H | direct bond | 0 | 1 | $N(CH_3)_2$ |
| Z4 a, b, or c | H | H | direct bond | 1 | 1 | H |
| Z5 a, b, or c | H | H | direct bond | 1 | 1 | $N(CH_3)_2$ |
| Z6 a, b, or c | H | H | $SO_2$ | 0 | 0 | absent |
| Z7 a, b, or c | H | H | $SO_2$ | 0 | 1 | H |
| Z8 a, b, or c | H | H | $SO_2$ | 0 | 1 | $N(CH_3)_2$ |
| Z9 a, b, or c | H | H | $SO_2$ | 1 | 1 | H |
| Z10 a, b, or c | H | H | $SO_2$ | 1 | 1 | $N(CH_3)_2$ |
| Z11 a, b, or c | H | $N(H)C(=O)E^3OH$ | direct bond | 0 | 0 | absent |
| Z12 a, b, or c | H | $N(H)C(=O)E^3OH$ | direct bond | 0 | 1 | H |
| Z13 a, b, or c | H | $N(H)C(=O)E^3OH$ | direct bond | 0 | 1 | $N(CH_3)_2$ |
| Z14 a, b, or c | H | $N(H)C(=O)E^3OH$ | direct bond | 1 | 1 | H |
| Z15 a, b, or c | H | $N(H)C(=O)E^3OH$ | direct bond | 1 | 1 | $N(CH_3)_2$ |

TABLE 28-continued

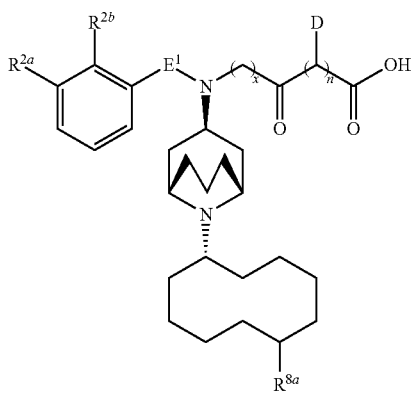

(a)

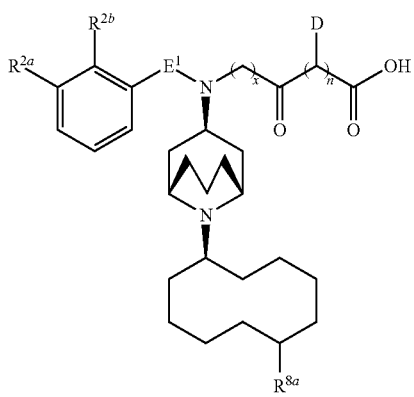

(b)

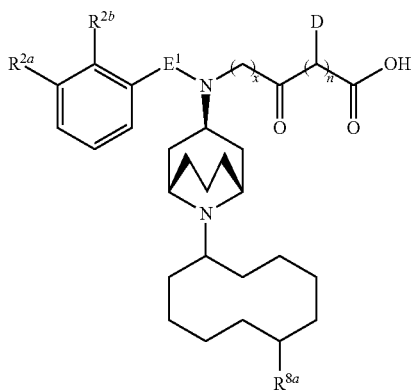

(c)

and pharmaceutically acceptable salts and solvates thereof, where:

| Compound | $R^{2a}$ | $R^{2b}$ | $E^1$ | x | n | D |
|---|---|---|---|---|---|---|
| Z16 a, b, or c | H | N(H)C(=O)$E^3$OH | $SO_2$ | 0 | 0 | absent |
| Z17 a, b, or c | H | N(H)C(=O)$E^3$OH | $SO_2$ | 0 | 1 | H |
| Z18 a, b, or c | H | N(H)C(=O)$E^3$OH | $SO_2$ | 0 | 1 | N(CH$_3$)$_2$ |
| Z19 a, b, or c | H | N(H)C(=O)$E^3$OH | $SO_2$ | 1 | 1 | H |
| Z20 a, b, or c | H | N(H)C(=O)$E^3$OH | $SO_2$ | 1 | 1 | N(CH$_3$)$_2$ |
| Z21 a, b, or c | H | OCH$_2$C(=O)OH | direct bond | 0 | 0 | absent |
| Z22 a, b, or c | H | OCH$_2$C(=O)OH | direct bond | 0 | 1 | H |
| Z23 a, b, or c | H | OCH$_2$C(=O)OH | direct bond | 0 | 1 | N(CH$_3$)$_2$ |
| Z24 a, b, or c | H | OCH$_2$C(=O)OH | direct bond | 1 | 1 | H |
| Z25 a, b, or c | H | OCH$_2$C(=O)OH | direct bond | 1 | 1 | N(CH$_3$)$_2$ |
| Z26 a, b, or c | H | OCH$_2$C(=O)OH | $SO_2$ | 0 | 0 | absent |
| Z27 a, b, or c | H | OCH$_2$C(=O)OH | $SO_2$ | 0 | 1 | H |
| Z28 a, b, or c | H | OCH$_2$C(=O)OH | $SO_2$ | 0 | 1 | N(CH$_3$)$_2$ |
| Z29 a, b, or c | H | OCH$_2$C(=O)OH | $SO_2$ | 1 | 1 | H |
| Z30 a, b, or c | H | OCH$_2$C(=O)OH | $SO_2$ | 1 | 1 | N(CH$_3$)$_2$ |

TABLE 28-continued

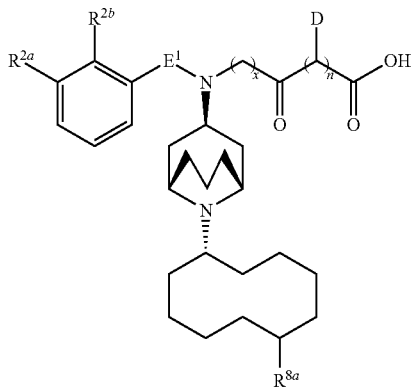

(a)

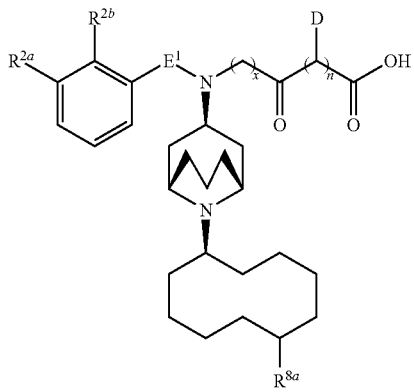

(b)

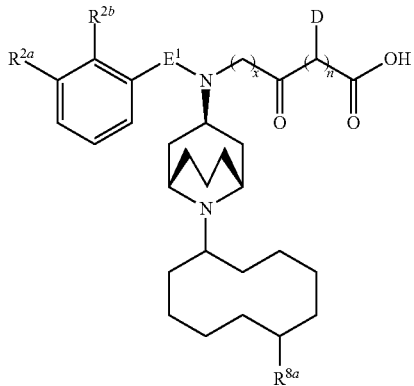

(c)

and pharmaceutically acceptable salts and solvates thereof, where:

| Compound | $R^{2a}$ | $R^{2b}$ | $E^1$ | x | n | D |
|---|---|---|---|---|---|---|
| Z31 a, b, or c | N(H)C(=O)E³OH | H | direct bond | 0 | 0 | absent |
| Z32 a, b, or c | N(H)C(=O)E³OH | H | direct bond | 0 | 1 | H |
| Z33 a, b, or c | N(H)C(=O)E³OH | H | direct bond | 0 | 1 | N(CH₃)₂ |
| Z34 a, b, or c | N(H)C(=O)E³OH | H | direct bond | 1 | 1 | H |
| Z35 a, b, or c | N(H)C(=O)E³OH | H | direct bond | 1 | 1 | N(CH₃)₂ |
| Z36 a, b, or c | N(H)C(=O)E³OH | H | SO₂ | 0 | 0 | absent |
| Z37 a, b, or c | N(H)C(=O)E³OH | H | SO₂ | 0 | 1 | H |
| Z38 a, b, or c | N(H)C(=O)E³OH | H | SO₂ | 0 | 1 | N(CH₃)₂ |
| Z39 a, b, or c | N(H)C(=O)E³OH | H | SO₂ | 1 | 1 | H |
| Z40 a, b, or c | N(H)C(=O)E³OH | H | SO₂ | 1 | 1 | N(CH₃)₂ |
| Z41 a, b, or c | OCH₂C(=O)OH | H | direct bond | 0 | 0 | absent |
| Z42 a, b, or c | OCH₂C(=O)OH | H | direct bond | 0 | 1 | H |
| Z43 a, b, or c | OCH₂C(=O)OH | H | direct bond | 0 | 1 | N(CH₃)₂ |
| Z44 a, b, or c | OCH₂C(=O)OH | H | direct bond | 1 | 1 | H |
| Z45 a, b, or c | OCH₂C(=O)OH | H | direct bond | 1 | 1 | N(CH₃)₂ |

TABLE 28-continued
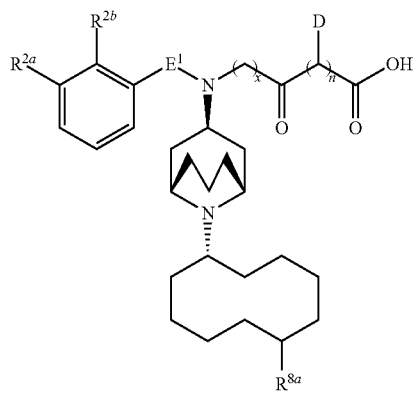
(a)
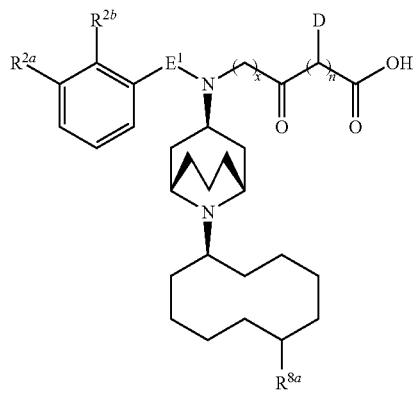
(b)
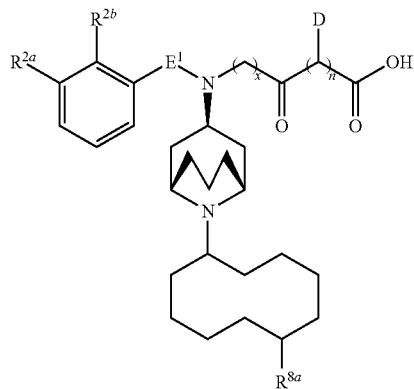
(c)
and pharmaceutically acceptable salts and solvates thereof, where:
| Compound | $R^{2a}$ | $R^{2b}$ | $E^1$ | x | n | D |
|---|---|---|---|---|---|---|
| Z46 a, b, or c | $OCH_2C(=O)OH$ | H | $SO_2$ | 0 | 0 | absent |
| Z47 a, b, or c | $OCH_2C(=O)OH$ | H | $SO_2$ | 0 | 1 | H |
| Z48 a, b, or c | $OCH_2C(=O)OH$ | H | $SO_2$ | 0 | 1 | $N(CH_3)_2$ |
| Z49 a, b, or c | $OCH_2C(=O)OH$ | H | $SO_2$ | 1 | 1 | H |
| Z50 a, b, or c | $OCH_2C(=O)OH$ | H | $SO_2$ | 1 | 1 | $N(CH_3)_2$ |
$R^{8a}$ is (i) H or (ii) $CH_3$; $E^3$ is (iii) a direct bond or (iv) $C(=O)$.

TABLE 29

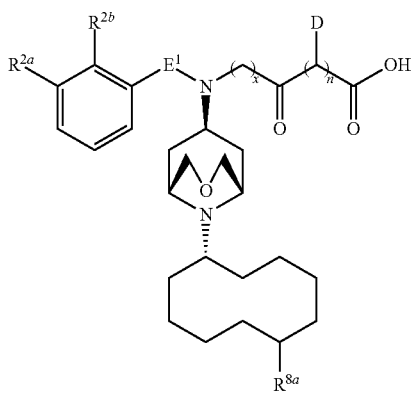

(a)

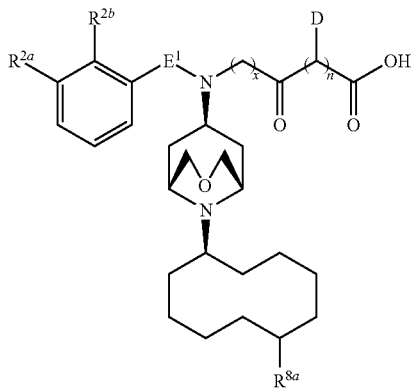

(b)

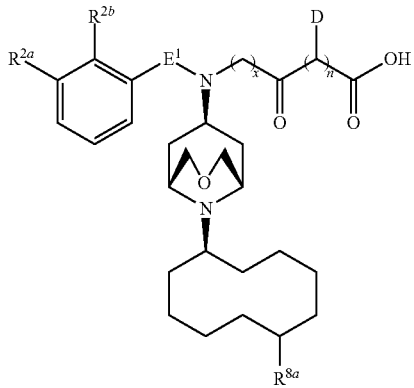

(c)

and pharmaceutically acceptable salts and solvates thereof, where:

| Compound | $R^{2a}$ | $R^{2b}$ | $E^1$ | x | n | D |
|---|---|---|---|---|---|---|
| AA1 a, b, or c | H | H | direct bond | 0 | 0 | absent |
| AA2 a, b, or c | H | H | direct bond | 0 | 1 | H |
| AA3 a, b, or c | H | H | direct bond | 0 | 1 | $N(CH_3)_2$ |
| AA4 a, b, or c | H | H | direct bond | 1 | 1 | H |
| AA5 a, b, or c | H | H | direct bond | 1 | 1 | $N(CH_3)_2$ |
| AA6 a, b, or c | H | H | $SO_2$ | 0 | 0 | absent |
| AA7 a, b, or c | H | H | $SO_2$ | 0 | 1 | H |
| AA8 a, b, or c | H | H | $SO_2$ | 0 | 1 | $N(CH_3)_2$ |
| AA9 a, b, or c | H | H | $SO_2$ | 1 | 1 | H |
| AA10 a, b, or c | H | H | $SO_2$ | 1 | 1 | $N(CH_3)_2$ |
| AA11 a, b, or c | H | $N(H)C(=O)E^3OH$ | direct bond | 0 | 0 | absent |
| AA12 a, b, or c | H | $N(H)C(=O)E^3OH$ | direct bond | 0 | 1 | H |
| AA13 a, b, or c | H | $N(H)C(=O)E^3OH$ | direct bond | 0 | 1 | $N(CH_3)_2$ |
| AA14 a, b, or c | H | $N(H)C(=O)E^3OH$ | direct bond | 1 | 1 | H |
| AA15 a, b, or c | H | $N(H)C(=O)E^3OH$ | direct bond | 1 | 1 | $N(CH_3)_2$ |

TABLE 29-continued

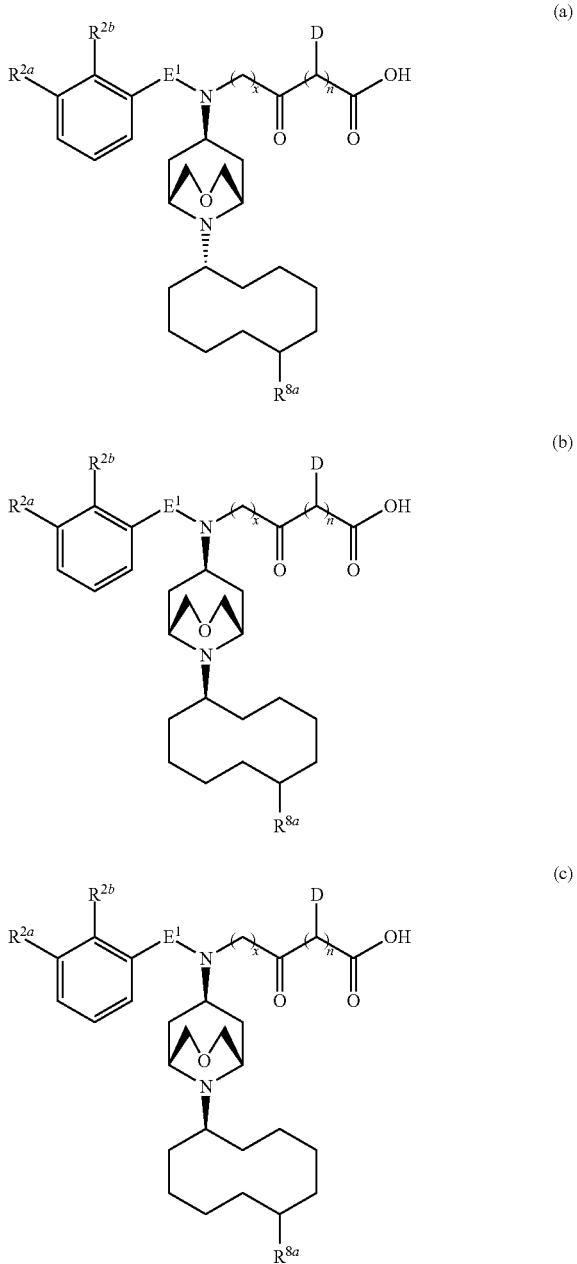

and pharmaceutically acceptable salts and solvates thereof, where:

| Compound | $R^{2a}$ | $R^{2b}$ | $E^1$ | x | n | D |
|---|---|---|---|---|---|---|
| AA16 a, b, or c | H | N(H)C(=O)E$^3$OH | SO$_2$ | 0 | 0 | absent |
| AA17 a, b, or c | H | N(H)C(=O)E$^3$OH | SO$_2$ | 0 | 1 | H |
| AA18 a, b, or c | H | N(H)C(=O)E$^3$OH | SO$_2$ | 0 | 1 | N(CH$_3$)$_2$ |
| AA19 a, b, or c | H | N(H)C(=O)E$^3$OH | SO$_2$ | 1 | 1 | H |
| AA20 a, b, or c | H | N(H)C(=O)E$^3$OH | SO$_2$ | 1 | 1 | N(CH$_3$)$_2$ |
| AA21 a, b, or c | H | OCH$_2$C(=O)OH | direct bond | 0 | 0 | absent |
| AA22 a, b, or c | H | OCH$_2$C(=O)OH | direct bond | 0 | 1 | H |
| AA23 a, b, or c | H | OCH$_2$C(=O)OH | direct bond | 0 | 1 | N(CH$_3$)$_2$ |
| AA24 a, b, or c | H | OCH$_2$C(=O)OH | direct bond | 1 | 1 | H |
| AA25 a, b, or c | H | OCH$_2$C(=O)OH | direct bond | 1 | 1 | N(CH$_3$)$_2$ |
| AA26 a, b, or c | H | OCH$_2$C(=O)OH | SO$_2$ | 0 | 0 | absent |
| AA27 a, b, or c | H | OCH$_2$C(=O)OH | SO$_2$ | 0 | 1 | H |
| AA28 a, b, or c | H | OCH$_2$C(=O)OH | SO$_2$ | 0 | 1 | N(CH$_3$)$_2$ |
| AA29 a, b, or c | H | OCH$_2$C(=O)OH | SO$_2$ | 1 | 1 | H |
| AA30 a, b, or c | H | OCH$_2$C(=O)OH | SO$_2$ | 1 | 1 | N(CH$_3$)$_2$ |

TABLE 29-continued

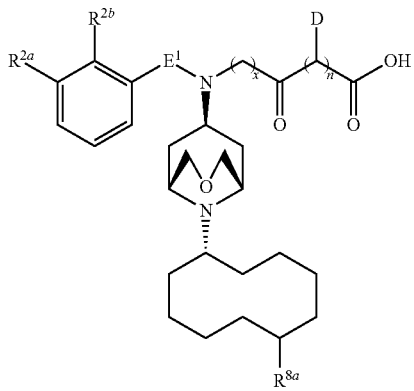

(a)

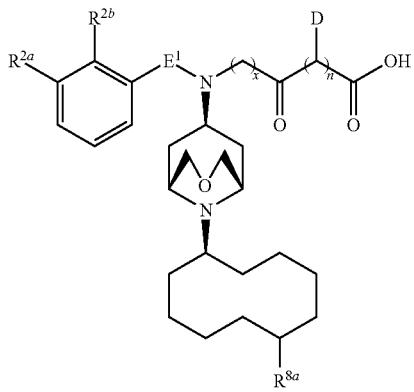

(b)

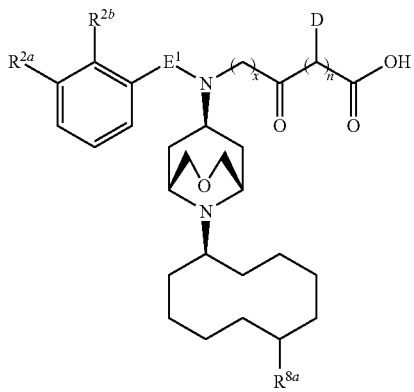

(c)

and pharmaceutically acceptable salts and solvates thereof, where:

| Compound | $R^{2a}$ | $R^{2b}$ | $E^1$ | x | n | D |
|---|---|---|---|---|---|---|
| AA31 a, b, or c | N(H)C(=O)E$^3$OH | H | direct bond | 0 | 0 | absent |
| AA32 a, b, or c | N(H)C(=O)E$^3$OH | H | direct bond | 0 | 1 | H |
| AA33 a, b, or c | N(H)C(=O)E$^3$OH | H | direct bond | 0 | 1 | N(CH$_3$)$_2$ |
| AA34 a, b, or c | N(H)C(=O)E$^3$OH | H | direct bond | 1 | 1 | H |
| AA35 a, b, or c | N(H)C(=O)E$^3$OH | H | direct bond | 1 | 1 | N(CH$_3$)$_2$ |
| AA36 a, b, or c | N(H)C(=O)E$^3$OH | H | SO$_2$ | 0 | 0 | absent |
| AA37 a, b, or c | N(H)C(=O)E$^3$OH | H | SO$_2$ | 0 | 1 | H |
| AA38 a, b, or c | N(H)C(=O)E$^3$OH | H | SO$_2$ | 0 | 1 | N(CH$_3$)$_2$ |
| AA39 a, b, or c | N(H)C(=O)E$^3$OH | H | SO$_2$ | 1 | 1 | H |
| AA40 a, b, or c | N(H)C(=O)E$^3$OH | H | SO$_2$ | 1 | 1 | N(CH$_3$)$_2$ |
| AA41 a, b, or c | OCH$_2$C(=O)OH | H | direct bond | 0 | 0 | absent |
| AA42 a, b, or c | OCH$_2$C(=O)OH | H | direct bond | 0 | 1 | H |
| AA43 a, b, or c | OCH$_2$C(=O)OH | H | direct bond | 0 | 1 | N(CH$_3$)$_2$ |
| AA44 a, b, or c | OCH$_2$C(=O)OH | H | direct bond | 1 | 1 | H |
| AA45 a, b, or c | OCH$_2$C(=O)OH | H | direct bond | 1 | 1 | N(CH$_3$)$_2$ |

TABLE 29-continued
(a)
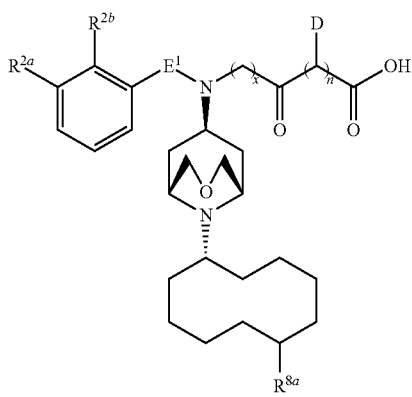
(b)
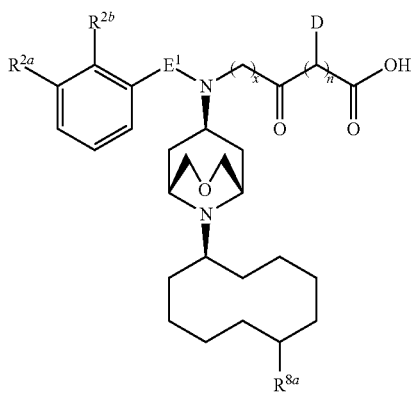
(c)
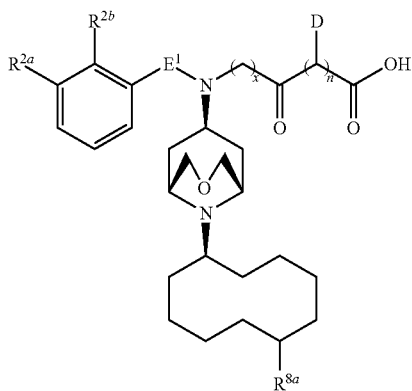
and pharmaceutically acceptable salts and solvates thereof, where:
| Compound | $R^{2a}$ | $R^{2b}$ | $E^1$ | x | n | D |
|---|---|---|---|---|---|---|
| AA46 a, b, or c | OCH$_2$C(=O)OH | H | SO$_2$ | 0 | 0 | absent |
| AA47 a, b, or c | OCH$_2$C(=O)OH | H | SO$_2$ | 0 | 1 | H |
| AA48 a, b, or c | OCH$_2$C(=O)OH | H | SO$_2$ | 0 | 1 | N(CH$_3$)$_2$ |
| AA49 a, b, or c | OCH$_2$C(=O)OH | H | SO$_2$ | 1 | 1 | H |
| AA50 a, b, or c | OCH$_2$C(=O)OH | H | SO$_2$ | 1 | 1 | N(CH$_3$)$_2$ |
$R^{8a}$ is (i) H or (ii) CH$_3$; $E^3$ is (iii) a direct bond or (iv) C(=O).

TABLE 30

(a)

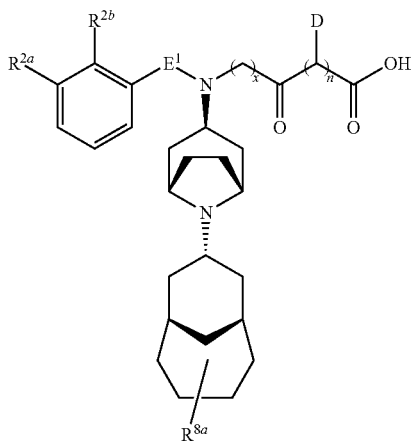

(b)

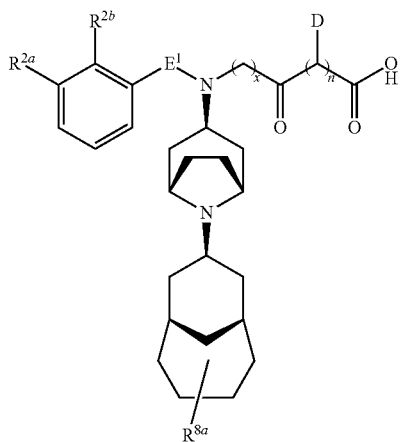

| Compound | $R^{2a}$ | $R^{2b}$ | $E^1$ | x | n | D |
|---|---|---|---|---|---|---|
| BB1 a or b | H | H | direct bond | 0 | 0 | absent |
| BB2 a or b | H | H | direct bond | 0 | 1 | H |
| BB3 a or b | H | H | direct bond | 0 | 1 | $N(CH_3)_2$ |
| BB4 a or b | H | H | direct bond | 1 | 1 | H |
| BB5 a or b | H | H | direct bond | 1 | 1 | $N(CH_3)_2$ |
| BB6 a or b | H | H | $SO_2$ | 0 | 0 | absent |
| BB7 a or b | H | H | $SO_2$ | 0 | 1 | H |
| BB8 a or b | H | H | $SO_2$ | 0 | 1 | $N(CH_3)_2$ |
| BB9 a or b | H | H | $SO_2$ | 1 | 1 | H |
| BB10 a or b | H | H | $SO_2$ | 1 | 1 | $N(CH_3)_2$ |
| BB11 a or b | H | $N(H)C(=O)E^3OH$ | direct bond | 0 | 0 | absent |
| BB12 a or b | H | $N(H)C(=O)E^3OH$ | direct bond | 0 | 1 | H |
| BB13 a or b | H | $N(H)C(=O)E^3OH$ | direct bond | 0 | 1 | $N(CH_3)_2$ |
| BB14 a or b | H | $N(H)C(=O)E^3OH$ | direct bond | 1 | 1 | H |
| BB15 a or b | H | $N(H)C(=O)E^3OH$ | direct bond | 1 | 1 | $N(CH_3)_2$ |
| BB16 a or b | H | $N(H)C(=O)E^3OH$ | $SO_2$ | 0 | 0 | absent |
| BB17 a or b | H | $N(H)C(=O)E^3OH$ | $SO_2$ | 0 | 1 | H |
| BB18 a or b | H | $N(H)C(=O)E^3OH$ | $SO_2$ | 0 | 1 | $N(CH_3)_2$ |
| BB19 a or b | H | $N(H)C(=O)E^3OH$ | $SO_2$ | 1 | 1 | H |
| BB20 a or b | H | $N(H)C(=O)E^3OH$ | $SO_2$ | 1 | 1 | $N(CH_3)_2$ |
| BB21 a or b | H | $OCH_2C(=O)OH$ | direct bond | 0 | 0 | absent |
| BB22 a or b | H | $OCH_2C(=O)OH$ | direct bond | 0 | 1 | H |
| BB23 a or b | H | $OCH_2C(=O)OH$ | direct bond | 0 | 1 | $N(CH_3)_2$ |
| BB24 a or b | H | $OCH_2C(=O)OH$ | direct bond | 1 | 1 | H |
| BB25 a or b | H | $OCH_2C(=O)OH$ | direct bond | 1 | 1 | $N(CH_3)_2$ |
| BB26 a or b | H | $OCH_2C(=O)OH$ | $SO_2$ | 0 | 0 | absent |
| BB27 a or b | H | $OCH_2C(=O)OH$ | $SO_2$ | 0 | 1 | H |
| BB28 a or b | H | $OCH_2C(=O)OH$ | $SO_2$ | 0 | 1 | $N(CH_3)_2$ |
| BB29 a or b | H | $OCH_2C(=O)OH$ | $SO_2$ | 1 | 1 | H |

TABLE 30-continued (a)

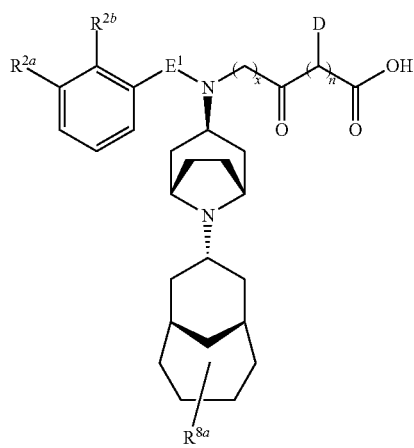

(b)

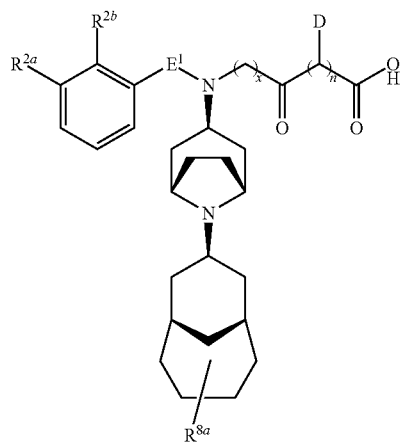

and pharmaceutically acceptable salts and solvates thereof, where:

| Compound | $R^{2a}$ | $R^{2b}$ | $E^1$ | x | n | D |
|---|---|---|---|---|---|---|
| BB30 a or b | H | OCH$_2$C(=O)OH | SO$_2$ | 1 | 1 | N(CH$_3$)$_2$ |
| BB31 a or b | N(H)C(=O)E$^3$OH | H | direct bond | 0 | 0 | absent |
| BB32 a or b | N(H)C(=O)E$^3$OH | H | direct bond | 0 | 1 | H |
| BB33 a or b | N(H)C(=O)E$^3$OH | H | direct bond | 0 | 1 | N(CH$_3$)$_2$ |
| BB34 a or b | N(H)C(=O)E$^3$OH | H | direct bond | 1 | 1 | H |
| BB35 a or b | N(H)C(=O)E$^3$OH | H | direct bond | 1 | 1 | N(CH$_3$)$_2$ |
| BB36 a or b | N(H)C(=O)E$^3$OH | H | SO$_2$ | 0 | 0 | absent |
| BB37 a or b | N(H)C(=O)E$^3$OH | H | SO$_2$ | 0 | 1 | H |
| BB38 a or b | N(H)C(=O)E$^3$OH | H | SO$_2$ | 0 | 1 | N(CH$_3$)$_2$ |
| BB39 a or b | N(H)C(=O)E$^3$OH | H | SO$_2$ | 1 | 1 | H |
| BB40 a or b | N(H)C(=O)E$^3$OH | H | SO$_2$ | 1 | 1 | N(CH$_3$)$_2$ |
| BB41 a or b | OCH$_2$C(=O)OH | H | direct bond | 0 | 0 | absent |
| BB42 a or b | OCH$_2$C(=O)OH | H | direct bond | 0 | 1 | H |
| BB43 a or b | OCH$_2$C(=O)OH | H | direct bond | 0 | 1 | N(CH$_3$)$_2$ |
| BB44 a or b | OCH$_2$C(=O)OH | H | direct bond | 1 | 1 | H |
| BB45 a or b | OCH$_2$C(=O)OH | H | direct bond | 1 | 1 | N(CH$_3$)$_2$ |
| BB46 a or b | OCH$_2$C(=O)OH | H | SO$_2$ | 0 | 0 | absent |
| BB47 a or b | OCH$_2$C(=O)OH | H | SO$_2$ | 0 | 1 | H |
| BB48 a or b | OCH$_2$C(=O)OH | H | SO$_2$ | 0 | 1 | N(CH$_3$)$_2$ |
| BB49 a or b | OCH$_2$C(=O)OH | H | SO$_2$ | 1 | 1 | H |
| BB50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

TABLE 31

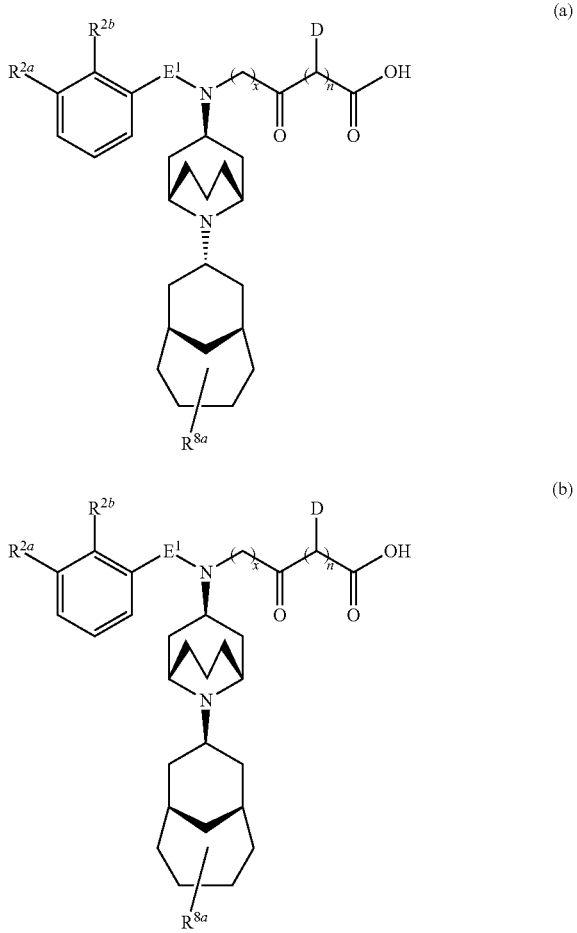

and pharmaceutically acceptable salts and solvates thereof, where:

| Compound | $R^{2a}$ | $R^{2b}$ | $E^1$ | x | n | X |
|---|---|---|---|---|---|---|
| CC1 a or b | H | H | direct bond | 0 | 0 | absent |
| CC2 a or b | H | H | direct bond | 0 | 1 | H |
| CC3 a or b | H | H | direct bond | 0 | 1 | $N(CH_3)_2$ |
| CC4 a or b | H | H | direct bond | 1 | 1 | H |
| CC5 a or b | H | H | direct bond | 1 | 1 | $N(CH_3)_2$ |
| CC6 a or b | H | H | $SO_2$ | 0 | 0 | absent |
| CC7 a or b | H | H | $SO_2$ | 0 | 1 | H |
| CC8 a or b | H | H | $SO_2$ | 0 | 1 | $N(CH_3)_2$ |
| CC9 a or b | H | H | $SO_2$ | 1 | 1 | H |
| CC10 a or b | H | H | $SO_2$ | 1 | 1 | $N(CH_3)_2$ |
| CC11 a or b | H | $N(H)C(=O)E^3OH$ | direct bond | 0 | 0 | absent |
| CC12 a or b | H | $N(H)C(=O)E^3OH$ | direct bond | 0 | 1 | H |
| CC13 a or b | H | $N(H)C(=O)E^3OH$ | direct bond | 0 | 1 | $N(CH_3)_2$ |
| CC14 a or b | H | $N(H)C(=O)E^3OH$ | direct bond | 1 | 1 | H |
| CC15 a or b | H | $N(H)C(=O)E^3OH$ | direct bond | 1 | 1 | $N(CH_3)_2$ |
| CC16 a or b | H | $N(H)C(=O)E^3OH$ | $SO_2$ | 0 | 0 | absent |
| CC17 a or b | H | $N(H)C(=O)E^3OH$ | $SO_2$ | 0 | 1 | H |
| CC18 a or b | H | $N(H)C(=O)E^3OH$ | $SO_2$ | 0 | 1 | $N(CH_3)_2$ |
| CC19 a or b | H | $N(H)C(=O)E^3OH$ | $SO_2$ | 1 | 1 | H |
| CC20 a or b | H | $N(H)C(=O)E^3OH$ | $SO_2$ | 1 | 1 | $N(CH_3)_2$ |
| CC21 a or b | H | $OCH_2C(=O)OH$ | direct bond | 0 | 0 | absent |
| CC22 a or b | H | $OCH_2C(=O)OH$ | direct bond | 0 | 1 | H |
| CC23 a or b | H | $OCH_2C(=O)OH$ | direct bond | 0 | 1 | $N(CH_3)_2$ |
| CC24 a or b | H | $OCH_2C(=O)OH$ | direct bond | 1 | 1 | H |
| CC25 a or b | H | $OCH_2C(=O)OH$ | direct bond | 1 | 1 | $N(CH_3)_2$ |
| CC26 a or b | H | $OCH_2C(=O)OH$ | $SO_2$ | 0 | 0 | absent |
| CC27 a or b | H | $OCH_2C(=O)OH$ | $SO_2$ | 0 | 1 | H |
| CC28 a or b | H | $OCH_2C(=O)OH$ | $SO_2$ | 0 | 1 | $N(CH_3)_2$ |
| CC29 a or b | H | $OCH_2C(=O)OH$ | $SO_2$ | 1 | 1 | H |
| CC30 a or b | H | $OCH_2C(=O)OH$ | $SO_2$ | 1 | 1 | $N(CH_3)_2$ |
| CC31 a or b | $N(H)C(=O)E^3OH$ | H | direct bond | 0 | 0 | absent |

TABLE 31-continued

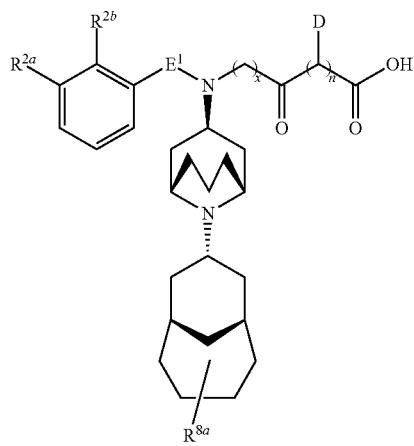

(a)

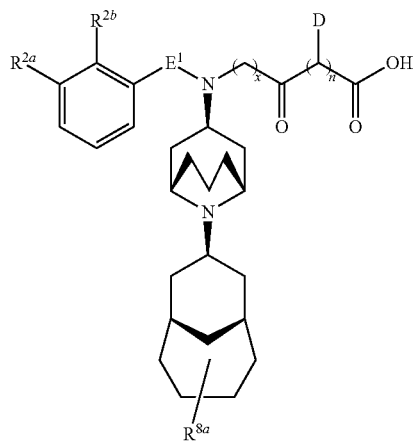

(b)

and pharmaceutically acceptable salts and solvates thereof, where:

| Compound | $R^{2a}$ | $R^{2b}$ | $E^1$ | x | n | X |
|---|---|---|---|---|---|---|
| CC32 a or b | N(H)C(=O)E³OH | H | direct bond | 0 | 1 | H |
| CC33 a or b | N(H)C(=O)E³OH | H | direct bond | 0 | 1 | N(CH₃)₂ |
| CC34 a or b | N(H)C(=O)E³OH | H | direct bond | 1 | 1 | H |
| CC35 a or b | N(H)C(=O)E³OH | H | direct bond | 1 | 1 | N(CH₃)₂ |
| CC36 a or b | N(H)C(=O)E³OH | H | SO₂ | 0 | 0 | absent |
| CC37 a or b | N(H)C(=O)E³OH | H | SO₂ | 0 | 1 | H |
| CC38 a or b | N(H)C(=O)E³OH | H | SO₂ | 0 | 1 | N(CH₃)₂ |
| CC39 a or b | N(H)C(=O)E³OH | H | SO₂ | 1 | 1 | H |
| CC40 a or b | N(H)C(=O)E³OH | H | SO₂ | 1 | 1 | N(CH₃)₂ |
| CC41 a or b | OCH₂C(=O)OH | H | direct bond | 0 | 0 | absent |
| CC42 a or b | OCH₂C(=O)OH | H | direct bond | 0 | 1 | H |
| CC43 a or b | OCH₂C(=O)OH | H | direct bond | 0 | 1 | N(CH₃)₂ |
| CC44 a or b | OCH₂C(=O)OH | H | direct bond | 1 | 1 | H |
| CC45 a or b | OCH₂C(=O)OH | H | direct bond | 1 | 1 | N(CH₃)₂ |
| CC46 a or b | OCH₂C(=O)OH | H | SO₂ | 0 | 0 | absent |
| CC47 a or b | OCH₂C(=O)OH | H | SO₂ | 0 | 1 | H |
| CC48 a or b | OCH₂C(=O)OH | H | SO₂ | 0 | 1 | N(CH₃)₂ |
| CC49 a or b | OCH₂C(=O)OH | H | SO₂ | 1 | 1 | H |
| CC50 a or b | OCH₂C(=O)OH | H | SO₂ | 1 | 1 | N(CH₃)₂ |

$R^{8a}$ is (i) H or (ii) CH₃; $E^3$ is (iii) a direct bond or (iv) C(=O).

TABLE 32

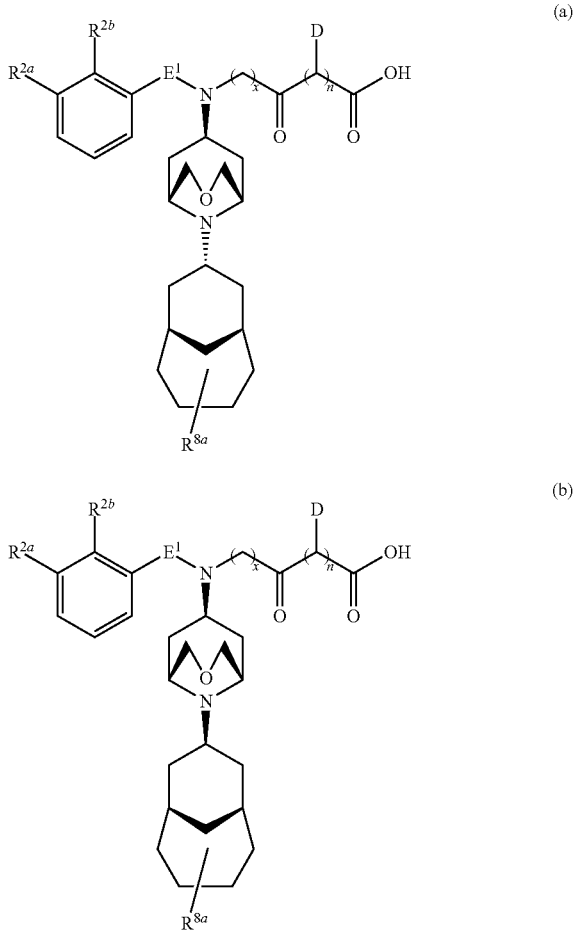

and pharmaceutically acceptable salts and solvates thereof, where:

| Compound | $R^{2a}$ | $R^{2b}$ | $E^1$ | x | n | X |
|---|---|---|---|---|---|---|
| DD1 a or b | H | H | direct bond | 0 | 0 | absent |
| DD2 a or b | H | H | direct bond | 0 | 1 | H |
| DD3 a or b | H | H | direct bond | 0 | 1 | $N(CH_3)_2$ |
| DD4 a or b | H | H | direct bond | 1 | 1 | H |
| DD5 a or b | H | H | direct bond | 1 | 1 | $N(CH_3)_2$ |
| DD6 a or b | H | H | $SO_2$ | 0 | 0 | absent |
| DD7 a or b | H | H | $SO_2$ | 0 | 1 | H |
| DD8 a or b | H | H | $SO_2$ | 0 | 1 | $N(CH_3)_2$ |
| DD9 a or b | H | H | $SO_2$ | 1 | 1 | H |
| DD10 a or b | H | H | $SO_2$ | 1 | 1 | $N(CH_3)_2$ |
| DD11 a or b | H | $N(H)C(=O)E^3OH$ | direct bond | 0 | 0 | absent |
| DD12 a or b | H | $N(H)C(=O)E^3OH$ | direct bond | 0 | 1 | H |
| DD13 a or b | H | $N(H)C(=O)E^3OH$ | direct bond | 0 | 1 | $N(CH_3)_2$ |
| DD14 a or b | H | $N(H)C(=O)E^3OH$ | direct bond | 1 | 1 | H |
| DD15 a or b | H | $N(H)C(=O)E^3OH$ | direct bond | 1 | 1 | $N(CH_3)_2$ |
| DD16 a or b | H | $N(H)C(=O)E^3OH$ | $SO_2$ | 0 | 0 | absent |
| DD17 a or b | H | $N(H)C(=O)E^3OH$ | $SO_2$ | 0 | 1 | H |
| DD18 a or b | H | $N(H)C(=O)E^3OH$ | $SO_2$ | 0 | 1 | $N(CH_3)_2$ |
| DD19 a or b | H | $N(H)C(=O)E^3OH$ | $SO_2$ | 1 | 1 | H |
| DD20 a or b | H | $N(H)C(=O)E^3OH$ | $SO_2$ | 1 | 1 | $N(CH_3)_2$ |
| DD21 a or b | H | $OCH_2C(=O)OH$ | direct bond | 0 | 0 | absent |
| DD22 a or b | H | $OCH_2C(=O)OH$ | direct bond | 0 | 1 | H |
| DD23 a or b | H | $OCH_2C(=O)OH$ | direct bond | 0 | 1 | $N(CH_3)_2$ |
| DD24 a or b | H | $OCH_2C(=O)OH$ | direct bond | 1 | 1 | H |
| DD25 a or b | H | $OCH_2C(=O)OH$ | direct bond | 1 | 1 | $N(CH_3)_2$ |
| DD26 a or b | H | $OCH_2C(=O)OH$ | $SO_2$ | 0 | 0 | absent |
| DD27 a or b | H | $OCH_2C(=O)OH$ | $SO_2$ | 0 | 1 | H |
| DD28 a or b | H | $OCH_2C(=O)OH$ | $SO_2$ | 0 | 1 | $N(CH_3)_2$ |
| DD29 a or b | H | $OCH_2C(=O)OH$ | $SO_2$ | 1 | 1 | H |
| DD30 a or b | H | $OCH_2C(=O)OH$ | $SO_2$ | 1 | 1 | $N(CH_3)_2$ |
| DD31 a or b | $N(H)C(=O)E^3OH$ | H | direct bond | 0 | 0 | absent |

TABLE 32-continued

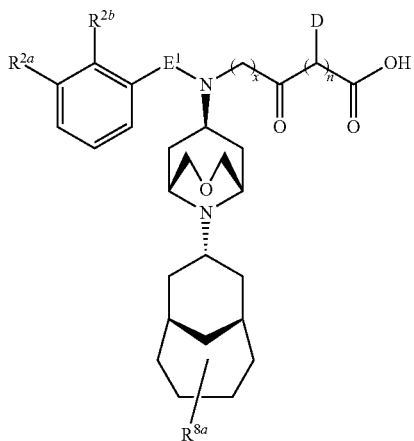

(a)

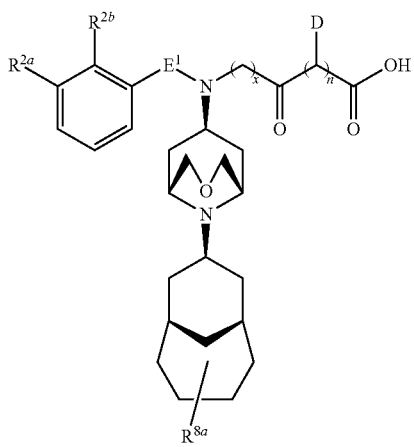

(b)

and pharmaceutically acceptable salts and solvates thereof, where:

| Compound | $R^{2a}$ | $R^{2b}$ | $E^1$ | x | n | X |
|---|---|---|---|---|---|---|
| DD32 a or b | N(H)C(=O)E³OH | H | direct bond | 0 | 1 | H |
| DD33 a or b | N(H)C(=O)E³OH | H | direct bond | 0 | 1 | N(CH$_3$)$_2$ |
| DD34 a or b | N(H)C(=O)E³OH | H | direct bond | 1 | 1 | H |
| DD35 a or b | N(H)C(=O)E³OH | H | direct bond | 1 | 1 | N(CH$_3$)$_2$ |
| DD36 a or b | N(H)C(=O)E³OH | H | SO$_2$ | 0 | 0 | absent |
| DD37 a or b | N(H)C(=O)E³OH | H | SO$_2$ | 0 | 1 | H |
| DD38 a or b | N(H)C(=O)E³OH | H | SO$_2$ | 0 | 1 | N(CH$_3$)$_2$ |
| DD39 a or b | N(H)C(=O)E³OH | H | SO$_2$ | 1 | 1 | H |
| DD40 a or b | N(H)C(=O)E³OH | H | SO$_2$ | 1 | 1 | N(CH$_3$)$_2$ |
| DD41 a or b | OCH$_2$C(=O)OH | H | direct bond | 0 | 0 | absent |
| DD42 a or b | OCH$_2$C(=O)OH | H | direct bond | 0 | 1 | H |
| DD43 a or b | OCH$_2$C(=O)OH | H | direct bond | 0 | 1 | N(CH$_3$)$_2$ |
| DD44 a or b | OCH$_2$C(=O)OH | H | direct bond | 1 | 1 | H |
| DD45 a or b | OCH$_2$C(=O)OH | H | direct bond | 1 | 1 | N(CH$_3$)$_2$ |
| DD46 a or b | OCH$_2$C(=O)OH | H | SO$_2$ | 0 | 0 | absent |
| DD47 a or b | OCH$_2$C(=O)OH | H | SO$_2$ | 0 | 1 | H |
| DD48 a or b | OCH$_2$C(=O)OH | H | SO$_2$ | 0 | 1 | N(CH$_3$)$_2$ |
| DD49 a or b | OCH$_2$C(=O)OH | H | SO$_2$ | 1 | 1 | H |
| DD50 a or b | OCH$_2$C(=O)OH | H | SO$_2$ | 1 | 1 | N(CH$_3$)$_2$ |

$R^{8a}$ is (i) H or (ii) CH$_3$; $E^3$ is (iii) a direct bond or (iv) C(=O).

4.2 Definitions

As used in connection with the Substituted Piperidin-4-amino-Type Compounds herein, the terms used herein have the following meaning:

"—(C$_1$-C$_{10}$)alkyl" means a straight chain or branched non-cyclic hydrocarbon having 1, 2, 3, 4, 5, 6, 7, 8, 9, or 10 carbon atoms. Representative straight chain —(C$_1$-C$_{10}$) alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —(C$_1$-C$_8$)alkyl groups, such as methyl, ethyl or propyl, replace one or both hydrogens in a —CH$_2$— group of a straight chain alkyl. A branched non-cyclic hydrocarbon means that one or more straight chain —(C$_1$-C$_{10}$)alkyl groups, such as methyl, ethyl or propyl, replace one or both hydrogens in a —CH$_2$— group of a straight chain non-cyclic hydrocarbon. Representative branched —(C$_1$-C$_{10}$)alkyls include -iso-propyl, -sec-butyl, -iso-butyl, -terl-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

In connection with the Z group, "—(C$_1$-C$_{10}$)alkyl-" means a straight chain or branched non-cyclic hydrocarbon moiety having 1, 2, 3, 4, 5, 6, 7, 8, 9, or 10 carbon atoms where two hydrogen atoms on the same or a different carbon atom of the moiety are each figuratively removed and replaced by a bond to one of the two adjoining groups. Representative —(C$_1$-C$_{10}$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, n-deca-1,1-diyl, n-deca-1,2-diyl, n-deca-1,3-diyl, n-deca-1,4-diyl, n-deca-1,5-diyl, n-deca-1,6-diyl, n-deca-1,7-diyl, n-deca-1,8-diyl, n-deca-1,9-diyl, n-deca-1,10-diyl, and the like.

"—(C$_2$-C$_{10}$)alkyl" means a straight chain or branched non-cyclic hydrocarbon having 2, 3, 4, 5, 6, 7, 8, 9, or 10 carbon atoms. Representative straight chain —(C$_2$-C$_{10}$)alkyls include -ethyl, -n-propyl, -n-butyl, -n-pentyl, -n-hexyl, -n-heptyl, -n-octyl, -n-nonyl, and -n-decyl. A branched alkyl means that one or more straight chain —(C$_2$-C$_8$)alkyl groups, such as ethyl or propyl, replace one or both hydrogens in a —CH$_2$— group of a straight chain alkyl. A branched non-cyclic hydrocarbon means that one or more straight chain —(C$_2$-C$_{10}$)alkyl groups, such as ethyl or propyl, replace one or both hydrogens in a —CH$_2$— group of a straight chain non-cyclic hydrocarbon. Representative branched —(C$_2$-C$_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_3$-C$_{10}$)alkyl" means a straight chain or branched non-cyclic hydrocarbon having 3, 4, 5, 6, 7, 8, 9, or 10 carbon atoms. Representative straight chain —(C$_3$-C$_{10}$)alkyls include -n-propyl, -n-butyl, -n-pentyl, -n-hexyl, -n-heptyl, -n-octyl, -n-nonyl, and -n-decyl. A branched alkyl means that one or more straight chain —(C$_3$-C$_8$)alkyl groups, such as propyl, butyl or pentyl, replace one or both hydrogens in a —CH$_2$— group of a straight chain alkyl. A branched non-cyclic hydrocarbon means that one or more straight chain —(C$_3$-C$_{10}$)alkyl groups, such as propyl, replace one or both hydrogens in a —CH$_2$— group of a straight chain non-cyclic hydrocarbon. Representative branched —(C$_3$-C$_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_1$-C$_6$)alkyl" means a straight chain or branched non-cyclic hydrocarbon having 1, 2, 3, 4, 5, or 6 carbon atoms. Representative straight chain —(C$_1$-C$_6$)alkyls include -methyl, -ethyl, -n-propyl, -n-butyl, -n-pentyl, and -n-hexyl. Representative branched —(C$_1$-C$_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl. In connection with the Z group, "—(C$_1$-C$_6$)alkyl-" means a straight chain or branched non-cyclic hydrocarbon moiety having 1, 2, 3, 4, 5, or 6 carbon atoms where two hydrogen atoms on the same or a different carbon atom of the moiety are each figuratively removed and replaced by a bond to one of the two adjoining groups. Representative —(C$_1$-C$_6$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, and the like.

"—(C$_1$-C$_4$)alkyl" means a straight chain or branched non-cyclic hydrocarbon having 1, 2, 3, or 4 carbon atoms. Representative straight chain —(C$_1$-C$_4$)alkyls include -methyl, -ethyl, -n-propyl, and -n-butyl. Representative branched —(C$_1$-C$_4$)alkyls include -iso-propyl, -sec-butyl, -iso-butyl, and -tert-butyl.

In connection with the Z group, "—(C$_1$-C$_4$)alkyl-" means a straight chain or branched non-cyclic hydrocarbon moiety having 1, 2, 3, or 4 carbon atoms where two hydrogen atoms on the same or a different carbon atom of the moiety are each figuratively removed and replaced by a bond to one of the two adjoining groups. Representative —(C$_1$-C$_4$)alkyl- moieties include meth-1,1-diyl, eth-1,1-diyl, eth-1,2-diyl, n-prop-1,1-diyl, n-prop-1,2-diyl, n-prop-1,3-diyl, n-but-1,2-diyl, n-but-1,3-diyl, n-but-1,4-diyl, and the like.

"—(C$_1$-C$_3$)alkyl" means a straight chain or branched non-cyclic hydrocarbon having 1, 2, or 3 carbon atoms. Representative straight chain —(C$_1$-C$_3$)alkyls include -methyl, -ethyl, -n-propyl. Representative branched —(C$_1$-C$_3$)alkyls include -iso-propyl.

In connection with the Z group, "—(C$_1$-C$_3$)alkyl-" means a straight chain or branched non-cyclic hydrocarbon moiety having 1, 2, or 3 carbon atoms where two hydrogen atoms on the same or a different carbon atom of the moiety are each figuratively removed and replaced by a bond to one of the two adjoining groups. Representative —(C$_1$-C$_3$)alkyl- moieties include meth-1,1-diyl, eth-1,1-diyl, eth-1,2-diyl, n-prop-1, 1-diyl, n-prop-1,2-diyl, n-prop-1,3-diyl, and the like.

"—(C$_1$-C$_2$)alkyl" means a straight chain non-cyclic hydrocarbon having 1 or 2 carbon atoms. Representative —(C$_1$-C$_2$)alkyls include -methyl and -ethyl.

In connection with the Z group, "—(C$_1$-C$_2$)alkyl-" means a straight chain non-cyclic hydrocarbon moiety having 1 or 2 carbon atoms where two hydrogen atoms on the same or a different carbon atom of the moiety are each figuratively removed and replaced by a bond to one of the two adjoining groups. Representative —$(C_1\text{-}C_2)$alkyl- moieties include meth-1,1-diyl, eth-1,1-diyl, and eth-1,2-diyl.

"—$(C_2\text{-}C_{10})$alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —$(C_1\text{-}C_8)$alkyl groups, such as methyl, ethyl or propyl, replace one or both hydrogens in a —$CH_2$— or —CH= group of a straight chain alkenyl. Representative straight chain and branched $(C_2\text{-}C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

In connection with the Z group, "—$(C_2\text{-}C_{10})$alkenyl-" means a straight chain or branched non-cyclic hydrocarbon moiety having 2, 3, 4, 5, 6, 7, 8, 9, or 10 carbon atoms and including at least one carbon-carbon double bond where two hydrogen atoms on the same or a different carbon atom of the moiety are each figuratively removed and replaced by a bond to one of the two adjoining groups. Representative —$(C_2\text{-}C_{10})$alkenyl- moieties include vin-1, -diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—$(C_2\text{-}C_6)$alkenyl" means a straight chain or branched non-cyclic hydrocarbon having 2, 3, 4, 5, or 6 carbon atoms and including at least one carbon-carbon double bond. Representative straight chain and branched $(C_2\text{-}C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

In connection with the Z group, "—$(C_2\text{-}C_6)$alkenyl-" means a straight chain or branched non-cyclic hydrocarbon moiety having 2, 3, 4, 5, or 6 carbon atoms and including at least one carbon-carbon double bond where two hydrogen atoms on the same or a different carbon atom of the moiety are each figuratively removed and replaced by a bond to one of the two adjoining groups. Representative —$(C_2\text{-}C_6)$alkenyl- moieties include vin-1,1-diyl, vin-1,2-diyl, prop-1-en-1,1-diyl, prop-1-en-1,2-diyl, prop-1-en-1,3-diyl, prop-2-en-1, 1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—$(C_2\text{-}C_3)$alkenyl" means a straight chain non-cyclic hydrocarbon having 2 or 3 carbon atoms and including at least one carbon-carbon double bond. Representative $(C_2\text{-}C_3)$alkenyls include -vinyl, -allyl, and 1-prop-1-enyl.

In connection with the Z group, "—$(C_2\text{-}C_3)$alkenyl-" means a straight chain or branched non-cyclic hydrocarbon moiety having 2 or 3 carbon atoms and including at least one carbon-carbon double bond where two hydrogen atoms on the same or a different carbon atom of the moiety are each figuratively removed and replaced by a bond to one of the two adjoining groups. Representative —$(C_2\text{-}C_3)$alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, and prop-2-en-1,3-diyl.

"—$(C_2\text{-}C_{10})$alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —$(C_1\text{-}C_8)$alkyl groups, such as methyl, ethyl or propyl, replace one or both hydrogens in a —$CH_2$— group of a straight chain alkynyl. Representative straight chain and branched —$(C_2\text{-}C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2\text{-}C_6)$alkynyl" means a straight chain or branched non-cyclic hydrocarbon having 2, 3, 4, 5, or 6 carbon atoms and including at least one carbon-carbon triple bond. Representative straight chain and branched $(C_2\text{-}C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1\text{-}C_6)$alkoxy" means a straight chain or branched non-cyclic hydrocarbon having one or more ether groups and 1, 2, 3, 4, 5, or 6 carbon atoms. Representative straight chain and branched $(C_1\text{-}C_6)$alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)tri methoxymethyl-, (2,2,2-trimethoxyethoxy)-, and the like.

"—$(C_1\text{-}C_4)$alkoxy" means a straight chain or branched non-cyclic hydrocarbon having one or more ether groups and 1, 2, 3, or 4 carbon atoms. Representative straight chain and branched $(C_1\text{-}C_4)$alkoxys include -methoxy, -ethoxy, -methoxymethyl, -2-methoxyethyl, (methoxymethoxy) methyl-, 1-(methoxy)-1-methoxyethyl-, trimethoxymethyl-, and the like.

"—$(C_3\text{-}C_{14})$cycloalkyl" means a saturated monocyclic hydrocarbon having 3, 4, 5, 6, 7, 8, 9, 10, 11, 12, 13, or 14 carbon atoms. Representative $(C_3\text{-}C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—$(C_4\text{-}C_{14})$cycloalkyl" means a saturated monocyclic hydrocarbon having 4, 5, 6, 7, 8, 9, 10, 11, 12, 13, or 14 carbon atoms. Representative $(C_3\text{-}C_{14})$cycloalkyls are -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—$(C_3\text{-}C_{12})$cycloalkyl" means a saturated monocyclic hydrocarbon having 3, 4, 5, 6, 7, 8, 9, 10, 11, or 12 carbon atoms. Representative $(C_3\text{-}C_{12})$cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—$(C_3\text{-}C_{10})$cycloalkyl" means a saturated monocyclic hydrocarbon having 3, 4, 5, 6, 7, 8, 9, or 10 carbon atoms. Representative $(C_3\text{-}C_{10})$cycloalkyls are -cyclopropyl, -cyclobutyl, -cyclopentyl, -cyclohexyl, -cycloheptyl, -cyclooctyl, -cyclononyl, and -cyclodecyl.

"—$(C_6\text{-}C_{10})$cycloalkyl" means a saturated monocyclic hydrocarbon having 6, 7, 8, 9, or 10 carbon atoms. Representative $(C_6\text{-}C_{10})$cycloalkyls are -cyclohexyl, -cycloheptyl, -cyclooctyl, -cyclononyl, and -cyclodecyl.

"—$(C_6\text{-}C_{12})$cycloalkyl" means a saturated monocyclic hydrocarbon having 6, 7, 8, 9, 10, 11, or 12 carbon atoms.

Representative $(C_6-C_{12})$cycloalkyls are -cyclohexyl, -cycloheptyl, -cyclooctyl, -cyclononyl, -cyclodecyl, -cycloundecyl, and -cyclododecyl.

"—$(C_4-C_8)$cycloalkyl" or "4- to 8-member cycloalkyl ring" means a saturated monocyclic hydrocarbon having 4, 5, 6, 7, or 8 carbon atoms. Representative —$(C_4-C_8)$cycloalkyls are -cyclobutyl, -cyclopentyl, -cyclohexyl, -cycloheptyl, and -cyclooctyl.

"—$(C_3-C_8)$cycloalkyl" means a saturated monocyclic hydrocarbon having 3, 4, 5, 6, 7, or 8 carbon atoms. Representative $(C_3-C_8)$cycloalkyls include -cyclopropyl, -cyclobutyl, -cyclopentyl, -cyclohexyl, -cycloheptyl, and -cyclooctyl.

"—$(C_3-C_7)$cycloalkyl" means a saturated monocyclic hydrocarbon having 3, 4, 5, 6, or 7 carbon atoms. Representative $(C_3-C_7)$cycloalkyls include cyclopropyl, -cyclobutyl, -cyclopentyl, -cyclohexyl, and -cycloheptyl.

"—$(C_6-C_{14})$bicycloalkyl" means a bicyclic hydrocarbon ring system having 6, 7, 8, 9, 10, 11, 12, 13, or 14 carbon atoms and at least one saturated cyclic alkyl ring. In one embodiment, the —$(C_6-C_{14})$bicycloalkyl has one saturated cyclic alkyl ring. In another embodiment, the —$(C_6-C_{14})$bicycloalkyl has two saturated cyclic alkyl rings. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

"—$(C_8-C_{20})$tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring; thus, one of the rings can comprise, e.g., benzo. In one embodiment, the —$(C_8-C_{20})$tricycloalkyl has one saturated cyclic alkyl ring. In another embodiment, the —$(C_8-C_{20})$tricycloalkyl has two saturated cyclic alkyl rings. In another embodiment, the —$(C_8-C_{20})$tricycloalkyl has three saturated cyclic alkyl rings. Representative —$(C_8-C_{20})$tricycloalkyls include -pyrenyl, -adamantyl, -noradamantyl, -1,2,3,4-tetrahydroanthracenyl, -1,2,3,4,4a,9,9a, 10-octahydroanthracenyl, -perhydroanthracenyl -aceanthrenyl, -1,2,3,4-tetrahydropenanthrenyl, -5,6,7,8-tetrahydrophenanthrenyl, -1,2,3, 4,4a,9, 10, 10a-octahydrophenanthrenyl, -perhydrophenanthrenyl, -tetradecahydro-1H-cyclohepta[a]naphthalenyl, -tetradecahydro-1H-cycloocta[e]indenyl, -tetradecahydro-1H-cyclohepta[e]azulenyl, -hexadecahydrocycloocta[b]naphthalenyl, -hexadecahydrocyclohepta[a]heptalenyl, -tricyclo-pentadecanyl, -tricyclo-octadecanyl, -tricyclo-nonadecanyl, -tricyclo-icosanyl, -2,3-benzobicyclo[2.2.2]octanyl, -6,7-benzobicyclo[3.2.1]octanyl, -9,10-benzobicyclo[3.3.2]decanyl, -2,3,4,4a,9,9a-hexahydro-1H-fluorenyl, -1,2,3,4,4a,8b-hexahydrobiphenylenyl, and the like.

"—$(C_5-C_{14})$cycloalkenyl" means a cyclic non-aromatic hydrocarbon having at least one carbon-carbon double bond in the cyclic system and 5, 6, 7, 8, 9, 10, 11, 12, 13, or 14 carbon atoms. Representative $(C_5-C_{14})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—$(C_5-C_8)$cycloalkenyl" means a cyclic non-aromatic hydrocarbon having at least one carbon-carbon double bond in the cyclic system and 5, 6, 7, or 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—$(C_5-C_{10})$cycloalkenyl" means a cyclic non-aromatic hydrocarbon having at least one carbon-carbon double bond in the cyclic system and 5, 6, 7, 8, 9, or 10 carbon atoms. Representative $(C_5-C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, and the like.

"—$(C_7-C_{14})$bicycloalkenyl" means a bicyclic hydrocarbon ring system having at least one carbon-carbon double bond in each ring and 7, 8, 9, 10, 11, 12, 13, or 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, -norbornenyl, and the like.

"—$(C_8-C_{20})$tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —$(C_8-C_{20})$tricycloalkenyls include -anthracenyl, -phenanthrenyl, -phenalenyl, -acenaphthalenyl, -as-indacenyl, -s-indacenyl, -2,3,6, 7,8,9,10,11-octahydro-1H-cycloocta[e]indenyl, 2,3,4,7,8,9, 10,111-octahydro-1H-cyclohepta[a]naphthalenyl, -8,9,10, 11-tetrahydro-7H-cyclohepta[a]naphthalenyl, -2,3,4,5,6,7,8, 9,10,11,12,13-dodecahydro-1H-cyclohepta[a]heptalenyl, -1,2,3,4,5,6,7,8,9,10, 11,12,13,14-tetradecahydro-dicyclohepta[a,c]cyclooctenyl), -2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(3- to 9-membered)heterocycle" or "-(3- to 9-membered)heterocyclo" means a 3- to 9-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, a 7-membered heterocycle can contain 1, 2, 3, 4, or 5 heteroatoms, an 8 membered heterocycle can contain 1, 2, 3, 4, 5, or 6 heteroatoms, and a 9 membered heterocycle can contain 1, 2, 3, 4, 5, 6, or 7 heteroatoms. Each heteroatom is independently selected from nitrogen, which can be quaternized; oxygen; and sulfur, including sulfoxide and sulfone. The -(3- to 9-membered)heterocycle can be attached via a nitrogen or carbon atom. Representative -(3- to 9-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(7- to 10-membered)bicycloheterocycle" or "-(7- to 10-membered)bicycloheterocyclo" means a 7- to 10-membered bicyclic, heterocyclic ring, each ring of which is independently either saturated, unsaturated non-aromatic or aromatic, i.e., where at least one ring comprises at least one heteroatom. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered) bicycloheterocycle can be attached via a nitrogen or carbon atom. Representative -(7- to 10-membered)bicycloheterocycles include -quinolinyl, -isoquinolinyl, -2,3-dihydrobenzofuranyl, -1,3-dihydroisobenzofuranyl, -benzo[d][1,3]dioxolyl, -2,3-dihydrobenzo[b]thiophenyl, -1,3-dihydrobenzo[c]thiophenyl, -benzo[d][1,3]dithiolyl, -chromonyl, -chromanyl, -2,3-dihydrobenzo[b][1,4]dioxinyl, -thiochromonyl, -thiochromanyl, -2,3-dihydrobenzo[b][1,4]dithiinyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -indolinyl, -isoindolinyl, -1,2,3,4-tetrahydroquinolinyl, -1,2,3,4-tetrahydroisoquinolinyl, and the like.

"—($C_3$-$C_{12}$)cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative ($C_3$-$C_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—($C_3$-$C_7$)cycloalkoxy" means a saturated monocyclic hydrocarbon having 3, 4, 5, 6, or 7 carbon atoms where at least one of the carbon atoms is replaced by an oxygen atom. Representative ($C_3$-$C_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"(6-membered)aryl" means a 6-membered aromatic carbocyclic moiety such as -phenyl.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 10-membered)heteroaryl comprises at least two heteroatoms independently selected from nitrogen, oxygen, and sulfur. In another embodiment, a bicyclic -(5- to 10-membered)heteroaryl comprises at least two heteroatoms, present in the same or in different rings, each heteroatom being independently selected from nitrogen, oxygen, and sulfur. In another embodiment, one of the -(5- to 10-membered)heteroaryl's rings contain at least one carbon atom. In another embodiment, both of the bicyclic -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- to 9-membered)heteroaryl" means an aromatic heterocycle ring of 5 to 9 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 9-membered)heteroaryl comprises at least two heteroatoms independently selected from nitrogen, oxygen, and sulfur. In another embodiment, a bicyclic -(5- to 9-membered)heteroaryl comprises at least two heteroatoms, present in the same or in different rings, each heteroatom being independently selected from nitrogen, oxygen, and sulfur. In another embodiment, one of the -(5- to 9-membered)heteroaryl's rings contain at least one carbon atom. In another embodiment, both of the bicyclic -(5- to 9-membered)heteroaryl's rings contain at least one carbon atom. Representative -(5- to 9-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have each been independently replaced with a halogen. Representative —CH(halo)$_2$ groups include —CHF$_2$, —CHCl$_2$, —CHBR$^2$, —CHBrCl, —CHClI, and —CHI$_2$.

"—C(halo)$_3$" means a methyl group where each of the hydrogens of the methyl group has been independently replaced with a halogen. Representative —C(halo)$_3$ groups include —CF$_3$, —CCl$_3$, —CBR$^3$, —CI$_3$, —CF$_2$Br, —CF$_2$Cl, —CCl$_2$F, and —CFClBr.

"—Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"(C$_2$-C$_6$)bridge" as used herein means a hydrocarbon chain containing 2 to 6 carbon atoms joining two atoms of the piperidine ring of Substituted Piperidin-4-amino-Type Compounds to form a fused bicyclic ring system. For example, compounds of the disclosure can comprise a (C$_2$-C$_6$)bridge joining positions 2 and 6 of the piperidine ring (A-B can together form a (C$_2$-C$_6$)bridge). Exemplary compounds of the disclosure include those with an unsubstituted (C$_2$)bridge, —CH$_2$—CH$_2$—, joining positions 2 and 6 of the piperidine ring (A-B can together form a (C$_2$) bridge); an unsubstituted (C$_3$)bridge, —CH$_2$—CH$_2$—CH$_2$—, joining positions 2 and 6 of the piperidine ring (A-B can together form a (C$_3$)bridge); an unsubstituted (C$_4$) bridge, —CH$_2$—CH$_2$—CH$_2$—CH$_2$—, joining positions 2 and 6 of the piperidine ring (A-B can together form a (C$_4$)bridge); an unsubstituted (C$_5$)bridge, —CH$_2$—CH$_2$—CH$_2$—CH$_2$—CH$_2$—, joining positions 2 and 6 of the piperidine ring (A-B can together form a (C$_5$)bridge); or an unsubstituted (C$_6$)bridge, —CH$_2$—CH$_2$CH$_2$—CH$_2$—CH$_2$—CH$_2$—, joining positions 2 and 6 of the piperidine ring (A-B can together form a (C$_6$)bridge). Examples of compounds where A-B can together form a (C$_2$-C$_6$)bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a (C$_2$-C$_6$)bridge which contains —HC=CH— within the (C$_2$-C$_6$)bridge include —HC=CH—, —CH$_2$—HC=CH—, —HC=CH—CH$_2$—, —CH$_2$—HC=CH—CH$_2$—, and the like. Examples of a (C$_2$-C$_6$)bridge which contains —O— within the (C$_2$-C$_6$)bridge include —CH$_2$—O—CH$_2$— (containing 2 carbon atoms), —CH$_2$—O—CH$_2$—CH$_2$— and —CH$_2$—CH$_2$—O—CH$_2$— (each containing 3 carbon atoms), —CH$_2$—CH$_2$—O—CH$_2$—CH$_2$—, —CH$_2$—O—CH$_2$—CH$_2$—CH$_2$— and —CH$_2$—CH$_2$—CH$_2$—O—CH$_2$— (each containing 4 carbon atoms), and the like.

In compounds of the disclosure comprising a bridge joining positions 2 and 6 of the piperidine ring (e.g., A-B can together form a (C$_2$-C$_6$)bridge), for, e.g., a Substituted Piperidin-4-amino-Type Compound, the exemplary endo bridge:

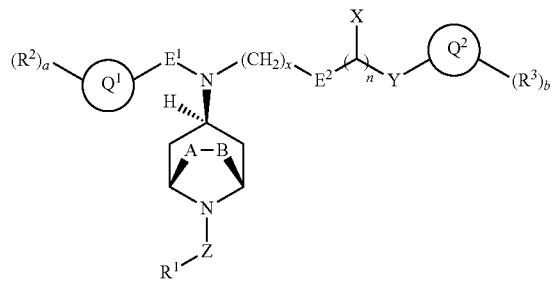

is equivalent to

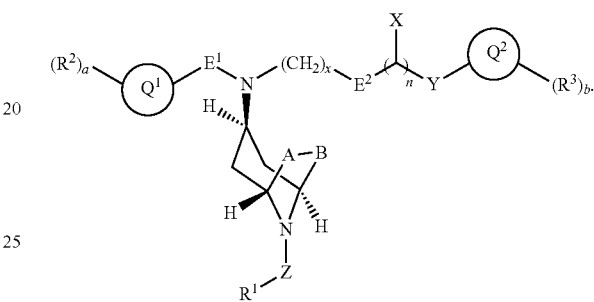

In Substituted Piperidin-4-amino-Type Compounds comprising a bridge joining positions 2 and 6 of the piperidine ring (e.g., A-B can together form a (C$_2$-C$_6$)bridge), for, e.g., a Substituted Piperidin-4-amino-Type Compound, the exemplary exo bridge:

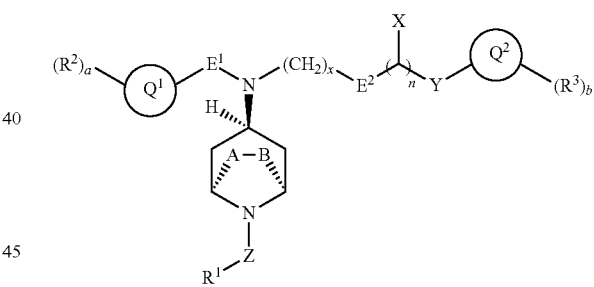

is equivalent to

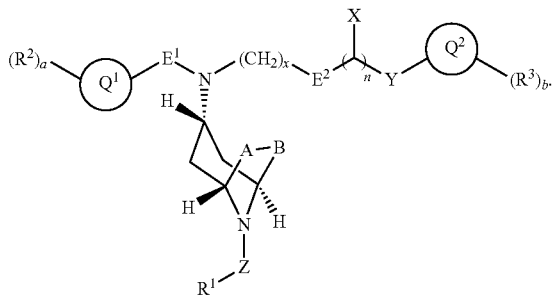

In Substituted Piperidin-4-amino-Type Compounds where the —Z—R$^1$ group comprises a bicyclic group, that bicyclic group can have two orientations. For example, for a —Z—R$^1$ group that is a —(C$_6$-C$_{14}$)bicycloalkyl, e.g., bicyclo[3.3.1]nonanyl, attached directly to the piperidine ring nitrogen, the following orientations are possible:

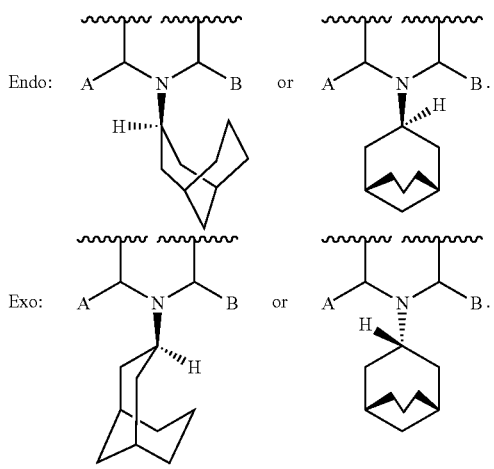

Endo:

Exo:

As used herein in connection with "—[(C$_1$-C$_{10}$)alkyl optionally substituted by R$^{13}$]$_h$—", when h is 1 means that the Z—R$^1$ bonded to the piperidine ring bearing A and B substituents is understood to appear as follows:

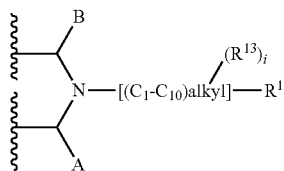

where, when i is 0, the —(C$_1$-C$_{10}$)alkyl- is unsubstituted by a R$^{13}$ group and, when i is 1, the —(C$_1$-C$_{10}$)alkyl- is substituted by a R$^1$ group at the carbon atom furthest removed from the piperidine ring bearing A and B substituents and substituted by a R$^{13}$ group at any carbon atom of the —(C$_1$-C$_{10}$)alkyl-including at the carbon atom furthest removed from the piperidine ring bearing A and B substituents. In one embodiment, R$^{13}$ is selected from:
(a) -halo, —OH, —CH$_2$OH, —CH$_2$CH$_2$OH, —N(R$^6$)$_2$, and —C(=O)OV$^1$; and
(b) —(C$_1$-C$_{10}$)alkyl, —(C$_2$-C$_{10}$)alkenyl, —O(C$_1$-C$_6$)alkyl, —(C$_5$-C$_{14}$)cycloalkenyl, and -(5- or 6-membered)heterocycle, each of which is unsubstituted or substituted with 1, 2, 3, or 4 independently selected R$^8$ groups; and
(c)

(iv)

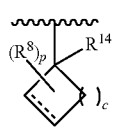

wherein R$^{14}$ is —H and c is an integer selected from 2, 3, 4, 5, 6, and 7;
(d) -phenyl and -(5- or 6-membered)heteroaryl, each of which is unsubstituted or substituted with 1 or 2 independently selected R$^7$ groups.

In another embodiment, R$^{13}$ is selected from:
(a) -halo, —OH, —CH$_2$OH, —CH$_2$CH$_2$OH, —N(R$^6$)$_2$, and —C(=O)OV$^1$; and
(b) —(C$_1$-C$_6$)alkyl, —(C$_2$-C$_6$)alkenyl, —O(C$_1$-C$_4$)alkyl, and -(5- or 6-membered)heterocycle, each of which is unsubstituted or substituted with 1 or 2 independently selected R$^8$ groups; and
(c)

(i)

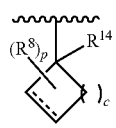

wherein R$^{14}$ is —H and c is an integer selected from 2, 3, 4, 5, 6, and 7;
(d) -phenyl and -(5- or 6-membered)heteroaryl, each of which is unsubstituted or substituted with 1 or 2 independently selected R$^7$ groups.

"—[(C$_2$-C$_{10}$)alkenyl optionally substituted by R$^{13}$]—" as used herein in connection with Z—R$^1$ means that the Z—R$^1$ bonded to the piperidine ring bearing A and B substituents is understood to appear as follows:

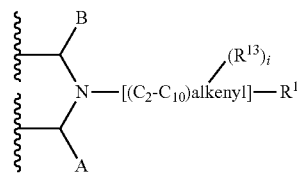

where, when i is 0, the —(C$_2$-C$_{10}$)alkenyl- is unsubstituted by a R$^{13}$ group and, when i is 1, the —(C$_2$-C$_{10}$)alkenyl- is substituted by a R$^1$ group at the carbon atom furthest removed from the piperidine ring bearing A and B substituents and substituted by a R$^{13}$ group at any carbon atom of the —(C$_2$-C$_{10}$)alkenyl-including at the carbon atom furthest removed from the piperidine ring bearing A and B substituents.

As used herein in connection with formula (i) of R$^1$, the dashed line denotes the presence or absence of at bond at that position. When the dashed line denotes the presence of a bond (i.e., there is a double bond at that position), then formula (i) is understood to appear as follows (i)

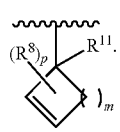

As used herein in connection with formula (i) of R$^1$, when the dashed line denotes the absence of a bond (i.e., there is a single bond at that position), then formula (i) is understood to appear as follows

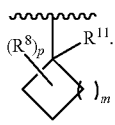

(i)

As used herein in connection with formula (iv) of $R^{13}$, the dashed line denotes the presence or absence of at bond at that position. When the dashed line denotes the presence of a bond (i.e., there is a double bond at that position), then formula (iv) is understood to appear as follows

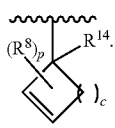

(iv)

When the dashed line denotes the absence of a bond (i.e., there is a single bond at that position), then formula (iv) is understood to appear as follows

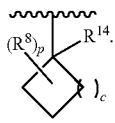

(iv)

The terms "phenyl," "phenyl group" and the like, when used in connection with the $Q^1$ ring, means

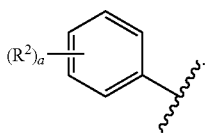

where $R^2$ and a are defined above.

The terms "naphthalenyl," "naphthalenyl group" and the like, when used in connection with the $Q^1$ ring, means

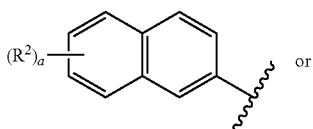

or

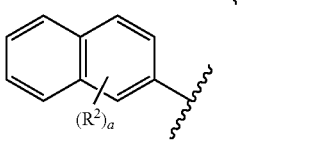

where $R^2$ and a are defined above.

In one embodiment, the naphthalenyl $Q^1$ group is

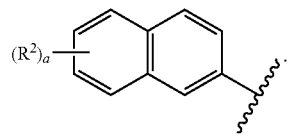

In another embodiment, the naphthalenyl $Q^1$ group is

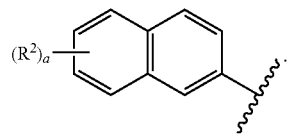

The terms "pyridinyl," "pyridinyl group" and the like, when used in connection with the $Q^1$ ring, means

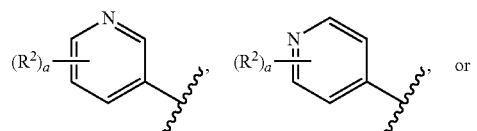

or

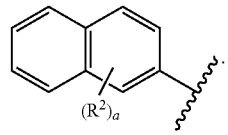

where $R^2$ and a are defined above.

In one embodiment, the pyridinyl $Q^1$ ring is

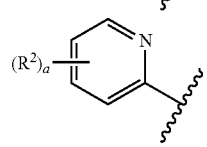

In another embodiment, the pyridinyl $Q^1$ ring is

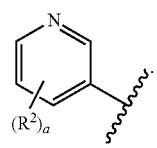

In another embodiment, the pyridinyl $Q^1$ ring is

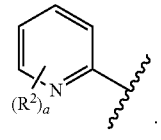

The terms "pyridazinyl", "pyridazinyl group" and the like, when used in connection with the $Q^1$ ring, means

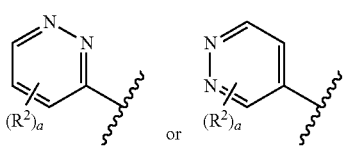 or where R² and a are defined above.

In one embodiment, the pyridazinyl Q¹ ring is

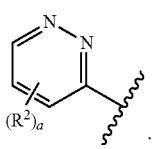

In another embodiment, the pyridazinyl Q¹ ring is

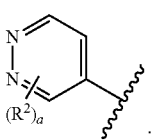

The terms "pyrimidinyl", "pyrimidinyl group" and the like, when used in connection with the Q¹ ring, means

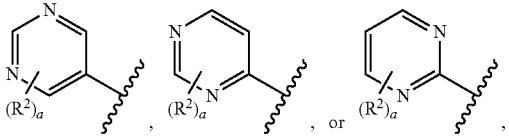

where R² and a are defined above. In one embodiment, the pyrimidinyl Q¹ ring is

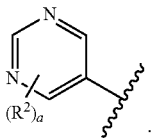

In another embodiment, the pyrimidinyl Q¹ ring is

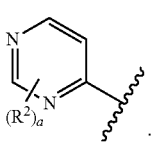

In another embodiment, the pyrimidinyl Q¹ ring is

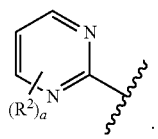

The terms "pyrazinyl", "pyrazinyl group" and the like, when used in connection with the Q¹ ring, means

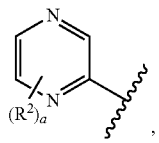, where R² and a are defined above.

The terms "triazinyl", "triazynyl group" and the like, when used in connection with the Q¹ ring, means

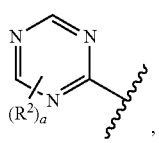, where R² and a are defined above.

The terms "pyrrolidinyl," "pyridinyl group" and the like, when used in connection with the Q² ring, means

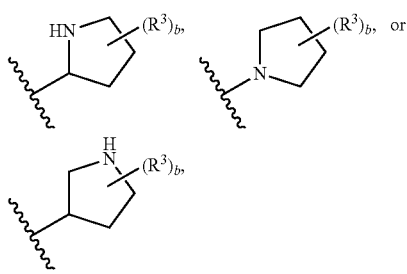

where R² and b are defined above.

In one embodiment, the pyrrolidinyl Q² ring is

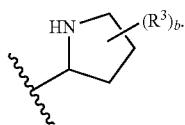

In another embodiment, the pyrrolidinyl Q² ring is

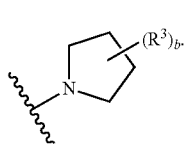

In another embodiment, the pyrrolidinyl $Q^2$ ring is

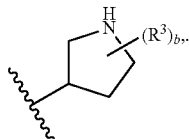

In one embodiment, the term "optionally substituted bicyclo[3.3.1]nonyl" and the like when used in connection with the optionally-substituted $R^1$ group is understood to refer to one of the structures below:

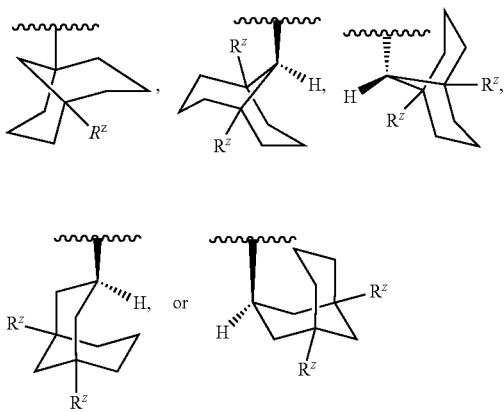

where the substituents are as defined above; and where in one or more embodiments, the optionally substituted $R^1$ group comprises one or more of the above-recited optionally substituted bicycle[3.3.1]nonyl structures.

In one embodiment, the term "optionally substituted —($C_6$-$C_{14}$)bicycloalkyl" means

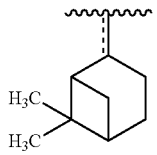

where the dashed line denotes the presence or absence of a bond. When the dashed line is present as a bond to provide one bond of a double bond, then the group above is understood to appear as follows

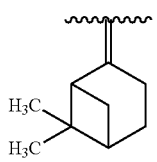

and when the dashed line is absent, then the optionally substituted —($C_6$-$C_{14}$)bicycloalkyl group above is understood to appear as follows

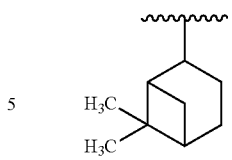

The terms "tetrazolyl," "tetrazolyl group" and the like means

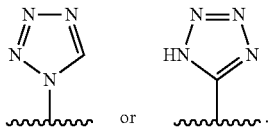 [SMILES: *n1cnnn1 ; "or" ; *c1nnn[nH]1]

In one embodiment, the tetrazolyl group is

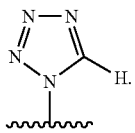

In another embodiment, the tetrazolyl group is

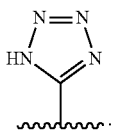

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

In one embodiment, the Substituted Piperidin-4-amino-Type Compound is in the form of a pharmaceutically acceptable salt, solvate, radiolabeled form, stereoisomer, enantiomer, diastereomer, racemic mixture, or tautomer thereof.

The term "pharmaceutically acceptable salt", as used herein, is any pharmaceutically acceptable salt that can be prepared from a Substituted Piperidin-4-amino-Type Compound including a salt formed from an acid and a basic functional group, such as a nitrogen group, of a Substituted Piperidin-4-amino-Type Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. For example, for a Substituted Piperidin-4-amino-Type Compound where D is N(R*)$_2$, a chloride salt can be formed by reacting the compound with HCl to provide the hydrochloride of the Substituted Piperidin-4-amino-Type Compound, e.g., D is N(H)(R*). The term "pharmaceutically acceptable salt" also includes a salt prepared from a Substituted Piperidin-4-amino-Type Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Substituted Piperidin-4-amino-Type Compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Substituted Piperidin-4-amino-Type Compound and 0.5 equivalents of fumaric acid. One skilled in the art will recognize that, e.g., acid addition salts, of a Substituted Piperidin-4-amino-Type Compound can be prepared by reaction of the compounds with the appropriate acid by a variety of known methods.

The Substituted Piperidin-4-amino-Type Compound can be in the form of an anhydrate. The term "anhydrate" as used herein, is any crystalline form of a Substituted Piperidin-4-amino-Type Compound in which water molecules are a non-integral part of the crystal. An anhydrate of a Substituted Piperidin-4-amino-Type Compound can be prepared, for example, by crystallization from a solvent substantially free of water. In one embodiment, the Substituted Piperidin-4-amino-Type Compound is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Substituted Piperidin-4-amino-Type Compound has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Substituted Piperidin-4-amino-Type Compound.

The Substituted Piperidin-4-amino-Type Compound includes all solvates thereof. "Solvates" are known in the art and are considered in view of the this disclosure to be a combination, physical association and/or solvation of a Substituted Piperidin-4-amino-Type Compound with a solvent molecule. This physical association can involve varying degrees of ionic and covalent bonding, including hydrogen bonding. When the solvate is of the stoichiometric type, there is a fixed ratio of the solvent molecule to Substituted Piperidin-4-amino-Type Compound, e.g., a disolvate, monosolvate or hemisolvate when the solvent molecule:Substituted Piperidin-4-amino-Type Compound molecule molar ratio is 2:1, 1:1 or 1:2, respectively. In other embodiments, the solvate is of the nonstoichiometric type. For example, the Substituted Piperidin-4-amino-Type Compound crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. A Substituted Piperidin-4-amino-Type Compound can be present as a solvated form with a pharmaceutically acceptable solvent, such as water, methanol, ethanol, and the like, and it is intended that the disclosure include both solvated and unsolvated Substituted Piperidin-4-amino-Type Compound forms. As "hydrate" relates to a particular subgroup of solvates, i.e., where the solvent molecule is water, hydrates are included within the solvates of the disclosure. In one embodiment, the Substituted Piperidin-4-amino-Type Compound is present as a monohydrate, i.e., as a free base where the water:Substituted Piperidin-4-amino-Type Compound molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and I Hemisolvate," *AAPS Pharm. Sci. Tech.*, 5(1):Article 12 (2004), and Bingham et al., "Over one hundred solvates of sulfathiazole," *Chem. Comm.*, pp. 603-604 (2001). In one embodiment, a non-limiting, process involves dissolving the Substituted Piperidin-4-amino-Type Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

In addition, one or more hydrogen, carbon or other atoms of a Substituted Piperidin-4-amino-Type Compound can be replaced by a radioactive isotope of the hydrogen, carbon or other atoms. Such a "radiolabeled", "radiolabeled form", and the like of a Substituted Piperidin-4-amino-Type Compound, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Substituted Piperidin-4-amino-Type Compound of the disclosure include isotopes of hydrogen, carbon, nitrogen, oxygen, phosphorous, sulfur, fluorine, chlorine, bromine, and iodine, such as $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$C, $^{76}$Br, $^{77}$Br, $^{81}$Br, $^{123}$I, $^{124}$I, $^{125}$I, and $^{131}$I, respectively. In one embodiment, a radiolabeled Substituted Piperidin-4-amino-Type Compound contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Substituted Piperidin-4-amino-Type Compound contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Substituted Piperidin-4-amino-Type Compound contains I radioactive isotope which is selected from hydrogen, carbon, nitrogen, oxygen, phosphorous, sulfur, fluorine, chlorine, bromine, and iodine. In another embodiment, a radiolabeled Substituted Piperidin-4-amino-Type Compound contains 1, 2, 3, 4, or more radioactive isotopes, each of which is independently selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Substituted Piperidin-4-amino-Type Compound contains 1 or 2 radioactive isotopes, each of which is independently selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$C, $^{76}$Br, $^{77}$Br, $^{81}$Br, $^{123}$I, $^{124}$I, $^{125}$I, and $^{131}$I. In another embodiment, a radiolabeled Substituted Piperidin-4-amino-Type Compound contains 1 radioactive isotope which is selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$C, $^{37}$Cl, $^{76}$Br, $^{77}$Br, $^{81}$Br, $^{123}$I, $^{124}$I, $^{125}$I, and $^{131}$I. In another embodiment, a radiolabeled Substituted Piperidin-4-amino-Type Compound contains 1, 2, 3, 4, or more radioactive isotopes, each of which is independently selected from $^{2}$H, $^{3}$H, $^{13}$C, $^{14}$C, $^{15}$N, $^{18}$O, $^{32}$P, and $^{125}$I. In another embodiment, a radiolabeled Substituted Piperidin-4-amino-Type Compound contains 1 or 2 radioactive isotopes, each of which is independently selected from $^{3}$H, $^{14}$C, $^{15}$N, $^{18}$O, $^{32}$P, and $^{125}$I. In another embodiment, a radiolabeled Substituted Piperidin-4-amino-Type Compound contains 1 radioactive isotope which is selected from $^{3}$H, $^{14}$C, $^{15}$N, $^{18}$O, $^{32}$P, and $^{125}$I.

Radiolabeled compounds of the disclosure can be prepared by methods known in the art. For example, tritiated Substituted Piperidin-4-amino-Type Compounds can be prepared by introducing tritium into the particular Substituted Piperidin-4-amino-Type Compound, for example, by catalytic dehalogenation with tritium. This method can include reacting a suitably halogen-substituted precursor of a Substituted Piperidin-4-amino-Type Compound with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences*, Vol. 1, *Labeled Compounds* (Part A), E. Buncel et al, eds., Chapter 6, pp. 155-192 (1987). $^{14}$C-labeled compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2. Radiolabeled compounds containing $^{18}$F at the 6-position of an aniline ring can be prepared as described in column 27 of U.S. Pat. No. 6,562,319 B2.

A Substituted Piperidin-4-amino-Type Compound can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When a Substituted Piperidin-4-amino-Type Compound contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Substituted Piperidin-4-amino-Type Compound can be obtained by known techniques such as chiral chromatography or formation of diastereomeric salts from an optically active acid or base.

Optical purity can be stated in terms of enantiomeric excess (% ee) and/or diastereomeric excess (% de), each which is determined by the appropriate formula below:

$$\% \ ee = \left[\frac{\text{major enantiomer (mol)} - \text{minor enantiomer (mol)}}{\text{major enantiomer (mol)} + \text{minor enantiomer (mol)}}\right] \times 100\%$$

$$\% \ de = \left[\frac{\text{major diastereomer (mol)} - \text{minor diastereomers (mol)}}{\text{major diastereomer (mol)} + \text{minor diastereomers (mol)}}\right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or CH$_2$Cl$_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "NMP" means N-methylpyrrolidinone, i.e., 1-methylpyrrolidin-2-one. The term "DMA" means N,N-dimethylacetamide. The term "MTBE" means tert-butyl methyl ether, i.e., 2-methoxy-2-methylpropane. The term "AcOH" means acetic acid. The term "TFA" means 2,2,2-trifluoroacetic acid. The terms "TEA" and "Et$_3$N" means triethylamine. The term "DIEA" means diisopropylethylamine, i.e., N-ethyl-N-isopropylpropan-2-amine. The term "Bn" means benzyl, i.e.:

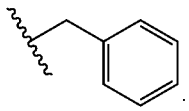

The term "BOC" means tert-butyloxycarbonyl, i.e.:

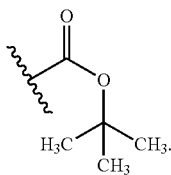

The term "IBD" means inflammatory-bowel disease. The term "IBS" means irritable-bowel syndrome. The term "ALS" means amyotrophic lateral sclerosis.

The term "effective amount", when used in connection with a Substituted Piperidin-4-amino-Type Compound, means an amount effective for: (a) treating or preventing a Condition or symptom thereof; (b) detectably inhibiting ORL-1 receptor function in a cell; or (c) detectably activating ORL-1 receptor function in a cell.

The term "effective amount", when used in connection with a second therapeutic agent means an amount for providing the therapeutic effect of the second therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10$^{th}$ Ed., McGraw-Hill, New York 2001)).

The terms "treatment of", "treating", and the like include the amelioration or cessation of a Condition or a symptom thereof. In one embodiment, treating includes inhibiting, for example, decreasing the overall frequency of episodes of a Condition or a symptom thereof.

The terms "prevention of", "preventing", and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.3 Methods for Making Substituted Piperidin-4-amino-Type Compounds

Substituted Piperidin-4-amino-Type Compounds can be made using conventional organic synthesis, in view of the present disclosure, and including the following illustrative methods shown in the schemes below where R$^1$, R$^2$, R$^3$, R*, E$^1$, E$^2$, Q$^1$, Q$^2$, D, W, a, b, x, and n are defined above, L is a halogen leaving group such as Br or I, and R is —(C$_1$-C$_4$)alkyl or —CF$_3$. For simplicity, in the following schemes the exemplary Q$^1$ group is phenyl which is sometimes unsubstituted with R$^2$; however, the schemes are also applicable to substituted phenyl and any of the Q$^1$ groups described herein, whether unsubstituted or substituted. Also for simplicity, in the following schemes A to F, E$^1$ is shown as a direct bond; however, the schemes are also applicable where E$^1$ is CH$_2$. When E$^1$ is C(=O), C(=S) or S(=O)$_q$, substituted Piperidin-4-amino-Type Compounds can be made as shown in the following schemes G, H and I. Also for simplicity, in the following scheme G, E$^1$ is shown as C(=O); however, the scheme is also applicable where E$^1$ is S(=O)$_2$.

Section 4.3.1 describes a general scheme for making Substituted Piperidin-4-amino Type Compounds. Section 4.3.2 describes a scheme for making Substituted Piperidin- 4-amino Type Compounds where x is 0, $E^2$ is C(=O), W is a direct bond, and $Q^2$ is a nitrogen containing heterocycle (referred to as a compound of Formula (Ia)), and Substituted Piperidin-4-amino Type Compounds of Formula (I) where x is 0, $E^2$ is C(=O), and W is N(R*) (referred to as a compound of Formula (Ib)). Section 4.3.3 describes a scheme for making Substituted Piperidin-4-amino Type Compounds of Formula (I) having the same substituent attached to the 4-amino nitrogen and the nitrogen which is part of an $R^2$ group (referred to as a compound of Formula (Ic)).

4.3.1 Methods for Making Substituted Piperidin-4-amino Type Compounds (Scheme A)

Preparation of Substituted Piperidin-4-amino Type Compounds can be carried out as shown in Scheme A below.

sium carbonate, as described in reference "Lit 1" to provide the 1-(substituted)piperidine-4-one Compound A3. As described in reference "Lit 2," Compound A3 can also be prepared by alkylation of a piperidine-4-one of structure A2 with an alkyl bromide or alkyl iodide in a suitable solvent, such as dimethyl formamide, MeCN or DMSO, in the presence of an inorganic base, such as potassium carbonate, or an organic base, such as DIEA. As described in reference "Lit 2," Compound A3 can also be prepared by reductive amination of Compound A2 with an aldehyde or ketone using either sodium triacetoxyborohydride or sodium cyanoborohydride in a suitable solvent, such as DCM or MeOH, respectively. Compound A3 can then be reductively aminated with a substituted or unsubstituted phenylamine using sodium triacetoxyborohydride or sodium cyanoborohydride

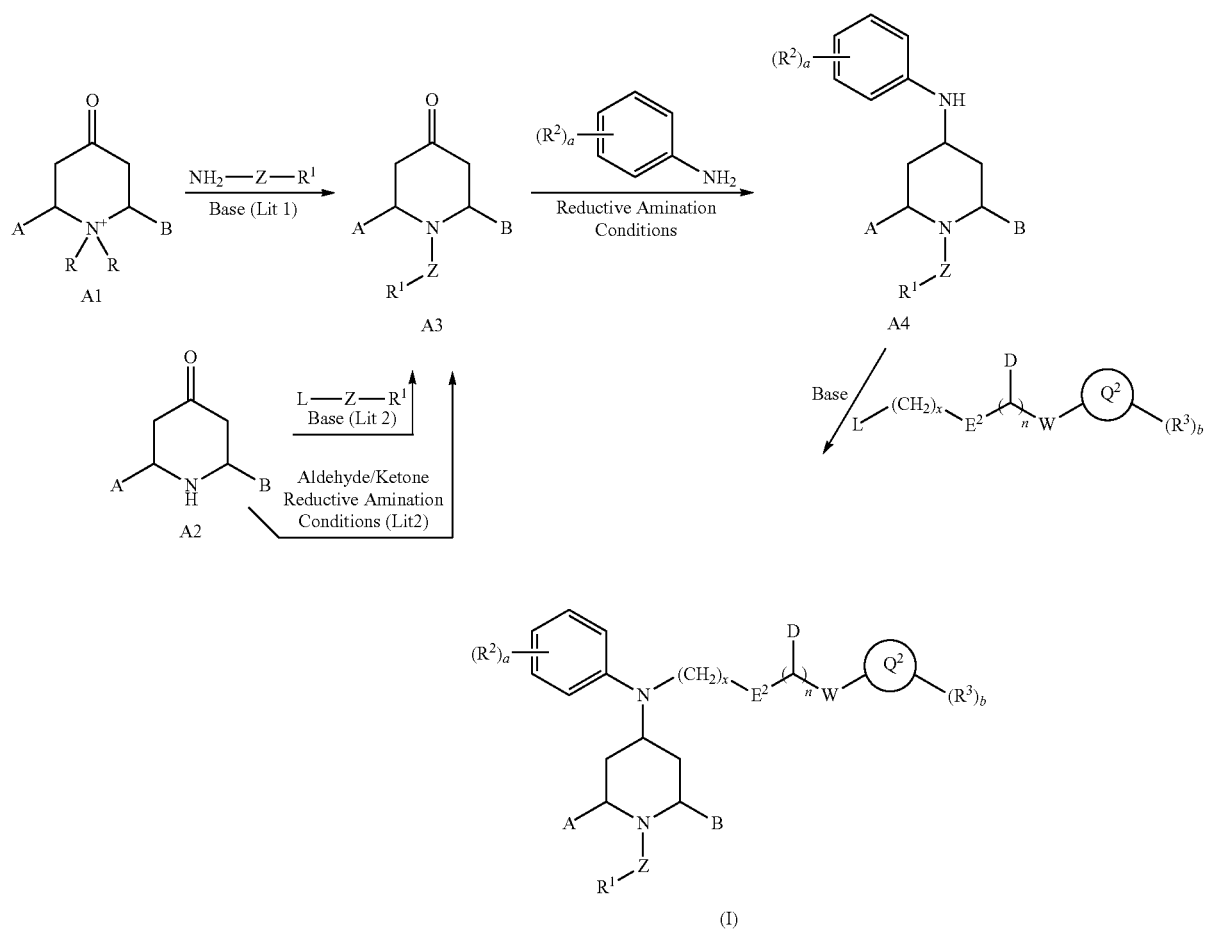

Scheme A

In Scheme A and the other schemes, "Lit 1" refers to the procedures described in the publications Tortolani et al., "A Convenient Synthesis to N-Aryl-Substituted 4-Piperidones," *Org. Lett.* 1:1261-1262 (1999) and/or International PCT Publication No. WO 2005/075459 A1 of Euro-Celtique S.A., and "Lit 2" refers to the procedures described in U.S. Pat. No. 6,635,653 by Goehring et al.

Compounds A1 and A2 are commercially available or can be prepared by methods known to the art.

A piperidinium salt of structure A1 can be reacted with a primary amine in a suitable solvent, such as EtOH, under reflux conditions in the presence of a base, such as potasin a suitable solvent, such as DCM or MeOH, respectively, to provide Compound A4. Compound A4 can be dissolved in a suitable solvent, such as toluene, and reacted with a halocarbon compound in the presence of a base, such as NaH, to provide a Compound of Formula (I).

4.3.2 Method for Making Substituted Piperidin-4-amino Type Compounds of Formula (Ia) and Formula (Ib) (Scheme B)

Preparation of Substituted Piperidin-4-amino Type Compounds of Formula (Ia) and (Ib) can be carried out as shown in Scheme B below.

Scheme B

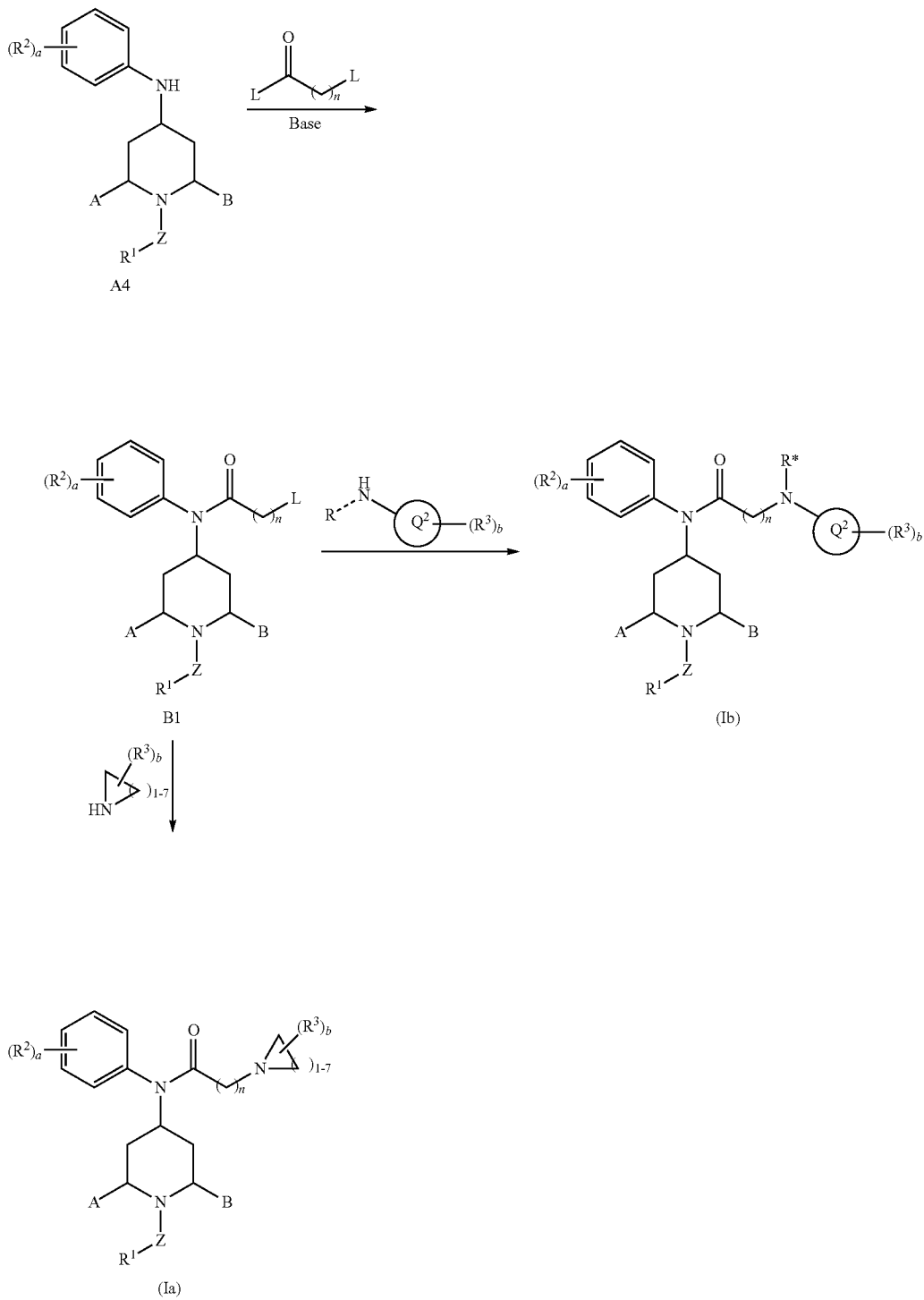

Compound A4 can be prepared by the methods described in Section 4.3.1.

Compound A4 can be dissolved in a suitable solvent, such as ethyl acetate, and reacted with a dihalogenated aldehyde as shown in Scheme B in the presence of a base, such as TEA, to provide Compound B1. Compound B1 can be dissolved in a suitable solvent, such as DMF, and reacted with an cyclic or cyclic amine as shown in Scheme B to provide Substituted Piperidin-4-amino-Type Compounds of Formula (Ia) or (Ib), respectively.

4.3.3 Method for Making Substituted Piperidin-4-amino Type Compounds of Formula (Ic) (Scheme C)

Preparation of Substituted Piperidin-4-amino Type Compounds of Formula (Ic) can be carried out as shown in Scheme C below.

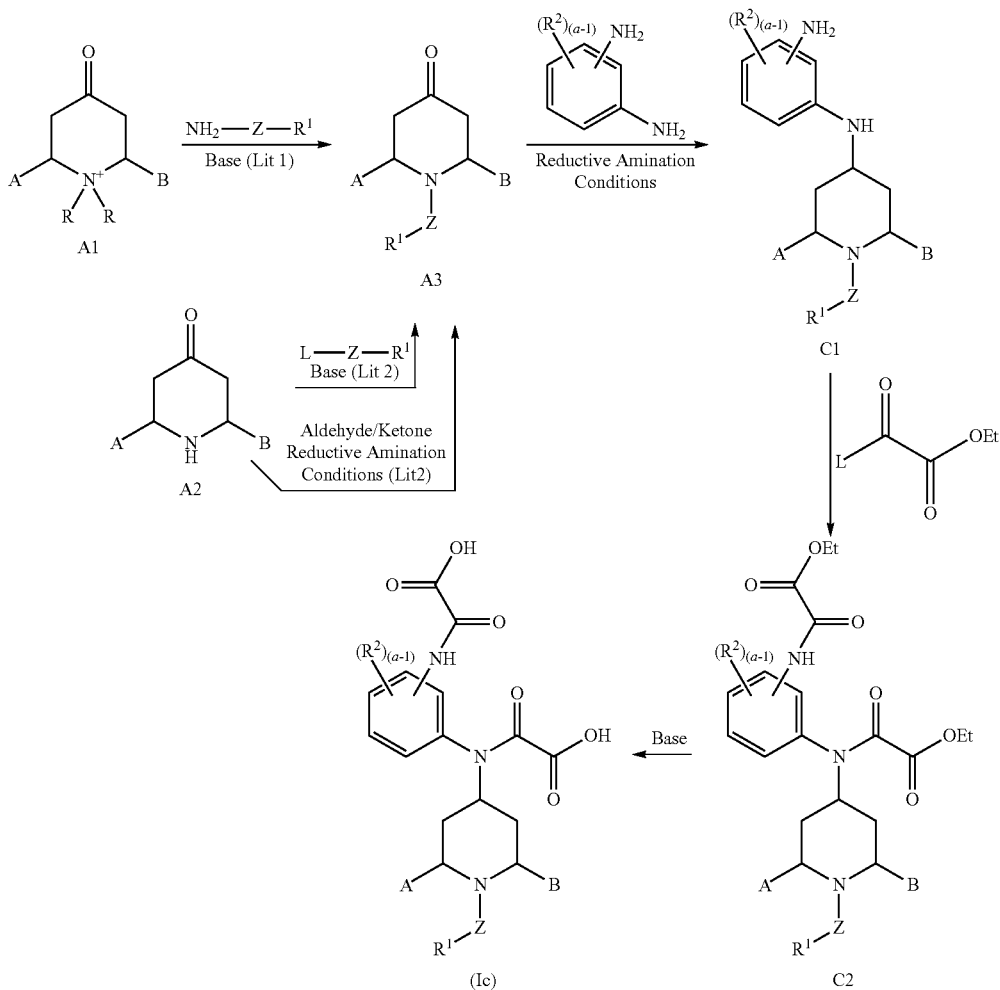

Scheme C

Compounds A1, A2, and A3 can be obtained as described in Section 4.3.1. Compound A3 can be reductively aminated with a substituted or unsubstituted phenylenediamine using sodium triacetoxyborohydride or sodium cyanoborohydride in a suitable solvent, such as DCM or MeOH, respectively, to provide compound C1. Compound C1 can be dissolved in a suitable solvent, such as DCM, and reacted with ethyl 2-halo-2-oxoacetate to provide compound C2. For simplicity, ethyl 2-halo-2-oxoacetate is shown in Scheme C; however, the scheme is applicable to reactions using other halogenated reagents providing compounds of Formula I as defined herein. Compound C2 can be dissolved in a suitable solvent, such as ethanol, and reacted with a suitable base, such as NaOH, to provide a Substituted Piperidin-4-amino-Type Compound of Formula (Ic).

4.3.4 Methods for Making Specific Stereoisomeric Forms of Substituted Piperidin-4-amino-Type Compounds Specific stereoisomeric forms of Substituted Piperidin-4-amino-Type Compounds can be prepared using methods described above. As described below, the desired stereochemical form can be introduced into the optionally-bridged piperidine portion of the molecule prior to the addition of the portion of the molecule attached at the 4 position of the piperidine ring.

4.3.4.1 Synthesis of Stereoisomeric Forms of Substituted Piperidin-4-amino-Type Precursors (Scheme D)

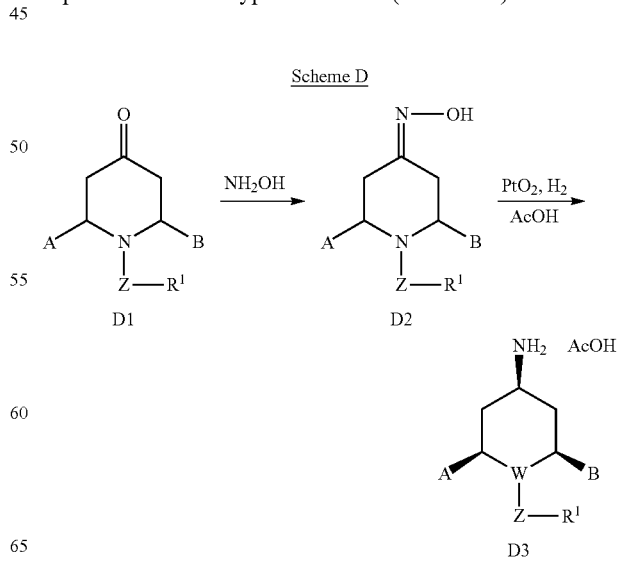

Scheme D

In Scheme D, Compound D3 can be prepared according to the methods described in U.S. Patent Application Publication US 2010/0216726 A1, for example, at paragraph [1745] and thereafter. Briefly, Compound D1 can be converted to oxime Compound D2 using aqueous hydroxylamine in an acidic solvent, such as AcOH. Compound D2 can be reduced to an endo amine Compound D3 by hydrogenation using a noble metal catalyst, such as platinum oxide, in a solvent, such as AcOH.

4.3.4.2 Alternative Synthesis of Stereoisomeric Forms of Substituted Piperidin-4-amino-Type Precursors (Scheme E)

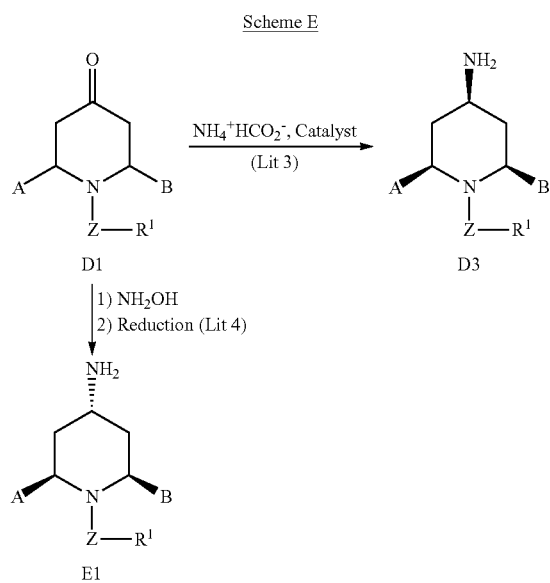

In Scheme T and the other schemes, "Lit 3" refers to Berdini et al., "A Modified Palladium Catalyzed Reductive Amination Procedure," *Tetrahedron,* 58:5669-5674 (2002) and "Lit 4" refers to Lewin et al., "Molecular Features Associated with Polyamine Modulation of NMDA Receptors," *J. Med. Chem.* 41:988-995 (1998).

Compound S1, where substituent groups A and B together form a bridge, e.g., a two carbon bridge, is commercially available or can be prepared by methods known to the art.

When substituent groups A and B together form a bridge, e.g., a two carbon bridge, Compound D1 can be converted to Compound D3, the "endo" isomer, under reductive amination conditions using, e.g., ammonium formate and a noble metal catalyst, e.g., palladium on carbon, in a solvent, such as EtOH or MeOH, as described in reference "Lit 3." Similarly, where substituent groups A and B together form a bridge, e.g., a two carbon bridge, Compound D1 can be reacted with aqueous hydroxylamine in a solvent, such as hexanes, to form an intermediate hydroxylamine, which can be converted to its oxime by dehydration in a solvent with a high boiling point, such as toluene, under Dean-stark conditions. The oxime intermediate can be converted to Compound E1, the "exo" isomer, by reduction using, e.g., sodium in propanol as described in reference "Lit 4."

4.3.4.3 Synthesis of Stereoisomeric Forms of Substituted Piperidin-4-amino-Type Compounds from Compound D3 (Scheme F)

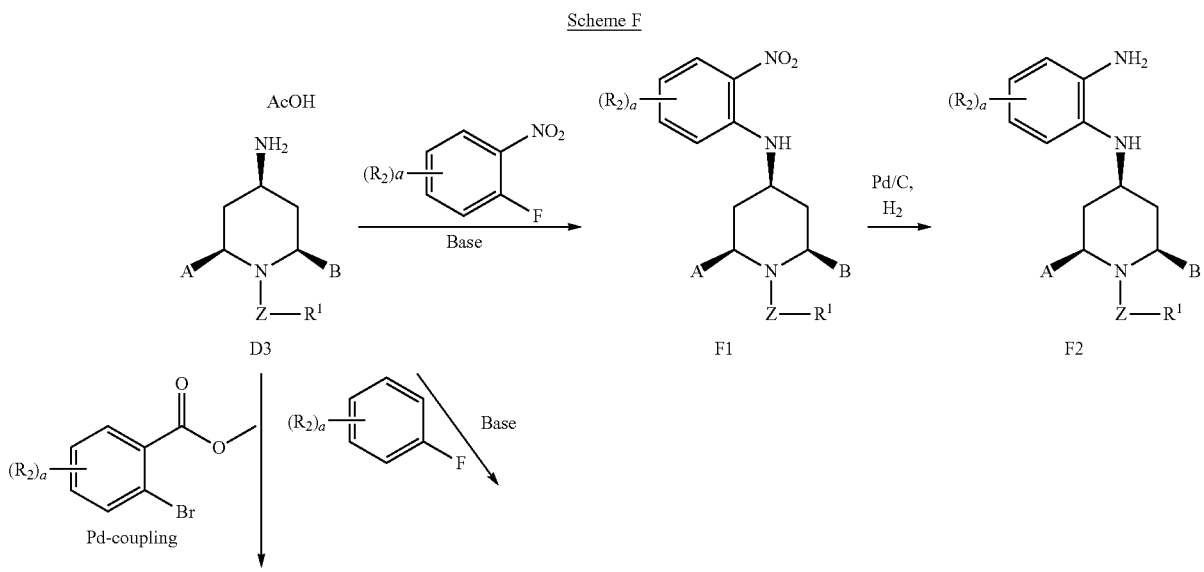

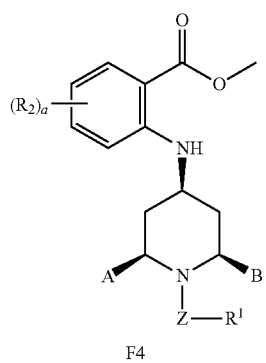

F4

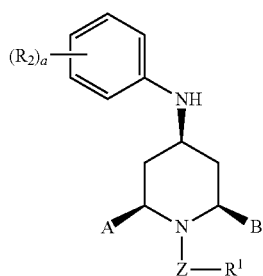

F3

In Scheme F, Compound F2 can be prepared according to the methods described in U.S. Patent Application Publication US 2010/0216726 A1, for example, at paragraph [1745] and thereafter. Briefly, amine Compound D3 or its salt, such as the acetate, can be reacted with a substituted or unsubstituted 2-fluoronitrobenzene in a polar solvent, such as MeCN or DMF, and a base, such as TEA or potassium carbonate, to provide Compound F1. Compound F1 can be reduced to Compound F2 by hydrogenation using a noble metal catalyst, such as palladium on charcoal or Raney nickel, in a solvent, such as EtOAc or DCM. Thereafter, a Substituted Piperidin-4-amino-Type Compound of Formula (Ic) can be prepared using methods described in Section 4.3.3. Compound F3 can be prepared by reacting compound D3 or its salt, such as the acetate, with a substituted or unsubstituted fluorobenzene in a polar solvent, such as MeCN or DMF, and a base, such as TEA or potassium carbonate, to provide Compound F3. Compound F4 can be prepared by reacting compound D3 or its salt, such as the acetate, with a substituted or unsubstituted methyl 2-bromobenzoate in a toluene and cesium carbonate as the base to provide Compound F4. Thereafter, a Substituted Piperidin-4-amino-Type Compound can be prepared using methods described in Sections 4.3.1-4.3.2.

4.3.4 Method for Making Substituted Piperidin-4-amino Type Compounds of Formula (I) where $E^1$ is C(=O) or S(=O)$_2$ (Scheme G)

Preparation of Substituted Piperidin-4-amino Type Compounds of Formula (I) where $E^1$ is C(=O) or S(=O)$_2$ can be carried out as shown in Scheme G below.

Scheme G

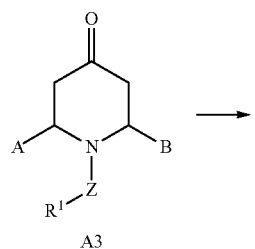

A3

-continued

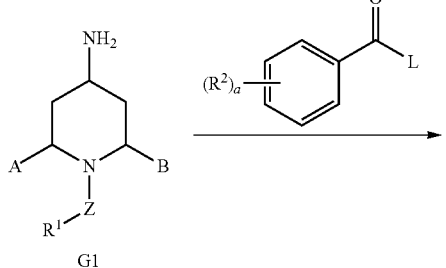

G1

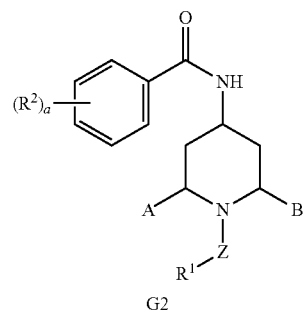

G2

In Scheme G, Compound G1 can be prepared according to Scheme D or Scheme E. Compound G1 can be dissolved in a suitable solvent, such as toluene, CH$_3$CN, THF or CH$_2$Cl$_2$, and reacted with a halocarbon compound in the presence of a base, such as NaH, K$_2$CO$_3$, Et$_3$N or pyridine, to provide Compound G2. Thereafter, a Substituted Piperidin-4-amino-Type Compound of Formula (I) can be prepared using methods described in Sections 4.3.1-4.3.2.

4.3.4 Method for Making Substituted Piperidin-4-amino Type Compounds of Formula (I) where $E^1$ is C(=S) (Scheme H)

Preparation of Substituted Piperidin-4-amino Type Compounds of Formula (I) where $E^1$ is C(=S) can be carried out as shown in Scheme H below.

Scheme H

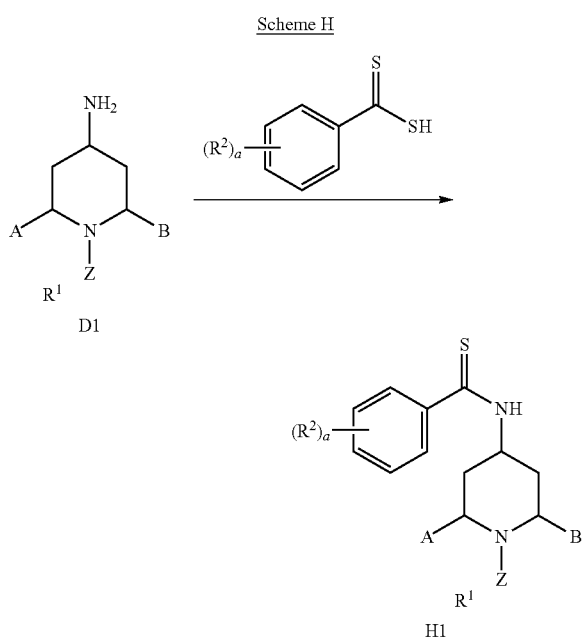

In Scheme H, Compound D1 can be dissolved in a suitable solvent, such as $CCl_4$, and reacted with a dithioic acid compound in the presence of $SCl_4$ to provide Compound H1. Thereafter, a Substituted Piperidin-4-amino-Type Compound of Formula (I) can be prepared using methods described in Sections 4.3.1-4.3.2.

4.3.4 Method for Making Substituted Piperidin-4-amino Type Compounds of Formula (I) where $E^1$ is $S(=O)$ (Scheme I)

Preparation of Substituted Piperidin-4-amino Type Compounds of Formula (I) where $E^1$ is $S(=O)$ can be carried out as shown in Scheme I below.

Scheme I

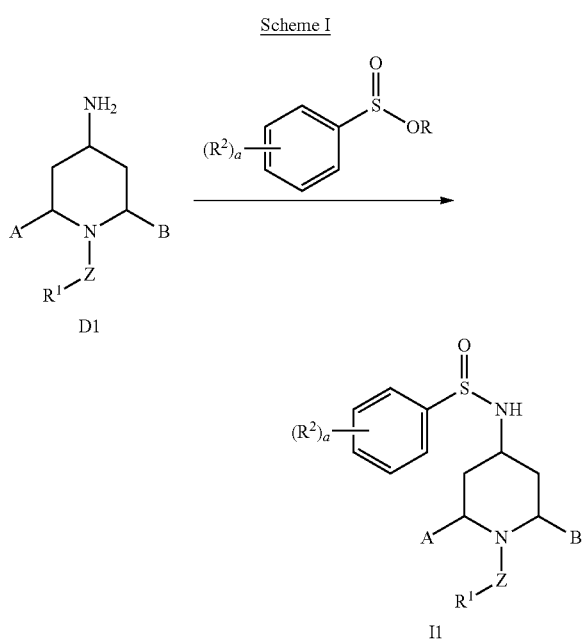

In Scheme I, Compound D1 can be dissolved in a suitable solvent, such as THF, and reacted with a sulfinic ester compound in the presence of a base, such as BuLi, to provide Compound 11. Thereafter, a Substituted Piperidin-4-amino-Type Compound of Formula (I) can be prepared using methods described in Sections 4.3.1-4.3.2.

In these embodiments, the final product of the reaction, i.e., the Substituted Piperidin-4-amino-Type Compound, has a percent diastereomeric excess (% de) of at least about 90%. In another embodiment, the final product of the reaction has a % de of at least about 95%. In another embodiment, the final product of the reaction has a % de of at least about 97%. In another embodiment, the final product of the reaction has a % de of at least about 98%. In another embodiment, the final product of the reaction has a % de of at least about 99%. In another embodiment, the final product of the reaction has a % de of greater than 99% (e.g., 99.1% to 99.9%).

4.4 Therapeutic Uses of the Substituted Piperidin-4-Amino-Type Compounds

In accordance with the disclosure, the Substituted Piperidin-4-amino-Type Compounds are administered to an animal in need of treatment or prevention of a Condition.

In one embodiment, an effective amount of a Substituted Piperidin-4-amino-Type Compound can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, and Parkinsonism.

In another embodiment, an effective amount of a Substituted Piperidin-4-amino-Type Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Substituted Piperidin-4-amino-Type Compounds can be used to treat or prevent acute or chronic pain. Examples of pain that can be treated or prevented using a Substituted Piperidin-4-amino-Type Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Substituted Piperidin-4-amino-Type Compounds can also be used to treat or prevent pain associated with inflammation or with an inflammatory disease in an animal. Such pain can arise where there is an inflammation of the body tissue, which can be a local inflammatory response or a systemic inflammation. For example, a Substituted Piperidin-4-amino-Type Compound can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immunecomplex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Substituted Piperidin-4-amino-Type Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Substituted Piperidin-4-amino-Type Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Substituted Piperidin-4-amino-Type Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Substituted Piperidin-4-amino-Type Piperidine Compounds can be used to treat or prevent a sleep disorder including, but not limited to, insomnia, hypersomnia, sleep deprivation, sleep apnea, dysomnia, delayed sleep phase syndrome (DSPS), advanced sleep phase syndrome (ASPS), non-24-hour sleep-wake syndrome (e.g., circadian rhythm sleep disorder), situational circadian rhythm sleep disorders (e.g., jet lag, shift work sleep disorders), hypopnea, irregular sleep wake rhythm, nightmares, night terror, parasomnia, restless leg syndrome (RLS), nocturnal mycolonus/periodic limb movement disorder (PLMD), rapid eye movement (REM) sleep disorder, somnambulism/sleep walking, somniloquy/sleep talking, and somniphobia. For example, U.S. Pat. No. 8,003,669 discloses a class of ORL-1 agonists said to be therapeutic agents for circadian rhythm sleep disorder and Miyakawa et al. disclose that administration of the ORL-1 receptor agonist known as W-212393 induces phase advance of locomotor activity circadian rhythm in mice ("ORL1 receptor-mediated down-regulation of mPER2 in the suprachiasmatic nucleus accelerates re-entrainment of the circadian clock following a shift in the environmental light/dark cycle," *Neuropharmacol.* 52:1055-1064 (2007)).

Metabolic disorders can be caused by an abnormal metabolic process and can be acquired, e.g., failure of a metabolically important organ such as the liver or disease of an endocrine organ, or congenital, e.g., an inherited enzyme abnormality. A congenital metabolic disorder can be caused by a defect in a single gene; some of the more well-known inborn metabolic errors include sickle cell anemia, hypothyroidism, Tay-Sachs disease, phenylketonuria, and cystic fibrosis. The Substituted Piperidin-4-amino-Type Piperidine Compounds can be used to treat or prevent a metabolic disorder including, but not limited to, anorexia nervosa, bulimia, and obesity. For example, U.S. Pat. No. 7,241,770 discloses a class of hydronopol derivative ORL-1 agonists said to be therapeutic agents for metabolic disorders.

A renal disorder may be acute or chronic. An acute renal disorder can be caused by impaired blood flow to the kidneys due to, e.g., blood loss, heart attack, or liver failure; kidney damage due to, e.g., blood clots, hemolytic uremic syndrome, or vasculitis; or urine blockage due to, e.g., bladder cancer, an enlarged prostate, or kidney stones. A chronic renal disorder can be caused by, e.g., diabetes mellitus, hypertension, or polycystic kidney disease. The Substituted Piperidin-4-amino-Type Piperidine Compounds can be used to treat or prevent a renal disorder including, but not limited to, those renal disorders characterized by the syndrome of inappropriate antidiuretic hormone secretion (SIADH) or by imbalances of water retention and/or water excretion or salt excretion. For example, U.S. Pat. No. 6,869,960 discloses a class of spiropiperidine ORL-1 ligands said to be therapeutic agents for renal disorders.

Cardiovascular disorders represent the leading cause of death in the United States, responsible for about 27% of yearly deaths. Cardiovascular disorders can be caused by tobacco use, alcohol abuse, obesity, diabetes mellitus, high cholesterol, high blood pressure, and other factors. The Substituted Piperidin-4-amino-Type Piperidine Compounds can be used to treat or prevent a cardiovascular disorder including, but not limited to, myocardial infarction, arrhythmias, bradycardia, hypertension, hypotension, thrombosis, anemia, arteriosclerosis, and angina pectoris. For example, U.S. Pat. No. 7,241,770 discloses a class of hydronopol derivative ORL-1 agonists said to be therapeutic agents for cardiovascular disorders.

According to the disclosure, some of the Substituted Piperidin-4-amino-Type Compounds are agonists at the ORL-1 receptor, some of the Substituted Piperidin-4-amino-Type Compounds are partial agonists at the ORL-1 receptor, and some of the Substituted Piperidin-4-amino-Type Compounds are antagonists at the ORL-1 receptor. In another embodiment, a Substituted Piperidin-4-amino-Type Compound is an agonist at the ORL-1 receptor and an agonist at a μ, κ and/or δ opioid receptor, particularly at a μ opioid receptor. In another embodiment, a Substituted Piperidin-4-amino-Type Compound is a partial agonist at the ORL-1 receptor and an agonist at a μ, κ and/or δ opioid receptor, particularly at a μ opioid receptor. In another embodiment, a Substituted Piperidin-4-amino-Type Compound is an antagonist at the ORL-1 receptor and an agonist at a μ, κ and/or δ opioid receptor, particularly at a μ opioid receptor. In another embodiment, a Substituted Piperidin-4-amino-Type Compound is an agonist at the ORL-1 receptor and an antagonist at a μ, κ and/or δ opioid receptor, particularly at a opioid receptor. In another embodiment, a Substituted Piperidin-4-amino-Type Compound is a partial agonist at the ORL-1 receptor and an antagonist at a μ, κ and/or δ opioid receptor, particularly at a opioid receptor. In another embodiment, a Substituted Piperidin-4-amino-Type Compound is an antagonist at the ORL-1 receptor and an antagonist at a μ, κ and/or δ opioid receptor, particularly at a μ opioid receptor.

The disclosure also provides methods for inhibiting ORL-1 receptor function in a cell, comprising contacting a cell capable of expressing the ORL-1 receptor with an amount of a Substituted Piperidin-4-amino-Type Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Substituted Piperidin-4-amino-Type Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The disclosure also relates to methods for activating ORL-1 receptor function in a cell, comprising contacting a cell capable of expressing the ORL-1 receptor with an amount of a Substituted Piperidin-4-amino-Type Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Substituted Piperidin-4-amino-Type Compound. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "IIdentification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

4.5 Therapeutic/Prophylactic Administration and Compositions of the Disclosure

Due to their activity, the Substituted Piperidin-4-amino-Type Compounds are advantageously useful in human and veterinary medicine. As described above, the Substituted Piperidin-4-amino-Type Compounds are useful for treating or preventing a Condition in an animal in need thereof. The Substituted Piperidin-4-amino-Type Compounds of the disclosure can be administered to any animal requiring modulation of the opioid and/or ORL-1 receptors.

When administered to an animal, a Substituted Piperidin-4-amino-Type Compound can be administered as a component of a composition that comprises a pharmaceutically acceptable carrier or excipient. The compositions, which comprise a Substituted Piperidin-4-amino-Type Compound, can be administered orally. A Substituted Piperidin-4-amino-Type Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Substituted Piperidin-4-amino-Type Compound.

Methods of administration include, but are not limited to, intradermal, intramuscular, intraperitoneal, parenteral, intravenous, subcutaneous, intranasal, epidural, oral, sublingual, intracerebral, intravaginal, transdermal (e.g., via a patch), rectal, by inhalation, transmucosal, or topical, particularly to the ears, nose, eyes, or skin. The method of administration is left to the discretion of the practitioner. In some instances, administration will result in the release of a Substituted Piperidin-4-amino-Type Compound into the bloodstream. In other instances, administration will result in only local release of a Substituted Piperidin-4-amino-Type Compound.

In specific embodiments, it can be desirable to administer a Substituted Piperidin-4-amino-Type Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Substituted Piperidin-4-amino-Type Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Substituted Piperidin-4-amino-Type Compound can be formulated as a suppository, with traditional binders and excipients such as triglycerides.

When a Substituted Piperidin-4-amino-Type Compound is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Substituted Piperidin-4-amino-Type Compound can also be in the form of a powder for reconstitution as an injectable formulation.

In another embodiment, a Substituted Piperidin-4-amino-Type Compound can be delivered in a vesicle, in particular a liposome (see Langer, "New Methods of Drug Delivery," *Science* 249:1527-1533 (1990); and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, a Substituted Piperidin-4-amino-Type Compound can be delivered in a controlled-release system or sustained-release system (see, e.g., Goodson, "Dental Applications," in *Medical Applications of Controlled Release*, Vol. 2, Applications and Evaluation, Langer and Wise, eds., CRC Press, Chapter 6, pp. 115-138 (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105-112 (1989)). In yet another embodiment, a controlled- or sustained-release system can be placed in proximity of a target of a Substituted Piperidin-4-amino-Type Compound, e.g., the spinal column, brain, or gastrointestinal tract, thus requiring only a fraction of the systemic dose.

Compositions of the disclosure can preferably further comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Substituted Piperidin-4-amino-Type Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, EtOH, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, DC, 1986), incorporated herein by reference.

Compositions of the disclosure can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences Vol.* 2 (Gennaro, ed., 19$^{th}$ Ed., Mack Publishing, Easton, Pa., 1995), incorporated herein by reference.

In one embodiment, the Substituted Piperidin-4-amino-Type Compounds are formulated in accordance with routine procedures as a composition adapted for oral administration to human beings. A Substituted Piperidin-4-amino-Type Compound to be orally delivered can be in the form of tablets, capsules, gelcaps, caplets, lozenges, aqueous or oily solutions, suspensions, granules, powders, emulsions, syrups, or elixirs, for example. When a Substituted Piperidin-4-amino-Type Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman et al., eds., 2$^{nd}$ Ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in

*Remington's Pharmaceutical Sciences* (Osol, ed., 16th Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., $2^{nd}$ Ed., Marcel Dekker, Inc., 1996 & 1998).

When a Substituted Piperidin-4-amino-Type Compound is to be injected parenterally, it can be, e.g., in the form of an isotonic sterile solution. Alternatively, when a Substituted Piperidin-4-amino-Type Compound is to be inhaled, it can be formulated into a dry aerosol or can be formulated into an aqueous or partially aqueous solution.

An orally administered Substituted Piperidin-4-amino-Type Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Substituted Piperidin-4-amino-Type Compounds can be formulated for intravenous administration. In certain embodiments, compositions for intravenous administration comprise sterile isotonic aqueous buffer. Where necessary, the compositions can also include a solubilizing agent. A Substituted Piperidin-4-amino-Type Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Substituted Piperidin-4-amino-Type Compound is to be administered by infusion, it can be dispensed, for example, with an infusion bottle containing sterile pharmaceutical grade water or saline. Where a Substituted Piperidin-4-amino-Type Compound is administered by injection, an ampule of sterile water for injection or saline can be provided so that the ingredients can be mixed prior to administration.

A Substituted Piperidin-4-amino-Type Compound can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Substituted Piperidin-4-amino-Type Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Substituted Piperidin-4-amino-Type Compound, and can thus reduce the occurrence of adverse side effects.

Controlled- or sustained-release compositions can initially release an amount of a Substituted Piperidin-4-amino-Type Compound that promptly produces the desired therapeutic or prophylactic effect, and gradually and continually release other amounts of the Substituted Piperidin-4-amino-Type Compound to maintain this level of therapeutic or prophylactic effect over an extended period of time. To maintain a constant level of the Substituted Piperidin-4-amino-Type Compound in the body, the Substituted Piperidin-4-amino-Type Compound can be released from the dosage form at a rate that will replace the amount of Substituted Piperidin-4-amino-Type Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Substituted Piperidin-4-amino-Type Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Substituted Piperidin-4-amino-Type Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Substituted Piperidin-4-amino-Type Compound is administered, the effective dosage amounts correspond to the total amount administered.

Where a cell capable of expressing the ORL-1 receptor, the g-opioid receptor, the κ-opioid receptor and/or the δ-opioid receptor is contacted with a Substituted Piperidin-4-amino-Type Compound in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Substituted Piperidin-4-amino-Type Compound will be from about 0.01 μL to about 1 mL. In another embodiment, the volume of solution or suspension will be about 200 μL.

A Substituted Piperidin-4-amino-Type Compound has a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, a Substituted Piperidin-4-amino-Type Compound has a $K_i$ (nM) of about 300 or less for binding to ORL-1 receptors. In one embodiment, a Substituted Piperidin-4-amino-Type Compound has a $K_i$ (nM) of about 100 or less. In another embodiment, a Substituted Piperidin-4-amino-Type Compound has a $K_i$ (nM) of about 35 or less. In another embodiment, a Substituted Piperidin-4-amino-Type Compound has a $K_i$ (nM) of about 20 or less. In another embodiment, a Substituted Piperidin-4-amino-Type Compound has a $K_i$ (nM) of about 15 or less. In another embodiment, a Substituted Piperidin-4-amino-Type Compound has a $K_i$ (nM) of about 10 or less. In another embodiment, a Substituted Piperidin-4-amino-Type Compound has a $K_i$ (nM) of about 4 or less. In another embodiment, a Substituted Piperidin-4-amino-Type Compound has a $K_i$ (nM) of about 1 or less. In another embodiment, a Substituted Piperidin-4-amino-Type Compound has a $K_i$ (nM) of about 0.4 or less. In another embodiment, a Substituted Piperidin-4-amino-Type Compound has a $K_i$ (nM) of about 0.1 or less.

ORL-1 GTP $EC_{50}$ is the concentration of a compound providing 50% of the maximal response for the compound at an ORL-1 receptor. In one embodiment, a Substituted Piperidin-4-amino-Type Compound has an ORL-1 GTP $EC_{50}$ (nM) of about 5000 or less to stimulate ORL-1 receptor function. In another embodiment, a Substituted Piperidin-4-amino-Type Compound has an ORL-1 GTP $EC_{50}$ (nM) of about 1000 or less. In another embodiment, a Substituted Piperidin-4-amino-Type Compound has an ORL-1 GTP $EC_{50}$ (nM) of about 100 or less. In another embodiment, a Substituted Piperidin-4-amino-Type Compound has an ORL-1 GTP $EC_{50}$ (nM) of about 80 or less. In another embodiment, a Substituted Piperidin-4-amino-Type Compound has an ORL-1 GTP $EC_{50}$ (nM) of about 50 or less. In another embodiment, a Substituted Piperidin-4-amino-Type Compound has an ORL-1 GTP $EC_{50}$ (nM) of about 35 or less. In another embodiment, a Substituted Piperidin-4-amino-Type Compound has an ORL-1 GTP $EC_{50}$ (nM) of about 15 or less. In another embodiment, a Substituted Piperidin-4-amino-Type Compound has an ORL-1 GTP $EC_{50}$ (nM) of about 10 or less. In another embodiment, a Substituted Piperidin-4-amino-Type Compound has an ORL-1 GTP $EC_{50}$ (nM) of about 4 or less. In another embodiment, a Substituted Piperidin-4-amino-Type Compound has an ORL-1 GTP $EC_{50}$ (nM) of about 1 or less. In another embodiment, a Substituted Piperidin-4-amino-Type Compound has an ORL-1 GTP $EC_{50}$ (nM) of about 0.4 or less. In another embodiment, a Substituted Piperidin-4-amino-Type Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In certain embodiments, a Substituted Piperidin-4-amino-Type Compound acting as an agonist has an ORL-1 GTP Emax (%) of about 50% or greater. In one embodiment, agonist Substituted Piperidin-4-amino-Type Compounds has an ORL-1 GTP Emax (%) of about 75% or greater. In another embodiment, agonist Substituted Piperidin-4-amino-Type Compounds has an ORL-1 GTP Emax (%) of about 85% or greater. In another embodiment, agonist Substituted Piperidin-4-amino-Type Compounds has an ORL-1 GTP Emax (%) of about 95% or greater. In another embodiment, agonist Substituted Piperidin-4-amino-Type Compounds has an ORL-1 GTP Emax (%) of about 100% or greater. In certain embodiments, a Substituted Piperidin-4-amino-Type Compound acting as a partial agonist has an ORL-1 GTP Emax (%) of less than about 10%. In one embodiment, partial agonist Substituted Piperidin-4-amino-Type Compounds has an ORL-1 GTP Emax (%) of less than about 20%. In another embodiment, partial agonist Substituted Piperidin-4-amino-Type Compounds has an ORL-1 GTP Emax (%) of less than about 30%. In another embodiment, partial agonist Substituted Piperidin-4-amino-Type Compounds has an ORL-1 GTP Emax (%) of less than about 40%. In another embodiment, partial agonist Substituted Piperidin-4-amino-Type Compounds has an ORL-1 GTP Emax (%) of less than about 50%.

In certain embodiments, a Substituted Piperidin-4-amino-Type Compound has a binding affinity ($K_i$) for the human μ-opioid receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

In certain embodiments, a Substituted Piperidin-4-amino-Type Compound has a $K_i$ (nM) for the human μ-opioid receptor of about 3000 or less for binding to a human g-opioid receptor, or about 1000 or less, or about 650 or less, or about 525 or less, or about 250 or less, or about 100 or less, or about 10 or less, or about 1 or less. In one embodiment, a Substituted Piperidin-4-amino-Type Compound has substantially no activity.

μ GTP $EC_{50}$ is the concentration of a compound providing 50% of the maximal response for the compound at a human μ-opioid receptor. In certain embodiments, a Substituted Piperidin-4-amino-Type Compound has a μ GTP $EC_{50}$ (nM) of about 20,000 or less to stimulate human μ-opioid receptor function, or about 10,000 or less. In other embodiments, a Substituted Piperidin-4-amino-Type Compound has a μ GTP $EC_{50}$ (nM) of about 5000 or less to stimulate human μ-opioid receptor function, or about 4100 or less, or about 3100 or less, or about 2000 or less, or about 1000 or less, or about 100 or less, or about 10 or less, or about 1 or less, or about 0.4 or less.

μ GTP Emax (%) is the maximal effect elicited by a compound relative to the effect elicited by DAMGO, a standard p agonist. In certain embodiments, a Substituted Piperidin-4-amino-Type Compound has a μ GTP Emax (%) of about 10% or greater, or about 20% or greater, or about 50% or greater, or about 65% or greater, or about 75% or greater, or about 88% or greater. In other embodiments, a Substituted Piperidin-4-amino-Type Compound has a μ GTP Emax (%) of about 10% or less, or about 5% or less, or about 2% or less.

In one embodiment, a Substituted Piperidin-4-amino-Type Compound has a $K_i$ (nM) of about 20,000 or less for binding to a human κ-opioid receptor. In another embodiment, a Substituted Piperidin-4-amino-Type Compound has substantially no activity. In certain embodiments, a Substituted Piperidin-4-amino-Type Compound that bind to the human κ-opioid receptor has a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, a Substituted Piperidin-4-amino-Type Compound has a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, a Substituted Piperidin-4-amino-Type Compound has a κ GTP Emax (%) of about 10% or greater, or about 15% or greater, or about 30% or greater, or about 40% or greater, or about 45% or greater, or about 75% or greater, or about 90% or greater. In other embodiments, a Substituted Piperidin-4-amino-Type Compound has a κ GTP Emax (%) of about 10% or less, or about 5% or less, or about 2% or less.

In one embodiment, a Substituted Piperidin-4-amino-Type Compound has a $K_i$ (nM) of about 20,000 or less for binding to a human δ-opioid receptor. In another embodiment, a Substituted Piperidin-4-amino-Type Compound has substantially no activity. In other embodiments, a Substituted Piperidin-4-amino-Type Compound that binds to the human δ-opioid receptor has a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, a Substituted Piperidin-4-amino-Type Compound has a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, a Substituted Piperidin-4-amino-Type Compound has a 6 GTP Emax (%) of about 10% or greater, or about 30% or greater, or about 50% or greater, or about 75% or greater, or about 90% or greater, or about 100% or greater. In other embodiments, a Substituted Piperidin-4-amino-Type Compound has a δ GTP Emax (%) of about 10% or less, or about 5% or less, or about 2% or less.

The Substituted Piperidin-4-amino-Type Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Substituted Piperidin-4-amino-Type Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. A Substituted Piperidin-4-amino-Type Compound and the second therapeutic agent combined can act either additively or synergistically to treat the same Condition, or they may act independently of each other such that the Substituted Piperidin-4-amino-Type Compound treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Substituted Piperidin-4-amino-Type Compound will be less than its minimal effective amount would be where the second therapeutic agent is not administered. In this embodiment, the Substituted Piperidin-4-amino-Type Compound and the second therapeutic agent can act synergistically to treat or prevent a Condition. In one embodiment, a Substituted Piperidin-4-amino-Type Compound is administered concurrently with a second therapeutic agent as a single composition comprising an effective amount of a Substituted Piperidin-4-amino-Type Compound and an effective amount of the second therapeutic agent. Alternatively, a composition comprising an effective amount of a Substituted Piperidin-4-amino-Type Compound and a second composition comprising an effective amount of the second therapeutic agent are concurrently administered. In another embodiment, an effective amount of a Substituted Piperidin-4-amino-Type Compound is administered prior or subsequent to administration of an effective amount of the second therapeutic agent. In this embodiment, the Substituted Piperidin-4-amino-Type Compound is administered while the second therapeutic agent exerts its therapeutic effect, or the second therapeutic agent is administered while the Substituted Piperidin-4-amino-Type Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., eds., 9$^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy* Vol. II (Gennaro, ed., 19$^{th}$ Ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocomine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the disclosure is prepared by a method comprising admixing a Substituted Piperidin-4-amino-Type Compound with a pharmaceutically acceptable carrier or excipient. Admixing can be accomplished using methods known for admixing a compound (or derivative) and a pharmaceutically acceptable carrier or excipient. In one embodiment, the Substituted Piperidin-4-amino-Type Compound is present in the composition in an effective amount.

4.6 Kits

The disclosure further provides kits that can simplify the handling and administration of a Substituted Piperidin-4-amino-Type Compound to an animal.

A typical kit of the disclosure comprises a unit dosage form of a Substituted Piperidin-4-amino-Type Compound. In one embodiment, the unit dosage form comprises a first container, which can be sterile, containing an effective amount of a Substituted Piperidin-4-amino-Type Compound and a pharmaceutically acceptable carrier or excipient. The kit can further comprise a label or printed instructions instructing the use of the Substituted Piperidin-4-amino-Type Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Substituted Piperidin-4-amino-Type Compound, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Certain Examples below relate to the synthesis of illustrative Substituted Piperidin-4-amino-Type Compounds.

5.1 Example 1: Synthesis of Substituted Piperidin-4-amino Type Compound Za

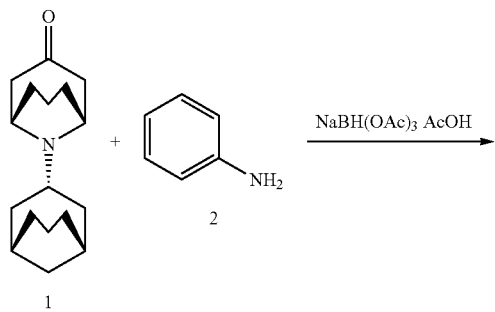

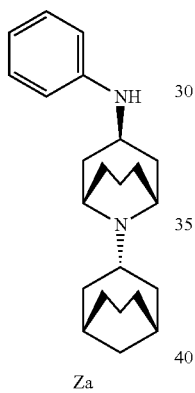

(1R,1'R,3r,5S,5'S)-9'-aza[3,9'-bi(bicyclo[3.3.1]nonan)]-3'-one (20.00 g, 77 mmol) (1) prepared as described in International PCT Publication No. WO 2012/085648, aniline (16.24 ml, 178 mmol, Sigma-Aldrich, St. Louis, Mo.) (2), acetic acid (120 ml, 2097 mmol), and DCM (200 ml) were combined and stirred. Sodium triacetoxyborohydride (133.2 g, 630 mmol) was added portionwise. The mixture was allowed to stir for 16 hours at a temperature of about 25° C. The mixture was poured into deionized water (400 ml) and basified using KOH to pH 5-6. The DCM layer was cut away, dried over MgSO₄, filtered, and adsorbed onto silica gel. The adsorbed material was chromatographed eluting first with neat DCM followed by 30% EtOAc in hexanes. Product fractions were combined and concentrated to dryness affording 11.2 g (18.91% yield) of (1R,1R,3r,3'R,5S,5'S)—N-phenyl-9'-aza[3,9'-bi(bicyclo[3.3.1]nonan)]-3'-amine (Za).

5.2 Example 2: Synthesis of Substituted Piperidin-4-amino Type Compound Zb

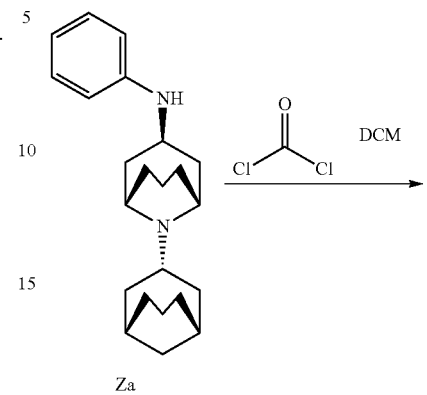

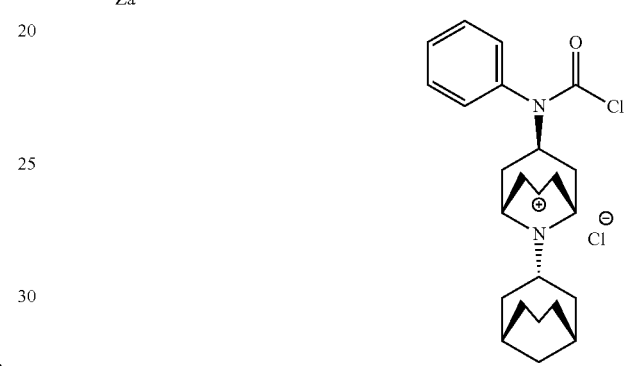

(1R,1'R,3r,3'R,5S,5'S)—N-phenyl-9'-aza[3,9'-bi(bicyclo[3.3.1]nonan)]-3'-amine (1.00 g, 2.95 mmol) (Za) prepared as described in Example 1 was dissolved in DCM (20 ml) with stirring in a 40 ml scintillation vial. The vial was capped and the mixture cooled to 0° C. Phosgene (15% wt solution in toluene) (4.216 ml, 5.90 mmol, Sigma-Aldrich) was added and the mixture was allowed to warm to a temperature of about 25° C. The reaction was concentrated to dryness affording (1R,1'R,3r,5S,5'S,7'R)-7'-((chlorocarbonyl)(phenyl)amino)-9'-aza[3,9'-bi(bicyclo[3.3.1]nonan)]-3'-ylium chloride (Zb) as a white solid (1.161 g; 90% yield).

5.3 Example 3: Synthesis of Substituted Piperidin-4-amino Type Compound B21a(i)

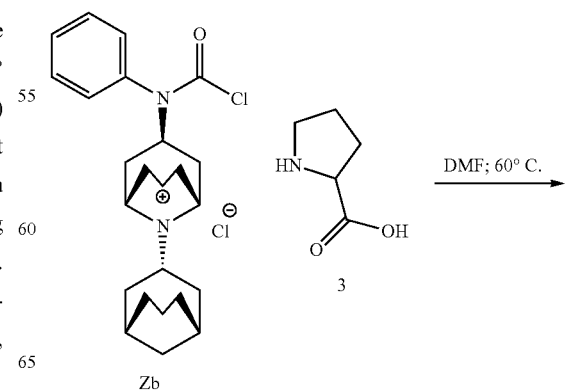

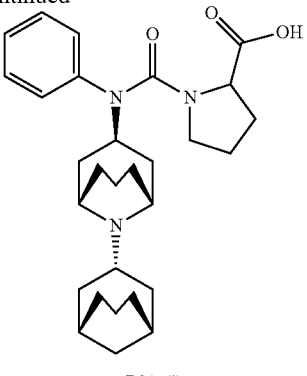

B21a(i)

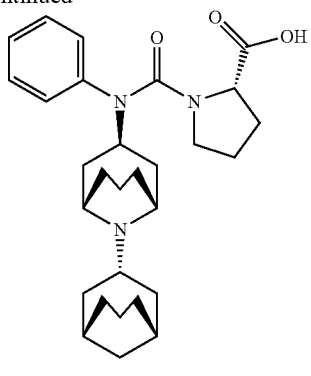

(S)-B21a(i)

(1R,1'R,3r,5S,5'S,7'R)-7'-((chlorocarbonyl)(phenyl) amino)-9'-aza[3,9'-bi(bicyclo[3.3.1]nonan)]-3'-ylium chloride (Zb) (0.1062 g, 0.220 mmol) prepared as described in Example 2 was suspended in DMF (5 ml) and cooled to 5° C. with stirring. Pyrrolidine-2-carboxylic acid (3) (0.025 g, 0.220 mmol, Sigma-Aldrich) was added and the mixture was allowed to stir and warm to 60° C. The mixture was stirred at this temperature for 1 hour. The mixture was then purified directly using preparatory HPLC. Pure product fractions were combined and concentrated to dryness. The resulting purified material was treated with aqueous saturated sodium bicarbonate solution (20 ml) and extracted into DCM (20 ml). The DCM layer was cut away and concentrated to dryness. The remaining material was triturated with MeOH and stripped to dryness affording 1-((1R,1'R,3r,3'R,5S,5'S)-[3,9'-bi(9'-azabicyclo[3.3.1]nonan)]-3'-yl(phenyl)carbamoyl)pyrrolidine-2-carboxylic acid (B21a(i)) as a white solid.

The identity of Substituted Piperidin-4-amino Type Compound B21a(i) was confirmed using $^1$H-NMR and LC/MS:

Substituted Piperidin-4-amino Type Compound B21a(i): $^1$H NMR, {400 MHz MeOD} δ 7.31 (m, 2H), 7.25 (m, 3H), 4.52-4.35 (m, 1H), 4.29-3.80 (m, 4H), 2.95-2.78 (m, 1H), 2.60-2.18 (m, 4H), 2.21-1.72 (m, 9H), 2.75-1.28 (m, 16H).

LC/MS [MH]+=480.3; >99.5% purity at 223 Nm.

5.4 Example 4 : Synthesis of Substituted Piperidin-4-amino Type Compound (S)-B21a(i)

(1R,1'R,3r,5 S,5'S,7'R)-7'-((chlorocarbonyl)(phenyl) amino)-9'-aza[3,9'-bi(bicyclo[3.3.1]nonan)]-3'-ylium chloride (Zb) (0.1062 g, 0.220 mmol) prepared as described in Example 2 was suspended in DMF (5 mil) and cooled to 5° C. with stirring. (S)-pyrrolidine-2-carboxylic acid (4) (0.025 g, 0.220 mmol, Sigma-Aldrich) was added and the mixture was allowed to stir and warm to 60° C. The mixture was stirred at this temperature for 1 hour. The mixture was then purified directly using preparatory HPLC. Pure product fractions were combined and concentrated to dryness. The resulting purified material was treated with aqueous saturated sodium bicarbonate solution (20 ml) and extracted into DCM (20 ml). The DCM layer was cut away and concentrated to dryness. The remaining material was triturated with MeOH and stripped to dryness affording (S)-1-((1R,1'R,3r, 3'R,5S,5'S)-[3,9'-bi(9'-azabicyclo[3.3.1]nonan)]-3'-yl(phenyl)carbamoyl)pyrrolidine-2-carboxylic acid ((S)-B21a(i)) as a white solid.

The identity of Substituted Piperidin-4-amino Type Compound (S)-B21a(i) was confirmed using $^1$H-NMR and LC/MS:

Substituted Piperidin-4-amino Type Compound (S)-B21a (i): H NMR, {400 MHz MeOD} δ 7.31 (m, 2H), 7.25 (m, 3H), 4.52-4.35 (m, 1H), 4.29-3.80 (m, 4H), 2.95-2.78 (m, 1H), 2.60-2.18 (m, 4H), 2.21-1.72 (m, 9H), 2.75-1.28 (m, 16H).

LC/MS [MH]+=480.3; 99.34% purity at 223 Nm.

5.5 Example 5 : Synthesis of Substituted Piperidin-4-amino Type Compound (R)-B21a(i)

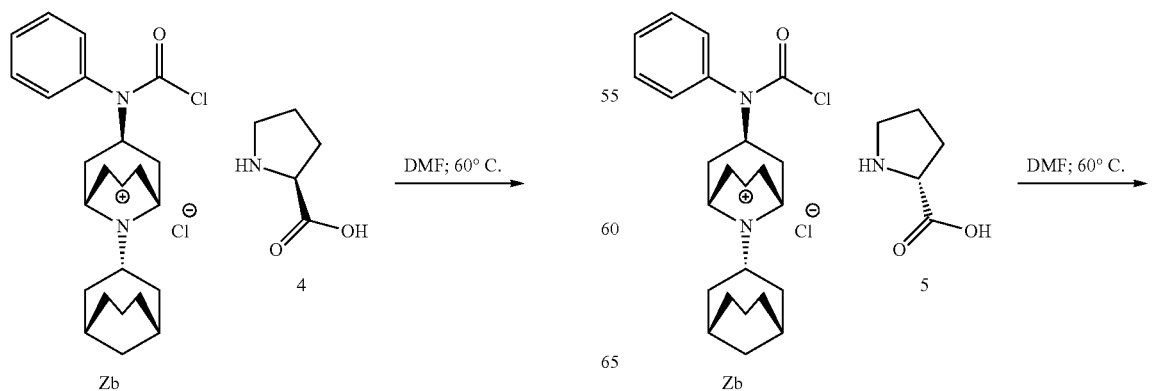

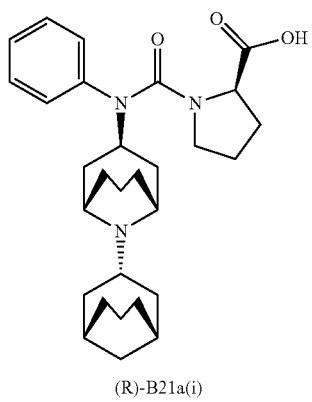

(R)-B21a(i)

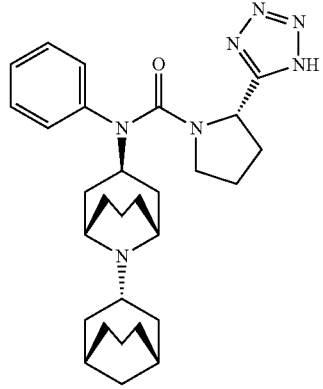

(S)-B61a(i)

(1R,1'R,3r,5S5'S,7'R)-7'-((chlorocarbonyl)(phenyl) amino)-9'-aza[3,9'-bi(bicyclo[3.3.1]nonan)]-3'-ylium chloride (Zb) (0.1062 g, 0.220 mmol) prepared as described in Example 2 was suspended in DMF (5 ml) and cooled to 5° C. with stirring. (R)-pyrrolidine-2-carboxylic acid (5) (0.025 g, 0.220 mmol, Sigma-Aldrich) was added and the mixture was allowed to stir and warm to 60° C. The mixture was stirred at this temperature for 1 hour. The mixture was then purified directly using preparatory HPLC. Pure product fractions were combined and concentrated to dryness. The resulting purified material was treated with aqueous saturated sodium bicarbonate solution (20 ml) and extracted into DCM (20 ml). The DCM layer was cut away and concentrated to dryness. The remaining material was triturated with MeOH and stripped to dryness affording (R)-1-((1R,1'R,3r,3'R,5S,5'S)-[3,9'-bi(9'-azabicyclo[3.3.1]nonan)]-3'-yl(phenyl)carbamoyl)pyrrolidine-2-carboxylic acid ((R)-B21a(i)) as a white solid.

The identity of Substituted Piperidin-4-amino Type Compound (R)-B21a(i) was confirmed using $^1$H-NMR and LC/MS:

Substituted Piperidin-4-amino Type Compound (R)-B21a (i): {400 MHz MeOD} δ 7.31 (m, 2H), 7.25 (m, 3H), 4.52-4.35 (m, 1H), 4.29-3.80 (m, 4H), 2.95-2.78 (m, 1H), 2.60-2.18 (m, 4H), 2.21-1.72 (m, 9H), 2.75-1.28 (m, 16H).

LC/MS [MH]+=480.3; >99.5% purity at 223 Nm.

5.6 Example 6 : Synthesis of Substituted Piperidin-4-amino Type Compound (S)-B61(a)(i)

(1R,1'R,3r,5S,5'S,7'R)-7'-((chlorocarbonyl)(phenyl) amino)-9'-aza[3,9'-bi(bicyclo[3.3.1]nonan)]-3'-ylium chloride (Zb) (0.1062 g, 0.220 mmol) prepared as described in Example 2 was suspended in DMF (5 ml) and cooled to 5° C. with stirring. (S)-5-(pyrrolidin-2-yl)-1H-tetrazole (6) (0.031 g, 0.220 mmol, Sigma-Aldrich) was added and the mixture was allowed to stir and warm to 60° C. The mixture was stirred at this temperature for 1 hour. The mixture was then purified directly using preparatory HPLC. Pure product fractions were combined and concentrated to dryness.

The resulting purified material was treated with aqueous saturated sodium bicarbonate solution (20 ml) and extracted into DCM (20 ml). The DCM layer was cut away and concentrated to dryness. The remaining material was triturated with MeOH and stripped to dryness affording (S)—N-((1R,1'R,3r,3'R,5S,5'S)-[3,9'-bi(9'-azabicyclo[3.3.1] nonan)]-3'-yl)-N-phenyl-2-(1H-tetrazol-5-yl)pyrrolidine-1-carboxamide ((S)-B61a(i)) as a white solid.

The identity of Substituted Piperidin-4-amino Type Compound (S)-B61(a)(i) was confirmed using $^1$H-NMR and LC/MS:

Substituted Piperidin-4-amino Type Compound (S)-B61 (a)(i): H-NMR, {400 MHz MeOD} δ 7.49 (m, 2H), 7.38 (m, 1H), 7.21 (m, 2H), 5.20 (m, 1H), 4.65-4.40 (m, 1H), 4.91-3.92 (m, 3H), 3.10 (m, 1H), 2.79 (m, 1H), 2.59-1.31 (m, 27H).

LC/MS [MH]+=504.3; >99.5% purity at 223 Nm.

5.7 Example 7 : Synthesis of Substituted Piperidin-4-amino Type Compound (R)-B41a(i)

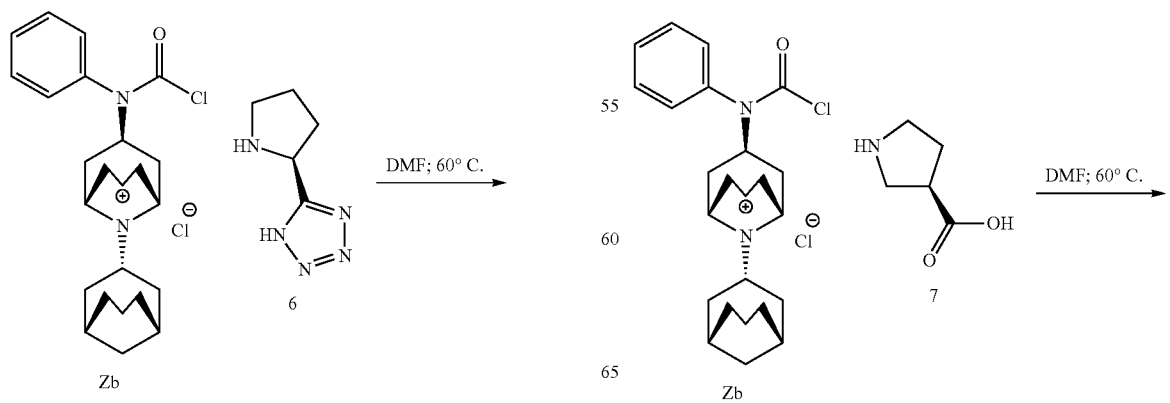

483
-continued

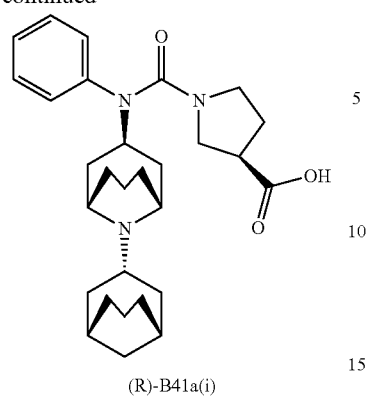

(R)-B41a(i)

484
-continued

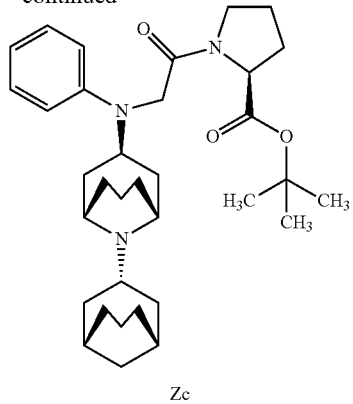

Zc (1R,1'R,3r,5S,5'S,7'R)-7'-((chlorocarbonyl)(phenyl)amino)-9'-aza[3,9'-bi(bicyclo[3.3.1]nonan)]-3'-ylium chloride (Zb) (0.1062 g, 0.220 mmol) prepared as described in Example 2 was suspended in DMF (5 ml) and cooled to 5° C. with stirring. (R)-pyrrolidine-3-carboxylic acid (7) (0.025 g, 0.220 mmol, Sigma-Aldrich) was added and the mixture was allowed to stir and warm to 60° C. The mixture was stirred at this temperature for 1 hour. The mixture was then purified directly using preparatory HPLC. Pure product fractions were combined and concentrated to dryness. The resulting purified material was treated with aqueous saturated sodium bicarbonate solution (20 ml) and extracted into DCM (20 ml). The DCM layer was cut away and concentrated to dryness. The remaining material was triturated with MeOH and stripped to dryness affording (R)-1-((1R,1'R,3r,3'R,5S,5'S)-[3,9'-bi(9'-azabicyclo[3.3.1]nonan)]-3'-yl(phenyl)carbamoyl)pyrrolidine-3-carboxylic acid ((R)-B41a(i)) as a white solid.

The identity of Substituted Piperidin-4-amino Type Compound (R)-B41a(i) was confirmed using ¹H-NMR and LC/MS:

Substituted Piperidin-4-amino Type Compound (R)-B41a (i): ¹H-NMR, {400 MHz MeOD} δ 7.49 (m, 2H), 7.35 (m, 1H), 7.23 (m, 2H), 4.75-4.50 (m, 1H), 4.39-4.01 (m, 3H), 3.40-2.80 (m, 4H), 2.62-2.27 (m, 4H), 2.30-1.85 (m, 9H), 1.88-1.40 (m, 14H).

LC/MS [MH]+=480.3; >99.5% purity at 223 Nm.

5.8 Example 8 : Synthesis of Substituted Piperidin-4-amino Type Compound Zc (1R,1'R,3r,3'R,5S,5'S)—N-phenyl-9'-aza[3,9'-bi(bicyclo[3.3.1]nonan)]-3'-amine (Za) (0.513 g, 1.515 mmol) prepared as described in Example 1 was taken up in anhydrous toluene (15 ml) with stirring under an atmosphere of nitrogen. Sodium hydride (90%) (0.364 g, 9.09 mmol) was added and the mixture was stirred and warmed to 110° C. for 30 minutes. (S)-tert-butyl 1-(2-chloroacetyl)pyrrolidine-2-carboxylate (0.413 g, 1.667 mmol, Sigma-Aldrich) (8) was added via syringe in 1 ml anhydrous toluene. The mixture was allowed to stir at 110° C. for 48 hours. The reaction was cooled to a temperature of about 25° C. and partitioned between DCM (20 ml) and DI water (20 ml). The DCM layer was cut away and concentrated to dryness. The resulting crude material was taken up in MeOH and purified using preparatory HPLC. Pure product fractions combined and concentrated to dryness. The resulting material was treated with aqueous saturated sodium bicarbonate and extracted with DCM. The DCM layer was cut away, dried over MgSO₄, filtered, and concentrated to dryness. This afforded 100 mg (12% yield) of (S)-tert-butyl 1-(2-((1R,1'R,3r,3'R,5S,5'S)-[3,9'-bi(9'-azabicyclo[3.3.1]nonan)]-3'-yl(phenyl)amino)acetyl)pyrrolidine-2-carboxylate (Zc).

5.9 Example 9 : Synthesis of Substituted Piperidin-4-amino Type Compound (S)-B22a(i)

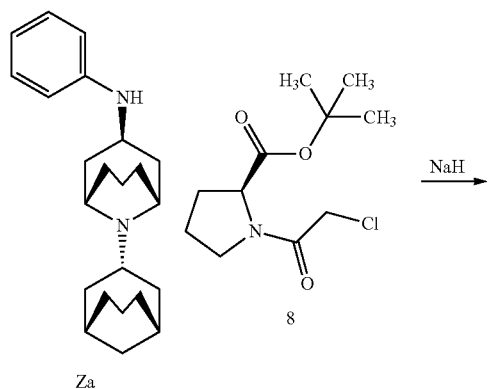

Za

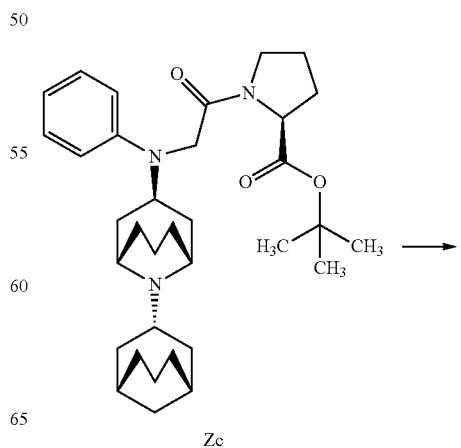

Zc

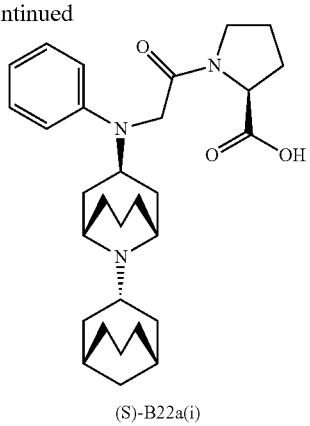

(S)-B22a(i)

(S)-tert-butyl 1-(2-((1R,1'R,3r,3'R,5S,5'S)-[3,9'-bi(9'-azabicyclo[3.3.1]nonan)]-3'-yl(phenyl)amino)acetyl)pyrrolidine-2-carboxylate (Zc) (0.063 g, 0.115 mmol) prepared as described in Example 8 was taken up in MeOH (5 ml). To this was added sodium hydroxide (0.630 ml, 2.52 mmol) and the resulting yellow solution was allowed to stir at a temperature of about 25° C. for 10 minutes. The reaction was then warmed to 70° C. for 24 hours. The reaction was cooled to a temperature of about 25° C. and concentrated to dryness. The remaining crude material was triturated with deionized water and vacuum filtered affording (S)-1-(2-((1R,1'R,3r,3'R,5S,5'S)-[3,9'-bi(9'-azabicyclo[3.3.1]nonan)]-3'-yl(phenyl)amino)acetyl)pyrrolidine-2-carboxylic acid ((S)-B22a(i)) as a white solid. The (S)-1-(2-((1R,1'R,3r,3'R,5S,5'S)-[3,9'-bi(9'-azabicyclo[3.3.1]nonan)]-3'-yl(phenyl)amino)acetyl)pyrrolidine-2-carboxylic acid ((S)-B22a(i)) was suspended in diethyl ether and stirred for 1 hour. A white solid precipitate was obtained, filtered and washed with diethyl ether. This material was dried under reduced pressure at 65° C. for 6 hours affording (S)-1-(2-((1R,1'R,3r,3'R,5S,5'S)-[3,9'-bi(9'-azabicyclo[3.3.1]nonan)]-3'-yl(phenyl)amino)acetyl)pyrrolidine-2-carboxylic acid ((S)-B22a(i)) as a white solid (0.050 g; 88% yield).

The identity of Substituted Piperidin-4-amino Type Compound (S)-B22a(i) was confirmed using $^1$H-NMR and LC/MS:

Substituted Piperidin-4-amino Type Compound (S)-B22a (i):$^1$H-NMR, {400-MHz MeOD} δ 7.15 (m, 2H), 6.71 (d, 2H), 6.61 (m, 1H), 4.45 (m, 2H), 4.19-3.91 (m, 2H), 3.89-3.38 (m, 5H), 2.37 (m, 1H), 2.30-1.17 (m, 26H), 1.13 (m, 2H).

LC/MS [MH]+=494.2; >99.5% purity at 223 Nm.

5.10 Example 10 : Synthesis of Substituted Piperidin-4-amino Type Compound Zd

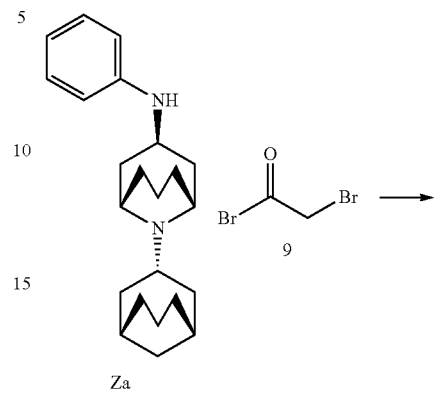

Za

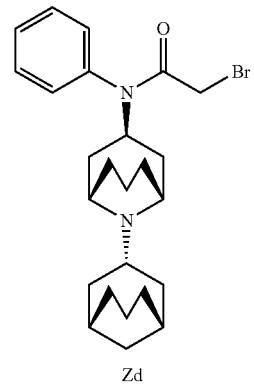

Zd (1R,1'R,3r,3'R,5S,5'S)—N-phenyl-9'-aza[3,9'-bi(bicyclo[3.3.1]nonan)]-3'-amine (Za) (1.00 g, 2.95 mmol) prepared as described in Example 1 was taken up in ethyl acetate (20 ml) with stirring. The vial was capped and the mixture cooled to 0° C. 2-bromoacetyl bromide (9) (0.257 ml, 2.95 mmol, Sigma-Aldrich) was then added followed by triethylamine (0.412 ml, 2.95 mmol). The mixture was allowed to stir and warm from 0° C. to a temperature of about 25° C. for 1 hour. Additional 2-bromoacetyl bromide (9) (1.028 ml, 11.80 mmol) was added and the mixture was allowed to stir for 18 hours. Deionized water (50 ml) was added and the mixture was transferred to a seperatory funnel. The organic layer was cut away, dried over MgSO$_4$, filtered, and concentrated onto silica gel. The adsorbed material was chromatographed on a CombiFlash column, eluting with neat ethyl acetate. Product fractions were combined and concentrated to dryness. The resulting material was dried under reduced pressure for 18 hours affording N-((1R,1'R,3r,3'R,5S,5'S)-[3,9'-bi(9'-azabicyclo[3.3.1]nonan)]-3'-yl)-2-bromo-N-phenylacetamide (Zd) (0.948 g; 56%) as a fluffy brown solid. Substituted Piperidin-4-amino Type Compound Zd was determined to be 80% pure by LC/MS.

5.11 Example 11 : Synthesis of Substituted Piperidin-4-amino Type Compound B24a(i)

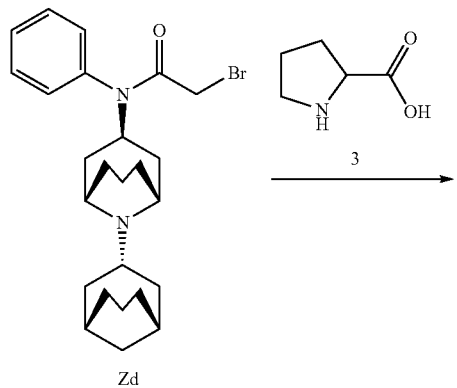

N-((1R,1'R,3r,3'R,5S,5'S)-[3,9'-bi(9'-azabicyclo[3.3.1]nonan)]-3'-yl)-2-bromo-N-phenylacetamide (0.200 g, 0.435 mmol) (Zd) prepared as described in Example 10 and triethylamine (0.182 ml, 1.306 mmol) were taken up in DMF (5 ml). Pyrrolidine-2-carboxylic acid (0.050 g, 0.435 mmol, Sigma-Aldrich) (3) was added and the mixture was warmed to 100° C. for 1 hour. The mixture was cooled to a temperature of about 25° C. and purified directly using preparatory HPLC. All pure product fractions were combined and concentrated to dryness. The resulting material was triturated with saturated sodium bicarbonate and extracted into DCM. The DCM layer was cut away and evaporated to dryness. The resulting material was taken up in MeOH and evaporated to dryness affording 1-(2-((1R,1'R,3r,3'R,5S,5'S)-[3,9'-bi(9'-azabicyclo[3.3.1]nonan)]-3'-yl(phenyl)amino)-2-oxoethyl)pyrrolidine-2-carboxylic acid (B24a(i)) as a white solid (0.001 g; <5% yield).

The identity of Substituted Piperidin-4-amino Type Compound B24a(i) was confirmed using H-NMR and LC/MS:

Substituted Piperidin-4-amino Type Compound B24a(i):
$^1$H-NMR, {400 MHz MeOD} δ 7.35 (m, 3H), 7.10 (m, 2H), 6.97 (m, 1H), 5.01 (m, 1H), 4.15-3.85 (m, 1H), 3.38 (m, 3H), 2.98-2.65 (m, 1H), 2.48-2.12 (m, 2H), 2.18-1.01 (m, 27H), 0.77 (m, 2H).

LC/MS [MH]+=494.2; 97.6% purity at 223 Nm.

5.12 Example 12 : Synthesis of Substituted Piperidin-4-amino Type Compound Ze

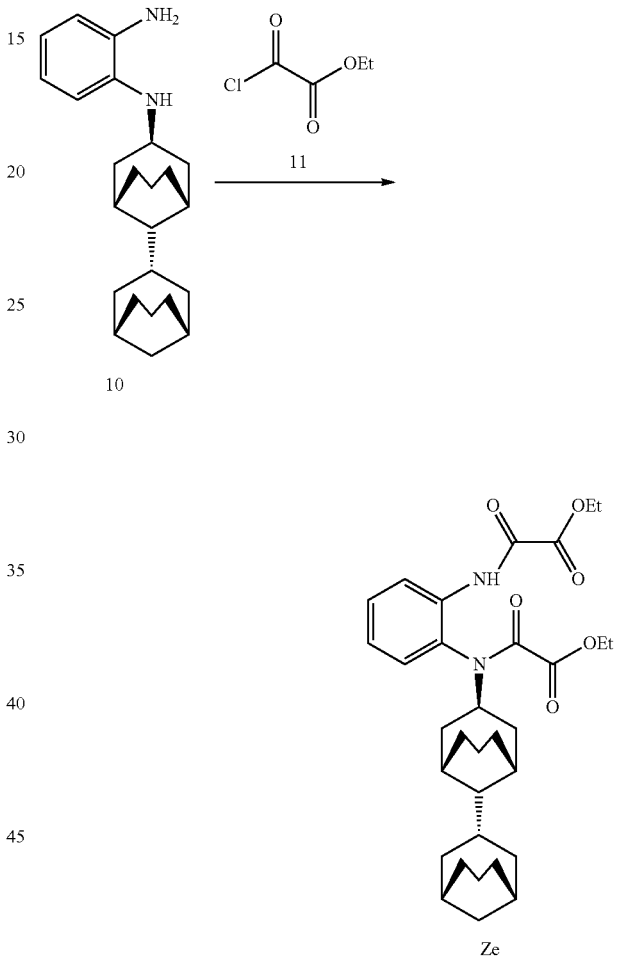

N1-((1R,1'R,3r,3'R,5S,5'S,9's)-[3,9'-bi(bicyclo[3.3.1]nonan)]-3'-yl)benzene-1,2-diamine (0.35 g, 0.994 mmol) (10) prepared as described in International PCT Publication No. WO 2012/085648 was taken up in DCM. Ethyl 2-chloro-2-oxoacetate (1.5 eq, 0.2 ml) (11) was added dropwise. The reaction mixture was stirred at a temperature of about 25° C. for 2 hours to produce ethyl 2-((1R,1'R,3r,3'R,5S,5'S,9's)-[3,9'-bi(bicyclo[3.3.1]nonan)]-3'-yl(2-(2-ethoxy-2-oxoacetamido)phenyl)amino)-2-oxoacetate (Ze).

The identity of Substituted Piperidin-4-amino Type Compound Ze was confirmed using LC/MS.

5.13 Example 13 : Synthesis of Substituted Piperidin-4-amino Type Compound Q11a(i)(iv)

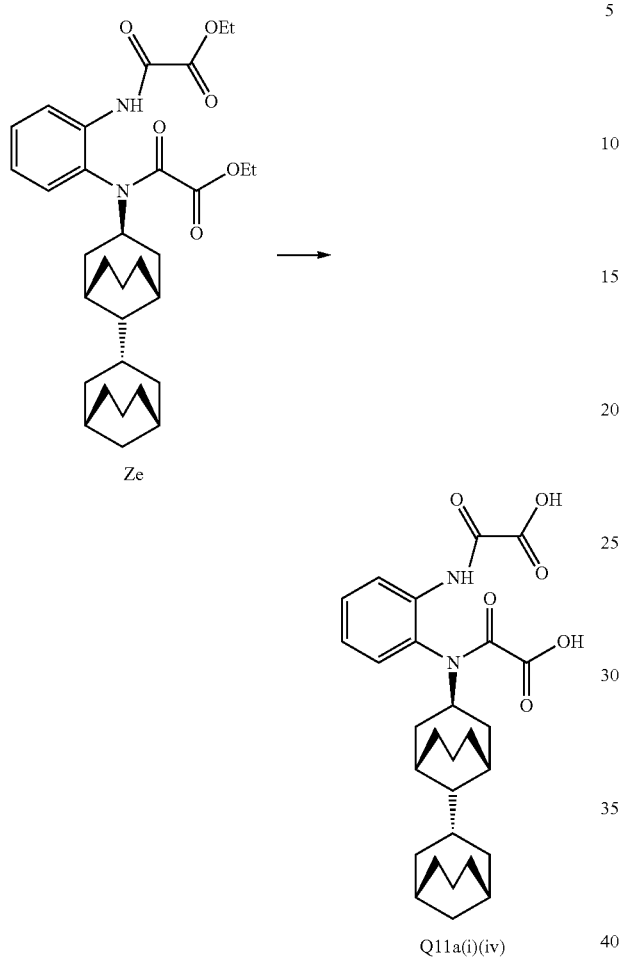

The crude ethyl 2-((1R,1'R,3r,3'R,5S,5'S,9's)-[3,9'-bi(bicyclo[3.3.1]nonan)]-3'-yl(2-(2-ethoxy-2-oxoacetamido)phenyl)amino)-2-oxoacetate (Ze) prepared in Example 12 was taken up in 5 ml of EtOH and (2 ml) of 2N NaOH and allowed to stir for 1 hour at a temperature of about 25° C. The mixture was evaporated and the product was then dissolved in H₂O (3 ml) and acidified to pH=4 with 2N HCl. The solution was extracted from DCM. Most of the product remained in the aqueous layer. After evaporating the aqueous layer, the crude product was purified by preparatory HPLC to obtain the desired product 2-((1R,1'R,3r,3'R,5S,5'S,9's)-[3,9'-bi(bicyclo[3.3.1]nonan)]-3'-yl(2-(carboxyformamido)phenyl)amino)-2-oxoacetic acid (Q11a(i)(iv)).

The identity of Substituted Piperidin-4-amino Type Compound Q11a(i)(iv) was confirmed using ¹H-NMR and LC/MS:

Substituted Piperidin-4-amino Type Compound Q11a(i)(iv): ¹HNMR (CD3OD) δ:07-7:94 (br, 1H), 7:34-7:49 (br, 1H), 7:06-7:31 (br, 1H), 3:85-4:19 (br, 3H), 2:34-2:62 (br, 3H), 1:07-2:19 (br, 24H), ppm; MS: (m/e): 498.1 (M+1).

5.14 Example 14 : Synthesis of Substituted Piperidin-4-amino Type Compound Zf N1-((1R,1'R,3r,3'R,5S,5'S,7S,9's)-7-methyl-[3,9' bi(bicyclo[3.3.1]nonan)]-3'-yl)benzene-1,2-diamine (0.359 g, 0.9534 mmol) (12) prepared as described in International PCT Publication No. WO 2012/085648 was taken up in DCM. Ethyl 2-chloro-2-oxoacetate (1.5 eq, 0.2 ml) (11) was added dropwise. The reaction mixture was stirred at a temperature of about 25° C. for 2 hours to produce ethyl 2-((2-(2-ethoxy-2-oxoacetamido)phenyl)((1R,1'R,3r,3'R,5S,5'S,7S,9's)-7-methyl-[3,9'-bi(bicyclo[3.3.1]nonan)]-3'-yl)amino)-2-oxoacetate (Zf).

The identity of Substituted Piperidin-4-amino Type Compound Zf was confirmed using LC/MS.

5.15 Example 15 : Synthesis of Substituted Piperidin-4-amino Type Compound (7S)-Q11a(ii)(iv)

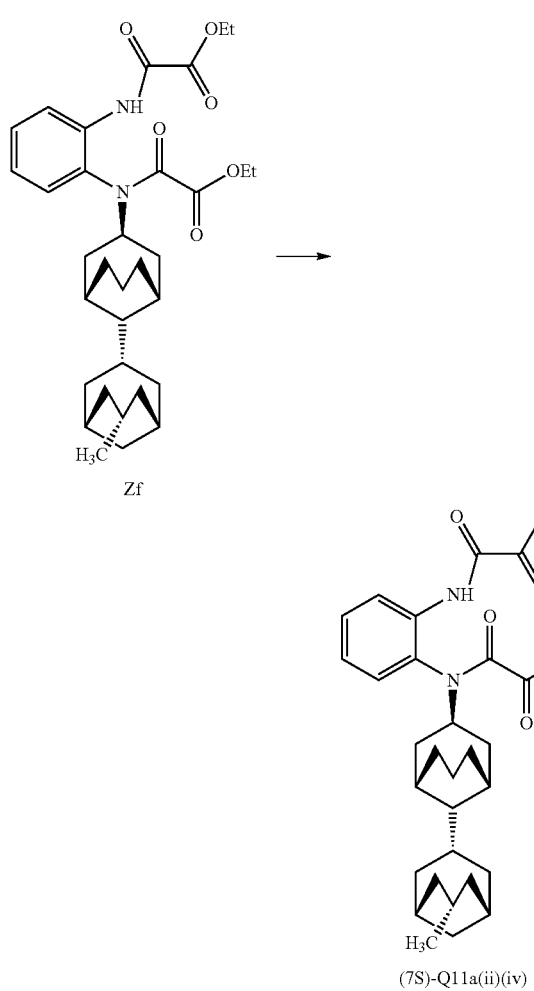

The crude ethyl 2-((2-(2-ethoxy-2-oxoacetamido)phenyl)((1R,1'R,3r,3'R,5S,5'S,7S,9's)-7-methyl-[3,9'-bi(bicyclo[3.3.1]nonan)]-3'-yl)amino)-2-oxoacetate (Zf) prepared in Example 14 was taken up in 5 ml of EtOH and (2 ml) of 2N NaOH and allowed to stir for 1 hour at a temperature of about 25° C. The mixture was evaporated and the product was then dissolved in H$_2$O (3 ml) and acidified to pH=4 with 2N HCl. The solution was extracted from DCM. Most of the product remained in the aqueous layer. After evaporating the aqueous layer, the crude product was purified by preparatory HPLC to obtain the desired product 2-((2-(1-carboxy-N-((1R,1'R,3r,3'R,5S,5'S,7S,9's)-7-methyl-[3,9'-bi(bicyclo[3.3.1]nonan)]-3'-yl)formamido)phenyl)amino)-2-oxoacetic acid ((7S)-Q11a(ii)(iv)).

The identity of Substituted Piperidin-4-amino Type Compound (7S)-Q11a(ii)(iv) was confirmed using $^1$H-NMR and LC/MS:

Substituted Piperidin-4-amino Type Compound (7S)-Q11a(ii)(iv):$^1$HNMR (CD3OD) δ 8:07-7:94 (br, 1H), 7:34-7:49 (br, 1H), 7:06-7:31 (br, 1H), 3:85-4:19 (br, 3H), 2:34-2:62 (br, 3H), 1:07-2:19 (br, 26H), ppm; MS: (m/e): 498.1 (M+1).

5.16 Example 16 : Synthesis of Substituted Piperidin-4-amino Type Compound Zh

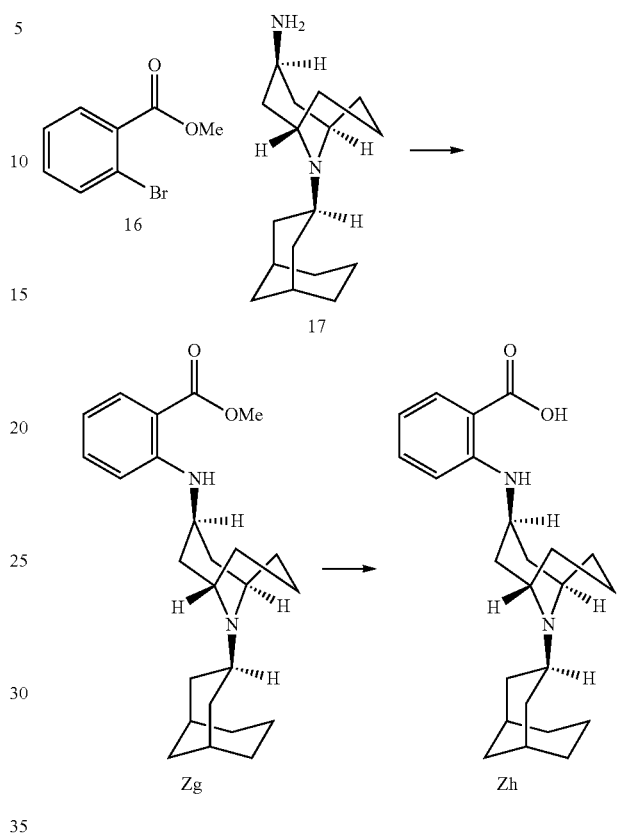

To a solution of methyl 2-bromobenzoate (16) (1.15 ml, 10 mmol) in toluene (45 ml), the following were added at a temperature of about 25° C. under N$_2$: (1R,1'R,3r,3'R,5S,5'S)-9'-aza[3,9'-bi(bicyclo[3.3.1]nonan)]-3'-amine (17) (2624 mg, 10 mmol) prepared as described in International PCT Publication No. WO 2009/027820, Cs$_2$CO$_3$ (9774 mg, 30 mmol), xantphos (289 mg, 0.5 mmol) and Pd$_2$(dba)$_3$ (183 mg, 0.2 mmol). The mixture was stirred at 110° C. for 12 hours. After quenching with water, the mixture was extracted with DCM/H$_2$O twice. The combined organic phases were dried over MgSO$_4$ and concentrated in vacuo. The resulting oil was chromatographed by column chromatography (ISCO, 120 g, CHCl$_3$/10% NH$_3$ in MeOH=99/1-85/15) to give methyl 2-((1R,1'R,3r,3'R,5S,5'S)-[3,9'-bi(9'-azabicyclo[3.3.1]nonan)]-3'-ylamino)benzoate (Zg) (yield; 770 mg, 21%).

The identity of Substituted Piperidin-4-amino Type Compound Zg was confirmed using $^1$H-NMR and LC/MS:

Substituted Piperidin-4-amino Type Compound Zg: $^1$H-NMR (400 MHz, CDCl$_3$) δ: 1.00 (d, J=12.0 Hz, 3.0H), 1.21-2.12 (m, 24.0H), 2.42 (s, 1.0H), 3.42 (s, 2.0H), 3.88 (br, 1.0H), 6.50 (t, J=7.4 Hz, 1.0H), 6.73 (d, J=8.2 Hz, 1.0H), 7.32 (t, J=4.5 Hz, 1.0H), 7.62 (s, 1.0H), 7.85 (d, J=8.0 Hz, 1.0H).

LC/MS: m/z=397.2 [M+H]$^+$.

To a solution of Compound Zg (770 mg, 1.942 mmol) in THF (15.4 ml) and MeOH (5 ml), 2N NaOH (4.9 ml, 9.7 mmol) was added at a temperature of about 25° C. The mixture was stirred at 90° C. for 7.5 hours. After concentration in vacuo, 2N HCl was added dropwise and adjusted to pH4-5, then extracted with DCM/H$_2$O twice. The combined organic phases were dried over Na$_2$SO$_4$ and concentrated in vacuo. To the resulting oil, a solution of AcOEt/ Et$_2$O/MeOH (1/8/1) was added at 0° C. and sonicated to give a yellow precipitate which was filtrated and washed with Et$_2$O to give 2-((1R,1'R,3r,3'R,5S,5'S)-[3,9'-bi(9'-azabicyclo[3.3.1]nonan)]-3'-ylamino)benzoic acid (Zh) as a pale yellow solid (yield; 707 mg, 95%).

The identity of Substituted Piperidin-4-amino Type Compound Zh was confirmed using $^1$H-NMR and LC/MS:

Substituted Piperidin-4-amino Type Compound Zh: $^1$H-NMR (400 MHz, DMSO+DCl) δ: 1.44-1.63 (m, 16.0H), 1.92-2.05 (m, 9.0H), 2.26-2.33 (m, 3.0H), 2.60-2.64 (m, 2.0H), 3.83 (s, 1.0H), 3.94-4.06 (m, 3.0H), 4.75 (br, 1.0H), 6.60 (t, J=7.5 Hz, 1.0H), 7.03 (d, J=8.6 Hz, 1.0H), 7.37 (t, J=7.1 Hz, 1.0H), 7.78 (d, J=8.0 Hz, 1.0H). LC/MS: m/z=381.6 [M+H]$^+$.

5.17 Example 17 : Synthesis of Substituted Piperidin-4-amino Type Compound Zi

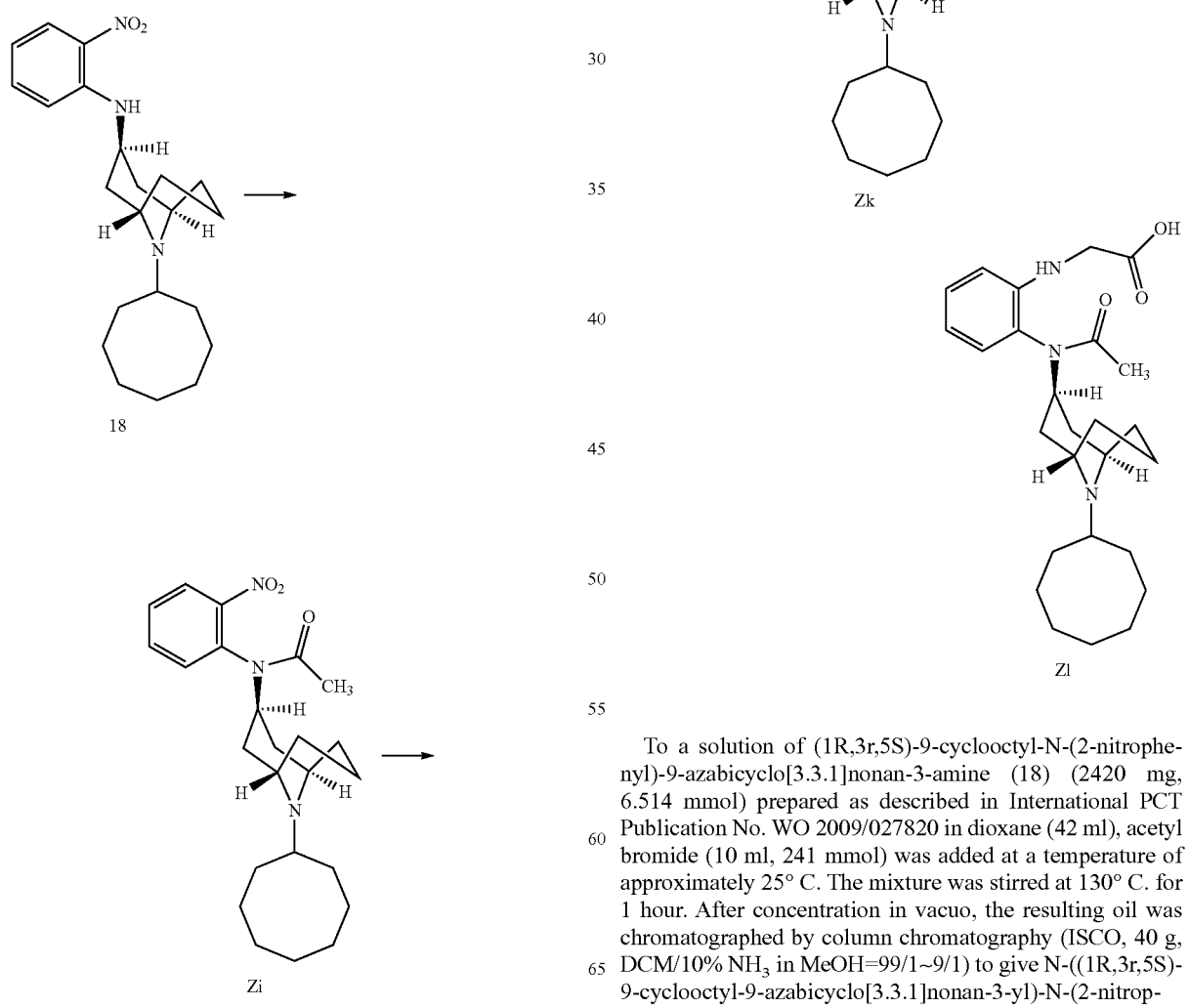

To a solution of (1R,3r,5S)-9-cyclooctyl-N-(2-nitrophenyl)-9-azabicyclo[3.3.1]nonan-3-amine (18) (2420 mg, 6.514 mmol) prepared as described in International PCT Publication No. WO 2009/027820 in dioxane (42 ml), acetyl bromide (10 ml, 241 mmol) was added at a temperature of approximately 25° C. The mixture was stirred at 130° C. for 1 hour. After concentration in vacuo, the resulting oil was chromatographed by column chromatography (ISCO, 40 g, DCM/10% NH$_3$ in MeOH=99/1~9/1) to give N-((1R,3r,5S)-9-cyclooctyl-9-azabicyclo[3.3.1]nonan-3-yl)-N-(2-nitrophenyl)acetamide (Zi) (Yield; 2330 mg, 87%).

The identity of Substituted Piperidin-4-amino Type Compound Zi was confirmed using $^1$H-NMR and LC/MS:

Substituted Piperidin-4-amino Type Compound Zi: $^1$H-NMR (400 MHz, CDCl$_3$) δ: 0.83-0.90 (m, 3.0H), 1.20-1.67 (m, 18.0H), 1.83 (s, 3.0H), 1.92 (s, 1.0H), 2.31 (s, 1.0H), 2.85 (s, 1.0H), 3.27-3.31 (m, 2.0H), 4.88-4.92 (m, 1.0H), 7.26 (d, J=9.0 Hz, 1.0H), 7.55 (t, J=6.7 Hz, 1.0H), 7.67 (t, J=6.3H, 1.0H), 7.95 (d, J=6.8 Hz, 1.0H). LC/MS: m/z=414.3 [M+H]$^+$.

To a solution of Compound Zi (2330 mg, 5.634 mmol) in MeOH (45 ml), 10% Pd—C (350 mg) was added at a temperature of approximately 25° C. The mixture was stirred at a temperature of approximately 25° C. for 3 hours. After filtration through a celite pad, the filtrate was concentrated in vacuo and to give N-(2-aminophenyl)-N-((1R,3r,5S)-9-cyclooctyl-9-azabicyclo[3.3.1]nonan-3-yl)acetamide (Zj) as a colorless solid (yield; 1190 mg, 55%).

The identity of Substituted Piperidin-4-amino Type Compound Zj was confirmed using $^1$H-NMR and LC/MS:

Substituted Piperidin-4-amino Type Compound Zj: $^1$H-NMR (400 MHz, CDCl$_3$) δ: 0.86-0.90 (m, 1.0H), 1.20-1.77 (m, 18.0H), 2.05 (s, 1.0H), 2.20 (s, 1.0H), 2.89 (s, 1.0H), 3.34(dd, J=10.3 Hz, J=21.6 Hz, 1.0H), 3.80 (s, 1H), 4.94 (br, 1.0H), 6.73-6.77 (m, 2.0H), 6.93 (d, J=7.3 Hz, 1.0H), 7.15 (dd, J=1.4 Hz, J=14 Hz, 1.0H). LC/MS: m/z=384.2 [M+H]$^+$.

To a solution of Compound Zj (1000 mg, 2.61 mmol) in THF (30 ml), K$_2$CO$_3$ (637 mg, 4.611 mmol), KI (510 mg, 3.074 mmol) and methylbromoacetate (0.219 ml, 2.31 mmol) were added at a temperature of approximately 25° C. and stirred at 85° C. for twelve hours. After quenching with water, the mixture was extracted with DCM/H$_2$O twice. The combined organic phases were dried over MgSO$_4$ and concentrated in vacuo. The resulting oil was chromatographed by column chromatography (ISCO, 24 g, DCM/10% NH$_3$ in MeOH=99/1-9/1) to give methyl 2-((2-(N-((1R,3r,5S)-9-cyclooctyl-9-azabicyclo[3.3.1]nonan-3-yl)acetamido)phenyl)amino)acetate (Zk) (yield; 160 mg, 14%).

The identity of Substituted Piperidin-4-amino Type Compound Zk was confirmed using $^1$H-NMR and LC/MS:

Substituted Piperidin-4-amino Type Compound Zk: $^1$H-NMR (400 MHz, CDCl$_3$) δ: 1.21-1.80 (m, 24.0H), 1.81 (s, 3.0H), 2.00-2.41 (m, 1.0H), 3.30 (br, 1.0H), 3.71(s, 3.0H), 3.91 (d, J=6.0 Hz, 2.0H), 4.91 (br, 1.0H), 6.55 (d, J=8.1 Hz, 1.0H), 6.75 (t, J=7.1 Hz, 1.0H), 6.91 (d, J=5.4 Hz, 1.0H), 7.25 (br, 1.0 Hz). LC/MS: m/z=456.3 [M+H]$^+$.

To a solution of Compound Zk (130 mg, 0.28 mmol) in THF (1 ml) and MeOH (1 ml), 2N NaOH (0.7 ml, 1.4 mmol) was added and stirred at at a temperature of approximately 25° C. for 3 hours. After concentration in vacuo, 2N HCl was added to the mixture and adjusted to pH5-6. The mixture was then extracted with DCM/H$_2$O twice. The combined organic phases were dried over MgSO$_4$ and concentrated in vacuo. The resulting solid was chromatographed by column chromatography (ISCO, 12 g, DCM/10% NH$_3$ in MeOH=99/1-9/1) to give 2-((2-(N-((1R,3r,5S)-9-cyclooctyl-9-azabicyclo[3.3.1]nonan-3-yl)acetamido)phenyl)amino)acetic acid (Zl) as a colorless solid (yield; 89 mg, 70%).

The identity of Substituted Piperidin-4-amino Type Compound Zl was confirmed using $^1$H-NMR and LC/MS:

Substituted Piperidin-4-amino Type Compound Zl: $^1$H-NMR (400 MHz, CD$_3$OD) δ: 1.50-1.96 (m, 24.0H), 2.66-2.86 (m, 1.0H), 3.67 (s, 3.0H), 4.06 (dd, J=10.3 Hz, J=25.5 Hz, 2.0H) 4.87 (br, 1.0H), 6.69-6.73 (m, 2.0H), 7.04 (d, J=6.4 Hz, 1.0H), 7.28 (t, J=6.7 Hz, 1.0H). LC/MS: m/z=442.6 [M+H]$^+$.

5.18 Example 18 : Synthesis of Substituted Piperidin-4-amino Type Compounds Zm and Zn Using procedures similar to those described in Examples 16 and 17, the Substituted Piperidin-4-amino Type Compounds 2-(((1R,3R,5S)-9-((3 S,5S,7S)-adamantan-1-yl)-9-azabicyclo[3.3.1]nonan-3-yl)amino)benzoic acid (Zm) and 2-((2-(N-((1R,1'R,3r,3'R,5S,5'S)-[3,9'-bi(9'-azabicyclo[3.3.1]nonan)]-3'-yl)acetamido)phenyl)amino)acetic acid (Zn) were prepared.

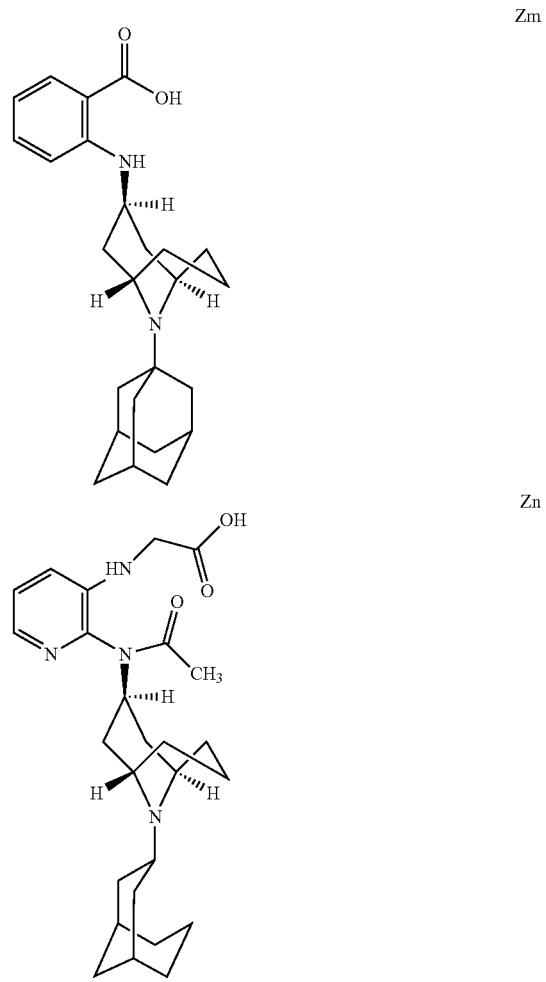 [SMILES: O=C(O)c1ccccc1N[C@H]1C[C@H]2CCC[C@@H](C1)N2C12CC3CC(CC(C3)C1)C2 ; CC(=O)N(c1ncccc1NCC(=O)O)[C@H]1C[C@H]2CCC[C@@H](C1)N2C1CC2CCCC(C2)C1]

The identity of Substituted Piperidin-4-amino Type Compound Zm was confirmed using $^1$H-NMR and LC/MS:

Substituted Piperidin-4-amino Type Compound Zm: $^1$H-NMR (400 MHz, DMSO) δ: 1.51-1.76 (m, 14.0H), 2.23 (s, 4.0H), 2.44 (s, 1.0H), 2.50 (s, 2.0H), 2.85-2.89 (m, 2.0H), 3.36 (s, 1.0H), 3.91-4.15 (m, 3.0H), 6.58-6.73 (m, 2.0H), 7.38 (t, J=7.1 Hz, 1.0H), 7.82 (d, J=7.8 Hz, 1.0H), 8.28 (s, 1.0H). LC/MS: m/z=395.2 [M+H]$^+$.

The identity of Substituted Piperidin-4-amino Type Compound Zn was confirmed using $^1$H-NMR and LC/MS:

Substituted Piperidin-4-amino Type Compound Zn: $^1$H-NMR (400 MHz, CDCl$_3$) δ: 1.41-2.02 (m, 21.0H), 2.23 (s, 1.0H), 2.53 (s, 1.0H), 2.74 (s, 2.0H), 2.94-3.02 (m, 3.0H), 3.48 (br, 2.0H), 3.84 (d, J=10.5 Hz, 1.0H), 4.06 (br, 2.0H), 4.39 (s, 1.0H), 4.92 (s, 1.0H), 6.41(d, J=7.2 Hz, 1.0H), 6.58 (t, J=6.5 Hz, 1.0H), 6.83 (d, J=7.4 Hz, 1.0H), 7.24 (t, J=7.5 Hz, 1.0H). LC/MS: m/z=454.6 [M+H]$^+$.

5.19 Example 19 : Synthesis of Compound 21

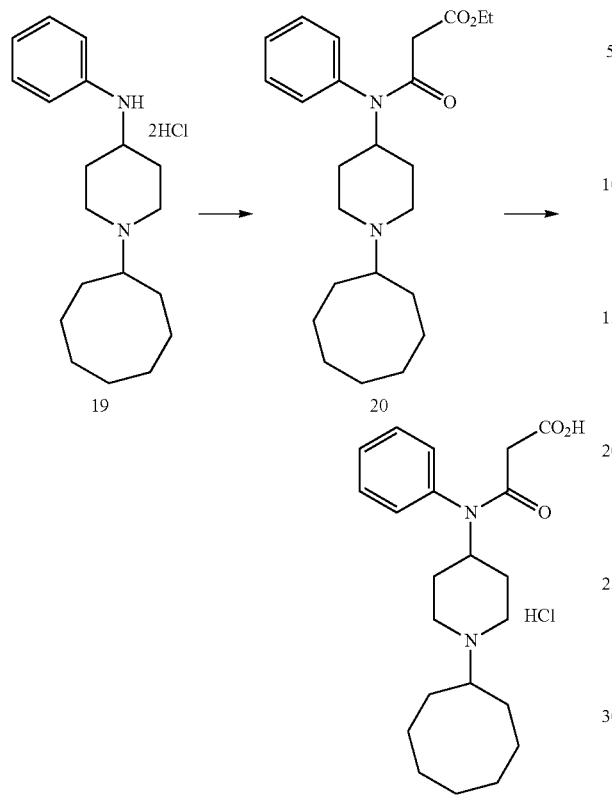

Using procedures similar to those described in Example 1, Compound 19 was prepared.

To a solution of Compound 19 (200 mg, 0.557 mmol) in 1,2-dichloroethane (8 ml), Et$_3$N (233 µl, 1.671 mmol) and ethyl 3-chloro-3-oxopropanoate (105 µl, 0.836 mmol) were added at a temperature of about 25° C. The mixture was stirred at a temperature of about 25° C. for 1.5 hours. Saturated NaHCO$_3$ (aq.) was then added to the mixture. The mixture was then extracted with EtOAc twice. The organic layers were washed with brine, dried over MgSO$_4$ and concentrated in vacuo. The resulting brown oil was chromatographed by column chromatography (Hexane/EtOAc=4/1 to 3/1 to CHCl$_3$/10% NH$_3$ in MeOH=10/1) to give Compound 20 as a pale yellow oil (yield; 115.2 mg, 52%).

The identity of Compound 20 was confirmed using LC/MS: m/z=401.4 [M+H]+.

To a solution of Compound 20 (52 mg, 0.13 mmol) in Ethanol (1 ml), 1M NaOH (0.156 ml, 0.156 mmol) was added at a temperature of about 25° C. The mixture was stirred at a temperature of about 25° C. for 1 hour. After concentration in vacuo, saturated NaHCO$_3$ (aq.) was added to the mixture. The mixture was then extracted with EtOAc twice. The aqueous layers were neutralized by 1M HCl to pH 4 and then extracted with CH$_2$Cl$_2$ twice. The organic layers were dried over MgSO$_4$ and concentrated in vacuo. The resulting oil was chromatographed by C18 column chromatography (H$_2$O/CH$_3$CN=100/0 to 0/100). To a solution of the chromatography product in DCM (1 ml), 4N HCl-Dioxane (50 pal) was added at a temperature of about 25° C. The solution was then concentrated in vacuo. Et$_2$O was added to the concentrate and the resulting solid was filtrated and washed with Et$_2$O to give Compound 21 as a pale brown solid (yield; 2.5 mg, 5%) The identity of Compound 21 was confirmed using $^1$H-NMR and LC/MS:

Compound 21: $^1$H-NMR (400 MHz, CDCl$_3$) δ: 1.38-1.96 (m, 18H), 2.92 (s, 2H), 3.16-3.56 (m, 5H), 4.75 (t, J=12.0 Hz, 1H), 7.25 (d, J=6.5 Hz, 2H), 7.45 (m, 3H), 8.97 (brs, 1H), 12.45 (brs, 1H). LC/MS: m/z=373.3 [M+H]$^+$.

A Substituted Piperidin-4-amino Type Compound of the disclosure can be prepared by Substituting Compound 19 in this Example with a compound having groups A and B as defined herein but which is otherwise identical to Compound 19.

5.20 Example 20 : Synthesis of Compound 25

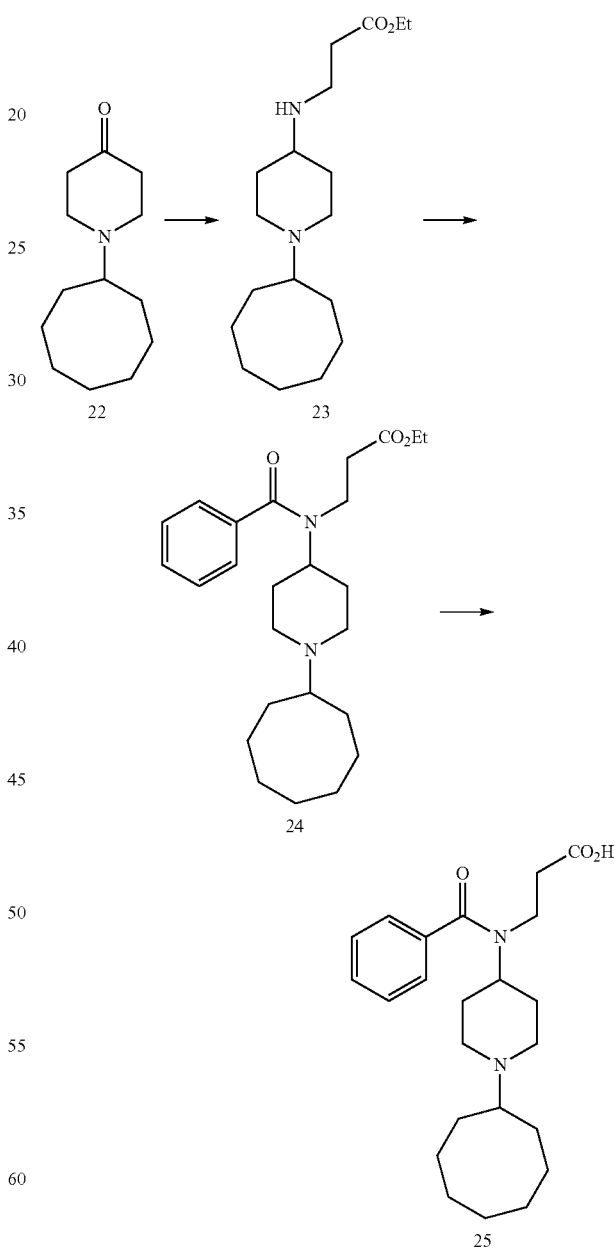

Using procedures similar to those described in Example 1, Compound 23 was prepared using Compound 22 as a starting material.

The identity of Compound 23 was confirmed by ¹H-NMR:

Compound 23: ¹H-NMR (400 MHz, CDCl₃) δ: 1.26 (t, J=7.12 Hz, 3H), 1.32 (d, J=8.4 Hz, 2H), 1.43-1.60 (m, 11H), 1.72 (m, 4H), 1.86 (d, J=12.2 Hz, 2H), 2.21 (m, 2H), 2.40 (m, 1H), 2.49 (t, J=6.56 Hz, 2H), 2.60 (m, 1H), 2.76 (d, J=11.96 Hz, 2H), 2.89 (t, J=6.64 Hz, 2H), 4.14 (q, J=7.16 Hz, 2H).

Using procedures similar to those described in Example 10, Compound 24 was prepared using Compound 23 as a starting material. Compound 25 was prepared using Compound 24 as a starting material and using procedures similar to those described in Example 13.

The identity of Compound 25 was confirmed by LC/MS:
Compound 25: LC/MS: m/z=387.6 [M+H]+.

A Substituted Piperidin-4-amino Type Compound of the disclosure can be prepared by Substituting Compound 22 in this Example with a compound having groups A and B as defined herein but which is otherwise identical to Compound 22.

5.21 Example 21 : Synthesis of Compound 28

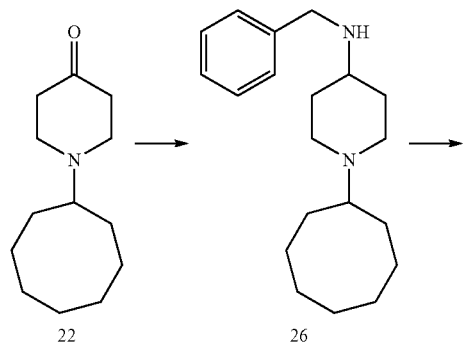

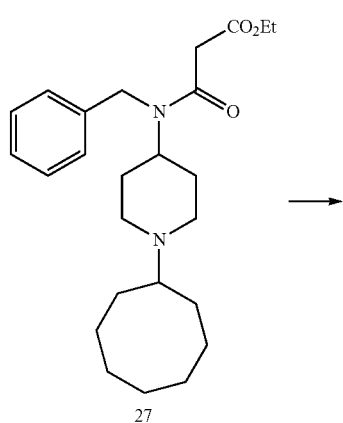

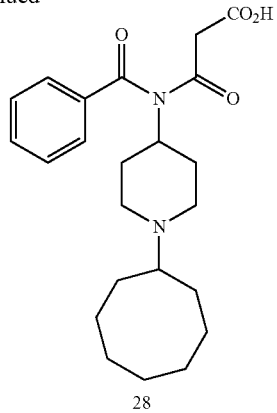

Using procedures similar to those described in Example 1, Compound 26 was prepared using Compound 22 as a starting material.

The identity of Compound 26 was confirmed by LC/MS:
Compound 26: LC/MS: m/z=301.3 [M+H]+.

To a solution of Compound 26 (300 mg, 1.00 mmol) in DMF (6 ml), 3-ethoxy-3-oxopropanoic acid (177 µl, 11.50 mmol), 1-Hydroxybenzotriazole hydrate (13.5 mg, 0.10 mmol) and N-(3-dimethylaminopropyl)-n'-ethylcarbodiimide hydrochloride (293 mg, 1.50 mmol) were added at a temperature of about 25° C. The mixture was stirred at a temperature of about 25° C. for 12 hours. Saturated NaHCO₃ (aq.) was added to the mixture The mixture was then extracted with EtOAc twice. The organic layers were washed with H₂O, dried over MgSO₄ and concentrated in vacuo. The resulting oil was chromatographed by column chromatography (CHCl₃/10% NH₃ in MeOH=95/5 to 9/1) to give Compound 27 as a colorless oil (yield; 414.5 mg, quant.).

The identity of Compound 27 was confirmed by LC/MS:
Compound 27: LC/MS: m/z=415.6 [M+H]⁺.

Using procedures similar to those described in Example 13, Compound 28 was prepared using Compound 27 as a starting material.

The identity of Compound 28 was confirmed by LC/MS:
Compound 28: LC/MS: m/z=387.3 [M+H]+.

A Substituted Piperidin-4-amino Type Compound of the disclosure can be prepared by Substituting Compound 22 in this Example with a compound having groups A and B as defined herein but which is otherwise identical to Compound 22.

5.22 Example 22 : In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) are prepared by lysing cells in ice-cold hypotonic buffer (2.5 mM MgCl₂, 50 mM HEPES, pH 7.4) (10 mL/10 cm dish) followed by homogenization with a tissue grinder/Teflon pestle. Membranes are collected by centrifugation at 30,000×g for 15 min at 4° C. and pellets resuspended in hypotonic buffer to a final concentration 1-3 mg/mL. Protein concentrations are determined using the BioRad protein assay reagent with bovine serum albumen as a standard. Aliquots of the ORL-1 receptor membranes are stored at −80° C.

Radioligand binding assays (screening and dose-displacement) use 0.1 nM [³H]-nociceptin (NEN; 87.7 Ci/mmole)

with 10-20 μg membrane protein in a final volume of 500 μL binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at about 25° C. Binding reactions are terminated by rapid filtration onto 96-well Unifilter GF/C filter plates (Packard) presoaked in 0.5% polyethylenimine (Sigma-Aldrich). Harvesting is performed using a 96-well tissue harvester (Packard) followed by three filtration washes with 500 μL ice-cold binding buffer. Filter plates are subsequently dried at 50° C. for 2-3 hours. Fifty μL/well scintillation cocktail (BetaScint; Wallac) is added and plates are counted in a Packard Top-Count for 1 min/well. The data from screening and dose-displacement experiments are analyzed using Microsoft Excel and the curve fitting functions in GraphPad PRISM™, v. 3.0, respectively, or an in-house function for one-site competition curve-fitting.

5.23 Example 23 : In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) are prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/mL. Protein concentrations are determined using the BioRad protein assay reagent with bovine serum albumen as a standard. Aliquots of the ORL-1 receptor membranes are stored at −80° C.

Functional binding assays are conducted as follows. ORL-1 membrane solution is prepared by sequentially adding final concentrations of 0.066 μg/μL ORL-1 membrane protein, 10 g/mL saponin, 3 M GDP and 0.20 nM [35S] GTPγS to binding buffer (100 mM NaCl, 10 mM $MgCl_2$, 20 mM HEPES, pH 7.4) on ice. The prepared membrane solution (190 μL/well) is transferred to 96-shallow well polypropylene plates containing 10 μL of 20× concentrated stock solutions of agonist/nociceptin prepared in DMSO. Plates are incubated for 30 min at about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates are subsequently dried at 50° C. for 2-3 hours. Fifty μL/well scintillation cocktail (BetaScint; Wallac) is added and plates are counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In one embodiment, a Substituted Piperidin-4-amino-Type Compound has an ORL-1 GTP $EC_{50}$ (nM) of about 5000 or less to stimulate ORL-1 receptor function. In another embodiment, a Substituted Piperidin-4-amino-Type Compound has an ORL-1 GTP $EC_{50}$ (nM) of about 1000 or less. In another embodiment, a Substituted Piperidin-4-amino-Type Compound has an ORL-1 GTP $EC_{50}$ (nM) of about 100 or less. In another embodiment, a Substituted Piperidin-4-amino-Type Compound has an ORL-1 GTP $EC_{50}$ (nM) of about 80 or less. In another embodiment, a Substituted Piperidin-4-amino-Type Compound has an ORL-1 GTP $EC_{50}$ (nM) of about 50 or less. In another embodiment, a Substituted Piperidin-4-amino-Type Compound has an ORL-1 GTP $EC_{50}$ (nM) of about 35 or less. In another embodiment, a Substituted Piperidin-4-amino-Type Compound has an ORL-1 GTP $EC_{50}$ (nM) of about 15 or less. In another embodiment, a Substituted Piperidin-4-amino-Type Compound has an ORL-1 GTP $EC_{50}$ (nM) of about 10 or less. In another embodiment, a Substituted Piperidin-4-amino-Type Compound has an ORL-1 GTP $EC_{50}$ (nM) of about 4 or less. In another embodiment, a Substituted Piperidin-4-amino-Type Compound has an ORL-1 GTP $EC_{50}$ (nM) of about 1 or less. In another embodiment, a Substituted Piperidin-4-amino-Type Compound has an ORL-1 GTP $EC_{50}$ (nM) of about 0.4 or less. In another embodiment, a Substituted Piperidin-4-amino-Type Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, a Substituted Piperidin-4-amino-Type Compound has an ORL-1 GTP Emax (%) of about 50% or greater. In another embodiment, a Substituted Piperidin-4-amino-Type Compound has an ORL-1 GTP Emax (%) of about 75% or greater. In another embodiment, a Substituted Piperidin-4-amino-Type Compound has an ORL-1 GTP Emax (%) of about 85% or greater. In another embodiment, a Substituted Piperidin-4-amino-Type Compound has an ORL-1 GTP Emax (%) of about 95% or greater. In another embodiment, a Substituted Piperidin-4-amino-Type Compound has an ORL-1 GTP Emax (%) of about 100% or greater. In another embodiment, a Substituted Piperidin-4-amino-Type Compound has an ORL-1 GTP Emax (%) of about 110% or greater. In certain embodiments, a Substituted Piperidin-4-amino-Type Compound acting as a partial agonist has an ORL-1 GTP Emax (%) of less than about 10%. In one embodiment, partial agonist Substituted Piperidin-4-amino-Type Compounds has an ORL-1 GTP Emax (%) of less than about 20%. In another embodiment, partial agonist Substituted Piperidin-4-amino-Type Compounds has an ORL-1 GTP Emax (%) of less than about 30%. In another embodiment, partial agonist Substituted Piperidin-4-amino-Type Compounds has an ORL-1 GTP Emax (%) of less than about 40%. In another embodiment, partial agonist Substituted Piperidin-4-amino-Type Compounds has an ORL-1 GTP Emax (%) of less than about 50%.

5.24 Example 24 : In Vitro Mu-opioid Receptor Binding Assays

μ-Opioid Receptor Binding Assay Procedures: Radioligand binding assays are conducted using freshly thawed membranes expressing human μ-receptors (Perkin Elmer, Shelton, Conn.). Radioligand dose-displacement binding assays for human μ-opioid receptors used 0.2 nM [$^3$H]-diprenorphine (NEN, Boston, Mass.), with 5-20 mg membrane protein/well in a final volume of 500 μL binding buffer (10 mM $MgCl_2$, 1 mM EDTA, 5% DMSO, 50 mM HEPES, pH 7.4). Reactions are carried out in the absence or presence of increasing concentrations of unlabeled naloxone. All reactions are conducted in 96-deep well polypropylene plates for 1-2 hr at about 25° C. Binding reactions are terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 μL of ice-cold binding buffer. Filter plates are subsequently dried at 50° C. for 2-3 hours. BetaScint scintillation cocktail (Wallac, Turku, Finland) is added (50 µL/well), and plates are counted using a Packard Top-Count for 1 min/well. The data are analyzed using the one-site competition curve fitting functions in GraphPad PRISM v. 3.0 (San Diego, Calif.), or an in-house function for one-site competition curve-fitting.

µ-Opioid Receptor Binding Data: In certain embodiments, a Substituted Piperidin-4-amino-Type Compound has a $K_i$ (nM) of about 3000 or less for binding to µ-opioid receptors, or about 1000 or less, or about 650 or less, or about 525 or less, or about 250 or less, or about 100 or less, or about 10 or less, or about 1 or less, or about 0.1 or less.

5.25 Example 25 : In Vitro Mu-Opioid Receptor Functional Assays

µ-Opioid Receptor Functional Assay Procedures: [$^{35}$S] GTPγS functional assays are conducted using freshly thawed membranes expressing human µ-receptors. Assay reactions are prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 µL/well) is transferred to 96-shallow well polypropylene plates containing 10 µL of 20× concentrated stock solutions of the agonist DAMGO ([D-Ala2, N-methyl-Phe4 Gly-olS5]-enkephalin) prepared in DMSO. Plates are incubated for 30 min at about 25° C. with shaking. Reactions are terminated by rapid filtration onto 96-well Unifilter GF/B filter plates (Packard, Meriden, Conn.) using a 96-well tissue harvester (Brandel, Gaithersburg, Md.) followed by three filtration washes with 200 µL of ice-cold wash buffer (10 mM NaH$_2$PO$_4$, 10 mM Na$_2$HPO$_4$, pH 7.4). Filter plates are subsequently dried at 50° C. for 2-3 hr. BetaScint scintillation cocktail (Wallac, Turku, Finland) is added (50 µL/well) and plates are counted using a Packard Top-Count for 1 min/well. Data are analyzed using the sigmoidal dose-response curve fitting functions in GraphPad PRISM v. 3.0, or an in-house function for non-linear, sigmoidal dose-response curve-fitting.

µ-Opioid Receptor Functional Data: µ GTP $EC_{50}$ is the concentration of a compound providing 50% of the maximal response for the compound at a -opioid receptor. In certain embodiments, a Substituted Piperidin-4-amino-Type Compound has a µ GTP $EC_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

µ GTP Emax (%) is the maximal effect elicited by a compound relative to the effect elicited by DAMGO, a standard t agonist. In certain embodiments, a Substituted Piperidin-4-amino-Type Compound has a µ GTP Emax (%) of about 10% or greater, or about 20% or greater, or about 50% or greater, or about 65% or greater, or about 75% or greater, or about 88% or greater, or about 100% or greater. In other embodiments, a Substituted Piperidin-4-amino-Type Compound has a µ GTP Emax (%) of about 10% or less, or about 5% or less, or about 2% or less.

5.26 Example 26 : In Vitro Kappa-opioid Receptor Binding Assays

κ-Opioid Receptor Binding Assay Procedures: Membranes from recombinant HEK-293 cells expressing the human kappa opioid receptor (kappa) (cloned in house) are prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/mL. Protein concentrations are determined using the BioRad protein assay reagent with bovine serum albumen as a standard. Aliquots of kappa receptor membranes are stored at −80° C.

Radioligand dose displacement assays used 0.4-0.8 nM [$^3$H]-U69,593 (NEN; 40 Ci/mmole) with 10-20 µg membrane protein (recombinant kappa opioid receptor expressed in HEK 293 cells; in-house prep) in a final volume of 200 µL binding buffer (5% DMSO, 50 mM Trizma base, pH 7.4). Non-specific binding is determined in the presence of 10 µM unlabeled naloxone or U69,593. All reactions are performed in 96-well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 200 µL ice-cold binding buffer. Filter plates are subsequently dried at 50° C. for 1-2 hours. Fifty µL/well scintillation cocktail (MicroScint$^2$0, Packard) is added and plates are counted in a Packard Top-Count for 1 min/well.

κ-Opioid Receptor Binding Data: In one embodiment, a Substituted Piperidin-4-amino-Type Compound has substantially no activity at a κ-opioid receptor. In certain embodiments, a Substituted Piperidin-4-amino-Type Compound has a Ki (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

5.27 Example 27 : In Vitro Kappa-Opioid Receptor Functional Assays

κ-Opioid Receptor Functional Assay Procedures: Functional [$^{35}$S]GTPγS binding assays are conducted as follows. Kappa opioid receptor membrane solution is prepared by sequentially adding final concentrations of 0.026 µg/µL kappa membrane protein (in-house), 10 µg/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µL/well) are transferred to 96-shallow well polypropylene plates containing 10 µL of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates are subsequently dried at 50° C. for 2-3 hours. Fifty μL/well scintillation cocktail (MicroScinT²0, Packard) is added and plates are counted in a Packard Top-Count for 1 min/well.

κ-Opioid Receptor Functional Data: κ GTP $EC_{50}$ is the concentration of a compound providing 50% of the maximal response for the compound at a κ-opioid receptor. In certain embodiments, a Substituted Piperidin-4-amino-Type Compound has a κ GTP $EC_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, a Substituted Piperidin-4-amino-Type Compound has a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, a Substituted Piperidin-4-amino-Type Compound has a κ GTP Emax (%) of about 10% or less, or about 5% or less, or about 2% or less.

5.28 Example 28 : In Vitro Delta-opioid Receptor Binding Assays

δ-Opioid Receptor Binding Assay Procedures: Radioligand dose-displacement assays use 0.2 nM [³H]-Naltrindole (NEN; 33.0 Ci/mmole) with 10-20 μg membrane protein (recombinant delta opioid receptor expressed in CHO-K1 cells; Perkin Elmer) in a final volume of 500 μL binding buffer (5 mM $MgCl_2$, 5% DMSO, 50 mM Trizma base, pH 7.4). Non-specific binding is determined in the presence of 25 μM unlabeled naloxone. All reactions are performed in 96-deep well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 500 μL ice-cold binding buffer. Filter plates are subsequently dried at 50° C. for 1-2 hours. Fifty μL/well scintillation cocktail (MicroScinT²0, Packard) is added and plates are counted in a Packard Top-Count for 1 min/well.

δ-Opioid Receptor Binding Data: In one embodiment, a Substituted Piperidin-4-amino-Type Compound has substantially no activity at a δ-opioid receptor. In certain embodiments, a Substituted Piperidin-4-amino-Type Compound has a $K_i$ (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

5.29 Example 29 : In Vitro Delta-Opioid Receptor Functional Assays

δ-Opioid Receptor Functional Assay Procedures: Functional [³⁵S]GTPγS binding assays are conducted as follows using membranes expressing human δ-opioid receptors. Delta opioid receptor membrane solution is prepared by sequentially adding final concentrations of 0.026 μg/μL delta membrane protein (Perkin Elmer), 10 μg/mL saponin, 3 μM GDP and 0.20 nM [³⁵S]GTPγS to binding buffer (100 mM NaCl, 10 mM $MgCl_2$, 20 mM HEPES, pH 7.4) on ice. The prepared membrane solution (190 μL/well) is transferred to 96-shallow well polypropylene plates containing 10 L of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates are subsequently dried at 50° C. for 1-2 hours. Fifty μL/well scintillation cocktail (MicroScinT²0, Packard) is added and plates are counted in a Packard Top-count for 1 min/well.

δ-Opioid Receptor Functional Data: δ GTP $EC_{50}$ is the concentration of a compound providing 50% of the maximal response for the compound at a δ receptor. In certain embodiments, a Substituted Piperidin-4-amino-Type Compound has a δ GTP $EC_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, a Substituted Piperidin-4-amino-Type Compound has a δ GTP Emax (%) of about 10% or greater, or about 30% or greater, or about 50% or greater, or about 75% or greater, or about 90% or greater, or about 100% or greater, or about 110% or greater. In other embodiments, a Substituted Piperidin-4-amino-Type Compound has a δ GTP Emax (%) of about 10% or less, or about 5% or less, or about 2% or less.

5.30 Example 30 : Efficacy of Receptor Binding and Activity Response

Table 33 provides, for several Substituted Piperidin-4-amino-Type Compounds, results on the efficacy of binding and activity response to the ORL-1 receptor, the mu-opioid receptor, the kappa-opioid receptor, and/or the delta-opioid receptor and CYP2D6 response.

In Table 33, binding efficacy to the ORL-1 receptor was determined by the procedure in Example 22. Binding efficacy to the mu-opioid receptor was determined by the procedure in Example 24. Binding efficacy to the kappa-opioid receptor was determined by the procedure in Example 26. Binding efficacy to the delta-opioid receptor was determined by the procedure in Example 28. In Table 34, activity response to the ORL-1 receptor was determined by the procedure in Example 23. Activity response to the mu-opioid receptor was determined by the procedure in Example 25. Activity response to the kappa-opioid receptor was determined by the procedure in Example 27.

TABLE 33
| Reference Number | Compound | $K_i$ [Average ± Std Deviation] (nM) | | | |
|---|---|---|---|---|---|
| | | | Opioid Receptor | | |
| | | ORL-1 | Mu | Kappa | Delta |
| B21a(i) | 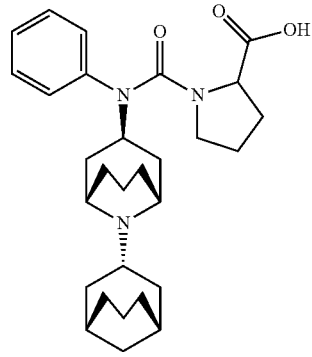 [SMILES: O=C(O)C1CCCN1C(=O)N(c1ccccc1)[C@H]1C[C@H]2CCC[C@@H](C1)N2[C@H]1C[C@@H]2CCC[C@@H](C2)C1] | 18.21 ± 3.69 | | | |
| S-B21a(i) | 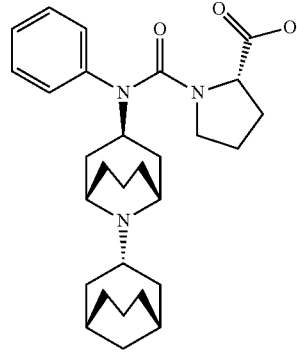 | 67.57 ± 11.21 | | | |
| (R)-B21a(i) | 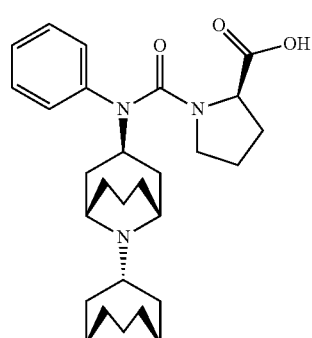 | 32.6 ± 7.64 | | | |
| (S)-B22a(i) | 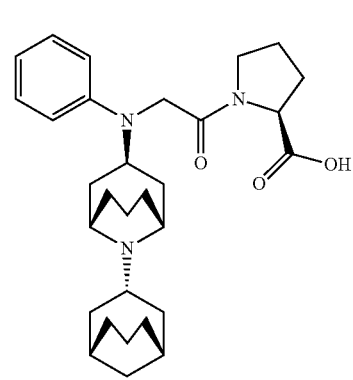 [SMILES: O=C(O)[C@@H]1CCCN1C(=O)CN(c1ccccc1)[C@H]1C[C@H]2CCC[C@@H](C1)N2[C@H]1C[C@@H]2CCC[C@@H](C2)C1] | 279.66 ± 67.8 | | | |

TABLE 33-continued
| | | $K_i$ [Average ± Std Deviation] (nM) | | | |
|---|---|---|---|---|---|
| Reference | | | Opioid Receptor | | |
| Number | Compound | ORL-1 | Mu | Kappa | Delta |
| (S)B61a(i) | 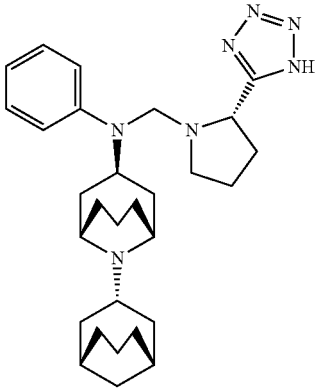 [SMILES: c1ccc(N(CN2CCC[C@H]2c2nnn[nH]2)[C@H]2C[C@H]3CCC[C@@H](C2)N3[C@H]2C[C@@H]3CCC[C@@H](C3)C2)cc1] | 410.8 ± 30.9 | | | |
| (R)-B41a(i) | 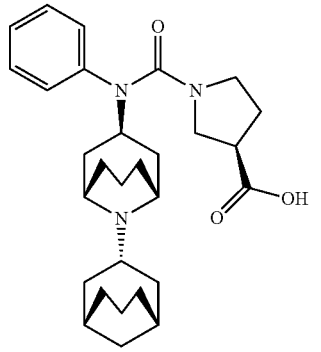 [SMILES: O=C(O)[C@@H]1CCN(C(=O)N(c2ccccc2)[C@H]2C[C@H]3CCC[C@@H](C2)N3[C@H]2C[C@@H]3CCC[C@@H](C3)C2)C1] | 780.2 ± 186.12 | | | |
| Q11a(i)(iv) | 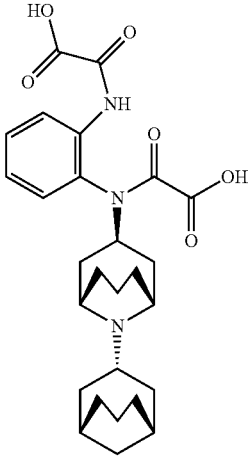 [SMILES: O=C(O)C(=O)Nc1ccccc1N(C(=O)C(=O)O)[C@H]1C[C@H]2CCC[C@@H](C1)N2[C@H]1C[C@@H]2CCC[C@@H](C2)C1] | 21.46 ± 2.79 | | | |

TABLE 33-continued
| Reference Number | Compound | K$_i$ [Average ± Std Deviation] (nM) | | | |
| --- | --- | --- | --- | --- | --- |
| | | | Opioid Receptor | | |
| | | ORL-1 | Mu | Kappa | Delta |
| (7S)-Q11a(ii)(iv) | 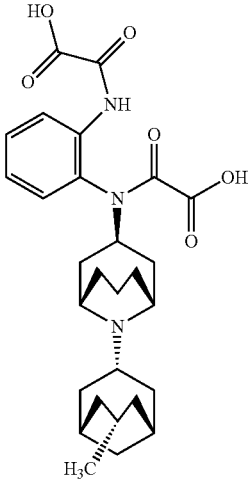 [SMILES: C[C@@H]1C[C@@H]2C[C@H](C1)C[C@@H](N1[C@@H]3CCC[C@H]1C[C@@H](N(C(=O)C(=O)O)c1ccccc1NC(=O)C(=O)O)C3)C2] | 9.14 ± 1.32 | 337.35 ± 82.72 | 289.34 ± 73.78 | >20,000 |
| Zh | 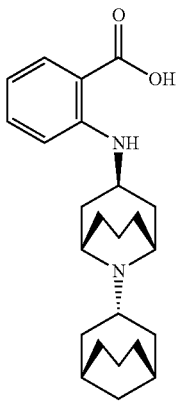 [SMILES: O=C(O)c1ccccc1N[C@H]1C[C@H]2CCC[C@@H](C1)N2[C@H]1C[C@@H]2CCC[C@@H](C2)C1] | 439.28 ± 71.43 | | | |
| Zl | 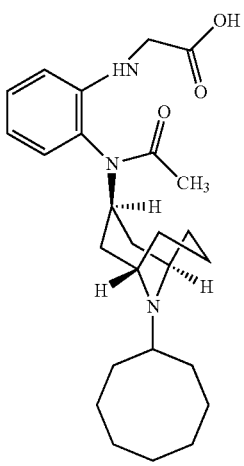 [SMILES: CC(=O)N(c1ccccc1NCC(=O)O)[C@H]1C[C@H]2CCC[C@@H](C1)N2C1CCCCCCC1] | >20,000 | | | |

TABLE 33-continued
| Reference Number | Compound | K$_i$ [Average ± Std Deviation] (nM) | | | |
| --- | --- | --- | --- | --- | --- |
| | | | Opioid Receptor | | |
| | | ORL-1 | Mu | Kappa | Delta |
| Zm |  | >20,000 | | | |
| Zn | 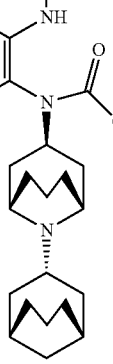 | 262.51 ± 36.9 | >20,000 | | >20,000 |
| 21 | 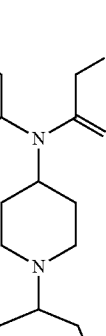 | 5606.23 ± 145.17 | | | |

TABLE 33-continued

| | | K_i [Average ± Std Deviation] (nM) | | | |
| | | | Opioid Receptor | | |
| Reference Number | Compound | ORL-1 | Mu | Kappa | Delta |
|---|---|---|---|---|---|
| 25 | 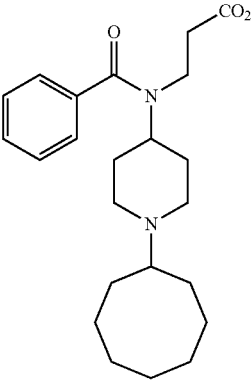 | >20,000 | | | |
| 28 | 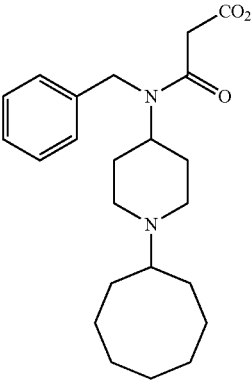 | >20,000 | | | |

TABLE 34

Activity Response of Substituted Piperidin-4-amino Type Compounds

| | GTPγS (EC$_{50}$: nM, Emax: %) [mean ± SEM] | | | |
| | ORL-1 | | Opioid Receptor EC$_{50}$ | |
| Reference Number | EC$_{50}$ | E$_{max}$ | Mu | Kappa |
|---|---|---|---|---|
| B21a(i) | >20,000 | 0.5 ± 0.5 | | |
| (S)-B21a(i) | >20,000 | | | |
| (R)-B21a(i) | >20,000 | | | |
| (S)-B22a(i) | | | | |
| (S)-B61a(i) | | | | |
| (R)-B41a(i) | | | | |
| Q11a(i)(iv) | 12.45 ± 1.75 | 23 ± 2.68 | | |
| (7S)-Q11a(ii)(iv) | 8.1 ± 1.57 | 31 ± 0.58 | >20,000 | >20,000 |
| Zh | | | | |
| Zl | | | | |
| Zm | | | | |
| Zn | 683.27 ± 52.63 | 38.25 ± 3.07 | | |

5.31 Example 31 : In Vivo Assays for Prevention or Treatment of Pain

Test Animals: Each experiment uses rats weighing between 200-260 g at the start of the experiment. The rats are group-housed and have free access to food and water at all times, except prior to oral administration of a Substituted Piperidin-4-amino-Type Compound when food is removed for 16 hours before dosing. A control group acts as a comparison to rats treated with a Substituted Piperidin-4-amino-Type Compound. The control group is administered the carrier for the Substituted Piperidin-4-amino-Type Compound. The volume of carrier administered to the control group is the same as the volume of carrier and Substituted Piperidin-4-amino-Type Compound administered to the test group.

Acute Pain: To assess the actions of a Substituted Piperidin-4-amino-Type Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Substituted Piperidin-4-amino-Type Compound. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \text{ s pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Substituted Piperidin-4-amino-Type Compound for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," Naunyn-Schmiedeberg's *Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/kg of either a Substituted Piperidin-4-amino-Type Compound; 30 mg/kg of a control selected from Celebrex, indomethacin, and naproxen; or carrier. Responses to noxious mechanical stimuli are then determined 1, 3, 5 and 24 hours post administration. Percentage reversal of hyperalgesia for each animal is defined as:

$$\% \ Reversal = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Substituted Piperidin-4-amino-Type Compound for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of male, 6-7 week old Jcl:SD rat is shaved. The sciatic nerve is exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. The wound area is then dusted with antibiotic powder. Sham treatment involves an identical surgical procedure except that the sciatic nerve is not manipulated or ligated.

Following surgery, animals are weighed and placed on a warm pad until they recovered from anesthesia. Animals are then returned to their home cages until behavioral testing began. The animal is assessed for response to noxious mechanical stimuli by determining PWT for the rear paw of the animal, as described below, prior to surgery (baseline), then immediately prior to and 1, 3, and 5 hours after oral drug-in-vehicle administration (for day 1). Thus, the 24 hour time point is the start of the next day when drug-in-vehicle is again orally administered (24 hours after the prior administration). On days 4 and 7, PWT response is determined 1, 3, and 5 hours thereafter. Percentage reversal of neuropathic hyperalgesia at each of the specified times after administration is defined as:

$$\% \ Reversal = \frac{[(\text{post administration } PWT) - (\text{pre-administration } PWT)]}{[(\text{baseline } PWT) - (\text{pre-administration } PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400 cP, Wako Pure Chemical Industries, Ltd.)/aqueous solution) is orally administered as controls. Eight rats that undergo partial ligation of the left sciatic nerve are used for each treatment group except for pregabalin, where six rats are treated. Dunnett's test is conducted for the % reversal; values with $p<0.05$ are considered to be statistically significant.

Additionally, as a control the rats undergo sham surgery in which an identical surgical procedure is followed with regard to the right thigh but the sciatic nerve is neither manipulated nor ligated.

Administration of 1, 3, or 10 mg/kg of Substituted Piperidin-4-amino-Type Compounds provide more effective reversal than the pregabalin control at all the measured time-points on the first day of administration. Once daily administration of Substituted Piperidin-4-amino-Type Compounds of the disclosure for seven days produces statistically significant effects against mechanical hyperalgesia in rats subjected to partial sciatic nerve ligation in the Seltzer model of neuropathic pain. Thus, Substituted Piperidin-4-amino-Type Compounds are effective in relieving neuropathic pain in vivo.

In particular, a single administration of a Substituted Piperidin-4-amino-Type Compound of the disclosure demonstrates analgesic effects in the Selzer model. Repeated administration for 7 days of Substituted Piperidin-4-amino-Type Compounds of the disclosure also demonstrate a dose-dependent significant analgesic effect.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Substituted Piperidin-4-amino-Type Compound for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," Pain 50(3):355-363 (1992).

Response to Mechanical Stimuli as an Assessment of Mechanical Hyperalgesia: The paw pressure assay is used to assess mechanical hyperalgesia. For this assay, hind paw withdrawal thresholds (PWT) to a noxious mechanical stimulus are determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," Pharmacol. Biochem. Behavior 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:
1. A compound of Formula (I):

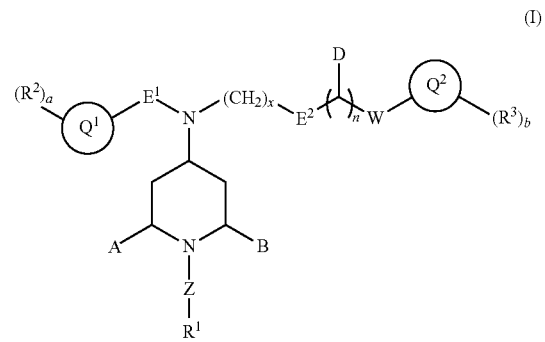

or a pharmaceutically acceptable salt or solvate thereof, wherein:
$Q^1$ is phenyl;
$Q^2$ is $(C_3\text{-}C_{10})$cycloalkyl, (3- to 9-membered)non-aromatic heterocycle, or a direct bond;
$E^1$ is $S(=O)_2$ or a direct bond;
$E^2$ is $C(=O)$, $S(=O)_2$, $CH_2$, or a direct bond;
W is $N(R^*)$ or a direct bond;
D is H, $NO_2$, or $N(R^*)_2$;
$R^*$ is, independently for each occurrence, H or $(C_1\text{-}C_6)$ alkyl unsubstituted or substituted with 1 or 2 substituents independently selected from —OH, —O($C_1\text{-}C_6$) alkyl, and =O;
each $R^2$ and $R^3$ is, independently for each occurrence, —H, -halo, —$NO_2$, —X, —C(=Y)YX, —N($T^1$)($T^2$), —YH, or —YX;
X is, independently for each occurrence, —H, —($C_1\text{-}C_6$) alkyl, —($C_2\text{-}C_6$)alkenyl, or -(5- or 6-membered)heterocycle, each of which is unsubstituted or substituted with 1 or 2 independently selected $R^8$ groups;
each Y is O;
each $R^5$ is independently $OR^9$ or =O;
each $R^8$ is independently —$OR^9$, =O, or —C(=O)$OR^9$;
each $R^9$ is independently —H or —($C_1\text{-}C_6$)alkyl;
a is an integer selected from 0 and 1;
b is an integer selected from 0 and 1;
n is an integer selected from 0 and 1;
x is an integer selected from 0 and 1;
each $T^1$ and $T^2$ is independently —H or —($C_1\text{-}C_{10}$)alkyl which is unsubstituted or substituted with 1, 2, or 3 independently selected $R^5$ groups;
A and B together form a bridge such that the bridged-piperidine is:

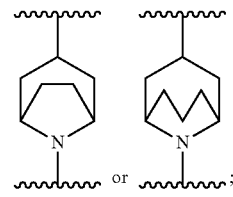

and

—Z—R¹ is:

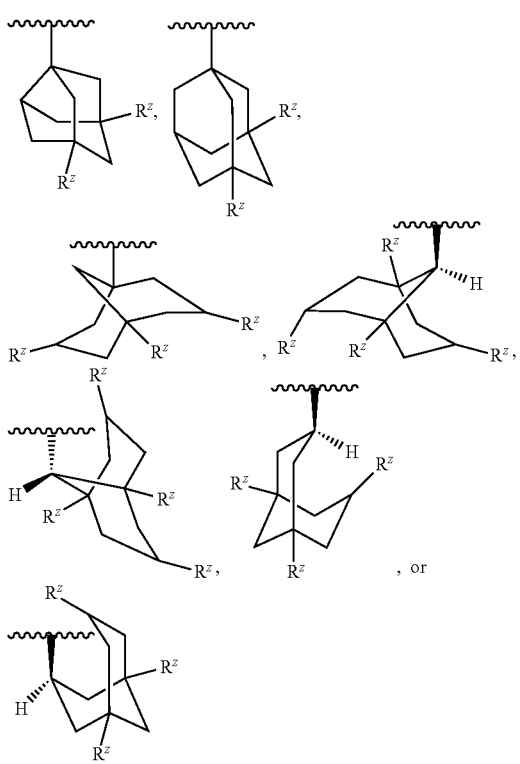

wherein each R$^z$ is independently —H, —(C$_1$-C$_4$)alkyl, —OH, or —CN.

2. The compound of claim 1 or a pharmaceutically acceptable salt or solvate thereof, wherein the R¹ group is in the exo-configuration with respect to the A-B bridge of the bridged piperidine.

3. The compound of claim 1 or a pharmaceutically acceptable salt or solvate thereof, wherein E¹ is S(=O)$_2$ or a direct bond.

4. The compound of claim 1 or a pharmaceutically acceptable salt or solvate thereof, wherein E² is C(=O) or a direct bond.

5. The compound of claim 1 or a pharmaceutically acceptable salt or solvate thereof, wherein D is selected from

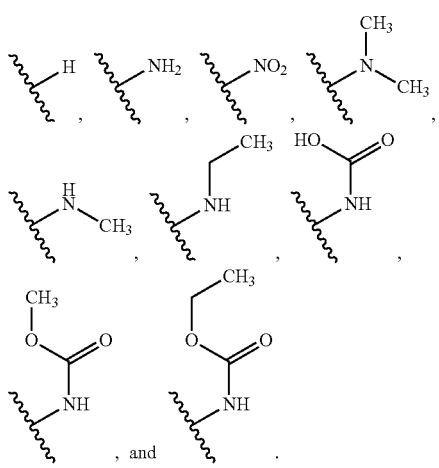

6. The compound of claim 1 or a pharmaceutically acceptable salt or solvate thereof, wherein W is NH or a direct bond, and Q² is (C$_3$-C$_6$)cycloalkyl, non-aromatic (3- to 6-membered)heterocycle, or a direct bond.

7. The compound of claim 1 or a pharmaceutically acceptable salt or solvate thereof, wherein Q²-(R³)$_b$ is selected from

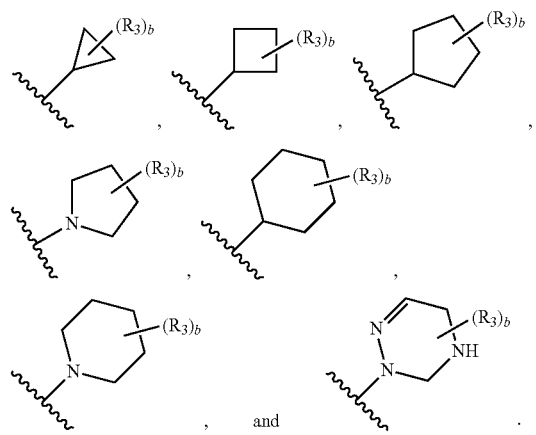

8. The compound of claim 1 or a pharmaceutically acceptable salt or solvate thereof, wherein:

E¹ is a direct bond or SO$_2$;

Q¹ is phenyl;

a is selected from 0 and 1;

R² is selected from

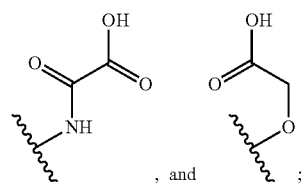 [SMILES: *NC(=O)C(=O)O ; *OCC(=O)O]

x is selected from 0 and 1;

E² is C(=O);

n is selected from 0 and 1;

D is selected from H and —N(CH$_3$)$_2$;

W is selected from —NH and a direct bond;

Q² is selected from pyrrolidinyl, cyclopropyl, cyclohexyl and a direct bond;

b is selected from 0 and 1; and

R³ is selected from

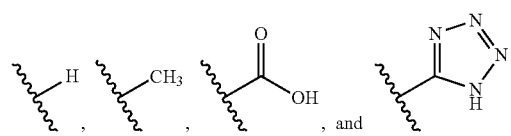

9. A compound which is:
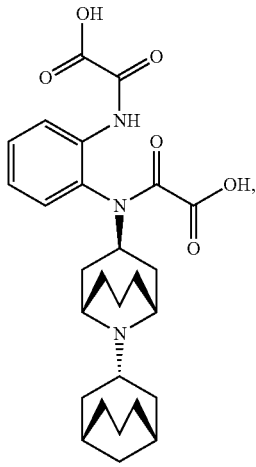
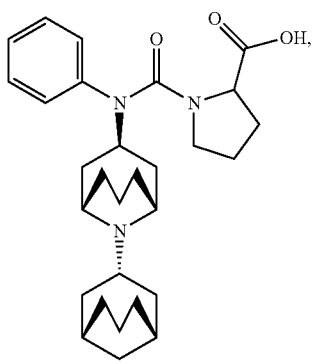
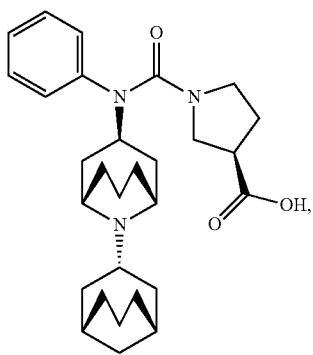
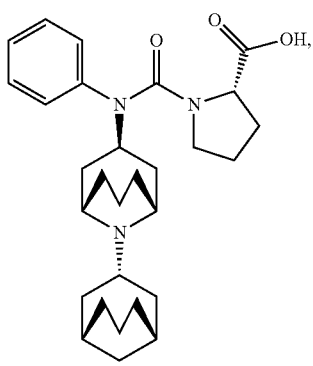
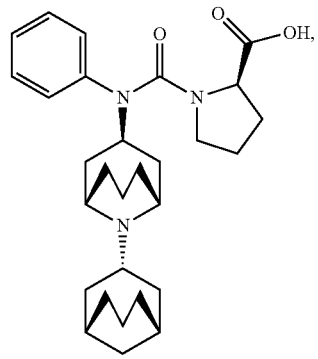
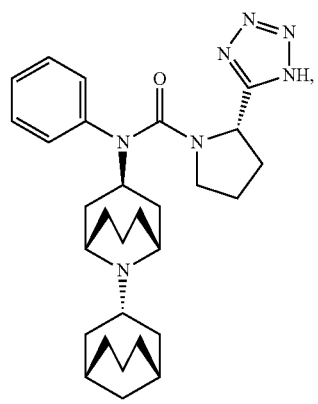
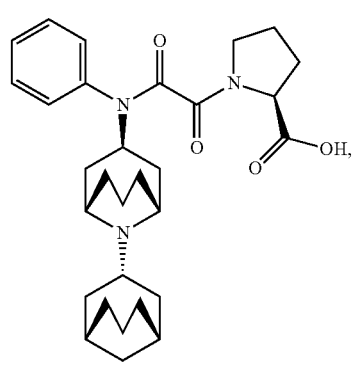
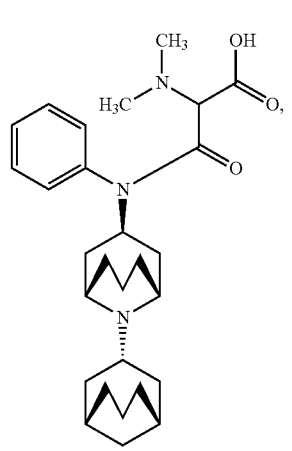

525
-continued
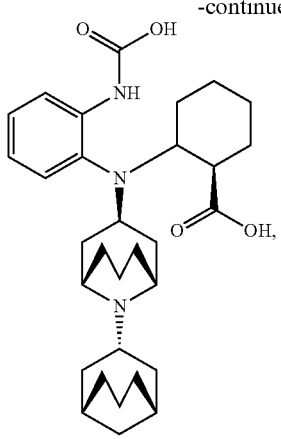
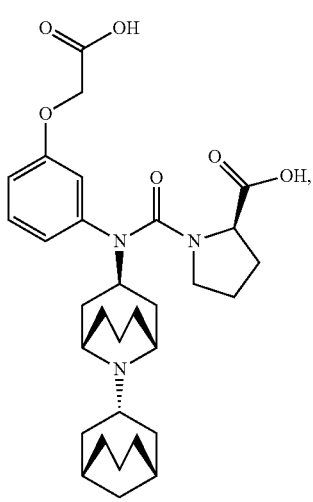
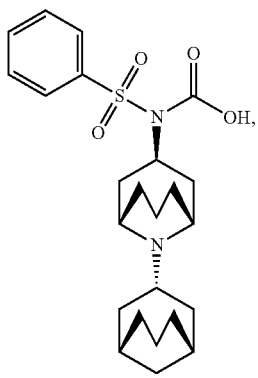
526
-continued
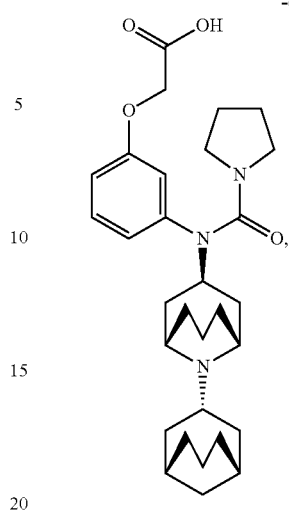
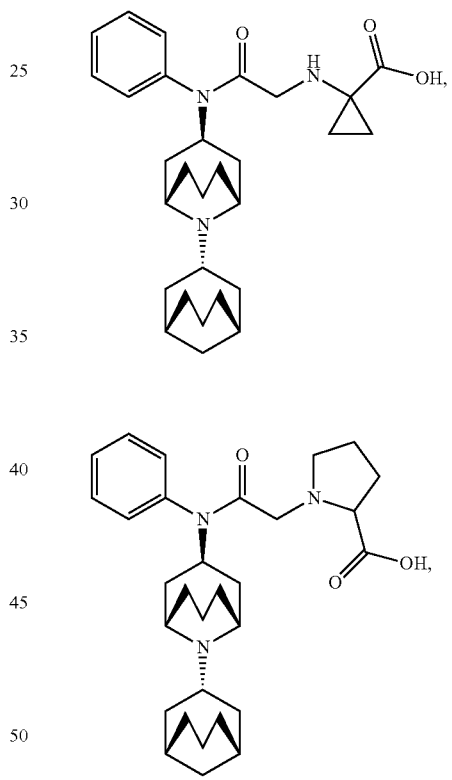
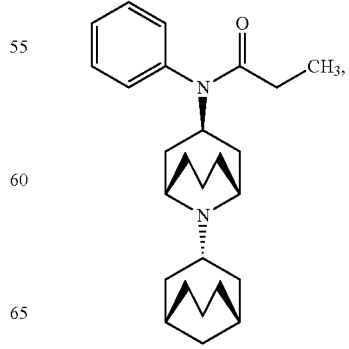

527
-continued
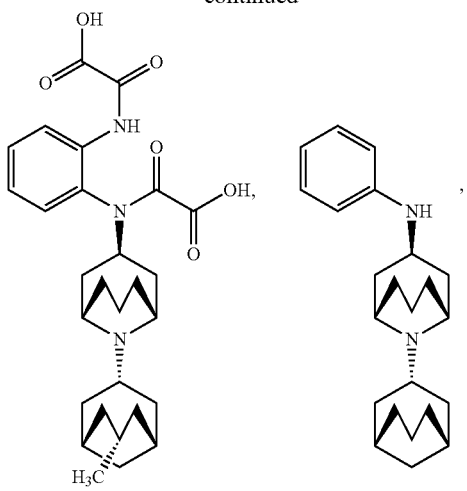
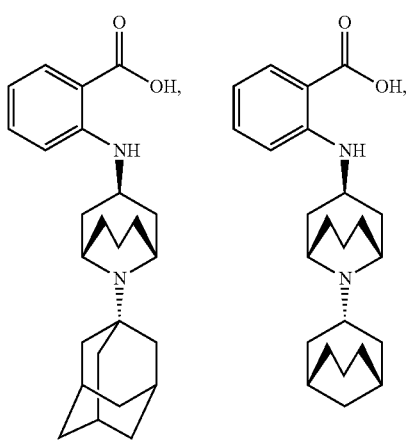
or a pharmaceutically acceptable salt or solvate thereof.
10. A compound which is:
528
-continued
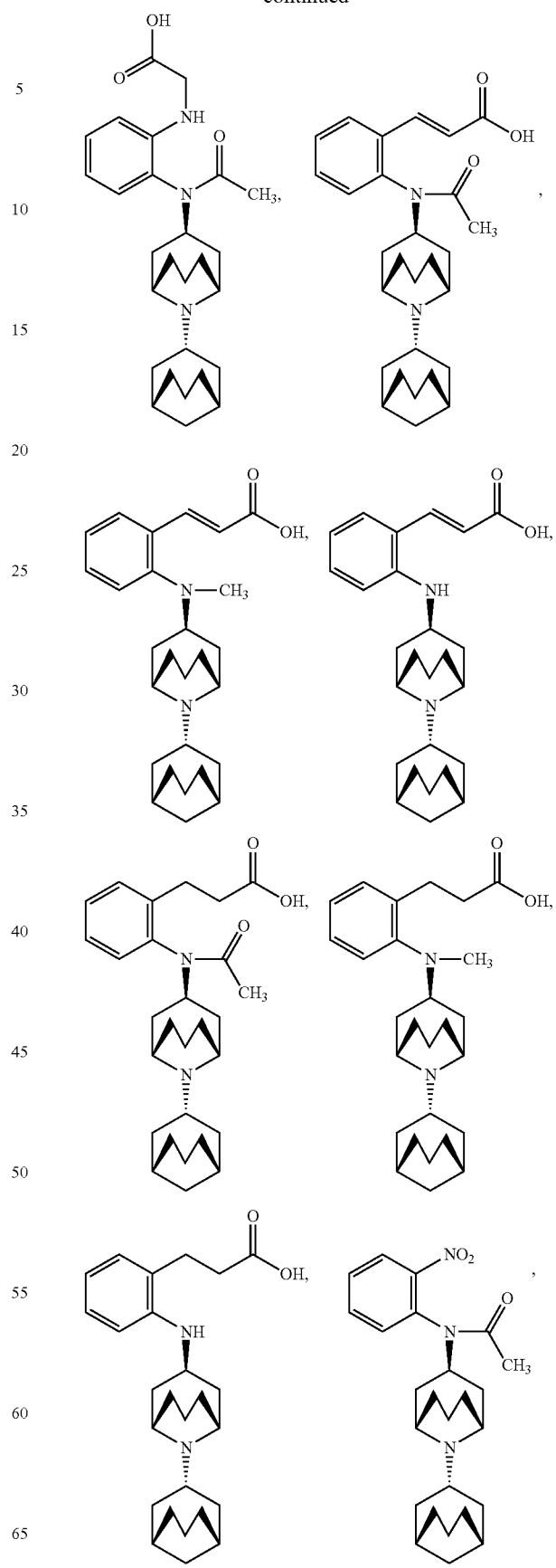

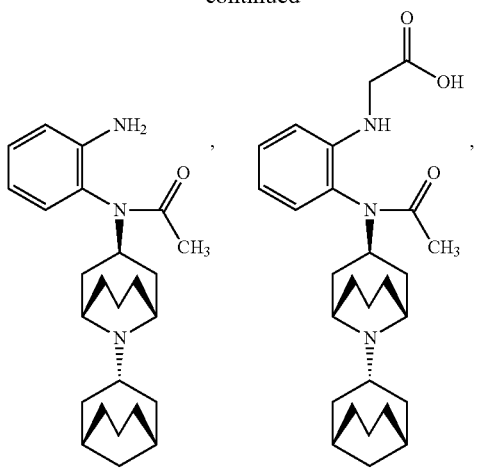

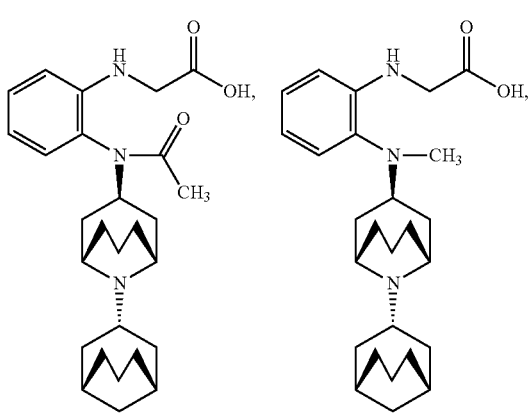

or a pharmaceutically acceptable salt or solvate thereof.

11. A pharmaceutical composition comprising the compound of claim 1 or a pharmaceutically acceptable salt or solvate thereof and a pharmaceutically acceptable carrier or excipient.

12. A method for modulating ORL-1 receptor function in a cell, comprising contacting a cell capable of expressing the ORL-1 receptor with the compound of claim 1 or a pharmaceutically acceptable salt or solvate thereof.

13. The method of claim 12, wherein the compound or the pharmaceutically acceptable salt or solvate thereof acts as an agonist or an antagonist at the ORL-1 receptor.

14. A method for treating pain in an animal, comprising administering to an animal in need thereof the compound of claim 1 or a pharmaceutically acceptable salt or solvate thereof.

15. The compound of claim 1 or a pharmaceutically acceptable salt or solvate thereof, wherein A and B together form a bridge such that the bridged-piperidine is

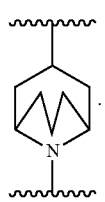

16. The compound of claim 1 or a pharmaceutically acceptable salt or solvate thereof, wherein —Z—R¹ is:

Wherein $R^z$ is —H, —CH$_3$, or —CH$_2$CH$_3$.

17. The compound of claim 1 or a pharmaceutically acceptable salt or solvate thereof, wherein the pharmaceutically acceptable salt is a hydrochloride salt, a sodium salt, a potassium salt, or a para-toluenesulfonic acid salt.

18. The compound of claim 1 or a pharmaceutically acceptable salt or solvate thereof, wherein the compound or pharmaceutically acceptable salt or solvate thereof is radiolabeled.

19. A pharmaceutical composition comprising the compound of claim 9 or a pharmaceutically acceptable salt or solvate thereof and a pharmaceutically acceptable carrier or excipient.

20. A method for modulating ORL-1 receptor function in a cell, comprising contacting a cell capable of expressing the ORL-1 receptor with the compound of claim 9 or a pharmaceutically acceptable salt or solvate thereof.

21. The method of claim 20, wherein the compound or the pharmaceutically acceptable salt or solvate thereof acts as an agonist or an antagonist at the ORL-1 receptor.

22. A method for treating pain in an animal, comprising administering to an animal in need thereof the compound of claim 9 or a pharmaceutically acceptable salt or solvate thereof.

* * * * *